(12) United States Patent
Chen et al.

(10) Patent No.: US 10,233,173 B2
(45) Date of Patent: Mar. 19, 2019

(54) SUBSTITUTED 1,2,3-TRIAZOLES AS NR2B-SELECTIVE NMDA MODULATORS

(71) Applicant: JANSSEN PHARMACEUTICA NV, Beerse (BE)

(72) Inventors: Gang Chen, San Diego, CA (US); Christa C Chrovian, La Jolla, CA (US); Heather R. Coate, San Diego, CA (US); Curt A. Dvorak, Poway, CA (US); Christine F. Gelin, San Diego, CA (US); Afton Hiscox, San Diego, CA (US); Michael A. Letavic, San Diego, CA (US); Jason C. Rech, San Diego, CA (US); Akinola Soyode-Johnson, San Diego, CA (US); Brice Stenne, La Jolla, CA (US); Jessica L. Wall, San Diego, CA (US); Wei Zhang, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/046,332

(22) Filed: Jul. 26, 2018

(65) Prior Publication Data

US 2018/0334451 A1 Nov. 22, 2018

Related U.S. Application Data

(62) Division of application No. 15/428,710, filed on Feb. 9, 2017, now Pat. No. 10,071,988.

(60) Provisional application No. 62/293,680, filed on Feb. 10, 2016.

(51) Int. Cl.
| | | |
|---|---|---|
| C07D 401/12 | (2006.01) |
| C07D 401/14 | (2006.01) |
| C07D 403/12 | (2006.01) |
| C07D 403/14 | (2006.01) |
| C07D 405/14 | (2006.01) |
| C07D 409/14 | (2006.01) |
| C07D 413/12 | (2006.01) |
| C07D 413/14 | (2006.01) |
| C07D 417/12 | (2006.01) |
| A61K 31/4192 | (2006.01) |
| A61K 31/427 | (2006.01) |
| A61K 31/4439 | (2006.01) |
| A61K 31/497 | (2006.01) |
| A61K 31/501 | (2006.01) |
| A61K 31/506 | (2006.01) |
| A61K 31/5377 | (2006.01) |

(52) U.S. Cl.
CPC ......... *C07D 403/12* (2013.01); *C07D 401/12* (2013.01); *C07D 401/14* (2013.01); *C07D 403/14* (2013.01); *C07D 405/14* (2013.01); *C07D 409/14* (2013.01); *C07D 413/12* (2013.01); *C07D 413/14* (2013.01); *C07D 417/12* (2013.01)

(58) Field of Classification Search
None
See application file for complete search history.

(56) References Cited

U.S. PATENT DOCUMENTS

| 8,785,438 | B2 | 7/2014 | Ohtsuka et al. |
| 9,434,743 | B2 | 9/2016 | Cheruvallath et al. |
| 9,963,447 | B2 | 5/2018 | Chrovian et al. |
| 9,981,950 | B2 | 5/2018 | Schindler et al. |
| 10,071,988 | B2 | 9/2018 | Gang et al. |
| 2007/0275965 | A1 | 11/2007 | Thomas et al. |
| 2008/0300239 | A1 | 12/2008 | Adams et al. |
| 2014/0275011 | A1 | 9/2014 | Mastracchio et al. |
| 2016/0024087 | A1 | 1/2016 | Gelbard et al. |
| 2017/0275254 | A1 | 9/2017 | Schindler et al. |
| 2018/0125826 | A1 | 5/2018 | Chovrian et al. |
| 2018/0208595 | A1 | 7/2018 | Chovrian et al. |

FOREIGN PATENT DOCUMENTS

| EP | 2194045 A1 | 6/2010 |
| WO | 2003082868 A1 | 10/2003 |
| WO | 2005080379 A1 | 9/2005 |
| WO | 2008145616 A1 | 12/2008 |
| WO | 2009058261 A1 | 5/2009 |
| WO | 2009118187 A1 | 10/2009 |
| WO | 2010043396 A1 | 4/2010 |
| WO | 2013130855 A1 | 9/2013 |
| WO | 2014124651 A1 | 8/2014 |
| WO | 2016025917 A1 | 2/2016 |

OTHER PUBLICATIONS

Addy, et al., Single-Dc3e Administration of MK-0657, an N112B-Selective NMDA Antagonist, Does Not Result in Clinically Meaningful Improvement in Motor Function in Patients 127ith Moderate ll'arkinson's Disease, Journal of Clinical Pharmacology, 2009, pp. 856-864, vol. 49.

Andreas Straube, Pharmacology of vertigo/nystagmus/oscillopsia, Current Opinion in Neurology, 2005, pp. 11-14, vol. 18 Issue 1.

(Continued)

*Primary Examiner* — Alicia L Otton

(74) *Attorney, Agent, or Firm* — Biospark Intellectual Property Law

(57) ABSTRACT

Substituted 1,2,3-triazoles as NR2B receptor ligands. Such compounds may be used in NR2B receptor modulation and in pharmaceutical compositions and methods for the treatment of disease states, disorders, and conditions mediated by NR2B receptor activity.

20 Claims, No Drawings

(56) References Cited

OTHER PUBLICATIONS

Arnold, et al., Glutamate receptor gene (GRIN2B) associated with reduced anterior cingulate glutamatergic concentration in pediatric obsessive-compulsive disorder, Psychiatry Research: Neuroimaging, Feb. 19, 2009, pp. 136-139, vol. 172 Issue 2.
Berberich, et al., The role of NMDAR subtypes and charge transfer during hippocampal LTP induction, Neuropharmacology, 2007, pp. 77-86, vol. 52 Issue 1.
Berge, et al., Pharmaceutical Salts, Journal of Pharmaceutical Sciences, 1977, pp. 1-19, vol. 66, No. 1.
Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.
Bullock, et al., An Open-Label Study of CP-101,606 in Subjects with a Severe Traumatic Head Injury or Spontaneous Intracerebral Hemorrhage, Annals New York Academy of Sciences, 1999, pp. 51-58, vol. 890.
Buonarati, et al., Role of sulfation and acetylation in the activation of 2-hydroxyamino-1-methyl-6-phenylimidazo [4,5-b]pyridine to intermediates which bind DNA, Mutation Research, Jun. 21, 1990, pp. 185-190, vol. 245.
Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.
Cull-Candy, et al., NMDA receptor subunits: diversity, development and disease, Current Opinion in Neurobiology, 2001, pp. 327-335, vol. 11 Issue 3.
Dalmau, et al., Anti-NMDA-receptor encephalitis: case series and analysis of the effects of antibodies, Lancet Neurol, Dec. 2008, pp. 1091-1098, vol. 7 Issue 12.
Dorval, et al., Association of the glutamate receptor subunit gene GRIN2B with attention-deficit/hyperactivity disorder, Genes, Brain and Behavior, 2007, pp. 444-452, vol. 6 Issue 5.
Farjam, et al., Inhibition of NR2B-Containing N-methyl-D-Aspartate Receptors (NMDARs) in Experimental Autoimmune Encephalomyelitis, a Model of Multiple Sclerosis, Iranian Journal of Pharmaceutical Research, 2014, pp. 695-705, vol. 13 Issue 2.
Fleisher, et al., Improved oral drug delivery: solubility limitations overcome by the use of prodrugs, Advanced Drug Delivery Reviews, 1996, pp. 115-130, vol. 19.
Fuller, et al., Differential expression of the NMDA NR2B receptor subunit in motoneuron populations susceptible and resistant to amyotrophic lateral sclerosis, Neuroscience Letters, Jan. 26, 2006, pp. 157-161, vol. 399 Issue (1-2).
Glenn D. Considine, Van Nostrand's Encyclopedia of Chemistry,, Encyclopedia of Chemistry, 2005, pp. 261, Chapter 5.
Grasselli, et al., Abnormal NMDA receptor function exacerbates experimental autoimmune encephalomyelitis, British Journal of Pharmacology, 2013, pp. 502-517, vol. 168 Issue 2.
Grimwood, et al., NR2B-containing NMDA receptors are upregulated in temporal cortex in schizophrenia, NeuroReport, Feb. 25, 1999, pp. 461-465, vol. 10 Issue 3.
Guitton, et al., Blockade of Cochlear NMDA Receptors Prevents Long-Term Tinnitus during a Brief Consolidation Window after Acoustic Trauma, Neural Plasticity, Dec. 12, 2007, pp. 1-11, Article ID 80904.
Haller, et al., NR2B subunit-specific NMDA antagonist Ro25-6981 inhibits the expression of conditioned fear: a comparison with the NMDA antagonist MK-801 and fluoxetine, Behavioural Pharmacology, 2011, pp. 113-121, vol. 22 Issue 2.
Hanson, et al., Altered GluN2B NMDA receptor function and synaptic plasticity during early pathology in the PS2APP mouse model of Alzheimer's disease, Neurobiology of Disease, 2015, pp. 254-262, vol. 74.
Hu, et al., Expression of immediate-early genes in the dorsal cochlear nucleus in salicylate-induced tinnitus, Eur Arch Otorhinolaryngol, 2016, pp. 325-332, vol. 273 Issue 2.
Ito, et al., A Medium-term rat liver bioassay for rapid in vivo detection of carcinogenic potential of chemicals, Cancer Sci, 2003, pp. 3-8, vol. 94 Issue 1.
Jozsef Nagy, The NR2B Subtype of NMDA Receptor: A Potential Target for the Treatment of Alcohol Dependence, Current Drug Targets—CNS & Neurological Disorders, 2004, pp. 169-179, vol. 3 Issue 3.
Jun Wu, et al., Targeting the NMDA Receptor Subunit NR2B for the Treatment of Neuropathic Pain, Neurotherapeutics:, 2009, pp. 693-702, vol. 6 Issue 4.
Kenneth D.Bagshawe, Antibody-Directed Enzyme prodrug Therapy : A Review, Drug Development Research, 1995, pp. 220-230, vol. 34.
Kolb, et al., Click Chemistry: Diverse Chemical Function from a Few Good Reactions, Angew. Chem. Int. Ed, 2001, pp. 2004-2021, vol. 40.
Kowal, et al., Human lupus autoantibodies against NMDA receptors mediate cognitive impairment, PNAS, Dec. 26, 2006, pp. 19854-19859, vol. 103 Issue 52.
Leaderbrand, et al., Co-activation of NR2A and NR2B subunits induces resistance to fear extinction, Neurobiol Learn Mem, 2013, pp. 35-40, vol. 113.
Leaver, et al., Neuroprotective Effects of a Selective N-Methyl-d-Aspartate NR2B Receptor Antagonist in the 6-Hydroxydopamine Rat Model of Parkinson's Disease, Clinical and Experimental Pharmacology and Physiology, May 27, 2008, pp. 1388-1394, vol. 35 Issue 11.
Leyva et al., Photochemistry of Fluorinated Aryl Azides in Toluene Solution and in Frozen Polycrystals, J. Org. Chem, May 8, 1989, pp. 5938-5945, vol. 54 Issue 25, American Chemical Society.
Li, et al., Enhanced Striatal NR2B-Containing N-Methyl-D-Aspartate Receptor-Mediated Synaptic Currents in a Mouse Model of Huntington Disease, J Neurophysiol, Jun. 3, 2004, pp. 2738-2746, vol. 92 Issue 5.
Li, et al., Glutamate N-methyl-D-aspartate Receptor Antagonists Rapidly Reverse Behavioral and Synaptic Deficits Caused by Chronic Stress Exposure, Biol Psychiatry, 2011, pp. 754-761, vol. 69 Issue 8.
Li, et al., Soluble Ab Oligomers Inhibit Long-Term Potentiation through a Mechanism Involving Excessive Activation of Extrasynaptic NR2B-Containing NMDA Receptors, The Journal of Neuroscience, May 4, 2011, pp. 6627-6638, vol. 31 Issue 18.
Lima-Ojeda, et al., Pharmacological blockade of GluN2B-containing NMDA receptors induces antidepressant-like effects lacking psychotomimetic action and neurotoxicity in the perinatal and adult rodent brain, Progress in Neuro-Psychopharmacology & Biological Psychiatry, Apr. 30, 2013, pp. 28-33, vol. 45.
Martucci, et al., N-methyl-d-aspartate receptor NR2B subunit gene GRIN2B in schizophrenia and bipolar disorder: Polymorphisms and mRNA levels, Schizophrenia Research, Mar. 20, 2006, pp. 214-221, vol. 84 Issue (2-3).
Massey, et al., Differential Roles of NR2A and NR2B-Containing NMDA Receptors in Cortical Long-Term Potentiation and Long-Term Depression, The Journal of Neuroscience, Sep. 8, 2004, pp. 7821-7828, vol. 24 Issue 36.
Miller, et al., GluN2B-containing NMDA receptors regulate depression-like behavior and are critical for the rapid antidepressant actions of ketamine, eLife, Oct. 23, 2014, pp. 1-22, vol. 3.
Morissette, et al., Prevention of Levodopa-Induced Dyskinesias by a Selective NR1A/2B N-Methyl-D-aspartate Receptor Antagonist in Parkinsonian Monkeys: Implication of Preproenkephalin, Movement Disorders, 2006, pp. 9-17, vol. 21 Issue 1.
Naskar, et al., Saving the Nerve from Glaucoma: Memantine to Caspaces, Seminars in Ophthalmology, Sep. 1999, pp. 152-158, vol. 14 Issue 3.
Naspolini, et al., Traxoprodil decreases pentylenetetrazol-induced seizures, Epilepsy Research, Jan. 24, 2012, pp. 12-19, vol. 100 Issue (1-2).

(56) References Cited

OTHER PUBLICATIONS

Nicholas Bodor, Novel Approaches to the Design of Safer Drugs: Soft Drugs and Site-Specific Chemical Delivery Systems, Advances in Drug Research, 1984, pp. 256-331, vol. 13.

Nutt, et al., Effects of a NR2B Selective NMDA Glutamate Antagonist, CP-101,606, on Dyskinesia and Parkinsonism, Movement Disorders, Aug. 29, 2008, pp. 1860-1866, vol. 23 Issue 13.

Orgogozo, et al., Efficacy and Safety of Memantine in Patients With Mild to Moderate Vascular Dementia A Randomized, Placebo-Controlled Trial (MMM 300), Stroke, 2002, pp. 1834-1839, vol. 33.

Paoletti, et al., NMDA receptor subunit diversity: impact on receptor properties, synaptic plasticity and disease, Nature Reviews | Neuroscience, 2013, pp. 383-400, vol. 14 Issue 6.

Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.

Peeters, et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, Jan. 24, 2007, pp. 564-572, vol. 321 Issue 2.

Porsolt, et al., Behavioural Despair in Mice: A Primary Screening Test for Antidepressants, Arch int Pharmacodyn, 1977, pp. 327-336, vol. 229.

Preskorn, et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology, Dec. 2008, pp. 631-637, vol. 28 Issue 6.

Remington, Remington Pharmaceutical Sciences., Pharmaceutical Sciences., 1985, pp. 1418, vol. 76.

Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.

Shan, et al., Prodrug Strategies Based on Intramolecular Cyclization Reactions, Journal of Pharmaceutical Sciences, Jul. 1977, pp. 765-767, vol. 86 Issue 7.

Shen, et al., Heroin relapse requires long-term potentiation-like plasticity mediated by NMDA2b-containing receptors, PNAS, Nov. 29, 2011, pp. 19407-19412, vol. 108 Issue 48.

Starck, et al., Drug therapy for acquired pendular nystagmus in multiple sclerosis, J Neurol, 1997, pp. 9-16, vol. 244 Issue 1.

Steece-Collier, et al., Antiparkinsonian Actions of CP-101,606, an Antagonist of NR2B Subunit-Containing N-Methyl-D-Aspartate Receptors, Experimental Neurology, Feb. 4, 2000, pp. 239-243, vol. 163 Issue 1.

STN Registry database entry for CAS RN 1394745-67-5, entered STN Sep. 18, 2012, Accessed Sep. 8, 2017.

Susan Duty, Targeting Glutamate Receptors to Tackle the Pathogenesis, Clinical Symptoms and Levodopa-Induced Dyskinesia Associated with Parkinson's Disease, CNS Drugs, Oct. 31, 2012, pp. 1017-1032, vol. 26 Issue 12.

Tang, et al., Disturbed Ca2+ signaling and apoptosis of medium spiny neurons in Huntington's disease, PNAS, Feb. 15, 2005, pp. 2602-2607, vol. 102 Issue 7.

Tang, et al., Genetic enchancement of learning and memory in mice, Nature, Sep. 2, 1999, pp. 63-69, vol. 401 Issue 6748.

Traynelis, et al., Glutamate Receptor Ion Channels: Structure, Regulation, and Function, Pharmacol Rev, 2010, pp. 405-496, vol. 62 Issue 3.

Wang, et al., Targeting the NMDA receptor subunit NR2B for treating or preventing age-related memory decline, Expert Opin. Ther. Targets, 2014, pp. 1121-1130, vol. 18 Issue 10.

Watanabe, et al., Distinct Distributions of Five N-Methyl-D-Aspartate Receptor Channel Subunit mRNAs in the Forebrain, The Journal of Comparative Neurology, Jul. 30, 1993, pp. 377-390, vol. 338 Issue 3.

Weickert, et al., Molecular evidence of N-methyl-D-aspartate receptor hypofunction in schizophrenia, Molecular Psychiatry, 2013, pp. 1185-1192, vol. 18.

Won, et al., Autistic-like social behaviour in Shank2-mutant mice improved by restoringNMDA receptor function, Nature, Jun. 14, 2012, pp. 261-265, vol. 486.

Yang, et al., Reduced brain infarct volume and improved neurological outcome by inhibition of the NR2B subunit of NMDA receptors by using CP101,606-27 alone and in combination with rt-PA in a thromboembolic stroke model in rats, J. Neurosurg, Feb. 2003, pp. 397-403, vol. 98 Issue 2.

Yuan, et al., Context-Dependent GluN2B-Selective Inhibitors of NMDA Receptor Function Are Neuroprotective with Minimal Side Effects, Neuron, Mar. 18, 2015, pp. 1305-1318, vol. 85 Issue 6.

Zarate, et al., A Randomized Trail of an N-methyl_D-aspartate Antagonist in Treatment-Resistant Major Depression, Arch Gen Psychiatry, 2006, pp. 856-864, vol. 63.

International Search Report for International Application No. PCT/US2015/045412, dated Nov. 10, 2015.

International Search Report for International Application No. PCT/US2015/045413, dated Nov. 27, 2015.

International Search Report for International Application No. PCT/US2016/041339 dated Sep. 27, 2016.

International Search Report for International Application No. PCT/US2017/017093, dated Apr. 7, 2017.

SUBSTITUTED 1,2,3-TRIAZOLES AS NR2B-SELECTIVE NMDA MODULATORS

This application is a divisional application of U.S. application Ser. No. 15/428,710 filed Feb. 9, 2017 which claims the benefit of U.S. Provisional Application No. 62/293,680, filed on Feb. 10, 2016, each of which is incorporated herein by reference in their entireties.

FIELD OF THE INVENTION

The present invention is related to compounds having NR2B modulating properties, pharmaceutical compositions comprising these compounds, chemical processes for preparing these compounds and their use in the treatment of diseases associated with NR2B receptor activity in animals, in particular humans.

BACKGROUND OF THE INVENTION

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., *Pharmacol Rev.* 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., *Neuropharmacology* 2007; 52(1):77-86) and long-term depression (LTD) (Massey, P V et al., *J Neurosci.* 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., *Nat Rev Neurosci.* 2013; 14(6):383-400; Watanabe M et al., *J Comp Neurol.* 1993; 338(3):377-90) and are implicated in learning, memory processing, mood, attention, emotion and pain perception (Cull-Candy S et al., *Curr Opin Neurobiol.* 2001; 11(3):327-35).

Compounds that modulate GluN2B-containing NMDA receptor function can be useful in treatment of many neurological and psychiatric disorders including but not limited to bipolar disorder (Martucci L et al., *Schizophrenia Res,* 2006; 84(2-3):214-21), major depressive disorder (Miller O H et al., *eLife.* 2014; 3:e03581; Li N et al., *Biol Psychiatry.* 2011; 69(8):754-61), treatment-resistant depression (Preskom S H et al. *J Clin Psychopharmacol.* 2008; 28(6): 631-7) and ther mood disorders (including schizophrenia (Grimwood S et al., *Neuroreport.* 1999; 10(3):461-5; Weickert C S et al. *Molecular Psychiatry* (2013) 18, 1185-1192), ante- and postpartum depression, seasonal affective disorder and the like), Alzheimer's disease (Hanson J E et al., *Neurobiol Dis.* 2015; 74:254-62; Li S et al., *J Neurosci.* 2011; 31(18):6627-38) and other dementias (Orgogozo J M et al. Stroke 2002, 33: 1834-1839), Parkinson's disease (Duty S, *CNS Drugs.* 2012; 26(12):1017-32; Steece-Collier K et al., *Exp Neurol.* 2000; 163(1):239-43; Leaver K R et al. *Clin Exp Pharmacol Physiol.* 2008; 35(11):1388-94), Huntington's chorea (Tang T S et al., *Proc Natl Acad Sci USA.* 2005; 102(7):2602-7; Ui L et al., *J Neurophysiol.* 2004; 92(5):2738-46), multiple sclerosis (Grasselli G et al., *Br J Pharmacol.* 2013; 168(2):502-17; Farjam M et al., *Iran J Pharm Res.* 2014; 13(2):695-705), cognitive impairment (Wang D et al. 2014, *Expert Opin Ther Targets Expert Opin Ther Targets.* 2014, 18(10):1121-30), head injury (Bullock M R et al., *Ann N Y Acad Sci.* 1999; 890:51-8), spinal cord injury, stroke (Yang Y et al., *J Neurosurg.* 2003; 98(2):397-403), epilepsy (Naspolini A P et al., *Epilepsy Res.* 2012 June; 100(1-2):12-9), movement disorders (e.g. dyskinesias) (Morissette M et al., *Mov Disord.* 2006; 21(1):9-17), various neurodegenerative diseases (e.g. amyotrophic lateral sclerosis (Fuller P I et al., *Neurosci Lett.* 2006; 399(1-2):157-61) or neurodegeneration associated with bacterial or chronic infections), glaucoma (Naskar R et al. *Semin Ophthalmol.* 1999 September; 14(3):152-8), pain (e.g. chronic, cancer, post-operative and neuropathic pain (Wu L J and Zhuo M, *Neurotherapeutics.* 2009; 6(4):693-702), diabetic neuropathy, migraine (Peeters M et al., *J Pharmacol Exp Ther.* 2007; 321(2):564-72), cerebral ischemia (Yuan H et al., *Neuron.* 2015; 85(6):1305-18), encephalitis (Dalmau J. et al., *Lancet Neurol.* 2008; 7(12):1091-8.), autism and autism spectrum disorders (Won H. et al., *Nature.* 2012; 486(7402):261-5), memory and learning disorders (Tang, Y. P. et al., *Nature.* 1999; 401(6748):63-9), obsessive compulsive disorder (Arnold P D et al., *Psychiatry Res.* 2009; 172(2):136-9.), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, *Neural Plast.* 2007; 80904; Hu S S et al. 2016; 273(2): 325-332), sleep disorders (like narcolepsy or excessive daytime sleepiness, patent WO 2009058261 A1), vertigo and nystagmus (Straube A. et al., *Curr Opin Neurol.* 2005; 18(1):11-4; Starck M et al. *J Neurol.* 1997 January; 244(1):9-16), anxiety autoimmunological disorders like neuropsychiatric systemic lupus erythematosus (Kowal C et al. *Proc. Nat. Acad. Sci. U.S.A.* 2006; 103, 19854-19859) and addictive illnesses (e.g. alcohol addiction, drug addiction) (Nagy J, 2004, *Curr Drug Targets CNS Neurol Disord.* 2004; 3(3):169-79; Shen H et al., *Proc Nat Acad Sci USA.* 2011; 108(48):19407-12).

In view of the clinical importance of NR2B, the identification of compounds that modulate NR2B receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

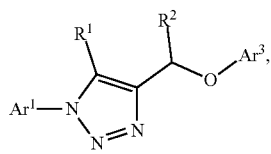
(I)

wherein:
$Ar^1$ is selected from the group consisting of:
(a) phenyl substituted with one substituent selected from the group consisting of: halo, $C_{1-6}$alkyl, $C_{1-6}$perhaloalkyl, and $OC_{1-6}$perhaloalkyl; phenyl substituted with two or three substituents each independently selected from the group consisting of: halo, $C_{1-6}$alkyl, $C_{1-6}$perhaloalkyl, $OC_{1-6}$alkyl, $OC_{1-6}$perhaloalkyl, $C_{3-6}$-cycloalkyl, and azetidinyl;
(b) pyridinyl; pyridinyl substituted with one or two members each independently selected from the group consisting of: halo, $CH_3$, $CF_3$, and $CF_2H$; and
(c) thienyl substituted with $CF_3$; 1-(2,2-difluorobenzo[d][1,3]dioxol-5-yl; or 2,3-dihydro-1H-inden-5-yl;
$R^1$ is H, halo, or $CH_3$;
$R^2$ is H or $CH_3$; and
$Ar^3$ is selected from the group consisting of:
(a) pyridinyl; pyridinyl substituted with one or two substituents each independently selected from the group consisting of: Cl, F, $CH_3$, $OCH_3$, $CF_3$, $C(CH_3)_2OH$; azetidin-1-yl; 3-fluoroazetidin-1-yl; and 3,3-difluoroazetidin-1-yl;
(b) pyridazinyl; pyridazinyl substituted with one or two substituents each independently selected from the group consisting of: $CH_3$, $OCH_3$, and $CF_3$;
(c) pyrimidin-4-yl; pyrimidin-4-yl substituted with one or two substituents each independently selected from the group consisting of: Cl, $CH_3$, $CF_3$, and $OCH_3$; pyrimidin-2-yl; pyrimidin-2-yl substituted one or two members each independently selected from the group consisting of: halo, $C_{1-6}$alkyl, $C_{1-6}$alkyl substituted with OH or $OCH_3$, $C(OH)(CH_3)(CF_3)$, $CH_2OCHF_2$, $CH_2OCF_3$, $CH_2OCH_2CH_3$, $CH(NH_2)CH_3$, $CH_2NH$($CH_3$), $C_{1-6}$perhaloalkyl, $OC_{1-6}$alkyl, $OC_{1-6}$perhaloalkyl, $C(=N-OH)(CH_3)$, $NH_2$, $NH(CH_3)$, $N(CH_3)_2$; $NH(CH_2CH_3)$, $NH(CH_2CHF_2)$, $NH$(cyclopropyl), $NH$(difluorocydobutyl), $NH$-oxetanyl, CN, $C(=O)CH_3$, $C(=O)NH(CH_3)$, $C(=O)N(CH_3)_2$, $SO_2CH_3$, $CO_2CH_3$, $C(CH_3)(=N-OH)$, cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholinyl, 1H-pyrrol-2-yl, 2-furyl, 1H-pyrazol-4-yl, 1H-pyrazol-5-yl, 1H-pyrazol-1-yl, 2-methyl-1H-imidazol-1-yl, 1-methylpyrazol-3-yl, and phenyl;
(d) 5-fluoro-pyrazin-2-yl; 5-methylpyrazin-2-yl; 6-methylpyrazin-2-yl; pyrazin-4-yl; (2-thienyl)pyrazin-2-yl, and 2,3-dimethylpyrazin-5-yl; and
(e) 5-methyl-1H-imidazol-2-yl; 5-methylthiazol-2-yl;
and pharmaceutically acceptable salts Formula (I).

One aspect of this invention concerns compounds of Formula (II):

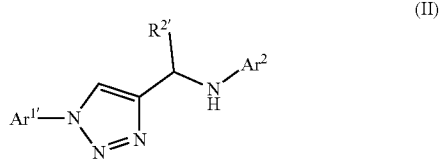
(II)

wherein:
$Ar^{1'}$ is phenyl substituted with $C_{1-3}$perhaloalkyl; or phenyl substituted with two substituents each independently selected from the group consisting of: halo, $C_{1-3}$alkyl, $C_{1-3}$perhaloalkyl, and $OC_{1-3}$perhaloalkyl;
$R^{2'}$ is H or $CH_3$; and
$Ar^2$ is selected from the group consisting of:
(a) pyridin-2-yl; pyridazin-3-yl; pyrimidin-4-yl; pyrimidin-2-yl; pyrimidin-2-yl substituted with one or two substituents each independently selected from the group consisting of halo, $C_{1-3}$alkyl, $C(CH_3)_2OH$, $C_{1-3}$perhaloalkyl, $OCH_3$, and cyclopropyl; and
(b) 1-methyl-imidazol-2-yl; oxazol-2-yl; 1-methyl-pyrazol-4-yl; 1-methyl-pyrazol-3-yl; and 1-methyl-1H-pyrazol-5-yl;
and pharmaceutically acceptable salts Formula (II).

Further embodiments are provided by pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II).

In certain embodiments, the compounds of Formula (I) are compounds selected from those species described or exemplified in the detailed description below.

In certain embodiments, the compounds of Formula (II) are compounds selected from those species described or exemplified in the detailed description below.

In a further aspect, the invention relates to enantiomers and diastereomers of the compounds of Formula (I) or Formula (II), as well as the pharmaceutically acceptable salts.

In a further aspect, the invention relates to pharmaceutical compositions for treating a disease, disorder, or medical condition mediated by NR2B receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

In a further aspect, the invention relates to pharmaceutical compositions for treating a disease, disorder, or medical condition mediated by NR2B receptor activity, comprising an effective amount of at least one compound selected from compounds of Formula (II), pharmaceutically acceptable salts of compounds of Formula (II), pharmaceutically acceptable prodrugs of compounds of Formula (II), and pharmaceutically active metabolites of Formula (II).

Pharmaceutical compositions according to the invention may further comprise one or more pharmaceutically acceptable excipients.

In another aspect, the chemical embodiments of the present invention are useful as NR2B receptor modulators. Thus, the invention is directed to a method for modulating NR2B receptor activity, including when such receptor is in a subject, comprising exposing NR2B receptor to an effective amount of at least one compound selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II).

In another aspect, the invention is directed to a method of treating a subject suffering from, or diagnosed with a disease, disorder, or medical condition mediated by NR2B receptor activity, comprising administering to the subject in need of such treatment an effective amount of at least one compound selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of Formula (I) or Formula (II).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION

In one aspect, provided herein are compounds of Formula (I), and pharmaceutically acceptable salts thereof,

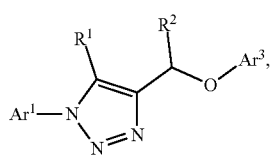

(I)

wherein:
Ar$^1$ is selected from the group consisting of:
(a) phenyl substituted with one substituent selected from the group consisting of: halo, $C_{1-6}$alkyl, $C_{1-6}$perhaloalkyl, and $OC_{1-6}$perhaloalkyl; phenyl substituted with two or three substituents each independently selected from the group consisting of: halo, $C_{1-6}$alkyl, $C_{1-6}$perhaloalkyl, $OC_{1-6}$alkyl, $OC_{1-6}$perhaloalkyl, $C_{3-6}$cycloalkyl, and azetidinyl;
(b) pyridinyl; pyridinyl substituted with one or two members each independently selected from the group consisting of: halo, $CH_3$, $CF_3$, and $CF_2H$; and
(c) thienyl substituted with $CF_3$; 1-(2,2-difluorobenzo[d][1,3]dioxol-5-yl; or 2,3-dihydro-1H-inden-5-yl;

R$^1$ is H, halo, or $CH_3$;
R$^2$ is H or $CH_3$; and
Ar$^3$ is selected from the group consisting of:
(a) pyridinyl; pyridinyl substituted with one or two substituents each independently selected from the group consisting of: Cl, F, $CH_3$, $OCH_3$, $CF_3$, $C(CH_3)_2OH$; azetidin-1-yl; 3-fluoroazetidin-1-yl; and 3,3-difluoroazetidin-1-yl;
(b) pyridazinyl; pyridazinyl substituted with one or two substituents each independently selected from the group consisting of: $CH_3$, $OCH_3$, and $CF_3$;
(c) pyrimidin-4-yl; pyrimidin-4-yl substituted with one or two substituents each independently selected from the group consisting of: Cl, $CH_3$, $CF_3$, and $OCH_3$; pyrimidin-2-yl; pyrimidin-2-yl substituted one or two members each independently selected from the group consisting of: halo, $C_{1-6}$alkyl, $C_{1-6}$alkyl substituted with OH or $OCH_3$, $C(OH)(CH_3)(CF_3)$, $CH_2OCHF_2$, $CH_2OCF_3$, $CH_2OCH_2CH_3$, $CH(NH_2)CH_3$, $CH_2NH(CH_3)$, $C_{1-6}$perhaloalkyl, $OC_{1-6}$alkyl, $OC_{1-6}$perhaloalkyl, $C(=N-OH)(CH_3)$, $NH_2$, $NH(CH_3)$, $N(CH_3)_2$; $NH(CH_2CH_3)$, $NH(CH_2CHF_2)$, $NH(cyclopropyl)$, $NH(difluorocydobutyl)$, NH-oxetanyl, CN, $C(=O)CH_3$, $C(=O)NH(CH_3)$, $C(=O)N(CH_3)_2$, $SO_2CH_3$, $CO_2CH_3$, $C(CH_3)(=N-OH)$, cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholinyl, 1H-pyrrol-2-yl, 2-furyl, 1H-pyrazol-4-yl, 1H-pyrazol-5-yl, 1H-pyrazol-1-yl, 2-methyl-1H-imidazol-1-yl, 1-methylpyrazol-3-yl, and phenyl;
(d) 5-fluoro-pyrazin-2-yl; 5-methylpyrazin-2-yl; 6-methylpyrazin-2-yl; pyrazin-4-yl; (2-thienyl)pyrazin-2-yl, and 2,3-dimethylpyrazin-5-yl; and
(e) 5-methyl-1H-imidazol-2-yl; 5-methylthiazol-2-yl.

An additional embodiment of the invention is a compound of Formula (I) wherein R$^1$ is H, F, I or $CH_3$.

An additional embodiment of the invention is a compound of Formula (I) wherein R$^1$ is H.

An additional embodiment of the invention is a compound of Formula (I) wherein R$^2$ is H.

An additional embodiment of the invention is a compound of Formula (I) wherein Ar$^1$ is phenyl substituted with one substituent selected from the group consisting of: Br, Cl, F, $CH_3$, $CF_3$, $CHF_2$, $CF_2CH_3$, $CH(CH_3)_2$, $OCHF_2$, and $OCF_3$.

An additional embodiment of the invention is a compound of Formula (I) wherein Ar$^1$ is 3-bromophenyl, 3-fluorophenyl, 4-fluorophenyl, 4-chlorophenyl, 2-methylphenyl, 3-methylphenyl, 4-methylphenyl, 3-isopropylphenyl, 3-(trifluoromethyl)phenyl, 3-(difluoromethyl)phenyl, 3-(1,1-difluoroethyl)phenyl, 3-(trifluoromethoxy)phenyl, 4-(trifluoromethoxy)phenyl, 3-(difluoromethoxy)phenyl, or 4-(difluoromethoxy)phenyl.

An additional embodiment of the invention is a compound of Formula (I) wherein Ar$^1$ is phenyl substituted with two substituents each independently selected from the group consisting of: Br, Cl, F, CH$_3$, CH$_2$CH$_3$, CH(CH$_3$)$_2$, CF$_3$, CF$_2$H, CF$_2$CH$_3$, CH$_2$CH$_2$CH$_2$Cl, CH$_2$CH$_2$CH$_2$F, OCH$_3$, OCF$_2$H, OCH$_2$CH$_2$F, cyclopropyl, and azetidin-1-yl.

An additional embodiment of the invention is a compound of Formula (I) wherein Ar$^1$ is 2,4-difluoro-5-methyl-phenyl, 3-(difluoromethyl)-2,4-difluoro-phenyl, or 2,4-difluoro-3-methyl-phenyl.

An additional embodiment of the invention is a compound of Formula (I) wherein Ar$^1$ is 6-methyl-pyridin-2-yl, 2-methyl-pyridin-4-yl, 5-methyl-pyridin-3-yl, 4-methyl-pyridin-2-yl, 2-bromo-pyridin-4-yl, 2-(trifluoromethyl)-pyridin-4-yl, 5-chloro-6-(trifluoromethyl)pyridin-2-yl, 2-(difluoromethyl)pyridin-4-yl, 5-(trifluoromethyl)pyridin-2-yl, 5-bromo-6-fluoropyridin-3-yl, or pyridin-4-yl.

An additional embodiment of the invention is a compound of Formula (I) wherein Ar$^1$ is 6-methyl-pyridin-2-yl, 2-methyl-pyridin-4-yl, 5-methyl-pyridin-3-yl, 4-methyl-pyridin-2-yl, 2-bromo-pyridin-4-yl, 2-(trifluoromethyl)-pyridin-4-yl; 1-(2,2-difluorobenzo[d][1,3]dioxol-5-yl; 5-(trifluoromethyl)thiophen-2-yl or 2,3-dihydro-1H-inden-5-yl.

An additional embodiment of the invention is a compound of Formula (I) wherein Ar$^1$ is 4-chloro-3-(difluoromethoxy)phenyl, 3-(difluoromethyl)-4-fluoro-phenyl, 4-chloro-3-(1,1-difluoroethyl)phenyl, 3-(1,1-difluoroethyl)-4-fluoro-phenyl, 3-(difluoromethoxy)-4-fluoro-phenyl, 4-chloro-3-(difluoromethyl)phenyl, 4-chloro-3-(2-fluoroethoxy)phenyl, 3-(3-chloropropyl)-4-fluoro-phenyl, or 5-(trifluoromethyl)thiophen-2-yl.

An additional embodiment of the invention is a compound of Formula (I) wherein Ar$^3$ is pyridin-2-yl, 3-fluoro-pyridin-2-yl, 6-fluoro-pyridin-2-yl, 3-chloro-pyridin-2-yl, 5-chloro-pyridin-2-yl, 4-methyl-pyridin-2-yl, 5-methyl-pyridin-2-yl, 6-methyl-pyridin-2-yl, 5-(trifluoromethyl)pyridine-2-yl, 6-(trifluoromethyl)pyridine-2-yl,pyridine-3-yl, 3-methoxy-pyridin-2-yl, 2-methoxy-pyridin-3-yl, 2-methyl-pyridin-5-yl, 2,3-dimethyl-pyridin-2-yl, 5-chloro-3-methoxy-pyridin-2-yl, or 2-chloro-5-methyl-pyridin-4-yl.

An additional embodiment of the invention is a compound of Formula (I) wherein Ar$^3$ is pyrimidin-2-yl; pyrimidin-2-yl substituted one or two members each independently selected from the group consisting of: halo, C$_{1-3}$alkyl, C$_{1-3}$alkyl substituted with OH or OCH$_3$, C(OH)(CH$_3$)(CF$_3$), CH(NH$_2$)CH$_3$, CH$_2$NH(CH$_3$), C$_{1-3}$perhaloalkyl, OC$_{1-3}$alkyl, OC$_{1-3}$perhaloalkyl, NH$_2$; NH(CH$_3$), N(CH$_3$)$_2$, NH(CH$_2$CH$_3$), NH(CH$_2$CHF$_2$), CN, C(=O)CH$_3$, C(=O)NH(CH$_3$), C(=O)N(CH$_3$)$_2$, SO$_2$CH$_3$, CO$_2$CH$_3$, cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoro-pyrrolidin-1-yl, 3,3-difluoropyrrolidin-1-yl, piperidin-1-yl, morpholinyl, 2-furyl, 1H-pyrazol-4-yl, and 1-methylpyrazol-3-yl.

An additional embodiment of the invention is a compound of Formula (I) wherein Ar$^3$ is pyrimidin-2-yl substituted one or two members each independently selected from the group consisting of: halo, C$_{1-6}$alkyl, C$_{1-6}$alkyl substituted with OH or CH$_3$, C$_{1-6}$perhaloalkyl, OC$_{1-6}$alkyl, OC$_{1-6}$perhaloalkyl, and azetidine-1-yl.

An additional embodiment of the invention is a compound of Formula (I) having the Formula (IA):

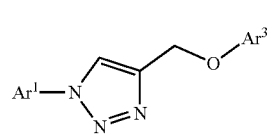

(IA)

wherein
Ar$^1$ is phenyl substituted with two substituents each independently selected from the group consisting of: halo, C$_{1-3}$perhaloalkyl, and OC$_{1-3}$perhaloalkyl; and
Ar$^3$ is selected from the group consisting of pyridin-2-yl, pyridin-3-yl, 3-chloro-pyridin-2-yl, 5-chloro-pyridin-2-yl, 3-fluoro-pyridin-2-yl, 6-fluoro-pyridin-2-yl, 4-methyl-pyridin-2-yl, 2-methyl-pyridin-5-yl, 5-methyl-pyridin-2-yl, 6-methyl-pyridin-2-yl, 2,3-dimethyl-pyridin-6-yl, 2-chloro-5-methylpyridin-4-yl, 3-methoxy-pyridin-2-yl, 2-methoxy-pyridin-3-yl, 2-(pyridin-3-yl)propan-2-ol, 5-chloro-3-methoxy-pyridin-2-yl, 5-(trifluoromethyl)pyridin-2-yl, 6-(trifluoromethyl)pyridin-2-yl, pyridazin-3-yl, pyrazin-2-yl, 5-methylpyrazin-2-yl, 5-fluoropyrazin-2-yl, and (2-thienyl)pyrazin-2-yl;
and pharmaceutically acceptable salts of compounds of Formula (IA).

An additional embodiment of the invention is a compound of Formula (I) having the Formula (IB):

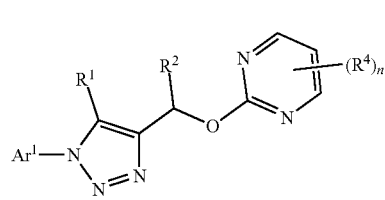

(IB)

wherein
Ar$^1$ is phenyl substituted with two substituents each independently selected from the group consisting of: halo, C$_{1-3}$alkyl, C$_{1-3}$perhaloalkyl, OCH$_3$, and OC$_{1-3}$perhaloalkyl;
R$^1$ is selected from the group consisting of: H, F, I, and CH$_3$;
R$^2$ is H or CH$_3$;
n is 0, 1, or 2; and
each R$^4$ is independently selected from the group consisting of: halo, C$_{1-6}$alkyl, C$_{1-6}$alkyl substituted with OH or OCH$_3$, C(OH)(CH$_3$)(CF$_3$), CH(NH$_2$)CH$_3$, CH$_2$NH(CH$_3$), C$_{1-6}$perhaloalkyl, OC$_{1-6}$alkyl, OC$_{1-6}$perhaloalkyl, NH$_2$, NH(CH$_3$), N(CH$_3$)$_2$, NH(CH$_2$CH$_3$), NH(CH$_2$CHF$_2$), CN, C(=O)CH$_3$, C(=O)NH(CH$_3$), C(=O)N(CH$_3$)$_2$, SO$_2$CH$_3$, CO$_2$CH$_3$, cyclopropyl, azetidin-1-yl, 3-fluoro-azetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholine, 2-furyl, 1H-pyrazol-4-yl, and 1-methylpyrazol-3-yl;
and pharmaceutically acceptable salts of compounds of Formula (IB).

An additional embodiment of the invention is a compound of Formula (I) having the Formula (IB) wherein:
Ar$^1$ is selected from the group consisting of: 4-chloro-3-(difluoromethoxy)phenyl, 3-(difluoromethoxy)-4-fluorophenyl, 3-(difluoromethoxy)-4-methyl-phenyl, 4-chloro-3-(1,1-difluoroethyl)phenyl, 3-(1,1-difluoroethyl)-4- fluoro-phenyl, 4-chloro-3-(2-fluoroethoxy)phenyl, 3-(3-chloropropyl)-4-fluoro-phenyl, 4-fluoro-3-(3-fluoropropyl)phenyl, 3-bromo-4-fluoro-phenyl, 2-fluoro-3-(trifluoromethyl)phenyl, 3-(difluoromethyl)-4-fluoro-phenyl, 4-chloro-3-(difluoromethyl)phenyl, 4-chloro-3-methoxy-phenyl), 4-fluoro-3-isopropyl-phenyl, 3-chloro-4-fluoro-phenyl, 3-ethyl-4-fluoro-phenyl, 3,4-difluorophenyl, 4-fluoro-3-methyl-phenyl, and 3,5-dimethylphenyl;

$R^1$ is H;

$R^2$ is H;

n is 1 or 2; and each $R^4$ is independently selected from the group consisting of: Cl, F, $C_{1-3}$alkyl, $C_{1-3}$perhaloalkyl, $CH_2OH$, $CH_2OCH_3$, $C(CH_3)_2(OH)$, $OCH_3$, $OC_{1-3}$perhaloalkyl, $C(=O)CH_3$, and azetidine-1-yl.

An additional embodiment of the invention is a compound of Formula (I) having the Formula (IC):

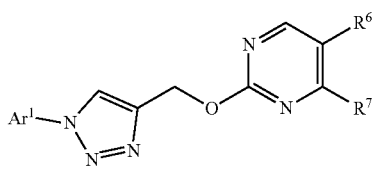

(IC)

wherein $Ar^1$ is selected from the group consisting of: 2-bromo-pyridin-4-yl, 6-methyl-pyridin-2-yl, 4-methyl-pyridin-2-yl, 2-methyl-pyridin-4-yl, 5-methyl-pyridin-3-yl, 2-(trifluoromethyl)-pyridin-4-yl, 5-(trifluoromethyl)pyridin-2-yl, 5-chloro-6-(trifluoromethyl)pyridin-2-yl, 5-bromo-6-methyl-pyridin-2-yl, 5-bromo-6-fluoropyridin-3-yl, and 5-(trifluoromethyl)-2-thienyl;

$R^6$ is selected from the group consisting of: Cl, F, $CH_3$, $CH_2CH_3$, $CF_3$, and $OCH_3$; and $R^7$ is H or $CH_3$;

and pharmaceutically acceptable salts of compounds of Formula (IC).

An additional embodiment of the invention is a compound of Formula (I) having the Formula (ID):

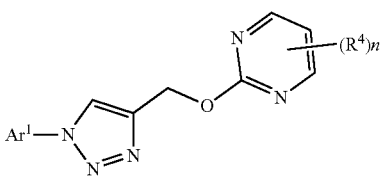

(ID)

wherein $Ar^1$ is phenyl substituted with one substituent selected from the group consisting of: Br, Cl, F, $C_{1-3}$alkyl, $C_{1-3}$perhaloalkyl, and $OC_{1-3}$perhaloalkyl;

n is 0, 1, or 2; and each $R^4$ is independently selected from the group consisting of: Br, Cl, F, $C_{1-3}$alkyl, $C_{1-3}$perhaloalkyl, $OCH_3$, $OCHF_2$, $CH_2OH$, $CH_2OCH_3$, $CH(CH_3)(OH)$, $C(OH)(CH_3)_2$, $C(OCH_3)(CH_3)_2$, $C(OH)(CH_3)(CF_3)$, $NH_2$, $NH(CH_3)$, $N(CH_3)_2$, $C(=O)CH_3$, cyclopropyl, azetidine-1-yl, 3-fluoroazetidin-1-yl, pyrrolidin-1-yl, and piperidin-1-yl;

and pharmaceutically acceptable salts of compounds of Formula (ID).

An additional embodiment of the invention is a compound of Formula (II) wherein:

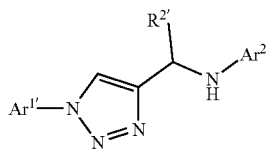

(II)

$Ar^{1'}$ is phenyl substituted with $C_{1-6}$perhaloalkyl; or phenyl substituted with two substituents each independently selected from the group consisting of: halo, $C_{1-3}$alkyl, $C_{1-3}$perhaloalkyl, and $OC_{1-3}$perhaloalkyl;

$R^{2'}$ is H or $CH_3$; and $Ar^2$ is selected from the group consisting of:
(a) pyridin-2-yl; pyridazin-3-yl; pyrimidin-4-yl; pyrimidin-2-yl; pyrimidin-2-yl substituted with one or two substituents each independently selected from the group consisting of halo, $C_{1-3}$alkyl, $C(CH_3)_2OH$, $C_{1-3}$perhaloalkyl, $OCH_3$, and cyclopropyl; and
(b) 1-methyl-imidazol-2-yl; oxazol-2-yl; 1-methyl-pyrazol-4-yl; 1-methyl-pyrazol-3-yl; and 1-methyl-1H-pyrazol-5-yl;

and pharmaceutically acceptable salts of compounds of Formula (II).

An additional embodiment of the invention is a compound of Formula (II) having the Formula (IIA):

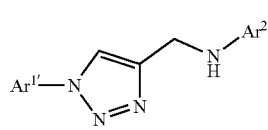

(IIA)

wherein:

$Ar^{1'}$ is selected from the group consisting of: 4-chloro-3-(difluoromethoxy)phenyl, 3-(difluoromethoxy)-4-fluoro-phenyl, 4-fluoro-3-(trifluoromethyl)phenyl, 3-(difluoromethyl)-4-fluoro-phenyl, and 4-chloro-3-(difluoromethyl) phenyl; and $Ar^2$ is selected from the group consisting of: oxazol-2-yl, pyrimidin-4-yl, 1-methyl-pyrazol-3-yl, 1-methyl-imidazol-2-yl, and 1-methyl-pyrazol-4-yl; and pharmaceutically acceptable salts of compounds of Formula (IIA).

An additional embodiment of the invention is a compound of Formula (II) having the Formula (IIB):

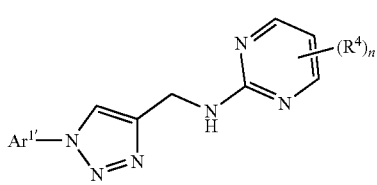

(IIB)

wherein:

$Ar^{1'}$ is selected from the group consisting of: 3-(difluoromethyl)phenyl, 4-fluoro-3-methyl-phenyl, 4-chloro-3-(difluoromethoxy)phenyl, 3-(difluoromethoxy)-4-fluoro-phenyl, 4-fluoro-3-(trifluoromethyl)phenyl, 3-(difluoromethyl)-4-fluoro-phenyl, 4-chloro-3-(difluoromethyl)phenyl, and 3-(1,1-difluoroethyl)-4-fluoro-phenyl;

n is 1 or 2; and each $R^4$ is independently selected from the group consisting of halo, $C_{1-3}$alkyl, $C(CH_3)_2OH$, $C_{1-3}$perhaloalkyl, $OCH_3$, and cyclopropyl;

and pharmaceutically acceptable salts of compounds of Formula (IIB).

A further embodiment of the current invention is a compound as shown below in Table 1.

| Ex #. | Compound Name |
|---|---|
| 1 | 2-((1-(4-Chloro-3-(difluoromethyl)phenyl)-1H-1,2,3-triazol-4-yl)methoxy)pyrimidine; |
| 4 | 2-[[1-[3-(Difluoromethoxy)-4-fluoro-phenyl]triazol-4-yl]methoxy]pyridine; |
| 5 | 3-[[1-[4-Chloro-3-(difluoromethoxy)phenyl]triazol-4-yl]methoxy]pyridine; |
| 8 | 2-[[1-[3-(Difluoromethoxy)-4-fluoro-phenyl]triazol-4-yl]methoxy]-6-methyl-pyridine; |
| 9 | 2-[[1-(3-Bromo-4-fluoro-phenyl)triazol-4-yl]methoxy]pyrimidine; |
| 10 | 2-[[1-[4-Chloro-3-(difluoromethoxy)phenyl]triazol-4-yl]methoxy]pyrimidine; |
| 11 | 2-[[1-[4-Chloro-3-(difluoromethyl)phenyl]triazol-4-yl]methoxy]pyridine; |
| 12 | 4-[[1-[4-Chloro-3-(difluoromethyl)phenyl]triazol-4-yl]methoxy]pyrimidine; |
| 13 | 4-[[1-[4-Chloro-3-(difluoromethoxy)phenyl]triazol-4-yl]methoxy]pyrimidine; |
| 14 | 3-[[1-[4-Chloro-3-(difluoromethoxy)phenyl]triazol-4-yl]methoxy]pyridazine; |
| 15 | 2-[[1-(4-Chloro-3-methoxy-phenyl)triazol-4-yl]methoxy]pyrimidine; |
| 16 | 2-[[1-(3-Bromo-4-fluoro-phenyl)triazol-4-yl]methoxy]-5-methyl-pyrimidine; |
| 17 | 2-[[1-(3-Bromo-4-fluoro-phenyl)triazol-4-yl]methoxy]-4-methyl-pyrimidine; |
| 18 | 2-[[1-(3-Bromo-4-fluoro-phenyl)triazol-4-yl]methoxy]-4,6-dimethyl-pyrimidine; |
| 19 | 2-[[1-(3-Bromo-4-fluoro-phenyl)triazol-4-yl]methoxy]-5-fluoro-pyrimidine; |
| 20 | 2-[[1-(4-Fluoro-3-methoxy-phenyl)triazol-4-yl]methoxy]pyrimidine; |
| 21 | 2-[[1-[4-Chloro-3-(difluoromethoxy)phenyl]triazol-4-yl]methoxy]-4-methyl-pyrimidine; |
| 22 | 2-[[1-[4-Chloro-3-(difluoromethoxy)phenyl]triazol-4-yl]methoxy]-5-methyl-pyrimidine; |
| 23 | 2-[[1-[4-Chloro-3-(difluoromethoxy)phenyl]triazol-4-yl]methoxy]pyrazine; |
| 25 | 2-[[1-3-(Difluoromethyl)-4-fluoro-phenyl]triazol-4-yl]methoxy]pyrimidine; |
| 26 | 2-[[1-[4-Chloro-3-(difluoromethoxy)phenyl]triazol-4-yl]methoxy]-5-methoxy-pyrimidine; |
| 27 | 2-[[1-[4-Chloro-3-(difluoromethoxy)phenyl]triazol-4-yl]methoxy]-5-ethyl-pyrimidine; |
| 28 | 5-Chloro-2-[[1-[4-chloro-3-(difluoromethoxy)phenyl]triazol-4-yl]methoxy]pyrimidine; |
| 29 | 2-[[1-[4-Chloro-3-(difluoromethoxy)phenyl]triazol-4-yl]methoxy]-4-methoxy-pyrimidine; |
| 30 | 2-[[1-[4-Chloro-3-(difluoromethyl)phenyl]triazol-4-yl]methoxy]-4-methyl-pyrimidine; |
| 31 | 2-[[1-[4-Chloro-3-(difluoromethoxy)phenyl]triazol-4-yl]methoxy]-5-methyl-pyrimidine; |
| 32 | 2-[[1-[4-Chloro-3-(difluoromethyl)phenyl]triazol-4-yl]methoxy]-5-ethyl-pyrimidine; |
| 33 | 2-[[1-[3-(Difluoromethoxy)-4-fluoro-phenyl]triazol-4-yl]methoxy]pyrimidine; |
| 34 | 2-[[1-[4-Chloro-3-(difluoromethoxy)phenyl]triazol-4-yl]methoxy]-5-methyl-pyrazine; |
| 35 | 2-[[1-[4-Chloro-3-(difluoromethoxy)phenyl]triazol-4-yl]methoxy]-5-(difluoromethoxy)pyrimidine; |
| 37 | 5-Chloro-2-[[1-(2,4-difluoro-3-methyl-phenyl)triazol-4-yl]methoxy]pyrimidine; |
| 38 | 2-[[1-(2,4-Difluoro-3-methyl-phenyl)triazol-4-yl]methoxy]-5-methyl-pyrimidine; |
| 39 | 2-[[1-(2,4-Difluoro-3-methyl-phenyl)triazol-4-yl]methoxy]-5-ethyl-pyrimidine; |
| 40 | 2-[[1-(3-Bromo-4-fluoro-phenyl)triazol-4-yl]methoxy]-5-ethyl-pyrimidine; |
| 41 | 2-[[1-(3-Bromo-4-fluoro-phenyl)triazol-4-yl]methoxy]-5-methoxy-pyrimidine; |
| 42 | 2-[[1-(3-Bromo-4-fluoro-phenyl)triazol-4-yl]methoxy]-5-chloro-pyrimidine; |
| 43 | 2-[[1-(3-Bromo-4-fluoro-phenyl)triazol-4-yl]methoxy]-5-isopropyl-pyrimidine; |
| 44 | 2-[[1-(3-Bromo-4-fluoro-phenyl)triazol-4-yl]methoxy]-5-(trifluoromethyl)pyrimidine; |
| 45 | 2-[[1-[4-Chloro-3-(difluoromethyl)phenyl]triazol-4-yl]methoxy]-5-(trifluoromethyl)pyrimidine; |
| 46 | 2-[[1-[4-Chloro-3-(difluoromethyl)phenyl]triazol-4-yl]methoxy]-5-methoxy-pyrimidine; |
| 47 | 5-Chloro-2-[[1-[4-chloro-3-(difluoromethyl)phenyl]triazol-4-yl]methoxy]pyrimidine; |
| 48 | 2-[[1-[4-Chloro-3-(difluoromethyl)phenyl]triazol-4-yl]methoxy]-5-isopropyl-pyrimidine; |
| 49 | 5-Chloro-2-[[1-[3-(difluoromethyl)-4-fluoro-phenyl]triazol-4-yl]methoxy]pyrimidine; |
| 50 | 2-[[1-[3-(Difluoromethyl)-4-fluoro-phenyl]triazol-4-yl]methoxy]-5-(trifluoromethyl)pyrimidine; |
| 51 | 2-[[1-[3-(Difluoromethyl)-4-fluoro-phenyl]triazol-4-yl]methoxy]-5-methyl-pyrimidine; |
| 52 | 2-[[1-[3-(Difluoromethyl)-4-fluoro-phenyl]triazol-4-yl]methoxy]-4-methyl-pyrimidine; |
| 53 | (R/S)-2-[1-[1-[4-Chloro-3-(difluoromethoxy)phenyl]triazol-4-yl]ethoxy]pyrimidine; |
| 54 | (R*)-2-[1-[1-[4-Chloro-3-(difluoromethoxy)phenyl]triazol-4-yl]ethoxy]pyrimidine; |
| 55 | (S*)-2-[1-[1-[4-Chloro-3-(difluoromethoxy)phenyl]triazol-4-yl]ethoxy]pyrimidine; |
| 56 | (R/S)-2-[1-[1-[4-Chloro-3-(difluoromethoxy)phenyl]triazol-4-yl]ethoxy]-5-methyl-pyrimidine; |
| 57 | (R*)-2-[1-[1-[4-Chloro-3-(difluoromethoxy)phenyl]triazol-4-yl]ethoxy]-5-methyl-pyrimidine; |
| 58 | (S*)-2-[1-[1-[4-Chloro-3-(difluoromethoxy)phenyl]triazol-4-yl]ethoxy]-5-methyl-pyrimidine; |
| 59 | (R/S)-2-[1-[1-[4-Chloro-3-(difluoromethoxy)phenyl]triazol-4-yl]ethoxy]-4-methyl-pyrimidine; |
| 60 | (R/S)-5-Chloro-2-[1-[1-[4-chloro-3-(difluoromethoxy)phenyl]-triazol-4-yl]ethoxy]pyrimidine; |
| 61 | 5-Chloro-2-[[1-[3-(difluoromethoxy)-4-fluoro-phenyl]triazol-4-yl]methoxy]pyrimidine; |
| 62 | 2-[[1-[3-(Difluoromethoxy)-4-fluoro-phenyl]triazol-4-yl]methoxy]-5-(trifluoromethyl)pyrimidine; |
| 63 | 2-[[1-[3-(Difluoromethoxy)-4-fluoro-phenyl]triazol-4-yl]methoxy]-5-methyl-pyrimidine; |
| 64 | 2-[[1-[3-(Difluoromethoxy)-4-fluoro-phenyl]triazol-4-yl]methoxy]-4-methyl-pyrimidine; |
| 65 | 2-[[1-[3-(Difluoromethyl)-4-fluoro-phenyl]triazol-4-yl]methoxy]-5-(trifluoromethyl)pyridine; |
| 66 | 2-[[1-[4-Chloro-3-(difluoromethyl)phenyl]triazol-4-yl]methoxy]-5-fluoro-pyrimidine; |
| 67 | 2-[[1-[3-(1,1-Difluoroethyl)-4-fluoro-phenyl]triazol-4-yl]methoxy]-5-ethyl-pyrimidine; |
| 68 | 2-[[1-[3-(1,1-Difluoroethyl)-4-fluoro-phenyl]triazol-4-yl]methoxy]-5-methoxy-pyrimidine; |
| 69 | 5-Chloro-2-[[1-[3-(1,1-difluoroethyl)-4-fluoro-phenyl]triazol-4-yl]methoxy]pyrimidine; |
| 70 | 2-[[1-[3-(1,1-Difluoroethyl)-4-fluoro-phenyl]triazol-4-yl]methoxy]-5-isopropyl-pyrimidine; |
| 71 | 2-[[1-[3-(1,1-Difluoroethyl)-4-fluoro-phenyl]triazol-4-yl]methoxy]-5-(trifluoromethyl)pyrimidine; |
| 72 | 5-Ethyl-2-[[1-[4-fluoro-3-(trifluoromethyl)phenyl]triazol-4-yl]methoxy]pyrimidine; |
| 73 | 2-[[1-[4-Fluoro-3-(trifluoromethyl)phenyl]triazol-4-yl]methoxy]-5-methoxy-pyrimidine; |
| 74 | 5-Chloro-2-[[1-[4-fluoro-3-(trifluoromethyl)phenyl]triazol-4-yl]methoxy]pyrimidine; |
| 75 | 2-[[1-[4-Fluoro-3-(trifluoromethyl)phenyl]triazol-4-yl]methoxy]-5-isopropyl-pyrimidine; |
| 76 | 2-[[1-[4-Fluoro-3-(trifluoromethyl)phenyl]triazol-4-yl]methoxy]-5-(trifluoromethyl)pyrimidine; |

| Ex #. | Compound Name |
|---|---|
| 77 | 2-[[1-[3-(1,1-Difluoroethyl)-4-fluoro-phenyl]triazol-4-yl]methoxy]-5-methyl-pyrimidine; |
| 78 | 2-[[1-[3-(1,1-Difluoroethyl)-4-fluoro-phenyl]triazol-4-yl]methoxy]pyrimidine; |
| 79 | 2-[[1-[3-(1,1-Difluoroethyl)-4-fluoro-phenyl]triazol-4-yl]methoxy]-4-methyl-pyrimidine; |
| 80 | 2-[[1-[3-(1,1-Difluoroethyl)-4-fluoro-phenyl]triazol-4-yl]methoxy]-5-fluoro-pyrimidine; |
| 81 | 2-[[1-[4-Fluoro-3-(trifluoromethyl)phenyl]triazol-4-yl]methoxy]-5-methyl-pyrimidine; |
| 82 | 2-[[1-[4-Fluoro-3-(trifluoromethyl)phenyl]triazol-4-yl]methoxy]pyrimidine; |
| 83 | 2-[[1-[4-Fluoro-3-(trifluoromethyl)phenyl]triazol-4-yl]methoxy]-4-methyl-pyrimidine; |
| 84 | 5-Fuoro-2-[[1-[4-fluoro-3-(trifluoromethyl)phenyl]triazol-4-yl]methoxy]pyrimidine; |
| 85 | 2-[[1-(3-Bromo-4-fluoro-phenyl)triazol-4-yl]methoxy]-4,5-dimethyl-pyrimidine; |
| 86 | 2-[[1-[4-Chloro-3-(difluoromethyl)phenyl]triazol-4-yl]methoxy]-4,5-dimethyl-pyrimidine; |
| 87 | 2-[[1-(4-Chloro-3-methoxy-phenyl)triazol-4-yl]methoxy]-5-methoxy-pyrimidine; |
| 88 | 2-[[1-(4-Chloro-3-methoxy-phenyl)triazol-4-yl]methoxy]-5-methyl-pyrimidine; |
| 89 | 2-[[1-[3-(Difluoromethyl)phenyl]triazol-4-yl]methoxy]-5-methyl-pyrimidine; |
| 90 | 2-[[1-[3-(Difluoromethyl)phenyl]triazol-4-yl]methoxy]-5-methoxy-pyrimidine; |
| 91 | 2-[[1-[3-(Difluoromethyl)phenyl]triazol-4-yl]methoxy]-5-ethyl-pyrimidine; |
| 92 | 5-Chloro-2-[[1-[3-(difluoromethyl)phenyl]triazol-4-yl]methoxy]pyrimidine; |
| 93 | 2-[[1-[3-(Difluoromethyl)phenyl]triazol-4-yl]methoxy]pyrimidine; |
| 94 | 2-[[1-(5-Bromo-6-methyl-2-pyridyl)triazol-4-yl]methoxy]-5-methyl-pyrimidine; |
| 95 | 2-[[1-[4-Chloro-3-(difluoromethoxy)phenyl]triazol-4-yl]methoxy]-5-fluoro-pyrimidine; |
| 96 | 2-[[1-[4-Chloro-3-(difluoromethoxy)phenyl]triazol-4-yl]methoxy]-5-(difluoromethyl)pyrimidine; |
| 103 | 3-[[1-[4-Chloro-3-(difluoromethoxy)phenyl]triazol-4-yl]methoxy]-2-methoxy-pyridine; |
| 104 | 5-[[1-[4-Chloro-3-(difluoromethoxy)phenyl]triazol-4-yl]methoxy]-2-methyl-pyridine; |
| 105 | 3-Chloro-2-[[1-[4-chloro-3-(difluoromethoxy)phenyl]triazol-4-yl]methoxy]pyridine; |
| 106 | 5-Chloro-2-[[1-[4-chloro-3-(difluoromethoxy)phenyl]triazol-4-yl]methoxy]-3-methoxy-pyridine; |
| 107 | 2-[[1-[4-Chloro-3-(difluoromethoxy)phenyl]triazol-4-yl]methoxy]-3-fluoro-pyridine; |
| 108 | 2-[[1-[4-Chloro-3-(difluoromethoxy)phenyl]triazol-4-yl]methoxy]-3-methoxy-pyridine; |
| 111 | 2-[[1-[3-(Difluoromethyl)-4-fluoro-phenyl]triazol-4-yl]methoxy]pyridine; |
| 112 | 5-Chloro-2[[1-[3-(difluoromethyl)-4-fluoro-phenyl]triazol-4-yl]methoxy]pyridine; |
| 113 | 2-[[1-[3-(Difluoromethyl)-4-fluoro-phenyl]triazol-4-yl]methoxy]-6-methyl-pyridine; |
| 114 | 2-[[1-[3-(Difluoromethyl)-4-fluoro-phenyl]triazol-4-yl]methoxy]-5-methyl-pyridine; |
| 115 | 2-[[1-[3-(Difluoromethy)-4-fluoro-phenyl]triazol-4-yl]methoxy]-4-methyl-pyridine; |
| 116 | 2-[[1-[3-(Difluoromethoxy)-4-fluoro-phenyl]triazol-4-yl]methoxy]-4-methyl-pyridine; |
| 117 | 5-Chloro-2-[[1-[3-(difluoromethoxy)-4-fluoro-phenyl]triazol-4-yl]methoxy]pyridine; |
| 118 | 2-[[1-[3-(Difluoromethoxy)-4-fluoro-phenyl]triazol-4-yl]methoxy]-5-methyl-pyridine; |
| 119 | 2-[[1-[3-(Difluoromethoxy)-4-fluoro-phenyl]triazol-4-yl]methoxy]-5-(trifluoromethyl)pyridine; |
| 120 | 5-Methyl-2-((1-(5-(trifluoromethyl)thiophen-2-yl)-1H-1,2,3-triazol-4-yl)methoxy)pyrimidine; |
| 121 | 5-Methyl-2-((1-(4-(trifluoromethyl)thiophen-2-yl)-1H-1,2,3-triazol-4-yl)methoxy)pyrimidine; |
| 122 | 2-((1-(3-(Difluoromethyl)-2-fluorophenyl)-1H-1,2,3-triazol-4-yl)methoxy)-5-methylpyrimidine; |
| 123 | 2-((1-(4-Chlorophenyl)-1H-1,2,3-triazol-4-yl)methoxy)-5-methylpyrimidine; |
| 124 | 2-((1-(4-Chloro-3-(oxetan-3-yl)phenyl)-1H-1,2,3-triazol-4-yl)methoxy)-5-methylpyrimidine; |
| 125 | 2-((1-(4-Chloro-3-(difluoromethyl)phenyl)-5-fluoro-1H-1,2,3-triazol-4-yl)methoxy)-5-methylpyrimidine; |
| 126 | 2-((1-(4-Chloro-3-(difluoromethyl)phenyl)-5-(trifluoromethyl)-1H-1,2,3-triazol-4-yl)methoxy)-5-methylpyrimidine; |
| 127 | 2-((1-(4-Chloro-3-(difluoromethyl)phenyl)-5-methyl-1H-1,2,3-triazol-4-yl)methoxy)-5-methylpyrimidine; |
| 128 | 2-((1-(4-Chloro-3-(difluoromethyl)phenyl)-1H-1,2,3-triazol-4-yl)methoxy)-5-methylthiazole; |
| 129 | 1-(4-Chloro-3-(difluoromethyl)phenyl)-4-(((5-methyl-1H-imidazol-2-yl)oxy)methyl)-1H-1,2,3-triazole; |
| 130 | 2-((1-(4-Chloro-3-(difluoromethoxy)phenyl)-1H-1,2,3-triazol-4-yl)methoxy)-5-methylpyridine; |
| 131 | 2-((1-(4-Chloro-3-(difluoromethoxy)phenyl)-1H-1,2,3-triazol-4-yl)methoxy)-6-methylpyridine; |
| 132 | 6-((1-(4-Chloro-3-(difluoromethoxy)phenyl)-1H-1,2,3-triazol-4-yl)methoxy)-2,3-dimethylpyridine; |
| 133 | 2-((1-(4-Chloro-3-(difluoromethoxy)phenyl)-1H-1,2,3-triazol-4-yl)methoxy)-6-methylpyrazine; |
| 134 | 5-((1-(4-Chloro-3-(difluoromethoxy)phenyl)-1H-1,2,3-triazol-4-yl)methoxy)-2,3-dimethylpyrazine; |
| 135 | 2-((1-(4-Chloro-3-(difluoromethoxy)phenyl)-1H-1,2,3-triazol-4-yl)methoxy)-2-methylpyrimidine; |
| 136 | 6-((1-(4-Chloro-3-(difluoromethoxy)phenyl)-1H-1,2,3-triazol-4-yl)methoxy)-3,4-dimethylpyridazine; |
| 137 | 3-((1-(4-Chloro-3-(difluoromethoxy)phenyl)-1H-1,2,3-triazol-4-yl)methoxy)-6-(trifluoromethyl)pyridazine; |
| 138 | 3-((1-(4-Chloro-3-(difluoromethoxy)phenyl)-1H-1,2,3-triazol-4-yl)methoxy)-6-methoxypyridazine; |
| 139 | 4-((1-(4-Chloro-3-(difluoromethoxy)phenyl)-1H-1,2,3-triazol-4-yl)methoxy)-2-methylpyrimidine; |
| 140 | 4-((1-(4-Chloro-3-(difluoromethoxy)phenyl)-1H-1,2,3-triazol-4-yl)methoxy)-2-(trifluoromethyl)pyrimidine; |
| 141 | 4-((1-(4-Chloro-3-(difluoromethoxy)phenyl)-1H-1,2,3-triazol-4-yl)methoxy)-2-methoxypyrimidine; |
| 142 | 2-((1-(5-Chloro-6-(trifluoromethyl)pyridin-2-yl)-1H-1,2,3-triazol-4-yl)methoxy)-5-methylpyrimidine; |
| 143 | 2-((1-(2-(Difluoromethyl)pyridin-4-yl)-1H-1,2,3-triazol-4-yl)methoxy)-5-methylpyrimidine; |
| 146 | 3-((1-(4-Chloro-3-(difluoromethoxy)phenyl)-1H-1,2,3-triazol-4-yl)methoxy)-4-methoxypyridine; |
| 147 | 4-Chloro-3-((1-(4-chloro-3-(difluoromethoxy)phenyl)-1H-1,2,3-triazol-4-yl)methoxy)pyridine; |
| 148 | 4-((1-(3-(Difluoromethoxy)phenyl)-1H-1,2,3-triazol-4-yl)methoxy)-5-methoxypyrimidine; |
| 149 | 2-((1-(3-(Difluoromethyl)phenyl)-5-methyl-1H-1,2,3-triazol-4-yl)methoxy)-5-methylpyrimidine; |
| 150 | 5-Methyl-2-((1-(5-(trifluoromethyl)pyridin-2-yl)-1H-1,2,3-triazol-4-yl)methoxy)pyrimidine; |
| 151 | 2-((1-(5-Bromo-6-fluoropyridin-3-yl)-1H-1,2,3-triazol-4-yl)methoxy)-5-methylpyrimidine; |
| 152 | 5-Methyl-2-((1-(pyridin-4-yl)-1H-1,2,3-triazol-4-yl)methoxy)pyrimidine; |
| 155 | 2-[[1-[3-(Difluoromethyl)phenyl]triazol-4-yl]methoxy]-4,5-dimethyl-pyrimidine; |
| 156 | 1-[2-[[1-[3-(Difluoromethyl)-4-fluoro-phenyl]triazol-4-yl]methoxy]pyrimidin-5-yl]ethanone; |
| 157 | (R/S)-1-[2-[[1-[3-(Difluoromethyl)-4-fluoro-phenyl]triazol-4-yl]methoxy]pyrimidin-5-yl]ethanol; |
| 158 | 2-[[1-[4-Fluoro-3-(trifluoromethyl)phenyl]triazol-4-yl]methoxy]pyridine; |
| 159 | [2-[[1-[3-(Difluoromethyl)phenyl]triazol-4-yl]methoxy]pyrimidin-4-yl]methanol; |
| 160 | [2-[[1-[3-(Difluoromethyl)phenyl]triazol-4-yl]methoxy]pyrimidin-5-yl]methanol; |
| 161 | 2-[[1-[3-(Difluoromethyl)phenyl]triazol-4-yl]methoxy]-5-methyl-pyrimidin-4-amine; |
| 162 | 2-[[1-[3-(Difluoromethyl)-4-fluoro-phenyl]triazol-4-yl]methoxy]-N-methyl-pyrimidine-4-carboxamide; |
| 163 | (R/S) 1-[2-[[1-[3-(Difluoromethyl)-4-fluoro-phenyl]triazol-4-yl]methoxy]pyrimidin-4-yl]ethanamine; |
| 164 | 5-Chloro-2-[[1-(4-fluorophenyl)triazol-4-yl]methoxy]pyrimidine; |
| 165 | 5-(Azetidin-1-yl)-2-[[1-[3-(difluoromethoxy)-4-fluoro-phenyl]-triazol-4-yl]methoxy]pyrimidine; |

| Ex #. | Compound Name |
|---|---|
| 166 | 2-[[1-[3-(Difluoromethoxy)-4-fluoro-phenyl]triazol-4-yl]methoxy]-4-(3,3-difluoropyrrolidin-1-yl)pyrimidine; |
| 167 | 2-((1-(3-(Difluoromethoxy)-4-fluorophenyl)-1H-1,2,3-triazol-4-yl)methoxy)-5-fluoropyrimidin-4-amine; |
| 168 | 2-[[1-[3-(Difluoromethoxy)-4-fluoro-phenyl]triazol-4-yl]methoxy]-4-pyrrolidin-1-yl-pyrimidine; |
| 169 | 2-[[1-[3-(Difluoromethoxy)-4-fluoro-phenyl]triazol-4-yl]methoxy]-4-(1-piperidyl)pyrimidine; |
| 170 | 4-[2-[[1-[3-(Difluoromethoxy)-4-fluoro-phenyl]triazol-4-yl]methoxy]pyrimidin-4-yl]morpholine; |
| 171 | 2-[[1-[4-Chloro-3-(difluoromethoxy)phenyl]triazol-4-yl]methoxy]-N-methyl-pyrimidin-4-amine; |
| 172 | 2-[[1-[3-(Difluoromethyl)phenyl]-5-methyl-triazol-4-yl]methoxy]-5-methoxy-pyrimidine; |
| 173 | 2-[[1-[3-(1,1-Difluoroethyl)-4-fluoro-phenyl]-5-methyl-triazol-4-yl]methoxy]-5-methyl-pyrimidine; |
| 174 | 5-Methyl-2-[[1-(6-methyl-2-pyridyl)triazol-4-yl]methoxy]-pyrimidine; |
| 175 | 5-Methyl-2-[[1-(2-methyl-4-pyridyl)triazol-4-yl]methoxy]-pyrimidine; |
| 176 | 5-Methyl-2-[[1-(5-methyl-3-pyridyl)triazol-4-yl]methoxy]-pyrimidine; |
| 177 | 2-[[1-(2-Bromo-4-pyridyl)triazol-4-yl]methoxy]-5-methyl-pyrimidine; |
| 178 | 2-[2-[[1-(3-Cyclobutyl-4-fluoro-phenyl)triazol-4-yl]methoxy]pyrimidin-5-yl]propan-2-ol; |
| 179 | 2-[2-[[1-(4-Fluoro-3-isopropyl-phenyl)triazol-4-yl]methoxy]pyrimidin-5-yl]propan-2-ol; |
| 180 | 2-[2-[[1-(3-Cyclopropyl-4-fluoro-phenyl)triazol-4-yl]methoxy]pyrimidin-5-yl]propan-2-ol; |
| 181 | 2-[2-[[1-(4-Fluoro-3-methyl-phenyl)triazol-4-yl]methoxy]-pyrimidin-5-yl]propan-2-ol; |
| 182 | 2-[2-[[1-(3-Ethyl-4-fluoro-phenyl)triazol-4-yl]methoxy]pyrimidin-5-yl]propan-2-ol; |
| 183 | 5-Bromo-2-[[1-[3-(1,1-difluoroethyl)-4-fluoro-phenyl]triazol-4-yl]methoxy]pyrimidine; |
| 184 | 2-[[1-[3-(1,1-Difluoromethyl)-4-fluoro-phenyl]triazol-4-yl]-methoxy]-5-(1-methylpyrazol-3-yl)pyrimidine; |
| 185 | 2-[[1-[3-(1,1-Difluoromethyl)-4-fluoro-phenyl]triazol-4-yl]-methoxy]-5-(1H-pyrazol-4-yl)pyrimidine; |
| 186 | 2-[[1-[3-(1,1-Difluoroethyl)-4-fluoro-phenyl]triazol-4-yl]methoxy]-4-(1H-pyrazol-4-yl)pyrimidine; |
| 187 | 4-(2-((1-(3-(1,1-Difluoroethyl)-4-fluorophenyl)-1H-1,2,3-triazol-4-yl)methoxy)pyrimidin-5-yl)morpholine; |
| 188 | 2-((1-(4-(Azetidin-1-yl)-3-(difluoromethyl)phenyl)-1H-1,2,3-triazol-4-yl)methoxy)pyrimidine; |
| 189 | 2-[[1-[4-Chloro-3-(difluoromethoxy)phenyl]triazol-4-yl]methoxy]-5-fluoro-pyrazine; |
| 190 | 4-Chloro-2-[[1-[4-chloro-3-(difluoromethoxy)phenyl]triazol-4-yl]methoxy]pyrimidine; |
| 191 | 2-[[1-[4-Chloro-3-(difluoromethoxy)phenyl]triazol-4-yl]methoxy]-4-fluoro-pyrimidine; |
| 192 | 2-[[1-[4-Chloro-3-(difluoromethoxy)phenyl]triazol-4-yl]methoxy]-5-(2-fluoroethoxy)pyrimidine; |
| 193 | 2-[[1-[4-Chloro-3-(2-fluoroethoxy)phenyl]triazol-4-yl]methoxy]-5-methoxy-pyrimidine; |
| 194 | 2-[[1-[4-Fluoro-3-(3-fluoropropyl)phenyl]triazol-4-yl]methoxy]-5-methoxy-pyrimidine; |
| 195 | 2-[[1-[3-(3-Chloropropyl)-4-fluoro-phenyl]triazol-4-yl]methoxy]-5-methoxy-pyrimidine; |
| 196 | 2-[[1-[4-Chloro-3-(difluoromethoxy)phenyl]triazol-4-yl]methoxy]-5-(3-fluoropropyl)pyrimidine; |
| 225 | 5-Chloro-2-[[1-(4-chlorophenyl)triazol-4-yl]methoxy]-pyrimidine; |
| 226 | 2-[[1-(4-Chlorophenyl)triazol-4-yl]methoxy]-5-(trifluoromethyl)pyrimidine; |
| 227 | 2-[[1-(4-Chlorophenyl)triazol-4-yl]methoxy]-5-(difluoromethoxy)pyrimidine; |
| 228 | 2-[[1-(3-Fluorophenyl)triazol-4-yl]methoxy]pyrimidine; |
| 229 | 5-Fluoro-2-[[1-(3-fluorophenyl)triazol-4-yl]methoxy]-pyrimidine; |
| 230 | 2-[[1-(3-Fluorophenyl)triazol-4-yl]methoxy]-5-methoxy-pyrimidine; |
| 231 | 5-Chloro-2-[[1-(3-fluorophenyl)triazol-4-yl]methoxy]-pyrimidine; |
| 232 | 2-[[1-(3-Fluorophenyl)triazol-4-yl]methoxy]-5-methyl-pyrimidine; |
| 233 | 5-Ethyl-2-[[1-(3-fluorophenyl)triazol-4-yl]methoxy]-pyrimidine; |
| 234 | 2-[[1-(3-Bromophenyl)triazol-4-yl]methoxy]-5-methyl-pyrimidine; |
| 235 | 2-[[1-(3-Bromophenyl)triazol-4-yl]methoxy]-4-methyl-pyrimidine; |
| 236 | 2-[[1-(o-Tolyl)triazol-4-yl]methoxy]pyrimidine; |
| 237 | 5-Fluoro-2-[[1-(o-tolyl)triazol-4-yl]methoxy]pyrimidine; |
| 238 | 5-Methoxy-2-[[1-(o-tolyl)triazol-4-yl]methoxy]pyrimidine; |
| 239 | 5-Chloro-2-[[1-(o-tolyl)triazol-4-yl]methoxy]pyrimidine; |
| 240 | 5-Methyl-2-[[1-(o-tolyl)triazol-4-yl]methoxy]pyrimidine; |
| 241 | 5-Ethyl-2-[[1-(o-tolyl)triazol-4-yl]methoxy]pyrimidine; |
| 242 | 2-[[1-(m-Tolyl)triazol-4-yl]methoxy]pyrimidine; |
| 243 | 5-Methyl-2-[[1-(m-tolyl)triazol-4-yl]methoxy]pyrimidine; |
| 244 | 4-Methyl-2-[[1-(m-tolyl)triazol-4-yl]methoxy]pyrimidine; |
| 245 | 5-Ethyl-2-[[1-(m-tolyl)triazol-4-yl]methoxy]pyrimidine; |
| 246 | 5-Chloro-2-[[1-(m-tolyl)triazol-4-yl]methoxy]pyrimidine; |
| 247 | 5-Fluoro-2-[[1-(m-tolyl)triazol-4-yl]methoxy]pyrimidine; |
| 248 | 5-Methoxy-2-[[1-(m-tolyl)triazol-4-yl]methoxy]pyrimidine; |
| 249 | 2-[2-[[1-(m-Tolyl)triazol-4-yl]methoxy]pyrimidin-5-yl]propan-2-ol; |
| 250 | 4-(Methoxymethyl)-2-[[1-(m-tolyl)triazol-4-yl]methoxy]-pyrimidine; |
| 251 | 4,5-Dimethyl-2-[[1-(m-tolyl)triazol-4-yl]methoxy]pyrimidine; |
| 252 | 5-Fluoro-4-methyl-2-[[1-(m-tolyl)triazol-4-yl]methoxy]-pyrimidine; |
| 253 | 5-Chloro-4-methyl-2-[[1-(m-tolyl)triazol-4-yl]methoxy]-pyrimidine; |
| 254 | 5-Methyl-2-[[1-(m-tolyl)triazol-4-yl]methoxy]pyrimidin-4-amine; |
| 255 | 1-[2-[[1-(m-Tolyl)triazol-4-yl]methoxy]pyrimidin-5-yl]ethanone; |
| 256 | 2-[[1-(p-Tolyl)triazol-4-yl]methoxy]pyrimidine; |
| 257 | 5-Fluoro-2-[[1-(p-tolyl)triazol-4-yl]methoxy]pyrimidine; |
| 258 | 5-Methoxy-2-[[1-(p-tolyl)triazol-4-yl]methoxy]pyrimidine; |
| 259 | 5-Chloro-2-[[1-(p-tolyl)triazol-4-yl]methoxy]pyrimidine; |
| 260 | 5-Methyl-2-[[1-(p-tolyl)triazol-4-yl]methoxy]pyrimidine; |
| 261 | 5-Ethyl-2-[[1-(p-tolyl)triazol-4-yl]methoxy]pyrimidine; |
| 262 | 2-[[1-(3-Isopropylphenyl)triazol-4-yl]methoxy]pyrimidine; |
| 263 | 5-Fluoro-2-[[1-(3-isopropylphenyl)triazol-4-yl]methoxy]-pyrimidine; |
| 264 | 2-[[1-(3-Isopropylphenyl)triazol-4-yl]methoxy]-5-methoxy-pyrimidine; |
| 265 | 5-Chloro-2-[[1-(3-isopropylphenyl)triazol-4-yl]methoxy]-pyrimidine; |
| 266 | 2-[[1-(3-Isopropylphenyl)triazol-4-yl]methoxy]-5-methyl-pyrimidine; |
| 267 | 5-Ethyl-2-[[1-(3-isopropylphenyl)triazol-4-yl]methoxy]-pyrimidine; |
| 268 | 2-[[1-[3-(Difluoromethyl)phenyl]triazol-4-yl]methoxy]-4-methyl-pyrimidine; |
| 269 | 2-[[1-[3-(Difluoromethyl)phenyl]triazol-4-yl]methoxy]-5-fluoro-pyrimidine; |
| 270 | 2-[[1-[3-(Difluoromethyl)phenyl]triazol-4-yl]methoxy]-4-isopropyl-pyrimidine; |
| 271 | 2-[[1-[3-(Difluoromethyl)phenyl]triazol-4-yl]methoxy]-4-(methoxymethyl)pyrimidine; |
| 272 | 2[2-[[1-[3-(Difluoromethyl)phenyl]triazol-4-yl]methoxy]-pyrimidin-5-yl]propan-2-ol; |
| 273 | 5-(Difluoromethyl)-2-[[1-[3-(difluoromethyl)phenyl]triazol-4-yl]methoxy]pyrimidine; |
| 274 | 4-(Difluoromethyl)-2-[[1-[3-(difluoromethyl)phenyl]triazol-4-yl]methoxy]pyrimidine; |
| 275 | 2-[[1-[3-(Difluoromethyl)phenyl]triazol-4-yl]methoxy]-5-(trifluoromethyl)pyrimidine; |
| 276 | 5-(Difluoromethoxy)-2-[[1-[3-difluoromethyl)phenyl]triazol-4-yl]methoxy]pyrimidine; |
| 277 | 2-[[1-[3-(Difluoromethyl)phenyl]triazol-4-yl]methoxy]-N,N-dimethyl-pyrimidin-4-amine; |
| 278 | 2-[[1-[3-(Difluoromethyl)phenyl]triazol-4-yl]methoxy]-5-fluoro-4-methyl-pyrimidine; |
| 279 | 5-Chloro-2-[[1-[3-(difluoromethyl)phenyl]triazol-4-yl]methoxy]-4-methyl-pyrimidine; |
| 280 | 2-Chloro-4[[1-[3-(difluoromethyl)phenyl]triazol-4-yl]methoxy]-5-methyl-pyrimidine; |

| Ex #. | Compound Name |
|---|---|
| 281 | 2-[[1-[3-(Difluoromethyl)phenyl]triazol-4-yl]methoxy]-N,N,5-trimethyl-pyrimidin-4-amine; |
| 282 | 5-Cyclopropyl-2-[[1-[3-(difluoromethyl)phenyl]triazol-4-yl]methoxy]pyrimidine; |
| 283 | 4-Cyclopropyl-2-[[1-[3-(difluoromethyl)phenyl]triazol-4-yl]methoxy]pyrimidine; |
| 284 | 2-[[1-[3-(Difluoromethyl)phenyl]triazol-4-yl]methoxy]-4-pyrrolidin-1-yl-pyrimidine; |
| 285 | 2-[[1-[3-(Difluoromethyl)phenyl]triazol-4-yl]methoxy]-4-(1-piperidyl)pyrimidine; |
| 286 | 5-Methyl-2-[[1-[3-(trifluoromethyl)phenyl]triazol-4-yl]methoxy]pyrimidine; |
| 287 | 5-Ethyl-2-[[1-[3-(trifluoromethyl)phenyl]triazol-4-yl]methoxy]pyrimidine; |
| 288 | 5-isopropyl-2-[[1-[3-(trifluoromethyl)phenyl]triazol-4-yl]methoxy]pyrimidine; |
| 289 | 5-(Difluoromethyl)-2-[[1-[3-(trifluoromethyl)phenyl]triazol-4-yl]methoxy]pyrimidine; |
| 290 | 4,5-Dimethyl-2-[[1-[3-(trifluoromethyl)phenyl]triazol-4-yl]methoxy]pyrimidine; |
| 291 | 5-Chloro-4-methyl-2-[[1-[3-(trifluoromethyl)phenyl]triazol-4-yl]methoxy]pyrimidine; |
| 292 | 2-[[1-[3-(1,1-Difluoroethyl)phenyl]triazol-4-yl]methoxy]-pyrimidine; |
| 293 | 5-Bromo-2-[[1-[3-(1,1-difluoroethyl)phenyl]triazol-4-yl]methoxy]pyrimidine; |
| 294 | 5-Chloro-2-[[1-[3-(1,1-difluoroethyl)phenyl]triazol-4-yl]methoxy]pyrimidine; |
| 295 | 2-[[1-[3-(1,1-Difluoroethyl)phenyl]triazol-4-yl]methoxy]-5-fluoro-pyrimidine; |
| 296 | 2-[[1-[3-(1,1-Difluoroethyl)phenyl]triazol-4-yl]methoxy]-4-methyl-pyrimidine; |
| 297 | 2-[[1-[3-(1,1-Difluoroethyl)phenyl]triazol-4-yl]methoxy]-5-methyl-pyrimidine; |
| 298 | [2-[[1-[3-(1,1-Difluoroethyl)phenyl]triazol-4-yl]methoxy]-pyrimidin-5-yl]methanol; |
| 299 | [2-[[1-[3-(1,1-Difluoroethyl)phenyl]triazol-4-yl]methoxy]-pyrimidin-4-yl]methanol; |
| 300 | 2-[[1-[3-(1,1-Difluoroethyl)phenyl]triazol-4-yl]methoxy]-4-(methoxymethyl)pyrimidine; |
| 301 | 2-[2-[[1-[3-(1,1-Difluoroethyl)phenyl]triazol-4-yl]methoxy]-pyrimidin-5-yl]propan-2-ol; |
| 302 | 2-[[1-[3-(1,1-Difluoroethyl)phenyl]triazol-4-yl]methoxy]-5-(difluoromethy)pyrimidine; |
| 303 | 2-[[1-[3-(1,1-Difluoroethyl)phenyl]triazol-4-yl]methoxy]-4-(difluoromethyl)pyrimidine; |
| 304 | 2-[[1-[3-(1,1-Difluoroethyl)phenyl]triazol-4-yl]methoxy]-4-(trifluoromethyl)pyrimidine; |
| 305 | (R/S)-2-[2-[[1-[3-(1,1-Difluoroethyl)phenyl]triazol-4-yl]methoxy]pyrimidin-5-yl]-1,1,1-trifluoro-propan-2-ol; |
| 306 | 2-[[1-[3-(1,1-Difluoroethyl)phenyl]triazol-4-yl]methoxy]-5-methoxy-pyrimidine; |
| 307 | 2-[[1-[3-(1,1-Difluoroethyl)phenyl]triazol-4-yl]methoxy]-4-methoxy-pyrimidine; |
| 308 | 2-[[1-[3-(1,1-Difluoroethyl)phenyl]triazol-4-yl]methoxy]-5-(difluoromethoxy)pyrimidine; |
| 309 | 1-[2-[[1-[3-(1,1-Difluoroethyl)phenyl]triazol-4-yl]methoxy]-pyrimidin-5-yl]ethanone; |
| 310 | (R/S)-1-[2-[[1-[3-(1,1-Difluoroethyl)phenyl]triazol-4-yl]methoxy]pyrimidin-5-yl]ethanol; |
| 311 | (R/S)-2-[[1-[3-(1,1-Difluoroethyl)phenyl]triazol-4-yl]methoxy]-5-(1-methoxyethyl)pyrimidine; |
| 312 | 5-Chloro-2-[[1-[3-(1,1-difluoroethyl)phenyl]triazol-4-yl]methoxy]-4-methyl-pyrimidine; |
| 313 | 2-[[1-[3-(1,1-Difluoroethyl)phenyl]triazol-4-yl]methoxy]-5-fluoro-4-methyl-pyrimidine; |
| 314 | 2-[[1-[3-(1,1-Difluoroethyl)phenyl]triazol-4-yl]methoxy]-5-methyl-pyrimidin-4-amine; |
| 315 | 2-[[1-[3-(1,1-Difluoroethyl)phenyl]triazol-4-yl]methoxy]-5-fluoro-N-methyl-pyrimidin-4-amine; |
| 316 | 2-[[1-[3-(1,1-Difluoroethyl)phenyl]triazol-4-yl]methoxy]-pyrimidin-4-amine; |
| 317 | 2-[[1-[3-(1,1-Difluoroethyl)phenyl]triazol-4-yl]methoxy]-N-methyl-pyrimidin-4-amine; |
| 318 | 2-[[1-[3-(1,1-Difluoroethyl)phenyl]triazol-4-yl]methoxy]-N,N-dimethyl-pyrimidin-4-amine; |
| 319 | 5-Cyclopropyl-2-[[1-[3-(1,1-difluoroethyl)phenyl]triazol-4-yl]methoxy]pyrimidine; |
| 320 | 5-(Azetidin-1-yl)-2-[[1-[3-(1,1-difluomethyl)phenyl]triazol-4-yl]methoxy]pyrimidine; |
| 321 | 2-[[1-[3-(1,1-Difluoroethyl)phenyl]triazol-4-yl]methoxy]-5-(3-fluoroazetidin-1-yl)pyrimidine; |
| 322 | 2-[[1-[3-(1,1-Difluoroethyl)phenyl]triazol-4-yl]methoxy]-4-pyrrolidin-1-yl-pyrimidine; |
| 323 | 2-[[1-[3-(Difluoromethoxy)phenyl]triazol-4-yl]methoxy]-pyrimidine; |
| 324 | 2-[[1-[3-(Difluoromethoxy)phenyl]triazol-4-yl]methoxy]-5-fluoro-pyrimidine; |
| 325 | 2-[[1-[3-(Difluoromethoxy)phenyl]triazol-4-yl]methoxy]-5-methoxy-pyrimidine; |
| 326 | 5-Chloro-2[[1-[3-(difluoromethoxy)phenyl]triazol-4-yl]methoxy]pyrimidine; |
| 327 | 2-[[1-[3-(Difluoromethoxy)phenyl]triazol-4-yl]methoxy]-5-methyl-pyrimidine; |
| 328 | 2-[[1-[3-(Difluoromethoxy)phenyl]triazol-4-yl]methoxy]-5-ethyl-pyrimidine; |
| 329 | 2-[[1-[4-(Difluoromethoxy)phenyl]triazol-4-yl]methoxy]-pyrimidine; |
| 330 | 2-[[1-[4-(Difluoromethoxy)phenyl]triazol-4-yl]methoxy]-5-fluoro-pyrimidine; |
| 331 | 2-[[1-[4-(Difluoromethoxy)phenyl]triazol-4-yl]methoxy]-5-methoxy-pyrimidine; |
| 332 | 5-Chloro-2-[[1-[4-(difluoromethoxy)phenyl]triazol-4-yl]methoxy]pyrimidine; |
| 333 | 2-[[1-[4-(Difluoromethoxy)phenyl]triazol-4-yl]methoxy]-5-methyl-pyrimidine; |
| 334 | 2-[[1-[4-(Difluoromethoxy)phenyl]triazol-4-yl]methoxy]-5-ethyl-pyrimidine; |
| 335 | 2-[[1-[4-(Trifluoromethoxy)phenyl]triazol-4-yl]methoxy]-pyrimidine; |
| 336 | 5-Fluoro-2-[[1-[4-(trifluoromethoxy)phenyl]triazol-4-yl]methoxy]pyrimidine; |
| 337 | 5-Methoxy-2-[[1-[4-(trifluoromethoxy)phenyl]triazol-4-yl]methoxy]pyrimidine; |
| 338 | 5-Chloro-2-[[1-[4-(trifluoromethoxy)phenyl]triazol-4-yl]methoxy]pyrimidine; |
| 339 | 5-Methyl-2-[[1-[4-(trifluoromethoxy)phenyl]triazol-4-yl]methoxy]pyrimidine; |
| 340 | 5-Ethyl-2-[[1-[4-(trifluoromethoxy)phenyl]triazol-4-yl]methoxy]pyrimidine; |
| 341 | 2-[[1-[3-(Trifluoromethoxy)phenyl]triazol-4-yl]methoxy]-pyrimidine; |
| 342 | 5-Methyl-2-[[1-[3-(trifluoromethoxy)phenyl]triazol-4-yl]methoxy]pyrimidine; |
| 343 | 5-Methyl-2-[[1-[3-(trifluoromethoxy)phenyl]triazol-4-yl]methoxy]pyrimidin-4-amine; |
| 344 | 1-[2-[[1-[3-(Trifluoromethoxy)phenyl]triazol-4-yl]methoxy]pyrimidin-5-yl]ethanone; |
| 345 | 2-[2-[[1-[3-(Trifluoromethoxy)phenyl]triazol-4-yl]methoxy]pyrimidin-5-yl]propan-2-ol; |
| 346 | 4-(Methoxymethyl)-2-[[1-[3-(trifluoromethoxy)phenyl]triazol-4-yl]methoxy]pyrimidine; |
| 347 | 4-Methyl-2-[[1-[3-(trifluoromethoxy)phenyl]triazol-4-yl]methoxy]pyrimidine; |
| 348 | 5-Fluoro-2-[[1-[3-(trifluoromethoxy)phenyl]triazol-4-yl]methoxy]pyrimidine; |
| 349 | 5-Methoxy-2-[[1-[3-(trifluoromethoxy)phenyl]triazol-4-yl]methoxy]pyrimidine; |
| 350 | 5-Chloro-2-[[1-[3-(trifluoromethoxy)phenyl]triazol-4-yl]methoxy]pyrimidine; |
| 351 | 5-Ethyl-2-[[1-[3-(trifluoromethoxy)phenyl]triazol-4-yl]methoxy]pyrimidine; |
| 352 | N-Methyl-2-[[1-[3-(trifluoromethoxy)phenyl]triazol-4-yl]methoxy]pyrimidin-4-amine; |
| 353 | 2-[[1-[3-(Trifluoromethoxy)phenyl]triazol-4-yl]methoxy]-pyrimidin-4-amine; |
| 354 | 2-[[1-(2,2-Difluoro-1,3-benzodioxol-5-yl)triazol-4-yl]methoxy]-5-methyl-pyrimidine; |
| 355 | 2-[[1-(2,2-Difluoro-1,3-benzodioxol-5-yl)triazol-4-yl]methoxy]pyrimidine; |
| 356 | 5-Chloro-2-[[1-(2,2-difluoro-1,3-benzodioxol-5-yl)triazol-4-yl]methoxy]pyrimidine; |

| Ex #. | Compound Name |
|---|---|
| 357 | 2-[[1-(2,2-Difluoro-1,3-benzodioxol-5-yl)triazol-4-yl]methoxy]-5-fluoro-4-methyl-pyrimidine; |
| 358 | 2-[[1-(2,2-Difluoro-1,3-benzodioxol-5-yl)triazol-4-yl]methoxy]-5-fluoro-pyrimidine; |
| 359 | 2-[[1-(2,2-Difluoro-1,3-benzodioxol-5-yl)triazol-4-yl]methoxy]-4,5-dimethyl-pyrimidine; |
| 360 | 2-[[1-(3,5-Dimethylphenyl)triazol-4-yl]methoxy]pyrimidine; |
| 361 | 2-[[1-(3,5-Dimethylphenyl)triazol-4-yl]methoxy]-5-fluoro-pyrimidine; |
| 362 | 2-[[1-(3,5-Dimethylphenyl)triazol-4-yl]methoxy]-5-methoxy-pyrimidine; |
| 363 | 5-Chloro-2-[[1-(3,5-dimethylphenyl)triazol-4-yl]methoxy]pyrimidine; |
| 364 | 2-[[1-(3,5-Dimethylphenyl)triazol-4-yl]methoxy]-5-methyl-pyrimidine; |
| 365 | 2-[[1-(3,5-Dimethylphenyl)triazol-4-yl]methoxy]-5-ethyl-pyrimidine; |
| 366 | 2-[(1-Indan-5-yltriazol-4-yl)methoxy]-5-methyl-pyrimidine; |
| 367 | 5-Chloro-2-[(1-indan-5-yltriazol-4-yl)methoxy]pyrimidine; |
| 368 | 2-[(1-Indan-5-yltriazol-4-yl)methoxy]-4-(methoxymethyl)-pyrimidine; |
| 369 | 2-[2-[(1-Indan-5-yltriazol-4-yl)methoxy]pyrimidin-5-yl]propan-2-ol; |
| 370 | 4-(Difluoromethyl)-2-[(1-indan-5-yltriazol-4-yl)methoxy]-pyrimidine; |
| 371 | 5-Chloro-2-[(1-indan-5-yltriazol-4-yl)methoxy]-4-methyl-pyrimidine; |
| 372 | 2-[[1-[4-Chloro-3-(difluoromethoxy)phenyl]triazol-4-yl]-methoxy]-4,5-dimethyl-pyrimidine; |
| 373 | 2-[[1-[4-Chloro-3-(difluoromethoxy)phenyl]triazol-4-yl]-methoxy]-5-isopropyl-pyrimidine; |
| 374 | 2-[(1R)-1-[1-[4-Chloro-3-(difluoromethoxy)phenyl]triazol-4-yl]ethoxy]pyrimidine; |
| 375 | 5-Chloro-2-[(1R)-1-[1-[4-chloro-3-(difluoromethoxy)phenyl]-triazol-4-yl]ethoxy]pyrimidine; |
| 376 | 2-[(1R)-1-[1-[4-Chloro-3-(difluoromethoxy)phenyl]triazol-4-yl]ethoxy]-5-methyl-pyrimidine; |
| 377 | 2-[(1R)-1-[1-[4-Chloro-3-(difluoromethoxy)phenyl]triazol-4-yl]ethoxy]-5-methoxy-pyrimidine; |
| 378 | 2-[(1S)-1-[1-[4-Chloro-3-(difluoromethoxy)phenyl]triazol-4-yl]ethoxy]pyrimidine; |
| 379 | 5-Chloro-2-[(1S)-1-[1-[4-chloro-3-(difluoromethoxy)phenyl]-triazol-4-yl]ethoxy]pyrimidine; |
| 380 | 2-[(1S)-1-[1-[4-Chloro-3-(difluoromethoxy)phenyl]triazol-4-yl]ethoxy]-5-methyl-pyrimidine; |
| 381 | 2-[(1S)-1-[1-[4-Chloro-3-(difluoromethoxy)phenyl]triazol-4-yl]ethoxy]-5-methoxy-pyrimidine; |
| 382 | 2-[[1-[4-Chloro-3-(difluoromethoxy)phenyl]triazol-4-yl]methoxy]pyrimidin-4-amine; |
| 383 | [2-[[1-[4-Chloro-3-(difluoromethoxy)phenyl]triazol-4-yl]methoxy]pyrimidin-4-yl]methanol; |
| 384 | 2-[[1-[4-Chloro-3-(difluoromethoxy)phenyl]triazol-4-yl]methoxy]-4-(methoxymethyl)pyrimidine; |
| 385 | 2-[2-[[1-[4-Chloro-3-(difluoromethoxy)phenyl]triazol-4-yl]methoxy]pyrimidin-5-yl]propan-2-ol; |
| 386 | 2-((1-(4-Chloro-3-(difluoromethoxy)phenyl)-1H-1,2,3-triazol-4-yl)methoxy)-4-isopropoxypyrimidine; |
| 387 | Methyl 2-((1-(4-chloro-3-(difluoromethoxy)phenyl)-1H-1,2,3-triazol-4-yl)methoxy)pyrimidine-4-carboxylate; |
| 388 | 2-[[1-[4-Chloro-3-(difluoromethoxy)phenyl]triazol-4-yl]methoxy]-N-(2,2-difluoroethyl)-5-fluoro-pyrimidin-4-amine; |
| 389 | 2-[[1-[4-Chloro-3-(difluoromethoxy)phenyl]triazol-4-yl]methoxy]-5-fluoro-N-methyl-pyrimidin-4-amine; |
| 390 | 2-((1-(4-Chloro-3-(difluoromethoxy)phenyl)-1H-1,2,3-triazol-4-yl)methoxy)-5-fluoropyrimidin-4-amine; |
| 391 | 5-(Azetidin-1-yl)-2-((1-(4-chloro-3-(difluoromethoxy)phenyl)-1H-1,2,3-triazol-4-yl)methoxy)pyrimidine; |
| 392 | 2-((1-(4-Chloro-3-(difluoromethoxy)phenyl)-1H-1,2,3-triazol-4-yl)methoxy)-5-(3-fluoroazetidin-1-yl)pyrimidine; |
| 393 | 2-((1-(4-Chloro-3-(difluoromethoxy)phenyl)-1H-1,2,3-triazol-4-yl)methoxy)-5-(3,3-difluoroazetidin-1-yl)pyrimidine; |
| 394 | 2-[[1-[4-Chloro-3-(difluoromethoxy)phenyl]triazol-4-yl]methoxy]-6-fluoro-pyridine; |
| 395 | 2-[[1-[3-(Difluoromethoxy)-4-fluoro-phenyl]triazol-4-yl]methoxy]-6-(trifluoromethy)pyridine; |
| 396 | 2-[[1-[3-(Difluoromethoxy)-4-fluoro-phenyl]triazol-4-yl]methoxy]-5-methyl-pyrazine; |
| 397 | 2-[[1-[3-(Difluoromethoxy)-4-fluoro-phenyl]triazol-4-yl]methoxy]-5-(2-thienyl)pyrazine; |
| 398 | 5-Bromo-2-[[1-[3-(difluoromethyl)-4-fluoro-phenyl]triazol-4-yl]methoxy]pyrimidine; |
| 399 | 2-[[1-[3-(Difluoromethyl)-4-fluoro-phenyl]triazol-4-yl]methoxy]-4-(methoxymethyl)pyrimidine; |
| 400 | [2-[[1-[3-(Difluoromethyl)-4-fluoro-phenyl]triazol-4-yl]methoxy]pyrimidin-4-yl]methanol; |
| 401 | 2-[2-[[1-[3-(Difluoromethyl)-4-fluoro-phenyl]triazol-4-yl]methoxy]pyrimidin-5-yl]propan-2-ol; |
| 402 | 4-(Difluoromethyl)-2-[[1-[3-(difluoromethyl)-4-fluoro-phenyl]triazol-4-yl]methoxy]pyrimidine; |
| 403 | 2-[[1-[3-(Difluoromethyl)-4-fluoro-phenyl]triazol-4-yl]methoxy]-4-(trifluoromethyl)pyrimidine; |
| 404 | (R/S)-2-[2-[[1-[3-(Difluoromethyl)-4-fluoro-phenyl]triazol-4-yl]methoxy]pyrimidin-5-yl]-1,1,1-trifluoro-propan-2-ol; |
| 405 | 5-(Difluoromethoxy)-2-[[1-[3-(difluoromethyl)-4-fluoro-phenyl]triazol-4-yl]methoxy]pyrimidine; |
| 406 | 5-Chloro-2-[[1-[3-(difluoromethyl)-4-fluoro-phenyl]triazol-4-yl]methoxy]-4-methyl-pyrimidine; |
| 407 | 2-[[1-[3-(Difluoromethyl)-4-fluoro-phenyl]triazol-4-yl]methoxy]-5-fluoro-4-methyl-pyrimidine; |
| 408 | 2-[[1-[3-(Difluoromethyl)-4-fluoro-phenyl]triazol-4-yl]methoxy]-4,5-dimethyl-pyrimidine; |
| 409 | 2-[[1-[3-(Difluoromethyl)-4-fluoro-phenyl]triazol-4-yl]methoxy]-N-methyl-pyrimidine-5-carboxamide; |
| 410 | 2-[[1-[3-(Difluoromethyl)-4-fluoro-phenyl]triazol-4-yl]methoxy]-N,N-dimethyl-pyrimidine-4-carboxamide; |
| 411 | 2-[[1-[3-(Difluoromethyl)-4-fluoro-phenyl]triazol-4-yl]methoxy]-4-methoxy-5-methyl-pyrimidine; |
| 412 | 2-[[1-[3-(Difluoromethyl)-4-fluoro-phenyl]triazol-4-yl]methoxy]pyrimidin-4-amine; |
| 413 | 2-[[1-[3-(Difluoromethyl)-4-fluoro-phenyl]triazol-4-yl]methoxy]-N-methyl-pyrimidin-4-amine; |
| 414 | 2-[[1-[3-(Difluoromethyl)-4-fluoro-phenyl]triazol-4-yl]methoxy]-5-fluoro-N-methyl-pyrimidin-4-amine; |
| 415 | 2-[[1-[3-(Difluoromethyl)-4-fluoro-phenyl]triazol-4-yl]methoxy]-N,N-dimethyl-pyrimidin-4-amine; |
| 416 | 2-((1-(3-(Difluoromethyl)-4-fluorophenyl)-1H-1,2,3-triazol-4-yl)methoxy)-5-(3-fluoroazetidin-1-yl)pyrimidine; |
| 417 | 5-(Azetidin-1-yl)-2-((1-(3-(difluoromethyl)-4-fluorophenyl)-1H-1,2,3-triazol-4-yl)methoxy)pyrimidine; |
| 418 | 2-((1-(3-(Difluoromethyl)-4-fluorophenyl)-1H-1,2,3-triazol-4-yl)methoxy)-5-(3-methoxyazetidin-1-yl)pyrimidine; |
| 419 | 5-(3,3-Difluoroazetidin-1-yl)-2-((1-(3-(difluoromethyl)-4-fluorophenyl)-1H-1,2,3-triazol-4-yl)methoxy)pyrimidine; |
| 420 | 2-((1-(3-(Difluoromethyl)-4-fluorophenyl)-1H-1,2,3-triazol-4-yl)methoxy)-5-(3-fluoro-3-methylazetidin-1-yl)pyrimidine; |
| 421 | 2-((1-(3-(Difluoromethyl)-4-fluorophenyl)-1H-1,2,3-triazol-4-yl)methoxy)-5-(3-(difluoromethyl)azetidin-1-yl)pyrimidine; |
| 422 | 2-((1-(3-(Difluoromethyl)-4-fluorophenyl)-1H-1,2,3-triazol-4-yl)methoxy)-5-(3,3-difluoropyrrolidin-1-yl)pyrimidine; |
| 423 | 5-Cyclopropyl-2-[[1-[3-(difluoromethyl)-4-fluoro-phenyl]triazol-4-yl]methoxy]pyrimidine; |
| 424 | 2-[[1-[3-(Difluoromethyl)-4-fluoro-phenyl]triazol-4-yl]methoxy]-4-(2-furyl)pyrimidine; |
| 425 | 2-[[1-[3-(Difluoromethyl)-4-fluoro-phenyl]-5-iodo-triazol-4-yl]methoxy]-5-methyl-pyrimidine; |
| 426 | [3H]-2-((1-(3-(Difluoromethyl)-4-fluorophenyl)-1H-1,2,3-triazol-4-yl-5-t)methoxy)-5-methylpyrimidine; |
| 427 | 3-Fluoro-2-[[1-[4-fluoro-3-(trifluoromethyl)phenyl]triazol-4-yl]methoxy]pyridine; |
| 428 | 5-Chloro-2-[[1-[4-fluoro-3-(trifluoromethyl)phenyl]triazol-4-yl]methoxy]pyridine; |
| 429 | 2-[[1-[4-Fluoro-3-(trifluoromethyl)phenyl]triazol-4-yl]methoxy]-4-methyl-pyridine; |
| 430 | 2-[[1-[4-Fluoro-3-(trifluoromethyl)phenyl]triazol-4-yl]methoxy]-6-methyl-pyridine; |
| 431 | 2-[[1-[4-Fluoro-3-(trifluoromethyl)phenyl]triazol-4-yl]methoxy]-5-methyl-pyridine; |
| 432 | 2-[[1-[4-Fluoro-3-(trifluoromethyl)phenyl]triazol-4-yl]methoxy]-5-(trifluoromethyl)pyridine; |
| 433 | 2-[6-[[1-[4-Fluoro-3-(trifluoromethyl)phenyl]triazol-4-yl]methoxy]-3-pyridyl]propan-2-ol; |

| Ex #. | Compound Name |
|---|---|
| 434 | 2-[[1-[4-Fluoro-3-(trifluoromethyl)phenyl]triazol-4-yl]methoxy]pyrazine |
| 435 | 2-[2-[[1-[4-Fluoro-3-(trifluoromethyl)phenyl]triazol-4-yl]methoxy]pyrimidin-5-yl]propan-2-ol; |
| 436 | 2-[[1-[4-Fluoro-3-(trifluoromethyl)phenyl]triazol-4-yl]methoxy]-5-(1-methoxy-1-methyl-ethyl)pyrimidine; |
| 437 | 2-[[1-[4-Fluoro-3-(trifluoromethyl)phenyl]triazol-4-yl]methoxy]-5-(methoxymethyl)pyrimidine; |
| 438 | 2-[[1-[4-Fluoro-3-(trifluoromethyl)phenyl]triazol-4-yl]methoxy]-4-(methoxymethyl)pyrimidine; |
| 439 | 5-(Difluoromethyl)-2-[[1-[4-fluoro-3-(trifluoromethyl)-phenyl]triazol-4-yl]methoxy]pyrimidine; |
| 440 | 4-(Difluoromethyl)-2-[[1-[4-fluoro-3-(trifluoromethyl)-phenyl]triazol-4-yl]methoxy]pyrimidine; |
| 441 | (R/S)-1,1,1-Trifluoro-2-[2-[[1-[4-fluoro-3-(trifluoromethyl)-phenyl]triazol-4-yl]methoxy]pyrimidin-5-yl]propan-2-ol; |
| 442 | 2-[[1-[4-Fluoro-3-(trifluoromethyl)phenyl]triazol-4-yl]methoxy]-4-methoxy-pyrimidine; |
| 443 | 5-Ethoxy-2-[[1-[4-fluoro-3-(trifluoromethyl)phenyl]-triazol-4-yl]methoxy]pyrimidine; |
| 444 | 5-Chloro-2-[[1-[4-fluoro-3-(trifluoromethyl)phenyl]triazol-4-yl]methoxy]-4-methyl-pyrimidine; |
| 445 | 5-Fluoro-2-[[1-[4-fluoro-3-(trifluoromethyl)phenyl]triazol-4-yl]methoxy]-4-methyl-pyrimidine; |
| 446 | 2-[[1-[4-Fluoro-3-(trifluoromethyl)phenyl]triazol-4-yl]methoxy]-4,5-dimethyl-pyrimidine; |
| 447 | 1-[2-[[1-[4-Fluoro-3-(trifluoromethyl)phenyl]triazol-4-yl]methoxy]pyrimidin-5-yl]ethanone; |
| 448 | (R/S)-1-[2-[[1-[4-Fluoro-3-(trifluoromethyl)phenyl]triazol-4-yl]methoxy]pyrimidin-5-yl]ethanol; |
| 449 | 2-[[1-[4-Fluoro-3-(trifluoromethyl)phenyl]triazol-4-yl]methoxy]-N-methyl-pyrimidin-4-amine; |
| 450 | 2-[[1-[4-Fluoro-3-(trifluoromethyl)phenyl]triazol-4-yl]methoxy]-N,N-dimethyl-pyrimidin-4-amine; |
| 451 | 5-Fluoro-2-[[1-[4-fluoro-3-(trifluoromethyl)phenyl]triazol-4-yl]methoxy]-N-methyl-pyrimidin-4-amine; |
| 452 | 2-[[1-[4-Fluoro-3-(trifluoromethyl)phenyl]triazol-4-yl]methoxy]-N-methyl-pyrimidine-5-carboxamide; |
| 453 | 5-Cyclopropyl-2-[[1-[4-fluoro-3-(trifluoromethyl)phenyl]-triazol-4-yl]methoxy]pyrimidine; |
| 454 | 5-Bromo-2-((1-(4-fluoro-3-(trifluoromethyl)phenyl)-1H-1,2,3-triazol-4-yl)methoxy)pyrimidine; |
| 455 | 2-(((1-(4-Fluoro-3-(trifluoromethyl)phenyl)-1H-1,2,3-triazol-4-yl)methoxy)-5-(3-fluoroazetidin-1-yl)pyrimidine; |
| 456 | 4-(2-(((1-(4-Fluoro-3-(trifluoromethyl)phenyl)-1H-1,2,3-triazol-4-yl)methoxy)pyrimidin-5-yl)morpholine; |
| 457 | 5-(Azetidin-1-yl)-2-((1-(3-(trifluoromethyl)-4-fluorophenyl)-1H-1,2,3-triazol-4-yl)methoxy)-4-methylpyrimidine; |
| 458 | 2-((1-(3-(Trifluoromethyl)-4-fluorophenyl)-1H-1,2,3-triazol-4-yl)methoxy)-N-ethyl-4-methylpyrimidin-5-amine; |
| 459 | 2-((1-(3-(Trifluoromethyl)-4-fluorophenyl)-1H-1,2,3-triazol-4-yl)methoxy)-N-ethylpyrimidin-5-amine; |
| 460 | 2-((1-(3-(Trifluoromethyl)-4-fluorophenyl)-1H-1,2,3-triazol-4-yl)methoxy)-5-(3-methoxyazetidin-1-yl)pyrimidine; |
| 461 | 5-Chloro-2-[[1-[2-fluoro-3-(trifluoromethyl)phenyl]triazol-4-yl]methoxy]pyrimidine; |
| 462 | 4-[[1-(4-Fluoro-3-methyl-phenyl)triazol-4-yl]methoxy]-6-methyl-pyrimidine; |
| 463 | 5-Chloro-2-[[1-(3-fluoro-2-methyl-phenyl)triazol-4-yl]methoxy]pyrimidine; |
| 464 | 2-[[1-(3-Fluoro-2-methyl-phenyl)triazol-4-yl]methoxy]-5-methyl-pyrimidine; |
| 465 | 5-Fluoro-2-[[1-(3-fluoro-2-methyl-phenyl)triazol-4-yl]methoxy]-4-methyl-pyrimidine; |
| 466 | 2-[2-[[1-(3-Fluoro-2-methyl-phenyl)triazol-4-yl]methoxy]-pyrimidin-5-yl]propan-2-ol; |
| 467 | 2-[[1-(2-Fluoro-3-methyl-phenyl)triazol-4-yl]methoxy]-5-methyl-pyrimidine; |
| 468 | 5-Chloro-2-[[1-(2-fluoro-3-methyl-phenyl)triazol-4-yl]methoxy]pyrimidine; |
| 469 | 2-[[1-(2-Fluoro-3-methyl-phenyl)triazol-4-yl]methoxy]-5-(trifluoromethyl)pyrimidine; |
| 470 | 5-Chloro-2-[[1-(2-fluoro-3-methyl-phenyl)triazol-4-yl]methoxy]-4-methyl-pyrimidine; |
| 471 | 5-(Difluoromethoxy)-2-[[1-(2-fluoro-3-methyl-phenyl)triazol-4-yl]methoxy]pyrimidine; |
| 472 | 2-[[1-(4-Fluoro-3-methyl-phenyl)triazol-4-yl]methoxy]-pyrimidin-4-amine; |
| 473 | 2-[[1-(4-Fluoro-3-methyl-phenyl)triazol-4-yl]methoxy]-pyrimidine; |
| 474 | 5-Fluoro-2-[[1-(4-fluoro-3-methyl-phenyl)triazol-4-yl]methoxy]pyrimidine; |
| 475 | 2-[[1-(4-Fluoro-3-methyl-phenyl)triazol-4-yl]methoxy]-5-methoxy-pyrimidine; |
| 476 | 5-Chloro-2-[[1-(4-fluoro-3-methyl-phenyl)triazol-4-yl]methoxy]pyrimidine; |
| 477 | 2-[[1-(4-Fluoro-3-methyl-phenyl)triazol-4-yl]methoxy]-5-methyl-pyrimidine; |
| 478 | 5-Ethyl-2-[[1-(4-fluoro-3-methyl-phenyl)triazol-4-yl]methoxy]pyrimidine; |
| 479 | 2-[[1-(4-Fluoro-3-methyl-phenyl)triazol-4-yl]methoxy]-4-(methoxymethyl)pyrimidine; |
| 480 | 2-[[1-(4-Fluoro-3-methyl-phenyl)triazol-4-yl]methoxy]-4,5-dimethyl-pyrimidine; |
| 481 | 5-Fluoro-2-[[1-(4-fluoro-3-methyl-phenyl)triazol-4-yl]methoxy]-4-methyl-pyrimidine; |
| 482 | 5-Chloro-2-[[1-(4-fluoro-3-methyl-phenyl)triazol-4-yl]methoxy]-4-methyl-pyrimidine; |
| 483 | 5-(2-Fluoroethoxy)-2-[[1-(4-fluoro-3-methyl-phenyl)triazol-4-yl]methoxy]pyrimidine; |
| 484 | 2-[[1-(2-Fluoro-5-methyl-phenyl)triazol-4-yl]methoxy]-5-methyl-pyrimidine; |
| 485 | 5-Chloro-2-[[1-(2-fluoro-5-methyl-phenyl)triazol-4-yl]methoxy]-4-methyl-pyrimidine; |
| 486 | 5-Fluoro-2-[[1-(2-fluoro-5-methyl-phenyl)triazol-4-yl]methoxy]-4-methyl-pyrimidine; |
| 487 | 5-Fluoro-2-[[1-(4-fluoro-2-methyl-phenyl)triazol-4-yl]methoxy]pyrimidine; |
| 488 | 2-[[1-(4-Fluoro-2-methyl-phenyl)triazol-4-yl]methoxy]-5-methoxy-pyrimidine; |
| 489 | 5-Chloro-2-[[1-(4-fluoro-2-methyl-phenyl)triazol-4-yl]methoxy]pyrimidine; |
| 490 | 2-[[1-(4-Fluoro-2-methyl-phenyl)triazol-4-yl]methoxy]-5-methyl-pyrimidine; |
| 491 | 5-Ethyl-2-[[1-(4-fluoro-2-methyl-phenyl)triazol-4-yl]methoxy]pyrimidine; |
| 492 | 2-[[1-[3-(Difluoromethoxy)-4-fluoro-phenyl]triazol-4-yl]methoxy]-5-fluoro-pyrimidine; |
| 493 | 2-[[1-[3-(Difluoromethoxy)-4-fluoro-phenyl]triazol-4-yl]methoxy]-5-fluoro-4-methyl-pyrimidine; |
| 494 | 5-Bromo-2-[[1-[3-(difluoromethoxy)-4-fluoro-phenyl]triazol-4-yl]methoxy]pyrimidine; |
| 495 | 2-[[1-[3-(Difluoromethoxy)-4-fluoro-phenyl]triazol-4-yl]methoxy]-4-ethyl-pyrimidine; |
| 496 | 2-[[1-[3-(Difluoromethoxy)-4-fluoro-phenyl]triazol-4-yl]methoxy]-4-isopropyl-pyrimidine; |
| 497 | 2-[[1-[3-(Difluoromethoxy)-4-fluoro-phenyl]triazol-4-yl]methoxy]-4-methoxy-pyrimidine; |
| 498 | [2-[[1-[3-(Difluoromethoxy)-4-fluoro-phenyl]triazol-4-yl]methoxy]pyrimidin-4-yl]methanol; |
| 499 | 2-[[1-[3-(Difluoromethoxy)-4-fluoro-phenyl]triazol-4-yl]methoxy]-4-(methoxymethyl)pyrimidine; |
| 500 | 2-[2-[[1-[3-(Difluoromethoxy)-4-fluoro-phenyl]triazol-4-yl]methoxy]pyrimidin-5-yl]propan-2-ol; |
| 501 | 2-[1-[3-(Difluoromethoxy)-4-fluoro-phenyl]triazol-4-yl]methoxy]pyrimidin-4-amine; |
| 502 | 2-[[1-[3-(Difluoromethoxy)-4-fluoro-phenyl]triazol-4-yl]methoxy]pyrimidin-5-amine; |
| 503 | 2-[[1-[3-(Difluoromethoxy)-4-fluoro-phenyl]triazol-4-yl]methoxy]-N-methyl-pyrimidin-4-amine; |
| 504 | 2-((1-(3-(Difluoromethoxy)-4-fluorophenyl)-1H-1,2,3-triazol-4-yl)methoxy)-N-ethylpyrimidin-4-amine; |
| 505 | 2-[[1-[3-(Difluoromethoxy)-4-fluoro-phenyl]triazol-4-yl]methoxy]-N,N-dimethyl-pyrimidin-4-amine; |
| 506 | 2-[[1-[3-(Difluoromethoxy)-4-fluoro-phenyl]triazol-4-yl]methoxy]-4-phenyl-pyrimidine; |
| 507 | 2-[[1-[3-(Difluoromethoxy)-4-fluoro-phenyl]triazol-4-yl]methoxy]-5-(3-fluoroazetidin-1-yl)pyrimidine; |
| 508 | 5-(3,3-Difluoroazetidin-1-yl)-2-[[1-[3-(difluoromethoxy)-4-fluoro-phenyl]triazol-4-yl]methoxy]pyrimidine; |
| 509 | 4-(Azetidin-1-yl)-2-[[1-[3-(difluoromethoxy)-4-fluoro-phenyl]triazol-4-yl]methoxy]pyrimidine; |

| Ex #. | Compound Name |
|---|---|
| 510 | 2-[[1-[3-(Difluoromethoxy)-4-fluoro-phenyl]triazol-4-yl]methoxy]-4-(3-fluoroazetidin-1-yl)pyrimidine; |
| 511 | 4-(3,3-Difluoroazetidin-1-yl)-2-[[1-[3-(difluoromethoxy)-4-fluoro-phenyl]triazol-4-yl]methoxy]pyrimidine; |
| 512 | (R)-2-[[1-[3-(Difluoromethoxy)-4-fluoro-phenyl]triazol-4-yl]methoxy]-4-[(3R)-3-fluoropyrrolidin-1-yl]pyrimidine; |
| 513 | 5-Chloro-2-[[1-[3-(difluoromethoxy)-4-fluoro-phenyl]-triazol-4-yl]methoxy]-4-methyl-pyrimidine; |
| 514 | 2-[[1-[3-(Difluoromethoxy)-4-fluoro-phenyl]triazol-4-yl]methoxy]-5-methyl-pyrimidin-4-amine; |
| 515 | 2-[[1-[3-(Difluoromethoxy)-4-fluoro-phenyl]triazol-4-yl]methoxy]-N,5-dimethyl-pyrimidin-4-amine; |
| 516 | 2-[[1-[3-(Difluoromethoxy)-4-fluoro-phenyl]triazol-4-yl]methoxy]-N,N,5-trimethyl-pyrimidin-4-amine; |
| 517 | N-(2,2-Difluoroethyl)-2-[[1-[3-(difluoromethoxy)-4-fluoro-phenyl]triazol-4-yl]methoxy]-5-fluoro-pyrimidin-4-amine; |
| 518 | 2-[[1-[3-(Difluoromethoxy)-4-fluoro-phenyl]triazol-4-yl]methoxy]-5-fluoro-N-methyl-pyrimidin-4-amine; |
| 519 | N-Cyclopropyl-2-((1-(3-(difluoromethoxy)-4-fluorophenyl)-1H-1,2,3-triazol-4-yl)methoxy)-5-fluoropyrimidin-4-amine; |
| 520 | 1-(2-((1-(3-(Difluoromethoxy)-4-fluorophenyl)-1H-1,2,3-triazol-4-yl)methoxy)pyrimidin-4-yl)-N-methylmethanamine; |
| 521 | 2-[[1-[3-(Difluoromethoxy)-4-methyl-phenyl]triazol-4-yl]methoxy]-5-methyl-pyrimidin-4-amine; |
| 522 | 1-[2-[[1-[3-(Difluoromethoxy)-4-methyl-phenyl]triazol-4-yl]methoxy]pyrimidin-5-yl]ethanone; |
| 523 | 2-[[1-[3-(Difluoromethoxy)-4-methyl-phenyl]triazol-4-yl]methoxy]-4-methyl-pyrimidine; |
| 524 | 2-[[1-[3-(Difluoromethoxy)-4-methyl-phenyl]triazol-4-yl]methoxy]-5-methyl-pyrimidine; |
| 525 | 5-Bromo-2-[[1-[3-(difluoromethoxy)-4-methyl-phenyl]-triazol-4-yl]methoxy]pyrimidine; |
| 526 | 2-[2-[[1-[3-(Difluoromethoxy)-4-methyl-phenyl]triazol-4-yl]methoxy]pyrimidin-5-yl]propan-2-ol; |
| 527 | 2-[[1-[3-(Difluoromethoxy)-4-methyl-phenyl]triazol-4-yl]methoxy]-4-(methoxymethyl)pyrimidine; |
| 528 | 2-[[1-[3-(Difluoromethyl)phenyl]-5-methyl-triazol-4-yl]methoxy]-4,5-dimethyl-pyrimidine; |
| 529 | 5-Chloro-2-[[1-[3-(difluoromethyl)phenyl]-5-methyl-triazol-4-yl]methoxy]pyrimidine; |
| 530 | 2-[[1-[4-Chloro-3-(1,1-difluoroethyl)phenyl]triazol-4-yl]methoxy]-5-methyl-pyrimidine; |
| 531 | 2-[[1-[4-Chloro-3-(1,1-difluoroethyl)phenyl]triazol-4-yl]methoxy]-4-methyl-pyrimidine; |
| 532 | 2-[2-[[1-[4-Chloro-3-(1,1-difluoroethyl)phenyl]triazol-4-yl]methoxy]pyrimidin-5-yl]propan-2-ol; |
| 533 | [2-[[1-[4-Chloro-3-(1,1-difluoroethyl)phenyl]triazol-4-yl]methoxy]pyrimidin-5-yl]methanol; |
| 534 | 2-[[1-[4-Chloro-3-(1,1-difluoroethyl)phenyl]triazol-4-yl]methoxy]-4-(methoxymethyl)pyrimidine; |
| 535 | 2-[[1-[4-Chloro-3-(1,1-difluoroethyl)phenyl]triazol-4-yl]methoxy]-5-(difluoromethy)pyrimidine; |
| 536 | 2-[[1-[4-Chloro-3-(1,1-difluoroethyl)phenyl]triazol-4-yl]methoxy]-4-(difluoromethy)pyrimidine; |
| 537 | 2-[[1-[4-Chloro-3-(1,1-difluoroethyl)phenyl]triazol-4-yl]methoxy]-5-(trifluoromethyl)pyrimidine; |
| 538 | 2-[[1-[4-Chloro-3-(1,1-difluoroethyl)phenyl]triazol-4-yl]methoxy]-4-(trifluoromethyl)pyrimidine; |
| 539 | (R/S)-2-[2-[[1-[4-Chloro-3-(1,1-difluoroethyl)phenyl]-triazol-4-yl]methoxy]pyrimidin-5-yl]-1,1,1-trifluoro-propan-2-ol; |
| 540 | [2-[[1-[4-Chloro-3-(1,1-difluoroethyl)phenyl]triazol-4-yl]methoxy]pyrimidin-4-yl]methanol; |
| 541 | 2-[[1-[4-Chloro-3-(1,1-difluoroethyl)phenyl]triazol-4-yl]methoxy]-4-methoxy-pyrimidine; |
| 542 | 2-[[1-[4-Chloro-3-(1,1-difluoroethyl)phenyl]triazol-4-yl]methoxy]-5-(difluoromethoxy)pyrimidine; |
| 543 | 5-Chloro-2-[[1-[4-chloro-3-(1,1-difluoroethyl)phenyl]-triazol-4-yl]methoxy]-4-methyl-pyrimidine; |
| 544 | 2-[[1-[4-Chloro-3-(1,1-difluoroethyl)phenyl]triazol-4-yl]methoxy]-5-fluoro-4-methyl-pyrimidine; |
| 545 | 2-[[1-[4-Chloro-3-(1,1-difluoroethyl)phenyl]triazol-4-yl]methoxy]-4,5-dimethyl-pyrimidine; |
| 546 | 2-[[1-[4-Chloro-3-(1,1-difluoroethyl)phenyl]triazol-4-yl]methoxy]-4,6-dimethyl-pyrimidine; |
| 547 | 2-[[1-[4-Chloro-3-(1,1-difluoroethyl)phenyl]triazol-4-yl]methoxy]pyrimidin-4-amine; |
| 548 | 2-[[1-[4-Chloro-3-(1,1-difluoroethyl)phenyl]triazol-4-yl]methoxy]-N-methyl-pyrimidin-4-amine; |
| 549 | 2-[[1-[4-Chloro-3-(1,1-difluoroethyl)phenyl]triazol-4-yl]methoxy]-5-fluoro-N-methyl-pyrimidin-4-amine; |
| 550 | 1-[2-[[1-[4-Chloro-3-(1,1-difluoroethyl)phenyl]triazol-4-yl]methoxy]pyrimidin-5-yl]ethanone; |
| 551 | (R/S)-1-[2-[[1-[4-Chloro-3-(1,1-difluoroethyl)phenyl]-triazol-4-yl]methoxy]pyrimidin-5-yl]ethanol; |
| 552 | 2-[[1-[4-Chloro-3-(1,1-difluoroethyl)phenyl]triazol-4-yl]methoxy]-5-cyclopropyl-pyrimidine; |
| 553 | 2-[[1-[4-Chloro-3-(1,1-difluoroethyl)phenyl]triazol-4-yl]methoxy]-4-pyrrolidin-1-yl-pyrimidine; |
| 554 | 2-[[1-[3-(1,1-Difluoroethyl)-4-fluoro-phenyl]triazol-4-yl]methoxy]pyridine; |
| 555 | 2-[[1-[3-(1,1-Difluoroethyl)-4-fluoro-phenyl]triazol-4-yl]methoxy]-3-fluoro-pyridine; |
| 556 | 2-[[1-[3-(1,1-Difluoroethyl)-4-fluoro-phenyl]triazol-4-yl]methoxy]-6-methyl-pyridine; |
| 557 | 2-[[1-[3-(1,1-Difluoroethyl)-4-fluoro-phenyl]triazol-4-yl]methoxy]-4-methyl-pyridine; |
| 558 | 2-[[1-[3-(1,1-Difluoroethyl)-4-fluoro-phenyl]triazol-4-yl]methoxy]-5-methyl-pyridine; |
| 559 | 2-[[1-[3-(1,1-Difluoroethyl)-4-fluoro-phenyl]triazol-4-yl]methoxy]-5-(trifluoromethyl)pyridine; |
| 560 | 6-[[1-[3-(1,1-Difluoroethyl)-4-fluoro-phenyl]triazol-4-yl]methoxy]-2,3-dimethyl-pyridine; |
| 561 | 3-[[1-[3-(1,1-Difluomethyl)-4-fluoro-phenyl]triazol-4-yl]methoxy]-2-methoxy-pyridine; |
| 562 | 2-[[1-[3-(1,1-Difluoroethyl)-4-fluoro-phenyl]triazol-4-yl]methoxy]-5-(difluoromethyl)pyrimidine; |
| 563 | 2-[[1-[3-(1,1-Difluoroethyl)-4-fluoro-phenyl]triazol-4-yl]methoxy]-4-(difluoromethyl)pyrimidine; |
| 564 | 2-[[1-[3-(1,1-Difluoroethyl)-4-fluoro-phenyl]triazol-4-yl]methoxy]-4-(trifluoromethyl)pyrimidine; |
| 565 | (R/S)-2-[2-[[1-[3-(1,1-Difluoroethyl)-4-fluoro-phenyl]triazol-4-yl]methoxy]pyrimidin-5-yl]-1,1,1-trifluoro-propan-2-ol; |
| 566 | 2-[2-[[1-[3-(1,1-Difluoroethyl)-4-fluoro-phenyl]triazol-4-yl]methoxy]pyrimidin-5-yl]propan-2-ol; |
| 567 | 2-[[1-[3-(1,1-Difluoroethyl)-4-fluoro-phenyl]triazol-4-yl]methoxy]-5-(1-methoxy-1-methyl-ethyl)pyrimidine; |
| 568 | [2-[[1-[3-(1,1-Difluoroethyl)-4-fluoro-phenyl]triazol-4-yl]methoxy]pyrimidin-4-yl]methanol; |
| 569 | 2-[[1-[3-(1,1-Difluoroethyl)-4-fluoro-phenyl]triazol-4-yl]methoxy]-5-(methoxymethyl)pyrimidine; |
| 570 | 2-[[1-[3-(1,1-Difluoroethyl)-4-fluoro-phenyl]triazol-4-yl]methoxy]-4-(methoxymethyl)pyrimidine; |
| 571 | [2-[[1-[3-(1,1-difluoroethyl)-4-fluoro-phenyl]triazol-4-yl]methoxy]pyrimidin-5-yl]methanol; |
| 572 | 2-[[1-[3-(1,1-Difluoroethyl)-4-fluoro-phenyl]triazol-4-yl]methoxy]-5-(difluoromethoxy)pyrimidine; |
| 573 | 2-[[1-[3-(1,1-Difluoroethyl)-4-fluoro-phenyl]triazol-4-yl]methoxy]-4,5-dimethyl-pyrimidine; |
| 574 | 5-Chloro-2-[[1-[3-(1,1-difluoroethyl)-4-fluoro-phenyl]-triazol-4-yl]methoxy]-4-methyl-pyrimidine; |
| 575 | 2-[[1-[3-(1,1-Difluoroethyl)-4-fluoro-phenyl]triazol-4-yl]methoxy]-5-fluoro-4-methyl-pyrimidine; |
| 576 | 2-[[1-[3-(1,1-Difluoroethyl)-4-fluoro-phenyl]triazol-4-yl]methoxy]-5-methyl-pyrimidin-4-amine; |
| 577 | 2-[[1-[3-(1,1-Difluoroethyl)-4-fluoro-phenyl]triazol-4-yl]methoxy]-N,5-dimethyl-pyrimidin-4-amine; |
| 578 | 2-[[1-[3-(1,1-Difluoroethyl)-4-fluoro-phenyl]triazol-4-yl]methoxy]-5-fluoro-N-methyl-pyrimidin-4-amine; |
| 579 | 2-[[1-[3-(1,1-Difluoroethyl)-4-fluoro-phenyl]triazol-4-yl]methoxy]-N,N,5-trimethyl-pyrimidin-4-amine; |
| 580 | 2-[[1-[3-(1,1-Difluoroethyl)-4-fluoro-phenyl]triazol-4-yl]methoxy]pyrimidin-4-amine; |
| 581 | 2-[[1-[3-(1,1-Difluoroethyl)-4-fluoro-phenyl]triazol-4-yl]methoxy]-N-methyl-pyrimidin-4-amine; |
| 582 | 2-[[1-[3-(1,1-Difluoroethyl)-4-fluoro-phenyl]triazol-4-yl]methoxy]-N,N-dimethyl-pyrimidin-4-amine; |
| 583 | 2-[[1-[3-(1,1-Difluoroethyl)-4-fluoro-phenyl]triazol-4-yl]methoxy]pyrimidine-5-carbonitrile; |
| 584 | 2-[[1-[3-(1,1-Difluoroethyl)-4-fluoro-phenyl]triazol-4-yl]methoxy]-5-methylsulfonyl-pyrimidine; |
| 585 | 1-[2-[[1-[3-(1,1-Difluoroethyl)-4-fluoro-phenyl]triazol-4-yl]methoxy]pyrimidin-5-yl]ethanone; |

| Ex #. | Compound Name |
|---|---|
| 586 | (R/S)-1-[2-[[1-[3-(1,1-Difluoroethyl)-4-fluoro-phenyl]triazol-4-yl]methoxy]pyrimidin-5-yl]ethanol; |
| 587 | 5-Cyclopropyl-2-[[1-[3-(1,1-difluoroethyl)-4-fluoro-phenyl]-triazol-4-yl]methoxy]pyrimidine; |
| 588 | 5-(Azetidin-1-yl)-2-[[1-[3-(1,1-difluoroethyl)-4-fluoro-phenyl]-triazol-4-yl]methoxy]pyrimidine; |
| 589 | 2-((1-(3-(1,1-Difluoroethyl)-4-fluorophenyl)-1H-1,2,3-triazol-4-yl)methoxy)-5-(3-fluoroazetidin-1-yl)pyrimidine; |
| 590 | 2-((1-(3-(1,1-Difluoroethyl)-4-fluorophenyl)-1H-1,2,3-triazol-4-yl)methoxy)-N,N-dimethylpyrimidin-5-amine; |
| 591 | 2-[[1-[3-(1,1-Difluoroethyl)-4-fluoro-phenyl]triazol-4-yl]methoxy]-4-pyrrolidin-1-yl-pyrimidine; |
| 592 | 2-[[1-[3-(1,1-Difluoroethyl)-4-fluoro-phenyl]triazol-4-yl]methoxy]-4-(1-piperidyl)pyrimidine; |
| 593 | 2-[[1-[3-(1,1-Difluoroethyl)-4-fluoro-phenyl]-5-methyl-triazol-4-yl]methoxy]-5-ethyl-pyrimidine; |
| 594 | 5-Cyclopropyl-2-[[1-[3-(1,1-difluoroethyl)-4-fluoro-phenyl]-5-methyl-triazol-4-yl]methoxy]pyrimidine; |
| 595 | 2-[[1-[3-(1,1-Difluoroethyl)-4-fluoro-phenyl]-5-methyl-triazol-4-yl]methoxy]-4,5-dimethyl-pyrimidine; |
| 596 | 5-Chloro-2-[[1-[3-(1,1-difluoroethyl)-4-fluoro-phenyl]-5-methyl-triazol-4-yl]methoxy]-4-methyl-pyrimidine; |
| 597 | 2-[[1-(3,4-Difluorophenyl)triazol-4-yl]methoxy]-pyrimidine; |
| 598 | 2-[[1-(3,4-Difluorophenyl)triazol-4-yl]methoxy]-5-fluoro-pyrimidine; |
| 599 | 2-[[1-(3,4-Difluorophenyl)triazol-4-yl]methoxy]-5-methoxy-pyrimidine; |
| 600 | 5-Chloro-2-[[1-(3,4-difluorophenyl)triazol-4-yl]methoxy]-pyrimidine; |
| 601 | 2-[[1-(3,4-Difluorophenyl)triazol-4-yl]methoxy]-5-methyl-pyrimidine; |
| 602 | 2-[[1-(3,4-Difluorophenyl)triazol-4-yl]methoxy]-5-ethyl-pyrimidine; |
| 603 | 2-[[1-(2,5-Difluorophenyl)triazol-4-yl]methoxy]-5-methyl-pyrimidine; |
| 604 | 2-[2-[[1-(2,5-Difluorophenyl)triazol-4-yl]methoxy]-pyrimidin-5-yl]propan-2-ol; |
| 605 | 5-Chloro-2-[[1-(2,3-difluorophenyl)triazol-4-yl]methoxy]-pyrimidine; |
| 606 | 2-[[1-(2,3-Difluorophenyl)triazol-4-yl]methoxy]-5-fluoro-pyrimidine; |
| 607 | 2-[[1-(2,3-Difluorophenyl)triazol-4-yl]methoxy]pyrimidine; |
| 608 | 2-[2-[[1-(2,3-Difluorophenyl)triazol-4-yl]methoxy]-pyrimidin-5-yl]propan-2-ol; |
| 609 | 2-[[1-(2,3-Difluorophenyl)triazol-4-yl]methoxy]-5-fluoro-4-methyl-pyrimidine; |
| 610 | 2-[[1-(3-Chloro-2-fluoro-phenyl)triazol-4-yl]methoxy]-5-methyl-pyrimidine; |
| 611 | 2-[[1-(3-Chloro-2-fluoro-phenyl)triazol-4-yl]methoxy]-pyrimidine; |
| 612 | 5-Chloro-2-[[1-(3-chloro-2-fluoro-phenyl)triazol]-4-yl]methoxy]pyrimidine; |
| 613 | 2-[[1-(3-Chloro-2-fluoro-phenyl)triazol-4-yl]methoxy]-5-fluoro-4-methyl-pyrimidine; |
| 614 | 2-[[1-(3-Chloro-2-fluoro-phenyl)triazol-4-yl]methoxy]-5-fluoro-pyrimidine; |
| 615 | 2-[2-[[1-(3-Chloro-2-fluoro-phenyl)triazol-4-yl]methoxy]-pyrimidin-5-yl]propan-2-ol; |
| 616 | [2-[[1-(3-Bromo-4-fluoro-phenyl)triazol-4-yl]methoxy]-pyrimidin-5-yl]methanol; |
| 617 | [2-[[1-(3-Bromo-4-fluoro-phenyl)triazol-4-yl]methoxy]-pyrimidin-4-yl]methanol; |
| 618 | 2-[[1-(3-Bromo-4-fluoro-phenyl)triazol-4-yl]methoxy]-5-(2-fluoroethoxy)pyrimidine; |
| 619 | 2-[[1-(3-Chloro-4-fluoro-phenyl)triazol-4-yl]methoxy]-pyrimidine; |
| 620 | 2-[[1-(3-Chloro-4-fluoro-phenyl)triazol-4-yl]methoxy]-5-methyl-pyrimidine; |
| 621 | 2-[[1-(3-Chloro-4-fluoro-phenyl)triazol-4-yl]methoxy]-5-ethyl-pyrimidine; |
| 622 | 2-[[1-(3-Chloro-4-fluoro-phenyl)triazol-4-yl]methoxy]-4-(methoxymethyl)pyrimidine; |
| 623 | 2-[[1-[4-Chloro-3-(difluoromethyl)phenyl]triazol-4-yl]methoxy]-4-isopropyl-pyrimidine; |
| 624 | [2-[[1-[4-Chloro-3-(difluoromethyl)phenyl]triazol-4-yl]methoxy]pyrimidin-5-yl]methanol; |
| 625 | [2-[[1-[4-Chloro-3-(difluoromethyl)phenyl]triazol-4-yl]methoxy]pyrimidin-4-yl]methanol; |
| 626 | 2-[2-[[1-[4-Chloro-3-(difluoromethyl)phenyl]triazol-4-yl]methoxy]pyrimidin-5-yl]propan-2-ol; |
| 627 | 2-[[1-[4-Chloro-3-(difluoromethyl)phenyl]triazol-4-yl]methoxy]-4-(methoxymethyl)pyrimidine; |
| 628 | 2-[[1-[4-Chloro-3-(difluoromethyl)phenyl]triazol-4-yl]methoxy]-4-(difluoromethyl)pyrimidine; |
| 629 | 2-[[1-[4-Chloro-3-(difluoromethyl)phenyl]triazol-4-yl]methoxy]-N,N-dimethyl-pyrimidin-4-amine; |
| 630 | 2-[[1-[4-Chloro-3-(difluoromethyl)phenyl]triazol-4-yl]methoxy]-5-cyclopropyl-pyrimidine; |
| 631 | 2-[[1-[4-Chloro-3-(difluoromethyl)phenyl]triazol-4-yl]methoxy]-4-cyclopropyl-pyrimidine; |
| 632 | 2-[[1-[4-chloro-3-(difluoromethyl)phenyl]triazol-4-yl]methoxy]-5-methyl-pyrimidin-4-amine; |
| 633 | 2-[[1-[4-Chloro-3-(difluoromethyl)phenyl]triazol-4-yl]methoxy]-N,N,5-trimethyl-pyrimidin-4-amine; |
| 634 | 2-[[1-[4-Chloro-3-(difluoromethyl)phenyl]triazol-4-yl]methoxy]-4-pyrrolidin-1-yl-pyrimidine; |
| 635 | 2-[[1-[4-Chloro-3-(difluoromethyl)phenyl]triazol-4-yl]methoxy]-4-(1-piperidyl)pyrimidine; |
| 636 | 2-[[1-[4-Chloro-3-(difluoromethyl)phenyl]triazol-4-yl]methoxy]-5-(2-fluoroethoxy)pyrimidine; |
| 637 | 2-[[1-[4-Chloro-3-(difluoromethyl)phenyl]triazol-4-yl]methoxy]-5-(3-fluoropropyl)pyrimidine; |
| 638 | 2-((1-(4-(Azetidin-1-yl)-3-(difluoromethyl)phenyl)-1H-1,2,3-triazol-4-yl)methoxy)-5-methylpyrimidine; |
| 639 | 2-[[1-(2,4-Difluoro-3-methyl-phenyl)triazol-4-yl]methoxy]-5-isopropyl-pyrimidine; |
| 640 | 2-[[1-(2,4-Difluoro-3-methyl-phenyl)triazol-4-yl]methoxy]-4-isopropyl-pyrimidine; |
| 641 | 5-(Difluoromethyl)-2-[[1-(2,4-difluoro-3-methyl-phenyl)triazol-4-yl]methoxy]pyrimidine; |
| 642 | 4-(Difluoromethyl)-2-[[1-(2,4-difluoro-3-methyl-phenyl)triazol-4-yl]methoxy]pyrimidine; |
| 643 | 2-[[1-(2,4-Difluoro-3-methyl-phenyl)triazol-4-yl]methoxy]-5-(trifluoromethyl)pyrimidine; |
| 644 | 2-[2-[[1-(2,4-Difluoro-3-methyl-phenyl)triazol-4-yl]methoxy]pyrimidin-5-yl]propan-2-ol; |
| 645 | 2-[[1-(2,4-Difluoro-3-methyl-phenyl)triazol-4-yl]methoxy]-4-(methoxymethyl)pyrimidine; |
| 646 | 5-(Difluoromethoxy)-2-[[1-(2,4-difluoro-3-methyl-phenyl)triazol-4-yl]methoxy]pyrimidine; |
| 647 | 5-Cyclopropyl-2-[[1-(2,4-difluoro-3-methyl-phenyl)triazol-4-yl]methoxy]pyrimidine; |
| 648 | 4-Cyclopropyl-2-[[1-(2,4-difluoro-3-methyl-phenyl)triazol-4-yl]methoxy]pyrimidine; |
| 649 | 2-[[1-(2,4-Difluoro-3-methyl-phenyl)triazol-4-yl]methoxy]-5-fluoro-4-methyl-pyrimidine; |
| 650 | 5-Chloro-2-[[1-(2,4-difluoro-3-methyl-phenyl)triazol-4-yl]methoxy]-4-methyl-pyrimidine; |
| 651 | 2-[[1-(2,4-Difluoro-3-methyl-phenyl)triazol-4-yl]methoxy]-5-methyl-pyrimidin-4-amine; |
| 652 | 2-[[1-[3-(Difluoromethyl)-2,4-difluoro-phenyl]triazol-4-yl]methoxy]-5-(trifluoromethyl)pyrimidine; |
| 653 | 5-Chloro-2-[[1-(2,4-difluoro-5-methyl-phenyl)triazol-4-yl]methoxy]pyrimidine; |
| 654 | 2-[[1-(2,4-Difluoro-5-methyl-phenyl)triazol-4-yl]methoxy]-5-methyl-pyrimidine; |
| 655 | 2-[[1-(2,4-Difluoro-5-methyl-phenyl)triazol-4-yl]methoxy]-5-ethyl-pyrimidine; |
| 656 | 5-(Difluoromethyl)-2-[[1-(2,4-difluoro-5-methyl-phenyl)triazol-4-yl]methoxy]pyrimidine; |
| 657 | 5-Chloro-2-[[1-(2,4-difluoro-5-methyl-phenyl)triazol-4-yl]methoxy]-4-methyl-pyrimidine; |
| 658 | 5-Cyclopropyl-2-[[1-(2,4-difluoro-5-methyl-phenyl)triazol-4-yl]methoxy]pyrimidine; |
| 659 | 5-Chloro-2-[[1-(6-methyl-2-pyridyl)triazol-4-yl]methoxy]-pyrimidine; |
| 660 | 5-Ethyl-2-[[1-(6-methyl-2-pyridyl)triazol-4-yl]methoxy]-pyrimidine; |
| 661 | 5-Chloro-4-methyl-2-[[1-(6-methyl-2-pyridyl)triazol-4-yl]methoxy]pyrimidine; |

| Ex #. | Compound Name |
|---|---|
| 662 | 5-Methyl-2-[[1-(4-methyl-2-pyridyl)triazol-4-yl]methoxy]-pyrimidine; |
| 663 | 5-Ethyl-2-[[1-(4-methyl-2-pyridyl)triazol-4-yl]methoxy]-pyrimidine; |
| 664 | 5-Ethyl-2-[[1-(2-methyl-4-pyridyl)triazol-4-yl]methoxy]-pyrimidine; |
| 665 | 2-[[1-(2-Bromo-4-pyridyl)triazol-4-yl]methoxy]-5-ethyl-pyrimidine; |
| 666 | 5-Methyl-2-[[1-[2-(trifluoromethyl)-4-pyridyl]triazol-4-yl]methoxy]pyrimidine; |
| 667 | 5-Ethyl-2-[[1-[2-(trifluoromethyl)-4-pyridyl]triazol-4-yl]methoxy]pyrimidine; |
| 668 | 5-Fluoro-4-methyl-2-((1-(5-(trifluoromethyl)thiophen-2-yl)-1H-1,2,3-triazol-4-yl)methoxy)pyrimidine; |
| 669 | 5-Methoxy-2-((1-(5-(trifluoromethyl)thiophen-2-yl)-1H-1,2,3-triazol-4-yl)methoxy)pyrimidine; |
| 670 | 5-(Trifluoromethyl)-2-((1-(5-(trifluoromethyl)thiophen-2-yl)-1H-1,2,3-triazol-4-yl)methoxy)pyrimidine; |
| 671 | 2-((1-(3-(Difluoromethoxy)-4-fluorophenyl)-1H-1,2,3-triazol-4-yl)methoxy)-N-(oxetan-3-yl)pyrimidin-4-amine; |
| 672 | 5-(Azetidin-1-yl)-2-((1-(3-(difluoromethoxy)-4-fluorophenyl)-1H-1,2,3-triazol-4-yl)methoxy)pyridine; |
| 673 | 2-((1-(3-(Difluoromethoxy)-4-fluorophenyl)-1H-1,2,3-triazol-4-yl)methoxy)-5-(3-fluoroazetidin-1-yl)pyridine; |
| 674 | 5-(3,3-Difluoroazetidin-1-yl)-2-((1-(3-(difluoromethoxy)-4-fluorophenyl)-1H-1,2,3-triazol-4-yl)methoxy)pyridine; |
| 675 | 2-(Azetidin-1-yl)-6-((1-(3-(difluoromethoxy)-4-fluorophenyl)-1H-1,2,3-triazol-4-yl)methoxy)pyridine; |
| 676 | 2-((1-(3-(Difluoromethoxy)-4-fluorophenyl)-1H-1,2,3-triazol-4-yl)methoxy)-6-(3-fluoroazetidin-1-yl)pyridine; |
| 677 | 2-(3,3-Difluoroazetidin-1-yl)-6-((1-(3-(difluoromethoxy)-4-fluorophenyl)-1H-1,2,3-triazol-4-yl)methoxy)pyridine; |
| 678 | 4-(Azetidin-1-yl)-2-((1-(3-(difluoromethoxy)-4-fluorophenyl)-1H-1,2,3-triazol-4-yl)methoxy)pyridine; |
| 679 | 2-((1-(3-(Difluoromethoxy)-4-fluorophenyl)-1H-1,2,3-triazol-4-yl)methoxy)-4-(3-fluoroazetidin-1-yl)pyridine; |
| 680 | 4-(3,3-Difluoroazetidin-1-yl)-2-((1-(3-(difluoromethoxy)-4-fluorophenyl)-1H-1,2,3-triazol-4-yl)methoxy)pyridine; |
| 681 | 2-((1-(3-(Difluoromethoxy)-4-fluorophenyl)-1H-1,2,3-triazol-4-yl)methoxy)-4-(1H-pyrrol-2-yl)pyrimidine; |
| 682 | 2-((1-(3-(Difluoromethoxy)-4-fluorophenyl)-1H-1,2,3-triazol-4-yl)methoxy)-4-(1H-pyrazol-5-yl)pyrimidine; |
| 683 | 2-((1-(3-(Difluoromethoxy)-4-fluorophenyl)-1H-1,2,3-triazol-4-yl)methoxy)-5-(1H-pyrrol-2-yl)pyrimidine; |
| 684 | 2-((1-(3-(Difluoromethoxy)-4-fluorophenyl)-1H-1,2,3-triazol-4-yl)methoxy)-5-(1H-pyrazol-5-yl)pyrimidine; |
| 685 | 2-((1-(3-(Difluoromethoxy)-4-fluorophenyl)-1H-1,2,3-triazol-4-yl)methoxy)-N-ethyl-5-fluoropyrimidin-4-amine; |
| 686 | 2-((1-(3-(Difluoromethoxy)-4-fluorophenyl)-1H-1,2,3-triazol-4-yl)methoxy)-5-fluoro-N-(oxetan-3-yl)pyrimidin-4-amine; |
| 687 | N-(3,3-Difluorocyclobutyl)-2-((1-(3-(difluoromethoxy)-4-fluorophenyl)-1H-1,2,3-triazol-4-yl)methoxy)-5-fluoropyrimidin-4-amine; |
| 688 | N-Cyclopropyl-2-((1-(3-(difluoromethoxy)-4-fluorophenyl)-1H-1,2,3-triazol-4-yl)methoxy)pyrimidin-4-amine; |
| 689 | N-(3,3-Difluorocyclobutyl)-2-((1-(3-(difluoromethoxy)-4-fluorophenyl)-1H-1,2,3-triazol-4-yl)methoxy)pyrimidin-4-amine; |
| 690 | N-Cyclopropyl-2-((1-(3-(difluoromethyl)-4-fluorophenyl)-1H-1,2,3-triazol-4-yl)methoxy)pyrimidin-4-amine; |
| 691 | N-Ethyl-2-((1-(3-(difluoromethyl)-4-fluorophenyl)-1H-1,2,3-triazol-4-yl)methoxy)pyrimidin-4-amine; |
| 692 | 2-((1-(3-(Difluoromethyl)-4-fluorophenyl)-1H-1,2,3-triazol-4-yl)methoxy)-4-(2-methyl-1H-imidazol-1-yl)pyrimidine; |
| 693 | 2-((1-(3-(Difluoromethyl)-4-fluorophenyl)-1H-1,2,3-triazol-4-yl)methoxy)-5-(2-methyl-1H-imidazol-1-yl)pyrimidine; |
| 694 | 2-((1-(3-(Difluoromethyl)-4-fluorophenyl)-1H-1,2,3-triazol-4-yl)methoxy)-5-(1H-pyrazol-5-yl)pyrimidine; |
| 695 | 2-((1-(3-(Difluoromethyl)-4-fluorophenyl)-1H-1,2,3-triazol-4-yl)methoxy)-4-(1H-pyrazol-5-yl)pyrimidine; |
| 696 | 4-(1,1-Difluoroethyl)-2-((1-(3-(difluoromethyl)-4-fluorophenyl)-1H-1,2,3-triazol-4-yl)methoxy)pyrimidine; |
| 697 | 4-((Difluoromethoxy)methyl)-2-((1-(3-(difluoromethyl)-4-fluorophenyl)-1H-1,2,3-triazol-4-yl)methoxy)pyrimidine; |
| 698 | 2-((1-(3-(Difluoromethyl)-4-fluorophenyl)-1H-1,2,3-triazol-4-yl)methoxy)-5-(1H-pyrazol-1-yl)pyrimidine; |
| 699 | 2-((1-(3-(Difluoromethyl)-4-fluorophenyl)-1H-1,2,3-triazol-4-yl)methoxy)-4-(1H-pyrazol-1-yl)pyrimidine; |
| 700 | (E)-1-(2-((1-(3-(Difluoromethyl)-4-fluorophenyl)-1H-1,2,3-triazol-4-yl)methoxy)pyrimidin-5-yl)ethan-1-one oxime; |
| 701 | 5-(1,1-Difluoroethyl)-2-((1-(3-(difluoromethyl)-4-fluorophenyl)-1H-1,2,3-triazol-4-yl)methoxy)pyrimidine; |
| 702 | (Z)-1-(2-((1-(3-(Difluoromethyl)-4-fluorophenyl)-1H-1,2,3-triazol-4-yl)methoxy)pyrimidin-4-yl)ethan-1-one oxime; |
| 703 | (2-((1-(3-(Difluoromethoxy)-4-fluorophenyl)-1H-1,2,3-triazol-4-yl)methoxy)-5-fluoropyrimidin-4-yl)methanol; |
| 704 | 2-((1-(3-(Difluoromethoxy)-4-fluorophenyl)-1H-1,2,3-triazol-4-yl)methoxy)-4-((difluoromethoxy)methyl)-5-fluoropyrimidine; |
| 705 | 2-((1-(3-(Difluoromethoxy)-4-fluorophenyl)-1H-1,2,3-triazol-4-yl)methoxy)-4-((difluoromethoxy)methyl)pyrimidine; |
| 706 | 2-((1-(3-(Difluoromethoxy)-4-fluorophenyl)-1H-1,2,3-triazol-4-yl)methoxy)-5-fluoro-4-((trifluoromethoxy)methyl)pyrimidine; |
| 707 | 2-((1-(3-(Difluoromethoxy)-4-fluorophenyl)-1H-1,2,3-triazol-4-yl)methoxy)-4-((trifluoromethoxy)methyl)pyrimidine; |
| 708 | 2-((1-(3-(Difluoromethoxy)-4-fluorophenyl)-1H-1,2,3-triazol-4-yl)methoxy)-4-(methoxymethyl-d2)pyrimidine; |
| 709 | 2-((1-(3-(Difluoromethoxy)-4-fluorophenyl)-1H-1,2,3-triazol-4-yl)methoxy)-4-((methoxy-d3)methyl-d2)pyrimidine; |
| 710 | 2-((1-(3-(Difluoromethoxy)-4-fluorophenyl)-1H-1,2,3-triazol-4-yl)methoxy)-4-((methoxy-d3)methyl)pyrimidine; |
| 711 | 2-((1-(3-(Difluoromethoxy)-4-fluorophenyl)-1H-1,2,3-triazol-4-yl)methoxy)-4-(ethoxymethyl)pyrimidine; |
| 712 | 2-((1-(3-(Difluoromethoxy)-4-fluorophenyl)-1H-1,2,3-triazol-4-yl)methoxy)-4-(1-methoxyethyl)pyrimidine; |
| 713 | 1-(2-((1-(3-(Difluoromethoxy)-4-fluorophenyl)-1H-1,2,3-triazol-4-yl)methoxy)pyrimidin-4-yl)ethan-1-ol; |
| 714 | 2-((1-(3-(Difluoromethoxy)-4-fluorophenyl)-1H-1,2,3-triazol-4-yl)methoxy)-4-(2-methoxypropan-2-yl)pyrimidine; |
| 715 | 2-(2-((1-(3-(Difluoromethoxy)-4-fluorophenyl)-1H-1,2,3-triazol-4-yl)methoxy)pyrimidin-4-yl)propan-2-ol; |
| 716 | 4-((2,2-Difluoroethoxy)methyl)-2-((1-(3-(difluoromethoxy)-4-fluorophenyl)-1H-1,2,3-triazol-4-yl)methoxy)pyrimidine; | and pharmaceutically acceptable salts thereof.

A further embodiment of the current invention is a compound as shown below in Table 2.

| Ex # | Compound Name |
|---|---|
| 2 | N-[[1-[4-Chloro-3-(difluoromethoxy)phenyl]triazol-4-yl]methyl]pyridin-2-amine; |
| 3 | N-[[1-[4-Fluoro-3-(trifluoromethyl)phenyl]triazol-4-yl]meth]pyrimidin-2-amine; |
| 6 | N-((1-(3-(Difluoromethyl)phenyl)-1H-1,2,3-triazol-4-yl)methyl)pyrimidin-2-amine; |
| 7 | N-[[1-[3-(Difluoromethoxy)-4-fluoro-phenyl]triazol-4-yl]methyl]-1-methyl-imidazol-2-amine; |
| 24 | N-[[1-[3-(Difluoromethyl)-4-fluoro-phenyl]triazol-4-yl]methyl]pyrimidin-2-amine; |
| 36 | N-[[1-[3-(Difluoromethoxy)-4-fluoro-phenyl]triazol-4-yl]methyl]pyrimidin-2-amine; |
| 97 | N-[[1-[4-Chloro-3-(difluoromethoxy)phenyl]triazol-4-yl]methyl]oxazol-2-amine; |
| 98 | N-[[1-[4-Chloro-3-(difluoromethoxy)phenyl]triazol-4-yl]methyl]pyrimdin-2-amine; |
| 99 | N-[[1[3-(Difluoromethyl)-4-fluoro-phenyl]triazol-4-yl]methyl]-1-methyl-pyrazo-4-amine, |
| 100 | N-[[1-[3-(Difluoromethyl)-4-fluoro-phenyl]triazol-4-yl]methyl]-1-methyl-pyrazol-3-amine; |
| 101 | N-[[1-[3-(Difluoromethoxy)-4-fluoro-phenyl]trazol-4-yl]methyl]-1-methyl-pyrazol-3-amine; |
| 102 | N-[[1-[3-(Difluoromethoxy)-4-fluoro-phenyl]triazol-4-yl]methyl]-1-methyl-pyrazol-4-amine; |
| 109 | N-[[1-[4-Chloro-3-(difluoromethyl)phenyl]triazol-4-yl]methyl]pyrimidin-2-amine; |
| 110 | N-[[1-[4-Chloro-3-(difluoromethyl)phenyl]triazol-4-yl]methyl]pyrimidin-4-amine; |
| 144 | N-((1-(4-Chloro-3-(difluoromethoxy)phenyl)-1H-1,2,3-triazol-4-yl)methyl)-5-methylpyrimidin-2-amine; |

| Ex # | Compound Name |
|---|---|
| 145 | N-((1-(4-Chloro-3-(difluoromethoxy)phenyl)-1H-1,2,3-triazol-4-yl)methyl)-4,5-dimethylpyrimidin-2-amine; |
| 153 | 5-Chloro-N-[[1-[3-(difluoromethyl)phenyl]triazol-4-yl]methyl]pyrimidin-2-amine; |
| 154 | N-[[1-[4-Chloro-3-(difluoromethyl)phenyl]triazol-4-yl]methyl]-5-methyl-pyrimidin-2-amine; |
| 197 | N-[[1-[3-(Difluoromethyl)phenyl]triazol-4-yl]methyl]-5-fluoro-pyrimidin-2-amine; |
| 198 | N-[[1-(4-Fluoro-3-methyl-phenyl)triazol-4-yl]methyl]-5-methyl-pyrimidin-2-amine; |
| 199 | 5-Chloro-N-[[1-(4-fluoro-3-methyl-phenyl)triazol-4-yl]methyl]-4-methyl-pyrimidin-2-amine; |
| 200 | 5-Chloro-N-[[1-[4-chloro-3-(difluoromethyl)phenyl]triazol-4-yl]methyl]pyrimidin-2-amine; |
| 201 | N-[[1-[4-Chloro-3-(difluoromethyl)phenyl]triazol-4-yl]methyl]-4-methyl-pyrimidin-2-amine; |
| 202 | N-[[1-[4-Chloro-3-(difluoromethyl)phenyl]triazol-4-yl]methyl]-5-ethyl-pyrimidin-2-amine; |
| 203 | N-[[1-[4-Chloro-3-(difluoromethyl)phenyl]triazol-4-yl]methyl]-5-methoxy-pyrimidin-2-amine; |
| 204 | N-[[1-[4-Chloro-3-(difluoromethy)phenyl]triazol-4-yl]methyl]-5-(difluoromethyl)pyrimidin-2-amine; |
| 205 | N-[[1-[4-Chloro-3-(difluoromethyl)phenyl]triazol-4-yl]methyl]-5-(trifluoromethyl)pyrimidin-2-amine; |
| 206 | N-[[1-[3-(1,1-Difluoroethyl)-4-fluoro-phenyl]triazol-4-yl]methyl]-5-methyl-pyrimidin-2-amine; |
| 207 | N-[[1-[3-(1,1-Difluoroethyl)-4-fluoro-phenyl]triazol-4-yl]methyl]-5-ethyl-pyrimidin-2-amine; |
| 208 | N-[[1-[3-(1,1-Difluoroethyl)-4-fluoro-phenyl]triazol-4-yl]methyl]-5-isopropyl-pyrimidin-2-amine; |
| 209 | 5-Cyclopropyl-N-[[1-[3-(1,1-difluoroethyl)-4-fluoro-phenyl]triazol-4-yl]methyl]pyrimidin-2-amine; |
| 210 | N-[[1-[3-(1,1-Difluoroethyl)-4-fluoro-phenyl]triazol-4-yl]methyl]-4,5-dimethyl-pyrimidin-2-amine; |
| 211 | N-[[1-[3-(Difluoromethyl)-4-fluoro-phenyl]triazol-4-yl]methyl]-5-methyl-pyrimidin-2-amine; |
| 212 | 5-Chloro-N-[[1-[3-(difluoromethyl)-4-fluoro-phenyl]triazol-4-yl]methyl]pyrimidin-2-amine; |
| 213 | N-[[1-[3-(Difluoromethyl)-4-fluoro-phenyl]triazol-4-yl]methyl]-5-(trifluoromethyl)pyrimidin-2-amine; |
| 214 | 2-[2-[[1-[3-(Difluoromethyl)-4-fluoro-phenyl]triazol-4-yl]methylamino]pyrimidin-5-yl]propan-2-ol; |
| 215 | N-((1-(3-(Difluoromethyl)-4-fluorophenyl)-1H-1,2,3-triazol-4-yl)methyl)pyridin-2-amine; |
| 216 | N-((1-(3-(Difluoromethyl)-4-fluorophenyl)-1H-1,2,3-triazol-4-yl)methyl)-5-ethylpyrimidin-2-amine; |
| 217 | N-((1-(3-(Difluoromethyl)-4-fluorophenyl)-1H-1,2,3-triazol-4-yl)methyl)-4,5-dimethylpyrimidin-2-amine; |
| 218 | 5-Chloro-N-((1-(3-(difluoromethyl)-4-fluorophenyl)-1H-1,2,3-triazol-4-yl)methyl)-4-methylpyrimidin-2-amine; |
| 219 | N-((1-(3-(Difluoromethyl)-4-fluorophenyl)-1H-1,2,3-triazol-4-yl)methyl)-1-methyl-1H-pyrazol-5-amine; |
| 220 | N-((1-(3-(Difluoromethyl)-4-fluorophenyl)-1H-1,2,3-triazol-4-yl)methyl)-1-methyl-1H-imidazol-2-amine; |
| 221 | N-((1-(3-(Difluoromethoxy)-4-fluorophenyl)-1H-1,2,3-triazol-4-yl)methyl)pyridin-2-amine; |
| 222 | N-((1-(3-(Difluoromethoxy)-4-fluorophenyl)-1H-1,2,3-triazol-4-yl)methyl)-5-methylpyrimidin-2-amine; |
| 223 | N-((1-(3-(Difluoromethoxy)-4-fluorophenyl)-1H-1,2,3-triazol-4-yl)methyl)-1-methyl-1H-pyrazol-5-amine; and |
| 224 | N-[(1R)-1-[1-[4-Chloro-3-(difluoromethoxy)phenyl]triazol-4-yl]ethyl]-5-methyl-pyrimidin-2-amine; | and pharmaceutically acceptable salts thereof.

A further embodiment of the current invention is a compound as shown below in Table 3.

| Compound Name |
|---|
| 2-[[1-[4-Chloro-3-(difluoromethoxy)phenyl]triazol-4-yl]methoxy]-5-methoxy-pyrimidine; |
| 2-[[1-[3-(Difluoromethyl)-4-fluoro-phenyl]triazol-4-yl]methoxy]-5-methyl-pyrimidine; |
| 2-[[1-[3-(Difluoromethoxy)-4-fluoro-phenyl]triazol-4-yl]methoxy]-5-methyl-pyrimidine; |
| 2-[[1-[4-Chloro-3-(difluoromethyl)phenyl]triazol-4-yl]methoxy]-4,5-dimethyl-pyrimidine; |
| 2-[[1-[4-Chloro-3-(difluoromethoxy)phenyl]triazol-4-yl]methoxy]-5-(2-fluoroethoxy)pyrimidine; |
| 2-[[1-[4-Chloro-3-(2-fluoroethoxy)phenyl]triazol-4-yl]methoxy]-5-methoxy-pyrimidine; |
| 2-[[1-[3-(3-Chloropropyl)-4-fluoro-phenyl]triazol-4-yl]methoxy]-5-methoxy-pyrimidine; |
| 2-[[1-[4-Chloro-3-(difluoromethoxy)phenyl]triazol-4-yl]methoxy]-5-(3-fluoropropyl)pyrimidine; |
| [2-[[1-[4-Chloro-3-(difluoromethoxy)phenyl]triazol-4-yl]methoxy]pyrimidin-4-yl]methanol; |
| 2-[[1-[4-Chloro-3-(difluoromethoxy)phenyl]triazol-4-yl]methoxy]-4-(methoxymethyl)pyrimidine; |
| 5-Chloro-2-[[1-[3-(difluoromethyl)-4-fluoro-phenyl]triazol-4-yl]methoxy]-4-methyl-pyrimidine; |
| [2-[[1-[3-(Difluoromethoxy)-4-fluoro-phenyl]triazol-4-yl]methoxy]pyrimidin-4-yl]methanol; |
| 2-[[1-[3-(Difluoromethoxy)-4-fluoro-phenyl]triazol-4-yl]methoxy]-4-(methoxymethyl)pyrimidine; |
| 2-[2-[[1-[4-Chloro-3-(1,1-difluoroethyl)phenyl]triazol-4-yl]methoxy]pyrimidin-5-yl]propan-2-ol; |
| 5-(Azetidin-1-yl)-2[[1-[3-(1,1-difluoroethyl)-4-fluoro-phenyl]triazol-4-yl]methoxy]pyrimidine; and |
| 5-Fluoro-4-methyl-2-((1-(5-(trifluoromethyl)thiophen-2-yl)-1H-1,2,3-triazol-4-yl)methoxy)pyrimidine; | and pharmaceutically acceptable salts thereof.

An additional embodiment of the invention is a pharmaceutical composition comprising:

(A) an effective amount of at least one compound selected from compounds of Formula (I):

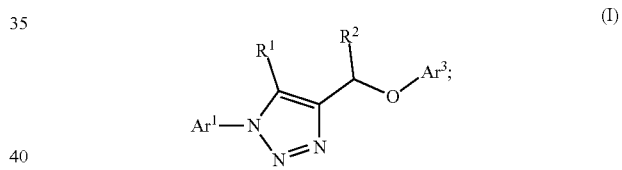

wherein:

$Ar^1$ is selected from the group consisting of:
- (a) phenyl substituted with one substituent selected from the group consisting of: halo, $C_{1-6}$alkyl, $C_{1-6}$perhaloalkyl, and $OC_{1-6}$perhaloalkyl; phenyl substituted with two or three substituents each independently selected from the group consisting of: halo, $C_{1-6}$alkyl, $C_{1-6}$perhaloalkyl, $OC_{1-6}$alkyl, $OC_{1-6}$perhaloalkyl, $C_{3-6}$cycloalkyl, and azetidinyl;
- (b) pyridinyl; pyridinyl substituted with one or two members each independently selected from the group consisting of: halo, $CH_3$, $CF_3$, and $CF_2H$; and
- (c) thienyl substituted with $CF_3$; 1-(2,2-difluorobenzo[d][1,3]dioxol-5-yl; or 2,3-dihydro-1H-inden-5-yl;

$R^1$ is H, halo, or $CH_3$;
$R^2$ is H or $CH_3$; and
$Ar^3$ is selected from the group consisting of:
- (a) pyridinyl; pyridinyl substituted with one or two substituents each independently selected from the group consisting of: Cl, F, $CH_3$, $OCH_3$, $CF_3$, $C(CH_3)_2OH$; azetidin-1-yl; 3-fluoroazetidin-1-yl; and 3,3-difluoroazetidin-1-yl;
- (b) pyridazinyl; pyridazinyl substituted with one or two substituents each independently selected from the group consisting of: $CH_3$, $OCH_3$, and $CF_3$;

(c) pyrimidin-4-yl; pyrimidin-4-yl substituted with one or two substituents each independently selected from the group consisting of: Cl, CH₃, CF₃, and OCH₃; pyrimidin-2-yl; pyrimidin-2-yl substituted one or two members each independently selected from the group consisting of: halo, $C_{1-6}$alkyl, $C_{1-6}$alkyl substituted with OH or OCH₃, C(OH)(CH₃)(CF₃), CH₂OCHF₂, CH₂OCF₃, CH₂OCH₂CH₃, CH(NH₂)CH₃, CH₂NH(CH₃), $C_{1-6}$perhaloalkyl, O$C_{1-6}$alkyl, O$C_{1-6}$perhaloalkyl, C(=N—OH)(CH₃), NH₂, NH(CH₃), N(CH₃)₂; NH(CH₂CH₃), NH(CH₂CHF₂), NH(cyclopropyl), NH(difluorocyclobutyl), NH-oxetanyl, CN, C(=O)CH₃, C(=O)NH(CH₃), C(=O)N(CH₃)₂, SO₂CH₃, CO₂CH₃, C(CH₃)(=N—OH), cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholinyl, 1H-pyrrol-2-yl, 2-furyl, 1H-pyrazol-4-yl, 1H-pyrazol-5-yl, 1H-pyrazol-1-yl, 2-methyl-1H-imidazol-1-yl, 1-methylpyrazol-3-yl, and phenyl;

(d) 5-fluoro-pyrazin-2-yl; 5-methylpyrazin-2-yl; 6-methylpyrazin-2-yl; pyrazin-4-yl; (2-thienyl)pyrazin-2-yl, and 2,3-dimethylpyrazin-5-yl; and (e) 5-methyl-1H-imidazol-2-yl; 5-methylthiazol-2-yl;

and pharmaceutically acceptable salts of compounds of Formula (I);

and (B) at least one pharmaceutically acceptable excipient.

An additional embodiment of the invention is a pharmaceutical composition comprising:

(A) an effective amount of at least one compound selected from compounds of Formula (II):

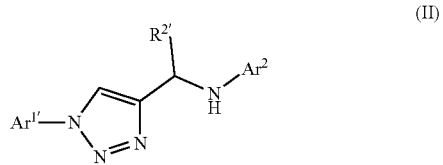

(II)

wherein:

$Ar^{1'}$ is phenyl substituted with $C_{1-6}$perhaloalkyl; or phenyl substituted with two substituents each independently selected from the group consisting of: halo, $C_{1-3}$alkyl, $C_{1-3}$perhaloalkyl, and O$C_{1-3}$perhaloalkyl;

$R^2$ is H or CH₃; and $Ar^2$ is selected from the group consisting of:

(a) pyridin-2-yl; pyridazin-3-yl; pyrimidin-4-yl; pyrimidin-2-yl; or pyrimidin-2-yl substituted with one or two substituents each independently selected from the group consisting of halo, $C_{1-3}$alkyl, C(CH₃)₂OH, $C_{1-3}$perhaloalkyl, OCH₃, and cyclopropyl; and (b) 1-methyl-imidazol-2-yl; oxazol-2-yl; 1-methyl-pyrazol-4-yl; 1-methyl-pyrazol-3-yl; or 1-methyl-1H-pyrazol-5-yl;

and pharmaceutically acceptable salts of compounds of Formula (II);

and (B) at least one pharmaceutically acceptable excipient.

An additional embodiment of the invention is a pharmaceutical composition comprising and effective amount of at least one compound of Formula (IA) (as well as Formulas (IB), (IC), and (ID)), as well as pharmaceutically acceptable salts, N-oxides or solvates of compounds of Formula (IA) (as well as Formulas (IB), (IC), and (ID)), pharmaceutically acceptable prodrugs of compounds of Formula (IA) (as well as Formulas (IB), (IC), and (ID)), and pharmaceutically active metabolites of Formula (IA) (as well as Formulas (IB), (IC), and (ID)); and at least one pharmaceutically acceptable excipient.

An additional embodiment of the invention is a pharmaceutical composition comprising and effective amount of at least one compound of Formula (IIA) (as well as Formula (IIB)), as well as pharmaceutically acceptable salts, N-oxides or solvates of compounds of Formula (IIA) (as well as Formula (IIB)), pharmaceutically acceptable prodrugs of compounds of Formula (IIA) (as well as Formula (IIB)), and pharmaceutically active metabolites of Formula (IIA) (as well as Formula (IIB)); and at least one pharmaceutically acceptable excipient.

An additional embodiment of the invention is a pharmaceutical composition comprising and effective amount of at least one compound in Table 1 (as well Table 2 and Table 3), as well as pharmaceutically acceptable salts, N-oxides or solvates of compounds of Table 1 (as well Table 2 and Table 3), pharmaceutically acceptable prodrugs of compounds of Table 1 (as well Table 2 and Table 3), and pharmaceutically active metabolites of Table 1 (as well Table 2 and Table 3); and at least one pharmaceutically acceptable excipient.

Also within the scope of the invention are enantiomers and diastereomers of the compounds of Formula (I) (as well as Formulas (IA), (IB), (IC), and (ID)). Also within the scope of the invention are the pharmaceutically acceptable salts, N-oxides or solvates of compounds of Formula (I) (as well as Formulas (IA), (IB), (IC), and (ID)). Also within the scope of the invention are the pharmaceutically acceptable prodrugs of compounds of Formula (I) (as well as Formulas (IA), (IB), (IC), and (ID)), and pharmaceutically active metabolites of the compounds of Formula (I) (as well as Formulas (IA), (IB), (IC), and (ID)).

Also within the scope of the invention are enantiomers and diastereomers of the compounds of Formula (II) (as well as Formulas (IIA) and (IB)). Also within the scope of the invention are the pharmaceutically acceptable salts, N-oxides or solvates of compounds of Formula (II) (as well as Formulas (IIA) and (IB)). Also within the scope of the invention are the pharmaceutically acceptable prodrugs of compounds of Formula (II) (as well as Formulas (IIA) and (IB)), and pharmaceutically active metabolites of the compounds of Formula (II) (as well as Formulas (IIA) and (IB)).

Also within the scope of the invention are isotopic variations of compounds of Formula (I) (as well as Formulas (IA), (IB), (IC), and (ID)), such as, e.g., deuterated compounds of Formula (I). Also within the scope of the invention are the pharmaceutically acceptable salts, N-oxides or solvates of the isotopic variations of the compounds of Formula (I) (as well as Formulas (IA), (IB), (IC), and (ID)). Also within the scope of the invention are the pharmaceutically acceptable prodrugs of the isotopic variations of the compounds of Formula (I) (as well as Formulas (IA), (IB), (IC), and (ID)), and pharmaceutically active metabolites of the isotopic variations of the compounds of Formula (I) (as well as Formulas (IA), (IB), (IC), and (ID)).

Also within the scope of the invention are isotopic variations of compounds of Formula (II) (as well as Formulas (IIA) and (IB)), such as, e.g., deuterated compounds of Formula (II). Also within the scope of the invention are the pharmaceutically acceptable salts, N-oxides or solvates of the isotopic variations of the compounds of Formula (II) (as well as Formulas (IIA) and (IB)). Also within the scope of the invention are the pharmaceutically acceptable prodrugs of the isotopic variations of the compounds of Formula (II) (as well as Formulas (IIA) and (IB)), and pharmaceutically active metabolites of the isotopic variations of the compounds of Formula (II) (as well as Formulas (IIA) and (IB)).

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I):

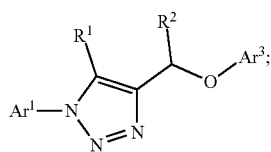

(I)

wherein:
Ar$^1$ is selected from the group consisting of:
  (a) phenyl substituted with one substituent selected from the group consisting of: halo, C$_{1-6}$alkyl, C$_{1-6}$perhaloalkyl, and OC$_{1-6}$perhaloalkyl; phenyl substituted with two or three substituents each independently selected from the group consisting of: halo, C$_{1-6}$alkyl, C$_{1-6}$perhaloalkyl, OC$_{1-6}$alkyl, OC$_{1-6}$perhaloalkyl, C$_{3-6}$-cycloalkyl, and azetidinyl;
  (b) pyridinyl; pyridinyl substituted with one or two members each independently selected from the group consisting of: halo, CH$_3$, CF$_3$, and CF$_2$H; and
  (c) thienyl substituted with CF$_3$; 1-(2,2-difluorobenzo[d][1,3]dioxol-5-yl; or 2,3-dihydro-1H-inden-5-yl;
R$^1$ is H, halo, or CH$_3$;
R$^2$ is H or CH$_3$; and
Ar$^3$ is selected from the group consisting of:
  (a) pyridinyl; pyridinyl substituted with one or two substituents each independently selected from the group consisting of: Cl, F, CH$_3$, OCH$_3$, CF$_3$, C(CH$_3$)$_2$OH; azetidin-1-yl; 3-fluoroazetidin-1-yl; and 3,3-difluoroazetidin-1-yl;
  (b) pyridazinyl; pyridazinyl substituted with one or two substituents each independently selected from the group consisting of: CH$_3$, OCH$_3$, and CF$_3$;
  (c) pyrimidin-4-yl; pyrimidin-4-yl substituted with one or two substituents each independently selected from the group consisting of: Cl, CH$_3$, CF$_3$, and OCH$_3$; pyrimidin-2-yl; pyrimidin-2-yl substituted one or two members each independently selected from the group consisting of: halo, C$_{1-6}$alkyl, C$_{1-6}$alkyl substituted with OH or OCH$_3$, C(OH)(CH$_3$)(CF$_3$), CH$_2$OCHF$_2$, CH$_2$OCF$_3$, CH$_2$OCH$_2$CH$_3$, CH(NH$_2$)CH$_3$, CH$_2$NH (CH$_3$), C$_{1-6}$perhaloalkyl, OC$_{1-6}$alkyl, OC$_{1-6}$perhaloalkyl, C(=N—OH)(CH$_3$), NH$_2$, NH(CH$_3$), N (CH$_3$)$_2$; NH(CH$_2$CH$_3$), NH(CH$_2$CHF$_2$), NH(cyclopropyl), NH(difluorocyclobutyl), NH-oxetanyl, CN, C(=O)CH$_3$, C(=O)NH(CH$_3$), C(=O)N(CH$_3$)$_2$, SO$_2$CH$_3$, CO$_2$CH$_3$, C(CH$_3$)(=N—OH), cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholinyl, 1H-pyrrol-2-yl, 2-furyl, 1H-pyrazol-4-yl, 1H-pyrazol-5-yl, 1H-pyrazol-1-yl, 2-methyl-1H-imidazol-1-yl, 1-methylpyrazol-3-yl, and phenyl;
  (d) 5-fluoro-pyrazin-2-yl; 5-methylpyrazin-2-yl; 6-methylpyrazin-2-yl; pyrazin-4-yl; (2-thienyl)pyrazin-2-yl, and 2,3-dimethylpyrazin-5-yl; and
  (e) 5-methyl-1H-imidazol-2-yl; 5-methylthiazol-2-yl;
and pharmaceutically acceptable salts thereof, to a subject in need thereof.

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (II):

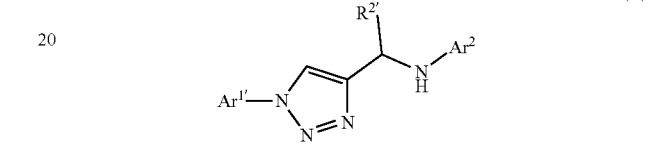

(II)

wherein:
Ar$^{1'}$ is phenyl substituted with C$_{1-3}$perhaloalkyl; or phenyl substituted with two substituents each independently selected from the group consisting of: halo, C$_{1-3}$alkyl, C$_{1-3}$perhaloalkyl, and OC$_{1-3}$perhaloalkyl;
R$^{2'}$ is H or CH$_3$; and
Ar$^2$ is selected from the group consisting of:
  (a) pyridin-2-yl; pyridazin-3-yl; pyrimidin-4-yl; pyrimidin-2-yl; or pyrimidin-2-yl substituted with one or two substituents each independently selected from the group consisting of halo, C$_{1-3}$alkyl, C(CH$_3$)$_2$OH, C$_{1-3}$perhaloalkyl, OCH$_3$, and cyclopropyl; and
  (b) 1-methyl-imidazol-2-yl; oxazol-2-yl; 1-methyl-pyrazol-4-yl; 1-methyl-pyrazol-3-yl; or 1-methyl-1H-pyrazol-5-yl;
and pharmaceutically acceptable salts thereof, to a subject in need thereof.

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I) (as well as (IA), (IB), (IC), (ID), (II), (IIA), and (IIB)), and pharmaceutically acceptable salts of all of the foregoing.

In preferred embodiments of the inventive method, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include, but are not limited to mental and behavioural disorders associated with childbirth, including but not limited to postnatal (postpartum) and prenatal depression; eating disorders, including but not limited to anorexia nervosa, bulimia nervosa, pica and binge eating disporder.

Examples of extrapyramidal and movement disorders that can be treated according to the present invention include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor, restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal)(partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myodonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-3}$alkyl as used here refers to a straight- or branched-chain alkyl group having from 1 to 3 carbon atoms in the chain. The term $C_{1-6}$alkyl as used here refers to a straight- or branched-chain alkyl group having from 1 to 6 carbon atoms in the chain.

The term "halo" represents chloro, fluoro, bromo or iodo.

The term "perhaloalkyl" or "haloalkyl" refers to a straight- or branched-chain alkyl group having from 1 to 6 carbon atoms in the chain optionally substituting hydrogens with halogens. The term "$C_{1-3}$perhaloalkyl" as used here refers to a straight- or branched-chain alkyl group having from 1 to 3 carbon atoms in the chain, optionally substituting hydrogens with halogens. The term "$C_{1-6}$perhaloalkyl" as used here refers to a straight- or branched-chain alkyl group having from 1 to 6 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), chloropropyl ($CH_2CH_2CH_2Cl$), and groups that in light of the ordinary skill in the art and the teachings provided herein would be considered equivalent to any one of the foregoing examples.

The term "cyano" refers to the group CN.

The term "cydoalkyl" refers to a saturated or partially saturated, monocyclic, fused polycydic, or spiro polycyclic carbocycle having from 3 to 12 ring atoms per carbocycle. Illustrative examples of cydoalkyl groups include the following entities, in the form of properly bonded moieties:

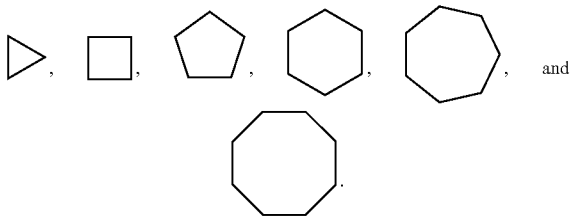 and

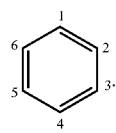

The term "phenyl" represents the following moiety:

The phenyl moiety can be attached through any one of the 1-, 2-, 3-4-, 5-, or 6-position carbon atoms.

The term "thienyl" represents the following moiety:

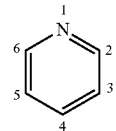

The term "pyridinyl" or "pyridyl" represents the following moiety:

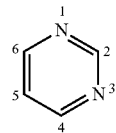

The pyridinyl or pyridyl moiety can be attached through any one of the 2-, 3-, 4-, 5-, or 6-position carbon atoms.

The term "pyrimidinyl" represents the following moiety:

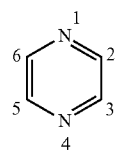

The pyrimidinyl moiety can be attached through any one of the 2-, 4-, 5-, or 6-position carbon atoms.

The term "pyrazinyl" represents the following moiety:

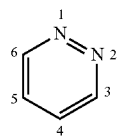

The pyrazinyl moiety can be attached through any one of the 2-, 3-, 5-, or 6-position carbon atoms.

The term "pyridazinyl" represents the following moiety:

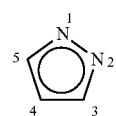

The pyridazinyl moiety can be attached through any one of the 3-, 4-, 5-, or 6-position carbon atoms.

The term "pyrazolyl" represents the following moiety:

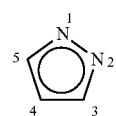

The pyrazolyl moiety can be attached through any one of the 1-, 2-, 3-, 4-, or 5-position carbon atoms.

The term "piperidinyl" represents the following moiety:

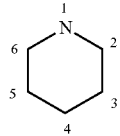

When the piperidinyl moiety is a substituent, it can be attached through any one of the 1-, 2-, 3-, 4-, 5-, or 6-position atoms, as permitted.

The term "pyrrolidinyl" represents the following moiety:

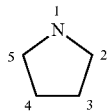

When the piperidinyl moiety is a substituent, it can be attached through any one of the 1-, 2-, 3-, 4-, or 5-position atoms, as permitted.

The term "azetidinyl" represents a 4-membered heterocycloalkyl moiety having one ring nitrogen. When the azetidinyl moiety is a substituent, it can be attached through any carbon atom or through the nitrogen atom, as permitted.

The term "morpholinyl" represents the following moiety:

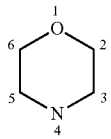

When the morpholinyl moiety is a substituent, it can be attached through any one of the 2-, 3-, 4-, 5-, or 6-position atoms, as permitted.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

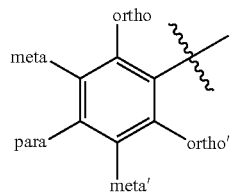

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols  and  are used as meaning the same spatial arrangement in chemical structures shown herein. Analogously, the symbols  and  are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) (as well as Formulas (IA), (IB), (IC), (ID), (II), (IIA), and (IIB)), or pharmaceutically acceptable salts of compounds of Formula (I) (as well as Formulas (IA), (IB), (IC), (ID), (II), (IIA), and (IIB)) may be obtained as solvates. Solvates include those formed from the interaction or complexation of compounds of the invention with one or more solvents, either in solution or as a solid or crystalline form. In some embodiments, the solvent is water and the solvates are hydrates.

In addition, certain crystalline forms of compounds of Formula (I) (as well as Formulas (IA), (IB), (IC), (ID), (II), (IIA), and (IIB)) or pharmaceutically acceptable salts of compounds of Formula (I) (as well as Formulas (IA), (IB), (IC), (ID), (II), (IIA), and (IIB)) may be obtained as co-crystals.

In other embodiments, pharmaceutically acceptable salts of compounds of Formula (I) may be obtained in a crystalline form. In still other embodiments, compounds of Formula (I) may be obtained in one of several polymorphic forms, as a mixture of crystalline forms, as a polymorphic form, or as an amorphous form. In other embodiments, compounds of Formula (I) may convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example deuterium (i.e., D or $^2$H); or tritium (i.e., T or $^3$H)), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as R$^1$, R$^{1'}$, R$^2$, R$^{2'}$, R$^4$, R$^{10}$, R$^{11}$, R$^{12}$, R$^{13}$, R$^{14}$, R$^{15}$, R$^{16}$, R$^{17}$, R$^{18}$, R$^{19}$, R$^f$, R$^g$, R$^h$, HAL, PG, LG, n, Ar$^1$, Ar$^{1'}$, Ar$^2$, Ar$^3$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as R$^1$, R$^{1'}$, R$^2$, R$^{2'}$, R$^4$, R$^{10}$, R$^{11}$, R$^{12}$, R$^{13}$, R$^{14}$, R$^{15}$, R$^{16}$, R$^{17}$, R$^{18}$, R$^{19}$, R$^f$, R$^g$, R$^h$, HAL, PG, LG, n, Ar$^1$, Ar$^{1'}$, Ar$^2$, Ar$^3$ and any other generic substituent symbol used herein.

The nomenclature "$C_{i\text{-}j}$" with j>i, when applied herein to a class of substituents, is meant to refer to embodiments of this invention for which each and every one of the number of carbon members, from i to j including i and j, is independently realized. By way of example, the term $C_{1\text{-}4}$ refers independently to embodiments that have one carbon member ($C_1$), embodiments that have two carbon members ($C_2$), embodiments that have three carbon members ($C_3$), and embodiments that have four carbon members ($C_4$).

The term $C_{n\text{-}m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), (IB), (IC), (ID), (II), (IIA), and (IIB)), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmcopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), (IB), (IC), (ID), (II), (IIA), and (IIB)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA), (IB), (IC), (ID), (II), (IIA), and (IIB)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), (IB), (IC), (ID), (II), (IIA), and (IIB)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), (IB), (IC), (ID), (II), (IIA), and (IIB)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) (as well as Formulas (IA), (IB), (IC), (ID), (II), (IIA), and (IIB)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1986.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), (IB), (IC), (ID), (II), (IIA), and (IIB)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), (IB), (IC), (ID), (II), (IIA), and (IIB)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), (IB), (IC), (ID), (II), (IIA), and (IIB)), which may also be used in the methods of the invention. A "pharmaceutically active metabolite" means a pharmacologically active product of metabolism in the body of a compound of Formula (I) (as well as Formulas (IA), (IB), (IC), (ID), (II), (IIA), and (IIB)) as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA), (IB), (IC), (ID), (II), (IIA), and (IIB)) and their pharmaceutically acceptable salts, pharmaceutically acceptable prodrugs, and pharmaceutically active metabolites of the present invention are useful as modulators of the NR2B receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the NR2B receptor expression or activity, and "activators" are compounds that increase, activate, facilitate, sensitize, or up-regulate NR2B receptor expression or activity.

The term "treat", "treatment" or "treating", as used herein, is intended to refer to administration of an active agent or composition of the invention to a subject for the purpose of affecting a therapeutic or prophylactic benefit through modulation of NR2B receptor activity. Treating includes reversing, ameliorating, alleviating, inhibiting the progress of, lessening the severity of, or preventing a disease, disorder, or condition, or one or more symptoms of such disease, disorder or condition mediated through modulation of NR2B receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by NR2B receptor activity, such as: bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, disruptive mood dysregulation disorder, depressive disorders with psychotic symptoms; persistent mood disorders, such as cyclothymia, dysthymia, euthymia; and premenstrual dysphoric disorder, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post traumatic stress disorder (PTSD); other neurotic disorders such as depersonalisation-derealisation syndrome; pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills; postnatal (postpartum) and prenatal depression; eating disorders, including but not limited to anorexia nervosa, bulimia nervosa, pica and binge eating disorder; Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome; dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); epilepsy, including localization-related (focal)(partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myodonic, tonic, tonic-clonic epileptic seizures; epilepsy with myodonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus; persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy; and acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis, and ALS; subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases; glaucoma and other neuopathies; dementias, vascular demensia, Lewy body dementia, frontotemporal dementia, and HIV-dementia; vertigo and nystagmus; tinnitus; neuropsychiatric systemic lupus erythematosus; disruptive mood dysregulation disorder; schizophrenia spectrum disorder; and sleep/wake disorders.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by NR2B activity, such as another NR2B modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following: Table 4:

| Term | Acronym |
| --- | --- |
| Acetonitrile | ACN |
| Aqueous | aq |
| Atmosphere | atm |
| tert-Butylcarbamoyl | Boc, or BOCa |
| Broad | br |
| Diatomaceous Earth | Celite ® |
| Diethylaminosulfur trifluoride | DAST |
| Di-tert-butyl azodicarboxylate | DBAD |
| 1,8-Diazabicyclo[5.4.0]undec-7-ene | DBU |
| Dichloromethane | DCM |
| Bis(2-methoxyethyl)aminosulfur trifluoride | Deoxo-Fluor ® |
| Diisopropylethylamine | DIPEA, DIEA, or Hunig's base |
| 4-Dimethylaminopyridine | DMAP |
| 1,2-Dimethoxyethane | DME |
| N,N-Dimethylformamide | DMF |
| Dimethylsulfoxide | DMSO |
| 1-Ethyl-3-(3-dimethylaminopropyl)carbodiimide | EDCI; EDAC, or EDC |
| Diethyl ether | Ether, $Et_2O$ |
| Ethyl Acetate | EtOAc, or EA |
| Ethanol | EtOH |
| Electrospray ionization | ESI |
| Normal-phase silica gel chromatography | FCC |
| Grams | g |
| Hours | h |
| Hydroxybenzotriazole | HOBt |
| High-pressure liquid chromatography | HPLC |
| Hertz | Hz |
| Isopropyl alcohol | iPrOH, IPA |
| Lithium aluminum hydride | LAH |
| Term | Acronym |
| Liquid chromatography and mass spectrometry | LCMS |
| Lithium bis(trimethylsilyl)amide | LHMDS |
| Molar | M |
| Mass to charge ratio | m/z |
| meta-Chloroperoxybenzoic acid | mCPBA |
| Methyl Iodide | MeI |
| Methanol | MeOH |
| Milligrams | mg |
| Minute | min |
| Milliliter | mL |
| Microliter | µL |
| Millimoles | mmol |
| Mass spectrometry | MS |
| Normal | N |
| Sodium tert-butoxide | NaOt-Bu |
| Nuclear magnetic resonance | NMR |
| $CF_3SO_3$- or triflate | OTf |
| Palladium (II) acetate | $Pd(OAc)_2$ |
| Palladium(II)bis(triphenylphosphine) dichloride | $Pd(PPh_3)_2Cl_2$ |
| Tetrakis(triphenylphosphine)palladium(0) | $Pd(PPh_3)_4$ |
| [1,1'-Bis(di-tert-butylphosphino)ferrocene]dichloropalladium(II) | $PdCl_2(dtbpf)$ or $Pd(dtbpf)_2Cl_2$ |
| [1,1'-Bis(diphenylphosphino)ferrocene]dichloropalladium (II) | $PdCl_2(dppf)$ or $Pd(dppf)_2Cl_2$ |
| Parts per million | ppm |
| Precipitate | ppt |
| Polytetrafluoroethylene | PTFE |
| Retention time | $R_t$ |
| Room temperature | rt |
| Saturated | sat |
| 1-Chloromethyl-4-fluoro-1,4-diazoniabicyclo[2.2.2]octane bis(tetrafluoroborate) | Selectfluor ® |
| [2-(Trimethylsilyl)ethoxy]methyl acetal | SEM |
| Supercritical Fluid Chromatography | SFC |
| Temperature | T |
| Tert-Butyl alcohol | tBuOH, t-BuOH |
| Tetra-n-butylammonium fluoride | TBAF |
| Triethylamine | TEA |
| Trifluoroacetic acid | TFA |
| Tetrahydrofuran | THF |
| Thin layer chromatography | TLC |
| Volume in milliliters of solvent per gram of substrate | V, or volumes |
| (Diethylamino)difluorosulfonium tetrafluoroborate | XtalFluor ® |

PREPARATIVE EXAMPLES

Exemplary compounds useful in methods of the invention will now be described by reference to the illustrative synthetic schemes for their general preparation below and the specific examples to follow.

SCHEME A

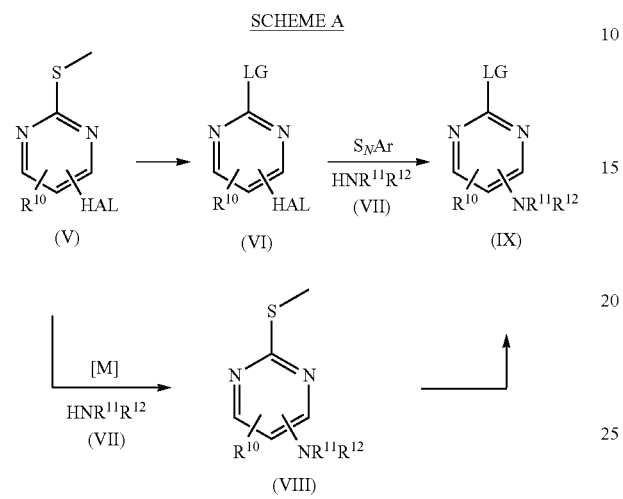

SCHEME B

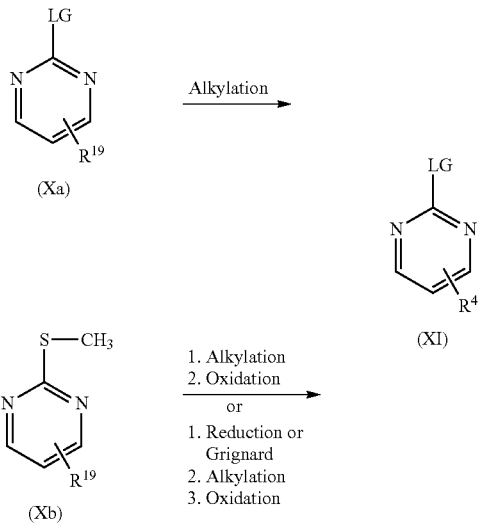

According to SCHEME A, a compound of formula (V) where HAL is Cl, and $R^{10}$ is F, is oxidized under conditions known to one skilled in the art, to afford a compound of formula (VI). For example, reaction of a compound of formula (V), where HAL is Cl, and $R^{10}$ is F, is oxidized with an oxidizing agent such as mCPBA, and the like, in a suitable solvent such as DCM, and the like, at temperatures ranging from 0° C. to rt, to provide a compound of formula (VI), where LG is $SO_2CH_3$.

Commercially available or synthetically accessible pyrimidines of formula (V), where HAL is Br, and $R^{10}$ is H, are reacted in a metal mediated cross coupling with an amine of formula (VII), to provide a compound of formula (VIII). For example, a pyrimidine of formula (V), where HAL is Br, and $R^{10}$ is H, is reacted with a palladium catalyst such as $Pd(OAc)_2$, a ligand such as Xantphos, and the like, a base such as NaOtBu, and the like, an amine such as azetidine, 3-fluoroazetidine, 3,3-difluoroazetidine, and the like, in a suitable solvent such as toluene, a temperatures ranging from 90-120° C., for a period of 2-5 h, to provide a compound of formula (VIII). A compound of formula (VIII), is oxidized, employing conditions previously described, to provide a compound of formula (IX).

Commercially available or synthetically accessible pyrimidines of formula (VI), where LG is Cl, $R^{10}$ is H, and HAL is Cl, are reacted with a suitable nucleophile such as an amine of formula (VII) (wherein the amine is an alkylamine or heterocycloalkyl amine which is optionally substituted with one or more halogen members), with or without a suitable base such as TEA, in a suitable solvent such as DMF, THF, DCM, and the like, for a period of 1-6 h, to provide a compound of formula (IX), where $NR^{11}R^{12}$ is $(N(C_{1-6}alkyl)_2)$ or heterocycloalkylamine and $R^{10}$ is H. In a preferred embodiment, the amine is azetidine, 3-fluoroazetidine, 3,3-difluoroazetidine, pyrrolidine, 3,3-difluoropyrrolidine piperidine, or morpholine, and the base is TEA.

According to SCHEME B, a compound of formula (Xa), where LG is Cl, $R^{19}$ is OH, or $CH_2OH$, is reacted with a silyl chloride reagent such as tert-butyl(chloro)dimethylsilane, and the like, a base such as imidazole, in a solvent such as DCM and the like, to provide silyl ether compound of formula (XI). Alternately a compound of formula (Xa) is alkylated with a suitable alkylating agent, such as 1-fluoro-2-iodoethane, employing a base such as NaH, $K_2CO_3$, $Na_2CO_3$, TEA, $Cs_2CO_3$, and the like, in a suitable solvent such as DMF, ACN, DCM, at temperatures ranging from 0° C. to 85° C., to afford a compound of formula (XI), where $R^4$ is O—$C_{1-6}$alkyl, $CH_2O$—$C_{1-6}$alkyl, O—$C_{1-6}$perhaloalkyl, or $CH_2O$—$C_{1-6}$perhaloalkyl, and LG is Cl.

A compound of formula (XI), where LG is $SO_2CH_3$ and $R^4$ is $CH_2O$—$C_{1-6}$alkyl, $CH_2O$—$C_{1-6}$perhaloalkyl, and $CH_2O$-$CD_3$, may be prepared in two steps from a compound of formula (Xb) where $R^{19}$ is $CH_2OH$. In a first step a compound of formula (Xb) may be alkylated employing conditions previously described, with a suitable base such as NaH, $K_2CO_3$, and the like, and an alkylating agent such as Et-I, $CD_3$-I, 2-chloro-2,2-difluoro-1-phenylethan-1-one, and the like. In a second step, oxidation of the thiomethyl employing previously described conditions, may provide a compound of formula (XI), where $R^4$ is $CH_2O$—$C_{1-6}$alkyl, $CH_2O$—$C_{1-6}$perhaloalkyl, or $CH_2O$-$CD_3$, and LG is $SO_2CH_3$.

A compound of formula (XI), where $R^4$ is $CH_2O$—$C_{1-6}$alkyl and LG is $SO_2CH_3$ may also be prepared in three steps from a compound of formula (Xb) where $R^{19}$ is C(=O)$CH_3$ or $CO_2CH_3$. In a first step, reduction of the kenone employing conditions known to one skilled in the art, for example with a reducing agent such as $LiBH_4$, $LiBD_4$, and the like, may provide a compound of formula (Xb), where $R^{19}$ is $CH_2OH$. Subsequent alkylation and oxidation may provide a compound of formula (XI), where $R^4$ is $CH_2O$—$C_{1-6}$alkyl and LG is $SO_2CH_3$. A compound of formula (Xb) may additionally be substituted with a halogen such as F.

A compound of formula (XI), where $R^4$ is $CH_2O$—$C_{1-6}$alkyl and LG is $SO_2CH_3$ may also be prepared in three steps from a compound of formula (Xb) where $R^{19}$ is C(=O)$CH_3$. Reaction of the ketone with a reagent such as MeMgBr, employing conditions known to one skilled in the art, may provide a compound of formula (Xb), where $R^{19}$ is C(CH$_3$)$_2$ OH. Subsequent alkylation and oxidation may provide a compound of formula (XI), where $R^4$ is $CH_2O$—$C_{1-6}$alkyl and LG is $SO_2CH_3$.

A compound of formula (Xb), where $R^{19}$ is $C(CH_3)_2OH$ or $CH_2OH$ may also be reacted with a silyl chloride reagent such as tert-butyl(chloro)dimethylsilane, under conditions previously described.

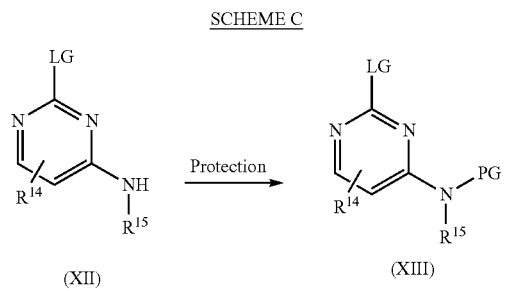

According to SCHEME C, a compound of formula (XII), where LG is Cl, $R^{14}$ is H, F, or $CH_3$, $R^{15}$ is $C_{1-6}$alkyl or $C_{1-6}$perhaloalkyl, is protected with a suitable nitrogen protecting group (PG) such as BOC (tert-butyloxycarbonyl), SEM (2-(trimethylsilyl)ethoxymethyl), and the like, under conditions known to one skilled in the art, to provide a compound of formula (XIII).

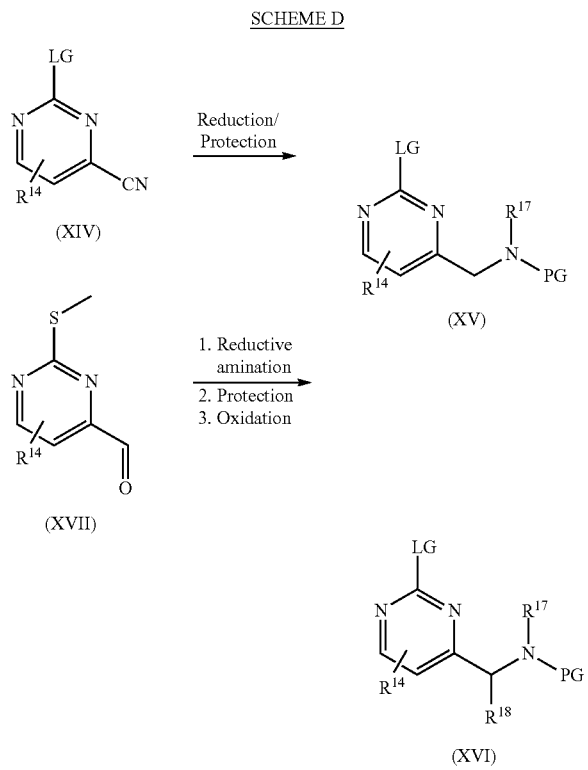

According to SCHEME D, a compound of formula (XIV), where LG is Cl, and $R^{14}$ is H, is reduced and subsequently protected in a one pot reaction to provide a compound of formula (XV), where PG is BOC, and $R^{17}$ is H. For example, 2-chloropyrimidine-4-carbonitrile, is reacted with di-tert-butyl dicarbonate, Pd/C, under an atmosphere of $H_2$, in a suitable solvent such as EtOH, and the like, to provide tert-butyl ((2-chloropyrimidin-4-yl)methyl)carbamate.

A compound of formula (XV) is also prepared from a compound of formula (XVII) in three steps. In a first step, a compound of formula (XVII), where $R^{14}$ is H, is reacted in a reductive amination reaction with a suitable amine such as methyl amine, a reducing agent such as $NaBH(OAc)_3$, $NaBH_4$, and the like, in a solvent such as THF, DCM and the like, for a period of 12-20 h. In a second step, the alkyl amine is protected with a suitable nitrogen protecting group such as BOC, employing conditions previously described. In a third step, the methylthioether is oxidized employing conditions previously described to provide a compound of formula (XV), where LG is $SO_2CH_3$, $R^{17}$ is $CH_3$, and PG is BOC.

A compound of formula (XV), where LG is Cl, PG is BOC, and $R^{17}$ is H, is alkylated employing conditions known to one skilled in the art. For example, alkylation with an alkyl halide agent such as MeI, and the like, a base such as NaH, in a solvent such as THF, DMF, and the like, provides a compound of formula (XVI), where $R^{18}$ is $CH_3$.

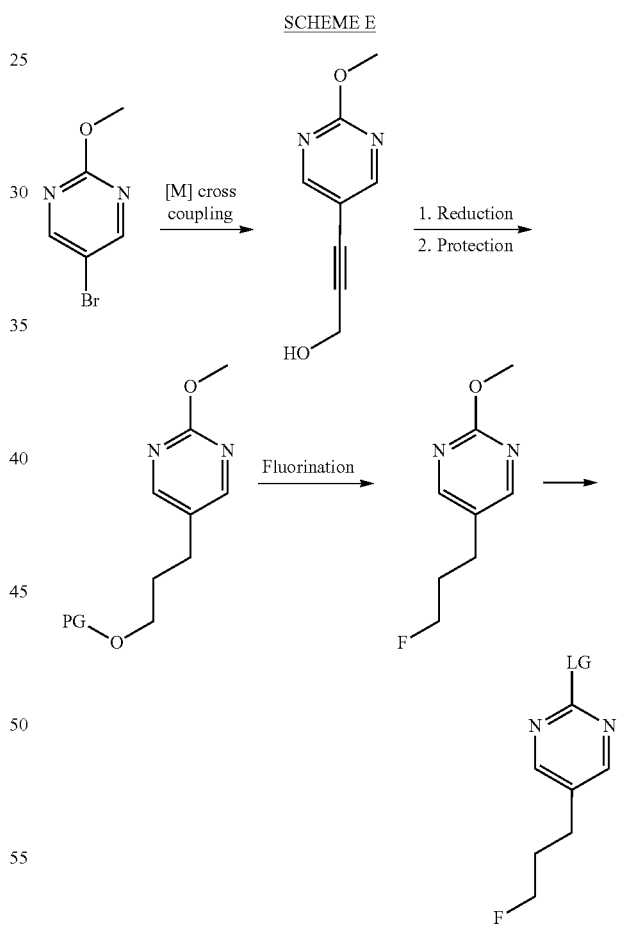

According to SCHEME E, 5-bromo-2-methoxypyrimidine is reacted in a metal mediated cross coupling with an alkyne such as prop-2-yn-1-ol, a palladium catalyst such as $PdCl_2(PPh_3)_2$, and the like, a base such trimethylamine, CuI, in a solvent such as DMF, and the like, to provide 3-(2-methoxypyrimidin-5-yl)prop-2-yn-1-ol. The alkyne is reduced, employing conditions previously described, to afford 3-(2-methoxypyrimidin-5-yl)propan-1-ol. The alcohol is protected with a suitable alkyl alcohol protecting group such as an alkyl tosylate. For example, 3-(2-methoxypyrimidin-5-yl)propan-1-ol is reacted with sulfonyl chloride, a base such as TEA, trimethylamine, and the like, in a solvent such DCM, for a period of 12-24 h, provides a compound of formula (XVIII). Fluorination of a compound of formula (XVIII), employing TBAF, in a solvent such as THF, provides 5-(3-fluoropropyl)-2-methoxypyrimidine. A compound of formula (XIX) is prepared in two steps from 5-(3-fluoropropyl)-2-methoxypyrimidine. In a first step, demethylation of the methyl ether is achieved with HCl/Dioxane, at a temperature of 100° C., for a period of 4-6 h. Chlorination of 5-(3-fluoropropyl)pyrimidin-2(1H)-one is achieved under chlorination conditions, for example, reaction with $POCl_3$, and the like, at temperatures ranging from 70-90° C., to afford a compound of formula (XIX), where LG is Cl.

SCHEME F

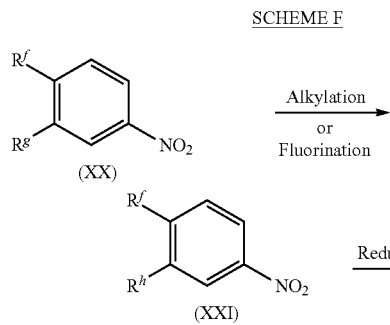

According to SCHEME F, a compound of formula (XXII), where $Ar^1$ is a substituted phenyl ring, is commercially available or synthetically accessible from a compound of formula (XX), where $R^f$ and $R^g$ are selected from: H, OH, halo, $C(O)C_{1-3}$alkyl, CHO, $C_{1-3}$alkyl, $OC_{1-3}$alkyl, $C_{1-6}$perhaloalkyl, and $OC_{1-6}$perhaloalkyl. A compound of formula (XX), where $R^1$ is defined as above and $R^g$ is OH, is alkylated with a reagent such as chlorodifluoroacetate, MeI, and the like, in the presence of a base, such as $K_2CO_3$, $Cs_2CO_3$, NaH, and the like, in a suitable solvent such as DMF, water, or a mixture thereof, at temperatures ranging from room temperature to 120° C., or conventional heating, for a period of 2 to 5 h, to provide a compound of formula (XXI), where $R^f$ is defined as above and $R^g$ is $OC_{1-6}$alkyl or $OC_{1-6}$perhaloalkyl. In a preferred method, a compound of formula (XX), where $R^f$ is Cl and $R^g$ is OH, is alkylated with chlorodifluoroacetate, in the presence of a base, such as $K_2CO_3$, in a suitable solvent such as DMF, water, or a mixture thereof, at 100° C., for 2.5 h, to afford compound of formula (XXI), where $R^f$ is Cl, and $R^h$ is $OCF_2H$. A compound of formula (XX), where $R^f$ is defined as above and $R^g$ is CHO, is fluorinated with a fluorinating agent such as, DAST, XtalFluor®, Deoxo-Fluor®, and the like, in a suitable solvent such as DCM, and the like, at temperatures ranging from −78° C. to 50° C., for a period of 2-24 h. In a preferred method, a compound of formula (XX), where $R^f$ is Cl and $R^g$ is CHO, is reacted with the a fluorinating agent such as DAST, in a solvent suitable solvent such as DCM, at room temperature, for 20 h, provides a compound of formula (XXI), where $R^f$ is Cl and $R^h$ is $CF_2H$.

A nitro compound of formula (XXI) is reduced, employing conditions known to one skilled in the art, to provide a compound of formula (XXII), where $Ar^1$ is a substituted phenyl ring as defined in Formula (I). A nitro compound of formula (XX), where $R^f$ and $R^g$ are selected from H, halo, $C(O)C_{1-4}$alkyl, $C_{1-4}$alkyl, $OC_{1-4}$alkyl, $C_{1-6}$perhaloalkyl, or $OC_{1-6}$perhaloalkyl, is reduced with a reducing agent, such as but not limited to: Pd/C under an atmosphere of $H_2$ (balloon); Fe powder in a solution of HCl; Zn powder in a solution of aqueous $NH_4Cl$; in a suitable solvent such as MeOH, EtOH, THF, acetone, and the like, at temperatures ranging from room temperature (23° C.) to about 50° C., for a period of 30 minutes to 16 h, to afford a compound of formula (XXII). In a preferred method, a nitro compound of formula (XXI), where $R^f$ is Cl and $R^h$ is $OCF_2H$, is reduced with Fe powder, concentrated HCl, in a solvent such as MeOH, at room temperature, for a period of about 2 h. In a preferred method, a nitro compound of formula (XXI), where $R^f$ is Cl and $R^h$ is $CF_2H$, is reduced with Zn powder, $NH_4Cl$, in a suitable solvent such as acetone/water, at temperatures ranging from 0° C. to rt, for a period of 16 h.

SCHEME G

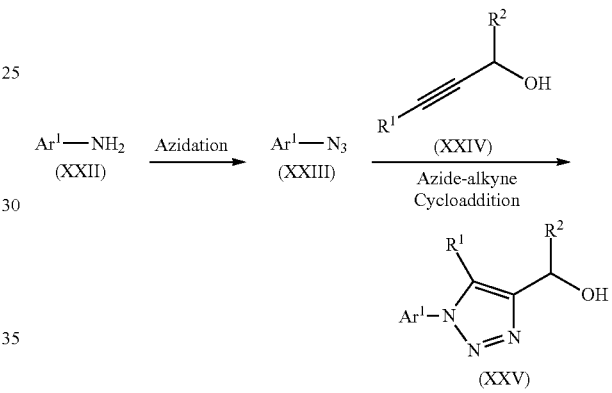

According to SCHEME G, an azide compound of formula (XXIII) is prepared from a compound of formula (XXII) employing azidation conditions known to one skilled in the art. In a preferred method, a compound of formula (XXII), where $Ar^1$ is a suitably substituted phenyl or pyridyl, in a suitable solvent such as iPrOH, THF, and the like, is treated with 6 N HCl in iPrOH, and reacted in flow, or conventional methods known to one skilled in the art, with sodium nitrite in a suitable solvent such as water, and sodium azide in a suitable solvent such as water, respectively, under acidic conditions (such as $H_2SO_4$, HCl, TFA, etc.) to afford an azide compound of formula (XXIII). Alternatively, aryl azides of formula (XXIII) may be prepared employing conditions known to one skilled in the art, for example, copper(II)-catalyzed conversion of organoboron compounds; arenediazonium tosylates and sodium azide in water at room temperature; $S_NAr$ reactions using sodium azide and a halogenated aryl. A compound of formula (XXIII), were $Ar^1$ is a suitably substituted thiophene may be made according to the methods recited above.

A compound of formula (XXV), where $R^1$ is H, $R^2$ is H or $CH_3$, and $Ar^1$ is a suitably substituted phenyl or pyridyl, is obtained thru a metal-catalyzed azide-alkyne 1,3-dipolar cycloaddition reaction of a compound of formula (XXIII) and an alkyne of formula (XXIV), in the presence of metal catalyst such as copper sulfate, $(CuOTf)_2 \cdot C_6He$, RuCp*Cl $(PPh_3)_2$, and the like, with or without a reducing agent such as L-sodium ascorbate and the like, in a solvent such as $H_2O$, tBuOH, isopropanol, dioxane, toluene, or a mixture thereof, at temperatures ranging from rt to 100° C., for a period of 30 min to 24 h. In a preferred method, the alkyne of formula (XXIV) where $R^1$ is H, $R^2$ is H or $CH_3$, is reacted with an azide compound of formula (XXIII), copper sulfate, L-sodium ascorbate, in tBuOH/$H_2O$, at room temperature overnight. In an alternate method, the alkyne is N-propargyl phthalimide.

A compound of formula (XXV), where Ar, is a suitably substituted phenyl or pyridyl, can be prepared as described in B. Chattopadhyay et al. *Org. Lett.* 2010, 12, 2166-2169. One skilled in the art will recognize that the azide-alkyne cycloaddition can also be accomplished by methods described in H. Kolb et al. *Angew. Chem. Int. Ed.* 2001, 40, 2004-2021.

SCHEME H

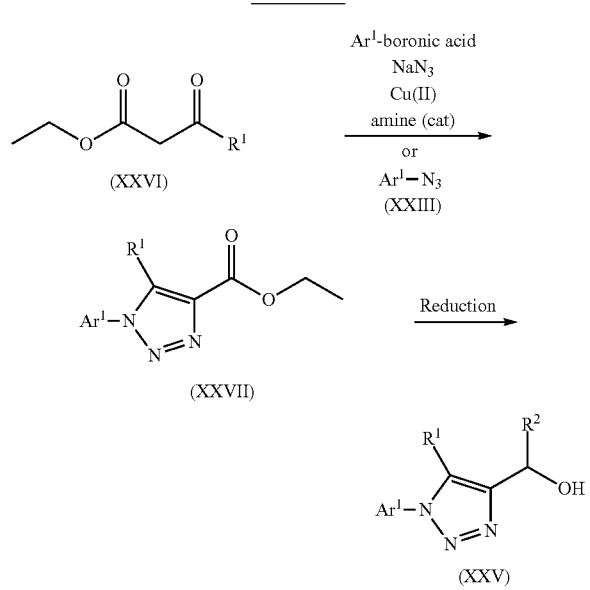

According to SCHEME H, a compound of formula (XXVI), where $R^1$ is $CH_3$, $CF_2H$, or $CF_3$, is reacted with an $Ar^1$-boronic acid, where $Ar^1$ is a suitably substituted phenyl ring, $NaN_3$, a transition metal catalyst such as $Cu(OAc)_2$, $Cu_2O$, CuBr, or Cu powder, a base such as piperidine, trimethylamine, $KzCO_3$ and the like, in a solvent such as DMSO, THF, DMF, and water, at temperatures ranging from room temperature to 80° C., for a period of 2 to 24 h, to provide a compound of formula (XXVII). Alternately, the addition of NaI in the previously described transformation of a compound of formula (XXVI) to a compound of formula (XXVII) provides a compound of formula (XXV) where $R^1$ is I.

A compound of formula (XXVI), where $R^1$ is $CH_3$, $CF_2H$, or $CF_3$, is reacted with an $Ar^1$—$N_3$ of formula (XXIII), where $Ar^1$ is a suitably substituted phenyl ring, an amine catalyst such as diethylamine, piperidine, proline, triethylamine, and the like, in a solvent such as DMSO, to provide a compound of formula (XXVII). Reduction of a compound of formula (XXVII), with a reducing agent, such as $LiAlH_4$, $LiBH_4$, and the like, in a solvent such as THF, and the like, affords a compound of formula (XXV), where $R^1$ is H or $CH_3$ and $R^2$ is H.

SCHEME I

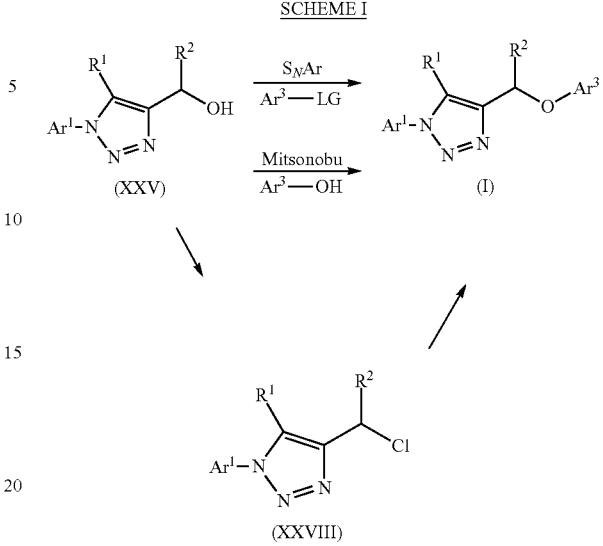

Referring to SCHEME I, a compound of Formula (I), where $Ar^3$ is pyrimidine, pyridine, or pyridazine substituted with one or two substituents, $R^1$ is H, and $R^2$ is H or $CH_3$, is obtained from a compound of formula (XXV), by a $S_NAr$, $S_N2$, or Mitsunobu reaction. For example, a compound of Formula (I) is obtained from a compound of formula (XXV), by $S_NAr$ reaction with LG-$Ar^3$, where $Ar^3$ is a commercially available or synthetically accessible heteroaromatic five or six membered ring, and LG is a suitable leaving group such as F, Cl, Br, I, $SO_2Me$, or OTf, in the presence of a base, such as NaH, $K_2CO_3$, $Cs_2CO_3$, and the like, in a solvent such as DMF, THF, ACN, and the like, at temperatures ranging from room temperature (about 23° C.) to about 140° C., employing conventional or microwave heating. In a preferred method the base is NaH, the solvent is DMF and the reaction is performed at room temperature.

A compound of Formula (I), where $Ar^3$ is pyrimidine, pyridine, or pyridazine substituted with one or two substituents, $R^1$ is H, and $R^2$ is H or $CH_3$, is also obtained from a compound of formula (XXV), by a Mitsunobu reaction with a compound of $Ar^3$—OH, where $Ar^3$—OH is a commercially available or synthetically accessible heteroaromatic five or six membered ring selected from is pyrimidine, pyridine, or pyridazine substituted with one or two substituents. For example, a compound of formula (XXV), where $R^1$ is H, and $R^2$ is H or $CH_3$, is reacted with $Ar^3$—OH, where $Ar^3$ is a commercially available or synthetically accessible heteroaromatic five or six membered ring, $PPh_3$, and the like, a base such as DEAD, DCAD, DIAD, DBAD, and the like, in a suitable solvent such as THF, DMF, and the like, at temperatures ranging from room temperature (about 23° C.) to about 50° C., to provide a compound of Formula (I). In a preferred method, a compound of formula (XXV) is reacted with $Ar^3$—OH, $PPh_3$, DBAD, in THF at room temperature to provide a compound of Formula (I).

A compound of Formula (I), where $Ar^{1'}$ is pyrimidine, pyridine, or pyridazine substituted with one or two substituents, $R^1$ is H, and $R^2$ is H or $CH_3$, is also obtained in two steps from a compound of formula (XXV), by $S_N2$ reaction. In the first step, a chloro compound of formula (XXVIII) is prepared from a compound of formula (XXV) employing chlorination conditions known to one skilled in the art, such as thionyl chloride, in a suitable solvent such as DCM, CHCl₃, and the like, at temperatures ranging from room temperature to about 50° C., for a period of 30 min to 6 h. In the second step, a compound of Formula (I) is prepared by reacting a chloro compound of formula (XXVIII) with a nucleophile such as Ar³—OH in a S_N2 reaction. For example, a chloro compound of formula (XXVIII) is reacted with a nucleophile of formula Ar³—OH, where a Ar³—OH is a suitable commercially available or synthetically accessible hydroxy-substituted heteroaryl compound, in the presence of a base, such as NaH, K₂CO₃ and the like, in a solvent such as DMF at temperatures ranging from room temperature (about 23° C.) to about 50° C. to provide a compound of Formula (I). In a preferred method, the base is K₂CO₃, the solvent is DMF and the reaction is performed at room temperature.

A compound of Formula (I) where Ar³ is substituted with Br, is reacted in a metal mediated cross coupling reaction to provide a compound of Formula (I) where Ar³ is xx. For example, a compound of Formula (I), where Ar³ is substituted with Br or Cl, is reacted with a suitably substituted commercially available or synthetically accessible aryl or heteroaryl boronic acid, boronate ester, trimethylboroxine, and the like, in the presence of a palladium catalyst such as XPhos Palladacyde Gen. 3, PdCl₂(dtbpf), Pd(PPh₃)₄, PdCl₂(dppf), Pd(PPh₃)₂Cl₂, and the like, a base such as K₃PO₄, aq. Na₂CO₃, Na₂CO₃, Cs₂CO₃, and the like, in a suitable solvent such as 1,2-dimethoxyethane, 1,4-dioxane, THF, DMF, water, or a mixture thereof, at a temperature ranging from 60 to 180° C., employing microwave or conventional heating, for a period of about 30 min to 16 h, to provide a compound of Formula (I), where 1-methylpyrazol-3-yl, 1H-pyrazol-4-yl, and the like.

In a similar fashion, a compound of Formula (I), where Ar¹ is substituted with a suitable halogen such as Br, is reacted in a metal mediated cross coupling reaction with an alkylzinc halide, cyclallkylzinc halide such as cyclobutylzinc bromide, 2-propylzinc bromide, and the like, a palladium catalyst such as Pd(t-Bu₃P)₂, and the like, in a suitable solvent such as THF, at a temperature of about 50° C., for a period of 12-24 h, to provide a compound of Formula (I), where Ar¹ is substituted with $C_{1-6}$alkyl or $C_{3-6}$cycloalkyl.

In a similar fashion, a compound of Formula (I), where Ar¹ is substituted with a suitable halogen such as Br, is reacted in a metal mediated cross coupling reaction with a suitably substituted commercially available or synthetically accessible boronic acid, potassium trifluoroborate, trimethylboroxine, and the like in the presence of a palladium catalyst such as RuPhos-Pd-G3, and the like, in a suitable solvent such as 1,4-dioxane, with a suitable base such as K₂CO₃, potassium phosphate tribasic, and the like at a temperature of about 100° C., for a period of 12-24 h, to provide a compound of Formula (I), where Ar¹ is substituted with $C_{1-6}$alkyl or $C_{3-6}$cycloalkyl.

A compound of Formula (I), where Ar¹ is substituted with a suitable halogen leaving group such as F, is reacted with a 4-6 membered heterocycloalkyl such as azetidine, pyrrolidine, piperidine or morpholine, a base such as DIPEA, and the like, in a suitable solvent such as ACN, and the like, at temperatures ranging from 50-100° C., for a period of 12-24 h, to provide a compound of Formula (I), where Ar¹ is substituted with 4-6 membered heterocycloalkyl.

A compound of Formula (I) where Ar¹ is substituted with an ester is saponified to a carboxylic acid using a base such as Cs₂CO₃, and the like, in a suitable solvent such as ACN, and the like, at a temperature of around 140° C. in a microwave reactor for 2 h, then the carboxylic acid is converted to an amide under conditions known to one skilled in the art, to privde and compound of Formula (I).

Conversion of a compound of Formula (I), where Ar³ is a pyrazine substituted with Cl, to a compound of Formula (I), where Ar³ is substituted with F, is achieved with CsF, in a solvent such as DMSO and the like, a temperatures ranging from 90-110° C., for a period of 2-4 h.

Conversion of a compounds of Formula (I), where Ar³ is a pyrimidine substituted with Cl, to a compound of Formula (I), where Ar¹' is substituted with. NH₂, is achieved with a solution of ammonia in MeOH, in a solvent such as THF, at a temperature around 100° C. under microwave irradiation for 8 h.

SCHEME J

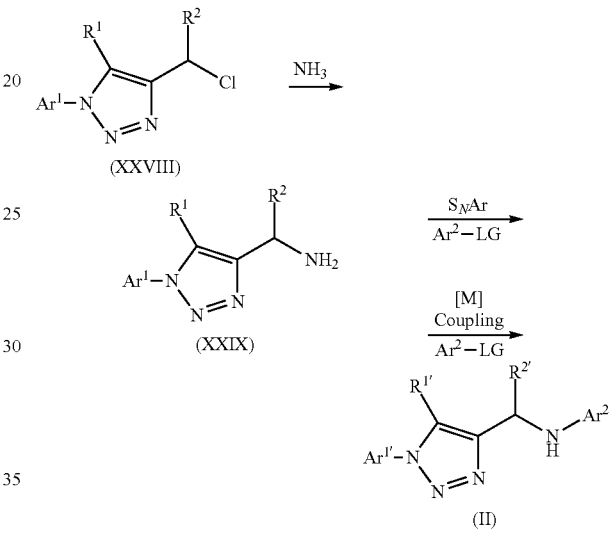

Referring to SCHEME J, a compound of Formula (II), where Ar² is pyrazole, oxazole, imidazole, pyrimidine, pyridine, or pyridazine substituted with one or two substituents, and R¹ and R² are H, is obtained from a compound of formula (XXVIII) by an S_NAr, S_N2, or metal mediated cross-coupling reaction.

A compound of Formula (II), where Ar² pyrimidine, pyridine, or pyridazine substituted with one or two substituents, and R¹ and R² are H, is obtained from a compound of formula (XXVIII) in two steps. In the first step, nucleophilic displacement of the chlorine in a compound of formula (XXVIII) with an amine, such as a solution of ammonia in methanol, provides the corresponding primary amine compound of formula (XXIX). Alternatively, nucleophilic displacement of the chlorine in a compound of formula (XXVIII) with phthalimide followed by deprotection using hydrazine hydrate provides the corresponding primary amine compound of formula (XXIX). In the second step, reaction of a compound of formula (XXIX) in a S_NAr reaction with Ar²-LG, where Ar² is a commercially available or synthetically accessible heteroaromatic five or six membered ring, and LG is a suitable leaving group such as F, Cl, Br, I, or OTf, in the presence of a base, such as NaH, Et₃N, K₂CO₃ and the like, in a solvent such as EtOH and the like, at temperatures ranging from room temperature (about 23° C.) to about 200° C., employing conventional or microwave heating. In a preferred method the base is Et₃N, the solvent is EtOH and the reaction was heated in a microwave reactor at 120° C. for 2 h and then at 150° C. for 10 min.

A compound of Formula (II), where Ar² is imidazole, pyrazole, pyrimidine, pyridine, or pyridazine substituted with one or two substituents, and R¹ and R² are H, is also obtained from a compound of formula (XXIX), by a metal mediated cross-coupling reaction with Ar²-LG, where Ar² is a commercially available or synthetically accessible heteroaromatic five or six membered ring, and LG is a suitable leaving group such as F, Cl, Br, I, or OTf, in the presence of a palladium catalyst such as Pd₂(dba)₃, Pd(OAc)₂, and the like, a phosphine ligand such as XPhos, tBuBrettPhos, and the like, a base such as KOtBu, LHMDS, and the like, in a suitable solvent such as toluene, DME, tBuOH, and DMF, at temperatures ranging from room temperature (about 23° C.) to about 110° C. In a preferred method the palladium catalyst is Pd₂(dba)₃, the ligand is tBuXPhos, the base is KOtBu, and the solvent is tBuOH.

A compound of Formula (II), where Ar² is pyrazole, pyrimidine, pyridine, or pyridazine substituted with one or two substituents, and R¹ and R² are H, is obtained from a compound of formula (XXVIII), in a S$_N$2 reaction with a compound of formula Ar²—NH₂. For example, a chloro compound of formula (XXVIII) is reacted with a compound of formula Ar²—NH₂, where a Ar²—NH₂ is a suitable commercially available or synthetically accessible amino-substituted heteroaryl compound, in the presence of a base, such as NaH, K₂CO₃, TEA, and the like, in a solvent such as DMF, EtOH, ACN and the like, at temperatures ranging from room temperature (about 23° C.) to about 100° C., for a period of about 3 h to 16 h, to provide a compound of Formula (II). In a preferred method the base is K₂CO₃, the solvent is DMF and the reaction is heated to 80° C.

SCHEME K

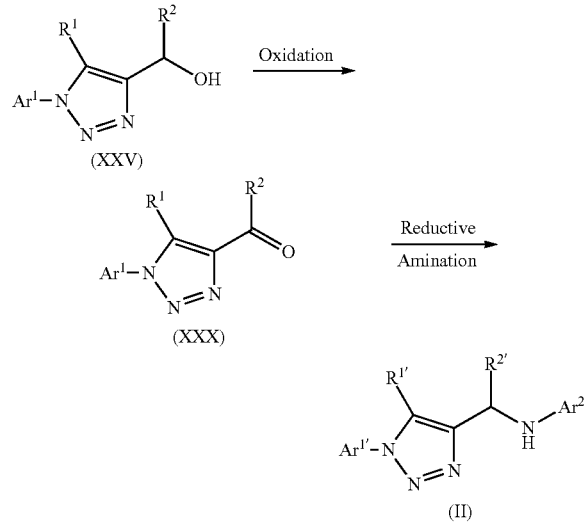

Referring to SCHEME K, a compound of Formula (II), where Ar² pyridine, oxazole, pyrazole, and R¹ and R² are H, is obtained from a compound of formula (XXV) in two steps. In the first step, a compound of formula (XXV) is oxidized to an aldehyde of formula (XXX) employing oxidation conditions known to one skilled in the art, for example, DMP (Dess-Martin periodinane), SO₃-pyridine, Swern conditions [(COCl)₂, DMSO, Et₃N], PCC, and the like, in a solvent such as EtOAc, DMSO, DCM, and the like, at temperatures ranging from about -78° C. to room temperature (about 23° C.). In a preferred method, a compound of formula (XXV) is oxidized to a compound of formula (XXX) with Dess-Martin periodinane, in DCM, at 20° C. for 4 hours. In the second step, a carbonyl compound of formula (XXX) is reacted with a compound of formula Ar²—NH₂, where a Ar²—NH₂ is a suitable commercially available or synthetically accessible amino-substituted heteroaryl compound, in a reductive amination reaction, a suitable reducing agent such as NaBH₄, NaHB(OAc)₃, NaBH₃CN and the like in a solvent such as MeOH, DCM and the like, at temperatures ranging from room temperature (about 23° C.) to about 50° C., for a period of 8-24 h to provide a compound of Formula (II). In a preferred method, the reducing agent is NaHB(OAc)₃ and the solvent is DCM.

Compounds of Formula (I) (as well as Formula (II)) may be converted to their corresponding salts using methods known to one of ordinary skill in the art. For example, an amine of Formula (I) (as well as Formula (II)) is treated with trifluoroacetic acid, HCl, or citric acid in a solvent such as Et₂O, CH₂Cl₂, THF, CH₃OH, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) (as well as Formula (II)) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na₂SO₄ or MgSO₄. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

Method A.

An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

Method B.

A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

Method C.

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

Method D.

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

or

Method E.

A Shimadzu LC-8A Series HPLC with a Sunfire C18 OBD column 15 (5 μm, 50×100 mm), mobile phase of 5% ACN in H2O (both with 0.05% TFA) was held for 1 min, then a gradient of 5-99% ACN over 14 min, then held at 99% ACN for 10 min, with a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

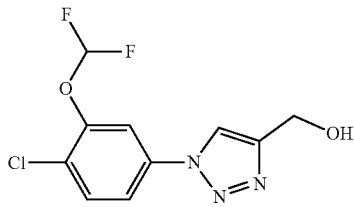 [SMILES: OCc1cn(-c2ccc(Cl)c(OC(F)F)c2)nn1]

Step A.
1-Chloro-2-(difluoromethoxy)-4-nitrobenzene

A mixture of 2-chloro-5-nitrophenol (10 g, 58 mmol), $K_2CO_3$ (9.4 g, 68 mmol), and sodium chlorodifluoroacetate (18 g, 115 mmol) in DMF (192 mL) and $H_2O$ (25 mL) was degassed with nitrogen for 5 minutes, and then the reaction mixture was heated to 100° C. for 2.5 h. The mixture was cooled to rt and 12 N HCl (17 mL) and $H_2O$ (25 mL) was added. The mixture was stirred at room temperature for 1 h. The resulting mixture was then cooled to 0° C., and an aqueous solution of 1 N NaOH (213 mL) was added portion wise. The reaction mixture was diluted with $H_2O$ and extracted with $Et_2O$ (2×). The organic layer was further washed with $H_2O$ (1×), dried ($Na_2SO_4$), filtered, and concentrated under reduced pressure. Purification (FCC, $SiO_2$, 0-50% DCM in hexanes) afforded the title compound (12 g, 55 mmol, 95% yield). $^1H$ NMR (400 MHz, $CDCl_3$) δ 8.15-8.12 (m, 1H), 8.08 (dd, J=8.8, 2.5 Hz, 1H), 7.65 (d, J=8.8 Hz, 1H), 6.65 (t, J=71.9 Hz, 1H).

Step B. 4-Chloro-3-(difluoromethoxy)aniline

To a solution of 1-chloro-2-(difluoromethoxy)-4-nitrobenzene (5 g, 22 mmol) in methanol (72 mL) was added Fe powder (5 g, 89 mmol) followed by the drop-wise addition of concentrated HCl (37% in $H_2O$, 19 mL). The reaction mixture was stirred at room temperature for 2 h. The reaction was quenched with ice water and basified with solid $NaHCO_3$. Celite® was added to the crude reaction mixture and stirred for 10 minutes. The heterogeneous mixture was filtered over a pad of Celite@ and the filtrate was concentrated under reduced pressure to remove MeOH. The resultant aqueous layer was extracted with DCM (3×). The combined organics were concentrated under reduced pressure to yield the title compound (3.3 g) as a light orange oil, which was used without further purification. MS (ESI) mass calcd. for $C_7H_6ClF_2NO$, 193.0; m/z found 194.1 $[M+H]^+$. $^1H$ NMR (400 MHz, $CDCl_3$) δ 7.16 (d, J=8.6 Hz, 1H), 6.68-6.28 (m, 3H), 3.77 (s, 2H).

Step C. (1-(4-Chloro-3-(difluoromethoxy)phenyl)-1H-1,2,3-triazol-4-yl)methanol

Two solutions, 4-chloro-3-(difluoromethoxy)aniline (2.5 g, 13 mmol) in 6 N HCl (6N HCl in iPrOH, 8 mL) and iPrOH (19 mL), and sodium nitrite (1 g, 15 mmol) in $H_2O$ (12 mL) were flowed through a LTF-MS mixer (0.2 mL) at 1 mL/min and 0.4 mL/min, respectively. The outcome was mixed with sodium azide (1 g, 15 mmol) in H₂O (12 mL) at 0.4 mL/min in a T-piece and flowed through a LTF-VS mixer (1 mL). The mixture was collected over K₂CO₃ (8.9 g, 65 mmol) in iPrOH (32 mL). The reaction mixture was stirred for 10 minutes after completion, and then propargyl alcohol (0.9 mL, 15 mmol), CuSO₄.5H₂O (322 mg, 1.29 mmol), and L-sodium ascorbate (256 mg, 1.29 mmol) were added to the crude reaction. The heterogeneous reaction mixture was stirred at rt overnight. The reaction was diluted with EtOAc, H₂O, and a saturated aqueous solution of NH₄Cl. The biphasic mixture was stirred for 5 min, and then the layers were separated and the aqueous layer further extracted with EtOAc (3×). The combined organics were dried (Na₂SO₄), filtered, and concentrated under reduced pressure to afford a dark orange solid. Purification (FCC, SiO₂, 40-100% EtOAc in hexanes) gave the title compound (2.9 g, 10 mmol, 80% yield). MS (ESI) mass calcd. for C₁₀H₈ClF₂N₃O₂, 275.0; m/z found 276.0 [M+H]⁺. ¹H NMR (400 MHz, CDCl₃) δ 8.04-7.94 (m, 1H), 7.74-7.67 (m, 1H), 7.64-7.60 (m, 1H), 7.59-7.54 (m, 1H), 6.64 (t, J=72.5 Hz, 1H), 4.91 (s, 2H).

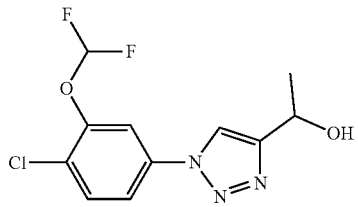 [SMILES: CC(O)c1cn(-c2ccc(Cl)c(OC(F)F)c2)nn1]

Step A.
4-Azido-1-chloro-2-(difluoromethoxy)benzene

Two solutions, 4-chloro-3-(difluoromethoxy)aniline (Intermediate 1, product from Step B, 0.8 g, 4.1 mmol) in 6 N HCl (6N HCl in PrOH, 2.6 mL) and iPrOH (6.4 mL), and sodium nitrite (342 mg, 4.96 mmol) in H₂O (12 mL) were flowed through a LTF-MS mixer (0.2 mL) at 1 ml/min and 0.4 mL/min, respectively. The outcome was mixed with sodium azide (322 mg, 4.96 mmol) in H₂O (4 mL) at 0.4 mL/min in a T-piece and flowed through a LTF-VS mixer (1 mL). The mixture was collected over K₂CO₃ (2.9 g, 21 mmol) in H₂O (10 mL). The reaction mixture was stirred for 10 minutes after completion. The crude reaction mixture was extracted with Et₂O (3×). The combined organics were dried (Na₂SO₄), filtered, and concentrated to a dark orange oil. The title compound was used crude in the next step without further purification.

Step B. R/S-1-(1-(4-Chloro-3-(difluoromethoxy)phenyl)-1H-1,2,3-triazol-4-yl)ethan-1-ol To a solution of the crude 4-azido-1-chloro-2-(difluoromethoxy)benzene (from Step A) 1:1 mixture of tBuOH/H₂O (14 mL) and 3-butyn-2-ol (0.37 mL, 4.96 mmol) was added CuSO₄.5H₂O (103 mg, 0.413 mmol), and L-sodium ascorbate (82 mg, 0.413 mmol). The reaction mixture stirred at room temperature over the weekend. The reaction was diluted with EtOAc, H₂O, and a saturated aqueous solution of NH₄Cl. The biphasic mixture was stirred for 5 min, and then the layers were separated and the aqueous layer further extracted with EtOAc (3×). The combined organics were dried (Na₂SO₄), filtered, and concentrated to a dark orange solid. Purification (FCC, SiO₂, 30-100% EtOAc in hexanes) afforded the title compound (785 mg, 2.71 mmol, 66% yield). MS (ESI) mass calcd. for C₁₁H₁₀ClF₂N₃O₂, 289.0; m/z found 290.1 [M+H]⁺. ¹H NMR (400 MHz, CDCl₃) δ 7.97-7.88 (m, 1H), 7.73-7.66 (m, 1H), 7.63-7.58 (m, 1H), 7.58-7.54 (m, 1H), 6.64 (t, J=72.6 Hz, 1H), 5.17 (q, J=6.5 Hz, 1H), 2.65 (s, 1H), 1.66 (d, J=6.5 Hz, 3H).

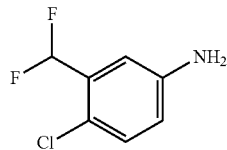 [SMILES: Nc1ccc(Cl)c(C(F)F)c1]

Step A. 1-Chloro-2-(difluoromethyl)-4-nitrobenzene

To 2-chloro-5-nitrobenzaldehyde (3.08 g, 16.61 mmol) stirring in DCM (50 mL) at rt was slowly added DAST (2.83 mL, 21.59 mmol), and the resulting solution was stirred at rt for 20 h. The completed reaction was poured over ice (100 g) and allowed to stir until all the ice was melted. The layers were separated and the aqueous layer was extracted with DCM (3×20 mL). The combined organics were washed once with brine (20 mL), dried (Na₂SO₄), and then concentrated under reduced pressure. The resulting orange residue (3.4 g, 98%) was carried forward without purification. ¹H NMR (500 MHz, CDCl₃) δ 8.55 (d, J=2.5 Hz, 1H), 8.33-8.27 (m, 1H), 7.67-7.62 (m, 1H), 6.98 (t, J=54.3 Hz, 1H).

Step B. 4-Chloro-3-(difluoromethyl)aniline

To a stirred mixture of 1-chloro-2-(difluoromethyl)-4-nitrobenzene (3.31 g, 15.95 mmol) and ammonium chloride (4.27 g, 79.73 mmol) in 5:1 acetone:water (90 mL) at 0° C. was added zinc powder (10.43 g, 159.46 mmol). The reaction was allowed to warm to rt and stirred for 16 h. Upon completion, the reaction was filtered through Celite@, concentrated under reduced pressure, and then taken in up in EtOAc (50 mL) and H₂O (50 mL). The layers were separated and the organic layer was washed with 1 M NaOH (3×15 mL), and then filtered again through Celite®. The resulting solution was dried (Na₂SO₄), and concentrated under reduced pressure to afford an orange oil that solidified upon standing (2.29 g, 78%). The material was carried forward crude without further purification. MS (ESI): mass calcd. for C₇H₆ClF₂N, 177.0; m/z found, 177.9 [M+H]⁺. ¹H NMR (500 MHz, CDCl₃) δ 7.19-7.13 (m, 1H), 6.94 (d, J=2.9 Hz, 1H), 6.87 (t, J=55.1 Hz, 1H), 6.73-6.67 (m, 1H).

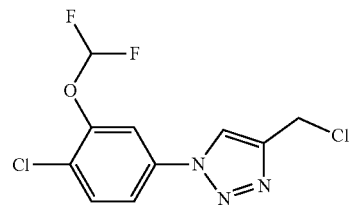 [SMILES: FC(F)Oc1cc(-n2cc(CCl)nn2)ccc1Cl]

To a solution of (1-(4-chloro-3-(difluoromethoxy)phenyl)-1H-1,2,3-triazol-4-yl)methanol (Intermediate 1, 243 mg, 0.882 mmol) in DCM (2 mL) was added thionyl chloride (2 mL). The reaction mixture was stirred at room temperature for 3 h. Upon completion the reaction mixture was poured over a solution of ice water and K₂CO₃. The biphasic mixture was stirred until all of the ice melted and the layers separated. The aqueous layer was further extracted with DCM (3×). The combined organics were dried (Na$_2$SO$_4$), filtered, and concentrated under reduced pressure to give the title compound as a yellow solid (231 mg), which was used without further purification. MS (ESI) mass calcd. for C$_{10}$H$_7$Cl$_2$F$_2$N$_3$O, 293.0; m/z found 294.1 [M+H]$^+$.

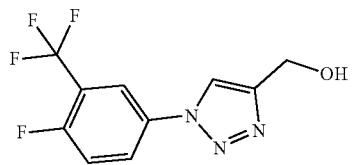 [SMILES: OCc1cn(-c2ccc(F)c(C(F)(F)F)c2)nn1]

Step A.
4-Azido-1-fluoro-2-(trifluoromethyl)benzene

4-Fluoro-3-(trifluoromethyl)aniline (1 mL, 7.77 mmol) was added via syringe to a cooled solution of TFA (6 mL)/H$_2$SO$_4$ (1.2 mL) at 0° C. A white ppt forms and the flask was removed from the ice bath and stirred until homogeneous (~15 min). The resulting solution was placed back in the ice bath and a solution of NaNO$_2$ (664 mg, 9.6 mmol) in water (5 mL) was added dropwise. After stirring for 30 min at 0° C. a solution of NaN$_3$ (880 mg, 13.5 mmol) in water (5 mL) was then added slowly. Caution: gas evolution observed. After the addition was complete the reaction mixture was warmed to rt. and stirred for an additional 30 min. Ether was added (75 mL) and the layers were separated. The organic layer was placed over aqueous NaHCO$_3$ (sat) and the acidic aqueous layer was extracted (1x) with ether and the organic layers combined, washed with aqueous NaHCO$_3$ (sat), brine, dried (MgSO$_4$), filtered, and concentrated under reduced pressure to afford the title compound which was used crude in the next step.

Step B. (1-(4-Fluoro-3-(trifluoromethyl)phenyl)-1H-1,2,3-triazol-4-yl)methanol

To a solution of 4-azido-1-fluoro-2-(trifluoromethyl)benzene in t-BuOH/water (20 mL; 1:1) was added prop-2-yn-1-ol (0.6 mL, 10.3 mmol); copper sulfate (195 mg, 0.78 mmol) and sodium ascorbate (152 mg, 0.77 mmol). The resulting mixture was stirred at rt overnight. The reaction was poured into water (200 mL) and extracted with EtOAc (3×50 mL). The combined organics were concentrated under reduced pressure. The residue was loaded directly onto SiO$_2$ (DCM/w trace MeOH). Purification (FCC, SiO$_2$, DCM/EtOAc (10% MeOH) 0-70%) afforded the title compound as an off white solid (87%). $^1$H NMR (500 MHz, CDCl$_3$) δ 8.02-7.98 (m, 2H), 7.98-7.93 (m, 1H), 7.43-7.36 (m, 1H), 4.97-4.87 (m, 2H), 2.24 (t, J=6.0 Hz, 1H).

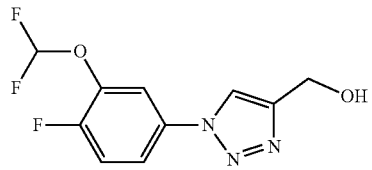 [SMILES: OCc1cn(-c2ccc(F)c(OC(F)F)c2)nn1]

Method A.

The title compound was prepared in a manner analogous to Intermediate 1. MS (ESI): mass calcd. for C$_{10}$H$_8$F$_3$N$_3$O$_2$, 259.1; m/z found, 260.1 [M+H]$^+$. $^1$H NMR (400 MHz, CDCl$_3$) δ 2.44 (s, 1H), 4.91 (s, 2H), 6.65 (t, J=72.6 Hz, 1H), 7.35 (t, J=9.2 Hz, 1H), 7.53-7.64 (m, 1H), 7.70 (dd, J=6.6, 2.7 Hz, 1H), 7.97 (s, 1H).

Method B.

Step A. 3-(Difluoromethoxy)-4-fluoroaniline

To a suspension of 2-(difluoromethoxy)-1-fluoro-4-nitrobenzene (1.4 g, 6.8 mmol) and Zn powder (4.0 g, 60.8 mmol) in acetone (31 mL) and water (3.1 mL) was added ammonium chloride (3.3 g, 60.8 mmol) at 0° C. Upon completion, the reaction mixture was filtered through a pad of Celite® and rinsed with MeOH. The filtrate was concentrated under vacuum. Purification (FCC, SiO$_2$, 0-10% EtOAc in hexanes) afforded (1.2 g, 6.6 mmol, 97%). MS (ESI): mass calcd. for C$_7$H$_6$F$_3$NO, 177.0; m/z found, 178.1 [M+H]$^+$. $^1$H NMR (400 MHz, DMSO-d$_6$) δ 7.10 (t, J=73.7 Hz, 1H), 6.99 (dd, J=10.8, 8.8 Hz, 1H), 6.49-6.45 (m, 1H), 6.39 (ddd, J=8.8, 3.8, 2.7 Hz, 1H), 5.20 (s, 2H).

Step B.
4-Azido-2-(difluoromethoxy)-1-fluorobenzene

Sodium nitrite (1.3 M in H$_2$O, 6.4 mL, 8.3 mmol) was added dropwise to a solution of 3-(difluoromethoxy)-4-fluoroaniline (1.2 g, 6.6 mmol) in TFA (5.1 mL, 66.1 mmol) and H$_2$SO$_4$ (1.1 mL, 19.8 mmol) at 0° C. The mixture was stirred at 0° C. for 30 min, and then sodium azide (1.3 M in H$_2$O, 8.9 mL, 11.6 mmol) was added dropwise at 0° C. The mixture was stirred at 0° C. for 30 min. Then, the mixture was diluted with Et$_2$O. The organic layer was collected, washed with a saturated aqueous solution of NaHCO$_3$ (until basic pH), dried (MgSO$_4$), filtered, and concentrated in vacuo to yield title product. The title product was carried as is to the next step.

Step C. (1-(3-(Difluoromethoxy)-4-fluorophenyl)-1H-1,2,3-triazol-4-yl)methanol

CuSO$_4$ (91 mg, 0.6 mmol) and (+)-sodium ascorbate (114 mg, 0.6 mmol) were added to a stirred solution of 4-azido-2-(difluoromethoxy)-1-fluorobenzene (1.2 g, 5.8 mmol) and propargyl alcohol (0.4 mL, 7.5 mmol) in distilled water (7.3 mL) and isopropanol (5.7 mL) at room temperature. Upon completion, water (40 mL) was added to the reaction mixture. The reaction mixture was extracted using EtOAc (3×60 mL). The combined organics were dried (MgSO$_4$), filtered, and concentrated under vacuum. Purification (FCC, SiO$_2$, 0-90% EtOAc in hexanes) afforded (1.3 g, 87%).

Method C.

Sodium azide (129 mg, 2.0 mmol) was added to a mixture of 2-(3-(difluoromethoxy)-4-fluorophenyl)-4,4,5,5-tetramethyl-1,3,2-dioxaborolane (380 mg, 1.3 mmol) and CuOAc$_2$ (48 mg, 0.3 mmol) in DMSO (4.5 mL) at room temperature. After 3 hours, propargyl alcohol (0.12 mL, 2.0) was added to the reaction mixture. After 16 h, water (20 mL) was added and the mixture was extracted using EtOAc (3×30 mL). The combined organics were dried (MgSO$_4$), filtered, and concentrated under vacuum. Purification (FCC, SiO$_2$, 0-40% EtOAc in hexanes) afforded (14 mg, 0.05, mmol, 4%). MS (ESI): mass calcd. for C$_{10}$H$_8$F$_3$N$_3$O$_2$, 259.1; m/z found, 259.9 [M+H]$^+$.

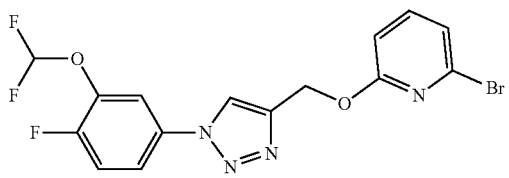 [SMILES: Fc1ccc(-n2cc(COc3cccc(Br)n3)nn2)cc1OC(F)F]

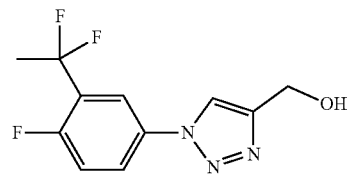

To a solution of (1-(3-(difluoromethoxy)-4-fluorophenyl)-1H-1,2,3-triazol-4-yl)methanol (Intermediate 6, 50 mg, 0.19 mmol) and 2-bromo-6-fluoropyridine (40.7 mg, 0.23 mmol) in DMF (1.2 mL) at 0° C. was added NaH (60% dispersion in mineral oil, 9.2 mg, 0.23 mmol). The reaction mixture was stirred at 0° C. for 2 h then quenched by the addition of water. The resulting precipitate was filtered to afford the title compound (75 mg, 93%) which was used crude without further purification. MS (ESI): mass calcd. for $C_{15}H_{10}BrF_3N_4O_2$, 413.99; m/z found, 414.0 [M+H]$^+$.

The title compound was prepared in a manner analogous to Intermediate 1. MS (ESI) mass calcd. for. $C_{11}H_{10}F_3N_3O$, 257.1; m/z found 258.0. $^1$H NMR (400 MHz, CDCl$_3$) δ 7.98 (t, J=0.7 Hz, 1H), 7.95-7.87 (m, 1H), 7.87-7.78 (m, 1H), 7.31 (dd, J=9.9, 8.9 Hz, 1H), 4.91 (d, J=0.7 Hz, 2H), 2.05 (td, J=18.6, 1.2 Hz, 3H).

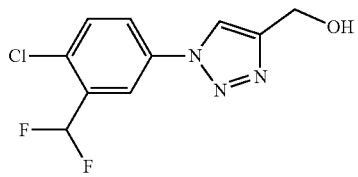 [SMILES: OCc1cn(-c2ccc(Cl)c(C(F)F)c2)nn1]

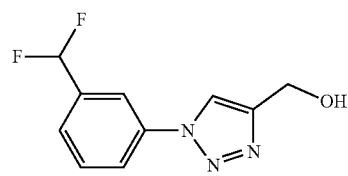 [SMILES: OCc1cn(-c2cccc(C(F)F)c2)nn1]

The title compound was prepared in a manner analogous to Intermediate 1. MS (ESI): mass calcd. for $C_{10}H_6ClF_2N_3O$, 259.0; m/z found, 260.0 [M+H]$^+$. $^1$H NMR (500 MHz, CDCl$_3$) δ 8.37 (s, 1H), 8.35 (d, J=2.6 Hz, 1H), 8.25-8.19 (m, 1H), 7.97-7.93 (m, 1H), 7.34 (t, J=54.6 Hz, 1H), 5.25 (s, 2H), 2.72 (s, 1H).

The title compound was prepared in a manner analogous to Intermediate 1, Step C, using 3-(difluoromethyl)aniline. MS (ESI): mass calcd. For $C_{10}H_9F_2N_3O$, 225.1; m/z found, 226.1 [M+H]$^+$.

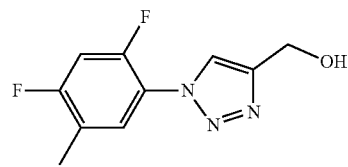 [SMILES: Cc1cc(-n2cc(CO)nn2)c(F)cc1F]

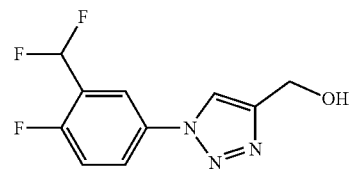

The title compound was prepared in a manner analogous to Intermediate 1, Step C, using 2,4-difluoro-5-methylaniline. MS (ESI): mass calcd. For $C_{10}H_9F_2N_3O$, 225.1; m/z found, 226.1 [M+H]$^+$.

The title compound was prepared in a manner analogous to Intermediate 1. MS (ESI): mass calcd. for $C_{10}H_6F_3N_3O$, 243.1; m/z found, 244.1 [M+H]$^+$. $^1$H NMR (400 MHz, CDCl$_3$) δ 2.26 (br t, J=5.78 Hz, 1H) 4.91 (d, J=5.32 Hz, 2H) 6.76-7.15 (m, 1H) 7.33 (t, J=9.02 Hz, 1H) 7.85-7.97 (m, 2H) 8.00 (s, 1H).

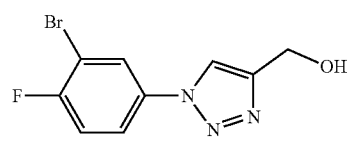

The title compound was prepared in a manner analogous to Intermediate 1. MS (ESI): mass calcd. for $C_9H_7BrFN_3O$, 270.98; m/z found, 274.0 [M+H+2]$^+$.

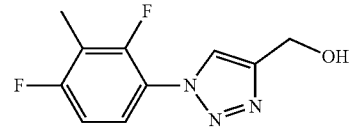

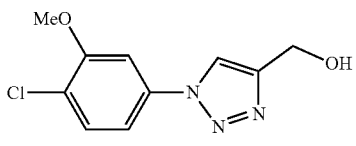 [SMILES: COc1cc(-n2cc(CO)nn2)ccc1Cl]

The title compound was prepared in a manner analogous to Intermediate 1. MS (ESI): mass calcd. for $C_{10}H_9F_2N_3O$, 225.1; m/z found, 226.2 [M+H]$^+$. Intermediate 11. (1-(3-(1,1-Difluoroethyl)-4-fluorophenyl)-1H-1,2,3-triazol-4-yl)methanol.

The title compound was prepared in a manner analogous to Intermediate 1. MS (ESI): mass calcd. for $C_{10}H_{10}ClN_3O_2$, 239.1; m/z found, 240.0 [M+H]$^+$. $^1$H NMR (400 MHz, CDCl$_3$) δ 7.97 (s, 1H), 7.49 (d, J=8.5 Hz, 1H), 7.46 (d, J=2.3 Hz, 1H), 7.15 (dd, J=8.5, 2.4 Hz, 1H), 4.90 (s, 2H), 4.00 (s, 3H).

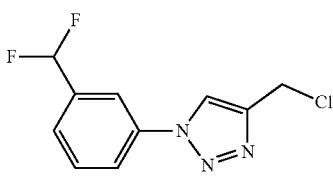 [SMILES: FC(F)c1cccc(-n2cc(CCl)nn2)c1]

The title compound was prepared in a manner analogous to Intermediate 4. MS (ESI) mass calcd. for $C_{10}H_9F_2N_3O$, 225.1; m/z found 226.1.

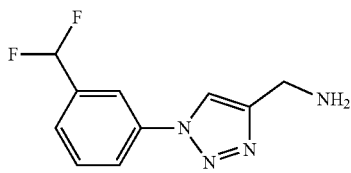 [SMILES: NCc1cn(-c2cccc(C(F)F)c2)nn1]

4-(Chloromethyl)-1-(3-(difluoromethyl)phenyl)-1H-1,2,3-triazole (Intermediate 16, 309.0 mg, 1.27 mmol) was placed in a pressure flask and then dissolved in $NH_3$ (7M in MeOH (13.73 mL, 7 M, 96.13 mmol). The flask was sealed, and the reaction was stirred at 45° C. for 20 h. The solvent evaporated under reduced pressure. Purification (FCC, $SiO_2$, 0-8% MeOH in DCM) afforded the title compound (124.7 mg, 44%). MS (ESI): mass calcd. for $C_{10}H_{10}F_2N_4$, 224.1; m/z found, 225.0 [M+H]$^+$. $^1$H NMR (600 MHz, $CD_3OD$) δ 8.63 (s, 1H), 8.14-8.11 (m, 1H), 8.09-8.05 (m, 1H), 7.82-7.77 (m, 1H), 7.77-7.73 (m, 1H), 6.97 (t, J=55.9 Hz, 1H), 4.26 (s, 2H).

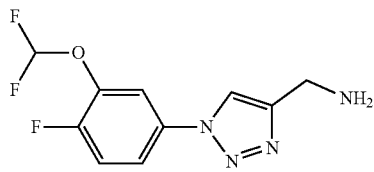 [SMILES: NCc1cn(-c2ccc(F)c(OC(F)F)c2)nn1]

The title compound was prepared in a manner analogous to Intermediate 17. MS (ESI): mass calcd. for $C_{10}H_9F_3N_4O$, 258.1; m/z found, 259.0 [M+H]$^+$. $^1$H NMR (400 MHz, DMSO-d$_6$) S ppm 4.20 (s, 2H) 7.45 (t, J=72.7 Hz, 1H) 7.68-7.77 (m, 1H) 7.85 (dt, J=8.8, 3.4 Hz, 1H) 7.98 (dd, J=6.9, 2.7 Hz, 1H) 8.64 (br s, 3H) 8.95 (s, 1H).

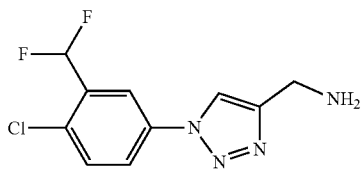 [SMILES: NCc1cn(-c2ccc(Cl)c(C(F)F)c2)nn1]

Step A. 1-(4-Chloro-3-(difluoromethyl)phenyl)-4-(chloromethyl)-1H-1,2,3-triazole To (1-(4-Chloro-3-(difluoromethyl)phenyl)-1H-1,2,3-triazol-4-yl)methanol (Intermediate 8, 1.65 g, 6.3 mmol) stirring in DCM (16 mL) was slowly added SOCl$_2$ (4 mL, 55 mmol). The mixture was stirred at rt overnight, then poured into a mixture of ice water and $K_2CO_3$. After all the ice was melted, the layers were separated and the aqueous layer was extracted with DCM (3×). The combined organic layers were washed with brine, dried ($Na_2SO_4$), then concentrated under reduced pressure to afford an orange solid that was used without purification (1.66 g, 94%).

Step B. 2-((1-(4-Chloro-3-(difluoromethyl)phenyl)-1H-1,2,3-triazol-4-yl)methyl)isoindoline-1,3-dione To 1-(4-chloro-3-(difluoromethyl)phenyl)-4-(chloromethyl)-1H-1,2,3-triazole (152 mg, 0.55 mmol) in DMF (2.7 mL) was added phthalimide (96 mg, 0.65 mmol) followed by $K_2CO_3$ (226 mg, 1.6 mmol). The reaction was stirred at 80° C. for 1 h, then cooled to rt and diluted with EtOAc and $H_2O$. The layers were separated and the aqueous layer was extracted with DCM (×3), then the combined organic layers were concentrated under reduced pressure to afford an orange solid that was used without purification.

Step C. (1-(4-Chloro-3-(difluoromethyl)phenyl)-1H-1,2,3-triazol-4-yl)methanamine To 2-((1-(4-chloro-3-(difluoromethyl)phenyl)-1H-1,2,3-triazol-4-yl)methyl)isoindoline-1,3-dione (212 mg, 0.55 mmol) stirring in EtOH (5 mL) was added hydrazine hydrate (0.03 mL, 0.65 mmol) and the mixture was stirred at reflux (80° C.) for 1 h. The reaction was cooled to rt and concentrated under reduced pressure. Purification (FCC, $SiO_2$, 10% 2 M $NH_3$ in MeOH/DCM 0-100%) afforded the title compound as pale yellow solid (116 mg, 82%). MS (ESI): mass calcd. for $C_{10}H_9ClF_2N_4$, 258.0; m/z found, 259.0 [M+H]$^+$.

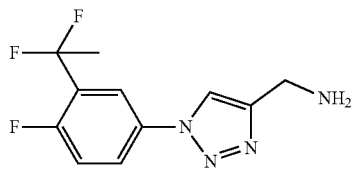 [SMILES: CC(F)(F)c1cc(-n2cc(CN)nn2)ccc1F]

The title compound was prepared in a manner analogous to Intermediate 19, steps A-C, using (1-(3-(1,1-difluoroethyl)-4-fluorophenyl)-1H-1,2,3-triazol-4-yl)methanol (Intermediate 11) in step A. MS (ESI): mass calcd. for $C_{11}H_{11}F_3N_4$, 256.1; m/z found, 257.1 [M+H]$^+$. $^1$H NMR (500 MHz, $CD_3OD$) δ 8.48-8.43 (m, 1H), 8.06 (dd, J=6.3, 2.8 Hz, 1H), 8.04-7.99 (m, 1H), 7.52-7.45 (m, 1H), 4.02 (s, 2H), 2.07 (td, J=18.8, 1.1 Hz, 3H).

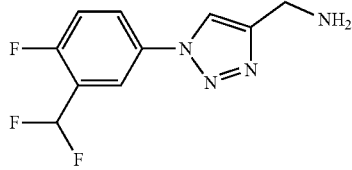 [SMILES: NCc1cn(-c2ccc(F)c(C(F)F)c2)nn1]

The title compound was prepared in a manner analogous to Intermediate 19, Steps A-C, using (1-(3-(difluoromethyl)-4-fluorophenyl)-1H-1,2,3-triazol-4-yl)methanol (Intermediate 9) in Step A. MS (ESI) mass calcd. for $C_{10}H_9F_3N_4$, 242.1; m/z found 243.0 [M+1].

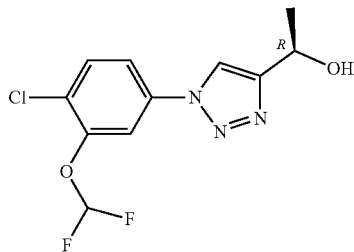

The title compound was prepared in a manner analogous to Intermediate 2 using 4-chloro-3-(difluoromethoxy)aniline and in Step A and (R)-(+)-3-butyn-2-ol in Step B. MS (ESI): mass calcd. for $C_{11}H_{10}ClF_2N_3O_2$, 289.7; m/z found, 290.1 [M+H]$^+$. $^1$H NMR (400 MHz, DMSO-d$_6$) δ 8.76 (s, 1H), 7.98 (d, J=2.3 Hz, 1H), 7.90-7.81 (m, 2H), 7.45 (t, J=72.8 Hz, 1H), 5.44 (d, J=4.8 Hz, 1H), 4.92 (qd, J=6.5, 4.7 Hz, 1H), 1.48 (d, J=6.5 Hz, 3H).

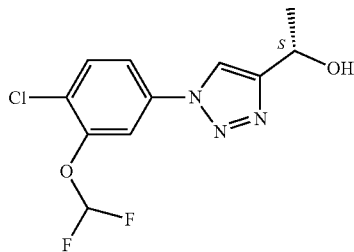

The title compound was prepared in a manner analogous to Intermediate 2 using 4-chloro-3-(difluoromethoxy)aniline and in Step A and (S)-(+)-3-butyn-2-ol in Step B. MS (ESI): mass calcd. for $C_{11}H_{10}ClF_2N_3O_2$, 289.7; m/z found, 290.1 [M+H]$^+$. $^1$H NMR (400 MHz, DMSO-d$_6$) δ 8.75 (s, 1H), 7.98 (d, J=2.3 Hz, 1H), 7.91-7.79 (m, 2H), 7.45 (t, J=72.8 Hz, 1H), 5.44 (d, J=4.8 Hz, 1H), 4.92 (qd, J=6.5, 4.6 Hz, 1H), 1.47 (d, J=6.5 Hz, 3H).

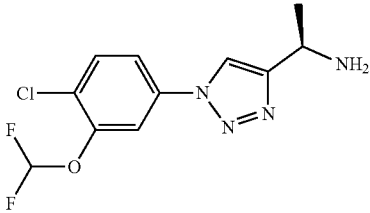 [SMILES: C[C@@H](N)c1cn(-c2ccc(Cl)c(OC(F)F)c2)nn1]

The title compound was made analogous to Intermediate 19 using (R)-1-(1-(4-chloro-3-(difluoromethoxy)phenyl)-1H-1,2,3-triazol-4-yl)ethan-1-ol (Intermediate 22) in step A.MS (ESI): mass calcd. for $C_{11}H_{11}ClF_2N_4O$, 288.1; m/z found, 289.0 [M+H]$^+$.

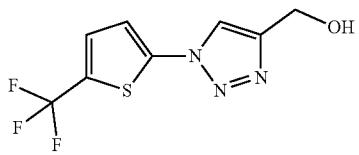 [SMILES: OCc1cn(-c2ccc(C(F)(F)F)s2)nn1]

Step A. tert-butyl (5-(Trifluoromethyl)thiophen-2-yl)carbamate

To a solution of 5-(trifluoromethyl)thiophene-2-carboxylic acid (2.5 g, 12.75 mmol) in tert-butyl alcohol (64 mL) was added triethylamine (1.78 mL, 12.75 mmol) followed by diphenylphosphorylazide (2.75 mL, 12.75 mmol). The resulting reaction mixture was heated to 90° C. and stirred overnight. The reaction was cooled to room temperature and the solvent was removed under reduced pressure. The resulting residue was redissolved in ethyl acetate (50 mL) and washed with a saturated aqueous solution of NaHCO$_3$, citric acid (10% aq) and brine. The combined organic layers were dried (Na$_2$SO$_4$), filtered, and concentrated into a brown oil which was purified via FCC (using 5-20% ethyl acetate/hexanes) to provide the desired product as a white solid (804 mg, 3.01 mmol, 23%). MS (ESI): mass calcd. for $C_{10}H_{12}F_3NO_2S$, 267.2; m/z found, 268.1 [M+H]$^+$. $^1$H NMR (500 MHz, CDCl$_3$) δ 7.16-7.14 (m, 1H), 6.40-6.37 (m, 1H), 1.55-1.50 (m, 9H).

Step B. 5-(Trifluoromethyl)thiophen-2-amine HCl salt

To a solution of tert-butyl (5-(trifluoromethyl)thiophen-2-yl)carbamate (804 mg, 3.01 mmol) in dioxane (8 mL) was added 4M HCl in dioxane (3.76 mL, 15.04 mmol). The resulting reaction mixture was allowed to stir overnight at room temperature. The reaction mixture was subsequently concentrated into a white solid (under reduced pressure), which was washed with ether to provide the desired product (584 mg, 2.868 mmol, 95.3%). Quantitative yield was assumed and the intermediate was used without further purification. MS (ESI): mass calcd. for $C_5H_4F_3NS$, 203.6; m/z found, 204.1 [M+H]$^+$. $^1$H NMR (500 MHz, DMSO-d$_6$) δ 7.13-7.09 (m, 1H), 5.90-5.84 (d, J=4.0 Hz, 1H).

Step C. 2-Azido-5-(trifluoromethyl)thiophene

To a solution of 5-(trifluoromethyl)thiophen-2-amine HCl salt (150 mg, 0.74 mmol) in TFA (0.56 mL, 7.4 mmol), H$_2$SO$_4$ (0.118 mL, 2.21 mmol) and water (4 mL) at 0° C. was slowly added a 1.3 M aq. solution of sodium nitirite (0.71 mL, 0.92 mmol). The resulting reaction mixture was stirred at 0° C. for 30 minutes and then a 1.3 M aq. solution of sodium azide (0.992 mL, 1.29 mmol) in water (4 mL) was added dropwise. The reaction mixture was stirred for an additional 30 minutes and then diluted with ether (10 mL). The organic layer was isolated and washed with saturated NaHCO$_3$ solution (until pH8), dried (Na$_2$SO$_4$), filtered, and concentrated under reduced pressure to yield the desired product (142 mg, 0.74 mmol). A quantitative yield was assumed and the crude material was carried forward without further purification.

Step D. (1-(5-(Trifluoromethyl)thiophen-2-yl)-1H-1,2,3-triazol-4-yl)methanol To a solution of 2-azido-5-(trifluoromethyl)thiophene (150 mg, 0.78 mmol) and propargyl alcohol (0.06 mL, 1.01 mmol) in isopropyl alcohol (1 mL) and water (1 mL) at room temperature was added copper (II) sulfate (14 mg, 0.08 mmol), and sodium ascorbate (15 mg, 0.08 mmol). The resulting reaction mixture was stirred for 3 hours and then diluted with water (10 mL) and extracted with ethyl acetate (3×20 mL). The combined organic layers were dried (MgSO$_4$), filtered, and concentrated under reduced pressure.

Purification (FCC, SiO$_2$, 0-90% ethyl acetate in hexanes) afforded the title compound (94 mg, 0.38 mmol, 48%). MS (ESI): mass calcd. for C$_8$H$_6$F$_3$N$_3$OS, 249.2; m/z found, 250.1 [M+H]$^+$. $^1$H NMR (400 MHz, CDCl$_3$) δ 8.06-7.86 (s, 1H), 7.46-7.32 (m, 1H), 7.23-7.10 (d, J=4.1 Hz, 1H), 4.98-4.76 (s, 2H), 2.79-2.63 (s, 1H).

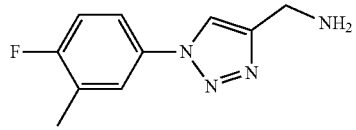

The title compound was prepared in a manner analogous to Intermediate 19, steps A-C, using (1-(4-fluoro-3-methylphenyl)-1H-1,2,3-triazol-4-yl)methanol in Step A. MS (ESI): mass calcd. for C$_{10}$H$_{11}$FN$_4$, 206.1; m/z found, 207.0 [M+H]$^+$.

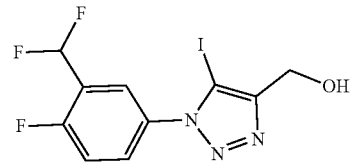 [SMILES: OCc1nnn(-c2ccc(F)c(C(F)F)c2)c1I]

Step A. 4-Azido-2-(difluoromethyl)-1-fluorobenzene

The title compound was prepared in a manner analogous to Intermediate 6, Method B, Steps A-B using 2-(difluoromethyl)-1-fluoro-4-nitrobenzene in Step A.

Step B. (1-(3-(Difluoromethyl)-4-fluorophenyl)-5-iodo-1H-1,2,3-triazol-4-yl)methanol 4-Azido-2-(difluoromethyl)-1-fluorobenzene (336 mg, 1.8 mmol), copper(II) perchlorate hexahydrate (1.3 g, 3.6 mmol) and NaI (1.1 g, 7.2 mmol) were pre-mixed in ACN (8 mL). After 5 minutes, propargyl alcohol (0.14 mL, 2.3 mmol) and DBU (0.27 mL, 1.8 mmol) were added. Upon completion, the reaction mixture was diluted in DCM (40 mL) and NH$_4$OH (28% NH$_3$ in water, 50 mL) was added. The crude material was triturated in DCM. The solids were collected by filtration, rinsed with DCM and dried under reduced pressure to yield the title compound (249 mg, 38%). MS (ESI): mass calcd. for C$_{10}$H$_7$F$_3$IN$_3$O, 369.0; m/z found, 369.8 [M+H]$^+$. $^1$H NMR (400 MHz, DMSO-d$_6$) δ 7.93-7.85 (m, 2H), 7.74-7.66 (m, 1H), 7.32 (t, J=53.9 Hz, 1H), 5.31 (t, J=5.4 Hz, 1H), 4.54 (d, J=5.4 Hz, 2H).

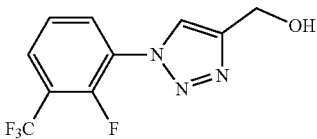

The title compound was prepared in a manner analogous to Intermediate 6, Method B, using 2-fluoro-1-nitro-3-(trifluoromethyl)benzene in Step A. MS (ESI): mass calcd. for C$_{10}$H$_7$F$_4$N$_3$O, 261.1; m/z found, 261.9 [M+H]$^+$. $^1$H NMR (500 MHz, DMSO-d$_6$) δ 8.56-8.54 (m, 1H), 8.21-8.15 (m, 1H), 8.02-7.98 (m, 1H), 7.66 (tt, J=8.0, 1.0 Hz, 1H), 5.38 (t, J=5.7 Hz, 1H), 4.64 (dd, J=5.6, 0.8 Hz, 2H).

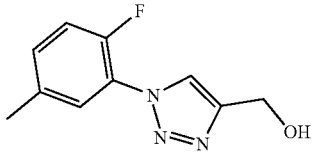

The title compound was prepared in a manner analogous to Intermediate 6, Method B, Steps B-C, using 2-fluoro-5-methylaniline in Step B. MS (ESI): mass calcd. for C$_{10}$H$_{10}$FN$_3$O, 207.1; m/z found, 208.0 [M+H]$^+$. $^1$H NMR (400 MHz, DMSO-d$_6$) δ 8.40 (dt, J=2.2, 0.7 Hz, 1H), 7.66-7.61 (m, 1H), 7.48-7.36 (m, 2H), 5.32 (t, J=5.6 Hz, 1H), 4.62 (d, J=5.2 Hz, 2H), 2.40-2.37 (m, 3H).

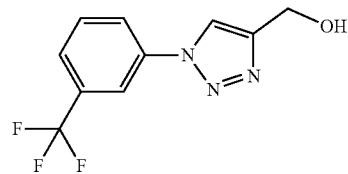 [SMILES: OCc1cn(-c2cccc(C(F)(F)F)c2)nn1]

The title compound was prepared in a manner analogous to Intermediate 6, Method B, using 3-(trifluoromethyl)aniline in Step B. MS (ESI): mass calcd. for C$_{10}$H$_6$F$_3$N$_3$O, 243.1; m/z found, 244.0 [M+H]$^+$. $^1$H NMR (500 MHz, DMSO-d$_6$) δ 8.88 (s, 1H), 8.31-8.25 (m, 2H), 7.88-7.82 (m, 2H), 5.38 (t, J=5.6 Hz, 1H), 4.63 (d, J=5.5 Hz, 2H).

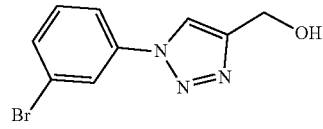 [SMILES: OCc1cn(-c2cccc(Br)c2)nn1]

The title compound was prepared in a manner analogous to Intermediate 6, Method B, Step B-C using 3-bromoaniline in Step B. $^1$H NMR (300 MHz, CDCl$_3$) δ 7.97 (s, 1H), 7.94 (t, J=1.7 Hz, 1H), 7.68 (dd, J=8.1, 0.9 Hz, 1H), 7.58 (d, J=8.6 Hz, 1H), 7.41 (t, J=8.1 Hz, 1H), 4.90 (s, 2H). OH was not observed.

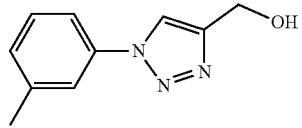

The title compound was prepared in a manner analogous to Intermediate 2 using m-toluidine in Step A and propargyl alcohol in Step B. MS (ESI): mass calcd. for C$_{10}$H$_{11}$N$_3$O, 189.2; m/z found, 190.1 [M+H]$^+$. $^1$H NMR (500 MHz, DMSO-d$_6$) δ 8.64 (d, J=0.7 Hz, 1H), 7.77-7.73 (m, 1H), 7.71-7.64 (m, 1H), 7.46 (t, J=7.8 Hz, 1H), 7.29 (ddt, J=7.6, 1.7, 0.9 Hz, 1H), 5.31 (t, J=5.6 Hz, 1H), 4.61 (dd, J=5.6, 0.7 Hz, 2H), 2.50 (p, J=1.9 Hz, 3H).

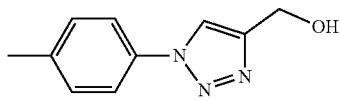

The title compound was prepared in a manner analogous to Intermediate 2 using p-toluidine in Step A and propargyl alcohol in Step B. MS (ESI): mass calcd. for $C_{10}H_{11}N_3O$, 189.2; m/z found, 190.1 [M+H]$^+$.

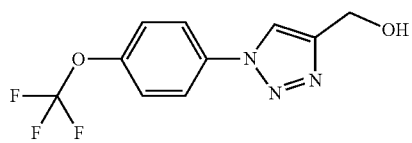 [SMILES: OCc1cn(-c2ccc(OC(F)(F)F)cc2)nn1]

The title compound was prepared in a manner analogous to Intermediate 2 using 4-(trifluoromethoxy)aniline in Step A and propargyl alcohol in Step B. MS (ESI): mass calcd. for $C_{10}H_8F_3N_3O_2$, 259.2; m/z found, 260.1 [M+H]$^+$.

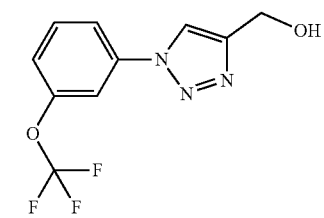 [SMILES: OCc1cn(-c2cccc(OC(F)(F)F)c2)nn1]

The title compound was prepared in a manner analogous to Intermediate 2 using 3-(trifluoromethoxy)aniline in Step A and propargyl alcohol in Step B. MS (ESI): mass calcd. for $C_{10}H_8F_3N_3O_2$, 259.2; m/z found, 260.1 [M+H]$^+$.

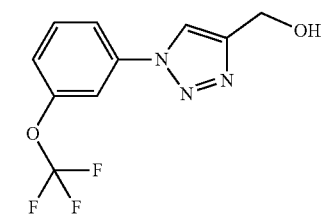

The title compound was prepared in a manner analogous to Intermediate 2 using 3,5-dimethylaniline in Step A and propargyl alcohol in Step B. MS (ESI): mass calcd. for $C_{11}H_{13}N_3O$, 203.2; m/z found, 204.2 [M+H]$^+$.

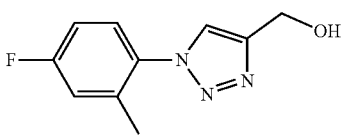

The title compound was prepared in a manner analogous to Intermediate 2 using 4-fluoro-2-methylaniline in Step A and propargyl alcohol in Step B. MS (ESI): mass calcd. for $C_{10}H_{10}FN_3O$, 207.2; m/z found, 208.1 [M+H]$^+$.

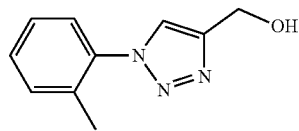

The title compound was prepared in a manner analogous to Intermediate 2 using o-toluidine in Step A. MS (ESI): mass calcd. for $C_{10}H_{11}N_3O$, 189.2; m/z found, 190.1 [M+H]$^+$.

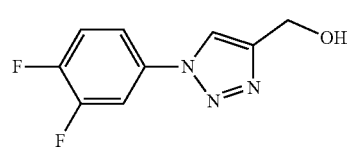

The title compound was prepared in a manner analogous to Intermediate 2 using 3,4-difluoroaniline in Step A and propargyl alcohol. MS (ESI): mass calcd. for $C_9H_7F_2N_3O$, 211.2; m/z found, 212.1 [M+H]$^+$.

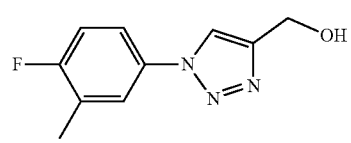

The title compound was prepared in a manner analogous to Intermediate 2 using 4-fluoro-3-methylaniline in Step A and propargyl alcohol in Step B. MS (ESI): mass calcd. for $C_{10}H_{10}FN_3O$, 207.2; m/z found, 208.1 [M+H]$^+$.

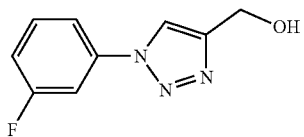 [SMILES: OCc1cn(-c2cccc(F)c2)nn1]

The title compound was prepared in a manner analogous to Intermediate 2 using 3-fluoroaniline in Step A and propargyl alcohol in Step B. MS (ESI): mass calcd. for $C_9H_8FN_3O$, 193.2; m/z found, 194.1 [M+H]$^+$.

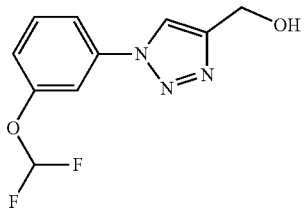 [SMILES: OCc1cn(-c2cccc(OC(F)F)c2)nn1]

The title compound was prepared in a manner analogous to Intermediate 2 using 3-(difluoromethoxy)aniline in Step A and propargyl alcohol in Step B. MS (ESI): mass calcd. for $C_{10}H_9F_2N_3O_2$, 241.2; m/z found, 242.0 [M+H]$^+$.

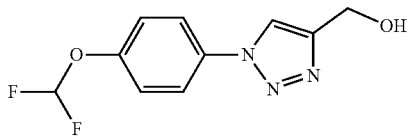 [SMILES: OCc1cn(-c2ccc(OC(F)F)cc2)nn1]

The title compound was prepared in a manner analogous to Intermediate 2 using 4-(difluoromethoxy)aniline in Step A and propargyl alcohol in Step B. MS (ESI): mass calcd. for $C_{10}H_6F_2N_3O_2$, 241.2; m/z found, 242.0 [M+H]$^+$.

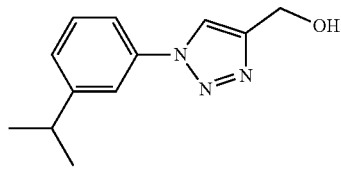 [SMILES: CC(C)c1cccc(-n2cc(CO)nn2)c1]

The title compound was prepared in a manner analogous to Intermediate 2 using 3-isopropylaniline in Step A and propargyl alcohol in Step B. MS (ESI): mass calcd. for $C_{10}H_8F_2N_3O_2$, 241.2; m/z found, 242.0 [M+H]$^+$.

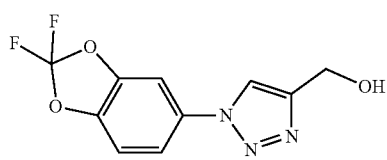 [SMILES: OCc1cn(-c2ccc3c(c2)OC(F)(F)O3)nn1]

The title compound was prepared in a manner analogous to Intermediate 2 using 2,2-difluoro-5-aminobenzodioxole in Step A and propargyl alcohol in Step B. MS calcd. for $C_{10}H_7F_2N_3O_3$, 255.2; m/z found, 256.1 [M+H]$^+$. $^1$H NMR (400 MHz, DMSO-d$_6$) δ 8.67 (d, J=0.7 Hz, 1H), 8.07 (d, J=2.2 Hz, 1H), 7.78 (dd, J=8.7, 2.2 Hz, 1H), 7.64 (d, J=8.7 Hz, 1H), 5.36 (t, J=5.5 Hz, 1H), 4.61 (dd, J=5.6, 0.7 Hz, 2H).

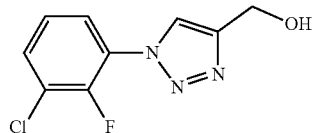 [SMILES: OCc1cn(-c2cccc(Cl)c2F)nn1]

The title compound was prepared in a manner analogous to Intermediate 2 using 3-chloro-2-fluoroaniline in Step A and propargyl alcohol in Step B. MS (ESI): mass calcd. for $C_9H_7ClFN_3O$, 227.6; m/z found, 228.0 [M+H]$^+$.

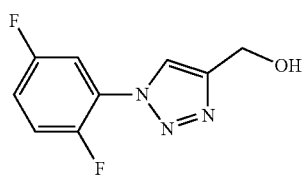 [SMILES: OCc1cn(-c2cc(F)ccc2F)nn1]

The title compound was prepared in a manner analogous to Intermediate 2 using 2,5-difluoroaniline in Step A and propargyl alcohol in Step B. MS (ESI): mass calcd. for $C_9H_7F_2N_3O$, 211.2; m/z found, 212.1 [M+H]$^+$.

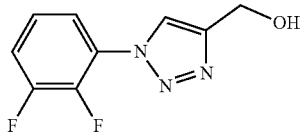 [SMILES: OCc1cn(-c2cccc(F)c2F)nn1]

The title compound was prepared in a manner analogous to Intermediate 2 using 2,3-difluoroaniline in Step A and propargyl alcohol in Step B. MS (ESI): mass calcd. for $CH_7F_2N_3O$, 211.2; m/z found, 212.1 [M+H]$^+$.

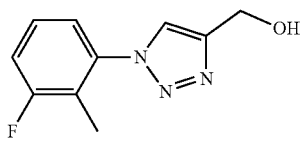

The title compound was prepared in a manner analogous to Intermediate 2 using 3-fluoro-2-methylaniline in Step A and propargyl alcohol in Step B. MS (ESI): mass calcd. for $C_{10}H_{10}FN_3O$, 207.2; m/z found, 208.1 [M+H]$^+$.

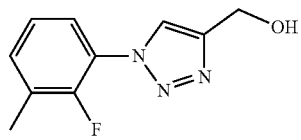

The title compound was prepared in a manner analogous to Intermediate 2 using 2-fluoro-3-methylaniline in Step A and propargyl alcohol in Step B. MS (ESI): mass calcd. for $C_{12}H_{13}N_3O$, 215.3; m/z found, 216.1 [M+H]$^+$.

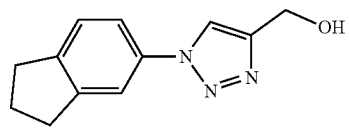 [SMILES: OCc1cn(-c2ccc3c(c2)CCC3)nn1]

The title compound was prepared in a manner analogous to Intermediate 2 using 5-aminoindan in Step A and propargyl alcohol in Step B. MS (ESI): mass calcd. for $C_{10}H_{10}FN_3O$, 207.2; m/z found, 208.1 [M+H]$^+$.

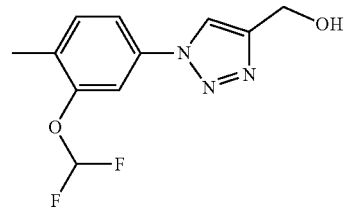 [SMILES: Cc1ccc(-n2cc(CO)nn2)cc1OC(F)F]

The title compound was prepared in a manner analogous to Intermediate 1, Step C, using 3-(difluoromethoxy)-4-methylaniline. MS (ESI): mass calcd. for $C_{11}H_{11}F_2N_3O_2$, 255.1; m/z found, 256.0 [M+H]$^+$.

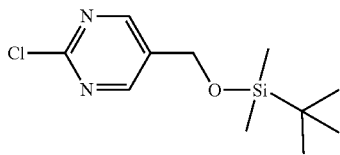 [SMILES: CC(C)(C)[Si](C)(C)OCc1cnc(Cl)nc1]

To (2-chloropyrimidin-5-yl)methanol (946 mg, 6.5 mmol) stirring in DCM (38 mL) at rt was added imidazole (477 mg, 7 mmol) followed by tert-butyl(chloro)dimethylsilane (1 g, 6.9 mmol). The reaction was stirred at rt for 30 mins, then diluted with water. The layers were separated and the aqueous layer was extracted with DCM (×3), dried (Na$_2$SO$_4$), and concentrated under reduced pressure. Purification (FCC, SiO$_2$, EtOAc/hexanes 0-10%) afforded the title compound as a clear, colorless oil that solidified upon standing (1.37 g, 81%). MS (ESI): mass calcd. for C$_{11}$H$_{19}$ClN$_2$OSi, 258.1; m/z found, 259.0 [M+H]$^+$.

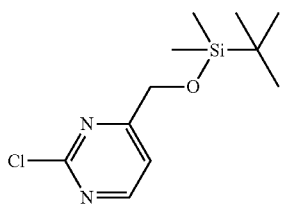 [SMILES: CC(C)(C)[Si](C)(C)OCc1ccnc(Cl)n1]

The title compound was prepared in a manner analogous to Intermediate 53 using (2-chloropyrimidin-4-yl)methanol. MS (ESI): mass calcd. for C$_{11}$H$_{11}$ClN$_2$OSi, 258.1; m/z found, 259.0 [M+H]$^+$.

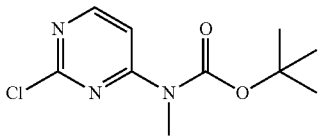 [SMILES: CN(C(=O)OC(C)(C)C)c1ccnc(Cl)n1]

A solution of 2-chloro-N-methylpyrimidin-4-amine (500 mg, 3.4 mmol), di-tert-butyl dicarbonate (1.49 mL, 6.9 mmol), TEA (0.96 mL, 6.9 mmol), DMAP (42.5 mg, 0.34 mmol) in THF (20 mL) was stirred at 70° C. for 3 h. The reaction mixture was cooled, and concentrated under reduced pressure. Purification (FCC, SiO$_2$, 0-20% EtOAc in hexanes) afforded the title compound (762 mg, 88%). MS (ESI): mass calcd. for C$_{10}$H$_{14}$ClN$_3$O$_2$, 243.1; m/z found, 244.0 [M+H]$^+$. $^1$H NMR (500 MHz, DMSO-d$_6$) δ 8.51 (d, J=5.9 Hz, 1H), 7.94 (d, J=5.9 Hz, 1H), 3.33 (s, 3H), 1.52 (s, 9H).

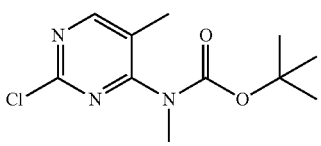 [SMILES: Cc1cnc(Cl)nc1N(C)C(=O)OC(C)(C)C]

The title compound was prepared in a manner analogous to Intermediate 55, using 2-chloro-N,5-dimethylpyrimidin-4-amine. MS (ESI): mass calcd. for C$_{11}$H$_{16}$ClN$_3$O$_2$, 257.1; m/z found, 258.0 [M+H]$^+$.

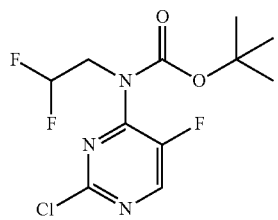

The title compound was prepared in a manner analogous to Intermediate 55, using 2-chloro-N-(2,2-difluoroethyl)-5-fluoropyrimidin-4-amine. MS (ESI): mass calcd. for C$_{10}$H$_{13}$ClF$_3$N$_3$O$_2$, 311.1; m/z found, 312.1 [M+H]$^+$. $^1$H NMR (400 MHz, DMSO-d$_6$) δ 8.92 (d, J=2.7 Hz, 1H), 6.47-6.15 (m, 1H), 4.22 (td, J=14.8, 3.8 Hz, 2H), 1.44 (s, 9H).

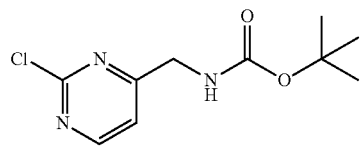 [SMILES: CC(C)(C)OC(=O)NCc1ccnc(Cl)n1]

A mixture of 2-chloropyrimidine-4-carbonitrile (1.5 g, 10.7 mmol), di-tert-butyl dicarbonate (2.8 mL, 12.9 mmol) and 10% Pd/C (572 mg, 0.5 mmol) in EtOH (25 mL) was stirred at room temperature under a hydrogen atmosphere (1 atm, balloon). After 4 h, the reaction mixture was filtered through a pad of Celite®. The filtrate was concentrated under vacuum. Purification (FCC, SiO$_2$, 0-99% EtOAc) to yield title product (720 mg, 27%). MS (ESI): mass calcd. for C$_{10}$H$_{14}$ClN$_3$O$_2$, 243.7; m/z found, 187.9 [M-t-Bu]$^+$. $^1$H NMR (400 MHz, DMSO-d$_6$) δ 8.72 (d, J=5.1 Hz, 1H), 7.56 (t, J=6.2 Hz, 1H), 7.39 (d, J=5.1 Hz, 1H), 4.21 (d, J=6.0 Hz, 2H), 1.40 (s, 9H).

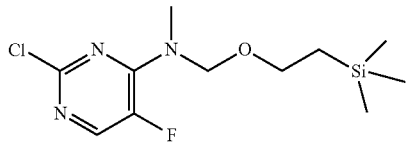 [SMILES: CN(COCC[Si](C)(C)C)c1nc(Cl)ncc1F]

A solution of 2-chloro-5-fluoro-N-methylpyrimidin-4-amine (500 mg, 3 mmol), (2-(chloromethoxy)ethyl)trimethylsilane (0.8 mL, 4.6 mmol), DIPEA (0.8 mL, 4.6 mmol) in DMF (28 mL) was stirred at rt for 16 h. Additional (2-(chloromethoxy)ethyl)trimethylsilane (0.8 mL, 4.6 mmol), DIPEA (0.8 mL, 4.6 mmol) was added and the reaction mixture was stirred for 6 h. To the reaction mixture was added brine (50 mL) and the reaction mix was extracted with EtOAc (3×60 mL). The combined organics were dried (MgSO$_4$), filtered, and concentrated under reduced pressure. Purification (FCC, SiO$_2$, 0-90% EtOAc in hexanes) afforded the title compound (528 mg, 58%). MS (ESI): mass calcd. for C$_{11}$H$_{19}$ClFN$_3$OSi, 291.1; m/z found, 292.1 [M+H]$^+$. $^1$H NMR (500 MHz, DMSO-d$_6$) δ 8.27 (d, J=6.1 Hz, 1H), 4.97 (d, J=1.4 Hz, 2H), 3.55-3.51 (m, 2H), 3.17 (d, J=2.5 Hz, 3H), 0.90-0.85 (m, 2H), −0.03--0.05 (m, 9H).

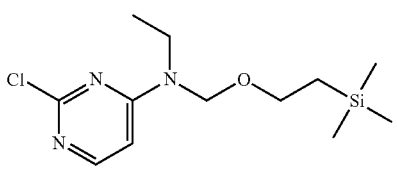 [SMILES: CCN(COCC[Si](C)(C)C)c1ccnc(Cl)n1]

The title compound was prepared in a manner analgous to Intermediate 59, using 2-chloro-N-ethylpyrimidin-4-amine. MS (ESI): mass calcd. for C₁₂H₂₂ClN₃OSi, 287.1; m/z found, 288.2 [M+H]⁺. ¹H NMR (400 MHz, DMSO-d₆) δ 8.13 (d, J=6.1 Hz, 1H), 6.79 (d, J=6.1 Hz, 1H), 4.92 (s, 2H), 3.65-3.46 (m, 4H), 1.12 (t, J=7.1 Hz, 3H), 0.92-0.84 (m, 2H), −0.02−−0.05 (m, 9H).

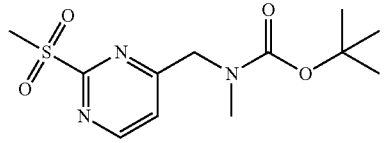 [SMILES: CN(Cc1ccnc(S(C)(=O)=O)n1)C(=O)OC(C)(C)C]

Step A. N-methyl-1-(2-(methylthio)pyrimidin-4-yl)methanamine

Sodium triacetoxyborohydride (825 mg, 3.9 mmol) was added to a mixture of 2-(methylthio)pyrimidine-4-carbaldehyde (300 mg, 1.9 mmol) and methyl amine (2 M in MeOH, 1.3 mL, 2.5 mmol)) in THF (28 mL) at room temperature. After 16 hours, the reaction mixture was quenched with a saturated aqueous solution of NaHCO₃ (50 mL). The mixture was extracted using EtOAc (3×75 mL). The combined organics were dried over MgSO₄, filtered and concentrated under vacuum. Purification (FCC, SiO₂, 0-90% EtOAc in hexanes followed by 0% DCM to 60% MeOH containing 10% 2 M NH₃ in MeOH) afforded the title compound (67 mg, 20%). MS (ESI): mass calcd. for C₇H₁₁N₃S, 169.1; m/z found, 170.1 [M+H]⁺.

Step B. tert-Butyl methyl((2-(methylthio)pyrimidin-4-yl)methyl)carbamate

A mixture of N-methyl-1-(2-(methylthio)pyrimidin-4-yl)methanamine (239 mg, 1.4 mmol), BOC-anhydride (0.9 mL, 4.2 mmol), DMAP (17 mg, 0.1 mmol), TEA (0.4 mL, 2.8 mmol) and THF (8 mL) was allowed to stir at room temperature. After 16 hours, water (30 mL) was added and the mixture was extracted using DCM (3×50 mL). The combined organics were dried over MgSO₄, filtered and concentrated under vacuum. Purification (FCC, SiO₂, 0-40% EtOAc in hexanes) afforded the title compound (151 mg, 40%). MS (ESI): mass calcd. for C₁₂H₁₉N₃O₂S, 269.1; m/z found, 270.1 [M+H]⁺. ¹H NMR (400 MHz, DMSO-d₆) δ 8.57 (d, J=5.1 Hz, 1H), 7.03-6.94 (m, 1H), 4.39 (s, 2H), 2.89 (s, 3H), 1.48-1.21 (m, 9H).

Step C. tert-Butyl methyl((2-(methylsulfonyl)pyrimidin-4-yl)methyl)carbamate mCPBA (276 mg, 1.2 mmol) was slowly added to a mixture of tert-butyl methyl((2-(methylthio)pyrimidin-4-yl)methyl)carbamate (151 mg, 0.6 mmol) in DCM (6 mL) at 0° C. After 3 hours, complete conversion was observed. The reaction mixture was quenched with saturated aqueous solution of NaHCO₃(aq) (60 mL). The mixture was extracted with DCM (3×80 mL). The combined organics were dried over MgSO₄, filtered and concentrated under vacuum. Purification (FCC, SiO₂, 0-99% EtOAc in hexanes) afforded the title compound (132 mg, 78%). MS (ESI): mass calcd. for C₁₂H₁₉N₃O₄S, 301.1; m/z found, 202.1 [M-tBu]⁺. ¹H NMR (400 MHz, DMSO-d₆) δ 9.05-8.99 (m, 1H), 7.68-7.58 (m, 1H), 4.59 (s, 2H), 3.40 (s, 3H), 2.94 (s, 3H), 1.51-1.19 (m, 9H).

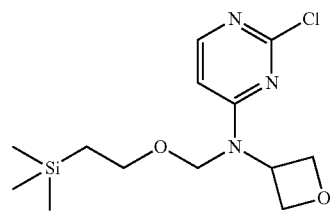 [SMILES: C[Si](C)(C)CCOCN(c1ccnc(Cl)n1)C1COC1]

Step A. 2-Chloro-N-(oxetan-3-yl)pyrimidin-4-amine

A mixture of 2,4-dichloropyrimidine (300 mg, 2.0 mmol), 3-oxetanamine (147 mg, 2.0 mmol) and DIPEA (0.7 mL, 4.0 mmol) in DMF (17 mL) was stirred at r.t. After 16 hours, conversion was observed. Water (20 mL) was added to the reaction mixture was extracted with EtOAc (3×30 mL). The combined organics were dried over MgSO₄, filtered and concentrated under vacuum. Purification (FCC, SiO₂, 0-99% EtOAc in hexanes) afforded the title compound. ¹H NMR (500 MHz, DMSO-d₆) δ 8.67-8.60 (m, 1H), 8.04-7.92 (m, 1H), 6.57-6.38 (m, 1H), 4.98-4.87 (m, 1H), 4.80 (t, J=6.7 Hz, 2H), 4.49-4.41 (m, 2H).

Step B. 2-Chloro-N-(oxetan-3-yl)-N-((2-(trimethylsilyl)ethoxy)methyl)pyrimidin-4-amine Under a nitrogen atmosphere was stirred a mixture of 2-chloro-N-(oxetan-3-yl)pyrimidin-4-amine (374 mg, 2.0 mmol), DIPEA (0.7 mL, 4.0 mmol) (2-(chloromethoxy)ethyl)trimethylsilane (0.7 mL, 4.0 mmol) and DMF (19 mL) at room temperature. After 16 hours, complete conversion was observed. Water (20 mL) was added and the mixture was extracted using EtOAc (3×30 mL). The combined organics were dried over MgSO₄, filtered and concentrated under vacuum. Purification (FCC, SiO₂, 0-99% EtOAc in hexanes) afforded the title compound (187 mg, 29%). MS (ESI): mass calcd. for C₁₃H₂₂ClN₃O₂Si, 315.1; m/z found, 316.1 [M+H]⁺. ¹H NMR (400 MHz, DMSO-d₆) 8.22 (d, J=6.1 Hz, 1H), 6.90-6.77 (m, 1H), 5.17-4.94 (m, 3H), 4.79-4.73 (m, 2H), 4.70-4.64 (m, 2H), 3.57-3.51 (m, 2H), 0.92-0.85 (m, 2H), −0.01−−0.04 (m, 9H).

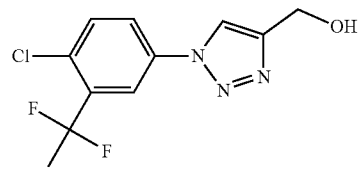 [SMILES: CC(F)(F)c1cc(-n2cc(CO)nn2)ccc1Cl]

Step A. 4-Chloro-3-(1,1-difluoroethyl)aniline

The title compound was prepared in a manner analogous to Intermediate 3, using 1-(2-chloro-5-nitrophenyl)ethan-1- one in step A and 1-chloro-2-(1,1-difluoroethyl)-4-nitrobenzene in step B. MS (ESI) mass calcd. for $C_8H_8ClF_2N_2O_2$, 191.0; m/z found 192.0 $[M+H]^+$. $^1H$ NMR (500 MHz, CDCl$_3$) δ 7.22-7.12 (m, 1H), 6.96-6.87 (d, J=2.8 Hz, 1H), 6.69-6.57 (m, 1H), 3.86-3.64 (s, 2H), 2.09-1.92 (t, J=18.5 Hz, 3H).

Step B. (1-(4-Chloro-3-(1,1-difluoroethyl)phenyl)-1H-1,2,3-triazol-4-yl)methanol The title compound was prepared in a manner analogous to Intermediate 1, using 4-chloro-3-(1,1-difluoroethyl)aniline. MS (ESI) mass calcd. for $C_{11}H_{10}ClF_2N_3O$, 273.0; m/z found 274.0 $[M+H]^+$. $^1H$ NMR (500 MHz, CDCl$_3$) δ 8.07-7.92 (m, 2H), 7.90-7.74 (m, 1H), 7.68-7.56 (d, J=8.6 Hz, 1H), 5.00-4.79 (s, 2H), 2.19-2.01 (t, J=18.5 Hz, 3H).

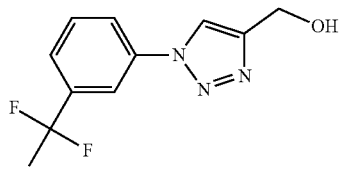 [SMILES: CC(F)(F)c1cccc(-n2cc(CO)nn2)c1]

The title compound was prepared in a manner analgous to Intermediate 2, using 3-(1,1-difluoroethyl) aniline. MS (ESI): mass calcd. for $C_{11}H_{11}F_2N_3O$, 239.1; m/z found, 240.0 $[M+H]^+$. 1H NMR (500 MHz, CDCl3) δ 8.11-7.99 (s, 1H), 7.99-7.86 (s, 1H), 7.86-7.72 (m, 1H), 7.69-7.53 (m, 2H), 5.00-4.83 (s, 2H), 2.08-1.88 (t, J=18.2 Hz, 3H).

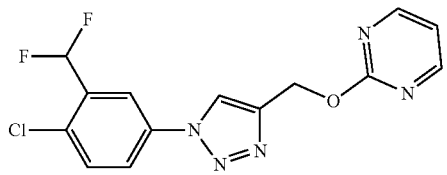 [SMILES: FC(F)c1cc(-n2cc(COc3ncccn3)nn2)ccc1Cl]

To a solution of (1-(4-chloro-3-(difluoromethyl)phenyl)-1H-1,2,3-triazol-4-yl)methanol (Intermediate 7, 25.3 mg, 0.097 mmol) in DMF (1.0 mL) at rt was added NaH (60% dispersion in mineral oil) (11.7 mg, 0.29 mmol). The resulting reaction was stirred for 5 min before the addition of 2-chloropyrimidine (14.5 mg, 0.127 mmol). The reaction was stirred at rt for 20 h, and then quenched by the addition of water (0.10 mL). The mixture was diluted with EtOAc (5 mL) and H$_2$O (5 mL). The layers were separated and the aqueous layer was extracted with EtOAc (3×5 mL). The combined organics were washed with H$_2$O (1×5 mL), with brine (1×5 mL), dried (Na$_2$SO$_4$), filtered, and concentrated under reduced pressure. Purification (FCC, SiO$_2$, 0-60% EtOAc in hexanes) afforded the title compound (19.2 mg, 58%). MS (ESI): mass calcd. for $C_{14}H_{10}ClF_2N_5O$, 337.1; m/z found, 338.0 $[M+H]^+$. $^1H$ NMR (400 MHz, CDCl$_3$) δ 8.58 (d, J=4.8 Hz, 2H), 8.18 (s, 1H), 8.02-8.00 (m, 1H), 7.92-7.86 (m, 1H), 7.63-7.59 (m, 1H), 7.14-6.84 (m, 2H), 5.71-5.65 (m, 2H).

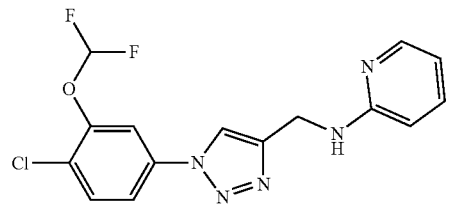

Step A. 1-(4-Chloro-3-(difluoromethoxy)phenyl)-1H-1,2,3-triazole-4-carbaldehyde

To a round bottom flask containing (1-(4-chloro-3-(difluoromethoxy)phenyl)-1H-1,2,3-triazol-4-yl)methanol (Intermediate 1, 150 mg, 0.54 mmol) was added Dess-Martin periodinane (461.6 mg, 1.09 mmol) and DCM (20 mL). The flask was sealed under ambient atmosphere and stirred rapidly at rt for 4 hours. The reaction was quenched with saturated aqueous sodium bicarbonate (2.5 mL) and 10% aqueous sodium thiosulfate (2.5 mL). The biphasic mixture is stirred vigorously until the white milky organic phase became clear and colorless (60 min). The layers were separated and aqueous layers was extracted with DCM (1×). The combined organics were washed with brine, dried (Na$_2$SO$_4$), filtered, and concentrated under reduced pressure. Purification (FCC, SiO$_2$, 0-30% EtOAc in hexanes) afforded the title compound (140 mg, 94%) as an off white solid. MS (ESI) mass calcd. for $C_{10}H_6ClF_2N_3O_2$, 273.0; m/z found 274.1 $[M+H]^+$.

Step B. N-((1-(4-Chloro-3-(difluoromethoxy)phenyl)-1H-1,2,3-triazol-4-yl)methyl)pyridin-2-amine A solution of 1-(4-chloro-3-(difluoromethoxy)phenyl)-1H-1,2,3-triazole-4-carbaldehyde (26 mg, 0.095 mmol) and 2-amino pyridine (10.7 mg, 0.114 mmol) in DCM (5 mL) was charged with 1 N HCl in Et$_2$O (0.5 mL). The resulting solution was stirred at rt for 10 min then charged with NaHB(OAc)$_3$ (30 mg, 0.143 mmol). The mixture was stirred at rt overnight. The completed reaction was diluted with DCM (5 mL) and quenched with water. The layers were separated and aqueous layer was extracted with DCM (1×). The combined organics were washed with brine, dried (Na$_2$SO$_4$), filtered, and concentrated under reduced pressure. Purification (FCC, SiO$_2$, 0-10% 2M NH$_3$ in MeOH/DCM) afforded the title compound (16 mg, 48%). MS (ESI) mass calcd. for $C_{15}H_{12}ClF_2N_5O$, 351.1; m/z found 352.0. $^1H$ NMR (400 MHz, CDCl$_3$) δ 8.17-8.05 (m, 1H), 8.00 (s, 1H), 7.69 (d, J=2.2 Hz, 1H), 7.63-7.43 (m, 3H), 6.86-6.42 (m, 3H), 5.67 (s, 1H), 4.81-4.71 (m, 2H).

Example 3. N-[[1-[4-Fluoro-3-(trifluoromethyl)phenyl]triazol-4-yl]methyl]pyrimidin-2-amine

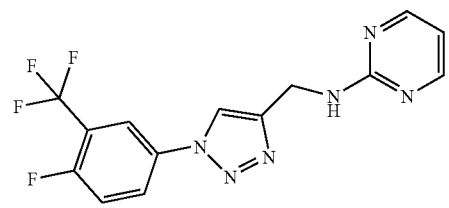 [SMILES: Fc1ccc(-n2cc(CNc3ncccn3)nn2)cc1C(F)(F)F]

Step A. 4-(Chloromethyl)-1-(4-fluoro-3-(trifluoromethyl)phenyl)-1H-1,2,3-triazole To a suspension of (1-(4-fluoro-3-(trifluoromethyl)phenyl)-1H-1,2,3-triazol-4-yl)methanol (Intermediate 5, 1.5 g, 5.7 mmol) in DCM (30 mL) in a flask equipped to vent into 2M $Na_2CO_3$ was added $SOCl_2$ (15 mL). The reaction turned homogeneous (~5 min) and the clear solution was stirred at rt for 3 h. Concentration under reduced pressure afforded 1.5 g of the title compound as an off white solid, which was used without further purification. $^1$H NMR (500 MHz, $CDCl_3$) δ 8.05 (s, 1H), 8.00 (dd, J=5.8, 2.7 Hz, 1H), 7.99-7.94 (m, 1H), 7.42 (t, J=9.1 Hz, 1H), 4.80 (s, 2H).

Step B. N-[[1-[4-Fluoro-3-(trifluoromethyl)phenyl]triazol-4-yl]methyl]pyrimidin-2-amine A mixture of 4-(chloromethyl)-1-(4-fluoro-3-(trifluoromethyl)phenyl)-1H-1,2,3-triazole (55 mg, 0.19 mmol), pyrimidin-2-amine (45 mg, 0.47 mmol), $K_2CO_3$ (130 mg, 0.94 mmol) in DMF (1.5 mL) was heated in a 80° C. heating block for 24 h. The mixture was poured into water (35 mL) and extracted with EtOAc. The solvent was removed under reduced pressure and the residue was loaded onto $SiO_2$. Purification (FCC, $SiO_2$, hexanes/EtOAc 0-100%) afforded the title compound (13 mg, 19%). MS (ESI): mass calcd. for $C_{14}H_{10}F_4N_6$, 338.1; m/z found, 339.0 [M+H]$^+$. $^1$H NMR (500 MHz, $CDCl_3$) δ 8.33 (d, J=4.8 Hz, 2H), 7.99-7.95 (m, 2H), 7.95-7.91 (m, 1H), 7.38 (t, J=9.1 Hz, 1H), 6.64-6.59 (m, 1H), 5.87-5.80 (m, 1H), 4.83 (d, J=6.2 Hz, 2H).

Example 4. 2-[[1-[3-(Difluoromethoxy)-4-fluorophenyl]triazol-4-yl]methoxy]pyridine

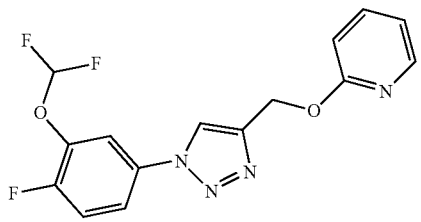 [SMILES: Fc1ccc(-n2cc(COc3ccccn3)nn2)cc1OC(F)F]

To a solution of (1-(3-(difluoromethoxy)-4-fluorophenyl)-1H-1,2,3-triazol-4-yl)methanol (Intermediate 6, 180 mg, 0.69 mmol), pyridin-2-ol (66 mg, 0.69 mmol), and triphenylphosphine (182 mg, 0.69 mmol) in THF (4.5 mL) was added DBAD (160 mg, 0.69 mmol). The resulting mixture was stirred at rt. for 3 h. The solvent was removed under reduced pressure. Purification (FCC, $SiO_2$, heptane/EtOAc (0 to 80%) afforded the title compound (28 mg, 11%). MS (ESI): mass calcd. for $C_{15}H_{11}F_3N_4O_2$, 336.1; m/z found, 337.1 [M+H]$^+$. $^1$H NMR (400 MHz, $CDCl_3$) δ 8.37-8.12 (m, 1H), 8.05 (s, 1H), 7.69 (dd, J=2.5, 6.7 Hz, 1H), 7.66-7.51 (m, 2H), 7.34 (t, J=9.2 Hz, 1H), 6.92 (ddd, J=0.7, 5.2, 7.1 Hz, 1H), 6.85-6.40 (m, 2H), 5.60 (s, 2H). 1-((3-(Difluoromethoxy)-4-fluorophenyl)-1H-1,2,3-triazol-4-yl)methyl)pyridin-2(1H)-one was also obtained (75 mg, 32%).

Example 5. 3-[[1-[4-Chloro-3-(difluoromethoxy)phenyl]triazol-4-yl]methoxy]pyridine

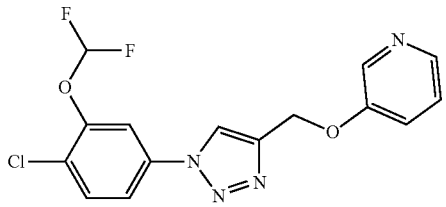 [SMILES: FC(F)Oc1cc(-n2cc(COc3cccnc3)nn2)ccc1Cl]

To a solution of pyridin-3-ol (11 mg, 0.12 mmol) and $K_2CO_3$ (64 mg, 0.46 mmol) in DMF (0.7 mL) was added a solution of 1-(4-chloro-3-(difluoromethoxy)phenyl)-4-(chloromethyl)-1H-1,2,3-triazole (Intermediate 4, 41 mg, 0.14 mmol) in DMF (0.5 mL). The reaction mixture was stirred at room temperature overnight. Upon completion, the reaction mixture was diluted with $H_2O$ and EtOAc. The aqueous layer was further extracted with EtOAc (3×).

The combined organics were dried ($Na_2SO_4$), filtered, and concentrated under reduced pressure. Purification (FCC, $SiO_2$, 0-100% EtOAc in hexanes) afforded title compound (24 mg, 58% yield). MS (ESI): mass calcd. for $C_{15}H_{11}ClF_2N_4O_2$, 352.1; m/z found, 353.0 [M+H]$^+$. $^1$H NMR (400 MHz, $CDCl_3$) δ 8.42 (d, J=3.0 Hz, 1H), 8.27 (dd, J=4.6, 1.4 Hz, 1H), 8.14-8.04 (m, 1H), 7.78-7.69 (m, 1H), 7.66-7.60 (m, 1H), 7.60-7.56 (m, 1H), 7.40-7.33 (m, 1H), 7.31-7.21 (m, 1H), 6.64 (t, J=72.5 Hz, 1H), 5.34 (s, 2H)

Example 6. N-((1-(3-(Difluoromethyl)phenyl-1H-1,2,3-triazol-4-yl)methyl)pyrimidin-2-amine

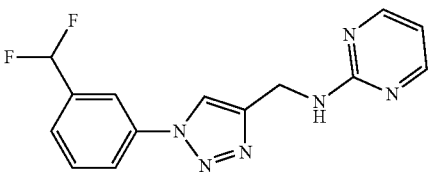 [SMILES: FC(F)c1cccc(-n2cc(CNc3ncccn3)nn2)c1]

(1-(3-(Difluoromethyl)phenyl)-1H-1,2,3-triazol-4-yl)methanamine (Intermediate 17, 32.4 mg, 0.145 mmol), 2-chloropyrimidine (21.5 mg, 0.188 mmol), TEA (0.03 mL, 0.217 mmol), and EtOH (0.723 mL) were combined in a microwave vial. The vial was purged with $N_2$, sealed, and heated in a microwave reactor at 120° C. for 2 h. Then at 150° C. for 10 min. The crude reaction mixture was concentrated under reduced pressure. Purification (FCC, $SiO_2$, 0-8% MeOH in DCM) afforded the title compound (21.3 mg, 49%). MS (ESI): mass calcd. for $C_{14}H_{12}F_2N_6$, 302.1; m/z found, 303.2 [M+H]$^+$. $^1$H NMR (400 MHz, $CDCl_3$) δ 8.33 (d, J=4.8 Hz, 2H), 8.00 (s, 1H), 7.92-7.82 (m, 2H), 7.68-7.55 (m, 2H), 6.72 (t, J=56.1 Hz, 1H), 6.61 (t, J=4.8 Hz, 1H), 5.66 (s, 1H), 4.83 (d, J=6.2 Hz, 2H).

Example 7. N-[[1-[3-(Difluoromethoxy)-4-fluorophenyl]triazol-4-yl]methyl]-1-methyl-imidazol-2-amine

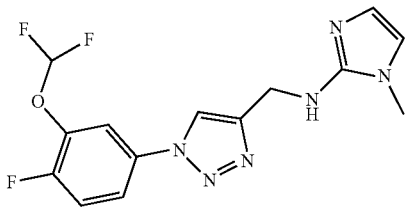 [SMILES: Cn1ccnc1NCc1cn(-c2ccc(F)c(OC(F)F)c2)nn1]

To a solution of (1-(3-(difluoromethoxy)-4-fluorophenyl)-1H-1,2,3-triazol-4-yl)methanamine (Intermediate 18, 50 mg, 0.17 mmol) and 2-bromo-1-methyl-1H-imidazole in tBuOH (4 mL) was added 2-di-tert-butylphosphino-2',4',6'-triisopropylbiphenyl (14.4 mg, 0.033 mmol), tris(dibenzylideneacetone)dipalladium(0) (15.5 mg, 0.017 mmol), and potassium tert-butoxide (76 mg, 0.68 mmol) under $N_2$ atmosphere. The mixture was stirred at 110° C. for 96 h. The resulting solids were filtered off and the solvent was evaporated under reduced pressure. Purification (FCC, $SiO_2$, EtOAc/Heptane 0-100%; then MeOH/DCM 0-90%) then further purified (RP HPLC; Stationary phase: $C^{18}$ XBridge 30×100 mm 5 μm), Mobile phase: Gradient from 81% 10 mM $NH_4CO_3H$ pH 9 solution in Water, 19% $CH_3CN$ to 64% 10 mM $NH_4CO_3H$ pH 9 solution in Water, 36% $CH_3CN$) to afford the title compound (11 mg, 19%) as white solid. MS (ESI): mass calcd. for $C_{14}H_{13}F_3N_6O$, 338.1; m/z found, 339.1 $[M+H]^+$. $^1H$ NMR (400 MHz, $CDCl_3$) δ 3.38 (s, 3H) 4.13-4.31 (m, 1H) 4.70 (d, J=6.24 Hz, 2H) 6.63 (t, J=72.83 Hz, 1H) 6.53 (d, J=1.39 Hz, 1H) 6.69 (d, J=1.39 Hz, 1H) 7.32 (t, J=9.25 Hz, 1H) 7.51-7.61 (m, 1H) 7.68 (dd, J=6.70, 2.54 Hz, 1H) 8.08 (s, 1H).

Example 8. 2-[[1-[3-(Difluoromethoxy)-4-fluorophenyl]triazol-4-yl]methoxy]-6-methyl-pyridine

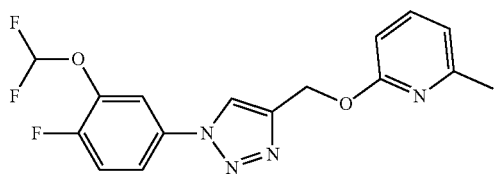 [SMILES: Cc1cccc(OCc2cn(-c3ccc(F)c(OC(F)F)c3)nn2)n1]

To a solution of 2-bromo-6-((1-(3-(difluoromethoxy)-4-fluorophenyl)-1H-1,2,3-triazol-4-yl)methoxy)pyridine (Intermediate 7, 75 mg, 0.18 mmol) in 1,4-dioxane (2 mL) was added trimethylboroxine (0.03 mL, 0.21 mmol), $Cs_2CO_3$ (118 mg, 0.36 mmol), and (2-dicydohexylphosphino-2',4',6'-triisopropyl-1,1'-biphenyl)[2-(2'-amino-1,1'-biphenyl)]palladium(II) methanesulfonate (15.3 mg, 0.018 mmol) to a sealed tube under $N_2$ atmosphere. The mixture was heated to 120° C. for 12 min under microwave irradiation. The mixture was concentrated under reduced pressure. Purification (FCC, $SiO_2$, EtOAc in heptane from 0-100%) afforded the title compound. The title compound was further purified (RP HPLC, Stationary phase: $^{18}C$ XBridge 30×100 mm 5 μm), Mobile phase: Gradient from 90% 10 mM $NH_4CO_3H$ pH 9 solution in Water, 10% $CH_3CN$ to 0% 10 mM $NH_4CO_3H$ pH 9 solution in Water, 100% $CH_3CN$) to afford the title compound (39 mg, 61%) HRMS=350.099. $^1H$ NMR (500 MHz, $CDCl_3$) δ ppm 2.49 (s, 3H) 5.59 (s, 2H) 6.49-6.81 (m, 1H) 6.61 (d, J=8.1 Hz, 1H) 6.77 (d, J=7.2 Hz, 1H) 7.35 (t, J=9.2 Hz, 1H) 7.49 (dd, J=8.2, 7.4 Hz, 1H) 7.59 (ddd, J=9.0, 3.9, 2.7 Hz, 1H) 7.70 (dd, J=6.4, 2.6 Hz, 1H) 8.04 (s, 1H)

Example 9. 2-[[1-(3-Bromo-4-fluoro-phenyl)triazol-4-yl]methoxy]pyrimidine

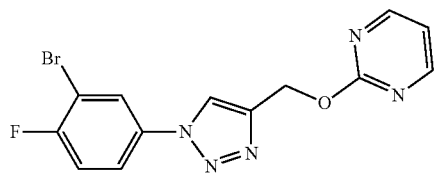 [SMILES: Fc1ccc(-n2cc(COc3ncccn3)nn2)cc1Br]

The title compound was prepared in a manner analogous to Example 1 using (1-(3-bromo-4-fluorophenyl)-1H-1,2,3-triazol-4-yl)methanol (Intermediate 14) and 2-chloropyrimidine. MS (ESI): mass calcd. for $C_{13}H_9BrFN_5O$, 349.0; m/z found, 350.0 $[M+H]^+$. $^1H$ NMR (600 MHz, $CDCl_3$) δ 8.57 (d, J=4.7 Hz, 2H), 8.09-8.08 (m, 1H), 7.99 (dd, J=5.8, 2.7 Hz, 1H), 7.67 (ddd, J=8.9, 4.0, 2.6 Hz, 1H), 7.30-7.28 (m, 1H), 7.00 (t, J=4.8 Hz, 1H), 5.68-5.65 (m, 2H).

Example 10. 2-[[1-[4-Chloro-3-(difluoromethoxy)phenyl]triazol-4-yl]methoxy]pyrimidine

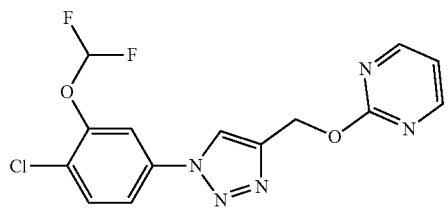 [SMILES: FC(F)Oc1cc(-n2cc(COc3ncccn3)nn2)ccc1Cl]

The title compound was prepared in a manner analogous to Example 1 using (1-(4-chloro-3-(difluoromethoxy)phenyl)-1H-1,2,3-triazol-4-yl)methanol (Intermediate 1) and 2-chloropyrimidine. MS (ESI): mass calcd. for $C_{14}H_{10}ClF_2N_5O_2$, 353.0; m/z found, 354.0 $[M+H]^+$. $^1H$ NMR (400 MHz, $CDCl_3$) δ 8.57 (d, J=4.8 Hz, 2H), 8.20-8.04 (m, 1H), 7.73-7.68 (m, 1H), 7.65-7.60 (m, 1H), 7.59-7.55 (m, 1H), 7.03-6.90 (m, 1H), 6.64 (t, J=72.5 Hz, 1H), 5.67 (s, 2H).

Example 11. 2-[[1-[4-Chloro-3-(difluoromethyl)phenyl]triazol-4-yl]methoxy]pyridine

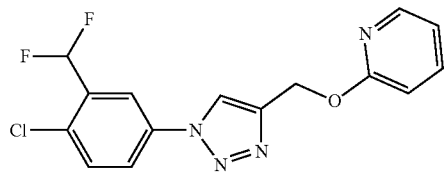 [SMILES: FC(F)c1cc(-n2cc(COc3ccccn3)nn2)ccc1Cl]

The title compound was prepared in a manner analogous to Example 1 using (1-(4-chloro-3-(difluoromethyl)phenyl)-

1H-1,2,3-triazol-4-yl)methanol (Intermediate 8) and 2-chloropyridine. MS (ESI): mass calcd. for C₁₅H₁₁ClF₂N₄O, 336.1; m/z found, 336.9 [M+H]⁺. ¹H NMR (400 MHz, CDCl₃) δ 8.21 (ddd, J=5.0, 2.0, 0.8 Hz, 1H), 8.12 (s, 1H), 8.02-7.99 (m, 1H), 7.92-7.87 (m, 1H), 7.64-7.58 (m, 2H), 7.14-6.85 (m, 1H), 6.95-6.90 (m, 1H), 6.81 (dt, J=8.3, 0.9 Hz, 1H), 5.64-5.57 (m, 2H).

Example 12. 4-[[1-[4-Chloro-3-(difluoromethyl)phenyl]triazol-4-yl]methoxy]pyrimidine

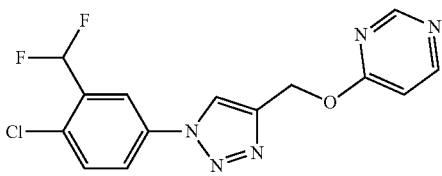 [SMILES: FC(F)c1cc(-n2cc(COc3ccncn3)nn2)ccc1Cl]

The title compound was prepared in a manner analogous to Example 1 using (1-(4-chloro-3-(difluoromethyl)phenyl)-1H-1,2,3-triazol-4-yl)methanol (Intermediate 8) and 4-chloropyrimidine. MS (ESI): mass calcd. for C₁₄H₁₀ClF₂N₅O, 337.1; m/z found, 338.0 [M+H]⁺. ¹H NMR (400 MHz, CDCl₃) δ 8.85 (s, 1H), 8.48 (d, J=5.8 Hz, 1H), 8.14 (s, 1H), 8.00 (d, J=2.7 Hz, 1H), 7.93-7.85 (m, 1H), 7.66-7.58 (m, 1H), 7.00 (t, J=54.5 Hz, 1H), 6.81 (dd, J=5.8, 1.2 Hz, 1H), 5.67 (s, 2H).

Example 13. 4-[[1-[4-Chloro-3-(difluoromethoxy)phenyl]triazol-4-yl]methoxy]pyrimidine

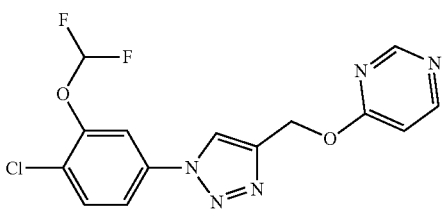 [SMILES: FC(F)Oc1cc(-n2cc(COc3ccncn3)nn2)ccc1Cl]

The title compound was prepared in a manner analogous to Example 1 using (1-(4-chloro-3-(difluoromethoxy)phenyl)-1H-1,2,3-triazol-4-yl)methanol (Intermediate 1) and 4-chloropyrimidine. MS (ESI): mass calcd. for C₁₄H₁₀ClF₂N₅O₂, 353.0; m/z found, 354.0 [M+H]⁺. ¹H NMR (400 MHz, CDCl₃) δ 8.83 (s, 1H), 8.47 (d, J=5.9 Hz, 1H), 8.10 (s, 1H), 7.73-7.67 (m, 1H), 7.64-7.59 (m, 1H), 7.59-7.54 (m, 1H), 6.80 (dd, J=5.9, 1.2 Hz, 1H), 6.64 (t, J=72.5 Hz, 1H), 5.65 (s, 2H)

Example 14. 3-[[1-[4-Chloro-3-(difluoromethoxy)phenyl]triazol-4-yl]methoxy]pyridazine

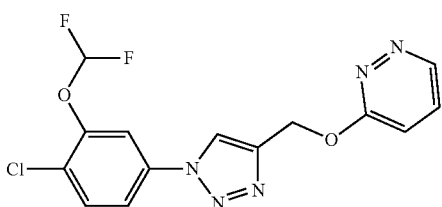

The title compound was prepared in a manner analogous to Example 1 using (1-(4-chloro-3-(difluoromethoxy)phenyl)-1H-1,2,3-triazol-4-yl)methanol (Intermediate 1) and 3-chloropyridazine. MS (ESI): mass calcd. for C₁₄H₁₀ClF₂N₅O₂, 353.0; m/z found, 354.0 [M+H]⁺. ¹H NMR (400 MHz, CDCl₃) δ 8.47 (d, J=5.9 Hz, 1H), 8.10 (s, 1H), 7.74-7.68 (m, 1H), 7.66-7.59 (m, 1H), 7.59-7.54 (m, 1H), 6.80 (dd, J=5.9, 1.2 Hz, 1H), 6.64 (t, J=72.5 Hz, 1H), 5.65 (s, 2H).

Example 15. 2-[[1-(4-Chloro-3-methoxy-phenyl)triazol-4-yl]methoxy]pyrimidine

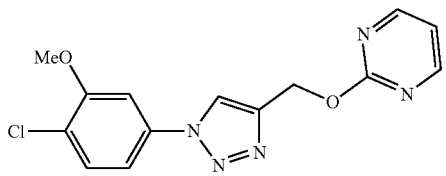 [SMILES: COc1cc(-n2cc(COc3ncccn3)nn2)ccc1Cl]

The title compound was prepared in a manner analogous to Example 1 using (1-(4-chloro-3-methoxyphenyl)-1H-1,2,3-triazol-4-yl)methanol (Intermediate 15) and 2-chloropyrimidine. MS (ESI): mass calcd. for C₁₄H₁₂ClN₅O₂, 317.1; m/z found, 318.0 [M+H]⁺. ¹H NMR (400 MHz, CDCl₃) δ 8.57 (d, J=4.8 Hz, 2H), 8.13 (s, 1H), 7.49 (d, J=8.5 Hz, 1H), 7.45 (d, J=2.4 Hz, 1H), 7.16 (dd, J=8.5, 2.4 Hz, 1H), 7.06-6.95 (m, 1H), 5.67 (s, 2H), 3.99 (s, 3H)

Example 16. 2-[[1-(3-Bromo-4-fluoro-phenyl)triazol-4-yl]methoxy]-5-methylpyrimidine

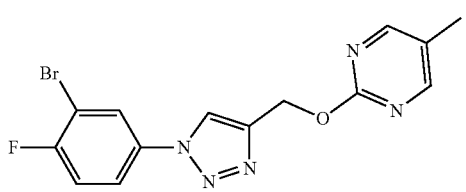 [SMILES: Cc1cnc(OCc2cn(-c3ccc(F)c(Br)c3)nn2)nc1]

The title compound was prepared in a manner analogous to Example 1 using (1-(3-bromo-4-fluorophenyl)-1H-1,2,3-triazol-4-yl)methanol (Intermediate 14) and 2-chloro-5-methylpyrimidine. MS (ESI): mass calcd. for C₁₄H₁₁BrFN₅O, 363.0; m/z found, 363.9 [M+H]⁺. ¹H NMR (400 MHz, CDCl₃) δ 8.38 (s, 2H), 8.07 (s, 1H), 7.98 (dd, J=5.8, 2.7 Hz, 1H), 7.67 (ddd, J=8.9, 4.0, 2.6 Hz, 1H), 7.30-7.27 (m, 1H), 5.63 (s, 2H), 2.26 (s, 3H).

Example 17. 2-[[1-(3-Bromo-4-fluoro-phenyl)triazol-4-yl]methoxy]-4-methylpyrimidine

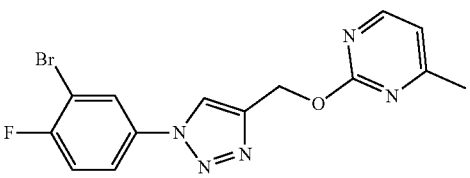 [SMILES: Cc1ccnc(OCc2cn(-c3ccc(F)c(Br)c3)nn2)n1]

The title compound was prepared in a manner analogous to Example 1 using (1-(3-bromo-4-fluorophenyl)-1H-1,2,3-triazol-4-yl)methanol (Intermediate 14) and 2-chloro-4-methylpyrimidine. MS (ESI): mass calcd. for $C_{14}H_{11}BrFN_5O$, 363.0; m/z found, 363.9 [M+H]$^+$. $^1$H NMR (400 MHz, CDCl$_3$) δ 8.40 (d, J=5.0 Hz, 1H), 8.08 (s, 1H), 7.99 (dd, J=5.8, 2.6 Hz, 1H), 7.66 (ddd, J=8.8, 4.0, 2.6 Hz, 1H), 7.31-7.28 (m, 1H), 6.87 (d, J=5.0 Hz, 1H), 5.65 (d, J=0.7 Hz, 2H), 2.50 (s, 3H).

Example 18. 2-[[1-(3-Bromo-4-fluoro-phenyl)triazol-4-yl]methoxy]-4,6-dimethyl-pyrimidine

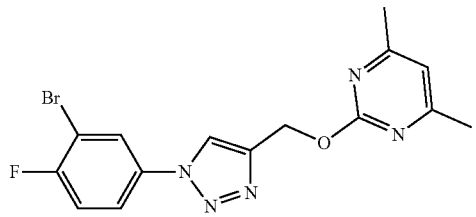 [SMILES: Cc1cc(C)nc(OCc2cn(-c3ccc(F)c(Br)c3)nn2)n1]

The title compound was prepared in a manner analogous to Example 1 using (1-(3-bromo-4-fluorophenyl)-1H-1,2,3-triazol-4-yl)methanol (Intermediate 14) and 2-chloro-4,6-dimethylpyrimidine. MS (ESI): mass calcd. for $C_{15}H_{13}BrFN_5O$, 377.0; m/z found, 378.0 [M+H]$^+$. $^1$H NMR (400 MHz, CDCl$_3$) δ 8.08 (s, 1H), 7.99 (dd, J=5.8, 2.7 Hz, 1H), 7.66 (ddd, J=8.9, 4.0, 2.7 Hz, 1H), 7.33-7.27 (m, 1H), 6.73 (s, 1H), 5.64 (d, J=0.8 Hz, 2H), 2.44 (s, 6H).

Example 19. 2-[[1-(3-Bromo-4-fluoro-phenyl)triazol-4-yl]methoxy]-5-fluoropyrimidine

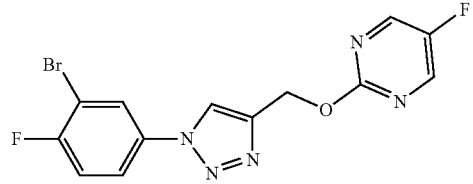 [SMILES: Fc1cnc(OCc2cn(-c3ccc(F)c(Br)c3)nn2)nc1]

The title compound was prepared in a manner analogous to Example 1 using (1-(3-bromo-4-fluorophenyl)-1H-1,2,3-triazol-4-yl)methanol (Intermediate 14) and 2-chloro-5-fluoropyrimidine. MS (ESI): mass calcd. for $C_{13}H_8BrF_2N_5O$, 367.0; m/z found, 368.0 [M+H]$^+$. $^1$H NMR (400 MHz, CDCl$_3$) δ 8.43 (s, 2H), 8.07 (s, 1H), 7.98 (dd, J=5.8, 2.7 Hz, 1H), 7.67 (ddd, J=8.9, 4.0, 2.6 Hz, 1H), 7.29 (dd, J=8.9, 7.8 Hz, 1H), 5.63 (s, 2H).

Example 20. 2-[[1-(4-Fluoro-3-methoxy-phenyl)triazol-4-yl]methoxy]pyrimidine

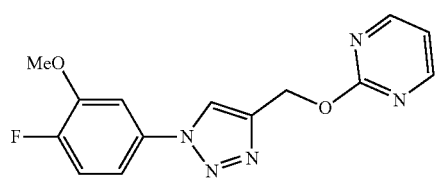 [SMILES: COc1cc(-n2cc(COc3ncccn3)nn2)ccc1F]

The title compound was prepared in a manner analogous to Example 1 using (1-(4-fluoro-3-methoxyphenyl)-1H-1,2,3-triazol-4-yl)methanol and 2-chloropyrimidine. MS (ESI): mass calcd. for $C_{14}H_{12}FN_5O_2$, 301.1; m/z found, 302.0 [M+H]$^+$. $^1$H NMR (400 MHz, CDCl$_3$) δ 8.57 (d, J=4.8 Hz, 2H), 8.09 (s, 1H), 7.46 (dd, J=7.4, 2.5 Hz, 1H), 7.23-7.12 (m, 2H), 7.05-6.94 (m, 1H), 5.66 (s, 2H), 3.97 (s, 3H)

Example 21. 2-[[1-[4-Chloro-3-(difluoromethoxy)phenyl]triazol-4-yl]methoxy]-4-methyl-pyrimidine

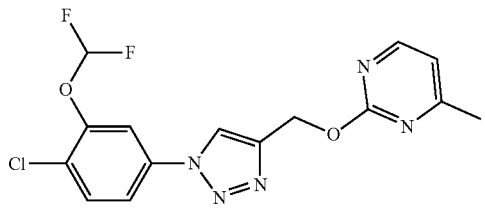 [SMILES: Cc1ccnc(OCc2cn(-c3ccc(Cl)c(OC(F)F)c3)nn2)n1]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-4-methylpyrimidine. MS (ESI): mass calcd. for $C_{15}H_{12}ClF_2N_5O_2$, 367.1; m/z found, 368.1 [M+H]$^+$. $^1$H NMR (400 MHz, CDCl$_3$) δ 8.39 (d, J=5.0 Hz, 1H), 8.13 (s, 1H), 7.74-7.65 (m, 1H), 7.63-7.58 (m, 1H), 7.60-7.52 (m, 1H), 6.86 (d, J=5.0 Hz, 1H), 6.63 (t, J=72.5 Hz, 1H), 5.64 (s, 2H), 2.48 (s, 3H).

Example 22. 2-[[1-[4-Chloro-3-(difluoromethoxy)phenyl]triazol-4-yl]methoxy]-5-methyl-pyrimidine

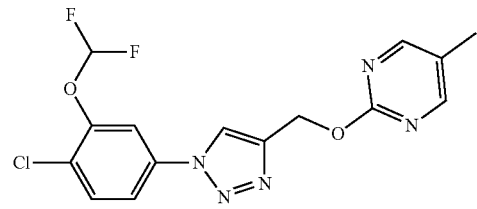 [SMILES: Cc1cnc(OCc2cn(-c3ccc(Cl)c(OC(F)F)c3)nn2)nc1]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-methylpyrimidine. MS (ESI): mass calcd. for $C_5H_{12}ClF_2N_5O_2$, 367.1; m/z found, 368.1 [M+H]$^+$. $^1$H NMR (400 MHz, CDCl$_3$) δ 8.37 (s, 2H), 8.12 (s, 1H), 7.75-7.67 (m, 1H), 7.64-7.58 (m, 2H), 7.58-7.53 (m, 1H), 6.63 (t, J=72.6 Hz, 1H), 5.62 (s, 2H), 2.25 (s, 3H).

Example 23. 2-[[1-[4-Chloro-3-(difluoromethoxy)phenyl]triazol-4-yl]methoxy]pyrazine

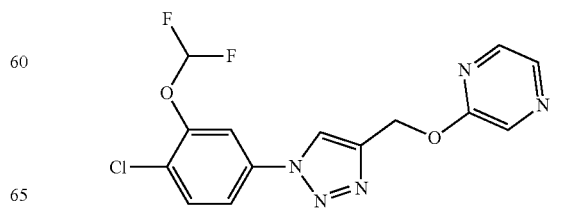

The title compound was prepared in a manner analogous to Example 1 using (1-(4-chloro-3-(difluoromethoxy)phenyl)-1H-1,2,3-triazol-4-yl)methanol (Intermediate 1) and 2-fluoropyrazine. MS (ESI): mass calcd. for $C_{14}H_{10}ClF_2N_5O_2$, 353.0; m/z found, 354.1 [M+H]$^+$. $^1$H NMR (400 MHz, CDCl$_3$) δ 8.30 (d, J=1.4 Hz, 1H), 8.19 (d, J=2.8 Hz, 1H), 8.13 (dd, J=2.8, 1.4 Hz, 1H), 8.08 (s, 1H), 7.74-7.68 (m, 1H), 7.65-7.60 (m, 1H), 7.60-7.55 (m, 1H), 6.64 (t, J=72.5 Hz, 1H), 5.61 (s, 2H).

Example 24. N-[[1-[3-(Difluoromethyl)-4-fluorophenyl]triazol-4-yl]methyl]pyrimidin-2-amine

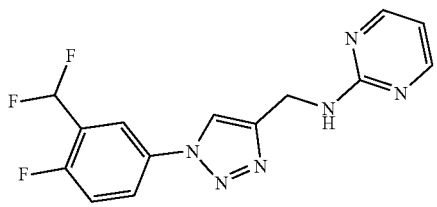 [SMILES: Fc1ccc(-n2cc(CNc3ncccn3)nn2)cc1C(F)F]

The title compound was prepared in a manner analogous to Example 3, Step B, using (1-(3-(difluoromethyl)-4-fluorophenyl)-1H-1,2,3-triazol-4-yl)methanamine (Intermediate 21) and 2-fluoropyrimidine. MS (ESI): mass calcd. for $C_{14}H_{11}F_3N_6$, 320.1; m/z found, 321.1 [M+H]$^+$. $^1$H NMR (400 MHz, CDCl$_3$) δ 4.82 (d, J=6.01 Hz, 2H), 5.80 (br s, 1H), 6.60 (t, J=4.62 Hz, 1H), 6.75-7.15 (m, 1H), 7.30 (br t, J=8.90 Hz, 1H), 7.77-7.93 (m, 2H), 7.97 (s, 1H), 8.33 (d, J=4.62 Hz, 2H).

Example 25. 2-[[1-[3-(Difluoromethyl)-4-fluorophenyl]triazol-4-yl]methoxy]pyrimidine

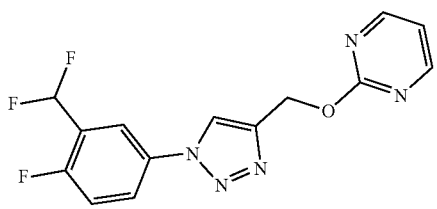 [SMILES: Fc1ccc(-n2cc(COc3ncccn3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 2-chloropyrimidine. MS (ESI): mass calcd. for $C_{14}H_{10}F_3N_5O$, 321.1; m/z found, 322.1 [M+H]$^+$. $^1$H NMR (400 MHz, CDCl$_3$) 5.67 (s, 2H), 6.78-7.12 (m, 2H), 7.33 (t, J=9.0 Hz, 1H), 7.82-8.01 (m, 2H), 8.14 (s, 1H), 8.58 (d, J=4.6 Hz, 2H).

Example 26. 2-[[1-[4-Chloro-3-(difluoromethoxy)phenyl]triazol-4-yl]methoxy]-5-methoxy-pyrimidine

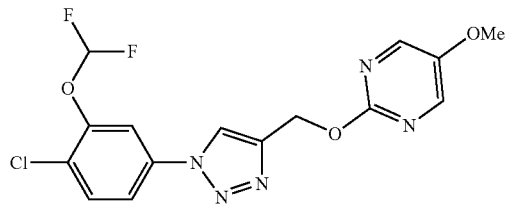 [SMILES: COc1cnc(OCc2cn(-c3ccc(Cl)c(OC(F)F)c3)nn2)nc1]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-methoxypyrimidine. MS (ESI): mass calcd. for $C_{15}H_{12}ClF_2N_5O_3$, 383.1; m/z found, 384.1 [M+H]$^+$. $^1$H NMR (400 MHz, CDCl$_3$) δ 8.24 (s, 2H), 8.15-8.08 (m, 1H), 7.74-7.67 (m, 1H), 7.66-7.59 (m, 1H), 7.59-7.55 (m, 1H), 6.63 (t, J=72.5 Hz, 1H), 5.61 (s, 2H), 3.88 (s, 3H).

Example 27. 2-[[1-[4-Chloro-3-(difluoromethoxy)phenyl]triazol-4-yl]methoxy]-5-ethyl-pyrimidine

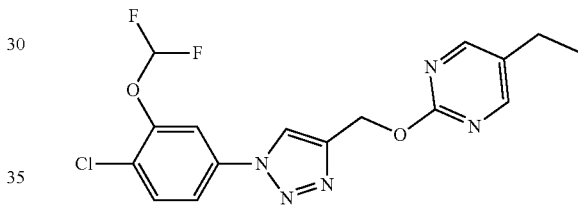

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-ethylpyrimidine. MS (ESI): mass calcd. for $C_{16}H_{14}ClF_2N_5O_2$, 381.1; m/z found, 382.1 [M+H]$^+$. $^1$H NMR (400 MHz, CDCl$_3$) δ 0.40 (s, 2H), 8.21-8.00 (m, 1H), 7.79-7.67 (m, 1H), 7.64-7.59 (m, 1H), 7.59-7.54 (m, 1H), 6.63 (t, J=72.5 Hz, 1H), 5.64 (s, 2H), 2.61 (q, J=7.6 Hz, 2H), 1.26 (t, J=7.6 Hz, 3H)

Example 28. 5-Chloro-2-[[1-[4-chloro-3-(difluoromethoxy)phenyl]triazol-4-yl]methoxy]pyrimidine

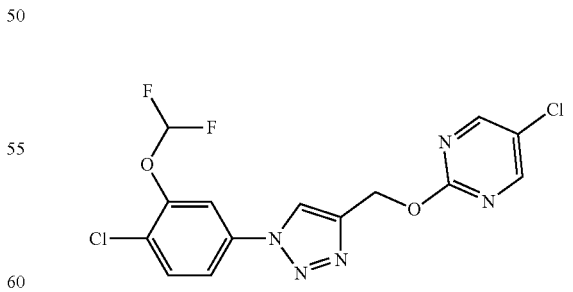

The title compound was prepared in a manner analogous to Example 1 using (1-(4-chloro-3-(difluoromethoxy)phenyl)-1H-1,2,3-triazol-4-yl)methanol (Intermediate 1) and 2,5-dichloropyrimidine. MS (ESI): mass calcd. for $C_{14}H_9Cl_2F_2N_5O_2$, 387.0; m/z found, 388.1 [M+H]$^+$. $^1$H NMR (400 MHz, CDCl$_3$) δ 8.51 (s, 2H), 8.16-8.02 (m, 1H), 7.73-7.68 (m, 1H), 7.65-7.60 (m, 1H), 7.59-7.53 (m, 1H), 6.64 (t, J=72.5 Hz, 1H), 5.64 (s, 2H).

Example 29. 2-[[1-[4-Chloro-3-(difluoromethoxy)phenyl]triazol-4-yl]methoxy]-4-methoxy-pyrimidine

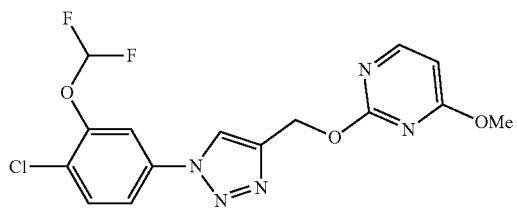 [SMILES: COc1ccnc(OCc2cn(-c3ccc(Cl)c(OC(F)F)c3)nn2)n1]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-4-methoxypyrimidine. MS (ESI): mass calcd. for $C_{15}H_{12}ClF_2N_5O_3$, 383.1; m/z found, 384.1 $[M+H]^+$. $^1$H NMR (400 MHz, CDCl$_3$) δ 8.22 (d, J=5.7 Hz, 1H), 8.12 (s, 1H), 7.75-7.68 (m, 1H), 7.63-7.59 (m, 1H), 7.58-7.53 (m, 1H), 6.64 (t, J=72.5 Hz, 1H), 6.43 (d, J=5.7 Hz, 1H), 5.64 (s, 2H), 3.98 (s, 3H).

Example 30. 2-[[1-[4-Chloro-3-(difluoromethyl)phenyl]triazol-4-yl]methoxy]-4-methyl-pyrimidine

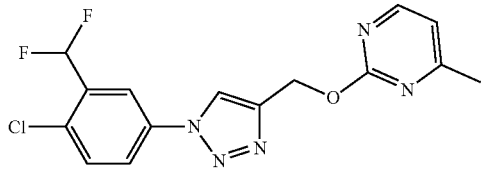 [SMILES: Cc1ccnc(OCc2cn(-c3ccc(Cl)c(C(F)F)c3)nn2)n1]

The title compound was prepared in a manner analogous to Example 1 using (1-(4-chloro-3-(difluoromethyl)phenyl)-1H-1,2,3-triazol-4-yl)methanol (Intermediate 8) and 2-chloro-4-methylpyrimidine. MS (ESI): mass calcd. for $C_{15}H_{12}ClF_2N_5O$, 351.1; m/z found, 352.1 $[M+H]^+$. $^1$H NMR (400 MHz, CDCl$_3$) δ 8.40 (d, J=5.0 Hz, 1H), 8.17 (s, 1H), 8.00 (d, J=2.5 Hz, 1H), 7.90-7.86 (m, 1H), 7.60 (d, J=8.7 Hz, 1H), 7.12-6.84 (m, 2H), 5.65 (d, J=0.7 Hz, 2H), 2.49 (s, 3H).

Example 31. 2-[[1-[4-Chloro-3-(difluoromethyl)phenyl]triazol-4-yl]methoxy]-5-methyl-pyrimidine

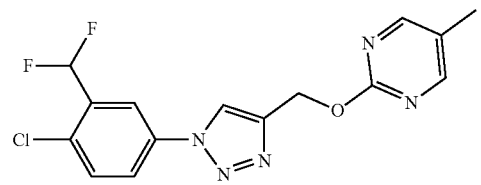 [SMILES: Cc1cnc(OCc2cn(-c3ccc(Cl)c(C(F)F)c3)nn2)nc1]

The title compound was prepared in a manner analogous to Example 1 using (1-(4-chloro-3-(difluoromethyl)phenyl)-1H-1,2,3-triazol-4-yl)methanol (Intermediate 8) and 2-chloro-5-methylpyrimidine. MS (ESI): mass calcd. for $C_{15}H_{12}ClF_2N_5O$, 351.1; m/z found, 352.1 $[M+H]^+$. $^1$H NMR (500 MHz, CDCl$_3$) δ 8.38 (d, J=0.9 Hz, 2H), 8.16 (s, 1H), 8.00 (d, J=2.6 Hz, 1H), 7.92-7.84 (m, 1H), 7.66-7.55 (m, 1H), 6.99 (t, J=54.6 Hz, 1H), 5.63 (d, J=0.7 Hz, 2H), 2.26 (s, 3H).

Example 32. 2-[[1-[4-Chloro-3-(difluoromethyl)phenyl]triazol-4-yl]methoxy]-5-ethyl-pyrimidine

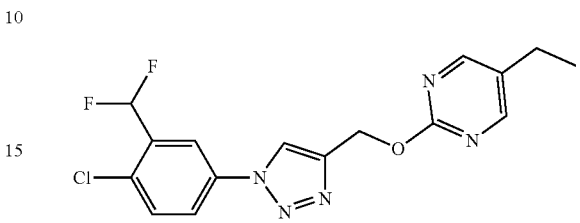

The title compound was prepared in a manner analogous to Example 1 using (1-(4-chloro-3-(difluoromethyl)phenyl)-1H-1,2,3-triazol-4-yl)methanol (Intermediate 8) and 2-chloro-5-ethylpyrimidine, using THF instead of DMF. MS (ESI): mass calcd. for $C_{16}H_{14}ClF_2N_5O$, 365.1; m/z found, 366.1 $[M+H]^+$. $^1$H NMR (500 MHz, CDCl$_3$) δ 8.40 (s, 1H), 8.17 (d, J=0.7 Hz, 1H), 8.01 (d, J=2.6 Hz, 1H), 7.92-7.86 (m, 1H), 7.63-7.59 (m, 1H), 6.99 (t, J=54.5 Hz, 1H), 5.65 (d, J=0.8 Hz, 2H), 2.61 (q, J=7.6 Hz, 3H), 1.27 (t, J=7.6 Hz, 3H).

Example 33. 2-[[1-[3-(Difluoromethoxy)-4-fluorophenyl]triazol-4-yl]methoxy]pyrimidine

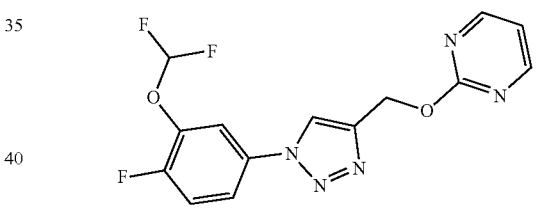

The title compound was prepared in a manner analogous to Example 1 using (1-(3-(difluoromethoxy)-4-fluorophenyl)-1H-1,2,3-triazol-4-yl)methanol (Intermediate 6) and 2-fluoropyrimidine. MS (ESI): mass calcd. for $C_{14}H_{10}F_3N_5O_2$, 337.1; m/z found, 338.1 $[M+H]^+$. $^1$H NMR (400 MHz, CDCl$_3$) δ 8.58 (d, J=4.9 Hz, 2H), 8.12 (s, 1H), 7.70 (dd, J=2.7, 6.6 Hz, 1H), 7.65-7.54 (m, 1H), 7.35 (t, J=9.1 Hz, 1H), 7.02 (t, J=4.7 Hz, 1H), 6.65 (t, J=72.6 Hz, 1H), 5.66 (s, 2H).

Example 34. 2-[[1-[4-Chloro-3-(difluoromethoxy)phenyl]triazol-4-yl]methoxy]-5-methyl-pyrazine

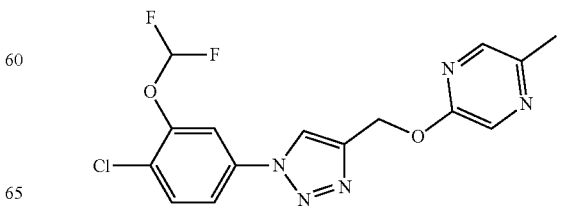

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-methylpyrazine. MS (ESI): mass calcd. for $C_{15}H_{12}ClF_2N_5O_2$, 367.1; m/z found, 368.1 [M+H]$^+$. $^1$H NMR (400 MHz, CDCl$_3$) δ 8.20 (d, J=1.5 Hz, 1H), 8.11-8.04 (m, 1H), 8.01-7.94 (m, 1H), 7.74-7.68 (m, 1H), 7.65-7.58 (m, 1H), 7.59-7.55 (m, 1H), 6.64 (t, J=72.5 Hz, 1H), 5.57 (s, 2H), 2.49 (s, 3H)

Example 35. 2-[[1-[4-Chloro-3-(difluoromethoxy)phenyl]triazol-4-yl]methoxy]-5-(difluoromethoxy)pyrimidine

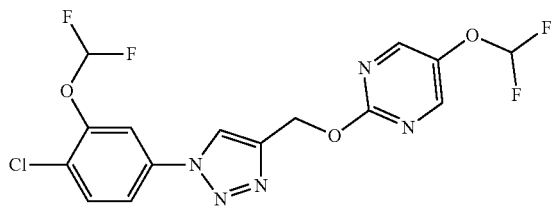 [SMILES: FC(F)Oc1cnc(OCc2cn(-c3ccc(Cl)c(OC(F)F)c3)nn2)nc1]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-(difluoromethoxy)pyrimidine. MS (ESI): mass calcd. for $C_{15}H_{10}ClF_4N_5O_3$, 419.0; m/z found, 420.0 [M+H]$^+$. $^1$H NMR (400 MHz, CDCl$_3$) δ 8.45 (s, 2H), 8.12 (s, 1H), 7.75-7.69 (m, 1H), 7.65-7.59 (m, 1H), 7.59-7.55 (m, 1H), 6.64 (t, J=72.5 Hz, 1H), 6.53 (t, J=71.9 Hz, 1H), 5.65 (s, 2H).

Example 36. N-[[1-[3-(Difluoromethoxy)-4-fluorophenyl]triazol-4-yl]methyl]pyrimidin-2-amine

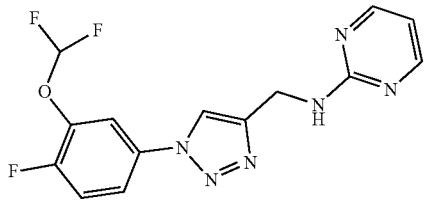 [SMILES: Fc1ccc(-n2cc(CNc3ncccn3)nn2)cc1OC(F)F]

The title compound was prepared in a manner analogous to Example 6 using (1-(3-(difluoromethoxy)-4-fluorophenyl)-1H-1,2,3-triazol-4-yl)methanamine (Intermediate 18) and 2-fluoropyrimidine. MS (ESI): mass calcd. for $C_{14}H_{11}F_3N_6O$, 336.1; m/z found, 337.1 [M+H]$^+$. $^1$H NMR (400 MHz, CDCl$_3$) δ 8.33 (d, J=4.9 Hz, 2H), 7.93 (s, 1H), 7.67 (dd, J=2.5, 6.5 Hz, 1H), 7.56 (ddd, J=2.7, 3.9, 9.0 Hz, 1H), 7.33 (t, J=9.2 Hz, 1H), 6.61 (s, 2H), 5.81-5.57 (m, 1H), 4.82 (d, J=6.2 Hz, 2H)

Example 37. 5-Chloro-2-[[1-(2,4-difluoro-3-methyl-phenyl)triazol-4-yl]methoxy]pyrimidine

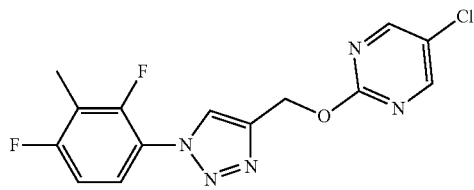 [SMILES: Cc1c(F)ccc(-n2cc(COc3ncc(Cl)cn3)nn2)c1F]

The title compound was prepared in a manner analogous to Example 1 using (1-(2,4-difluoro-3-methylphenyl)-1H-1,2,3-triazol-4-yl)methanol (Intermediate 10) and 2,5-dichloropyrimidine. MS (ESI): mass calcd. for $C_{14}H_{10}ClF_2N_5O$, 337.1; m/z found, 338.1 [M+H]$^+$. $^1$H NMR (500 MHz, CDCl$_3$) δ 8.50 (s, 2H), 8.13 (d, J=2.7 Hz, 1H), 7.73-7.66 (m, 1H), 7.07-6.99 (m, 1H), 5.68-5.62 (m, 2H), 2.30 (t, J=2.0 Hz, 3H).

Example 38. 2-[[1-(2,4-Difluoro-3-methyl-phenyl)triazol-4-yl]methoxy]-5-methyl-pyrimidine

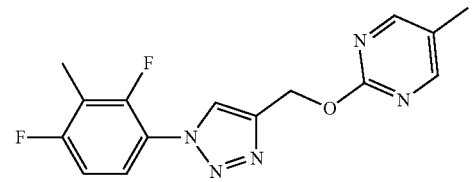 [SMILES: Cc1cnc(OCc2cn(-c3ccc(F)c(C)c3F)nn2)nc1]

The title compound was prepared in a manner analogous to Example 1 using (1-(2,4-difluoro-3-methylphenyl)-1H-1,2,3-triazol-4-yl)methanol (Intermediate 10) and 2-chloro-5-methylpyrimidine. MS (ESI): mass calcd. for $C_{15}H_{13}F_2N_5O$, 317.1; m/z found, 318.2 [M+H]$^+$. $^1$H NMR (500 MHz, CDCl$_3$) δ 8.38 (d, J=0.9 Hz, 2H), 8.15-8.11 (m, 1H), 7.69 (td, J=8.6, 5.7 Hz, 1H), 7.02 (td, J=8.7, 1.8 Hz, 1H), 5.64 (d, J=0.6 Hz, 2H), 2.30 (t, J=2.0 Hz, 3H), 2.25 (t, J=0.7 Hz, 3H).

Example 39. 2-[[1-(2,4-Difluoro-3-methyl-phenyl)triazol-4-yl]methoxy]-5-ethyl-pyrimidine

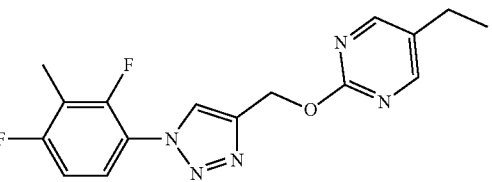

The title compound was prepared in a manner analogous to Example 1 using (1-(2,4-difluoro-3-methylphenyl)-1H-1,2,3-triazol-4-yl)methanol (Intermediate 10) and 2-chloro-5-ethylpyrimidine. MS (ESI): mass calcd. for $C_{16}H_{15}F_2N_5O$, 331.1; m/z found, 332.2 [M+H]$^+$. $^1$H NMR (500 MHz, CDCl$_3$) δ 8.39 (s, 2H), 8.14 (d, J=2.9 Hz, 1H), 7.73-7.66 (m, 1H), 7.02 (td, J=8.6, 1.9 Hz, 1H), 5.65 (d, J=0.7 Hz, 2H), 2.63-2.57 (m, 2H), 2.30 (t, J=2.0 Hz, 3H), 1.26 (t, J=7.6 Hz, 3H).

Example 40. 2-[[1-(3-Bromo-4-fluoro-phenyl)triazol-4-yl]methoxy]-5-ethyl-pyrimidine

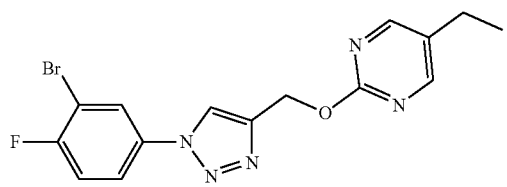 [SMILES: CCc1cnc(OCc2cn(-c3ccc(F)c(Br)c3)nn2)nc1]

The title compound was prepared in a manner analogous to Example 1 using (1-(3-bromo-4-fluorophenyl)-1H-1,2,3-triazol-4-yl)methanol (Intermediate 14) and 2-chloro-5-ethylpyrimidine, using THF instead of DMF. MS (ESI): mass calcd. for $C_{15}H_{13}BrFN_5O$, 377.0; m/z found, 380.1 [M+H]$^+$. $^1$H NMR (400 MHz, CDCl$_3$) δ 8.40 (s, 2H), 8.08 (s, 1H), 7.99 (dd, J=5.8, 2.7 Hz, 1H), 7.67 (ddd, J=8.9, 4.1, 2.7 Hz, 1H), 7.31-7.27 (m, 1H), 5.64 (s, 2H), 2.61 (q, J=7.6 Hz, 2H), 1.27 (t, J=7.6 Hz, 3H).

Example 41. 2-[[1-(3-Bromo-4-fluoro-phenyl)triazol-4-yl]methoxy]-5-methoxy-pyrimidine

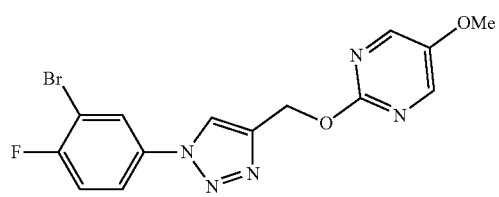 [SMILES: COc1cnc(OCc2cn(-c3ccc(F)c(Br)c3)nn2)nc1]

The title compound was prepared in a manner analogous to Example 1 using (1-(3-bromo-4-fluorophenyl)-1H-1,2,3-triazol-4-yl)methanol (Intermediate 14) and 2-chloro-5-methoxypyrimidine. MS (ESI): mass calcd. for $C_{14}H_{11}BrFN_5O_2$, 379.0; m/z found, 380.0 [M+H]$^+$. $^1$H NMR (400 MHz, CDCl$_3$) δ 8.24 (s, 2H), 8.07 (s, 1H), 7.98 (dd, J=5.8, 2.7 Hz, 1H), 7.67 (ddd, J=8.9, 4.1, 2.6 Hz, 1H), 7.31-7.27 (m, 1H), 5.60 (d, J=0.7 Hz, 2H), 3.88 (s, 3H).

Example 42. 2-[[1-(3-Bromo-4-fluoro-phenyl)triazol-4-yl]methoxy]-5-chloropyrimidine

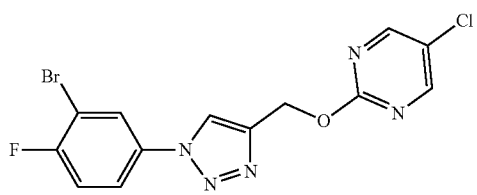 [SMILES: Fc1ccc(-n2cc(COc3ncc(Cl)cn3)nn2)cc1Br]

The title compound was prepared in a manner analogous to Example 1 using (1-(3-bromo-4-fluorophenyl)-1H-1,2,3-triazol-4-yl)methanol (Intermediate 14) and 2,5-dichloropyrimidine, using THF instead of DMF. MS (ESI): mass calcd. for $C_{13}H_8BrClFN_5O$, 383.0; m/z found, 384.0 [M+H]$^+$. $^1$H NMR (400 MHz, CDCl$_3$) δ 8.51 (s, 2H), 8.07 (s, 1H), 7.98 (dd, J=5.8, 2.7 Hz, 1H), 7.67 (ddd, J=8.9, 4.0, 2.6 Hz, 1H), 7.29 (dd, J=9.0, 7.9 Hz, 1H), 5.64 (d, J=0.7 Hz, 2H).

Example 43. 2-[[1-(3-Bromo-4-fluoro-phenyl)triazol-4-yl]methoxy]-5-isopropylpyrimidine

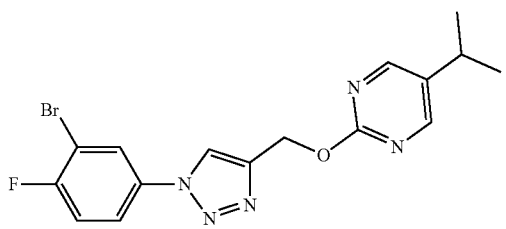 [SMILES: CC(C)c1cnc(OCc2cn(-c3ccc(F)c(Br)c3)nn2)nc1]

The title compound was prepared in a manner analogous to Example 1 using (1-(3-bromo-4-fluorophenyl)-1H-1,2,3-triazol-4-yl)methanol (Intermediate 14) and 2-chloro-5-isopropylpyrimidine, using THF instead of DMF. MS (ESI): mass calcd. for $C_{16}H_{15}BrFN_5O$, 391.0; m/z found, 392.1 [M+H]$^+$. $^1$H NMR (400 MHz, CDCl$_3$) δ 8.42 (d, J=0.5 Hz, 2H), 8.08 (s, 1H), 7.99 (dd, J=5.8, 2.7 Hz, 1H), 7.67 (ddd, J=8.9, 4.0, 2.7 Hz, 1H), 7.31-7.28 (m, 1H), 5.64 (d, J=0.7 Hz, 2H), 2.97-2.87 (m, 1H), 1.30 (d, J=7.0 Hz, 6H)

Example 44. 2-[[1-(3-Bromo-4-fluoro-phenyl)triazol-4-yl]methoxy]-5-(trifluoromethyl)pyrimidine

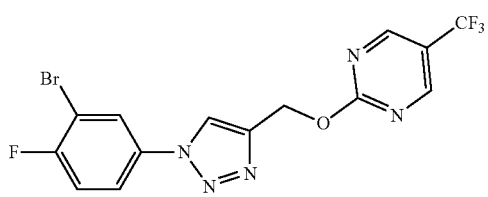 [SMILES: Fc1ccc(-n2cc(COc3ncc(C(F)(F)F)cn3)nn2)cc1Br]

The title compound was prepared in a manner analogous to Example 1 using (1-(3-bromo-4-fluorophenyl)-1H-1,2,3-triazol-4-yl)methanol (Intermediate 14) and 2-chloro-5-(trifluoromethyl)pyrimidine, using THF instead of DMF. MS (ESI): mass calcd. for $C_{14}H_8BrF_4N_5O$, 417.0; m/z found, 418.0 [M+H]$^+$. $^1$H NMR (400 MHz, CDCl$_3$) δ 8.82 (d, J=0.8 Hz, 2H), 8.09 (s, 1H), 7.99 (dd, J=5.7, 2.7 Hz, 1H), 7.68 (ddd, J=8.9, 4.0, 2.6 Hz, 1H), 7.29 (dd, J=8.9, 7.8 Hz, 1H), 5.73 (d, J=0.6 Hz, 2H).

Example 45. 2-[[1-[4-Chloro-3-(difluoromethyl)phenyl]triazol-4-yl]methoxy]-5-(trifluoromethyl)pyrimidine

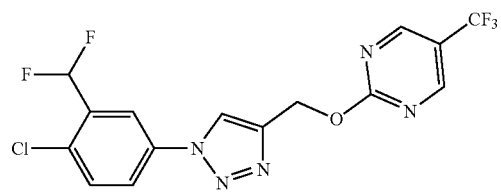 [SMILES: FC(F)c1cc(-n2cc(COc3ncc(C(F)(F)F)cn3)nn2)ccc1Cl]

The title compound was prepared in a manner analogous to Example 1 using (1-(4-chloro-3-(difluoromethyl)phenyl)-1H-1,2,3-triazol-4-yl)methanol (Intermediate 8) and 2-chloro-5-(trifluoromethyl)pyrimidine, using THF instead of DMF. MS (ESI): mass calcd. for $C_{15}H_9ClF_8N_5O$, 405.0; m/z found, 406.1 [M+H]$^+$. $^1$H NMR (500 MHz, CDCl3) δ 8.82 (d, J=0.8 Hz, 2H), 8.18 (s, 1H), 8.01 (d, J=2.7 Hz, 1H), 7.89 (dd, J=8.7, 2.5 Hz, 1H), 7.62 (d, J=8.6 Hz, 1H), 7.00 (t, J=54.5 Hz, 1H), 5.74 (d, J=0.7 Hz, 2H).

Example 46. 2-[[1-[4-Chloro-3-(difluoromethyl)phenyl]triazol-4-yl]methoxy]-5-methoxy-pyrimidine

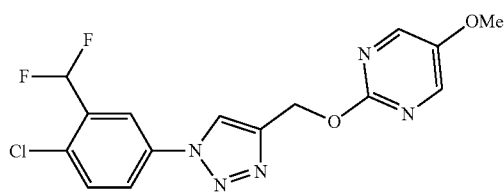 [SMILES: COc1cnc(OCc2cn(-c3ccc(Cl)c(C(F)F)c3)nn2)nc1]

The title compound was prepared in a manner analogous to Example 1 using (1-(4-chloro-3-(difluoromethyl)phenyl)-1H-1,2,3-triazol-4-yl)methanol (Intermediate 8) and 2-chloro-5-methoxypyrimidine, using THF instead of DMF. MS (ESI): mass calcd. for $C_{15}H_{12}ClF_2N_5O_2$, 367.1; m/z found, 368.1 [M+H]$^+$. $^1$H NMR (500 MHz, CDCl$_3$) δ 8.24 (s, 2H), 8.16 (s, 1H), 8.01 (d, J=2.6 Hz, 1H), 7.91-7.86 (m, 1H), 7.61 (dt, J=8.7, 1.2 Hz, 1H), 6.99 (t, J=54.6 Hz, 1H), 5.61 (d, J=0.7 Hz, 2H), 3.88 (s, 3H).

Example 47. 5-Chloro-2-[[1-[4-chloro-3-(difluoromethyl)phenyl]triazol-4-yl]methoxy]pyrimidine

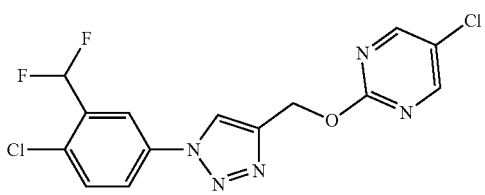 [SMILES: FC(F)c1cc(-n2cc(COc3ncc(Cl)cn3)nn2)ccc1Cl]

The title compound was prepared in a manner analogous to Example 1 using (1-(4-chloro-3-(difluoromethyl)phenyl)-1H-1,2,3-triazol-4-yl)methanol (Intermediate 8) and 2,5-dichloropyrimidine, using THF instead of DMF. MS (ESI): mass calcd. for $C_{14}H_9Cl_2F_2N_5O$, 371.0; m/z found, 372.0 [M+H]$^+$. $^1$H NMR (500 MHz, CDCl$_3$) δ 8.51 (s, 2H), 8.16 (s, 1H), 8.01 (d, J=2.6 Hz, 1H), 7.92-7.86 (m, 1H), 7.65-7.59 (m, 1H), 7.00 (t, J=54.5 Hz, 1H), 5.65 (d, J=0.7 Hz, 2H).

Example 48. 2-[[1-[4-Chloro-3-(difluoromethyl)phenyl]triazol-4-yl]methoxy]-5-isopropyl-pyrimidine

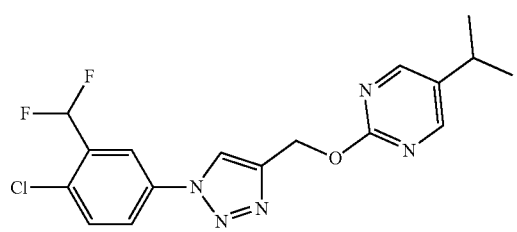 [SMILES: CC(C)c1cnc(OCc2cn(-c3ccc(Cl)c(C(F)F)c3)nn2)nc1]

The title compound was prepared in a manner analogous to Example 1 using (1-(4-chloro-3-(difluoromethyl)phenyl)-1H-1,2,3-triazol-4-yl)methanol (Intermediate 8) and 2-chloro-5-isopropylpyrimidine, using THF instead of DMF. MS (ESI): mass calcd. for $C_{17}H_{16}ClF_2N_5O$, 379.1; m/z found, 380.1 [M+H]$^+$. $^1$H NMR (500 MHz, CDCl$_3$) δ 8.43 (d, J=0.6 Hz, 2H), 8.17 (s, 1H), 8.01 (d, J=2.6 Hz, 1H), 7.90-7.87 (m, 1H), 7.61 (d, J=8.7 Hz, 1H), 6.99 (t, J=54.6 Hz, 1H), 5.65 (d, J=0.7 Hz, 2H), 2.97-2.88 (m, 1H), 1.30 (d, J=7.0 Hz, 6H).

Example 49. 5-Chloro-2-[[1-[3-(difluoromethyl)-4-fluoro-phenyl]triazol-4-yl]methoxy]pyrimidine

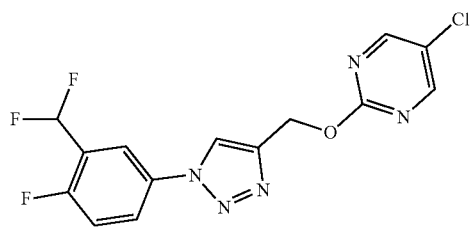 [SMILES: Fc1ccc(-n2cc(COc3ncc(Cl)cn3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 2,5-dichloropyrimidine. MS (ESI): mass calcd. for $C_{14}H_9ClF_3N_5O$, 355.0; m/z found, 356.0 [M+H]$^+$. $^1$H NMR (400 MHz, CDCl$_3$) δ 5.66 (s, 2H), 6.96 (t, J=55.02 Hz, 1H), 7.34 (t, J=9.02 Hz, 1H), 7.77-8.03 (m, 2H), 8.13 (s, 1H), 8.52 (s, 2H).

Example 50. 2-[[1-[3-(Difluoromethyl)-4-fluoro-phenyl]triazol-4-yl]methoxy]-5-(trifluoromethyl)pyrimidine

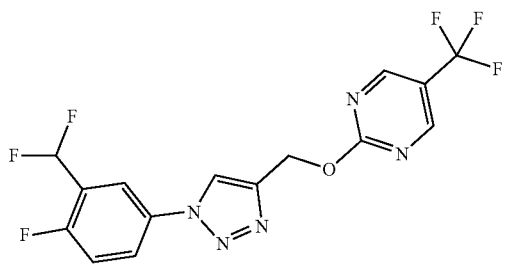 [SMILES: Fc1ccc(-n2cc(COc3ncc(C(F)(F)F)cn3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 2-chloro-5-(trifluoromethyl)pyrimidine. MS (ESI): mass calcd. for $C_{15}H_6F_6N_5O$, 389.1; m/z found, 390.0 [M+H]$^+$. $^1$H NMR (400 MHz, CDCl$_3$) δ 5.75 (s, 2H), 6.96 (t, J=54.56 Hz, 1H), 7.35 (t, J=9.02 Hz, 1H), 7.76-8.05 (m, 2H), 8.16 (s, 1H), 8.83 (s, 2H)

Example 51. 2-[[1-[3-(Difluoromethyl)-4-fluoro-phenyl]triazol-4-yl]methoxy]-5-methyl-pyrimidine

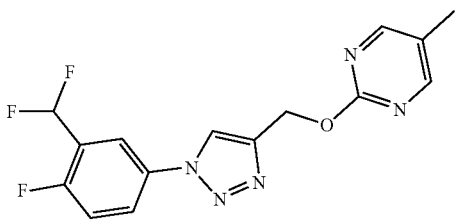 [SMILES: Cc1cnc(OCc2cn(-c3ccc(F)c(C(F)F)c3)nn2)nc1]

The title compound was prepared in a manner analogous to Example 1 using (1-(3-(difluoromethyl)-4-fluorophenyl)-1H-1,2,3-triazol-4-yl)methanol (Intermediate 9) and 2-chloro-5-methylpyrimidine, using THF instead of DMF. MS (ESI): mass calcd. for $C_{15}H_{12}F_3N_5O$, 335.1; m/z found, 336.1 [M+H]$^+$. $^1$H NMR (400 MHz, CDCl$_3$) δ 2.27 (s, 3H), 5.65 (s, 2H), 6.96 (t, J=54.56 Hz, 1H), 7.33 (t, J=8.90 Hz, 1H), 7.69-8.03 (m, 2H), 8.14 (s, 1H), 8.39 (s, 2H).

Example 52. 2-[[1-[3-(Difluoromethyl)-4-fluoro-phenyl]triazol-4-yl]methoxy]-4-methyl-pyrimidine

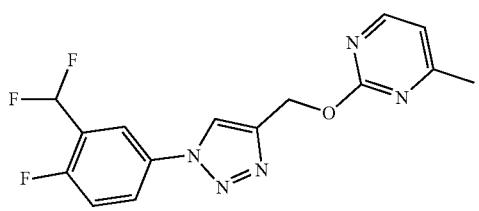 [SMILES: Cc1ccnc(OCc2cn(-c3ccc(F)c(C(F)F)c3)nn2)n1]

The title compound was prepared in a manner analogous to Example 1 using (1-(3-(difluoromethyl)-4-fluorophenyl)-1H-1,2,3-triazol-4-yl)methanol (Intermediate 9) and 2-chloro-4-methylpyrimidine, using THF instead of DMF. MS (ESI): mass calcd. for $C_{15}H_{12}F_3N_5O$, 335.1; m/z found, 336.1 [M+H]$^+$. $^1$H NMR (400 MHz, CDCl$_3$) δ 2.50 (s, 3H), 5.67 (s, 2H), 6.96 (t, J=54.56 Hz, 1H), 6.87 (d, J=4.85 Hz, 1H), 7.33 (t, J=9.02 Hz, 1H), 7.86-7.93 (m, 1H), 7.96 (dd, J=5.66, 2.66 Hz, 1H), 8.15 (s, 1H), 8.41 (d, J=4.85 Hz, 1H).

Example 53. (R/S)-2-[1-[1-[4-Chloro-3-(difluoromethoxy)phenyl]triazol-4-yl]ethoxy]pyrimidine

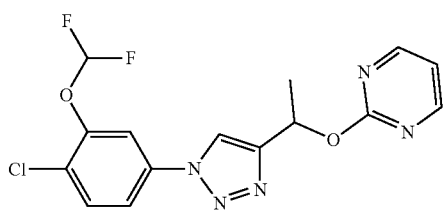 [SMILES: CC(Oc1ncccn1)c1cn(-c2ccc(Cl)c(OC(F)F)c2)nn1]

The title compound was prepared in a manner analogous to Example 1 using R/S-1-(1-(4-chloro-3-(difluoromethoxy)phenyl)-1H-1,2,3-triazol-4-yl)ethan-1-ol (Intermediate 2) and 2-chloropyrimidine. MS (ESI): mass calcd. for $C_{15}H_{12}ClF_2N_5O_2$, 367.1; m/z found, 368.0 [M+H]$^+$. $^1$H NMR (400 MHz, CDCl$_3$) δ 8.54 (d, J=4.8 Hz, 2H), 8.10-8.02 (m, 1H), 7.72-7.64 (m, 1H), 7.63-7.58 (m, 1H), 7.58-7.53 (m, 1H), 7.00-6.93 (m, 1H), 6.63 (t, J=72.5 Hz, 1H), 6.51 (q, J=6.6 Hz, 1H), 1.85 (d, J=6.6 Hz, 3H).

Example 54. (R*)-2-[1-[1-[4-Chloro-3-(difluoromethoxy)phenyl]triazol-4-yl]ethoxy]pyrimidine

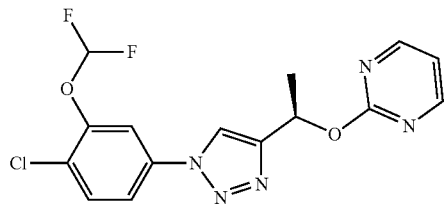 [SMILES: C[C@@H](Oc1ncccn1)c1cn(-c2ccc(Cl)c(OC(F)F)c2)nn1]

SFC Purification (Stationary phase: Chiralpak IF 5 μm 250×21 mm, Mobile phase: 20% methanol, 80% CO$_2$) Enantiomeric purity (SFC/Chiralpak IF): 100%. Retention time: 5.40 min. MS (ESI): mass calcd. for $C_{15}H_{12}ClF_2N_5O_2$, 367.1; m/z found, 368.1 [M+H]$^+$. $^1$H NMR (400 MHz, CDCl$_3$) δ 8.53 (d, J=4.8 Hz, 2H), 8.11-7.96 (m, 1H), 7.73-7.65 (m, 1H), 7.61-7.57 (m, 1H), 7.57-7.52 (m, 1H), 7.01-6.91 (m, 1H), 6.63 (t, J=72.5 Hz, 1H), 6.51 (q, J=6.6 Hz, 1H), 1.85 (d, J=6.6 Hz, 3H).

Example 55. (S*)-2-[1-[1-[4-Chloro-3-(difluoromethoxy)phenyl]triazol-4-yl]ethoxy]pyrimidine

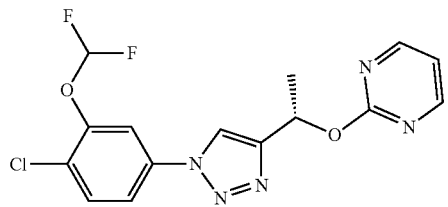 [SMILES: C[C@H](Oc1ncccn1)c1cn(-c2ccc(Cl)c(OC(F)F)c2)nn1]

SFC Purification (Stationary phase: Chiralpak IF 5 μm 250×21 mm, Mobile phase: 20% methanol, 80% CO$_2$) Enantiomeric purity (SFC/Chiralpak IF): 99.6%. Retention time: 7.05 min. MS (ESI): mass calcd. for $C_{15}H_{12}ClF_2N_5O_2$, 367.1; m/z found, 368.1 [M+H]$^+$. $^1$H NMR (400 MHz, CDCl$_3$) δ 8.54 (d, J=4.8 Hz, 2H), 8.11-7.97 (m, 1H), 7.75-7.65 (m, 1H), 7.63-7.58 (m, 1H), 7.57-7.53 (m, 1H), 7.01-6.92 (m, 1H), 6.63 (t, J=72.5 Hz, 1H), 6.51 (q, J=6.6 Hz, 1H), 1.85 (d, J=6.6 Hz, 3H).

Example 56. (R/S)-2-[1-[1-[4-Chloro-3-(difluoromethoxy)phenyl]triazol-4-yl]ethoxy]-5-methyl-pyrimidine

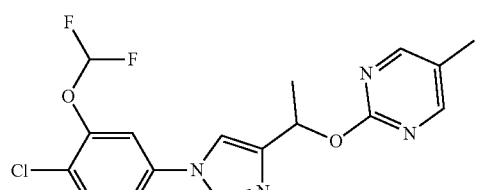

The title compound was prepared in a manner analogous to Example 1 using R/S-1-(1-(4-chloro-3-(difluoromethoxy)phenyl)-1H-1,2,3-triazol-4-yl)ethan-1-ol (Intermediate 2) and 2-chloro-5-methylpyrimidine. MS (ESI): mass calcd. for $C_{16}H_{14}ClF_2N_5O_2$, 381.1; m/z found, 382.0 [M+H]+. 1H NMR (400 MHz, CDCl3) δ 8.35 (s, 2H), 8.09-7.99 (m, 1H), 7.74-7.66 (m, 1H), 7.62-7.57 (m, 1H), 7.57-7.52 (m, 1H), 6.84-6.42 (m, 2H), 2.24 (s, 3H), 1.84 (d, J=6.6 Hz, 3H). Example 56 was subjected to Chiral SFC purification [Stationary phase: Chiralpak IF (5 μm, 4.6×250 mm), Mobile phase of 25% MeOH: 75% CO2] to provide the corresponding single enantiomers (Example 57 and Example 58) where the absolute stereochemistry was not determined. The enantiomeric purity was confirmed by analytical SFC using a Chiralpak IF column (5 μm 4.6×250 mm), mobile phase of 25% MeOH: 75% CO2, and a flow rate of 2 mL/min over 7 minutes (Temperature=35° C.). Elution was monitored following absorbance at 254 nm.

Example 57. (R*)-2-[1-[1-[4-Chloro-3-(difluoromethoxy)phenyl]triazol-4-yl]ethoxy]-5-methylpyrimidine

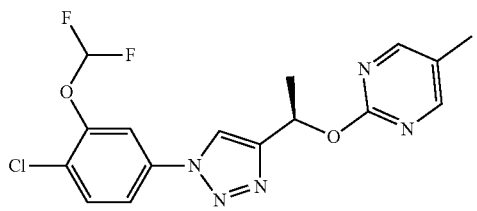 [SMILES: Cc1cnc(O[C@H](C)c2cn(-c3ccc(Cl)c(OC(F)F)c3)nn2)nc1]

Enantiomeric purity (SFC/Chiralpak IF): 100%. Retention time: 5.93 min. MS (ESI): mass calcd. for $C_{16}H_{14}ClF_2N_5O_2$, 381.1; m/z found, 382.0 [M+H]+. 1H NMR (400 MHz, CDCl3) δ 8.35 (s, 2H), 8.05-8.01 (m, 1H), 7.71-7.66 (m, 1H), 7.62-7.57 (m, 1H), 7.57-7.51 (m, 1H), 6.82-6.41 (m, 2H), 2.24 (s, 3H), 1.84 (d, J=6.6 Hz, 3H).

Example 58. (S*)-2-[1-[1-[4-Chloro-3-(difluoromethoxy)phenyl]triazol-4-yl]ethoxy]-5-methylpyrimidine

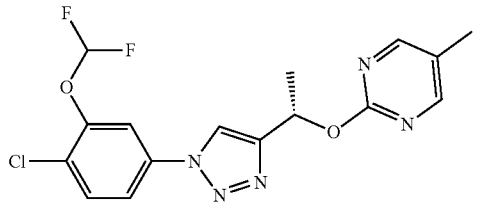 [SMILES: Cc1cnc(O[C@@H](C)c2cn(-c3ccc(Cl)c(OC(F)F)c3)nn2)nc1]

Enantiomeric purity (SFC/Chiralpak IF): 100%. Retention time: 8.74 min. MS (ESI): mass calcd. for $C_{16}H_{14}ClF_2N_5O_2$, 381.1; m/z found, 382.0 [M+H]+. 1H NMR (400 MHz, CDCl3) δ 8.34 (s, 2H), 8.13-7.97 (m, 1H), 7.73-7.65 (m, 1H), 7.60-7.57 (m, 1H), 7.57-7.52 (m, 1H), 6.84-6.39 (m, 2H), 2.23 (s, 3H), 1.83 (d, J=6.6 Hz, 3H).

Example 59. (R/S)-2-[1-[1-[4-Chloro-3-(difluoromethoxy)phenyl]triazol-4-yl]ethoxy]-4-methylpyrimidine

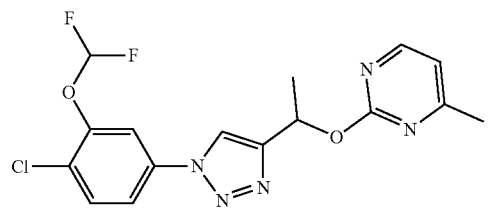 [SMILES: Cc1ccnc(OC(C)c2cn(-c3ccc(Cl)c(OC(F)F)c3)nn2)n1]

The title compound was prepared in a manner analogous to Example 1 using R/S-1-(1-(4-chloro-3-(difluoromethoxy)phenyl)-1H-1,2,3-triazol-4-yl)ethan-1-ol (Intermediate 2) and 2-chloro-4-methylpyrimidine. MS (ESI): mass calcd. for $C_{16}H_{14}ClF_2N_5O_2$, 381.1; m/z found, 382.0 [M+H]+. 1H NMR (500 MHz, CDCl3) δ 8.36 (d, J=5.0 Hz, 1H), 8.04 (d, J=0.7 Hz, 1H), 7.70-7.65 (m, 1H), 7.61-7.58 (m, 1H), 7.57-7.53 (m, 1H), 6.86-6.79 (m, 1H), 6.62 (t, J=72.5 Hz, 1H), 6.53 (q, J=6.6 Hz, 1H), 2.47 (s, 3H), 1.83 (d, J=6.6 Hz, 3H)

Example 60. (R/S)-5-Chloro-2-[1-[1-[4-chloro-3-(difluoromethoxy)phenyl]triazol-4-yl]ethoxy]pyrimidine

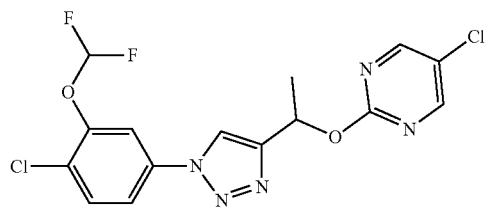 [SMILES: CC(Oc1ncc(Cl)cn1)c1cn(-c2ccc(Cl)c(OC(F)F)c2)nn1]

The title compound was prepared in a manner analogous to Example 1 using R/S-1-(1-(4-chloro-3-(difluoromethoxy)phenyl)-1H-1,2,3-triazol-4-yl)ethan-1-ol (Intermediate 2) and 2,5-dichloropyrimidine. MS (ESI): mass calcd. for $C_{15}H_{11}Cl_2F_2N_5O_2$, 401.0; m/z found, 402.0 [M+H]+. 1H NMR (500 MHz, CDCl3) δ 8.47 (s, 2H), 8.02 (d, J=0.7 Hz, 1H), 7.72-7.65 (m, 1H), 7.63-7.58 (m, 1H), 7.57-7.52 (m, 1H), 6.63 (t, J=72.5 Hz, 1H), 6.44 (q, J=6.6 Hz, 1H), 1.85 (d, J=6.6 Hz, 3H).

Example 61. 5-Chloro-2-[[1-[3-(difluoromethoxy)-4-fluoro-phenyl]triazol-4-yl]methoxy]pyrimidine

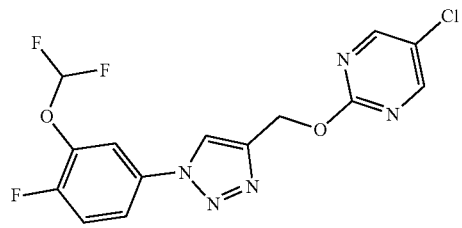 [SMILES: Fc1ccc(-n2cc(COc3ncc(Cl)cn3)nn2)cc1OC(F)F]

The title compound was prepared in a manner analogous to Example 1 using (1-(3-(difluoromethoxy)-4-fluorophenyl)-1H-1,2,3-triazol-4-yl)methanol (Intermediate 6) and 2,5-dichloropyrimidine, using THF instead of DMF. MS (ESI): mass calcd. for $C_{14}H_9ClF_3N_5O_2$, 371.0; m/z found, 372.1 [M+H]$^+$. $^1$H NMR (400 MHz, CDCl$_3$) δ 2.01-2.06 (m, 1H), 4.08-4.15 (m, 1H), 5.64 (s, 2H), 6.64 (t, J=72.36 Hz, 1H), 7.35 (t, J=9.13 Hz, 1H), 7.58 (ddd, J=8.90, 3.81, 2.77 Hz, 1H), 7.69 (dd, J=6.70, 2.54 Hz, 1H), 8.08 (s, 1H), 8.51 (s, 2H)

Example 62. 2-[[1-[3-(Difluoromethoxy)-4-fluorophenyl]triazol-4-yl]methoxy]-5-(trifluoromethyl)pyrimidine

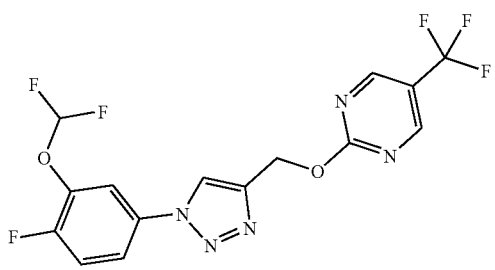 [SMILES: Fc1ccc(-n2cc(COc3ncc(C(F)(F)F)cn3)nn2)cc1OC(F)F]

The title compound was prepared in a manner analogous to Example 1 using (1-(3-(difluoromethoxy)-4-fluorophenyl)-1H-1,2,3-triazol-4-yl)methanol (Intermediate 6) and 2-chloro-5-(trifluoromethyl)pyrimidine, using THF instead of DMF. MS (ESI): mass calcd. for $C_{15}H_9F_6N_5O_2$, 405.1; m/z found, 406.1 [M+H]$^+$. $^1$H NMR (400 MHz, CDCl$_3$) δ 8.81 (s, 2H), 8.13 (s, 1H), 7.69 (dd, J=2.4, 6.6 Hz, 1H), 7.59 (br d, J=9.0 Hz, 1H), 7.34 (t, J=9.2 Hz, 1H), 6.65 (t, J=72.1 Hz, 1H), 5.72 (s, 2H).

Example 63. 2-[[1-[3-(Difluoromethoxy)-4-fluorophenyl]triazol-4-yl]methoxy]-5-methyl-pyrimidine

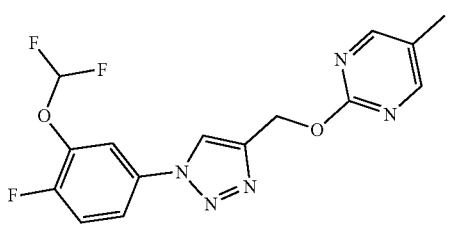 [SMILES: Cc1cnc(OCc2cn(-c3ccc(F)c(OC(F)F)c3)nn2)nc1]

The title compound was prepared in a manner analogous to Example 1 using (1-(3-(difluoromethoxy)-4-fluorophenyl)-1H-1,2,3-triazol-4-yl)methanol (Intermediate 6) and 2-chloro-5-methylpyrimidine, using THF instead of DMF. MS (ESI): mass calcd. for $C_{15}H_{12}F_3N_5O_2$, 351.1; m/z found, 352.1 [M+H]$^+$. $^1$H NMR (400 MHz, CDCl$_3$) δ 8.38 (s, 2H), 8.09 (s, 1H), 7.69 (dd, J=2.5, 6.5 Hz, 1H), 7.58 (td, J=3.2, 8.9 Hz, 1H), 7.34 (t, J=9.2 Hz, 1H), 6.64 (t, J=72.4 Hz, 1H), 5.83-5.41 (m, 2H), 2.26 (s, 3H)

Example 64. 2-[[1-[3-(Difluoromethoxy)-4-fluorophenyl]triazol-4-yl]methoxy]-4-methyl-pyrimidine

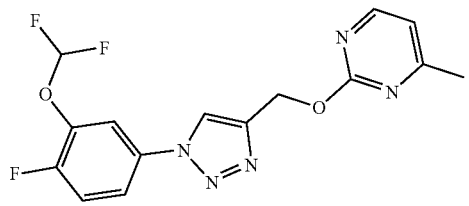 [SMILES: Cc1ccnc(OCc2cn(-c3ccc(F)c(OC(F)F)c3)nn2)n1]

The title compound was prepared in a manner analogous to Example 1 using (1-(3-(difluoromethoxy)-4-fluorophenyl)-1H-1,2,3-triazol-4-yl)methanol (Intermediate 6) and 2-chloro-4-methylpyrimidine, using THF instead of DMF. MS (ESI): mass calcd. for $C_{15}H_{12}F_3N_5O_2$, 351.1; m/z found, 352.1 [M+H]$^+$. $^1$H NMR (400 MHz, CDCl$_3$) δ 8.40 (d, J=5.1 Hz, 1H), 8.11 (s, 1H), 7.70 (dd, J=2.5, 6.5 Hz, 1H), 7.64-7.51 (m, 1H), 7.34 (t, J=9.2 Hz, 1H), 6.87 (d, J=5.1 Hz, 1H), 6.65 (t, J=72.6 Hz, 1H), 5.66 (s, 2H), 2.50 (s, 3H).

Example 65. 2-[[1-[3-(Difluoromethyl)-4-fluorophenyl]triazol-4-yl]methoxy]-5-(trifluoromethyl)pyridine

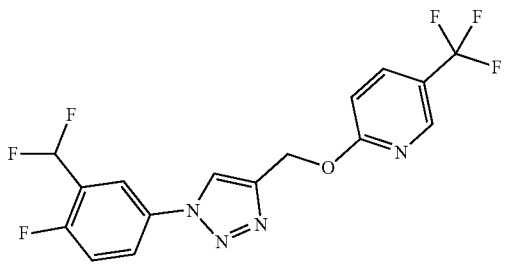 [SMILES: Fc1ccc(-n2cc(COc3ccc(C(F)(F)F)cn3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 2-chloro-5-(trifluoromethyl)pyridine, using THF instead of DMF. MS (ESI): mass calcd. for $C_{16}H_{10}F_6N_4O$, 388.1; m/z found, 389.0 [M+H]$^+$. $^1$H NMR (400 MHz, CDCl$_3$) δ 5.66 (s, 2H), 6.73-7.14 (m, 2H), 7.33 (t, J=9.02 Hz, 1H), 7.81 (dd, J=8.67, 2.43 Hz, 1H), 7.86-7.99 (m, 2H), 8.09 (s, 1H), 8.50 (s, 1H)

Example 66. 2-[[1-[4-Chloro-3-(difluoromethyl)phenyl]triazol-4-yl]methoxy]-5-fluoro-pyrimidine

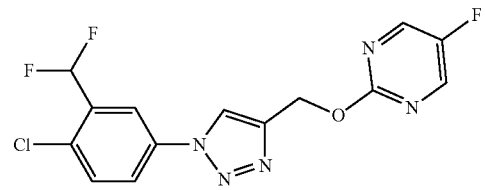 [SMILES: Fc1cnc(OCc2cn(-c3ccc(Cl)c(C(F)F)c3)nn2)nc1]

The title compound was prepared in a manner analogous to Example 1 using (1-(4-chloro-3-(difluoromethyl)phenyl)-

1H-1,2,3-triazol-4-yl)methanol (Intermediate 8) and 2-chloro-5-fluoropyrimidine, using THF instead of DMF. MS (ESI): mass calcd. for $C_{14}H_9ClF_3N_5O$, 355.0; m/z found, 356.0 [M+H]$^+$. $^1$H NMR (500 MHz, CDCl$_3$) δ 8.43 (s, 2H), 8.16 (s, 1H), 8.01 (d, J=2.6 Hz, 1H), 7.91-7.86 (m, 1H), 7.64-7.60 (m, 1H), 6.99 (t, J=54.6 Hz, 1H), 5.64 (d, J=0.7 Hz, 2H).

Example 67. 2-[[1-[3-(1,1-Difluoroethyl)-4-fluoro-phenyl]triazol-4-yl]methoxy]-5-ethyl-pyrimidine

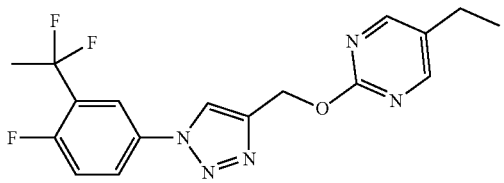 [SMILES: CCc1cnc(OCc2cn(-c3ccc(F)c(C(C)(F)F)c3)nn2)nc1]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-5-ethylpyrimidine, using THF instead of DMF. MS (ESI): mass calcd. for $C_{17}H_{16}F_3N_5O$, 363.1; m/z found, 364.0 [M+H]$^+$. $^1$H NMR (500 MHz, CDCl$_3$) δ 8.40 (s, 2H), 8.12 (t, J=0.7 Hz, 1H), 7.92-7.87 (m, 1H), 7.86-7.80 (m, 1H), 7.34-7.28 (m, 1H), 5.74-5.55 (m, 2H), 2.70-2.52 (m, 2H), 2.05 (t, J=18.6, 1.2 Hz, 3H), 1.27 (t, J=7.6 Hz, 3H).

Example 68. 2-[[1-[3-(1,1-Difluoroethyl)-4-fluoro-phenyl]triazol-4-yl]methoxy]-5-methoxy-pyrimidine

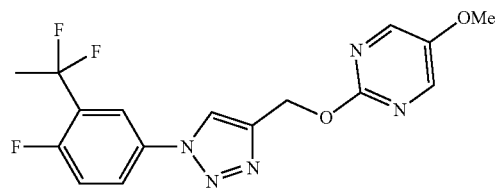 [SMILES: COc1cnc(OCc2cn(-c3ccc(F)c(C(C)(F)F)c3)nn2)nc1]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-5-methoxypyrimidine, using THF instead of DMF. MS (ESI): mass calcd. for $C_{16}H_{14}F_3N_5O_2$, 365.1; m/z found, 366.0 [M+H]$^+$. $^1$H NMR (500 MHz, CDCl$_3$) δ 8.24 (s, 2H), 8.11 (t, J=0.7 Hz, 1H), 7.89 (dd, J=6.2, 2.8 Hz, 1H), 7.82 (s, 1H), 7.30 (dd, J=9.8, 8.8 Hz, 1H), 5.61 (d, J=0.7 Hz, 2H), 3.88 (s, 3H), 2.05 (td, J=18.6, 1.2 Hz, 3H).

Example 69. 5-Chloro-2-[[1-[3-(1,1-difluoroethyl)-4-fluoro-phenyl]triazol-4-yl]methoxy]pyrimidine

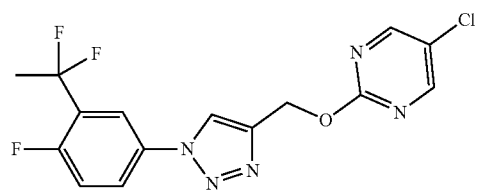 [SMILES: CC(F)(F)c1cc(-n2cc(COc3ncc(Cl)cn3)nn2)ccc1F]

The title compound was prepared in a manner analogous to Example 1 using (1-(3-(1,1-difluoroethyl)-4-fluorophenyl)-1H-1,2,3-triazol-4-yl)methanol (Intermediate 11) and 2,5-dichloropyrimidine, using THF instead of DMF. MS (ESI): mass calcd. for $C_{15}H_{11}ClF_3N_5O$, 369.1; m/z found, 370.0 [M+H]$^+$. $^1$H NMR (500 MHz, CDCl$_3$) δ 8.51 (s, 2H), 8.11 (t, J=0.7 Hz, 1H), 7.89 (dd, J=6.2, 2.7 Hz, 1H), 7.84 (d, J=12.9 Hz, 1H), 7.31 (dd, J=9.8, 8.9 Hz, 1H), 5.65 (d, J=0.7 Hz, 2H), 2.05 (td, J=18.6, 1.2 Hz, 3H).

Example 70. 2-[[1-[3-(1,1-Difluoroethyl)-4-fluoro-phenyl]triazol-4-yl]methoxy]-5-isopropyl-pyrimidine

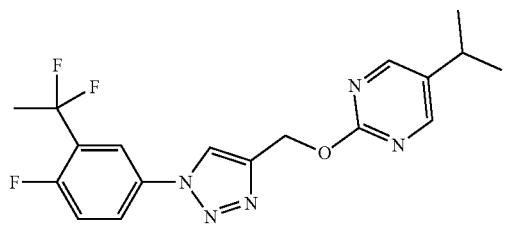 [SMILES: CC(C)c1cnc(OCc2cn(-c3ccc(F)c(C(C)(F)F)c3)nn2)nc1]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-5-isopropylpyrimidine, using THF instead of DMF. MS (ESI): mass calcd. for $C_{15}H_8F_3N_5O$, 377.1; m/z found, 378.0 [M+H]$^+$. $^1$H NMR (500 MHz, CDCl$_3$) δ 8.42 (d, J=0.5 Hz, 2H), 8.12 (t, J=0.7 Hz, 1H), 7.90 (dd, J=6.2, 2.7 Hz, 1H), 7.87-7.81 (m, 1H), 7.35-7.27 (m, 1H), 5.64 (s, 2H), 2.92 (t, J=7.0 Hz, 1H), 2.05 (td, J=18.6, 1.2 Hz, 6H), 1.30 (d, J=7.0 Hz, 3H).

Example 71. 2-[[1-[3-(1,1-Difluoroethyl)-4-fluoro-phenyl]triazol-4-yl]methoxy]-5-(trifluoromethyl) pyrimidine

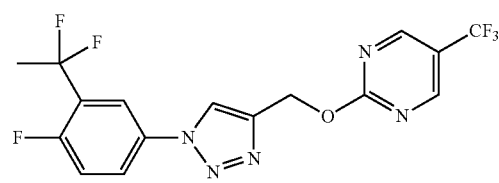 [SMILES: CC(F)(F)c1cc(-n2cc(COc3ncc(C(F)(F)F)cn3)nn2)ccc1F]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-5-(trifluoromethyl)pyrimidine, using THF instead of DMF. MS (ESI): mass calcd. for $C_{16}H_{11}FN_5O$, 403.1; m/z found, 404.0 [M+H]$^+$. $^1$H NMR (500 MHz, CDCl$_3$) δ 8.85-8.78 (m, 2H), 8.13 (s, 1H), 7.93-7.87 (m, 1H), 7.87-7.81 (m, 1H), 7.36-7.28 (m, 1H), 5.74 (s, 2H), 2.05 (td, J=18.6, 1.2 Hz, 3H).

Example 72. 5-Ethyl-2-[[1-[4-fluoro-3-(trifluoromethyl)phenyl]triazol-4-yl]methoxy]pyrimidine

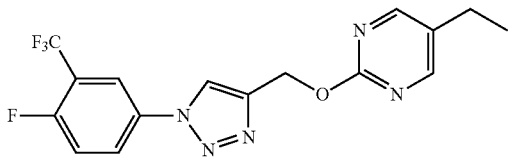 [SMILES: CCc1cnc(OCc2cn(-c3ccc(F)c(C(F)(F)F)c3)nn2)nc1]

The title compound was prepared in a manner analogous to Example 1 using (1-(4-fluoro-3-(trifluoromethyl)phenyl)-1H-1,2,3-triazol-4-yl)methanol (Intermediate 5) and 2-chloro-5-ethylpyrimidine, using THF instead of DMF. MS (ESI): mass calcd. for $C_{16}H_{13}F_4N_5O$, 367.1; m/z found, 368.1 [M+H]$^+$. $^1$H NMR (500 MHz, CDCl$_3$) δ 8.40 (t, J=0.7 Hz, 2H), 8.14 (t, J=0.7 Hz, 1H), 8.02-7.98 (m, 1H), 7.98-7.92 (m, 1H), 7.40 (t, J=9.1 Hz, 1H), 5.65 (d, J=0.7 Hz, 2H), 2.70-2.54 (m, 2H), 1.27 (t, J=7.6 Hz, 3H)

Example 73. 2-[[1-[4-Fluoro-3-(trifluoromethyl)phenyl]triazol-4-yl]methoxy]-5-methoxy-pyrimidine

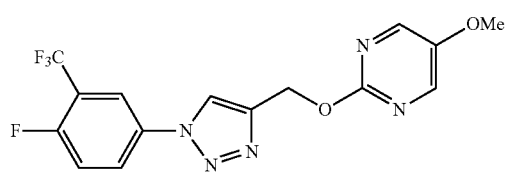 [SMILES: COc1cnc(OCc2cn(-c3ccc(F)c(C(F)(F)F)c3)nn2)nc1]

The title compound was prepared in a manner analogous to Example 1 using (1-(4-fluoro-3-(trifluoromethyl)phenyl)-1H-1,2,3-triazol-4-yl)methanol (Intermediate 5) and 2-chloro-5-methoxypyrimidine, using THF instead of DMF. MS (ESI): mass calcd. for $C_{15}H_{11}F_4N_5O_2$, 369.1; m/z found, 370.0 [M+H]$^+$. $^1$H NMR (500 MHz, CDCl$_3$) δ 8.24 (s, 2H), 8.16-8.09 (m, 1H), 8.04-7.98 (m, 1H), 7.99-7.93 (m, 1H), 7.40 (t, J=9.2 Hz, 1H), 5.61 (s, 2H), 3.88 (s, 3H).

Example 74. 5-Chloro-2-[[1-[4-fluoro-3-(trifluoromethyl)phenyl]triazol-4-yl]methoxy]pyrimidine

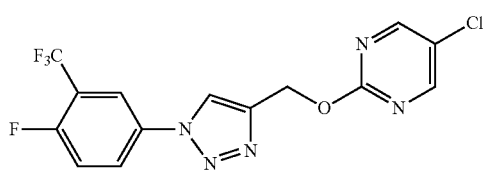 [SMILES: Fc1ccc(-n2cc(COc3ncc(Cl)cn3)nn2)cc1C(F)(F)F]

The title compound was prepared in a manner analogous to Example 1 using (1-(4-fluoro-3-(trifluoromethyl)phenyl)-1H-1,2,3-triazol-4-yl)methanol (Intermediate 5) and 2,5-dichloropyrimidine, using THF instead of DMF. MS (ESI): mass calcd. for $C_{14}H_6ClF_4N_5O$, 373.0; m/z found, 374.0 [M+H]$^+$. $^1$H NMR (500 MHz, CDCl$_3$) δ 8.51 (s, 2H), 8.16-8.11 (m, 1H), 8.04-7.98 (m, 1H), 7.98-7.92 (m, 1H), 7.41 (t, J=9.1 Hz, 1H), 5.65 (d, J=0.7 Hz, 2H).

Example 75. 2-[[1-[4-Fluoro-3-(trifluoromethyl)phenyl]triazol-4-yl]methoxy]-5-isopropyl-pyrimidine

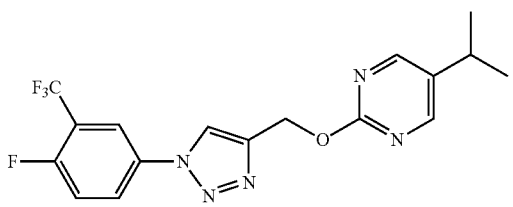 [SMILES: CC(C)c1cnc(OCc2cn(-c3ccc(F)c(C(F)(F)F)c3)nn2)nc1]

The title compound was prepared in a manner analogous to Example 1 using (1-(4-fluoro-3-(trifluoromethyl)phenyl)-1H-1,2,3-triazol-4-yl)methanol (Intermediate 5) and 2-chloro-5-isopropylpyrimidine, using THF instead of DMF. MS (ESI): mass calcd. for $C_{17}H_{15}F_4N_5O$, 381.1; m/z found, 382.0 [M+H]$^+$. $^1$H NMR (500 MHz, CDCl$_3$) δ 8.43 (s, 2H), 8.16-8.13 (m, 1H), 8.02-7.99 (m, 1H), 7.98-7.93 (m, 1H), 7.40 (t, J=9.1 Hz, 1H), 5.65 (s, 2H), 2.98-2.85 (m, 1H), 1.30 (d, J=7.0 Hz, 6H).

Example 76. 2-[[1-[4-Fluoro-3-(trifluoromethyl)phenyl]triazol-4-yl]methoxy]-5-(trifluoromethyl)pyrimidine

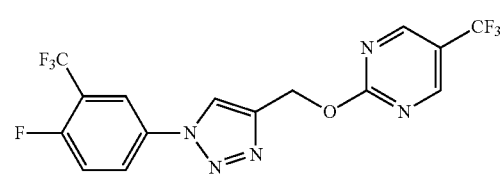 [SMILES: Fc1ccc(-n2cc(COc3ncc(C(F)(F)F)cn3)nn2)cc1C(F)(F)F]

The title compound was prepared in a manner analogous to Example 1 using (1-(4-fluoro-3-(trifluoromethyl)phenyl)-1H-1,2,3-triazol-4-yl)methanol (Intermediate 5) and 2-chloro-5-(trifluoromethyl)pyrimidine, using THF instead of DMF. MS (ESI): mass calcd. for $C_{15}H_8F_7N_5O$, 407.1; m/z found, 408.0 [M+H]$^+$. $^1$H NMR (500 MHz, CDCl$_3$) δ 8.86-8.79 (m, 2H), 8.15 (s, 1H), 8.04-7.98 (m, 1H), 7.98-7.93 (m, 1H), 7.41 (t, J=9.1 Hz, 1H), 5.74 (d, J=0.7 Hz, 2H).

Example 77. 2-[[1-[3-(1,1-Difluoroethyl)-4-fluorophenyl]triazol-4-yl]methoxy]-5-methyl-pyrimidine

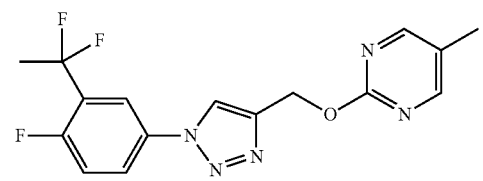 [SMILES: Cc1cnc(OCc2cn(-c3ccc(F)c(C(C)(F)F)c3)nn2)nc1]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-5-methylpyrimidine, using THF instead of DMF. MS (ESI): mass calcd. for $C_{16}H_{14}F_3N_5O$, 349.1; m/z found, 350.1 [M+H]$^+$. $^1$H NMR (400 MHz, CDCl$_3$) δ 8.38 (s, 2H), 8.12 (s, 1H), 7.97-7.78 (m, 2H), 7.37-7.27 (m, 1H), 5.64 (d, J=2.9 Hz, 2H), 2.27 (d, J=2.7 Hz, 3H), 2.17-1.94 (m, 3H).

Example 78. 2-[[1-[3-(1,1-Difluoroethyl)-4-fluorophenyl]triazol-4-yl]methoxy]pyrimidine

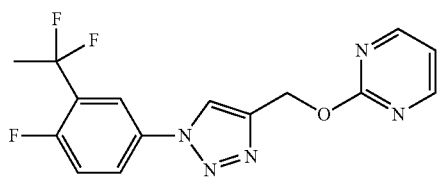 [SMILES: CC(F)(F)c1cc(-n2cc(COc3ncccn3)nn2)ccc1F]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloropyrimidine, using THF instead of DMF. MS (ESI): mass calcd. for $C_{15}H_{12}F_3N_5O$, 335.1; m/z found, 336.0 [M+H]$^+$. $^1$H NMR (400 MHz, CDCl$_3$) δ 8.58 (d, J=4.7 Hz, 2H), 8.13 (d, J=1.1 Hz, 1H), 7.93-7.87 (m, 1H), 7.88-7.79 (m, 1H), 7.36-7.27 (m, 1H), 7.01 (t, J=4.7 Hz, 1H), 5.67 (d, J=0.9 Hz, 2H), 2.19-1.91 (m, 3H).

Example 79. 2-[[1-[3-(1,1-Difluoroethyl)-4-fluorophenyl]triazol-4-yl]methoxy]-4-methyl-pyrimidine

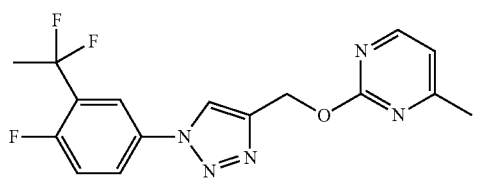 [SMILES: Cc1ccnc(OCc2cn(-c3ccc(F)c(C(C)(F)F)c3)nn2)n1]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-4-methylpyrimidine, using THF instead of DMF. MS (ESI): mass calcd. for $C_{16}H_{14}F_3N_5O$, 349.1; m/z found, 350.1 [M+H]$^+$. $^1$H NMR (400 MHz, CDCl$_3$) δ 8.41 (t, J=5.3 Hz, 1H), 8.13 (s, 1H), 7.96-7.77 (m, 2H), 7.36-7.28 (m, 2H), 6.86 (d, J=5.3 Hz, 1H), 5.66 (d, J=3.5 Hz, 2H), 2.66-2.31 (m, 2H), 2.05 (t, J=18.3 Hz, 3H)

Example 80. 2-[[1-[3-(1,1-Difluoroethyl)-4-fluorophenyl]triazol-4-yl]methoxy]-5-fluoro-pyrimidine

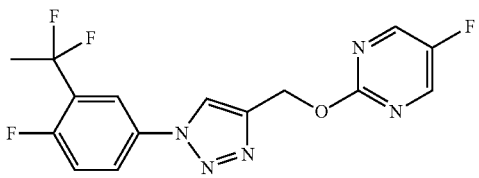 [SMILES: CC(F)(F)c1cc(-n2cc(COc3ncc(F)cn3)nn2)ccc1F]

The title compound was prepared in a manner analogous to Example 1 using (1-(3-(1,1-difluoroethyl)-4-fluorophenyl)-1H-1,2,3-triazol-4-yl)methanol (Intermediate 11) and 2-chloro-5-fluoropyrimidine, using THF instead of DMF. MS (ESI): mass calcd. for $C_{15}H_{11}F_4N_5O$, 353.1; m/z found, 354.0 [M+H]$^+$. $^1$H NMR (400 MHz, CDCl$_3$) δ 8.43 (s, 2H), 8.11 (s, 1H), 7.92-7.87 (m, 1H), 7.87-7.81 (m, 1H), 7.31 (t, J=9.4 Hz, 1H), 5.64 (s, 2H), 2.16-1.96 (m, 3H).

Example 81. 2-[[1-[4-Fluoro-3-(trifluoromethyl)phenyl]triazol-4-yl]methoxy]-5-methyl-pyrimidine

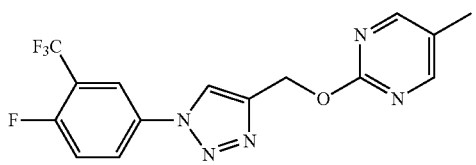 [SMILES: Cc1cnc(OCc2cn(-c3ccc(F)c(C(F)(F)F)c3)nn2)nc1]

The title compound was prepared analogous to Example 155, using (1-(4-fluoro-3-(trifluoromethyl)phenyl)-1H-1,2,3-triazol-4-yl)methanol (Intermediate 5) and 2-chloro-5-methylpyrimidine, using THF instead of DMF. MS (ESI): mass calcd. for $C_{15}H_{11}F_4N_5O$, 353.1; m/z found, 354.0 [M+H]$^+$. $^1$H NMR (400 MHz, CDCl$_3$) δ 8.39 (d, J=1.2 Hz, 2H), 8.13 (s, 1H), 8.04-7.92 (m, 2H), 7.40 (t, J=9.2 Hz, 1H), 5.68-5.60 (m, 2H), 2.34-2.18 (m, 3H).

Example 82. 2-[[1-[4-Fluoro-3-(trifluoromethyl)phenyl]triazol-4-yl]methoxy]pyrimidine

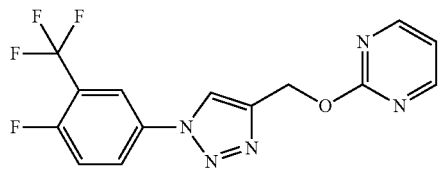 [SMILES: Fc1ccc(-n2cc(COc3ncccn3)nn2)cc1C(F)(F)F]

The title compound was prepared analogous to Example 155, using (1-(4-fluoro-3-(trifluoromethyl)phenyl)-1H-1,2,3-triazol-4-yl)methanol (Intermediate 5) and 2-chloropyrimidine, using THF instead of DMF. MS (ESI): mass calcd. for $C_{14}H_9F_4N_5O$, 339.1; m/z found, 340.0 [M+H]$^+$. $^1$H NMR (400 MHz, CDCl$_3$) δ 8.67-8.54 (m, 2H), 8.15 (s, 1H), 8.08-7.89 (m, 2H), 7.40 (t, J=9.2 Hz, 1H), 7.01 (t, J=4.7 Hz, 1H), 5.68 (d, J=0.8 Hz, 2H).

Example 83. 2-[[1-[4-Fluoro-3-(trifluoromethyl)phenyl]triazol-4-yl]methoxy]-4-methyl-pyrimidine

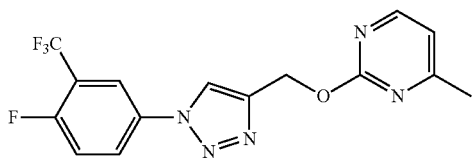 [SMILES: Cc1ccnc(OCc2cn(-c3ccc(F)c(C(F)(F)F)c3)nn2)n1]

The title compound was prepared analogous to Example 155, using (1-(4-fluoro-3-(trifluoromethyl)phenyl)-1H-1,2,3-triazol-4-yl)methanol (Intermediate 5) and 2-chloro-4-methylpyrimidine, using THF instead of DMF. MS (ESI): mass calcd. for $C_{15}H_{11}F_4N_5O$, 353.1; m/z found, 354.0 [M+H]$^+$. $^1$H NMR (400 MHz, CDCl$_3$) δ 8.40 (d, J=5.2 Hz, 1H), 8.14 (s, 1H), 8.08-7.90 (m, 2H), 7.40 (t, J=9.0 Hz, 1H), 6.87 (d, J=5.1 Hz, 1H), 5.66 (d, J=0.8 Hz, 2H), 2.50 (d, J=2.5 Hz, 3H).

Example 84. 5-Fuoro-2-[[1-[4-fluoro-3-(trifluoromethyl)phenyl]triazol-4-yl]methoxy]pyrimidine

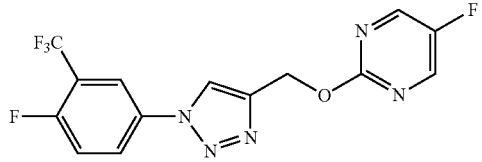 [SMILES: Fc1cnc(OCc2cn(-c3ccc(F)c(C(F)(F)F)c3)nn2)nc1]

The title compound was prepared analogous to Example 1, using (1-(4-fluoro-3-(trifluoromethyl)phenyl)-1H-1,2,3-triazol-4-yl)methanol (Intermediate 5) and 2-chloro-5-fluoropyrimidine, using THF instead of DMF. MS (ESI): mass calcd. for $C_{14}H_6F_5N_5O$, 357.1; m/z found, 358.0 [M+H]$^+$. $^1$H NMR (400 MHz, CDCl$_3$) δ 8.44 (d, J=3.1 Hz, 2H), 8.13 (s, 1H), 8.07-7.90 (m, 2H), 7.41 (t, J=9.3 Hz, 1H), 5.64 (d, J=3.0 Hz, 2H)

Example 85. 2-[[1-(3-Bromo-4-fluoro-phenyl)triazol-4-yl]methoxy]-4,5-dimethyl-pyrimidine

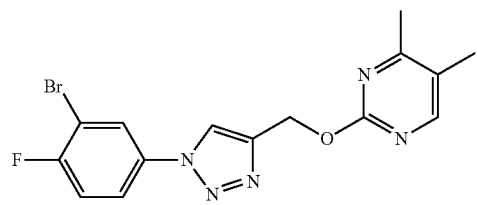 [SMILES: Cc1cnc(OCc2cn(-c3ccc(F)c(Br)c3)nn2)nc1C]

The title compound was prepared in a manner analogous to Example 1 using (1-(3-bromo-4-fluorophenyl)-1H-1,2,3-triazol-4-yl)methanol (Intermediate 14) and 2-chloro-4,5-dimethylpyrimidine, using THF instead of DMF. MS (ESI): mass calcd. for $C_{15}H_{13}BrFN_5O$, 377.0; m/z found, 378.0 [M+H]$^+$. $^1$H NMR (500 MHz, CDCl$_3$) δ 8.20 (s, 1H), 8.07 (s, 1H), 7.98 (dd, J=5.8, 2.7 Hz, 1H), 7.66 (ddd, J=8.9, 4.1, 2.7 Hz, 1H), 7.30-7.27 (m, 1H), 5.62 (d, J=0.7 Hz, 2H), 2.44 (s, 3H), 2.20 (s, 3H).

Example 86. 2-[[1-[4-Chloro-3-(difluoromethyl)phenyl]triazol-4-yl]methoxy]-4,5-dimethyl-pyrimidine

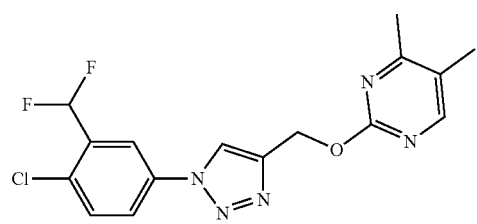 [SMILES: Cc1cnc(OCc2cn(-c3ccc(Cl)c(C(F)F)c3)nn2)nc1C]

The title compound was prepared in a manner analogous to Example 1 using (1-(4-chloro-3-(difluoromethyl)phenyl)-1H-1,2,3-triazol-4-yl)methanol (Intermediate 8) and 2-chloro-4,5-dimethylpyrimidine, using THF instead of DMF. MS (ESI): mass calcd. for $C_{16}H_{14}ClF_2N_5O$, 365.1; m/z found, 366.0 [M+H]$^+$. $^1$H NMR (500 MHz, CDCl$_3$) δ 8.22-8.20 (m, 1H), 8.17-8.16 (m, 1H), 8.00 (d, J=2.6 Hz, 1H), 7.90-7.86 (m, 1H), 7.62-7.58 (m, 1H), 6.99 (t, J=54.6 Hz, 1H), 5.63 (d, J=0.8 Hz, 2H), 2.45 (s, 3H), 2.20 (s, 3H)

Example 87. 2-[1-(4-Chloro-3-methoxy-phenyl)triazol-4-yl]methoxy)-5-methoxy-pyrimidine

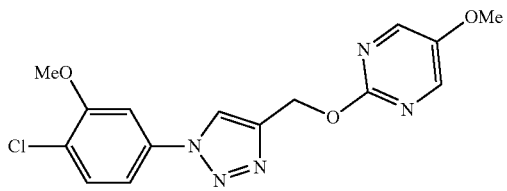 [SMILES: COc1cnc(OCc2cn(-c3ccc(Cl)c(OC)c3)nn2)nc1]

The title compound was prepared in a manner analogous to Example 1 using (1-(4-chloro-3-methoxyphenyl)-1H-1,2,3-triazol-4-yl)methanol (Intermediate 15) and 2-chloro-5-methoxypyrimidine, using THF instead of DMF. MS (ESI): mass calcd. for $C_{15}H_{14}ClN_5O_3$, 347.1; m/z found, 348.0 [M+H]$^+$. $^1$H NMR (400 MHz, CDCl$_3$) δ 8.24 (s, 2H), 8.15-8.04 (m, 1H), 7.49 (d, J=8.5 Hz, 1H), 7.45 (d, J=2.4 Hz, 1H), 7.16 (dd, J=8.5, 2.4 Hz, 1H), 5.60 (s, 2H), 3.99 (s, 3H), 3.88 (s, 3H).

Example 88. 2-[[1-(4-Chloro-3-methoxy-phenyl)triazol-4-yl]methoxy]-5-methyl-pyrimidine

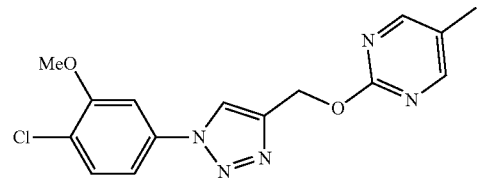 [SMILES: COc1cc(-n2cc(COc3ncc(C)cn3)nn2)ccc1Cl]

The title compound was prepared in a manner analogous to Example 1 using (1-(4-chloro-3-methoxyphenyl)-1H-1,2,3-triazol-4-yl)methanol (Intermediate 15) and 2-chloro-5-methylpyrimidine, using THF instead of DMF. MS (ESI): mass calcd. for $C_{15}H_{14}ClN_5O_2$, 331.1; m/z found, 332.1 [M+H]$^+$. $^1$H NMR (400 MHz, CDCl$_3$) δ 8.38 (s, 2H), 8.23-8.08 (m, 1H), 7.49 (d, J=8.5 Hz, 1H), 7.45 (d, J=2.3 Hz, 1H), 7.16 (dd, J=8.5, 2.4 Hz, 1H), 5.63 (s, 2H), 3.99 (s, 3H), 2.26 (s, 3H).

Example 89. 2-[[1-[3-(Difluoromethyl)phenyl]triazol-4-yl]methoxy]-5-methyl-pyrimidine

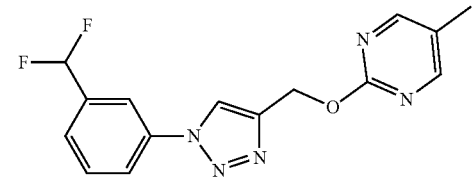 [SMILES: Cc1cnc(OCc2cn(-c3cccc(C(F)F)c3)nn2)nc1]

The title compound was prepared in a manner analogous to Example 1 using (1-(3-(difluoromethyl)phenyl)-1H-1,2,3-triazol-4-yl)methanol (Intermediate 12) and 2-chloro-5-methylpyrimidine, using THF instead of DMF. MS (ESI): mass calcd. for $C_{15}H_{13}F_2N_5O$, 317.1; m/z found, 318.0 [M+H]$^+$. $^1$H NMR (500 MHz, CDCl$_3$) δ 8.38 (s, 2H), 8.17 (s, 1H), 7.92-7.89 (m, 1H), 7.88-7.85 (m, 1H), 7.66-7.60 (m, 1H), 7.60-7.56 (m, 1H), 6.72 (t, J=56.1 Hz, 1H), 5.64 (d, J=0.7 Hz, 2H), 2.28-2.23 (m, 3H).

Example 90. 2-[[1-[3-(Difluoromethyl)phenyl]triazol-4-yl]methoxy]-5-methoxy-pyrimidine

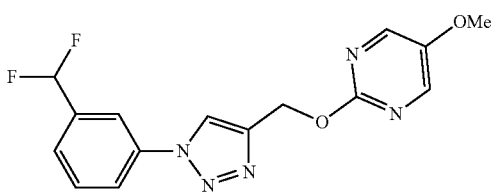 [SMILES: COc1cnc(OCc2cn(-c3cccc(C(F)F)c3)nn2)nc1]

The title compound was prepared in a manner analogous to Example 1 using (1-(3-(difluoromethyl)phenyl)-1H-1,2,3-triazol-4-yl)methanol (Intermediate 12) and 2-chloro-5-methoxypyrimidine, using THF instead of DMF. MS (ESI): mass calcd. for $C_{15}H_{13}F_2N_5O_2$, 333.1; m/z found, 334.0 [M+H]$^+$. $^1$H NMR (500 MHz, CDCl$_3$) δ 8.23 (s, 2H), 8.16 (s, 1H), 7.91-7.89 (m, 1H), 7.88-7.85 (m, 1H), 7.65-7.60 (m, 1H), 7.60-7.55 (m, 1H), 6.72 (t, J=56.1 Hz, 1H), 5.61 (d, J=0.7 Hz, 2H), 3.87 (s, 3H).

Example 91. 2-[[1-[3-(Difluoromethyl)phenyl]triazol-4-yl]methoxy]-5-ethyl-pyrimidine

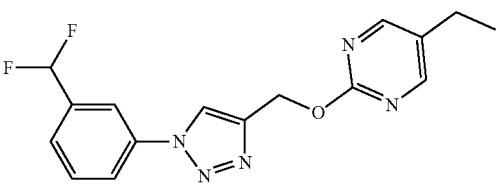 [SMILES: CCc1cnc(OCc2cn(-c3cccc(C(F)F)c3)nn2)nc1]

The title compound was prepared in a manner analogous to Example 1 using (1-(3-(difluoromethyl)phenyl)-1H-1,2,3-triazol-4-yl)methanol (Intermediate 12) and 2-chloro-5-ethylpyrimidine, using THF instead of DMF. MS (ESI): mass calcd. for $C_{15}H_{15}F_2N_5O$, 331.1; m/z found, 332.1 [M+H]$^+$. $^1$H NMR (500 MHz, CDCl$_3$) δ 8.38 (s, 2H), 8.17 (s, 1H), 7.91-7.88 (m, 1H), 7.87-7.83 (m, 1H), 7.64-7.58 (m, 1H), 7.58-7.54 (m, 1H), 6.71 (t, J=56.1 Hz, 1H), 5.63 (d, J=0.7 Hz, 2H), 2.59 (q, J=7.7 Hz, 2H), 1.24 (t, J=7.6 Hz, 3H).

Example 92. 5-Chloro-2-[[1-[3-(difluoromethyl)phenyl]triazol-4-yl]methoxy]pyrimidine

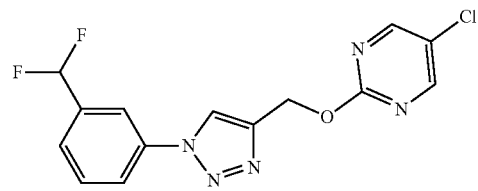 [SMILES: FC(F)c1cccc(-n2cc(COc3ncc(Cl)cn3)nn2)c1]

The title compound was prepared in a manner analogous to Example 1 using (1-(3-(difluoromethyl)phenyl)-1H-1,2,3-triazol-4-yl)methanol (Intermediate 12) and 2,5-dichloropyrimidine, using THF instead of DMF. MS (ESI): mass calcd. for $C_{14}H_{10}ClF_2N_5O$, 337.1; m/z found, 338.1 [M+H]$^+$. $^1$H NMR (500 MHz, CDCl$_3$) δ 8.50 (s, 2H), 8.17 (s, 1H), 7.92-7.88 (m, 1H), 7.88-7.85 (m, 1H), 7.66-7.61 (m, 1H), 7.61-7.57 (m, 1H), 6.72 (t, J=56.1 Hz, 1H), 5.64 (d, J=0.6 Hz, 2H).

Example 93. 2-[[1-[3-(Difluoromethyl)phenyl]triazol-4-yl]methoxy]pyrimidine

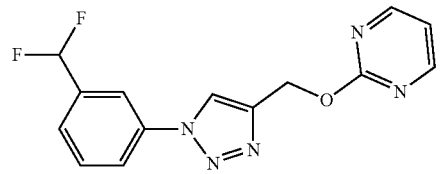 [SMILES: FC(F)c1cccc(-n2cc(COc3ncccn3)nn2)c1]

The title compound was prepared in a manner analogous to Example 1 using (1-(3-(difluoromethyl)phenyl)-1H-1,2,3-triazol-4-yl)methanol (Intermediate 12) and 2-chloropyrimidine, using THF instead of DMF. MS (ESI): mass calcd. for $C_{14}H_{11}F_2N_5O$, 303.1; m/z found, 304.0 [M+H]$^+$. $^1$H NMR (500 MHz, CDCl$_3$) δ 8.56 (d, J=4.8 Hz, 2H), 8.18 (s, 1H), 7.91-7.89 (m, 1H), 7.88-7.84 (m, 1H), 7.65-7.60 (m, 1H), 7.59-7.56 (m, 1H), 6.99 (t, J=4.8 Hz, 1H), 6.72 (t, J=56.1 Hz, 1H), 5.66 (d, J=0.7 Hz, 2H)

Example 94. 2-[[1-(5-Bromo-6-methyl-2-pyridyl)triazol-4-yl]methoxy]-5-methyl-pyrimidine

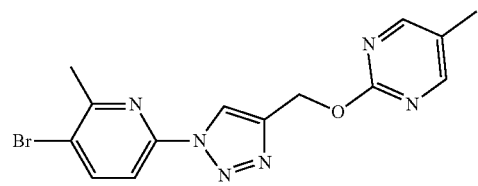 [SMILES: Cc1cnc(OCc2cn(-c3ccc(Br)c(C)n3)nn2)nc1]

The title compound was prepared in a manner analogous to Example 1 using (1-(5-bromo-6-methylpyridin-2-yl)-1H-1,2,3-triazol-4-yl)methanol and 2-chloro-5-methylpyrimidine, using THF instead of DMF. MS (ESI): mass calcd. for $C_{14}H_{13}BrN_6O$, 360.0; m/z found 361.0 [M+H]$^+$. $^1$H NMR (500 MHz, CDCl$_3$) δ 8.68 (s, 1H), 8.39-8.36 (m, 2H), 8.00-7.96 (m, 1H), 7.91-7.87 (m, 1H), 5.63 (d, J=0.8 Hz, 2H), 2.68 (s, 3H), 2.25 (s, 3H).

Example 95. 2-[[1-[4-Chloro-3-(difluoromethoxy)phenyl]triazol-4-yl]methoxy]-5-fluoro-pyrimidine

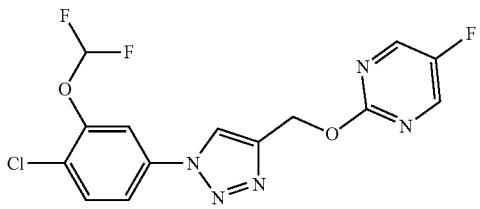 [SMILES: Fc1cnc(OCc2cn(-c3ccc(Cl)c(OC(F)F)c3)nn2)nc1]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-fluoropyrimidine. MS (ESI): mass calcd. for $C_{14}H_9ClF_3N_5O_2$, 371.0; m/z found, 372.1 [M+H]$^+$. $^1$H NMR (400 MHz, CDCl$_3$) δ 8.43 (s, 2H), 8.14-8.09 (m, 1H), 7.72-7.66 (m, 1H), 7.64-7.60 (m, 1H), 7.59-7.54 (m, 1H), 6.64 (t, J=72.5 Hz, 1H), 5.63 (s, 2H).

Example 96. 2-[[1-[4-Chloro-3-(difluoromethoxy)phenyl]triazol-4-yl]methoxy]-5-(difluoromethyl)pyrimidine

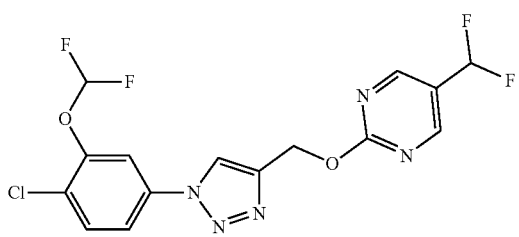 [SMILES: FC(F)Oc1cc(-n2cc(COc3ncc(C(F)F)cn3)nn2)ccc1Cl]

The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-(difluoromethyl)pyrimidine. MS (ESI): mass calcd. for $C_{15}H_{10}ClF_4N_5O_2$, 403.1; m/z found, 404.0 [M+H]$^+$. $^1$H NMR (400 MHz, CDCl$_3$) δ 8.76-8.63 (m, 2H), 8.22-8.07 (m, 1H), 7.75-7.64 (m, 1H), 7.64-7.60 (m, 1H), 7.59-7.54 (m, 1H), 6.73 (t, J=55.6 Hz, 1H), 6.64 (t, J=72.5 Hz, 1H), 5.71 (s, 2H).

Example 97. N-[[1-[4-Chloro-3-(difluoromethoxy)phenyl]triazol-4-yl]methyl]oxazol-2-amine

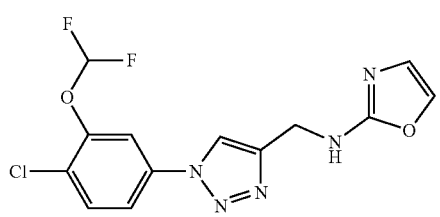 [SMILES: FC(F)Oc1cc(-n2cc(CNc3ncco3)nn2)ccc1Cl]

The title compound was prepared in a manner analogous to Example 2, using 1-(4-chloro-3-(difluoromethoxy)phenyl)-1H-1,2,3-triazole-4-carbaldehyde and oxazol-2-amine. MS (ESI): mass calcd. for $C_{13}H_{10}ClF_2N_5O_2$, 341.0; m/z found, 342.0 [M+H]$^+$. $^1$H NMR (400 MHz, CDCl$_3$) δ 8.09-7.97 (m, 1H), 7.74-7.64 (m, 1H), 7.65-7.51 (m, 2H), 7.22-7.14 (m, 1H), 6.87-6.40 (m, 2H), 5.30 (s, 1H), 4.70 (d, J=5.7 Hz, 2H).

Example 98. N-[[1-[4-Chloro-3-(difluoromethoxy)phenyl]triazol-4-yl]methyl]pyrimidin-2-amine

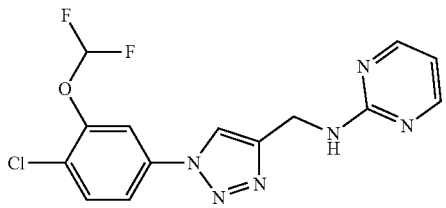

The title compound was prepared in a manner analogous Example 3, using 1-(4-chloro-3-(difluoromethoxy)phenyl)-4-(chloromethyl)-1H-1,2,3-triazole (Intermediate 4) in Step A and pyrimidin-2-amine in Step B. MS (ESI): mass calcd. for $C_{14}H_{11}ClF_2NO$, 352.1; m/z found, 353.0 [M+H]$^+$. $^1$H NMR (400 MHz, CDCl$_3$) δ 8.33 (d, J=4.8 Hz, 2H), 8.00-7.92 (m, 1H), 7.72-7.68 (m, 1H), 7.62-7.57 (m, 1H), 7.56-7.52 (m, 1H), 6.89-6.34 (m, 2H), 4.82 (dd, J=6.2, 0.7 Hz, 2H).

Example 99. N-[[1-[3-(Difluoromethyl)-4-fluorophenyl]triazol-4-yl]methyl]-1-methyl-pyrazol-4-amine

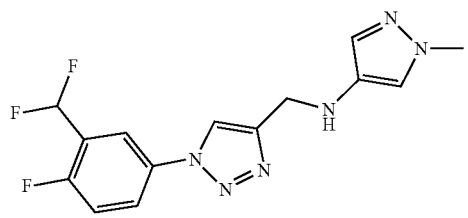 [SMILES: Cn1cc(NCc2cn(-c3ccc(F)c(C(F)F)c3)nn2)cn1]

The title compound was prepared in a manner analogous to Example 3, using (1-(3-(difluoromethyl)-4-fluorophenyl)-1H-1,2,3-triazol-4-yl)methanol (Intermediate 9) in Step A and 1-methyl-1H-pyrazol-4-amine in Step B. MS (ESI): mass calcd. for $C_{14}H_{13}F_3N_6$, 322.1; m/z found, 323.1 [M+H]$^+$. $^1$H NMR (400 MHz, CDCl$_3$) δ 3.48 (br s, 1H), 3.80 (s, 3H), 4.37 (s, 2H), 6.75-7.10 (m, 2H), 7.17 (s, 1H), 7.32 (br t, J=9.02 Hz, 1H), 7.75-8.05 (m, 3H).

Example 100. N-[[1-[3-(Difluoromethyl)-4-fluorophenyl]triazol-4-yl]methyl]-1-methyl-pyrazol-3-amine

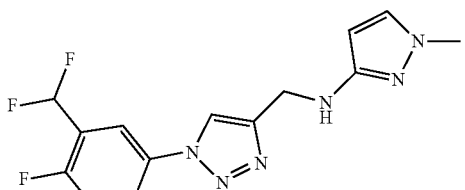

The title compound was prepared in a manner analogous to Example 3, using (1-(3-(difluoromethyl)-4-fluorophenyl)-1H-1,2,3-triazol-4-yl)methanol (Intermediate 9) in Step A and 1-methyl-1H-pyrazol-3-amine in Step B. MS (ESI): mass calcd. for $C_{14}H_{13}F_3N_6$, 322.1; m/z found, 323.1 [M+H]$^+$. $^1$H NMR (400 MHz, CDCl$_3$) δ 3.74 (s, 3H), 4.18 (br s, 1H), 4.56 (br s, 2H), 5.58 (br s, 1H), 6.75-7.20 (m, 2H), 7.31 (br t, J=9.02 Hz, 1H), 7.72-8.17 (m, 3H)

Example 101. N-[[1-[3-(Difluoromethoxy)-4-fluorophenyl]triazol-4-yl]methyl]-1-methyl-pyrazol-3-amine

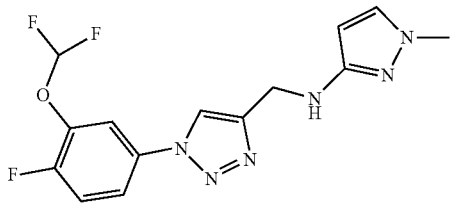 [SMILES: Cn1ccc(NCc2cn(-c3ccc(F)c(OC(F)F)c3)nn2)n1]

The title compound was prepared in a manner analogous to Example 3, using (1-(3-(difluoromethoxy)-4-fluorophenyl)-1H-1,2,3-triazol-4-yl)methanol (Intermediate 6) in Step A and 1-methyl-1H-pyrazol-3-amine in Step B. MS (ESI): mass calcd. for $C_{14}H_{13}F_3N_6O$, 338.1; m/z found, 339.1 [M+H]$^+$. $^1$H NMR (400 MHz, CDCl$_3$) δ 7.91 (s, 1H), 7.67 (br d, J=4.2 Hz, 1H), 7.61-7.48 (m, 1H), 7.33 (t, J=9.5 Hz, 1H), 7.12 (br d, J=1.6 Hz, 1H), 6.64 (t, J=72.4 Hz, 1H), 5.57 (d, J=2.1 Hz, 1H), 4.55 (br s, 2H), 4.20 (br s, 1H), 3.74 (s, 3H).

Example 102. N-[[1-[3-(Difluoromethoxy)-4-fluorophenyl]triazol-4-yl]methyl]-1-methyl-pyrazol-4-amine

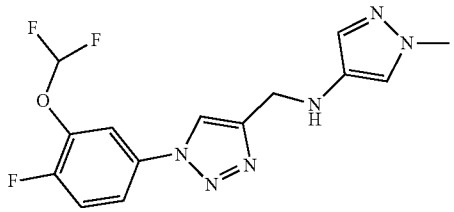 [SMILES: Cn1cc(NCc2cn(-c3ccc(F)c(OC(F)F)c3)nn2)cn1]

The title compound was prepared in a manner analogous to Example 3, using (1-(3-(difluoromethoxy)-4-fluorophenyl)-1H-1,2,3-triazol-4-yl)methanol (Intermediate 6) in Step A and 1-methyl-1H-pyrazol-4-amine in Step B. MS (ESI): mass calcd. for $C_{14}H_{13}F_3N_6O$, 338.1; m/z found, 339.1 [M+H]$^+$. $^1$H NMR (400 MHz, CDCl$_3$) δ 7.86 (s, 1H), 7.68 (br d, J=4.6 Hz, 1H), 7.61-7.47 (m, 1H), 7.33 (s, 1H), 7.17 (s, 1H), 6.97 (s, 1H), 6.87-6.40 (m, 1H), 4.36 (s, 2H), 3.80 (d, J=0.7 Hz, 3H)

Example 103. 3-[[1-[4-Chloro-3-(difluoromethoxy)phenyl]triazol-4-yl]methoxy]-2-methoxy-pyridine

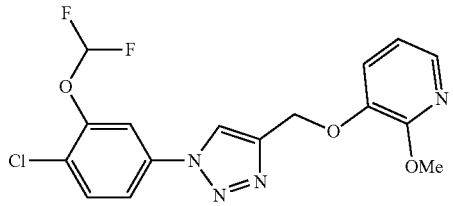 [SMILES: COc1ncccc1OCc1cn(-c2ccc(Cl)c(OC(F)F)c2)nn1]

The title compound was prepared in a manner analogous to Example 5 using 1-(4-chloro-3-(difluoromethoxy)phenyl)-4-(chloromethyl)-1H-1,2,3-triazole (Intermediate 4) and 2-methoxypyridin-3-ol. MS (ESI): mass calcd. for $C_{16}H_{13}ClF_2N_4O_3$, 382.1; m/z found, 383.1 [M+H]$^+$. $^1$H NMR (400 MHz, CDCl$_3$) δ 8.10 (s, 1H), 7.79 (dd, J=5.0, 1.5 Hz, 1H), 7.75-7.68 (m, 1H), 7.66-7.59 (m, 1H), 7.58-7.53 (m, 1H), 7.30 (dd, J=7.8, 1.5 Hz, 1H), 6.85 (dd, J=7.8, 5.0 Hz, 1H), 6.63 (t, J=72.5 Hz, 1H), 5.36 (s, 2H), 4.02 (s, 3H).

Example 104. 5-[[1-[4-Chloro-3-(difluoromethoxy)phenyl]triazol-4-yl]methoxy]-2-methyl-pyridine

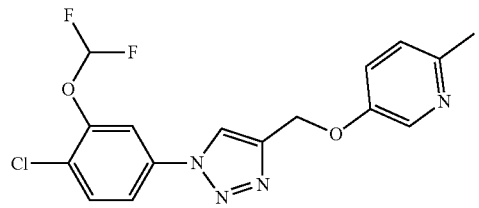 [SMILES: Cc1ccc(OCc2cn(-c3ccc(Cl)c(OC(F)F)c3)nn2)cn1]

The title compound was prepared in a manner analogous to Example 5 using 1-(4-chloro-3-(difluoromethoxy)phenyl)-4-(chloromethyl)-1H-1,2,3-triazole (Intermediate 4) and 6-methylpyridin-3-ol. MS (ESI): mass calcd. for $C_{16}H_{13}ClF_2N_4O_2$, 366.1; m/z found, 367.1 [M+H]$^+$. $^1$H NMR (400 MHz CDCl$_3$) δ 8.29 (d, J=3.0 Hz, 1H), 8.08-7.98 (m, 1H), 7.74-7.70 (m, 1H), 7.66-7.61 (m, 1H), 7.60-7.55 (m, 1H), 7.30-7.22 (m, 1H), 7.10 (d, J=8.5 Hz, 1H), 6.64 (t, J=72.5 Hz, 1H), 5.31 (s, 2H), 2.50 (s, 3H)

Example 105. 3-Chloro-2-[[1-[4-chloro-3-(difluoromethoxy)phenyl]triazol-4-yl]methoxy]pyridine

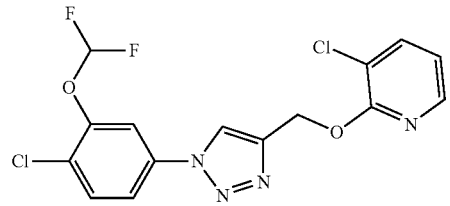 [SMILES: FC(F)Oc1cc(-n2cc(COc3ncccc3Cl)nn2)ccc1Cl]

The title compound was prepared in a manner analogous to Example 5 using 1-(4-chloro-3-(difluoromethoxy)phenyl)-4-(chloromethyl)-1H-1,2,3-triazole (Intermediate 4) and 3-chloropyridin-2-ol. MS (ESI): mass calcd. for $C_{15}H_{10}Cl_{12}F_2N_4O_2$, 386.0; m/z found, 387.0 [M+H]$^+$. $^1$H NMR (500 MHz, CDCl₃) δ 8.10 (dd, J=4.9, 1.7 Hz, 1H), 8.09-8.08 (m, 1H), 7.74-7.70 (m, 1H), 7.67 (dd, J=7.6, 1.7 Hz, 1H), 7.64-7.59 (m, 1H), 7.59-7.55 (m, 1H), 6.91 (dd, J=7.6, 4.9 Hz, 1H), 6.64 (t, J=72.6 Hz, 1H), 5.68 (s, 2H).

Example 106. 5-Chloro-2-[[1-[4-chloro-3-(difluoromethoxy)phenyl]triazol-4-yl]methoxy]-3-methoxy-pyridine

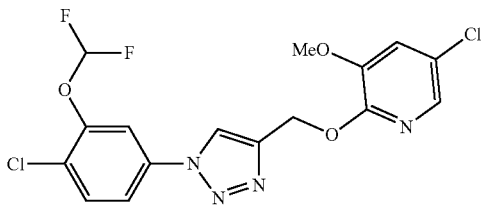 [SMILES: COc1cc(Cl)cnc1OCc1cn(-c2ccc(Cl)c(OC(F)F)c2)nn1]

The title compound was prepared in a manner analogous to Example 5 using 1-(4-chloro-3-(difluoromethoxy)phenyl)-4-(chloromethyl)-1H-1,2,3-triazole (Intermediate 4) and 5-chloro-3-methoxypyridin-2-ol. MS (ESI): mass calcd. for C₁₆H₁₂ClF₂N₄O₃, 416.0; m/z found, 417.0 [M+H]⁺. ¹H NMR (400 MHz, CDCl₃) δ 8.07 (s, 1H), 7.72 (d, J=2.2 Hz, 1H), 7.71-7.68 (m, 1H), 7.62-7.58 (m, 1H), 7.57-7.53 (m, 1H), 7.06 (d, J=2.1 Hz, 1H), 6.63 (t, J=72.6 Hz, 1H), 5.64 (s, 2H), 3.86 (s, 3H)

Example 107. 2-[[1-[4-Chloro-3-(difluoromethoxy)phenyl]triazol-4-yl]methoxy]-3-fluoro-pyridine

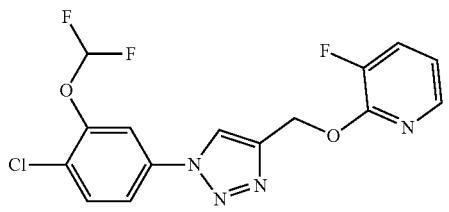 [SMILES: Fc1cccnc1OCc1cn(-c2ccc(Cl)c(OC(F)F)c2)nn1]

The title compound was prepared in a manner analogous to Example 5 using 1-(4-chloro-3-(difluoromethoxy)phenyl)-4-(chloromethyl)-1H-1,2,3-triazole (Intermediate 4) and 3-fluoropyridin-2-ol. MS (ESI): mass calcd. for C₁₅H₁₀ClF₃N₄O₂, 370.0; m/z found, 371.0 [M+H]⁺. ¹H NMR (500 MHz, CDCl₃) δ 8.17-8.06 (m, 1H), 7.97 (dd, J=5.0, 1.5 Hz, 1H), 7.72-7.70 (m, 1H), 7.64-7.60 (m, 1H), 7.59-7.55 (m, 1H), 7.40-7.34 (m, 1H), 6.97-6.85 (m, 1H), 6.64 (t, J=72.5 Hz, 1H), 5.68 (s, 2H).

Example 108. 2-[[1-[4-Chloro-3-(difluoromethoxy)phenyl]triazol-4-yl]methoxy]-3-methoxy-pyridine

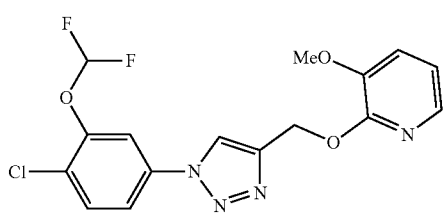 [SMILES: COc1cccnc1OCc1cn(-c2ccc(Cl)c(OC(F)F)c2)nn1]

The title compound was prepared in a manner analogous to Example 5 using 1-(4-chloro-3-(difluoromethoxy)phenyl)-4-(chloromethyl)-1H-1,2,3-triazole (Intermediate 4) and 3-methoxypyridin-2-ol. MS (ESI): mass calcd. for C₁₆H₁₃ClF₂N₄O₃, 382.1; m/z found, 383.0 [M+H]⁺. ¹H NMR (400 MHz, CDCl₃) δ 8.08 (s, 1H), 7.80-7.74 (m, 1H), 7.72-7.67 (m, 1H), 7.62-7.58 (m, 1H), 7.57-7.53 (m, 1H), 7.12-7.07 (m, 1H), 6.93-6.87 (m, 1H), 6.63 (t, J=72.6 Hz, 1H), 5.68 (s, 2H), 3.87 (s, 3H)

Example 109. N-[[1-[4-Chloro-3-(difluoromethyl)phenyl]triazol-4-yl]methyl]pyrimidin-2-amine

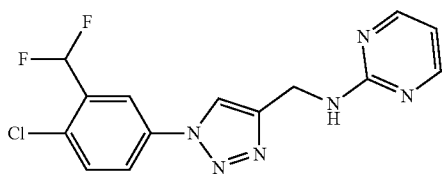 [SMILES: FC(F)c1cc(-n2cc(CNc3ncccn3)nn2)ccc1Cl]

The title compound was prepared in a manner analogous to Example 6 using (1-(4-chloro-3-(difluoromethyl)phenyl)-1H-1,2,3-triazol-4-yl)methanamine (Intermediate 19) and 2-chloropyrimidine. MS (ESI): mass calcd. for C₁₄H₁₁ClF₂N₆, 336.1; m/z found, 337.0 [M+H]⁺. ¹H NMR (500 MHz, CDCl₃) δ 8.34 (d, J=4.8 Hz, 2H), 8.00 (s, 1H), 7.98 (d, J=2.6 Hz, 1H), 7.89-7.85 (m, 1H), 7.61-7.57 (m, 1H), 6.98 (t, J=54.6 Hz, 1H), 6.61 (t, J=4.8 Hz, 1H), 5.69 (s, 1H), 4.83 (dd, J=6.2, 0.7 Hz, 2H).

Example 110. N-[[1-[4-Chloro-3-(difluoromethyl)phenyl]triazol-4-yl]methyl]pyrimidin-4-amine

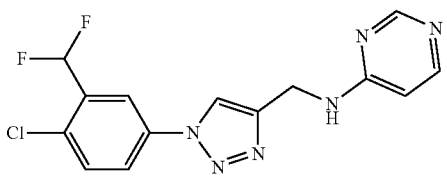 [SMILES: FC(F)c1cc(-n2cc(CNc3ccncn3)nn2)ccc1Cl]

The title compound was prepared in a manner analogous to Example 6 using (1-(4-chloro-3-(difluoromethyl)phenyl)-1H-1,2,3-triazol-4-yl)methanamine (Intermediate 19) and 4-chloropyrimidine. MS (ESI): mass calcd. for C₁₄H₁₁ClF₂N₆, 336.1; m/z found, 337.0 [M+H]⁺. ¹H NMR (500 MHz, CDCl₃) S 8.65 (s, 1H), 8.20 (d, J=6.0 Hz, 1H), 8.02 (s, 1H), 8.00 (d, J=2.6 Hz, 1H), 7.88-7.84 (m, 1H), 7.63-7.58 (m, 1H), 6.99 (t, J=54.5 Hz, 1H), 6.44 (dd, J=6.0, 1.3 Hz, 1H), 5.54 (s, 1H), 4.81 (d, J=5.8 Hz, 2H).

Example 111. 2-[[1-[3-(Difluoromethyl)-4-fluorophenyl]triazol-4-yl]methoxy]pyridine

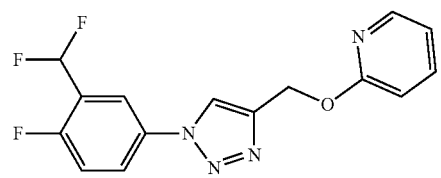 [SMILES: Fc1ccc(-n2cc(COc3ccccn3)nn2)cc1C(F)F]

The title compound was prepared in a manner analogous to Intermediate 7 using (1-(3-(difluoromethyl)-4-fluorophenyl)-1H-1,2,3-triazol-4-yl)methanol (Intermediate 9) and 2-fluoropyridine. MS (ESI): mass calcd. for $C_{15}H_{11}F_3N_4O$, 320.1; m/z found, 321.1 [M+H]$^+$. $^1$H NMR (400 MHz, CDCl$_3$) δ 5.62 (s, 2H), 6.73-7.15 (m, 3H), 7.33 (t, J=8.90 Hz, 1H), 7.55-7.73 (m, 1H), 7.84-8.01 (m, 2H), 8.09 (s, 1H), 8.15-8.30 (m, 1H).

Example 112. 5-Chloro-2-[[1-[3-(difluoromethyl)-4-fluoro-phenyl]triazol-4-yl]methoxy]pyridine

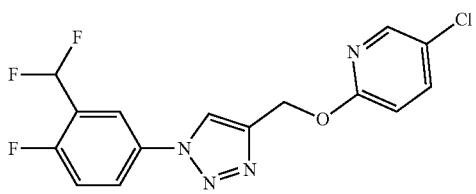 [SMILES: Fc1ccc(-n2cc(COc3ccc(Cl)cn3)nn2)cc1C(F)F]

The title compound was prepared in a manner analogous to Intermediate 7 using (1-(3-(difluoromethyl)-4-fluorophenyl)-1H-1,2,3-triazol-4-yl)methanol (Intermediate 9) and 5-chloro-2-fluoropyridine. MS (ESI): mass calcd. for $C_{15}H_{10}ClF_3N_4O$, 354.0; m/z found, 355.1 [M+H]$^+$. $^1$H NMR (400 MHz, CDCl$_3$) δ 5.57 (s, 2H), 6.77 (d, J=8.8 Hz, 1H), 6.80-7.13 (m, 1H), 7.33 (t, J=9.0 Hz, 1H), 7.56 (dd, J=8.8, 2.5 Hz, 1H), 7.84-7.98 (m, 2H), 8.07 (s, 1H), 8.15 (d, J=2.5 Hz, 1H).

Example 113. 2-[[1-[3-(Difluoromethyl)-4-fluorophenyl]triazol-4-yl]methoxy]-6-methyl-pyridine

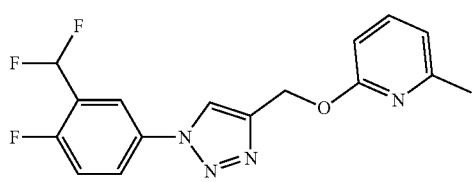 [SMILES: Cc1cccc(OCc2cn(-c3ccc(F)c(C(F)F)c3)nn2)n1]

Step A. 2-Bromo-6-((1-(3-(difluoromethyl)-4-fluorophenyl)-1H-1,2,3-triazol-4-yl)methoxy)pyridine The title compound was prepared in a manner analogous to Intermediate 7 using (1-(3-(difluoromethyl)-4-fluorophenyl)-1H-1,2,3-triazol-4-yl)methanol (Intermediate 9) and 2-bromo-6-fluoropyridine.

Step B. 2-[[1-[3-(Difluoromethyl)-4-fluoro-phenyl]triazol-4-yl]methoxy]-6-methyl-pyridine To a solution of 2-bromo-6-((1-(3-(difluoromethyl)-4-fluorophenyl)-1H-1,2,3-triazol-4-yl)methoxy)pyridine (25 mg, 0.06 mmol), Cs$_2$CO$_3$ (41 mg, 0.12 mmol), in 1,4 dioxane (0.65 mL) was added 2,4,6-trimethyl-1,3,5,2,4,6-trioxatriborinane (0.01 mL, 0.07 mmol) and (2-dicyclohexylphosphino-2',4',6'-triisopropyl-1,1'-biphenyl)[2-(2'-amino-1,1'-biphenyl)]palladium(II) methanesulfonate (Xphos Palladacycle Gen. 3) (5.3 mg, 0.006 mmol). The reaction mixture was heated under microwave irradiation at 120° C. for 12 minutes. The mixture was concentrated in vacuo. Purification (FCC, SiO$_2$, EtOAc in heptane from 0-100%). Purification (RP HPLC, Stationary phase: C18 XBridge 30×100 mm 5 um, Mobile phase: Gradient from 90% 10 mM NH$_4$CO$_3$H pH 9 solution in Water, 10% CH$_3$CN to 0% 10 mM NH$_4$CO$_3$H pH 9 solution in Water, 100% CH$_3$CN) afforded the title compound (46 mg, 68%). MS (ESI): mass calcd. for $C_{16}H_{13}F_3N_4O$, 334.1; m/z found, 335.1 [M+H]$^+$. $^1$H NMR (400 MHz, CDCl$_3$) δ 2.49 (s, 3H), 5.60 (s, 2H), 6.61 (d, J=8.3 Hz, 1H), 6.77 (d, J=7.4 Hz, 1H), 6.81-7.14 (m, 1H), 7.33 (t, J=9.0 Hz, 1H), 7.49 (t, J=7.6 Hz, 1H), 7.83-7.99 (m, 2H), 8.08 (s, 1H).

Example 114. 2-[[1-[3-(Difluoromethyl)-4-fluorophenyl]triazol-4-yl]methoxy]-5-methyl-pyridine

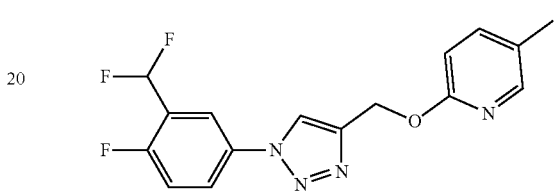

The title compound was prepared in a manner analogous to Example 1 using (1-(3-(difluoromethyl)-4-fluorophenyl)-1H-1,2,3-triazol-4-yl)methanol (Intermediate 9) and 2-fluoro-5-methylpyridine. MS (ESI): mass calcd. for $C_{16}H_{13}F_3N_4O$, 334.1; m/z found, 335.1 [M+H]$^+$. $^1$H NMR (400 MHz, CDCl$_3$) δ 2.27 (s, 3H), 5.58 (s, 2H), 6.73 (d, J=8.3 Hz, 1H), 6.79-7.16 (m, 1H), 7.33 (t, J=9.0 Hz, 1H), 7.43 (dd, J=8.4, 1.97 Hz, 1H), 7.84-7.97 (m, 2H), 8.01 (s, 1H), 8.08 (s, 1H)

Example 115. 2-[[1-[3-(Difluoromethyl)-4-fluorophenyl]triazol-4-yl]methoxy]-4-methyl-pyridine

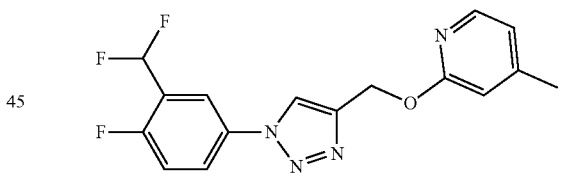

Step A. 4-Bromo-2-((1-(3-(difluoromethyl)-4-fluorophenyl)-1H-1,2,3-triazol-4-yl)methoxy)pyridine The title compound was prepared in a manner analogous to Intermediate 7 using (1-(3-(difluoromethyl)-4-fluorophenyl)-1H-1,2,3-triazol-4-yl)methanol (Intermediate 9) and 4-bromo-2-fluoropyridine.

Step B. 2-[[1-[3-(Difluoromethyl)-4-fluoro-phenyl]triazol-4-yl]methoxy]-4-methyl-pyridine The title compound was prepared in a manner analogous to Example 113 step B, using 4-bromo-2-((1-(3-(difluoromethyl)-4-fluorophenyl)-1H-1,2,3-triazol-4-yl)methoxy)pyridine. MS (ESI): mass calcd. for $C_{16}H_{13}F_3N_4O$, 334.1; m/z found, 335.1 [M+H]$^+$. $^1$H NMR (400 MHz, CDCl$_3$) δ 2.31

(s, 3H), 5.60 (s, 2H), 6.63 (s, 1H), 6.76 (d, J=5.1 Hz, 1H), 6.80-7.12 (m, 1H), 7.33 (t, J=9.0 Hz, 1H), 7.80-7.98 (m, 2H), 8.02-8.20 (m, 2H).

Example 116. 2-[[1-[3-(Difluoromethoxy)-4-fluoro-phenyl]triazol-4-yl]methoxy]-4-methyl-pyridine

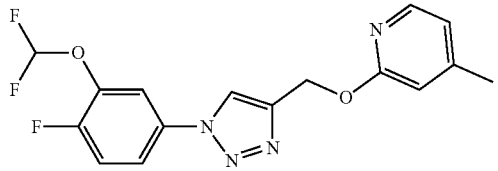 [SMILES: Cc1ccnc(OCc2cn(-c3ccc(F)c(OC(F)F)c3)nn2)c1]

Step A. 4-Bromo-2-((1-(3-(difluoromethoxy)-4-fluorophenyl)-1H-1,2,3-triazol-4-yl)methoxy)pyridine The title compound was prepared in a manner analogous to Intermediate 7 using (1-(3-(difluoromethoxy)-4-fluorophenyl)-1H-1,2,3-triazol-4-yl)methanol (Intermediate 6) and 4-bromo-2-fluoropyridine.

Step B. 2-[[1-[3-(Difluoromethoxy)-4-fluoro-phenyl]triazol-4-yl]methoxy]-4-methyl-pyridine The title compound was prepared in a manner analogous to Example 113 step B, using 4-bromo-2-((1-(3-(difluoromethoxy)-4-fluorophenyl)-1H-1,2,3-triazol-4-yl) methoxy)pyridine. MS (ESI): mass calcd. for $C_{16}H_{13}F_3N_4O_2$, 350.1; m/z found, 351.1 [M+H]$^+$. $^1$H NMR (500 MHz, CDCl$_3$) δ 2.30 (s, 3H), 5.58 (s, 2H), 6.42-6.84 (m, 3H), 7.33 (t, J=9.25 Hz, 1H), 7.58 (ddd, J=8.96, 3.90, 2.75 Hz, 1H), 7.68 (dd, J=6.65, 2.60 Hz, 1H), 8.02 (s, 1H), 8.05 (d, J=5.20 Hz, 1H).

Example 117. 5-Chloro-2-[[1-[3-(difluoromethoxy)-4-fluoro-phenyl]triazol-4-yl]methoxy]pyridine

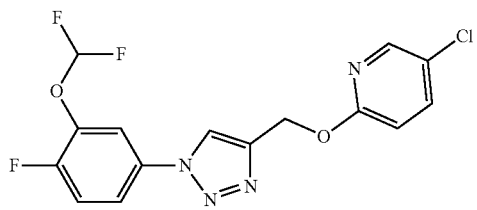 [SMILES: Fc1ccc(-n2cc(COc3ccc(Cl)cn3)nn2)cc1OC(F)F]

The title compound was prepared in a manner analgous to Example 1 using (1-(3-(difluoromethoxy)-4-fluorophenyl)-1H-1,2,3-triazol-4-yl)methanol (Intermediate 6) and 5-chloro-2-fluoropyridine. HRMS=370.044; $^1$H NMR (500 MHz, CDCl$_3$) δ 5.57 (s, 2H), 6.46-6.87 (m, 2H), 7.35 (t, J=9.25 Hz, 1H), 7.49-7.63 (m, 2H), 7.70 (dd, J=6.65, 2.60 Hz, 1H), 8.03 (s, 1H), 8.15 (d, J=2.60 Hz, 1H).

Example 118. 2-[[1-[3-(Difluoromethoxy)-4-fluoro-phenyl]triazol-4-yl]methoxy]-5-methyl-pyridine

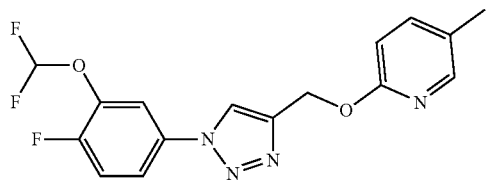 [SMILES: Cc1ccc(OCc2cn(-c3ccc(F)c(OC(F)F)c3)nn2)nc1]

Step A. 5-Chloro-2-((1-(3-(difluoromethoxy)-4-fluorophenyl)-1H-1,2,3-triazol-4-yl)methoxy)pyridine The title compound was prepared in a manner analogous to Intermediate 7 using (1-(3-(difluoromethoxy)-4-fluorophenyl)-1H-1,2,3-triazol-4-yl)methanol (Intermediate 6) and 5-chloro-2-fluoropyridine.

Step B. 2-[[1-[3-(Difluoromethoxy)-4-fluoro-phenyl]triazol-4-yl]methoxy]-5-methyl-pyridine The title compound was prepared in a manner analogous to Example 113 step B, using 5-chloro-2-((1-(3-(difluoromethoxy)-4-fluorophenyl)-1H-1,2,3-triazol-4-yl) methoxy)pyridine. MS (ESI): mass calcd. for $C_{16}H_{13}F_3N_4O_2$, 350.1; m/z found, 351.1 [M+H]$^+$. $^1$H NMR (500 MHz, CDCl$_3$) δ 2.26 (s, 3H), 5.56 (s, 2H), 6.44-6.81 (m, 2H), 7.33 (t, J=9.25 Hz, 1H), 7.42 (dd, J=8.38, 2.02 Hz, 1H), 7.58 (ddd, J=8.81, 3.90, 2.89 Hz, 1H), 7.68 (dd, J=6.65, 2.60 Hz, 1H), 7.94-8.01 (m, 1H), 8.03 (s, 1H).

Example 119. 2-[[1-[3-(Difluoromethoxy)-4-fluoro-phenyl]triazol-4-yl]methoxy]-5-(trifluoromethyl) pyridine

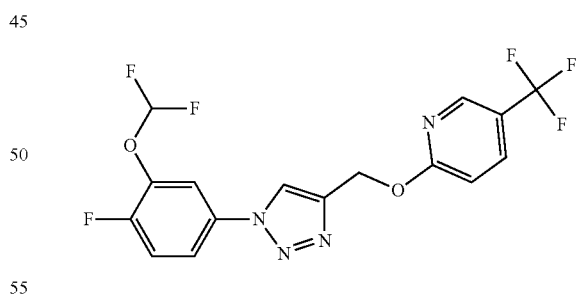

The title compound was prepared in a manner analogous to Intermediate 7 using (1-(3-(difluoromethoxy)-4-fluorophenyl)-1H-1,2,3-triazol-4-yl)methanol (Intermediate 6) and 2-fluoro-5-(trifluoromethyl)pyridine. HRMS=404.070; $^1$H NMR (500 MHz, CDCl$_3$) δ 5.65 (s, 2H), 6.45-6.81 (m, 1H), 6.89 (d, J=8.96 Hz, 1H), 7.34 (t, J=9.25 Hz, 1H), 7.52-7.63 (m, 1H), 7.70 (dd, J=6.36, 2.60 Hz, 1H), 7.81 (dd, J=8.81, 2.17 Hz, 1H), 8.05 (s, 1H), 8.37-8.58 (m, 1H).

Example 120-Example 152 may be prepared in a manner analogous to the methods described in the previous examples.

Example 120. 5-Methyl-2-((1-(5-(trifluoromethyl)thiophen-2-yl)-1H-1,2,3-triazol-4-yl)methoxy)pyrimidine

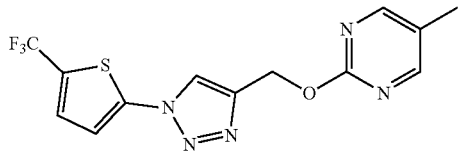 [SMILES: Cc1cnc(OCc2cn(-c3ccc(C(F)(F)F)s3)nn2)nc1]

MS (ESI): mass calcd. for $C_{13}H_{10}F_3N_5OS$, 341.06

Example 121. 5-Methyl-2-((1-(4-(trifluoromethyl)thiophen-2-yl)-1H-1,2,3-triazol-4-yl)methoxy)pyrimidine

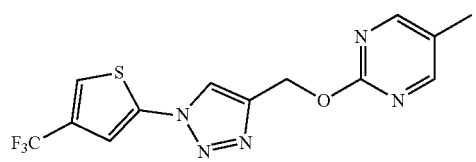 [SMILES: Cc1cnc(OCc2cn(-c3cc(C(F)(F)F)cs3)nn2)nc1]

MS (ESI): mass calcd. for $C_{13}H_{10}F_3N_5OS$, 341.06

Example 122. 2-((1-(3-(Difluoromethyl)-2-fluorophenyl-1H-1,2,3-triazol-4-yl)methoxy)-5-methylpyrimidine

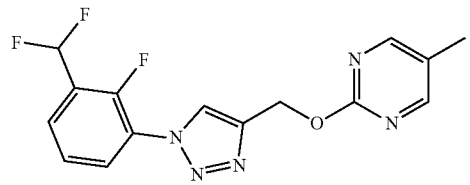 [SMILES: Cc1cnc(OCc2cn(-c3cccc(C(F)F)c3F)nn2)nc1]

MS (ESI): mass calcd. for $C_{15}H_{12}F_3N_5O$, 335.10

Example 123. 2-((1-(4-Chlorophenyl)-1H-1,2,3-triazol-4-yl)methoxy)-5-methylpyrimidine

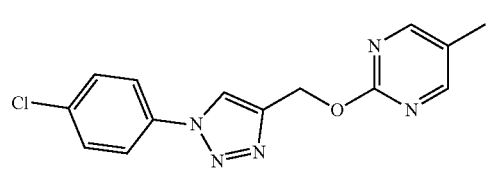 [SMILES: Cc1cnc(OCc2cn(-c3ccc(Cl)cc3)nn2)nc1]

MS (ESI): mass calcd. for $C_{14}H_{12}ClN_5O$, 301.07

Example 124. 2-((1-(4-Chloro-3-(oxetan-3-yl)phenyl)-1H-1,2,3-triazol-4-yl)methoxy)-5-methylpyrimidine

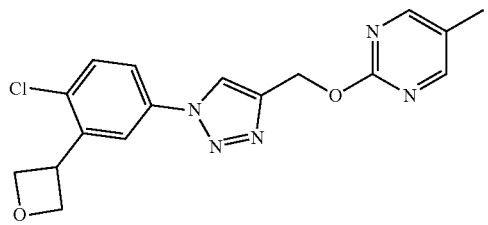 [SMILES: Cc1cnc(OCc2cn(-c3ccc(Cl)c(C4COC4)c3)nn2)nc1]

MS (ESI): mass calcd. for $C_{17}H_{16}ClN_5O_2$, 357.10

Example 125. 2-((1-(4-Chloro-3-(difluoromethyl)phenyl)-5-fluoro-1H-1,2,3-triazol-4-yl)methoxy)-5-methylpyrimidine

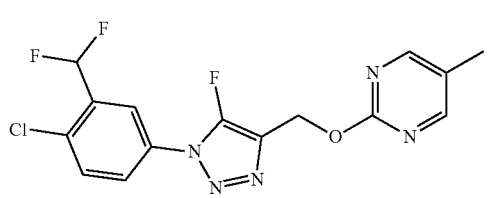 [SMILES: Cc1cnc(OCc2nnn(-c3ccc(Cl)c(C(F)F)c3)c2F)nc1]

MS (ESI): mass calcd. for $C15H11ClF3N5O$, 369.06

Example 126. 2-((1-(4-Chloro-3-(difluoromethyl)phenyl)-5-(trifluoromethyl)-1H-1,2,3-triazol-4-yl)methoxy)-5-methylpyrimidine

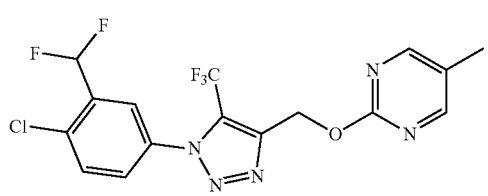 [SMILES: Cc1cnc(OCc2nnn(-c3ccc(Cl)c(C(F)F)c3)c2C(F)(F)F)nc1]

MS (ESI): mass calcd. for $C_{16}H_{11}ClF_5N_5O$, 419.06

Example 127. 2-((1-(4-Chloro-3-(difluoromethyl)phenyl)-5-methyl-1H-1,2,3-triazol-4-yl)methoxy)-5-methylpyrimidine

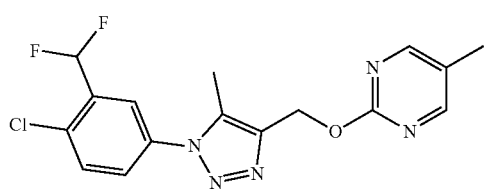 [SMILES: Cc1cnc(OCc2nnn(-c3ccc(Cl)c(C(F)F)c3)c2C)nc1]

MS (ESI): mass calcd. for $C_{16}H_{14}ClF_2N_5O$, 365.09

Example 128. 2-((1-(4-Chloro-3-(difluoromethyl)phenyl)-1H-1,2,3-triazol-4-yl)methoxy)-5-methylthiazole

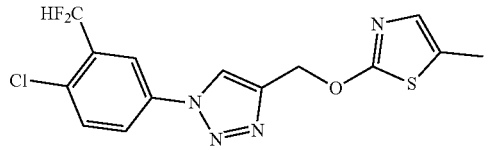

MS (ESI): mass calcd. for $C_{14}H_{11}ClF_2N_4OS$, 356.03.

Example 129. 1-(4-Chloro-3-(difluoromethyl)phenyl)-4-(((5-methyl-1H-imidazol-2-yl)oxy)methyl)-1H-1,2,3-triazole

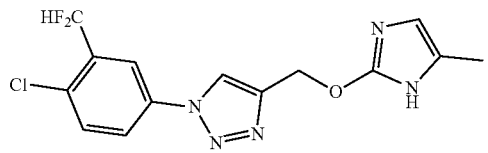

MS (ESI): mass calcd. for $C_{14}H_{12}ClF_2N_5O$, 339.07

Example 130. 2-((1-(4-Chloro-3-(difluoromethoxy)phenyl)-1H-1,2,3-triazol-4-yl)methoxy)-5-methylpyridine

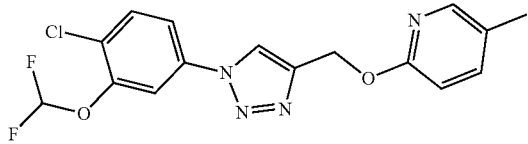 [SMILES: Cc1ccc(OCc2cn(-c3ccc(Cl)c(OC(F)F)c3)nn2)nc1]

MS (ESI): mass calcd. for $C_{16}H_{13}ClF_2N_4O_2$, 366.07

Example 131. 2-((1-(4-Chloro-3-(difluoromethoxy)phenyl)-1H-1,2,3-triazol-4-yl)methoxy-6-methylpyridine

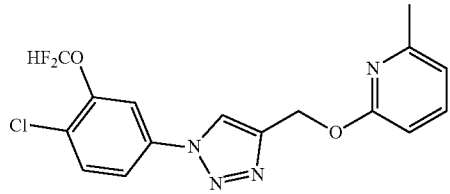

MS (ESI): mass calcd. for $C_{16}H_{13}ClF_2N_4O_2$, 366.07

Example 132. 6-((1-(4-Chloro-3-(difluoromethoxy)phenyl)-1H-1,2,3-triazol-4-yl)methoxy)-2,3-dimethylpyridine

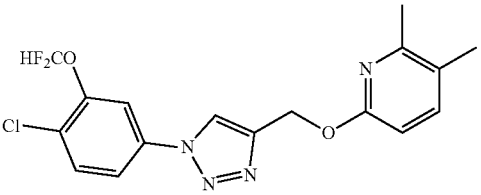

MS (ESI): mass calcd. for $C_{17}H_{15}ClF_2N_4O_2$, 380.09

Example 133. 2-((1-(4-Chloro-3-(difluoromethoxy)phenyl)-1H-1,2,3-triazol-4-yl)methoxy)-6-methylpyrazine

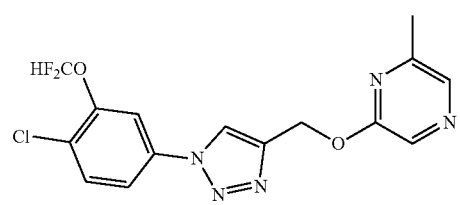

MS (ESI): mass calcd. for $C_{15}H_{12}ClF_2N_5O_2$, 367.06

Example 134. 5-((1-(4-Chloro-3-(difluoromethoxy)phenyl-1H-1,2,3-triazol-4-yl)methoxy)-2,3-dimethylpyrazine

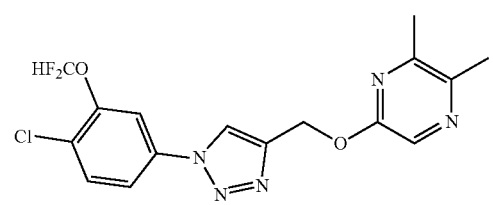

MS (ESI): mass calcd. for $C_{16}H_{14}ClF_2N_5O_2$, 381.08

Example 135. 5-((1-(4-Chloro-3-(difluoromethoxy)phenyl-1H-1,2,3-triazol-4-yl)methoxy)-2-methylpyrimidine

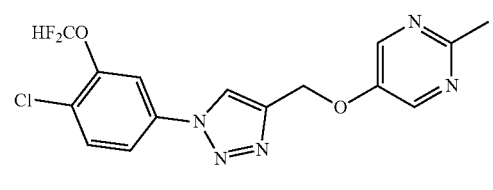

MS (ESI): mass calcd. for $C_{15}H_{12}ClF_2N_5O_2$, 367.06

Example 136. 6-((1-(4-Chloro-3-(difluoromethoxy)phenyl)-1H-1,2,3-triazol-4-yl)methoxy)-3,4-dimethylpyridazine

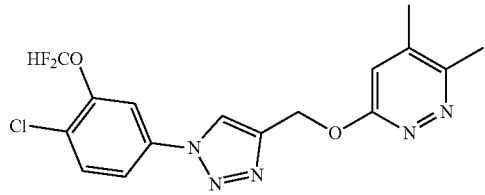

MS (ESI): mass calcd. for $C_{16}H_{14}ClF_2N_5O_2$, 381.08

Example 137. 3-((1-(4-Chloro-3-(difluoromethoxy)phenyl)-1H-1,2,3-triazol-4-yl)methoxy)-6-(trifluoromethyl)pyridazine

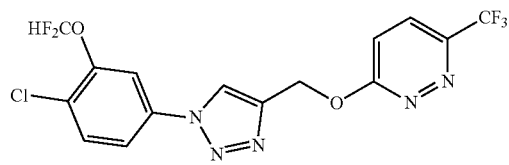

MS (ESI): mass calcd. for $C_{15}H_9ClF_5N_5O_2$, 421.04r

Example 138. 3-((1-(4-Chloro-3-(difluoromethoxy)phenyl)-1H-1,2,3-triazol-4-yl)methoxy)-6-methoxypyridazine

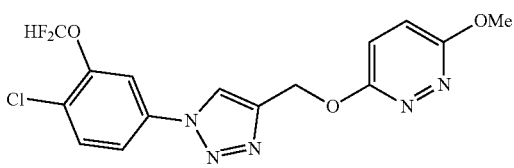

MS (ESI): mass calcd. for $C_{15}H_{12}ClF_2N_5O_3$, 383.06

Example 139. 4-((1-(4-Chloro-3-(difluoromethoxy)phenyl-1H-1,2,3-triazol-4-yl)methoxy-2-methylpyrimidine

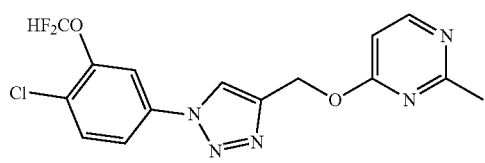

MS (ESI): mass calcd. for $C_{15}H_{12}ClF_2N_5O_2$, 367.06

Example 140. 4-((1-(4-Chloro-3-(difluoromethoxy)phenyl)-1H-1,2,3-triazol-4-yl)methoxy)-2-(trifluoromethyl)pyrimidine

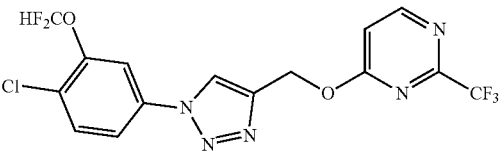

MS (ESI): mass calcd. for $C_{15}H_9ClF_5N_5O_2$, 421.04

Example 141. 4-((1-(4-Chloro-3-(difluoromethoxy)phenyl)-1H-1,2,3-triazol-4-yl)methoxy)-2-methoxypyrimidine

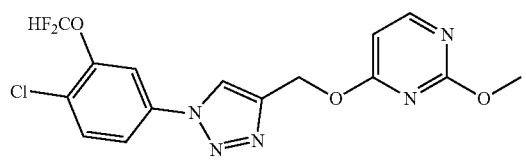

MS (ESI): mass calcd. for $C_{15}H_{12}ClF_2N_5O_3$, 383.06

Example 142. 2-((1-(5-Chloro-6-(trifluoromethyl)pyridin-2-yl)-1H-1,2,3-triazol-4-yl)methoxy)-5-methylpyrimidine

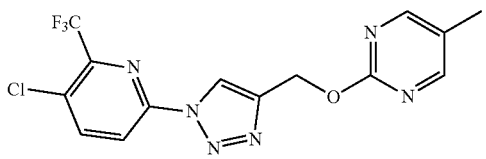 [SMILES: Cc1cnc(OCc2cn(-c3ccc(Cl)c(C(F)(F)F)n3)nn2)nc1]

MS (ESI): mass calcd. for $C_{14}H_{10}ClF_3N_6O$, 370.06

Example 143. 2-((1-(2-(Difluoromethyl)pyridin-4-yl)-1H-1,2,3-triazol-4-yl)methoxy)-5-methylpyrimidine

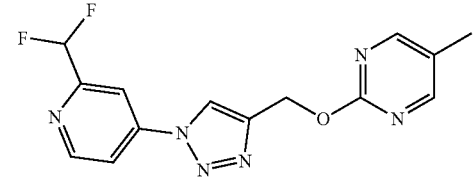 [SMILES: Cc1cnc(OCc2cn(-c3ccnc(C(F)F)c3)nn2)nc1]

MS (ESI): mass calcd. for $C_{14}H_{12}F_2N_6O$, 318.10

Example 144. N-((1-(4-Chloro-3-(difluoromethoxy)phenyl)-1H-1,2,3-triazol-4-yl)methyl)-5-methylpyrimidin-2-amine

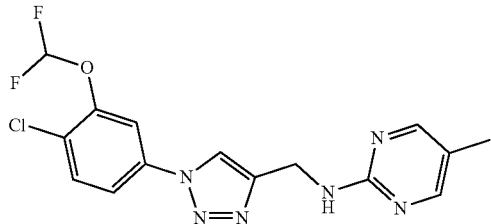 [SMILES: Cc1cnc(NCc2cn(-c3ccc(Cl)c(OC(F)F)c3)nn2)nc1]

MS (ESI): mass calcd. for $C_{15}H_{13}ClF_2N_6O$, 366.08

Example 145. N-((1-(4-Chloro-3-(difluoromethoxy)phenyl)-1H-1,2,3-triazol-4-yl)methyl)-4,5-dimethylpyrimidin-2-amine

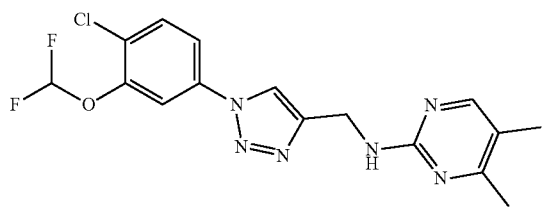 [SMILES: Cc1cnc(NCc2cn(-c3ccc(Cl)c(OC(F)F)c3)nn2)nc1C]

MS (ESI): mass calcd. for $C_{16}H_{15}ClF_2N_6O$, 380.10

Example 146. 3-((1-(4-Chloro-3-(difluoromethoxy)phenyl)-1H-1,2,3-triazol-4-yl) methoxy)-4-methoxypyridine.

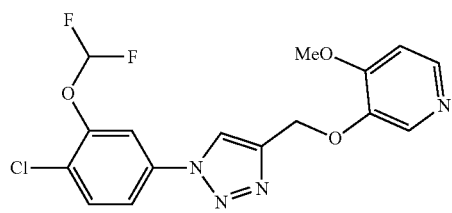 [SMILES: COc1ccncc1OCc1cn(-c2ccc(Cl)c(OC(F)F)c2)nn1]

MS (ESI): mass calcd. for $C_{16}H_{13}ClF_2N_4O_3$, 382.1

Example 147. 4-Chloro-3-((1-(4-chloro-3-(difluoromethoxy)phenyl)-1H-1,2,3-triazol-4-yl)methoxy)pyridine

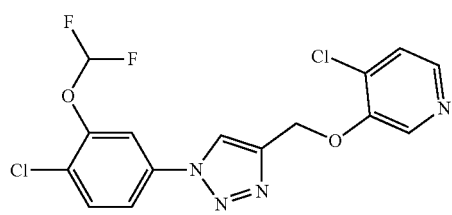 [SMILES: FC(F)Oc1cc(-n2cc(COc3cnccc3Cl)nn2)ccc1Cl]

MS (ESI): mass calcd. for $C_{15}H_{10}Cl_2F_2N_4O_2$, 386.0

Example 148. 4-((1-(3-(Difluoromethoxy)phenyl)-1H-1,2,3-triazol-4-yl)methoxy)-5-methoxypyrimidine

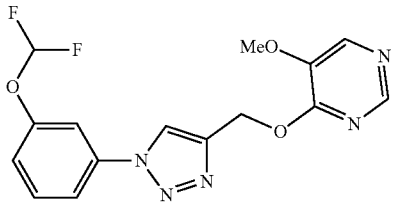 [SMILES: COc1cncnc1OCc1cn(-c2cccc(OC(F)F)c2)nn1]

MS (ESI): mass calcd. for $C_{15}H_{13}F_2N_5O_3$, 349.1

Example 149. 2-((1-(3-(Difluoromethyl)phenyl)-5-1H-1,2,3-triazol-4-yl)methoxy)-5-methoxypyrimidine

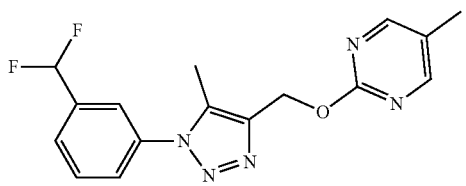 [SMILES: Cc1cnc(OCc2nnn(-c3cccc(C(F)F)c3)c2C)nc1]

MS (ESI): mass calcd. for $C_{16}H_{13}F_2N_5O$, 331.1

Example 150. 5-Methyl-2-((1-(5-(trifluoromethyl)pyridin-2-yl)-1H-1,2,3-triazol-4-yl)methoxy)pyrimidine

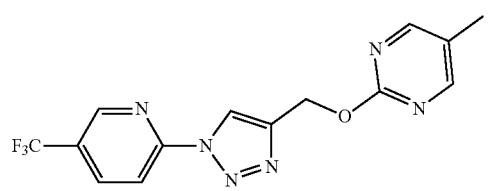 [SMILES: Cc1cnc(OCc2cn(-c3ccc(C(F)(F)F)cn3)nn2)nc1]

MS (ESI): mass calcd. for $C_{16}H_{15}F_2N_5O$, 336.1

Example 151. 2-((1-(5-Bromo-6-fluoropyridin-3-yl)-1H-1,2,3-triazol-4-yl)methoxy)-5-methylpyrimidine

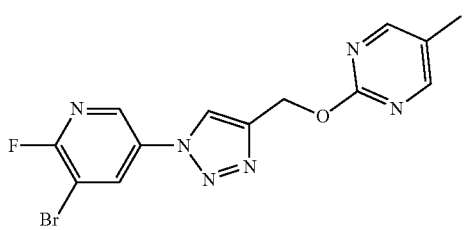 [SMILES: Cc1cnc(OCc2cn(-c3cnc(F)c(Br)c3)nn2)nc1]

MS (ESI): mass calcd. for $C_{13}H_{10}BrFN_6O$, 364.0

Example 152. 5-Methyl-2-((1-(pyridin-4-yl)-1H-1,2,3-triazol-4-yl)methoxy)pyrimidine

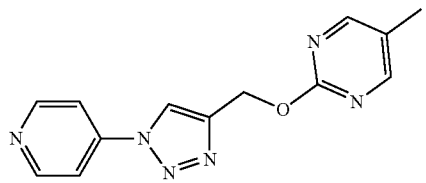 [SMILES: Cc1cnc(OCc2cn(-c3ccncc3)nn2)nc1]

MS (ESI): mass calcd. for $C_{13}H_{12}N_6O$, 268.1

Example 153: 5-Chloro-N-[[1-[3-(difluoromethyl)phenyl]triazol-4-yl]methyl]pyrimidin-2-amine

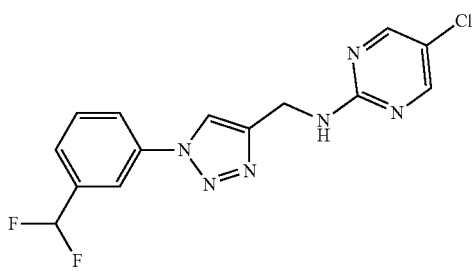 [SMILES: FC(F)c1cccc(-n2cc(CNc3ncc(Cl)cn3)nn2)c1]

To a solution of 4-(chloromethyl)-1-(3-(difluoromethyl)phenyl)-1H-1,2,3-triazole (25 mg, 0.103 mmol) and 2-amino-5-chloropyrimidine (17 mg, 0.13 mmol) in DMF (1.5 mL) was added $K_2CO_3$ (57 mg, 0.41 mmol). The resulting mixture was stirred at 100° C. for 72 h. The reaction mixture was diluted with water (8 mL) and extracted with EtOAc (3×10 mL). The combined organics were dried over $Na_2SO_4$, filtered, and concentrated under reduced pressure. Purification (FCC, $SiO_2$, 0-80% EtOAc/hexanes) afforded the title compound (6.2 mg, 18%). MS (ESI): mass calcd. for $C_{14}H_{11}ClF_2NS$, 336.07; m/z found, 337.0 [M+H]$^+$. $^1$H NMR (400 MHz, CDCl$_3$) δ 8.33-8.19 (m, 2H), 8.03-7.95 (m, 1H), 7.91-7.80 (m, 2H), 7.68-7.54 (m, 2H), 6.72 (t, J=56.1 Hz, 1H), 5.85 (s, 1H), 4.80 (dd, J=6.2, 0.6 Hz, 2H).

Example 154: N-[[1-[4-Chloro-3-(difluoromethyl)phenyl]triazol-4-yl]methyl]-5-methyl-pyrimidin-2-amine

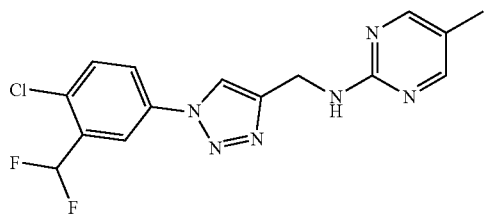 [SMILES: Cc1cnc(NCc2cn(-c3ccc(Cl)c(C(F)F)c3)nn2)nc1]

A solution of (1-(4-chloro-3-(difluoromethyl)phenyl)-1H-1,2,3-triazol-4-yl)methanamine (Intermediate 19) (35 mg, 0.14 mmol), 2-chloro-5-methylpyrimidine (22.6 mg, 0.18 mmol), and triethylamine (0.06 mL, 0.4 mmol) in EtOH (1 mL) was sealed and heated in a microwave reactor for 1 h at 180° C., then 200° C. for 1 h. The mixture was concentrated under reduced pressure. Purification (FCC, $SiO_2$, MeOH/DCM 0-8%) afforded the title compound (8.3 mg, 17%). MS (ESI): mass calcd. for $C_{15}H_{13}ClF_2N_6$, 350.1; m/z found, 351.0 [M+H]$^+$. $^1$H NMR (500 MHz, CDCl$_3$) δ 8.19 (s, 2H), 7.99 (s, 1H), 7.97 (d, J=2.6 Hz, 1H), 7.87 (dd, J=8.7, 2.6 Hz, 1H), 7.61-7.57 (m, 1H), 6.98 (t, J=54.6 Hz, 1H), 5.69 (s, 1H), 4.81 (d, J=6.2 Hz, 2H), 2.16 (s, 3H).

Example 155: 2-[[1-[3-(Difluoromethyl)phenyl]triazol-4-yl]methoxy]-4,5-dimethyl-pyrimidine

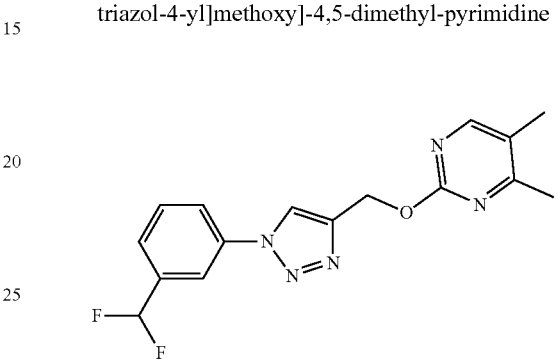

To a solution of (1-(3-(difluoromethyl)phenyl)-1H-1,2,3-triazol-4-yl)methanol (Intermediate 12, 50 mg, 0.22 mmol) in THF (1 mL) was added NaH (60% dispersion in mineral oil, 26.6 mg, 0.67 mmol). The mixture was stirred for 5 min, then 2-chloro-4,5-dimethylpyrimidine (38 mg, 0.27 mmol) was added. The reaction was stirred at rt overnight. The mixture was quenched with $H_2O$, and diluted with EtOAc and $H_2O$. The layers were separated and the aqueous layer was extracted with EtOAc (3×). The combined organic layers were dried ($Na_2SO_4$) and concentrated under reduced pressure. Purification (FCC, $SiO_2$, EtOAc/hexanes 0-50%) afforded the title compound (44 mg, 60%). MS (ESI): mass calcd. for $C_{16}H_{15}F_2N_5O$, 331.1; m/z found, 332.1 [M+H]$^+$. $^1$H NMR (400 MHz, CDCl$_3$) δ 8.23-8.12 (m, 2H), 7.93-7.83 (m, 2H), 7.67-7.54 (m, 2H), 6.72 (t, J=56.0 Hz, 1H), 5.64 (s, 2H), 2.44 (s, 3H), 2.20 (s, 3H).

Example 156: 1-[2-[[1-[3-(Difluoromethyl)-4-fluoro-phenyl]triazol-4-yl]methoxy]pyrimidin-5-yl]ethanone

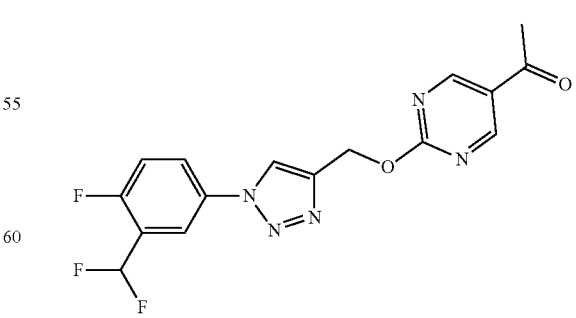

A solution of (1-(3-(difluoromethyl)-4-fluorophenyl)-1H-1,2,3-triazol-4-yl)methanol (Intermediate 9, 110 mg, 0.41 mmol), $Cs_2CO_3$ (535.9 mg, 1.64 mmol), and 1-(2-chloropyrimidin-5-yl)ethan-1-one (83.6 mg, 0.53 mmol) in ACN (0.02 mL) was heated at 110° C. overnight. The reaction mixture was cooled, diluted with EtOAc, and washed with sat aq. NH₄Cl. The organic layer was dried (Na₂SO₄), filtered, and concentrated under reduced pressure. Purification (FCC, SiO₂, 0-50% EtOAc in hexanes) afforded the title compound (12 mg, 8%). MS (ESI): mass calcd. for $C_{16}H_{12}F_3N_5O_2$, 363.1; m/z found, 364.1 [M+H]⁺. ¹H NMR (500 MHz, CDCl₃) δ 9.14-9.05 (s, 2H), 8.19-8.11 (s, 1H), 7.98-7.87 (m, 2H), 7.40-7.31 (m, 1H), 7.09-6.80 (t, J=54.6 Hz, 1H), 5.80-5.71 (s, 2H), 2.66-2.57 (s, 3H).

Example 157: (R/S)-1-[2-[[1-[3-(Difluoromethyl)-4-fluoro-phenyl]triazol-4-yl]methoxy]pyrimidin-5-yl]ethanol

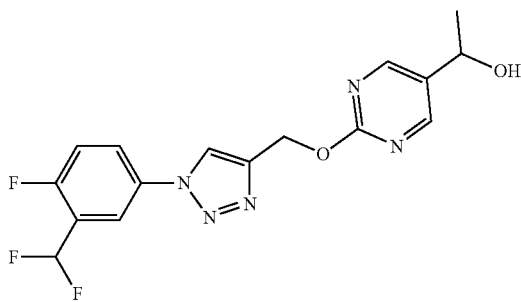 [SMILES: CC(O)c1cnc(OCc2cn(-c3ccc(F)c(C(F)F)c3)nn2)nc1]

A solution of 1-(2-((1-(3-(difluoromethyl)-4-fluorophenyl)-1H-1,2,3-triazol-4-yl)methoxy)pyrimidin-5-yl)ethan-1-one (Example 156, 14 mg, 0.04 mmol) in DCM/MeOH (15 mL/1 mL) is cool to 0° C. Sodium borohydride (4.4 mg, 0.12 mmol) was added in a single portion and the reaction mixture was stirred at 0° C. for 1 h. The completed reaction was quenched with water and extracted into DCM (5 mL×3). The organic layer is dried (Na₂SO₄), filtered, and concentrated. Purification (FCC, SiO₂, eluting with 0-3% MeOH in DCM) afforded the titled compound (7 mg, 50%). MS (ESI): mass calcd. for $C_{16}H_{14}F_3N_5O_2$, 365.1; m/z found, 366.0 [M+H]⁺. ¹H NMR (500 MHz, CDCl₃) δ 8.61-8.55 (s, 2H), 8.17-8.13 (s, 1H), 7.98-7.93 (m, 1H), 7.93-7.87 (m, 1H), 7.37-7.29 (m, 1H), 7.08-6.80 (t, J=54.6 Hz, 1H), 5.76-5.56 (d, J=0.7 Hz, 2H), 5.10-4.86 (m, 1H), 1.64-1.50 (d, J=6.5 Hz, 3H). OH proton not observed.

Example 158: 2-[[1-[4-Fluoro-3-(trifluoromethyl)phenyl]triazol-4-yl]methoxy]pyridine

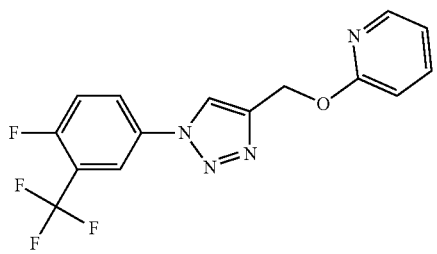 [SMILES: Fc1ccc(-n2cc(COc3ccccn3)nn2)cc1C(F)(F)F]

A stirred suspension of (1-(4-fluoro-3-(trifluoromethyl)phenyl)-1H-1,2,3-triazol-4-yl)methanol (Intermediate 5, 30 mg, 0.115 mmol), 2-chloropyridine (19.5 mg, 0.172 mmol), Cs₂CO₃ (75 mg, 0.23 mmol) and 2-(di-tert-butylphosphino)biphenyl (69 mg, 0.23 mmol) in toluene (2 mL) was charged with palladium (II) acetate (3 mg, 0.012 mmol). The mixture was stirred at 120° C. for 4 h under a nitrogen atmosphere. The completed reaction was filtered through a pad of diatomaceous earth and washed with EtOAc. The organics were concentrated under reduced pressure. Purification (FCC, SiO₂, 0-100% EtOAc in Hexanes) afforded the titled compound (18 mg, 47%). MS (ESI): mass calcd. for $C_{15}H_{10}F_4N_4O$, 338.1; m/z found, 339.0 [M+H]⁺. ¹H NMR (500 MHz, CDCl₃) δ 8.23-8.18 (m, 1H), 8.09 (t, J=0.7 Hz, 1H), 8.03-7.97 (m, 1H), 7.98-7.92 (m, 1H), 7.65-7.58 (m, 1H), 7.39 (t, J=9.1 Hz, 1H), 6.95-6.89 (m, 1H), 6.85-6.78 (m, 1H), 5.61 (d, J=0.7 Hz, 2H).

Example 159: [2-[[1-[3-(Difluoromethyl)phenyl]triazol-4-yl]methoxy]pyrimidin-4-yl]methanol

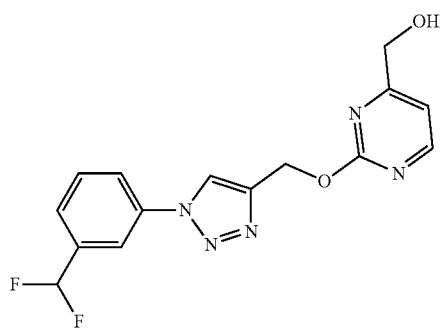 [SMILES: OCc1ccnc(OCc2cn(-c3cccc(C(F)F)c3)nn2)n1]

Step A. 4-(((tert-Butyldimethylsilyl)oxy)methyl)-2-((1-(3-(difluoromethyl)phenyl)-1H-1,2,3-triazol-4-yl)methoxy)pyrimidine The title compound was prepared analogous to Example 155, using 4-(((tert-butyldimethylsilyl)oxy)methyl)-2-chloropyrimidine (Intermediate 54).

Step B. [2-[[1-[3-(Difluoromethyl)phenyl]triazol-4-yl]methoxy]pyrimidin-4-yl]methanol To a solution of 4-(((tert-butyldimethylsilyl)oxy)methyl)-2-((1-(3-(difluoromethyl)phenyl)-1H-1,2,3-triazol-4-yl)methoxy)pyrimidine (78 mg, 0.17 mmol) in THF (2 mL) was added TBAF (1 M in THF, 0.2 mL, 0.2 mmol). The reaction was stirred at rt for 15 minutes, then quenched with a saturated solution of NH₄Cl and diluted with EtOAc. The layers were separated and the organic layer was dried (Na₂SO₄) then concentrated under reduced pressure. Purification (FCC, SiO₂, EtOAc/hexanes 0-80%) afforded the title compound (26 mg, 39%). MS (ESI): mass calcd. for $C_{15}H_{13}F_2N_5O_2$, 333.1; m/z found, 334.1 [M+H]⁺. ¹H NMR (500 MHz, CDCl₃) δ 8.50 (d, J=5.0 Hz, 1H), 8.19 (s, 1H), 7.91-7.89 (m, 1H), 7.88-7.84 (m, 1H), 7.65-7.60 (m, 1H), 7.60-7.56 (m, 1H), 7.02 (d, J=5.1 Hz, 1H), 6.72 (t, J=56.1 Hz, 1H), 5.67 (d, J=0.7 Hz, 2H), 4.73 (d, J=4.5 Hz, 2H), 3.33 (t, J=5.4 Hz, 1H)

Example 160: [2-[[1-[3-(Difluoromethyl)phenyl]triazol-4-yl]methoxy]pyrimidin-5-yl]methanol

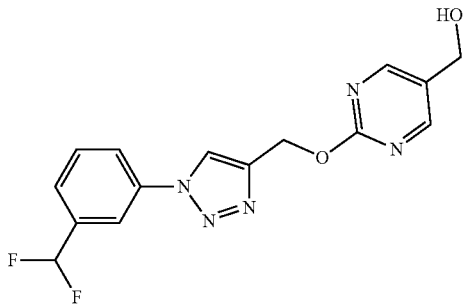 [SMILES: OCc1cnc(OCc2cn(-c3cccc(C(F)F)c3)nn2)nc1]

The title compound was prepared analogous to Example 159, using 5-(((tert-butyldimethylsilyl)oxy)methyl)-2-chloropyrimidine (Intermediate 53) in Step A. MS (ESI): mass calcd. for $C_{15}H_{13}F_2N_5O_2$, 333.1; m/z found, 334.1 [M+H]$^+$. $^1$H NMR (500 MHz, CDCl$_3$) δ 8.54 (s, 2H), 8.18 (s, 1H), 7.92-7.88 (m, 1H), 7.88-7.83 (m, 1H), 7.65-7.59 (m, 1H), 7.58-7.55 (m, 1H), 6.71 (t, J=56.1 Hz, 1H), 5.63 (d, J=0.7 Hz, 2H), 4.67 (s, 2H), 2.88 (s, 1H).

Example 161: 2-[[1-[3-(Difluoromethyl)phenyl]triazol-4-yl]methoxy]-5-methyl-pyrimidin-4-amine

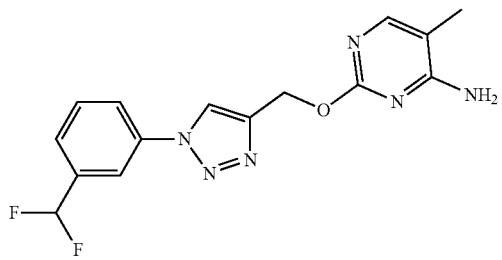 [SMILES: Cc1cnc(OCc2cn(-c3cccc(C(F)F)c3)nn2)nc1N]

(1-(3-(Difluoromethyl)phenyl)-1H-1,2,3-triazol-4-yl)methanol (Intermediate 12, 26 mg, 0.12 mmol), 2-chloro-5-methylpyrimidin-4-amine (20 mg, 0.14 mmol), and Cs$_2$CO$_3$ (113 mg, 0.35 mmol) were dissolved in ACN (0.7 mL) in a microwave vial. The reaction was heated in a microwave reactor at 140° C. for 2 h. The reaction was cooled to rt, diluted with EtOAC and H$_2$O, then the layers were separated and the aqueous layer was extracted with EtOAc (3×). The combined organic layers were dried (Na$_2$SO$_4$), and concentrated under reduced pressure. Purification (FCC, SiO$_2$, EtOAC/hexanes 0-70%) afforded the title compound (13.4 mg, 29%). MS (ESI): mass calcd. for $C_{15}H_{14}F_2N_6O$, 332.1; m/z found, 333.0 [M+H]$^+$. $^1$H NMR (500 MHz, CDCl$_3$) δ 8.15 (s, 1H), 7.93-7.82 (m, 3H), 7.66-7.54 (m, 2H), 6.71 (t, J=56.1 Hz, 1H), 5.55 (s, 2H), 5.02 (s, 2H), 2.07-1.99 (m, 3H)

Example 162: 2-[[1-[3-(Difluoromethyl)-4-fluorophenyl]triazol-4-yl]methoxy]-N-methyl-pyrimidine-4-carboxamide

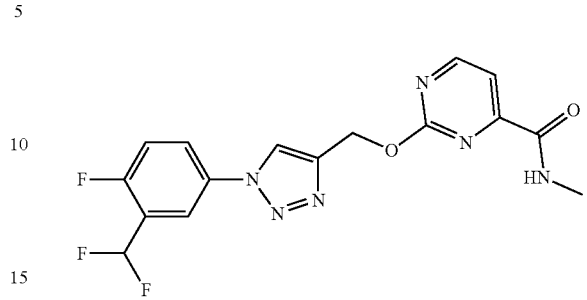

Step A: 2-((1-(3-(difluoromethyl)-4-fluorophenyl)-1H-1,2,3-triazol-4-yl)methoxy)pyrimidine-4-carboxylic acid The title compound was prepared in a manner analogous to Example 161, using (1-(3-(difluoromethyl)-4-fluorophenyl)-1H-1,2,3-triazol-4-yl)methanol (Intermediate 9) and methyl 2-chloropyrimidine-4-carboxylate. MS (ESI): mass calcd. for $C_{15}H_{10}F_3N_5O_3$, 335.1; m/z found, 366.0[M+H]$^+$.

Step B: 2-[[1-[3-(Difluoromethyl)-4-fluoro-phenyl]triazol-4-yl]methoxy]-N-methyl-pyrimidine-4-carboxamide To solution of 2-((1-(3-(difluoromethyl)-4-fluorophenyl)-1H-1,2,3-triazol-4-yl)methoxy)pyrimidine-4-carboxylic acid (15 mg, 0.041 mmol), methylamine (1.5 mg, 0.045 mmol), EDCl (16 mg, 0.082 mmol), and HOBt (11 mg, 0.082 mmol) in DCM (3 mL) was added DIEA (21 μL, 0.123 mmol). The resulting mixture was stirred at rt overnight. The reaction mixture was diluted with DCM and washed with water and brine. The organic layer was dried (Na$_2$SO$_4$), filtered, and concentrated under reduced pressure. Purification (FCC, SiO$_2$, 0-80% EtOAc/Hexanes) afforded the title compound (6.1 mg, 39%). MS (ESI): mass calcd. for $C_{16}H_{13}F_3N_6O_2$, 378.1; m/z found, 379.0 [M+H]$^+$. $^1$H NMR (500 MHz, CDCl$_3$) δ 8.77 (d, J=4.9 Hz, 1H), 8.17-8.09 (m, 2H), 7.98-7.92 (m, 1H), 7.93-7.86 (m, 1H), 7.82-7.75 (m, 1H), 7.39-7.30 (m, 1H), 6.95 (t, J=54.6 Hz, 1H), 5.70 (d, J=0.6 Hz, 2H), 3.06 (d, J=5.1 Hz, 3H).

Example 163: (R/S) 1-[2-[[1-[3-(Difluoromethoxy)-4-fluoro-phenyl]triazol-4-yl]methoxy]pyrimidin-4-yl]ethanamine

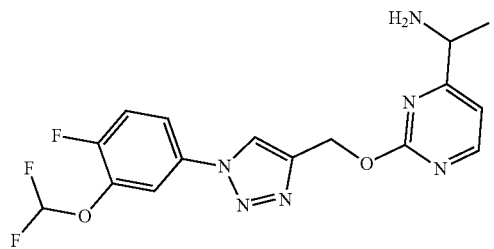 [SMILES: CC(N)c1ccnc(OCc2cn(-c3ccc(F)c(OC(F)F)c3)nn2)n1]

Step. A. (R/S) tert-Butyl (1-(2-chloropyrimidin-4-yl)ethyl)carbamate

Under a nitrogen atmosphere was added NaH (60% dispersion in mineral oil, 154 mg, 3.8 mmol) in small batches to a mixture of tert-butyl ((2-chloropyrimidin-4-yl)methyl)carbamate (Intermediate 58, 720 mg, 3.0 mmol) in DMF (50 mL) at room temperature. After 30 minutes, MeI (0.22 mL, 3.5 mmol) was added at 0° C. After 16 h, complete conversion was observed. EtOAc (200 mL) was added. The mixture was washed with brine (1×350 mL). The organic was dried (MgSO$_4$), filtered, and concentrated under vacuum. Purification (FCC, SiO$_2$, 0-99% EtOAc/hexanes) afforded the title compound (299 mg, 39%). MS (ESI): mass calcd. for $C_{11}H_{16}ClN_3O_2$, 257.1; m/z found, 201.9 [M-t-Bu]$^+$.

Step B. (R/S) tert-Butyl (1-(2-((1-(3-(difluoromethoxy)-4-fluorophenyl)-1H-1,2,3-triazol-4-yl)methoxy)pyrimidin-4-yl)ethyl)carbamate The title compound was prepared in a manner analogous to Example 1 using (1-(3-(difluoromethoxy)-4-fluorophenyl)-1H-1,2,3-triazol-4-yl)methanol (Intermediate 6) and R/S tert-butyl (1-(2-chloropyrimidin-4-yl)ethyl)carbamate, using THF instead of DMF. MS (ESI): mass calcd. for $C_{21}H_{23}F_3N_6O_4$, 480.1; m/z found, 480.9 [M+H].

Step C. (R/S) 1-[2-[[1-[3-(Difluoromethoxy)-4-fluoro-phenyl]triazol-4-yl]methoxy]pyrimidin-4-yl]ethanamine as the trifluoroacetic acid salt TFA (0.04 mL, 0.5 mmol) was added to a mixture of (R/S) tert-butyl (1-(2-((1-(3-(difluoromethoxy)-4-fluorophenyl)-1H-1,2,3-triazol-4-yl)methoxy)pyrimidin-4-yl)ethyl)carbamate (13 mg, 0.03 mmol) in DCM (5 mL). Upon completion, the reaction mixture was concentrated under reduced pressure. Purification (HPLC METHOD E) afforded the title compound (3.6 mg, 35%). MS (ESI): mass calcd. for $C_{16}H_{15}F_3N_6O_2$, 380.1; m/z found, 381.0 [M+H]$^+$. $^1$H NMR (500 MHz, CD$_2$Cl$_2$) δ8.47 (d, J=5.1 Hz, 1H), 8.21 (s, 1H), 7.72 (dd, J=6.7, 2.6 Hz, 1H), 7.60 (ddd, J=9.0, 3.9, 2.7 Hz, 1H), 7.37 (dd, J=9.7, 8.9 Hz, 1H), 7.03 (d, J=5.0 Hz, 1H), 6.69 (t, J=72.8 Hz, 1H), 5.63-5.57 (m, 2H), 4.04 (q, J=6.8 Hz, 1H), 1.39 (d, J=6.7 Hz, 3H).

Example 164: 5-Chloro-2-[[1-(4-fluorophenyl)triazol-4-yl]methoxy]pyrimidine. as the Trifluoroacetic Acid Salt

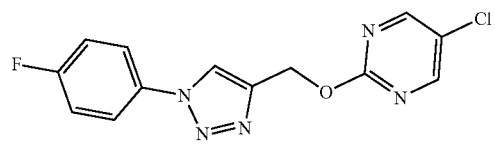 [SMILES: Fc1ccc(-n2cc(COc3ncc(Cl)cn3)nn2)cc1]

A microwave vial was charged with 2-((1-(3-bromo-4-fluorophenyl)-1H-1,2,3-triazol-4-yl)methoxy)-5-chloropyrimidine (Example 42, 25 mg, 0.07 mmol), azetidine (0.005 mL, 0.08 mmol), trans-bis(acetato)bis[o-(di-o-tolylphosphino)benzyl]dipalladium(II) (6 mg, 0.007 mmol), molybdenum hexacarbonyl (17 mg, 0.07 mmol), DBU (0.01 mL, 0.08 mmol) and THF (0.5 mL), purged with nitrogen, and heated to 150° C. under microwave irradiation for 20 minutes. The reaction mixture was concentrated under vacuum. Purification (FCC, SiO$_2$, 0-99% EtOAc in hexanes), followed by reversed phase HPLC (METHOD E) afforded the title compound (7 mg, 25%) as a by-product. MS (ESI): mass calcd. for $C_{13}H_{10}ClFN_5O$, 305.1; m/z found, 306.1 [M+H]$^+$. $^1$H NMR (500 MHz, DMSO-d$_6$) δ 8.89 (s, 1H), 8.77-8.75 (m, 2H), 7.98-7.93 (m, 2H), 7.49-7.42 (m, 2H), 5.54 (s, 2H).

Example 165: 5-(Azetidin-1-yl)-2-[[1-[3-(difluoromethoxy)-4-fluoro-phenyl]triazol-4-yl]methoxy]pyrimidine

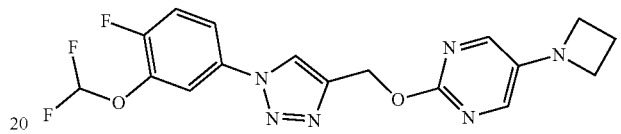

Step A. 5-(Azetidin-1-yl)-2-(methylthio)pyrimidine

A mixture of azetidine (0.03 mL, 0.5 mmol), 5-bromo-2-(methylthio)pyrimidine (100 mg, 0.49 mmol), Xantphos (4,5-Bis(diphenylphosphino)-9,9-dimethylxanthene) (9.9 mg, 0.02 mmol), Pd(OAc)$_2$ (2 mg, 0.01 mmol) and NaOt-Bu (140 mg, 1.5 mmol) in toluene (1.7 mL) was heated at 110° C. After 3 h, the reaction mixture was cooled to room temperature and concentrated under vacuum. Purification (FCC, SiO$_2$, 0-99% EtOAc in hexanes) afforded the title compound (39 mg, 44%). MS (ESI): mass calcd. for $C_8H_{11}N_3S$, 181.1; m/z found, 182.1 [M+H]$^+$. $^1$H NMR (400 MHz, DMSO-d$_6$) δ 7.96 (s, 2H), 3.87 (t, J=7.3 Hz, 4H), 2.45 (s, 3H), 2.40-2.32 (m, 2H).

Step B. 5-(Azetidin-1-yl)-2-(methylsulfonyl)pyrimidine mCPBA (1.6 g, 7.3 mmol) was slowly added to a mixture of 5-(azetidin-1-yl)-2-(methylthio)pyrimidine (531 mg, 2.9 mmol) in DCM (12 mL) at 0° C. After 16 hours, the reaction mixture was quenched with a saturated aqueous solution of NaHCO$_3$ (60 mL). The mixture was extracted with DCM (3×80 mL). The combined organics were dried (MgSO$_4$), filtered, and concentrated under vacuum. Purification (FCC, SiO$_2$, 0-99% EtOAc in hexanes) afforded the title compound (290 mg, 46%). MS (ESI): mass calcd. for $C_5H_{11}N_3O_2S$, 213.1; m/z found, 214.1 [M+H]$^+$. $^1$H NMR (500 MHz, DMSO-d$_6$) δ 8.10 (s, 2H), 4.08 (t, J=7.5 Hz, 4H), 3.24 (s, 3H), 2.48-2.40 (m, 2H).

Step C. 5-(Azetidin-1-yl)-2-[[1-[3-(difluoromethoxy)-4-fluoro-phenyl]triazol-4-yl]methoxy]pyrimidine The title compound was prepared in a manner analogous to Example 155 using (1-(3-(difluoromethoxy)-4-fluorophenyl)-1H-1,2,3-triazol-4-yl)methanol (Intermediate 6) and using 5-(azetidin-1-yl)-2-(methylsulfonyl)pyrimidine. MS (ESI): mass calcd. for $C_{17}H_{15}F_3N_6O_2$, 392.1; m/z found, 393.2 [M+H]$^+$. $^1$H NMR (400 MHz, DMSO-d$_6$) b 8.92 (s, 1H), 8.00 (dd, J=6.9, 2.6 Hz, 1H), 7.92 (s, 2H), 7.87 (ddd, J=9.0, 4.0, 2.6 Hz, 1H), 7.68 (dd, J=10.2, 9.0 Hz, 1H), 7.39 (t, J=72.8 Hz, 1H), 5.42 (s, 2H), 3.84 (t, J=7.2 Hz, 4H), 2.38-2.29 (m, 2H).

Example 166: 2-[[1-[3-(Difluoromethoxy)-4-fluorophenyl]triazol-4-yl]methoxy]-4-(3,3-difluoropyrrolidin-1-yl)pyrimidine

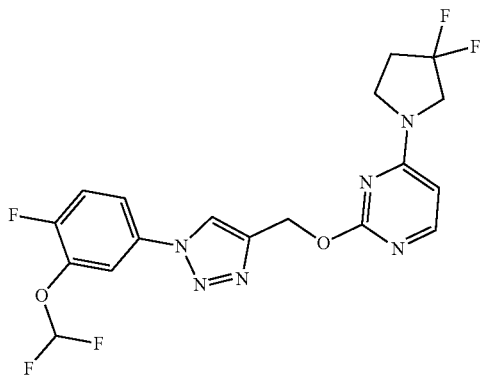 [SMILES: Fc1ccc(-n2cc(COc3nccc(N4CCC(F)(F)C4)n3)nn2)cc1OC(F)F]

Step A. 2-Chloro-4-(3,3-difluoropyrrolidin-1-yl)pyrimidine

A mixture of 2,4-dichloropyrimidine (500 mg, 3.4 mmol), 3,3-difluoropyrrolidine hydrochloride (481 mg, 3.4 mmol) and TEA (0.56 mL, 4.0 mmol) in DCM (23 mL) was stirred at rt. After 3 hours, water (50 mL) was added to the reaction mixture. The mixture was extracted with EtOAc (3×75 mL). The combined organics were dried (MgSO$_4$), filtered, and concentrated under vacuum. Purification (FCC, SiO$_2$, 0-100% EtOAc in hexanes) afforded the title compound (392 mg, 53%). MS (ESI): mass calcd. for C$_8$H$_8$ClF$_2$N$_3$, 219.0; m/z found, 220.0 [M+H]$^+$. $^1$H NMR (400 MHz, DMSO-d$_6$) δ 8.14 (d, J=6.0 Hz, 1H), 6.61 (br s, 1H), 3.89 (t, J=13.0 Hz, 2H), 3.75-3.61 (m, 2H).

Step B. 2-[[1-[3-(Difluoromethoxy)-4-fluoro-phenyl]triazol-4-yl]methoxy]-4-(3,3-difluoropyrrolidin-1-yl)pyrimidine The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-(3,3-difluoropyrrolidin-1-yl)pyrimidine. MS (ESI): mass calcd. for C$_{18}$H$_{15}$F$_8$N$_6$O$_2$, 442.1; m/z found, 442.9 [M+H]$^+$. $^1$H NMR (400 MHz, DMSO-d$_6$) δ 8.92 (s, 1H), 8.09 (d, J=5.9 Hz, 1H), 8.00 (dd, J=6.9, 2.6 Hz, 1H), 7.88 (ddd, J=9.0, 4.0, 2.6 Hz, 1H), 7.68 (dd, J=10.2, 9.0 Hz, 1H), 7.39 (t, J=72.8 Hz, 1H), 6.33-6.26 (m, 1H), 5.45 (s, 2H), 3.97-3.83 (m, 2H), 3.74-3.59 (m, 2H).

Example 167: 2-((1-(3-(Difluoromethoxy)-4-fluorophenyl)-1H-1,2,3-triazol-4-yl)methoxy)-5-fluoropyrimidin-4-amine

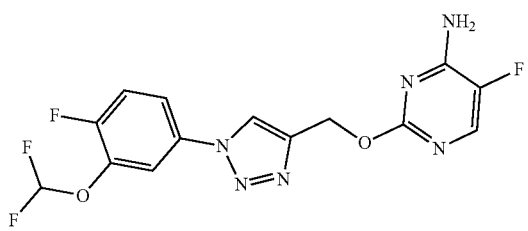 [SMILES: Nc1nc(OCc2cn(-c3ccc(F)c(OC(F)F)c3)nn2)ncc1F]

Step A: 4-Chloro-5-fluoro-2-(methylsulfonyl)pyrimidine mCPBA (77%, 2.5 g, 11.2 mmol) was slowly added to a mixture of 4-chloro-5-fluoro-2-(methylthio)pyrimidine (1.0 g, 5.6 mmol) in DCM (25 mL) at 0° C. After 16 hours, the reaction mixture was quenched with a saturated aqueous solution of NaHCO$_3$ (60 mL). The mixture was extracted with DCM (3×80 mL). The combined organics were dried (MgSO$_4$), filtered, and concentrated under vacuum. Purification (FCC, SiO$_2$, 0-99% EtOAc in hexanes) afforded the title compound (1.2 g, 98%). MS (ESI): mass calcd. for C$_5$H$_4$ClFN$_2$O$_2$S, 210.0; m/z found, 211.1 [M+H]$^+$. $^1$H NMR (400 MHz, DMSO-d$_6$) δ 9.26 (d, J=1.2 Hz, 1H), 3.43 (s, 3H).

Step B. 4-Chloro-2-((1-(3-(difluoromethoxy)-4-fluorophenyl)-1H-1,2,3-triazol-4-yl)methoxy)-5-fluoropyrimidine Under a nitrogen atmosphere was added ((1-(3-(difluoromethoxy)-4-fluorophenyl)-1H-1,2,3-triazol-4-yl)methanol (Intermediate 6, 50 mg, 0.2 mmol) to a suspension of NaH (60% dispersion in mineral oil, 15 mg, 0.4 mmol) in THF (2.7 mL). After 5 minutes, 4-chloro-5-fluoro-2-(methylsulfonyl)pyrimidine (49 mg, 0.2 mmol) was added at 0° C. Upon completion, brine (20 mL) was added and the mixture was extracted with EtOAc (3×30 mL). The combined organics were dried (MgSO$_4$), filtered, and concentrated under vacuum. MS (ESI): mass calcd. for C$_{14}$H$_8$ClF$_4$N$_5$O$_2$, 389.0; m/z found, 390.1 [M+H]$^+$.

Step C. 2-((1-(3-(Difluoromethoxy)-4-fluorophenyl)-1H-1,2,3-triazol-4-yl)methoxy)-5-fluoropyrimidin-4-amine A microwave vial was charged with 4-chloro-2-((1-(3-(difluoromethoxy)-4-fluorophenyl)-1H-1,2,3-triazol-4-yl)methoxy)-5-fluoropyrimidine (75 mg, 0.2 mmol), ammonia (2M in MeOH, 1.9 mL, 3.9 mmol) and THF (1.9 mL). The vial was heated to 100° C. under microwave irradiation for 8 hours. The reaction mixture was concentrated under vacuum and the crude material was purified using reversed phase HPLC (Agilent, H$_2$O/NH$_4$OH:MeCN gradient) to afford the title compound (14.9 mg, 21%). MS (ESI): mass calcd. for C$_{14}$H$_{10}$F$_4$N$_6$O$_2$, 370.1; m/z found, 371.1 [M+H]$^+$. $^1$H NMR (500 MHz, DMSO-d$_6$ δ 8.91 (s, 1H), 8.01-7.96 (m, 2H), 7.86 (ddd, J=9.0, 4.0, 2.7 Hz, 1H), 7.68 (dd, J=10.2, 9.0 Hz, 1H), 7.55-7.23 (m, 3H), 5.35 (s, 2H).

Example 168: 2-[[1-[3-(Difluoromethoxy)-4-fluorophenyl]triazol-4-yl]methoxy]-4-pyrrolidin-1-yl-pyrimidine. as the trifluoroacetic acid salt

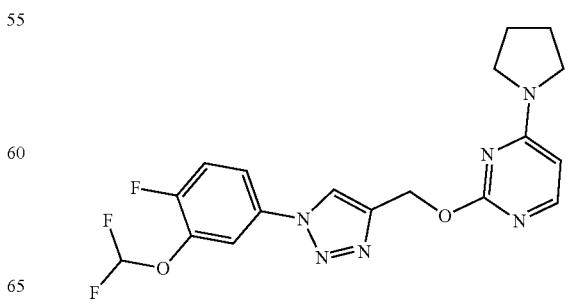

The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-(pyrrolidin-1-yl)pyrimidine. MS (ESI): mass calcd. for $C_{18}H_{17}F_3N_6O_2$, 406.1; m/z found, 406.9 [M+H]$^+$. $^1$H NMR (400 MHz, DMSO-d$_6$) δ 8.97 (s, 1H), 8.07 (d, J=6.7 Hz, 1H), 8.00 (dd, J=6.9, 2.7 Hz, 1H), 7.90-7.85 (m, 1H), 7.70 (dd, J=10.2, 9.0 Hz, 1H), 7.40 (t, J=72.7 Hz, 1H), 6.44 (d, J=6.7 Hz, 1H), 5.62 (s, 2H), 3.72-3.63 (m, 2H), 2.08-1.90 (m, 4H).

Example 169: 2-[[1-[3-(Difluoromethoxy)-4-fluoro-phenyl]triazol-4-yl]methoxy]-4-(1-piperidyl)pyrimidine

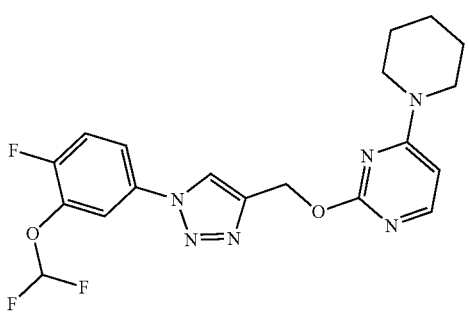 [SMILES: Fc1ccc(-n2cc(COc3nccc(N4CCCCC4)n3)nn2)cc1OC(F)F]

The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-(piperidin-1-yl)pyrimidine. MS (ESI): mass calcd. for $C_{19}H_{19}F_3N_6O_2$, 420.2; m/z found, 421.0 [M+H]$^+$. $^1$H NMR (400 MHz, DMSO-d$_6$) δ 8.90 (s, 1H), 8.03-7.96 (m, 2H), 7.87 (ddd, J=9.0, 4.0, 2.7 Hz, 1H), 7.68 (dd, J=10.2, 9.0 Hz, 1H), 7.39 (t, J=72.8 Hz, 1H), 6.49 (d, J=6.2 Hz, 1H), 5.41 (s, 2H), 3.67-3.53 (m, 4H), 1.70-1.57 (m, 2H), 1.54-1.42 (m, 4H).

Example 170: 4-[2-[[1-[3-(Difluoromethoxy)-4-fluoro-phenyl]triazol-4-yl]methoxy]pyrimidin-4-yl]morpholine

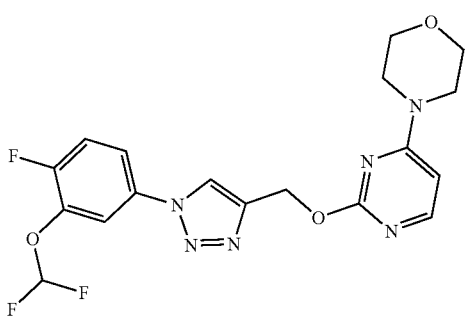 [SMILES: Fc1ccc(-n2cc(COc3nccc(N4CCOCC4)n3)nn2)cc1OC(F)F]

The title compound was prepared in a manner analogous to Example 155 using (1-(3-(difluoromethoxy)-4-fluorophenyl)-1H-1,2,3-triazol-4-yl)methanol (Intermediate 6) and 4-(2-chloropyrimidin-4-yl) morpholine. MS (ESI): mass calcd. for $C_{18}H_{17}F_3N_6O_3$, 422.1; m/z found, 422.9 [M+H]$^+$. $^1$H NMR (400 MHz, DMSO-d$_6$) δ 8.91 (s, 1H), 8.07 (d, J=6.1 Hz, 1H), 8.00 (dd, J=6.9, 2.7 Hz, 1H), 7.87 (ddd, J=9.0, 4.0, 2.6 Hz, 1H), 7.68 (dd, J=10.2, 9.0 Hz, 1H), 7.39 (t, J=72.8 Hz, 1H), 6.52 (d, J=6.1 Hz, 1H), 5.43 (s, 2H), 3.69-3.54 (m, 8H).

Example 171: 2-[[1-[4-Chloro-3-(difluoromethoxy)phenyl]triazol-4-yl]methoxy]-N-methyl-pyrimidin-4-amine

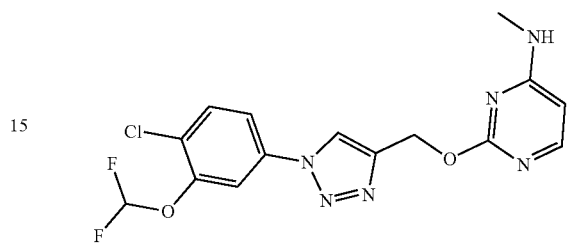

The title compound was prepared in a manner analogous to Example 163, Steps B-C, using (1-(4-chloro-3-(difluoromethoxy)phenyl)-1H-1,2,3-triazol-4-yl)methanol (Intermediate 1) and tert-butyl (2-chloropyrimidin-4-yl)(methyl)carbamate (Intermediate 55). MS (ESI): mass calcd. for $C_{15}H_{13}ClF_2N_6O_2$, 382.1; m/z found, 383.1 [M+H]$^+$. $^1$H NMR (500 MHz, DMSO-d$_6$) δ 8.96 (s, 1H), 8.00-7.98 (m, 1H), 7.90-7.80 (m, 3H), 7.60-7.28 (m, 2H), 6.15 (d, J=5.9 Hz, 1H), 5.41 (s, 2H), 2.82-2.73 (m, 3H).

Example 172: 2-[[1-[3-(Difluoromethyl)phenyl]-5-methyl-triazol-4-yl]methoxy]-5-methoxy-pyrimidine

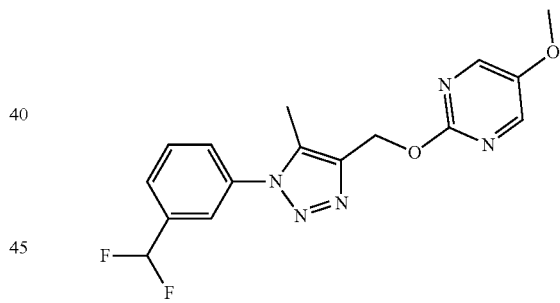

Step A. 1-Azido-3-(difluoromethyl)benzene

Method A

Two solutions, 3-(difluoromethyl)aniline (1.0 g, 7.0 mmol) in 6 N HCl (6N HCl in iPrOH, 4.4 mL) and iPrOH (5 mL), and sodium nitrite (0.58 g, 8.4 mmol) in H$_2$O (4 mL) were flowed through a LTF-MS mixer (0.2 mL) at 1 mL/min and 0.4 mL/min, respectively. The outcome was mixed with sodium azide (0.55 g, 8.4 mmol) in H$_2$O (4 mL) at 0.4 mL/min in a T-piece and flowed through a LTF-VS mixer (1 mL). The mixture was collected over K$_2$CO$_3$ (4.8 g, 35 mmol) in iPrOH (140 mL). The reaction mixture was extracted into ether and concentrated under reduced pressure. The crude residue was carried forward without purification.

Method B.

To 3-(difluoromethyl)aniline (1.47 g, 10.3 mmol) in a round bottom flask was slowly added H$_2$SO$_4$ (2 mL, 37.5 mmol) followed by TFA (10 mL, 130.7 mmol). The reaction was cooled to 0° C., then a solution of NaNO₂ (1 g, 15 mmol) in H₂O (10 mL) was added drop-wise with stirring. The reaction was stirred at 0° C. for 40 minutes, then a solution of sodium azide (1.26 g, 19.4 mmol) in H₂O (10 mL) was added drop-wise. The reaction was removed from the ice bath and stirred at rt for 2 h. The mixture was diluted with diethyl ether and basified to pH 12 with a solution of LiOH (4 N). The layers were separated and the aqueous layer was extracted with diethyl ether (3×). The combined organic layers were dried (Na₂SO₄) and concentrated under reduced pressure. The crude residue was carried forward without purification.

Step B. Ethyl 1-(3-(difluoromethyl)phenyl)-5-methyl-1H-1,2,3-triazole-4-carboxylate To a solution of 1-azido-3-(difluoromethyl)benzene (0.59 g, 3.5 mmol) in DMSO (3.5 mL) was added ethyl acetoacetate (0.7 mL, 5.2 mmol) followed by dimethylamine (0.02 mL, 0.17 mmol). The vial was purged with N₂ then sealed and stirred at 70° C. overnight. The reaction was cooled to rt then diluted with EtOAc and H₂O. The layers were separated and the aqueous layer was extracted with EtOAc (3×). The combined organic layers were washed with H₂O (×5), then brine (×3), then dried (Na₂SO₄) and concentrated under reduced pressure. Purification (FCC, SiO₂, EtOAc/hexanes 0-50%) afforded the title compound as a pale yellow oil that solidified upon standing (67%). MS (ESI): mass calcd. for $C_{13}H_{13}F_2N_3O_2$, 281.1; m/z found, 282.0 [M+H]⁺.

Step C. (1-(3-(Difluoromethyl)phenyl)-5-methyl-1H-1,2,3-triazol-4-yl)methanol To ethyl 1-(3-(difluoromethyl)phenyl)-5-methyl-1H-1,2,3-triazole-4-carboxylate (395 mg, 1.4 mmol) stirring in THF at −78° C. was added LAH (1 M in THF, 3.5 mL, 3.5 mmol) drop-wise. The reaction was stirred at −78° C. for 2 h, then warmed to rt and stirred for 1 h. The reaction was cooled to 0° C. and quenched slowly with EtOAc, then the mixture was warmed to rt and diluted with a saturated solution of L(+)-tartaric acid potassium sodium salt (Rochelle salt). The mixture was stirred vigorously for 1 h, then the layers were separated and the aqueous layer was extracted with EtOAc (3×). The combined organic layers were dried (Na₂SO₄) then concentrated under reduced pressure to afford a yellow oil that was used without purification (296 mg, 88%). MS (ESI) mass calcd. for $C_{11}H_{11}F_2N_3O$, 239.1; m/z found 240.0 [M+H]⁺. ¹H NMR (500 MHz, CDCl₃) δ 7.69-7.63 (m, 3H), 7.63-7.57 (m, 1H), 6.73 (t, J=56.1 Hz, 1H), 4.83 (s, 2H), 2.40 (s, 3H).

Step D. 2-[[1-[3-(Difluoromethyl)phenyl]-5-methyl-triazol-4-yl]methoxy]-5-methoxy-pyrimidine To (1-(3-(difluoromethyl)phenyl)-5-methyl-1H-1,2,3-triazol-4-yl)methanol (45 mg, 0.19 mmol) stirring in THF (1 mL) was added NaH (60% dispersion in mineral oil, 22.6 mg, 0.56 mmol) and the reaction was stirred for 5 min. 2-Chloro-5-methoxypyrimidine was then added and the reaction was stirred at rt for 1 h. The reaction was quenched with H₂O, then diluted with EtOAc and H₂O. The layers were separated and the aqueous layer was extracted with EtOAc (3×). The combined organic layers were washed with H₂O (1×), brine (IX), then dried (Na₂SO₄) and concentrated under reduced pressure. Purification (FCC, SiO₂, EtOAc/hexanes 0-60%) afforded the title compound (41 mg, 62%). MS (ESI): mass calcd. for $C_{16}H_{15}F_2N_5O_2$, 347.1; m/z found, 348.0 [M+H]⁺. ¹H NMR (400 MHz, CDCl₃) δ 8.24 (s, 2H), 7.71-7.56 (m, 4H), 6.73 (t, J=56.1 Hz, 1H), 5.56 (s, 2H), 3.88 (s, 3H), 2.45 (s, 3H).

Example 173: 2-[[1-[3-(1,1-Difluoroethyl)-4-fluoro-phenyl]-5-methyl-triazol-4-yl]methoxy]-5-methyl-pyrimidine

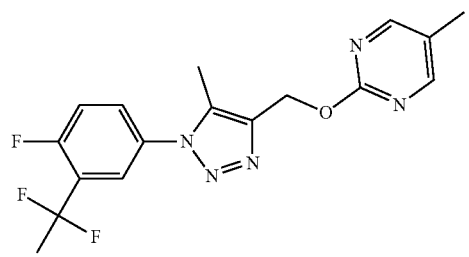 [SMILES: Cc1cnc(OCc2nnn(-c3ccc(F)c(C(C)(F)F)c3)c2C)nc1]

Step A. 2-(1,1-Difluoroethyl)-1-fluoro-4-nitrobenzene

To a solution of 1-(2-fluoro-5-nitrophenyl)ethanone (3.0 g, 16.5 mmol) stirring in DCM (50 mL) at −78° C. was added DAST (10 mL, 75.7 mmol). The mixture was warmed to rt and stirred for 5 days. The reaction was poured over ice, then the ice was allowed to melt and the layers were separated. The aqueous layer was extracted with DCM (2×), then the combined organic layers were washed with brine, dried (Na₂SO₄), filtered, and concentrated under reduced pressure. Purification (FCC, SiO₂, EtOAc/hexanes 0-20%) afforded the title compound (2.73 g, 81%). ¹H NMR (500 MHz, CDCl₃) δ 8.49 (dd, J=6.3, 2.8 Hz, 1H), 8.35 (dt, J=8.9, 3.5 Hz, 1H), 7.31 (t, J=9.3 Hz, 1H), 2.04 (t, J=18.5 Hz, 3H).

Step B. 3-(1,1-Difluoroethyl)-4-fluoroaniline

To 2-(1,1-difluoroethyl)-1-fluoro-4-nitrobenzene (1 g, 4.86 mmol) dissolved in EtOH (30 mL) was added 10% Pd/C (0.52 g, 0.49 mmol). The reaction was placed under an atmosphere of hydrogen and stirred at rt overnight. The reaction mixture was filtered through a pad of Celite®, rinsing with EtOAc, and the filtrate was concentrated under vacuum to afford the title compound that was used without purification (863 mg, 101%). MS (ESI): mass calcd. for $C_8H_8F_3N$, 175.1; m/z found, 176.1 [M+H]⁺.

Step C. 4-Azido-2-(1,1-difluoroethyl)-1-fluorobenzene

To 3-(1,1-difluoroethyl)-4-fluoroaniline (854 mg, 4.9 mmol) in a round bottom flask was slowly added H₂SO₄ (1 mL, 18.8 mmol) followed by TFA (5 mL, 65.3 mmol). The reaction was cooled to 0° C., then a solution of NaNO₂ (482 mg, 7 mmol) in H₂O (3 mL) was added drop-wise with stirring. The reaction was stirred at 0° C. for 15 minutes, then a solution of sodium azide (594.3 mg, 9 mmol) in H₂O (6 mL) was added drop-wise. The reaction was removed from the ice bath and stirred at rt for 30 min. The mixture was diluted with diethyl ether and basified to pH 12 with a solution of NaOH (3 N). The layers were separated and the aqueous layer was extracted with diethyl ether (3×). The combined organic layers were dried (Na₂SO₄) and concentrated under reduced pressure. The crude residue was carried forward without purification.

Step D. Ethyl 1-(3-(1,1-difluoroethyl)-4-fluorophenyl)-5-methyl-1H-1,2,3-triazole-4-carboxylate To a solution of 4-azido-2-(1,1-difluoroethyl)-1-fluorobenzene (0.981 g, 4.9 mmol) in DMSO (5 mL) was added ethyl acetoacetate (0.9 mL, 7.3 mmol) followed by dimethylamine (0.025 mL, 0.24 mmol). The vial was purged with N₂ then sealed and stirred at 70° C. for 2 days. The reaction was cooled to rt then diluted with EtOAc and H₂O. The layers were separated and the aqueous layer was extracted with EtOAc (3×). The combined organic layers were washed with H₂O (5×), then brine (3×), then dried (Na₂SO₄) and concentrated under reduced pressure. Purification (FCC, SiO₂, EtOAc/hexanes 0-50%) afforded the title compound as a yellow oil that solidified upon standing (1.32 g, 87%). MS (ESI): mass calcd. for $C_{14}H_{14}F_3N_3O_2$, 313.1; m/z found, 314.1 [M+H]⁺.

Step E. (1-(3-(1,1-difluoroethyl)-4-fluorophenyl)-5-methyl-1H-1,2,3-triazol-4-yl)methanol To ethyl 1-(3-(1,1-difluoroethyl)-4-fluorophenyl)-5-methyl-1H-1,2,3-triazole-4-carboxylate (537 mg, 1.7 mmol) stirring in THF at −78° C. was added LAH (1 M in THF, 4.5 mL, 4.5 mmol) drop-wise. The reaction was stirred at −78° C. for 1 h, then warmed to rt and stirred for 3 h. The reaction was cooled to 0° C. and quenched slowly with EtOAc, then the mixture was warmed to rt and diluted with a saturated solution of potassium sodium tartrate tetrahydrate. The mixture was stirred vigorously for 10 min, then the layers were separated and the aqueous layer was extracted with EtOAc. The combined organic layers were washed with brine, then dried (Na₂SO₄) and concentrated under reduced pressure to afford a yellow oil that was used without purification. MS (ESI) mass calcd. for $C_{12}H_{12}F_3N_3O$, 271.1; m/z found 272.1 [M+H]⁺

Step F. 2-[[1-[3-(1,1-difluoroethyl)-4-fluoro-phenyl]-5-methyl-triazol-4-yl]methoxy]-5-methyl-pyrimidine To (1-(3-(1,1-difluoroethyl)-4-fluorophenyl)-5-methyl-1H-1,2,3-triazol-4-yl)methanol (25 mg, 0.09 mmol) stirring in THF (0.8 mL) was added NaH (60% dispersion in mineral oil, 12.5 mg, 0.31 mmol) and the reaction was stirred for 5 min. 2-Chloro-5-methylpyrimidine was then added and the reaction was stirred at rt overnight. The reaction was quenched with H₂O, then concentrated under a stream of air. Purification (FCC, SiO₂, EtOAc/hexanes 0-80%) afforded the title compound (20 mg, 60%). MS (ESI): mass calcd. for $C_{17}H_{16}F_3N_5O$, 363.1; m/z found, 364.0 [M+H]⁺. ¹H NMR (500 MHz, CDCl₃) δ 8.37 (s, 2H), 7.66 (dd, J=6.3, 2.6 Hz, 1H), 7.53 (ddd, J=8.5, 4.1, 2.6 Hz, 1H), 7.32 (t, J=9.4 Hz, 1H), 5.56 (s, 2H), 2.42 (s, 3H), 2.25 (s, 3H), 2.11-1.96 (m, 3H).

Example 174: 5-Methyl-2-[[1-(6-methyl-2-pyridyl)triazol-4-yl]methoxy]pyrimidine

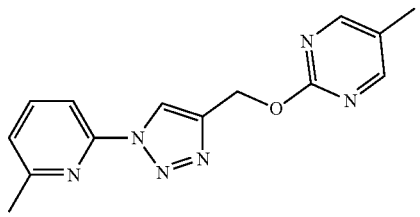 [SMILES: Cc1cnc(OCc2cn(-c3cccc(C)n3)nn2)nc1]

Step A. 5-Methyltetrazolo[1,5-a]pyridine

2-Methylpyridine N-oxide (400 mg, 3.7 mmol), diphenylphosphoryl azide (4 mL, 18.6 mmol), and pyridine (0.6 mL, 7.4 mmol) were combined and purged with nitrogen, sealed, and stirred at 120° C. overnight. The mixture was cooled to rt, then loaded directly onto a silica gel column. Purification (FCC, SiO₂, 10% 2N NH₃ in MeOH/DCM 0-5%) afforded the title compound as a white solid (257 mg, 52%). MS (ESI): mass calcd. for $C_6H_6N_4$, 134.1; m/z found, 135.1 [M+H]⁺.

Step B. (1-(6-Methylpyridin-2-yl-1H-1,2,3-triazol-4-yl)methanol

To a solution of 5-methyltetrazolo[1,5-a]pyridine (257 mg, 1.9 mmol) and copper (I) trifluoromethanesulfonate benzene complex (96.4 mg, 0.19 mmol) in toluene (7.7 mL) was added propargyl alcohol (0.13 mL, 2.3 mmol). The vial was purged with nitrogen, then sealed and stirred at 100° C. overnight. The mixture was diluted with DCM, washed with water (×1), brine (×1), then dried (Na₂SO₄) and concentrated under reduced pressure to afford a pale orange solid (191 mg, 53%). The crude product was used without purification. MS (ESI): mass calcd. for $CH_{10}N_4O$, 190.1; m/z found, 191.1 [M+H]⁺. ¹H NMR (500 MHz, CD₃OD) δ 8.68 (s, 1H), 7.96-7.88 (m, 2H), 7.37-7.33 (m, 1H), 4.77 (d, J=0.7 Hz, 2H), 2.59 (s, 3H).

Step C. 5-Methyl-2-[[1-(6-methyl-2-pyridyl)triazol-4-yl]methoxy]pyrimidine

The title compound was prepared in a manner analgous to Example 1 using (1-(6-methylpyridin-2-yl)-1H-1,2,3-triazol-4-yl)methanol and 2-chloro-5-methylpyrimidine, using THF instead of DMF. MS (ESI): mass calcd. for $C_{14}H_{14}N_6O$, 282.1; m/z found, 283.0 [M+H]⁺. ¹H NMR (400 MHz, CDCl₃) b 8.71 (s, 1H), 8.37 (d, J=0.8 Hz, 2H), 7.96 (d, J=8.1 Hz, 1H), 7.76 (t, J=7.8 Hz, 1H), 7.17 (d, J=7.6 Hz, 1H), 5.63 (d, J=0.7 Hz, 2H), 2.57 (s, 3H), 2.24 (s, 3H).

Example 175: 5-Methyl-2-[[1-(2-methyl-4-pyridyl)triazol-4-yl]methoxy]pyrimidine

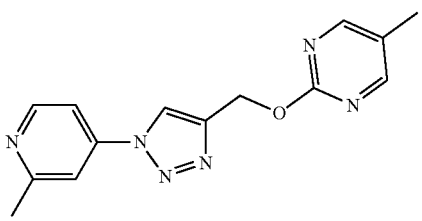 [SMILES: Cc1cnc(OCc2cn(-c3ccnc(C)c3)nn2)nc1]

Step A. 4-Azido-2-methylpyridine

To 4-chloro-2-picoline hydrochloride (600 mg, 3.7 mmol) stirring in H$_2$O (2.5 mL) was added a solution of NaOH (1 M in H$_2$O) until the pH measured 7. Sodium azide (476 mg, 7.3 mmol) was then added and the reaction was heated at reflux overnight. The reaction was cooled to rt then extracted with ether (3×). The combined organic layers were dried (Na$_2$SO$_4$) and concentrated under reduced pressure to afford a colorless oil that was used without purification.

Step B. (1-(2-Methylpyridin-4-yl)-1H-1,2,3-triazol-4-yl)methanol

4-Azido-2-methylpyridine (491 mg, 3.7 mmol) was dissolved in a mixture of tBuOH (4.5 mL) and H$_2$O (4.5 mL). Propargyl alcohol (0.26 mL, 4.4 mmol) was then added, followed by copper (II) sulfate pentahydrate (91 mg, 0.37 mmol) and L-sodium ascorbate (72.5 mg, 0.37 mmol). The reaction was stirred at rt overnight, then diluted with NH$_4$OH (28% in H$_2$O) and H$_2$O. The layers were separated and the aqueous layer was extracted with EtOAc (6×) and DCM (3×). The combined organic layers were washed with brine, dried (Na$_2$SO$_4$), and concentrated under reduced pressure to afford the title compound that was used without purification (356 mg, 51%). MS (ESI): mass calcd. for C$_9$H$_{10}$N$_4$O, 190.1; m/z found, 191.1 [M+H]$^+$. $^1$H NMR (400 MHz, CD$_3$OD) δ 8.66 (s, 1H), 8.61 (d, J=5.7 Hz, 1H), 7.93-7.90 (m, 1H), 7.83 (dd, J=5.8, 2.1 Hz, 1H), 4.80 (s, 2H), 2.67 (s, 3H).

Step C. 5-Methyl-2-[[1-(2-methyl-4-pyridyl)triazol-4-yl]methoxy]pyrimidine

The title compound was prepared in a manner analgous to Example 1 using (1-(2-methylpyridin-4-yl)-1H-1,2,3-triazol-4-yl)methanol and 2-chloro-5-methylpyrimidine, using THF instead of DMF. MS (ESI): mass calcd. for C$_{14}$H$_{14}$N$_6$O, 282.1; m/z found, 283.0 [M+H]$^+$. $^1$H NMR (400 MHz, CDCl$_3$) δ 8.65 (d, J=5.6 Hz, 1H), 8.38 (d, J=0.8 Hz, 2H), 8.21 (s, 1H), 7.61 (d, J=2.1 Hz, 1H), 7.49 (ddd, J=5.4, 2.1, 0.7 Hz, 1H), 5.64 (d, J=0.7 Hz, 2H), 2.67 (s, 3H), 2.26 (s, 3H).

Example 176: 5-Methyl-2-[[1-(5-methyl-3-pyridyl)triazol-4-yl]methoxy]pyrimidine

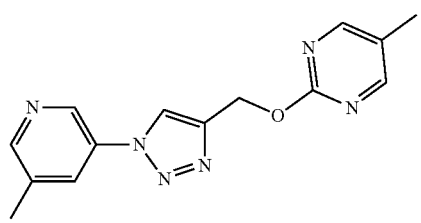 [SMILES: Cc1cnc(OCc2cn(-c3cncc(C)c3)nn2)nc1]

Step A. 3-Azido-5-methylpyridine

To 3-amino-5-methylpyridine (483 mg, 4.5 mmol) in a round bottom flask was slowly added H$_2$SO$_4$ (0.9 mL, 17.2 mmol) followed by TFA (4.6 mL, 59.9 mmol). The reaction was cooled to 0° C., then a solution of NaNO$_2$ (442 mg, 6.4 mmol) in H$_2$O (3 mL) was added drop-wise with stirring. The reaction was stirred at 0° C. for 15 minutes, then a solution of sodium azide (544 mg, 8.4 mmol) in H$_2$O (3 mL) was added drop-wise. The reaction was removed from the ice bath and stirred at rt for 30 min. The mixture was diluted with diethyl ether and basified to pH 12 with a solution of NaOH (3 N). The layers were separated and the aqueous layer was extracted with diethyl ether (3×). The combined organic layers were dried (Na$_2$SO$_4$) and concentrated under reduced pressure. The crude residue was carried forward without purification

Step B. (1-(5-Methylpyridin-3-yl)-1H-1,2,3-triazol-4-yl)methanol

To 3-azido-5-methylpyridine (599 mg, 4.5 mmol) dissolved in tBuOH (6 mL) and H$_2$O (6 mL) was added propargyl alcohol (0.3 mL, 5.2 mmol) followed by copper (II) sulfate pentahydrate (109 mg, 0.44 mmol) and L-sodium ascorbate (90 mg, 0.45 mmol). The reaction was stirred at rt overnight. In the morning LCMS indicated no conversion. The mixture was basified to pH=8 with K$_2$CO$_3$ (approx. 200 mg, then stirred at rt for an additional 5 h. The reaction was diluted with EtOAc and NH$_4$OH (28% in H$_2$O), then the layers were separated and the aqueous layer was extracted with EtOAc (×3). The combined organic layers were dried (Na$_2$SO$_4$) and concentrated under reduced pressure. Purification (FCC, SiO$_2$, MeOH/DCM 0-5%) afforded the title compound (57.5 mg, 6.7%). MS (ESI): mass calcd. for C$_9$H$_{10}$N$_4$O, 190.1; m/z found, 191.1 [M+H]$^+$.

Step C. 5-Methyl-2-[[1-(5-methyl-3-pyridyl)triazol-4-yl]methoxy]pyrimidine

The title compound was prepared in a manner analgous to Example 1 using (1-(5-methylpyridin-3-yl)-1H-1,2,3-triazol-4-yl) and 2-chloro-5-methylpyrimidine using THF instead of DMF. MS (ESI): mass calcd. for C$_{14}$H$_{14}$N$_6$O, 282.1; m/z found, 283.0 [M+H]$^+$. $^1$H NMR (500 MHz, CDCl$_3$) δ 8.77 (d, J=2.4 Hz, 1H), 8.53 (d, J=1.8 Hz, 1H), 8.38 (s, 2H), 8.19-8.13 (m, 1H), 7.97-7.94 (m, 1H), 5.65 (s, 2H), 2.47 (s, 3H), 2.26 (s, 3H).

Example 177: 2-[[1-(2-Bromo-4-pyridyl)triazol-4-yl]methoxy]-5-methyl-pyrimidine

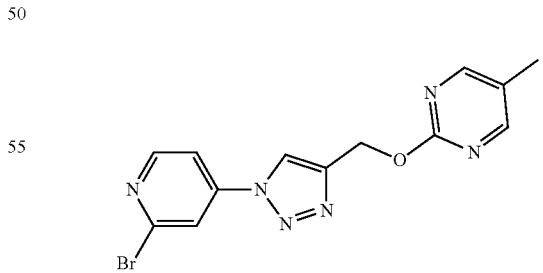

The title compound was prepared in a manner analogous to Example 176, using 2-bromopyridin-4-amine in Step A. MS (ESI): mass calcd. for C$_{13}$H$_{11}$BrN$_6$O, 346.0; m/z found, 347.0 [M+H]$^+$. $^1$H NMR (400 MHz, CD$_3$OD) δ 8.87 (s, 1H), 8.53 (d, J=5.5 Hz, 1H), 8.46 (s, 2H), 8.24 (d, J=2.0 Hz, 1H), 8.01 (dd, J=5.6, 1.9 Hz, 1H), 5.60 (s, 2H), 2.27 (s, 3H)

Example 178: 2-[2-[[1-(3-Cyclobutyl-4-fluoro-phenyl)triazol-4-yl]methoxy]pyrimidin-5-yl]propan-2-ol

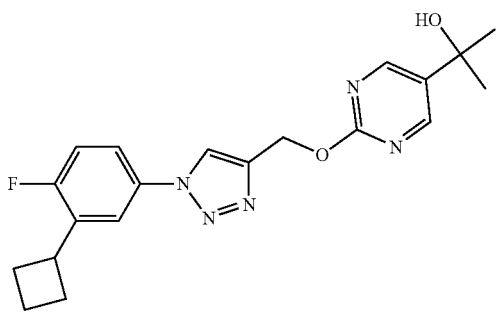 [SMILES: CC(C)(O)c1cnc(OCc2cn(-c3ccc(F)c(C4CCC4)c3)nn2)nc1]

Step A. 2-(2-((1-(3-Bromo-4-fluorophenyl)-1H-1,2,3-triazol-4-yl)methoxy)pyrimidin-5-yl)propan-2-ol The title compound was prepared in a manner analogous to Example 1 using (1-(3-bromo-4-fluorophenyl)-1H-1,2,3-triazol-4-yl)methanol (Intermediate 14) and 2-(2-chloropyrimidin-5-yl)propan-2-ol, using THF instead of DMF. MS (ESI): mass calcd. for $C_{16}H_{15}BrN_5O_2$, 407.0; m/z found, 408.0 [M+H]$^+$. $^1$H NMR (500 MHz, CDCl$_3$) δ 8.67 (s, 2H), 8.09 (s, 1H), 7.99 (dd, J=5.8, 2.7 Hz, 1H), 7.67 (ddd, J=8.8, 4.0, 2.7 Hz, 1H), 7.30-7.26 (m, 2H), 5.65 (d, J=0.8 Hz, 2H), 1.63 (s, 6H).

Step B. 2-[2-[[1-(3-Cyclobutyl-4-fluoro-phenyl)triazol-4-yl]methoxy]pyrimidin-5-yl]propan-2-ol To a solution of 2-(2-((1-(3-bromo-4-fluorophenyl)-1H-1,2,3-triazol-4-yl)methoxy)pyrimidin-5-yl)propan-2-ol (30 mg, 0.07 mmol) in THF (1 mL) was added cyclobutylzinc bromide (0.5 M in THF, 0.3 mL, 0.15 mmol) and Pd(t-Bu$_3$P)$_2$ (1.9 mg, 0.004 mmol). The mixture was stirred at 50° C. overnight. The mixture was purified (FCC, SiO$_2$, MeOH/DCM 0-10%), however the product contained impurities. The compound was re-purified by basic HPLC (Gilson, waters Xbridge 50×150 mm, 5-95% MeCN/20 mM NH$_4$OH over 15 min, 80 mL/min) to afford the title compound (15.8 mg, 56%). MS (ESI): mass calcd. for $C_{20}H_{22}FN_5O_2$, 383.2; m/z found, 384.1 [M+H]$^+$. $^1$H NMR (500 MHz, CDCl$_3$) δ 8.67 (s, 2H), 8.09 (s, 1H), 7.61 (ddd, J=6.3, 2.7, 0.8 Hz, 1H), 7.46 (dddd, J=8.8, 4.2, 2.7, 0.6 Hz, 1H), 7.11 (t, J=9.0 Hz, 1H), 5.65 (d, J=0.7 Hz, 2H), 3.83-3.72 (m, 1H), 2.46-2.36 (m, 2H), 2.28-2.16 (m, 2H), 2.14-2.03 (m, 1H), 1.96-1.87 (m, 1H), 1.62 (s, 6H).

Example 179: 2-[2-[[1-(4-Fluoro-3-isopropyl-phenyl)triazol-4-yl]methoxy]pyrimidin-5-yl]propan-2-ol

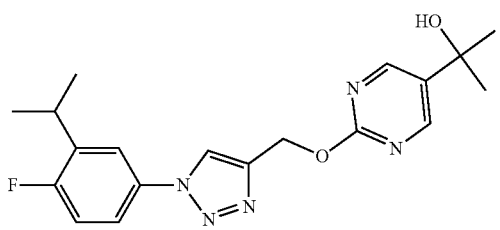 [SMILES: CC(C)c1cc(-n2cc(COc3ncc(C(C)(C)O)cn3)nn2)ccc1F]

The title compound was prepared in a manner analogous to Example 178 step B, using 2-(2-((1-(3-bromo-4-fluorophenyl)-1H-1,2,3-triazol-4-yl)methoxy)pyrimidin-5-yl)propan-2-ol (Example 178, product from Step A) and 2-propylzinc bromide. MS (ESI): mass calcd. for $C_{19}H_{22}FN_5O_2$, 371.2; m/z found, 372.0 [M+H]$^+$.

Example 180: 2-[2-[[1-(3-Cyclopropyl-4-fluoro-phenyl)triazol-4-yl]methoxy]pyrimidin-5-yl]propan-2-ol

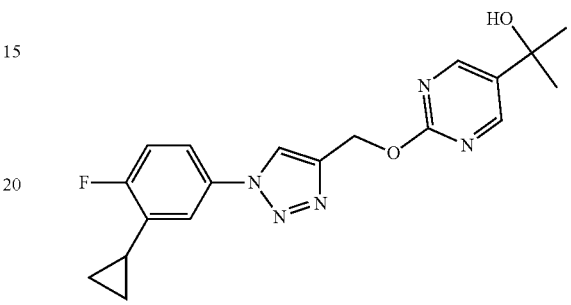

To a solution of 2-(2-((1-(3-bromo-4-fluorophenyl)-1H-1,2,3-triazol-4-yl)methoxy)pyrimidin-5-yl)propan-2-ol (Example 178, product from Step A, 42 mg, 0.1 mmol), K$_2$CO$_3$ (43 mg, 0.31 mmol), and RuPhos-Pd-G3 (4.3 mg, 0.005 mmol) was in 1,4-dioxane (1 mL) and water (0.2 mL) was added cyclopropylboronic acid (19.3 mg, 0.23 mmol). The vial was sealed and the reaction was stirred at 100° C. overnight. The reaction was diluted with water, capped with a septum, and left to stand at rt for 9 days. The mixture was then filtered through a plug of silica, rinsing with EtOAc and DCM, then concentrated under reduced pressure. The residue was re-dissolved in MeOH, filtered through a 0.45 μm syringe, and purified by preparatory HPLC (Gilson, waters Xbridge 50×150 mm, 5-95% MeCN/20 mM NH$_4$OH over 15 min, 80 mL/min). Fractions containing the pure product was frozen and lyophilized over 2 days to afford the title compound (8 mg, 21%). MS (ESI): mass calcd. for $C_{19}H_{20}FN_5O_2$, 369.2; m/z found, 370.0 [M+H]$^+$. $^1$H NMR (500 MHz, CDCl$_3$) δ 8.67 (s, 2H), 8.04 (s, 1H), 7.42 (ddd, J=8.8, 4.2, 2.8 Hz, 1H), 7.28-7.27 (m, 1H), 7.14 (t, J=9.1 Hz, 1H), 5.65 (d, J=0.7 Hz, 2H), 2.15 (ddd, J=13.7, 8.6, 5.2 Hz, 1H), 1.76 (s, 1H), 1.63 (s, 6H), 1.11-1.05 (m, 2H), 0.81 (dt, J=6.7, 4.8 Hz, 2H).

Example 181: 2-[2-[[1-(4-Fluoro-3-methyl-phenyl)triazol-4-yl]methoxy]pyrimidin-5-yl]propan-2-ol

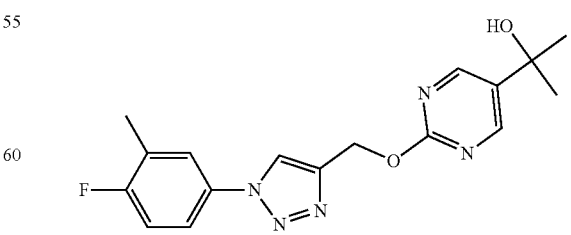

To a solution of 2-(2-((1-(3-bromo-4-fluorophenyl)-1H-1,2,3-triazol-4-yl)methoxy)pyrimidin-5-yl)propan-2-ol (Example 178, product from Step A, 42 mg, 0.1 mmol), K$_2$CO$_3$ (44 mg, 0.32 mmol), and RuPhos-Pd-G3 (4.3 mg, 0.005 mmol) in 1,4-dioxane (1.05 mL) was added trimethylboroxine (0.04 mL, 0.3 mmol). The vial was sealed and the reaction was stirred at 90° C. for 3 h. The mixture was then filtered through a plug of silica, rinsing with DCM, and concentrated under reduced pressure. Purification (FCC, SiO$_2$, MeOH/DCM 0-10%) afforded the title compound (20.9 mg, 59%). MS (ESI): mass calcd. for $C_{17}H_{18}FN_5O_2$, 343.1; m/z found, 344.1 [M+H]$^+$. $^1$H NMR (500 MHz, CDCl$_3$) δ 8.67 (s, 2H), 8.06 (s, 1H), 7.59 (ddd, J=6.5, 2.7, 0.9 Hz, 1H), 7.50-7.45 (m, 1H), 7.14 (t, J=8.8 Hz, 1H), 5.66 (d, J=0.7 Hz, 2H), 2.37 (d, J=2.0 Hz, 3H), 1.77 (s, 1H), 1.63 (s, 6H).

Example 182: 2-[2-[[1-(3-Ethyl-4-fluoro-phenyl)triazol-4-yl]methoxy]pyrimidin-5-yl]propan-2-ol

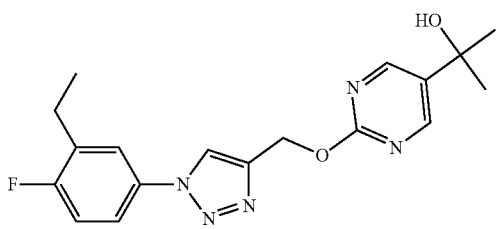 [SMILES: CCc1cc(-n2cc(COc3ncc(C(C)(C)O)cn3)nn2)ccc1F]

A solution of 2-(2-((1-(3-bromo-4-fluorophenyl)-1H-1,2,3-triazol-4-yl)methoxy)pyrimidin-5-yl)propan-2-ol (Example 178, product from Step A, 32 mg, 0.08 mmol), potassium ethyltrifluoroborate (10.7 mg, 0.08 mmol), potassium phosphate tribasic (50 mg, 0.24 mmol), RuPhos-Pd-G3 (3.3, 0.004 mmol), in 1,4-dioxane (0.5 mL), and water (0.2 mL) was purged with nitrogen, sealed and stirred at 90° C. for 2 days. The reaction was filtered through a plug of silica, rinsing with EtOAc, then evaporated under reduced pressure. The residue was dissolved in MeOH then purified by preparatory HPLC (Gilson, waters Xbridge 50×150 mm, 5-95% MeCN/20 mM NH$_4$OH over 15 min, 80 mL/min), and the fractions containing pure product were frozen and lyophilized over 2 days to afford the title compound (5.7 mg, 20%). MS (ESI): mass calcd. for $C_{18}H_{20}FN_5O_2$, 357.2; m/z found, 358.0 [M+H]$^+$. $^1$H NMR (500 MHz, CDCl$_3$) δ 8.67 (s, 2H), 8.07 (s, 1H), 7.59 (dd, J=6.4, 2.7 Hz, 1H), 7.48 (ddd, J=8.8, 4.2, 2.8 Hz, 1H), 7.14 (t, J=8.9 Hz, 1H), 5.65 (s, 2H), 2.75 (q, J=8.0 Hz, 2H), 1.62 (s, 6H), 1.28 (t, J=7.6 Hz, 3H).

Example 183: 5-Bromo-2-[[1-[3-(1,1-difluoroethyl)-4-fluoro-phenyl]triazol-4-yl]methoxy]pyrimidine

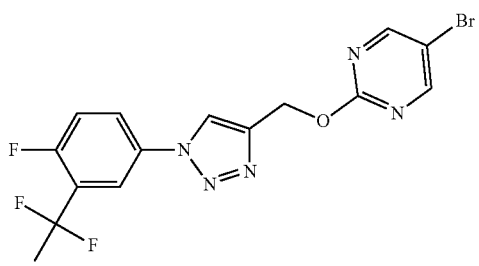 [SMILES: CC(F)(F)c1cc(-n2cc(COc3ncc(Br)cn3)nn2)ccc1F]

The title compound was prepared in a manner analogous to Example 153 using (1-(3-(1,1-difluoroethyl)-4-fluorophenyl)-1H-1,2,3-triazol-4-yl)methanol (Intermediate 11) and 5-bromo-2-chloropyrimidine, using ACN instead of DMF. MS (ESI): mass calcd. for $C_{15}H_{11}BrF_3N_5O$, 413.0; m/z found, 414.0 [M+H]$^+$. $^1$H NMR (500 MHz, CDCl$_3$) δ 8.66-8.54 (s, 2H), 8.15-8.09 (m, 1H), 7.93-7.87 (m, 1H), 7.85-7.78 (m, 1H), 7.37-7.28 (m, 1H), 5.69-5.58 (m, 2H), 2.14-1.94 (m, 3H).

Example 184: 2-[[1-[3-(1,1-Difluoroethyl)-4-fluoro-phenyl]triazol-4-yl]methoxy]-5-(1-methylpyrazol-3-yl)pyrimidine

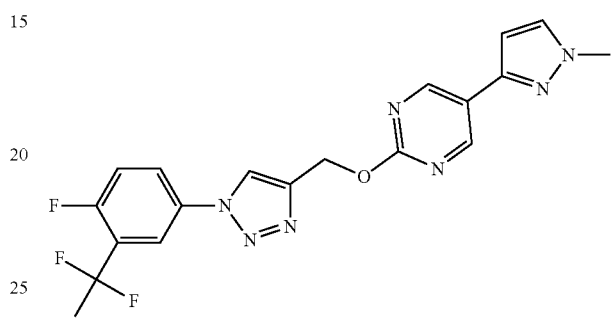

In a vial a suspension of 5-bromo-2-[[1-[3-(1,1-difluoroethyl)-4-fluoro-phenyl]triazol-4-yl]methoxy]pyrimidine (Example 183, 25 mg, 0.060 mmol), 1-methyl-3-(4,4,5,5-tetramethyl-1,3,2-dioxaborolan-2-yl)-1H-pyrazole (15.07 mg, 0.072 mmol), Na$_2$CO$_3$ (20 mg, 0.181 mmol) and PdCl$_2$(dppf) (4 mg, 0.006 mmol) in THF/H$_2$O (3 mL/0.3 mL) was capped and heated under microwave irradiation for 1.5 h at 100° C. The completed reaction was diluted with EtOAc and washed with water, brine, dried (Na$_2$SO$_4$), filtered, and concentrated under reduced pressure. Purification (FCC, SiO$_2$, eluting with 0-50% EtOAc in hexanes) afforded the title compound (13.8 mg, 55%). MS (ESI): mass calcd. for $C_{19}H_{16}F_3N_7O$, 415.1; m/z found, 416.1 [M+H]$^+$. $^1$H NMR (400 MHz, CDCl$_3$) δ 8.96-8.90 (s, 2H), 8.17-8.12 (s, 1H), 7.94-7.87 (m, 1H), 7.87-7.79 (m, 1H), 7.46-7.39 (d, J=2.3 Hz, 1H), 7.36-7.27 (t, J=9.4 Hz, 1H), 6.55-6.48 (d, J=2.3 Hz, 1H), 5.74-5.67 (d, J=0.7 Hz, 2H), 4.06-3.90 (s, 3H), 2.17-1.96 (m, 3H).

Example 185: 2-[[1-[3-(1,1-Difluoroethyl)-4-fluoro-phenyl]triazol-4-yl]methoxy]-5-(1H-pyrazol-4-yl)pyrimidine

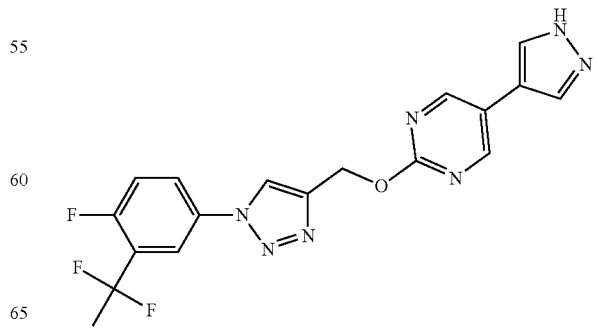

Step A: 2-((1-(3-(1,1-Difluoroethyl)-4-fluorophenyl)-1H-1,2,3-triazol-4-yl)methoxy)-5-(1-(tetrahydro-2H-pyran-2-yl)-1H-pyrazol-4-yl)pyrimidine The title compound was prepared in an manner analogous to Example 184 using 5-bromo-2-[[1-[3-(1,1-difluoroethyl)-4-fluoro-phenyl]triazol-4-yl]methoxy]pyrimidine (Example 183) and 1-(tetrahydro-2H-pyran-2-yl)-4-(4,4,5,5-tetramethyl-1,3,2-dioxaborolan-2-yl)-1H-pyrazole. MS (ESI): mass calcd. for $C_{23}H_{22}F_3N_7O_2$, 485.2; m/z found, 486.1 [M+H]$^+$.

Step B: 2-[[1-[3-(1,1-Difluoroethyl)-4-fluoro-phenyl]triazol-4-yl]methoxy]-5-(1H-pyrazol-4-yl)pyrimidine A solution of 2-((1-(3-(1,1-difluoroethyl)-4-fluorophenyl)-1H-1,2,3-triazol-4-yl)methoxy)-5-(1-(tetrahydro-2H-pyran-2-yl)-1H-pyrazol-4-yl)pyrimidine (27 mg, 0.06 mmol) in MeOH (3 mL) was charged with 3M HCl (3 mL) and stirred at rt for 4 hours. The completed reaction was concentrated under reduced pressure and re-suspended in DCM. The organics were washed with sat. aq. NaHCO$_3$, water, then brine. The organics were dried (Na$_2$SO$_4$), filtered, and concentrated under reduced pressure. Purification (FCC, SiO$_2$, 0-3% MeOH in DCM) afforded the title compound (15.3 mg, 32%). MS (ESI): mass calcd. for $C_{18}H_{14}F_3N_7O$, 401.1; m/z found, 402.0 [M+H]$^+$. $^1$H NMR (400 MHz, CDCl$_3$) δ 8.73-8.68 (s, 2H), 8.36-8.32 (s, 1H), 7.99-7.94 (m, 1H), 7.92-7.83 (m, 2H), 7.39-7.32 (t, J=9.4 Hz, 1H), 5.72-5.63 (s, 2H), 3.40-3.32 (s, 2H), 2.15-1.97 (t, J=18.6 Hz, 2H).

Example 186: 2-[[1-[3-(1,1-Difluoroethyl)-4-fluoro-phenyl]triazol-4-yl]methoxy]-4-(1H-pyrazol-4-yl)pyrimidine

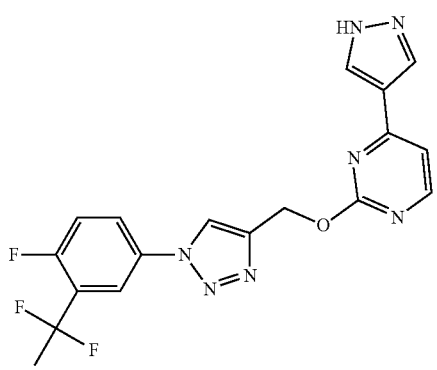 [SMILES: CC(F)(F)c1cc(-n2cc(COc3nccc(-c4cn[nH]c4)n3)nn2)ccc1F]

Step A: 2-Chloro-4-(1-(tetrahydro-2H-pyran-2-yl)-1H-pyrazol-4-yl)pyrimidine

To a flask with 2-chloro-4-(1H-pyrazol-4-yl)pyrimidine (284 mg, 1.6 mmol) and 3,4-dihydro-2H-pyran (661 mg, 7.9 mmol) in THF (9 mL) was charged with TFA (12 μL, 0.16 mmol) and stirred at 77° C. overnight. The completed reaction was diluted with EtOAc and washed with water, brine, dried (Na$_2$SO$_4$), filtered, and concentrated under reduced pressure. Purification (FCC, SiO$_2$, 0-60% EtOAc in hexanes) afforded the title compound (360 mg, 86%). MS (ESI): mass calcd. for $C_{12}H_{13}ClN_4O$, 264.1; m/z found, 265.0 [M+H]$^+$.

Step B: 2-((1-(3-(1,1-Difluoroethyl)-4-fluorophenyl)-1H-1,2,3-triazol-4-yl)methoxy)-4-(1-(tetrahydro-2H-pyran-2-yl)-1H-pyrazol-4-yl)pyrimidine The title compound was prepared in a manner analogous to Example 156 using (1-(3-(1,1-difluoroethyl)-4-fluorophenyl)-1H-1,2,3-triazol-4-yl)methanol (Intermediate 11) and 2-chloro-4-(1-(tetrahydro-2H-pyran-2-yl)-1H-pyrazol-4-yl)pyrimidine. MS (ESI): mass calcd. for $C_{23}H_{22}F_3N_7O_2$, 485.2; m/z found, 486.1 [M+H]$^+$.

Step C. 2-[[1-[3-(1,1-Difluoroethyl)-4-fluoro-phenyl]triazol-4-yl]methoxy]-4-(1H-pyrazol-4-yl)pyrimidine The title compound was prepared in a manner analogous to Example 185, step B, using 2-((1-(3-(1,1-Difluoroethyl)-4-fluorophenyl)-1H-1,2,3-triazol-4-yl)methoxy)-4-(1-(tetrahydro-2H-pyran-2-yl)-1H-pyrazol-4-yl)pyrimidine. MS (ESI): mass calcd. for $C_{18}H_{14}F_3N_7O$, 401.1; m/z found, 402.0 [M+H]$^+$. $^1$H NMR (500 MHz, CDCl$_3$) δ 8.52-8.44 (d, J=5.2 Hz, 1H), 8.25-8.17 (d, J=2.6 Hz, 3H), 7.96-7.87 (m, 1H), 7.89-7.80 (m, 1H), 7.36-7.26 (m, 1H), 7.18-7.10 (d, J=5.2 Hz, 1H), 5.76-5.64 (s, 2H), 5.34-5.25 (s, 1H), 2.11-1.98 (m, 3H).

Example 187: 4-(2-((1-(3-(1,1-Difluoroethyl)-4-fluorophenyl)-1H-1,2,3-triazol-4-yl)methoxy)pyrimidin-5-yl)morpholine

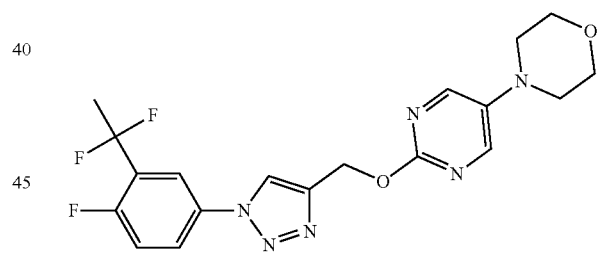

To a vial was added 5-bromo-2-((1-(3-(1,1-difluoroethyl)-4-fluorophenyl)-1H-1,2,3-triazol-4-yl)methoxy)pyrimidine (Example 183, 28 mg, 0.07 mmol), morpholine (0.01 mL, 0.08 mmol), NaOtBu (8 mg, 0.08 mmol), 2-dicyclohexylphosphino-2',6'-diisopropoxy-1,1'-biphenyl)[2-(2'-amino-1,1'-biphenyl)]palladium(II) methanesulfonate (RuPhos-Pd-G3) (6 mg, 0.01 mmol), 2-dicyclohexylphosphino-2',6'-diisopropoxybiphenyl (RuPhos) (4 mg, 0.01 mmol) in THF (1 mL) under N$_2$. The resulting reaction mixture was sealed and heated to 85° C. then allowed to stir overnight. The reaction mixture was then cooled to room temperature, filtered through a pad of Celite® and concentrated under reduced pressure. Purification (basic HPLC, Agilent prep system, Waters XBridge C18 5 μm 50×100 mm column, 5-95% MeCN/20 nM NH$_4$OH over 22 min at 80 mL/min) afforded the title compound (13 mg, 45%). MS (ESI): mass calcd. for $C_{19}H_{19}F_3N_6O_2$, 420.3; m/z found, 421.1 [M+H]$^+$. $^1$H NMR (400 MHz, CDCl$_3$) δ 8.18-8.14 (s, 2H), 8.06-8.03

(s, 1H), 7.85-7.80 (m, 1H), 7.79-7.73 (m, 1H), 7.27-7.20 (m, 1H), 5.57-5.50 (s, 2H), 3.85-3.77 (m, 4H), 3.08-3.00 (m, 4H), 2.05-1.90 (m, 3H).

Example 188: 2-((1-(4-(Azetidin-1-yl)-3-(difluoromethyl)phenyl)-1H-1,2,3-triazol-4-yl)methoxy)pyrimidine

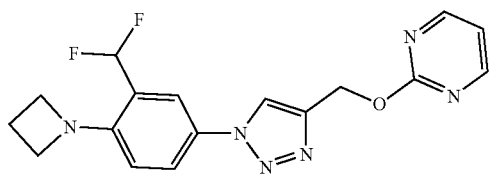 [SMILES: FC(F)c1cc(-n2cc(COc3ncccn3)nn2)ccc1N1CCC1]

To a solution of 2-((1-(3-(difluoromethyl)-4-fluorophenyl)-1H-1,2,3-triazol-4-yl)methoxy)pyrimidine (Example 25, 30 mg, 0.09 mmol) in ACN (2 mL) was added azetidine (5.3 mg, 0.09 mmol) and DIPEA (30 mg, 0.23 mmol). The resulting reaction mixture was heated to 90° C. and allowed to stir overnight. The reaction mixture was cooled to room temperature and diluted with EtOAc then washed with $NH_4Cl$ solution. The organic layer was isolated, dried ($MgSO_4$), filtered, and concentrated under reduced pressure. Purification (FCC, $SiO_2$, 0-100% ethyl acetate in hexanes) afforded the title compound (19 mg, 0.05 mmol, 57%). MS (ESI): mass calcd. for $C_{17}H_{16}F_2N_6O$, 358.3; m/z found, 359.1 $[M+H]^+$. $^1H$ NMR (500 MHz, $CDCl_3$) δ 8.58-8.54 (d, J=4.7 Hz, 2H), 8.05-8.01 (t, J=0.7 Hz, 1H), 7.75-7.70 (d, J=2.5 Hz, 1H), 7.67-7.62 (m, 1H), 7.00-6.96 (m, 1H), 6.90-6.65 (m, 1H), 6.57-6.53 (d, J=8.9 Hz, 1H), 5.68-5.62 (d, J=0.6 Hz, 2H), 4.14-4.08 (m, 4H), 2.45-2.36 (m, 2H).

Example 189: 2-[[1-[4-Chloro-3-(difluoromethoxy)phenyl]triazol-4-yl]methoxy]-5-fluoro-pyrazine

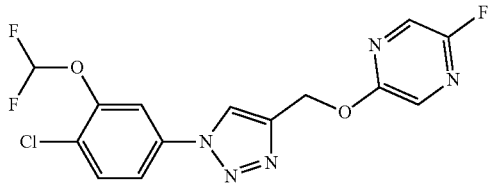 [SMILES: Fc1cnc(OCc2cn(-c3ccc(Cl)c(OC(F)F)c3)nn2)cn1]

Step A. 2-Chloro-5-((1-(4-chloro-3-(difluoromethoxy)phenyl)-1H-1,2,3-triazol-4-yl)methoxy)pyrazine The title compound was prepared in a manner analogous to Example 1 using (1-(3-(difluoromethoxy)-4-chlorophenyl)-1H-1,2,3-triazol-4-yl)methanol (Intermediate 1) and 2,4-dichloropyrazine. MS (ESI): mass calcd. for $C_{14}H_9Cl_{12}F_2N_5O_2$, 387.0; m/z found, 388.0 $[M+H]^+$.

Step B. 2-[[1-[4-Chloro-3-(difluoromethoxy)phenyl]triazol-4-yl]methoxy]-5-fluoro-pyrazine To a solution of 2-chloro-5-((1-(4-chloro-3-(difluoromethoxy)phenyl)-1H-1,2,3-triazol-4-yl)methoxy)pyrazine (42 mg, 0.108 mmol) in DMSO (0.8 mL) was added CsF (164 mg, 1.1 mmol). The mixture was heated in a sealed reaction vessel to 100° C. for 2.5 h. The reaction mixture was cooled to rt, then diluted with water, ACN and few drops of HCl (1M, aq). Purification (semi-prep RP-HPLC, equipped with Phenomenex C18 Gemini 5 um, 250×4.6 mm; 5-95% Acetonitrile in water with 0.1% TFA addition) afforded the title compound (8 mg, 20%) after free base with $NaHCO_3$ (aq). MS (ESI): mass calcd. for $C_{14}H_9ClF_3N_5O_2$, 371.0; m/z found, 372.0 $[M+H]^+$. $^1H$ NMR (400 MHz, $CD_3CN$) δ 8.47-8.36 (m, 1H), 8.27-8.19 (m, 1H), 8.10 (dd, J=8.2, 0.7 Hz, 1H), 7.82-7.67 (m, 3H), 7.12 (t, J=76 Hz, 1H), 5.59 (s, 2H).

Example 190: 4-Chloro-2-[[1-[4-chloro-3-(difluoromethoxy)phenyl]triazol-4-yl]methoxy]pyrimidine

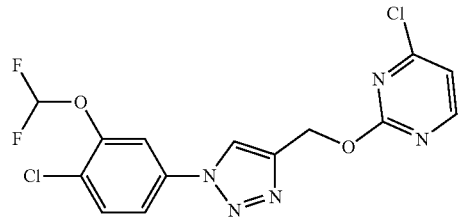 [SMILES: FC(F)Oc1cc(-n2cc(COc3nccc(Cl)n3)nn2)ccc1Cl]

To a solution of 2-((1-(4-chloro-3-(difluoromethoxy)phenyl)-1H-1,2,3-triazol-4-yl)methoxy)pyrimidin-4-amine (Example 382, 25 mg, 0.068 mmol) in ACN (1 mL) at rt, were added isopentyl nitrite (0.0137 ml, 0.1 mmol) and copper(II) chloride (9.6 mg, 1.071 mmol). The mixture was heated to reflux for 3 hours The reaction mixture was diluted with water (5 mL) and few drops of HCl, filtered through a syringe filter (0.25 um). Purification (semi-prep HPLC (95% to 5% Water in MeCN with 0.1% TFA addition, Phenomenex C18 Gemini, 5 um, 250×4.6 mm)), afforded the title compound which was free based by neutralization with $NaHCO_3$ (aq) and extraction with EtOAc to afford the title compound (7 mg, 27%). MS (ESI): mass calcd. for $C_{14}H_9Cl_{12}F_2N_5O_2$, 387.0; m/z found, 388.1 $[M+H]^+$. $^1H$ NMR (400 MHz, $CD_3CN$) δ 8.55-8.48 (m, 1H), 8.45 (t, J=1.3 Hz, 1H), 7.82-7.68 (m, 3H), 7.24-7.16 (m, 1H), 6.94 (t, J=60 Hz, 1H), 5.63 (s, 1H).

Example 191: 2-[[1-[4-Chloro-3-(difluoromethoxy)phenyl]triazol-4-yl]methoxy]-4-fluoro-pyrimidine

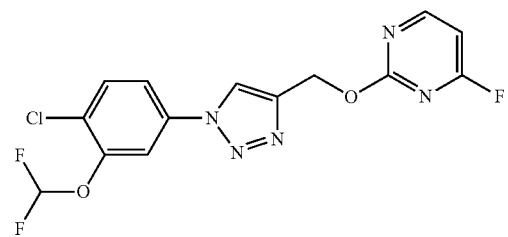 [SMILES: Fc1ccnc(OCc2cn(-c3ccc(Cl)c(OC(F)F)c3)nn2)n1]

The title compound was prepared in a manner analgous to Example 189, Step B, using 4-chloro-2-((1-(4-chloro-3-(difluoromethoxy)phenyl)-1H-1,2,3-triazol-4-yl)methoxy)pyrimidine (Example 190) using MeCN instead of DMSO. MS (ESI): mass calcd. for $C_{14}H_9ClF_3N_5O_2$, 371.0; m/z found, 372.1 $[M+H]^+$. 1H NMR (500 MHz, $CDCl_3$) δ 8.59 (dd, J=11.5, 5.5 Hz, 1H), 8.15 (s, 1H), 7.73 (d, J=2.1 Hz, 1H), 7.66-7.62 (m, 1H), 7.61-7.56 (m, 1H), 6.69 (dd, J=5.5, 2.6 Hz, 1H), 6.66 (t, J=72.5 Hz, 1H).

Example 192: 2-[[1-[4-Chloro-3-(difluoromethoxy) phenyl]triazol-4-yl]methoxy]-5-(2-fluoroethoxy) pyrimidine

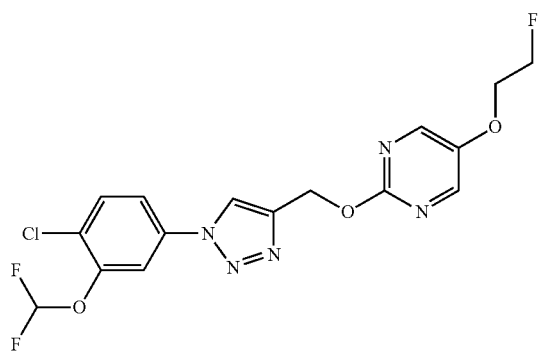 [SMILES: FCCOc1cnc(OCc2cn(-c3ccc(Cl)c(OC(F)F)c3)nn2)nc1]

Step A. 2-Chloro-5-(2-fluoroethoxy)pyrimidine

To a mixture of 2-chloropyrimidin-5-ol (1 g, 7.6 mmol) and 1-fluoro-2-iodoethane (1.73 g, 9.9 mmol) in DMF (2.9 mL) was added $Cs_2CO_3$ (3.2 g, 9.9 mmol). The mixture was stirred vigorously for 3 h. The reaction mixture was diluted with EtOAc (20 mL) and filtered, and the solid was washed with EtOAc (20 mL). The filtrate was washed with water (3×30 mL) and dried ($Na_2SO_4$) and concentrated. Purification (FCC, $SiO_2$, DCM/EtOAc) afforded the title compound as a white solid (847 mg, 62.6%). MS (ESI): mass calcd. for $C_6H_6ClFN_2O$, 176.0; m/z found, 171.1 [M+H]$^+$.

Step B. 2-[[1-[4-Chloro-3-(difluoromethoxy)phenyl] triazol-4-yl]methoxy]-5-(2-fluoroethoxy)pyrimidine The title compound was prepared in a manner analogous to Example 1 using (1-(4-chloro-3-(difluoromethoxy)phenyl)-1H-1,2,3-triazol-4-yl)methanol (Intermediate 1) (41.2 mg, 0.15 mmol) and 2-chloro-5-(2-fluoroethoxy)pyrimidine. MS (ESI): mass calcd. for $C_{16}H_{13}ClF_3N_5O_3$, 415.1; m/z found, 416.1[M+H]$^+$. $^1$H NMR (500 MHz, $CD_3OD$) δ 8.56 (s, 1H), 8.34 (s, 2H), 7.83 (s, 1H), 7.75-7.66 (m, 3H), 6.87 (m, 1H), 5.59 (s, 2H), 4.81-4.80 (m, 1H), 4.71-4.70 (m, 1H), 4.36-4.34 (m, 1H), 4.30-4.29 (m, 1H).

Example 193: 2-[[1-[4-Chloro-3-(2-fluoroethoxy) phenyl]triazol-4-yl]methoxy]-5-methoxy-pyrimidine

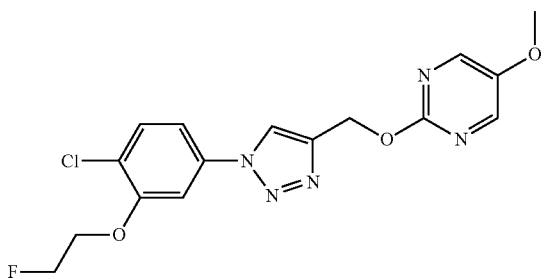 [SMILES: COc1cnc(OCc2cn(-c3ccc(Cl)c(OCCF)c3)nn2)nc1]

Step A. 2-Chloro-5-(4-(hydroxymethyl)-1H-1,2,3-triazol-1-yl)phenol

A mixture of (1-(4-chloro-3-(difluoromethoxy)phenyl)-1H-1,2,3-triazol-4-yl)methanol (Intermediate 1) (110 mg, 0.4 mmol) and tBuOK (134 mg, 1.2 mmol) in dry DMSO was stirred at rt for 15 h. The reaction was quenched by adding acetic acid (3 mL). The mixture was subjected to C18 reversed phase HPLC purification (TFA buffered MeCN/water) to afford the title compound as a white solid (18 mg, 20%). MS (ESI): mass calcd. for $C_9H_8ClN_3O_2$, 225.0; m/z found, 226.1[M+H]$^+$.

Step B. (1-(4-Chloro-3-(2-fluoroethoxy)phenyl)-1H-1,2,3-triazol-4-yl)methanol

To 2-chloro-5-(4-(hydroxymethyl)-1H-1,2,3-triazol-1-yl) phenol (18 mg, 0.08 mg) and $Cs_2CO_3$ (65 mg, 0.2 mmol) in DMF (0.8 mL) was added 1-fluoro-2-iodoethane (16.6 mg, 0.096 mmol). The mixture was stirred at rt for 3 h, and then diluted with EtOAc (30 mL), washed with water 3×20 mL), dried ($Na_2SO_4$), and concentrated. Purification (FCC, $SiO_2$, DCM/EtOAc) afforded the title compound (19 mg, 87%). MS (ESI): mass calcd. for $C_{11}H_{11}ClFN_3O_2$, 271.0; m/z found, 272.1[M+H]$^+$.

Step C. 2-[[1-[4-Chloro-3-(2-fluoroethoxy)phenyl] triazol-4-yl]methoxy]-5-methoxy-pyrimidine The title compound was prepared in a manner analogous to Example 1 using (1-(4-chloro-3-(2-fluoroethoxy)phenyl)-1H-1,2,3-triazol-4-yl)methanol and 2-chloro-5-methoxypyrimidine. MS (ESI): mass calcd. for $C_{16}H_{15}ClFN_5O_3$, 379.1; m/z found, 380.1 [M+H]$^+$. $^1$H NMR (600 MHz, $CD_3OD$) δ 8.39 (s, 1H), 8.25 (s, 2H), 7.52 (t, J=1.1 Hz, 2H), 7.31 (dd, J=8.5, 2.4 Hz, 1H), 5.56 (s, 2H), 4.87-4.83 (m, 1H), 4.80-4.75 (m, 1H), 4.43-4.39 (m, 1H), 4.39-4.33 (m, 1H), 3.88 (s, 2H).

Example 194: 2-[[1-[4-Fluoro-3-(3-fluoropropyl) phenyl]triazol-4-yl]methoxy]-5-methoxy-pyrimidine

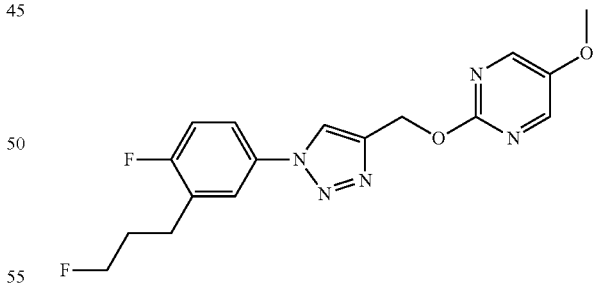

Step A. (E)-2-((1-(4-Fluoro-3-(3-((tetrahydro-2H-pyran-2-yl)oxy)prop-1-en-1-yl)phenyl)-1H-1,2,3-triazol-4-yl)methoxy)-5-methoxypyrimidine A mixture of 2-((1-(3-bromo-4-fluorophenyl)-1H-1,2,3-triazol-4-yl)methoxy)-5-methoxypyrimidine (Example 41, 80 mg, 0.21 mmol), (E)-4,4,5,5-tetramethyl-2-(3-((tetrahydro-2H-pyran-2-yl)oxy)prop-1-en-1-yl)-1,3,2-dioxaborolane (84 mg, 0.31 mmol), Pd(PPh$_3$)$_4$(12 mg, 0.01 mmol), and Na$_2$CO$_3$ solution (1.0 M, 0.63 mL, 0.62 mmol) in a microwave tube was heated at 110° C. for 20 min under microwave irradiation. The reaction mixture was diluted with EtOAc (10 mL) and washed with water (2×10 mL). The organic phase was dried (Na$_2$SO$_4$), filtered, and concentrated under reduced pressure. Purification (FCC, SiO$_2$, hexane/EtOAc) afforded the title compound (68 mg, 73.2%). MS (ESI): mass calcd. for C$_{22}$H$_{24}$FN$_5$O$_4$, 441.2; m/z found, 442.3 [M+H]$^+$.

Step B. 2-((1-(4-Fluoro-3-(3-((tetrahydro-2H-pyran-2-yl)oxy)propyl)phenyl)-1H-1,2,3-triazol-4-yl)methoxy)-5-methoxypyrimidine A solution of (E)-2-((1-(4-fluoro-3-(3-((tetrahydro-2H-pyran-2-yl)oxy)prop-1-en-1-yl)phenyl)-1H-1,2,3-triazol-4-yl)methoxy)-5-methoxypyrimidine (22 mg, 0.05 mmol) in MeOH (10 mL) was purged with nitrogen. Pd/C (10%, 30 mg) was added. The mixture was purged with hydrogen twice. The mixture was stirred under hydrogen atmosphere at rt for 15 min. The mixture was filtered and the filtrate was concentrated. Purification (FCC, SiO$_2$, hexane/EtOAc) afforded the title compound (22 mg, 99%). MS (ESI): mass calcd. for C$_{22}$H$_{22}$FN$_5$O$_4$, 443.2; m/z found, 444.3 [M+H]$^+$.

Step C. 3-(2-Fluoro-5-(4-(((5-methoxypyrimidin-2-yl)oxy)methyl)-1H-1,2,3-triazol-1-yl)phenyl)propan-1-ol To 2-((1-(4-fluoro-3-(3-((tetrahydro-2H-pyran-2-yl)oxy)propyl)phenyl)-1H-1,2,3-triazol-4-yl)methoxy)-5-methoxypyrimidine (22 mg, 0.05 mmol) in MeOH (10 mL) was added concentrated HCl dropwise at rt. The mixture was stirred at rt for 15 min. To the mixture was added 0.1 mL of water and the volatiles were removed under reduced pressure and dried under high vacuum. Purification (FCC, SiO$_2$, DCM/methanol) afforded the title compound. mass calcd. for C$_{17}$H$_{18}$FN$_5$O$_3$, 359.1; m/z found, 360.2 [M+H]$^+$.

Step D. 2-((1-(4-Fluoro-3-(3-fluoropropyl)phenyl)-1H-1,2,3-triazol-4-yl)methoxy)-5-methoxypyrimidine To 3-(2-fluoro-5-(4-(((5-methoxypyrimidin-2-yl)oxy)methyl)-1H-1,2,3-triazol-1-yl)phenyl)propan-1-ol (21 mg, 0.058 mmol) in 0.2 mL of DCM at −78° C. was added (diethylamino)sulfur trifluoride (0.072 mL, 0.6 mmol) with stirring. The reaction was allowed to warm slowly to rt with stirring and concentrated under reduced pressure. Purification (semi-prep RP-HPLC (95% to 5% Water in MeCN with 0.1% TFA addition, Phenomenex C18 Gemini, 5 um, 250× 4.6 mm) afforded the title compound (1.2 mg, 6%) and 2-[[1-[3-(3-chloropropyl)-4-fluoro-phenyl]triazol-4-yl]methoxy]-5-methoxy-pyrimidine. MS (ESI): mass calcd. for C$_{17}$H$_{17}$F$_2$N$_5$O$_2$, 361.1; m/z found, 362.2 [M+H]$^+$. $^1$H NMR (400 MHz, CD$_3$OD) δ 8.50 (s, 1H), 8.23 (s, 2H), 7.70 (dd, J=6.4, 2.8 Hz, 1H), 7.65-7.58 (m, 1H), 7.19 (t, J=9.1 Hz, 1H), 5.45 (s, 2H), 4.45 (t, J=5.9 Hz, 2H), 4.33 (t, J=5.9 Hz, 1H), 3.80 (s, 3H), 2.78 (t, J=7.9 Hz, 2H).

Example 195: 2-[[1-[3-(3-Chloropropyl)-4-fluorophenyl]triazol-4-yl]methoxy]-5-methoxy-pyrimidine

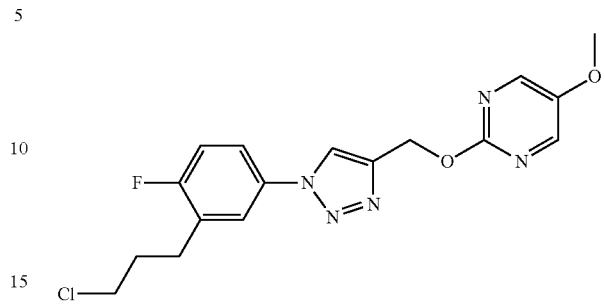

The title compound was obtained as a by-product from the synthesis of Example 194, step D. (1.3 mg, 6%). MS (ESI): mass calcd. for C$_{17}$H$_{17}$ClFN$_5$O$_2$, 377.1; m/z found, 378.1 [M+H]$^+$. $^1$H NMR (400 MHz, CD$_3$OD) δ 8.62 (s, 1H), 8.35 (s, 2H), 7.82 (dd, J=6.3, 2.7 Hz, 1H), 7.78-7.71 (m, 1H), 7.31 (t, J=9.1 Hz, 1H), 5.57 (s, 2H), 3.92 (s, 3H), 3.64 (t, J=6.4 Hz, 2H), 2.94 (t, J=7.6 Hz, 2H), 2.15 (ddd, J=7.7, 6.3, 1.3 Hz, 2H)

Example 196: 2-[[1-[4-Chloro-3-(difluoromethoxy)phenyl]triazol-4-yl]methoxy]-5-(3-fluoropropyl)pyrimidine

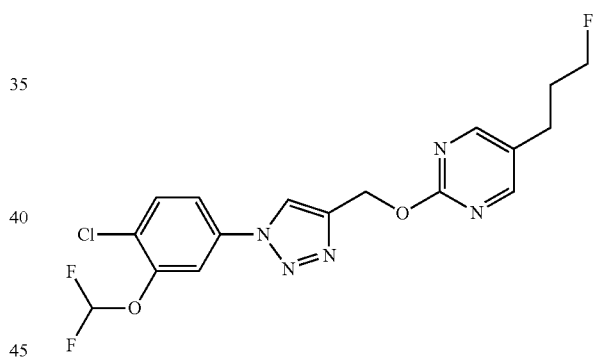

Step A: 3-(2-Methoxypyrimidin-5-yl)prop-2-yn-1-ol

To a degassed solution of 5-bromo-2-methoxypyrimidine (4.0 g, 21 mmol), trimethylamine (5.9 mL, 42 mmol), PdCl$_2$(PPh$_3$)$_2$(1.5 g, 2.1 mmol) and CuI (0.4 g, 2.1 mmol) in DMF (33 mL) was added prop-2-yn-1-ol (3.1 mL, 53 mmol) was added. The reaction was sealed and heated at 90° C. for 4 hours. The reaction was diluted with brine and extracted with EtOAc (50 mL×3). The combined organics were dried, filtered, concentrated under reduced pressure. Purification (FCC, SiO$_2$, hexanes/EtOAc; 4:1) afforded the title compound (1.8 g, 52%) MS (ESI): mass calcd. for C$_8$H$_8$N$_2$O$_2$, 164.1; m/z found, [M+H]$^+$ 165.1.

Step B: 3-(2-Methoxypyrimidin-5-yl)propan-1-ol

An ethanol solution (65 mL) of 3-(2-methoxypyrimidin-5-yl)prop-2-yn-1-ol (1.8 g, 11 mmol) was added to Pd/C (10% wt, 583 mg). The reaction mixture was stirred under hydrogen atmosphere (1 atm) for 3 hours. The reaction mixture was filtered through diatomaceous earth and concentrated under reduced pressure to afford the title compound (1.5 g, 81%) MS (ESI): mass calcd. for $C_8H_{12}N_2O_2$, 168.1; m/z found, $[M+H]^+$ 169.1.

Step C: 3-(2-Methoxypyrimidin-5-yl)propyl 4-methylbenzenesulfonate

To a solution of 3-(2-methoxypyrimidin-5-yl)propan-1-ol (450 mg, 2.7 mmol) in DCM (17 mL), were added trimethylamine (1.1 mL, 8.0 mmol) and sulfonyl chloride (1.02 g, 5.35 mmol). The reaction mixture was stirred at rt overnight. The reaction was diluted with $NaHCO_3$ (aq, 25 mL) and the aqueous layers were extracted with EtOAc (30 mL×3). The combined organic extracts was dried, filtered, and concentrated under reduced pressure. Purification (FCC, $SiO_2$, hexanes/EtOAc; 5:1) afforded the title compound (540 mg, 63%) MS (ESI): mass calcd. for $C_{15}H_{18}N_2O_4S$, 322.1; m/z found, $[M+H]^+$ 323.1.

Step D: 5-(3-Fluoropropyl)-2-methoxypyrimidine

To a solution of 3-(2-methoxypyrimidin-5-yl)propyl 4-methylbenzenesulfonate (750 mg, 2.3 mmol) in THF (10 mL) was added TBAF (1.0 M in THF, 3.5 mL, 3.5 mmol). The reaction mixture was heated to 60° C. for 30 min. The reaction mixture was concentrated under reduced pressure. The crude product was diluted with EtOAc (50 mL), washed with $NaHCO_3$ (aq, 30 mL) and brine (30 mL). The combined organics were dried, filtered, and concentrated under reduced pressure. Purification (FCC, $SiO_2$, hexanes EtOAc; 5:1) afforded the title compound (290 mg, 73%) MS (ESI): mass calcd. for $C_8H_{11}FN_2O$, 170.1; m/z found, $[M+H]^+$ 171.1.

Step E: 5-(3-Fluoropropyl)pyrimidin-2(1H)-one hydrochloride salt

A solution of 5-(3-fluoropropyl)-2-methoxypyrimidine (250 mg, 1.47 mmol) in HCl (4M in dioxane, 1.1 mL, 4.4 mmol) and water (0.26 mL, 14.7 mmol) was heated to 100° C. for 5 hours. The mixture was concentrated under reduced pressure to afford the title compound as a white HCl salt which was used in next step without further purification. MS (ESI): mass calcd. for $C_7H_9FN_2O$, 156.1; m/z found, $[M+H]^+$ 157.1.

Step F. 2-Chloro-5-(3-fluoropropyl)pyrimidine

A mixture of 5-(3-fluoropropyl)pyrimidin-2(1H)-one hydrochloride (120 mg, 0.62 mmol) in $POCl_3$ (2 mL) was heated at 95° C. for 20 h. The reaction mixture was cooled and concentrated under reduced pressure. The residue was diluted with EtOAc (30 mL) and washed with $NaHCO_3$ (aq, sat. 3×20 mL). The organics were dried, filtered, and concentrated under reduced pressure. Purification (FCC, $SiO_2$, hexane/EtOAc) afforded the title compound (66 mg, 66%). MS (ESI): mass calcd. for $C_7H_6ClFN_2$, 174.0; m/z found, 175.0 $[M+H]^+$.

Step G. 2-[[1-[4-Chloro-3-(difluoromethoxy)phenyl] triazol-4-yl]methoxy]-5-(3-fluoropropyl)pyrimidine The title compound was prepared in a manner analogous to Example 1 using (1-(4-chloro-3-(difluoromethoxy)phenyl)-1H-1,2,3-triazol-4-yl)methanol (Intermediate 1) and 2-chloro-5-(3 fluoropropyl)pyrimidine. MS (ESI): mass calcd. for $C_{17}H_{15}ClF_3N_5O_2$, 413.1; m/z found, 414.1 $[M+H]^+$. $^1$H NMR (400 MHz, $CDCl_3$) δ 8.45 (s, 2H), 8.17 (s, 1H), 7.74 (d, J=2.2 Hz, 1H), 7.67-7.56 (m, 2H), 6.68 (t, J=72.5 Hz, 1H), 5.67 (d, J=0.7 Hz, 2H), 4.57 (t, J=5.7 Hz, 1H), 4.46 (t, J=5.7 Hz, 1H), 2.76 (t, J=7.7 Hz, 2H), 2.15-1.92 (m, 2H).

Example 197: N-[[1-[3-(Difluoromethyl)phenyl] triazol-4-yl]methyl]-5-fluoro-pyrimidin-2-amine

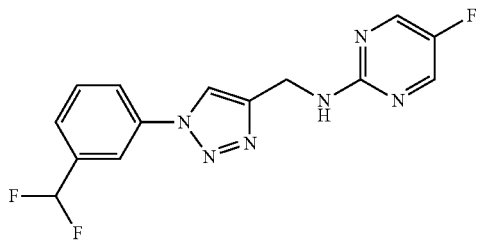 [SMILES: Fc1cnc(NCc2cn(-c3cccc(C(F)F)c3)nn2)nc1]

The title compound was prepared in a manner analogous to Example 153 using 2-amino-5-fluoropyrimidine. MS (ESI): mass calcd. for $C_{14}H_{11}F_3N_6$, 320.1; m/z found, 321.0 $[M+H]^+$. $^1$H NMR (500 MHz, $CDCl_3$) δ 8.23 (d, J=2.2 Hz, 2H), 7.99 (s, 1H), 7.98-7.77 (m, 2H), 7.70-7.53 (m, 2H), 6.72 (t, J=56.1 Hz, 1H), 5.73 (s, 1H), 4.79 (d, J=6.4 Hz, 2H).

Example 198: N-[[1-(4-Fluoro-3-methyl-phenyl) triazol-4-yl]methyl]-5-methyl-pyrimidin-2-amine

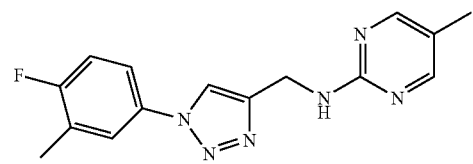 [SMILES: Cc1cnc(NCc2cn(-c3ccc(F)c(C)c3)nn2)nc1]

The title compound was prepared in a manner analogous to Example 6, using (1-(4-fluoro-3-methylphenyl)-1H-1,2,3-triazol-4-yl)methanamine (Intermediate 26) and 2-chloro-5-methylpyrimidine. MS (ESI): mass calcd. for $C_{15}H_{15}FN_6$, 298.1; m/z found, 299.0 $[M+H]^+$. $^1$H NMR (400 MHz, DMSO-$d_6$) δ 8.52-8.50 (m, 1H), 8.18-8.14 (m, 2H), 7.88-7.83 (m, 1H), 7.75-7.69 (m, 1H), 7.40-7.30 (m, 2H), 4.58 (d, J=6.1 Hz, 2H), 2.34-2.29 (m, 3H), 2.08-2.04 (m, 3H).

Example 199: 5-Chloro-N-[[1-(4-fluoro-3-methyl-phenyl)triazol-4-yl]methyl]-4-methyl-pyrimidin-2-amine

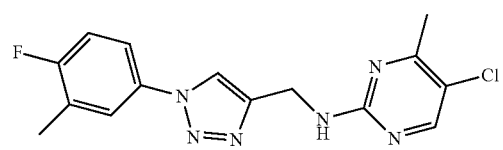 [SMILES: Cc1cc(-n2cc(CNc3ncc(Cl)c(C)n3)nn2)ccc1F]

The title compound was prepared in a manner analogous to Example 6, using (1-(4-fluoro-3-methylphenyl)-1H-1,2,3-triazol-4-yl)methanamine (Intermediate 26) and 2,5-dichloro-4-methylpyrimidine. MS (ESI): mass calcd. for $C_{15}H_{14}ClFN_6$, 332.1; m/z found, 332.9 [M+H]$^+$. $^1$H NMR (400 MHz, DMSO-$d_6$) δ 8.54 (s, 1H), 8.25 (s, 1H), 7.88-7.79 (m, 2H), 7.76-7.70 (m, 1H), 7.35 (t, J=9.1 Hz, 1H), 4.59 (d, J=6.0 Hz, 2H), 2.36 (s, 3H), 2.32 (d, J=2.0 Hz, 3H).

Example 200: 5-Chloro-N-[[1-[4-chloro-3-(difluoromethyl)phenyl]triazol-4-yl]methyl]pyrimidin-2-amine

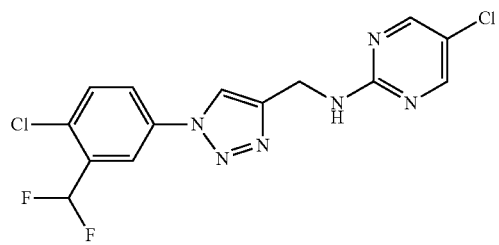 [SMILES: FC(F)c1cc(-n2cc(CNc3ncc(Cl)cn3)nn2)ccc1Cl]

The title compound was prepared in a manner analogous to Example 154 using 2,5-dichloropyrimidine. MS (ESI): mass calcd. for $C_{14}H_{10}Cl_2F_2N_6$, 370.0; m/z found, 371.0 [M+H]$^+$. $^1$H NMR (500 MHz, CDCl$_3$) δ 8.26 (s, 2H), 8.00-7.95 (m, 2H), 7.90-7.83 (m, 1H), 7.62-7.55 (m, 1H), 6.98 (t, J=54.5 Hz, 1H), 5.88 (t, J=6.4 Hz, 1H), 4.79 (d, J=6.1 Hz, 2H).

Example 201: N-[[1-[4-Chloro-3-(difluoromethyl)phenyl]triazol-4-yl]methyl]-4-methyl-pyrimidin-2-amine

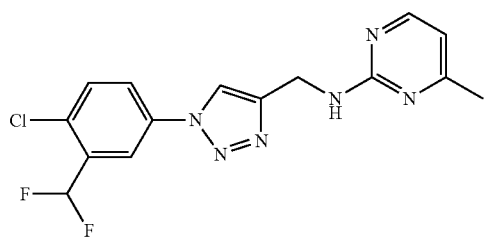 [SMILES: Cc1ccnc(NCc2cn(-c3ccc(Cl)c(C(F)F)c3)nn2)n1]

The title compound was prepared in a manner analogous to Example 154 using, using 2-chloro-4-methylpyrimidine. MS (ESI): mass calcd. for $C_{15}H_{13}ClF_2N_6$, 350.1; m/z found, 351.1 [M+H]$^+$. $^1$H NMR (500 MHz, CDCl$_3$) δ 8.20 (d, J=5.0 Hz, 1H), 8.01 (s, 1H), 7.99-7.95 (m, 1H), 7.88-7.83 (m, 1H), 7.63-7.55 (m, 1H), 6.98 (t, J=54.5 Hz, 1H), 6.52 (d, J=5.0 Hz, 1H), 6.12 (s, 1H), 4.85 (d, J=6.1 Hz, 2H), 2.39 (s, 3H).

Example 202: N-[[1-[4-Chloro-3-(difluoromethyl)phenyl]triazol-4-yl]methyl]-5-ethyl-pyrimidin-2-amine

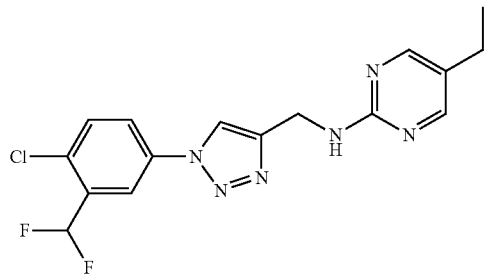 [SMILES: CCc1cnc(NCc2cn(-c3ccc(Cl)c(C(F)F)c3)nn2)nc1]

The title compound was prepared in a manner analogous to Example 154 using 2-chloro-5-ethylpyrimidine. MS (ESI): mass calcd. for $C_{15}H_{15}ClF_2N_6$, 364.1; m/z found, 365.1 [M+H]$^+$. $^1$H NMR (500 MHz, CDCl$_3$) δ 8.26 (s, 2H), 8.11 (s, 1H), 7.99 (d, J=2.5 Hz, 1H), 7.85 (dd, J=8.7, 2.5 Hz, 1H), 7.58 (d, J=8.7 Hz, 1H), 7.10 (s, 1H), 6.97 (t, J=54.5 Hz, 1H), 4.89 (d, J=5.5 Hz, 2H), 2.54 (q, J=7.6 Hz, 2H), 1.23 (t, J=7.6 Hz, 3H).

Example 203: N-[[1-[4-Chloro-3-(difluoromethyl)phenyl]triazol-4-yl]methyl]-5-methoxy-pyrimidin-2-amine

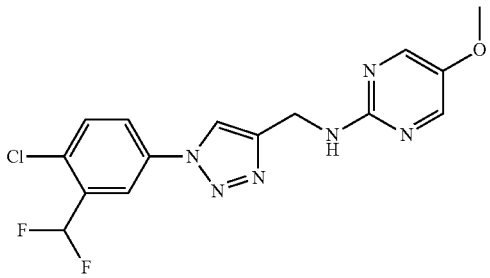 [SMILES: COc1cnc(NCc2cn(-c3ccc(Cl)c(C(F)F)c3)nn2)nc1]

The title compound was prepared in a manner analogous to Example 154 using 2-chloro-5-methoxypyrimidine. MS (ESI): mass calcd. for $C_{15}H_{13}ClF_2N_6O$, 366.1; m/z found, 367.0 [M+H]$^+$. $^1$H NMR (500 MHz, CDCl$_3$) δ 8.10 (s, 2H), 7.99-7.96 (m, 2H), 7.89-7.83 (m, 1H), 7.61-7.57 (m, 1H), 6.98 (t, J=54.5 Hz, 1H), 5.55-5.42 (m, 1H), 4.78 (d, J=6.2 Hz, 2H), 3.81 (s, 3H)

Example 204: N-[[1-[4-Chloro-3-(difluoromethyl)phenyl]triazol-4-yl]methyl]-5-(difluoromethyl)pyrimidin-2-amine

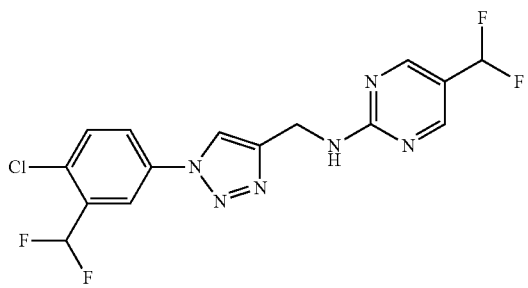 [SMILES: FC(F)c1cnc(NCc2cn(-c3ccc(Cl)c(C(F)F)c3)nn2)nc1]

The title compound was prepared in a manner analogous to Example 154 using 2-chloro-5-difluoromethylpyrimidine. MS (ESI): mass calcd. for $C_{15}H_{11}ClF_4N_6$, 386.1; m/z found, 387.0 [M+H]$^+$. $^1$H NMR (500 MHz, CDCl$_3$) δ 8.45 (s, 2H), 8.02-7.99 (m, 1H), 7.98 (d, J=2.5 Hz, 1H), 7.89-7.84 (m, 1H), 7.60 (dd, J=8.6, 1.0 Hz, 1H), 6.99 (t, J=54.5 Hz, 1H), 6.59 (t, J=56.0 Hz, 1H), 6.05 (s, 1H), 4.86 (d, J=6.2 Hz, 2H).

Example 205: N-[[1-[4-Chloro-3-(difluoromethyl)phenyl]triazol-4-yl]methyl]-5-(trifluoromethyl)pyrimidin-2-amine

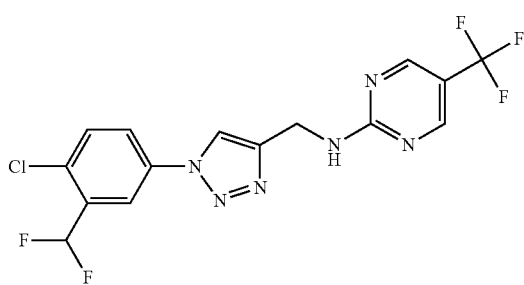 [SMILES: FC(F)c1cc(-n2cc(CNc3ncc(C(F)(F)F)cn3)nn2)ccc1Cl]

The title compound was prepared in a manner analogous to Example 154 using 2-chloro-5-trifluoromethylpyrimidine. MS (ESI): mass calcd. for $C_{15}H_{10}ClF_5N_6$, 404.1; m/z found, 405.0 [M+H]$^+$. $^1$H NMR (400 MHz, CDCl$_3$) δ 8.54 (s, 2H), 8.02 (s, 1H), 7.98 (d, J=2.6 Hz, 1H), 7.90-7.84 (m, 1H), 7.63-7.56 (m, 1H), 6.98 (t, J=54.5 Hz, 1H), 6.43-6.31 (m, 1H), 4.87 (d, J=6.0 Hz, 2H).

Example 206: N-[[1-[3-(1,1-Difluoroethyl)-4-fluoro-phenyl]triazol-4-yl]methyl]-5-methyl-pyrimidin-2-amine

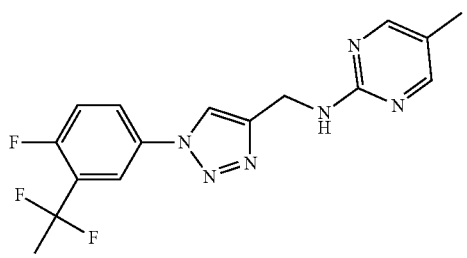 [SMILES: Cc1cnc(NCc2cn(-c3ccc(F)c(C(C)(F)F)c3)nn2)nc1]

The title compound was prepared in a manner analogous to Example 154 using (1-(3-(1,1-difluoroethyl)-4-fluorophenyl)-1H-1,2,3-triazol-4-yl)methanamine (Intermediate 20). MS (ESI): mass calcd. for $C_{16}H_{15}F_3N_6$, 348.1; m/z found, 349.0 [M+H]$^+$. $^1$H NMR (400 MHz, CD$_3$OD) δ 8.46-8.44 (m, 1H), 8.20 (d, J=0.7 Hz, 2H), 8.07-8.03 (m, 1H), 8.02-7.96 (m, 1H), 7.46 (t, J=9.7 Hz, 1H), 4.74 (s, 2H), 2.16 (s, 3H), 2.06 (td, J=18.7, 1.1 Hz, 3H).

Example 207: N-[[1-[3-(1,1-Difluoroethyl)-4-fluoro-phenyl]triazol-4-yl]methyl]-5-ethyl-pyrimidin-2-amine

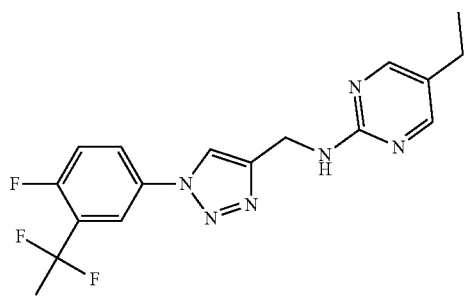 [SMILES: CCc1cnc(NCc2cn(-c3ccc(F)c(C(C)(F)F)c3)nn2)nc1]

The title compound was prepared in a manner analogous to Example 154 using (1-(3-(1,1-difluoroethyl)-4-fluorophenyl)-1H-1,2,3-triazol-4-yl)methanamine (Intermediate 20) and 2-chloro-5-ethylpyrimidine. MS (ESI): mass calcd. for $C_{17}H_{17}F_3N_6$, 362.1; m/z found, 363.1 [M+H]$^+$. $^1$H NMR (400 MHz, CD$_3$OD) δ 8.45 (s, 1H), 8.22 (s, 2H), 8.07-7.95 (m, 2H), 7.45 (t, J=9.6 Hz, 1H), 4.74 (s, 2H), 2.52 (q, J=7.6 Hz, 2H), 2.14-1.99 (m, 3H), 1.21 (t, J=7.6 Hz, 3H).

Example 208: N-[[1-[3-(1,1-Difluoroethyl)-4-fluoro-phenyl]triazol-4-yl]methyl]-5-isopropyl-pyrimidin-2-amine

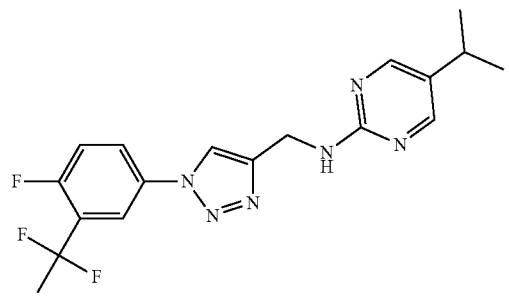 [SMILES: CC(C)c1cnc(NCc2cn(-c3ccc(F)c(C(C)(F)F)c3)nn2)nc1]

The title compound was prepared in a manner analogous to Example 154 using (1-(3-(1,1-difluoroethyl)-4-fluorophenyl)-1H-1,2,3-triazol-4-yl)methanamine (Intermediate 20) and 2-chloro-4-isopropylpyrimidine. MS (ESI): mass calcd. for $C_{18}H_{19}F_3N_6$, 376.2; m/z found, 377.2 [M+H]$^+$. $^1$H NMR (400 MHz, CD$_3$OD) δ 8.46 (s, 1H), 8.25 (s, 2H), 8.07-8.03 (m, 1H), 8.02-7.97 (m, 1H), 7.46 (t, J=9.6 Hz, 1H), 4.75 (d, J=0.7 Hz, 2H), 2.89-2.78 (m, 1H), 2.06 (td, J=18.7, 1.1 Hz, 3H), 1.27 (d, J=7.0 Hz, 6H).

Example 209: 5-Cyclopropyl-N-[[1-[3-(1,1-difluoroethyl)-4-fluoro-phenyl]triazol-4-yl]methyl]pyrimidin-2-amine

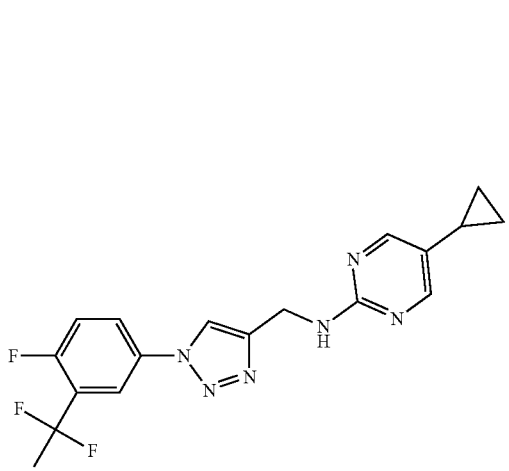 [SMILES: CC(F)(F)c1cc(-n2cc(CNc3ncc(C4CC4)cn3)nn2)ccc1F]

The title compound was prepared in a manner analogous to Example 154 using (1-(3-(1,1-difluoroethyl)-4-fluorophenyl)-1H-1,2,3-triazol-4-yl)methanamine (Intermediate 20) and 2-chloro-4-cyclopropylpyrimidine. MS (ESI): mass calcd. for $C_{18}H_{17}F_3N_6$, 374.1; m/z found, 375.1 [M+H]$^+$. $^1$H NMR (400 MHz, CD$_3$OD) δ 8.45 (s, 1H), 8.15 (s, 2H), 8.07-8.02 (m, 1H), 8.02-7.95 (m, 1H), 7.46 (t, J=9.6 Hz, 1H), 4.74 (s, 2H), 2.13-1.99 (m, 3H), 1.84-1.73 (m, 1H), 0.99-0.88 (m, 2H), 0.68-0.60 (m, 2H).

Example 210: N-[[1-[3-(1,1-Difluoroethyl)-4-fluoro-phenyl]triazol-4-yl]methyl]-4,5-dimethyl-pyrimidin-2-amine

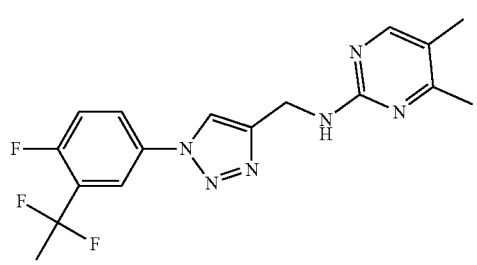 [SMILES: Cc1cnc(NCc2cn(-c3ccc(F)c(C(C)(F)F)c3)nn2)nc1C]

The title compound was prepared in a manner analogous to Example 154 using (1-(3-(1,1-difluoroethyl)-4-fluorophenyl)-1H-1,2,3-triazol-4-yl)methanamine (Intermediate 20) and 2-chloro-4,5-dimethylpyrimidine. MS (ESI): mass calcd. for $C_{17}H_{17}F_3N_6$, 362.1; m/z found, 363.1 [M+H]$^+$. $^1$H NMR (400 MHz, CD$_3$OD) δ 8.44 (s, 1H), 8.07-7.96 (m, 3H), 7.49-7.42 (m, 1H), 4.74 (s, 2H), 2.35 (s, 3H), 2.14-2.11 (m, 3H), 2.11-2.00 (m, 3H).

Example 211: N-[[1-[3-(Difluoromethyl)-4-fluoro-phenyl]triazol-4-yl]methyl]-5-methyl-pyrimidin-2-amine

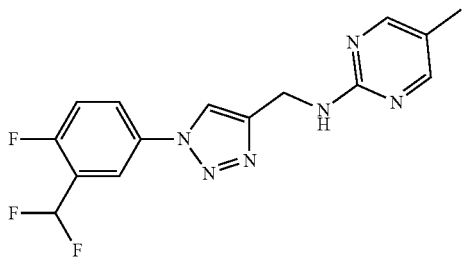 [SMILES: Cc1cnc(NCc2cn(-c3ccc(F)c(C(F)F)c3)nn2)nc1]

The title compound was prepared in a manner analogous to Example 154 using (1-(3-(difluoromethyl)-4-fluorophenyl)-1H-1,2,3-triazol-4-yl)methanamine (Intermediate 21) and 2-chloro-5-methylpyrimidine. MS (ESI): mass calcd. for $C_{15}H_{13}F_3N_6$, 334.1; m/z found, 335.1 [M+H]$^+$. $^1$H NMR (500 MHz, CDCl$_3$) δ 8.19-8.16 (m, 2H), 7.96-7.94 (m, 1H), 7.92-7.86 (m, 2H), 7.30 (t, J=9.0 Hz, 1H), 6.94 (t, J=54.7 Hz, 1H), 5.52 (s, 1H), 4.87-4.75 (m, 2H), 2.21-2.07 (m, 3H).

Example 212: 5-Chloro-N-[[1-[3-(difluoromethyl)-4-fluoro-phenyl]triazol-4-yl]methyl]pyrimidin-2-amine

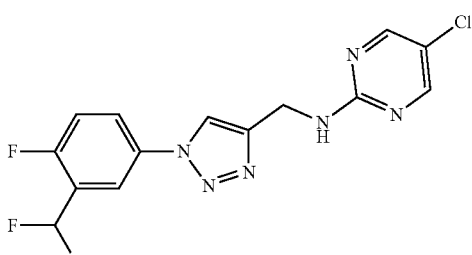

The title compound was prepared in a manner analogous to Example 154 using (1-(3-(difluoromethyl)-4-fluorophenyl)-1H-1,2,3-triazol-4-yl)methanamine (Intermediate 21) and 2,5-dichloropyrimidine. MS (ESI): mass calcd. for $C_{14}H_{10}ClF_3N_6$, 354.1; m/z found, 355.0 [M+H]$^+$. $^1$H NMR (500 MHz, CDCl$_3$) δ 8.27 (s, 2H), 7.97-7.94 (m, 1H), 7.94-7.85 (m, 2H), 7.31 (t, J=9.0 Hz, 1H), 6.94 (t, J=54.5 Hz, 1H), 5.73 (s, 1H), 4.79 (d, J=6.4 Hz, 2H).

Example 213: N-[[1-[3-(Difluoromethyl)-4-fluorophenyl]triazol-4-yl]methyl]-5-(trifluoromethyl)pyrimidin-2-amine

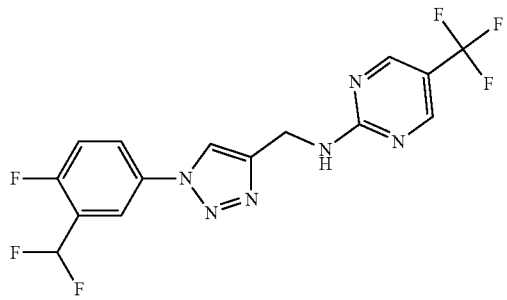 [SMILES: Fc1ccc(-n2cc(CNc3ncc(C(F)(F)F)cn3)nn2)cc1C(F)F]

The title compound was prepared in a manner analogous to Example 154 using (1-(3-(difluoromethyl)-4-fluorophenyl)-1H-1,2,3-triazol-4-yl)methanamine (Intermediate 21) and 2-chloro-5-trifluoromethylpyrimidine. MS (ESI): mass calcd. for $C_{15}H_{10}F_6N_6$, 388.1; m/z found, 389.0 [M+H]$^+$. $^1$H NMR (500 MHz, CDCl$_3$) δ 8.54 (s, 2H), 7.98 (s, 1H), 7.95-7.85 (m, 2H), 7.32 (t, J=9.0 Hz, 1H), 6.95 (t, J=54.6 Hz, 1H), 6.16 (s, 1H), 4.86 (d, J=6.5 Hz, 2H).

Example 214: 2-[2-[[1-[3-(Difluoromethyl)-4-fluoro-phenyl]triazol-4-yl]methylamino]pyrimidin-5-yl]propan-2-ol

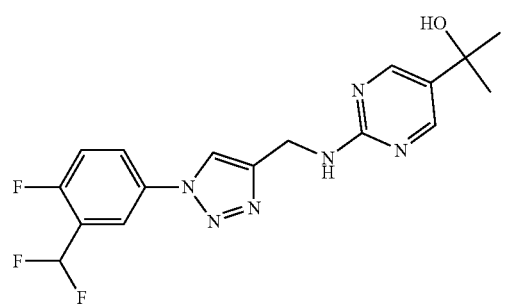 [SMILES: CC(C)(O)c1cnc(NCc2cn(-c3ccc(F)c(C(F)F)c3)nn2)nc1]

The title compound was prepared in a manner analogous to Example 154 using (1-(3-(difluoromethyl)-4-fluorophenyl)-1H-1,2,3-triazol-4-yl)methanamine (Intermediate 21) and 2-(2-chloropyrimidin-5-yl)propan-2-ol. MS (ESI): mass calcd. for $C_{17}H_{17}F_3N_6O$, 378.1; m/z found, 379.0 [M+H]$^+$. $^1$H NMR (500 MHz, CDCl$_3$) δ 8.47 (s, 2H), 7.99-7.94 (m, 1H), 7.94-7.86 (m, 2H), 7.31 (t, J=9.0 Hz, 1H), 6.94 (t, J=54.6 Hz, 1H), 5.66 (s, 1H), 4.87-4.77 (m, 2H), 1.58 (s, 6H).

Example 215. N-((1-(3-(Difluoromethyl)-4-fluorophenyl)-1H-1,2,3-triazol-4-yl)methyl)pyridin-2-amine

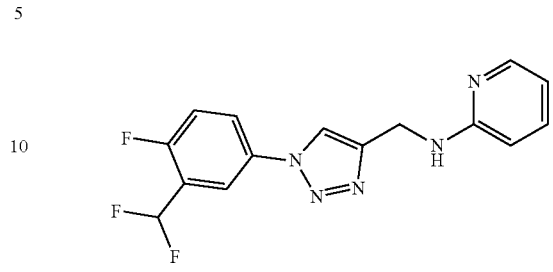

A mixture of (1-(3-(difluoromethyl)-4-fluorophenyl)-1H-1,2,3-triazol-4-yl)methanamine (Intermediate 21) (69 mg, 0.29 mmol), 2-iodopyridine (0.03 mL, 0.29 mmol), cuprous iodide (27.1 mg, 0.14 mmol), 1-(5,6,7,8-tetrahydroquinolin-8-yl)ethan-1-one (0.045 mL, 0.29 mmol), and Cs$_2$CO$_3$ (185.6 mg, 0.57 mmol) in DMF (0.9 mL) under N$_2$ in a sealed tube was stirred at rt for 16 h. The mixture was concentrated un vacuo. Purification (FCC, EtOAc/heptane from 0-100%) and re-purification (HPLC, Stationary phase: C18 XBridge 30×100 mm 5 um), Mobile phase: Gradient from 90% 10 mM NH$_4$CO$_3$H pH 9 solution in Water, 10% CH$_3$CN to 0% 10 mM NH$_4$CO$_3$H pH 9 solution in Water, 100% CH$_3$CN) afforded the title compound (12 mg, 13%). MS (ESI): mass calcd. for $C_{15}H_{12}F_3N_6$, 319.1; m/z found, 320.1 [M+H]$^+$. $^1$H NMR (500 MHz, CDCl$_3$) δ 4.77 (d, J=5.49 Hz, 2H), 5.06 (br s, 1H), 6.49 (dt, J=8.4, 0.9 Hz, 1H), 6.64 (ddd, J=7.2, 5.0, 0.9 Hz, 1H), 6.77-7.09 (m, 1H), 7.31 (t, J=9.1 Hz, 1H), 7.43 (ddd, J=8.5, 6.9, 1.9 Hz, 1H), 7.82-7.91 (m, 1H), 7.93 (dd, J=5.6, 2.8 Hz, 1H), 7.96 (s, 1H), 8.08-8.26 (m, 1H).

Example 216: N-((1-(3-(Difluoromethyl)-4-fluorophenyl)-1H-1,2,3-triazol-4-yl)methyl)-5-ethylpyrimidin-2-amine

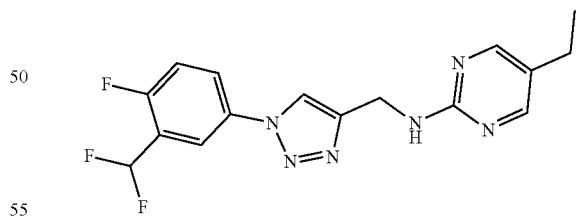

The title compound was prepared in a manner analogous to Example 153 using (1-(3-(difluoromethyl)-4-fluorophenyl)-1H-1,2,3-triazol-4-yl)methanamine (Intermediate 21) and 2-chloro-5-ethylpyrimidine. MS (ESI): mass calcd. for $C_{16}H_{15}F_3N_6$, 348.1; m/z found, 349.0 [M+H]$^+$. $^1$H NMR (300 MHz, DMSO-d$_6$) δ 8.62 (s, 1H), 8.13 (s, 2H), 8.11-7.97 (m, 2H), 7.55 (t, J=9.4 Hz, 1H), 7.45-6.88 (m, 2H), 4.53 (d, J=6.0 Hz, 2H), 2.35 (q, J=7.5 Hz, 2H), 1.05 (t, J=7.6 Hz, 3H).

Example 217: N-((1-(3-(Difluoromethyl)-4-fluorophenyl)-1H-1,2,3-triazol-4-yl)methyl)-4,5-dimethylpyrimidin-2-amine

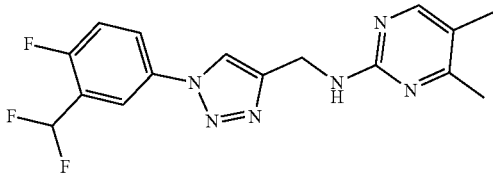 [SMILES: Cc1cnc(NCc2cn(-c3ccc(F)c(C(F)F)c3)nn2)nc1C]

The title compound was prepared in a manner analogous to Example 153 using (1-(3-(difluoromethyl)-4-fluorophenyl)-1H-1,2,3-triazol-4-yl)methanamine (Intermediate 21) and 2-chloro-4,5-dimethylpyrimidine. MS (ESI): mass calcd. for $C_{16}H_{15}F_3N_6$, 348.1; m/z found, 349.0 [M+H]$^+$. $^1$H NMR (300 MHz, DMSO-d$_6$) δ 8.66 (s, 1H), 8.15 (dd, J=12.0, 4.6 Hz, 2H), 7.99 (s, 1H), 7.62 (t, J=9.4 Hz, 1H), 7.29 (t, J=72.0, 1H), 7.24 (t, J=5.8 Hz, 1H), 4.59 (d, J=6.0 Hz, 2H), 2.24 (s, 3H), 2.03 (s, 3H).

Example 218: 5-Chloro-N-((1-(3-(difluoromethyl)-4-fluorophenyl)-1H-1,2,3-triazol-4-yl)methyl)-4-methylpyrimidin-2-amine

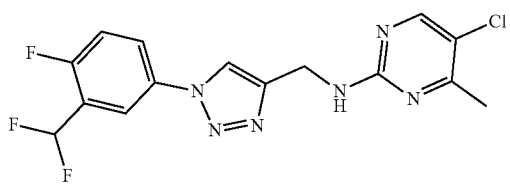 [SMILES: Cc1nc(NCc2cn(-c3ccc(F)c(C(F)F)c3)nn2)ncc1Cl]

The title compound was prepared in a manner analogous to Example 153 using (1-(3-(difluoromethyl)-4-fluorophenyl)-1H-1,2,3-triazol-4-yl)methanamine (Intermediate 21) and 2,5-dichloro-4-methylpyrimidine. MS (ESI): mass calcd. for $C_{15}H_{12}ClF_3N_6$, 368.1; m/z found, 369.0 [M+H]$^+$. $^1$H NMR (300 MHz, DMSO-d$_6$) δ 8.70 (s, 1H), 8.24 (s, 1H), 8.15 (dd, J=10.6, 4.7 Hz, 2H), 7.84 (t, J=5.6 Hz, 1H), 7.63 (t, J=9.4 Hz, 1H), 7.29 (t, J=53.9 Hz, 1H), 4.60 (d, J=5.9 Hz, 2H), 2.36 (s, 3H).

Example 219: N-((1-(3-(Difluoromethyl)-4-fluorophenyl)-1H-1,2,3-triazol-4-yl)methyl)-1-methyl-1H-pyrazol-5-amine

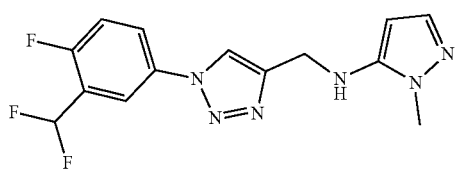 [SMILES: Cn1nccc1NCc1cn(-c2ccc(F)c(C(F)F)c2)nn1]

Step A. 1-(3-(Difluoromethyl)-4-fluorophenyl)-1H-1,2,3-triazole-4-carbaldehyde

To a solution of (1-(3-(difluoromethyl)-4-fluorophenyl)-1H-1,2,3-triazol-4-yl)methanol (Intermediate 9) (50 mg, 0.21 mmol) and sodium acetate (50.6 mg, 0.62 mmol) stirring in DCM (2 mL) was added pyridinium chlorochromate (PCC) (88.6 mg, 0.41 mmol), and the mixture was stirred at rt for 2 h. The suspension was filtered and the solvent removed under vacuum. The crude product was used without purification.

Step B. N-((1-(3-(Difluoromethyl)-4-fluorophenyl)-1H-1,2,3-triazol-4-yl)methyl)-1-methyl-1H-pyrazol-5-amine To 1-(3-(Difluoromethyl)-4-fluorophenyl)-1H-1,2,3-triazole-4-carbaldehyde (42 mg, 0.17 mmol) and 1-methyl-1H-pyrazol-5-amine (18.9 mg, 0.19 mmol) stirring in MeOH (2.2 mL) and AcOH (0.2 mL) was added NaBH$_3$CN, and the mixture was stirred at rt for 90 min. The suspension was filtered and the solvent was removed under vacuum. The residue was purified by HPLC ((Stationary phase: C18 XBridge 30×100 mm 5 um), Mobile phase: Gradient from 74% 10 mM NH$_4$CO$_3$H pH 9 solution in Water, 26% CH$_3$CN to 58% 10 mM NH$_4$CO$_3$H pH 9 solution in Water, 42% CH$_3$CN)) to afford the product (12 mg, 18%). MS (ESI): mass calcd. for $C_{14}H_{13}F_3N_6$, 322.1; m/z found, 323.1 [M+H]$^+$. $^1$H NMR (500 MHz, CDCl$_3$) δ 8.20-7.75 (m, 3H), 7.45-7.29 (m, 1H), 7.58-7.29 (m, 1H), 7.17-6.77 (m, 1H), 5.59 (s, 1H), 4.49 (s, 2H), 4.03 (br s, 1H), 3.68 (s, 3H).

Example 220: N-((1-(3-(Difluoromethyl)-4-fluorophenyl)-1H-1,2,3-triazol-4-yl)methyl)-1-methyl-1H-imidazol-2-amine

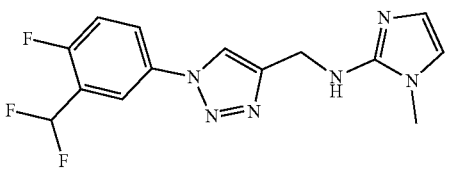 [SMILES: Cn1ccnc1NCc1cn(-c2ccc(F)c(C(F)F)c2)nn1]

The title compound was prepared in a manner analogous to Example 7 using (1-(3-(difluoromethyl)-4-fluorophenyl)-1H-1,2,3-triazol-4-yl)methanamine (Intermediate 21). MS (ESI): mass calcd. for $C_{14}H_{13}F_3N_6$, 322.1; m/z found, 323.1 [M+H]$^+$. 1H NMR (500 MHz, CDCl$_3$) δ 8.12 (s, 1H), 7.95 (dd, J=2.9, 5.8 Hz, 1H), 7.92-7.82 (m, 1H), 7.31 (t, J=9.0 Hz, 1H), 6.95 (t, J=54.6 Hz, 1H), 6.71 (d, J=1.7 Hz, 1H), 6.54 (d, J=1.4 Hz, 1H), 4.72 (d, J=6.4 Hz, 2H), 4.19 (br t, J=6.1 Hz, 1H), 3.39 (s, 3H).

Example 221: N-((1-(3-(Difluoromethoxy)-4-fluorophenyl)-1H-1,2,3-triazol-4-yl)methyl)pyridin-2-amine

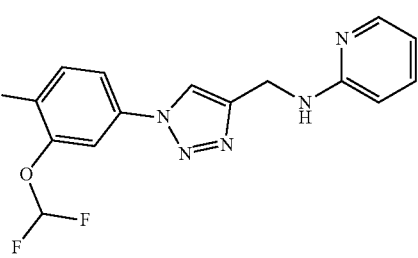

The title compound was prepared in a manner analogous to Example 215 using (1-(3-(difluoromethoxy)-4-fluorophenyl)-1H-1,2,3-triazol-4-yl)methanamine (Intermediate 18). MS (ESI): mass calcd. for $C_{15}H_{12}F_3N_5O$, 335.1; m/z found, 336.1 [M+H]$^+$. 1H NMR (500 MHz, CDCl$_3$) δ 4.75 (d, J=6.1 Hz, 2H) 5.05 (br s, 1H) 6.38-6.87 (m, 3H) 7.32 (t, J=9.3 Hz, 1H) 7.42 (ddd, J=8.5, 6.9, 1.9 Hz, 1H) 7.50-7.61 (m, 1H) 7.67 (dd, J=6.7, 2.6 Hz, 1H) 7.9 (s, 1H) 8.07-8.26 (m, 1H).

Example 222: N-((1-(3-(Difluoromethoxy)-4-fluorophenyl)-1H-1,2,3-triazol-4-yl)methyl)-5-methylpyrimidin-2-amine

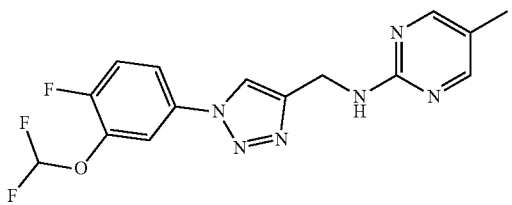 [SMILES: Cc1cnc(NCc2cn(-c3ccc(F)c(OC(F)F)c3)nn2)nc1]

The title compound was prepared in a manner analogous to Example 153 using (1-(3-(difluoromethoxy)-4-fluorophenyl)-1H-1,2,3-triazol-4-yl)methanamine (Intermediate 18) and 2-chloro-5-methylpyrimidine. MS (ESI): mass calcd. for $C_{15}H_{13}F_3N_6O$, 350.1; m/z found, 350.9 [M+H]$^+$. $^1$H NMR (300 MHz, DMSO-d$_6$) δ 8.63 (s, 1H), 8.17 (s, 2H), 8.04-7.90 (m, 1H), 7.91-7.77 (m, 1H), 7.64 (t, J=9.6 Hz, 1H), 7.46-7.35 (m, 1H), 7.38 (t, J=72.5 Hz, 1H), 4.59 (d, J=6.0 Hz, 2H), 2.06 (s, 3H).

Example 223: N-((1-(3-(Difluoromethoxy)-4-fluorophenyl)-1H-1,2,3-triazol-4-yl)methyl)-1-methyl-1H-pyrazol-5-amine

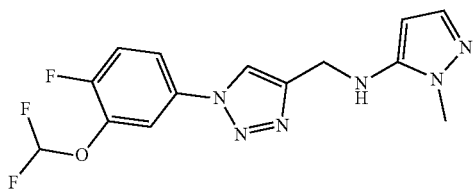 [SMILES: Cn1nccc1NCc1cn(-c2ccc(F)c(OC(F)F)c2)nn1]

The title compound was prepared in a manner analogous to Example 219 using (1-(3-(difluoromethoxy)-4-fluorophenyl)-1H-1,2,3-triazol-4-yl)methanamine (Intermediate 18) in step A. MS (ESI): mass calcd. for $C_{14}H_{13}F_3N_6O$, 338.1; m/z found, 339.1 [M+H]$^+$. $^1$H NMR (500 MHz, CDCl$_3$) δ 7.88 (s, 1H), 7.69 (dd, J=2.5, 6.5 Hz, 1H), 7.62-7.53 (m, 1H), 7.35 (t, J=9.2 Hz, 1H), 7.30 (d, J=1.2 Hz, 1H), 6.65 (t, J=72.8 Hz, 1H), 5.57 (d, J=1.7 Hz, 1H), 4.48 (s, 2H), 3.95 (br s, 1H), 3.68 (s, 3H).

Example 224: N-[(1R)-1-[1-[4-Chloro-3-(difluoromethoxy)phenyl]triazol-4-yl]ethyl]-5-methyl-pyrimidin-2-amine

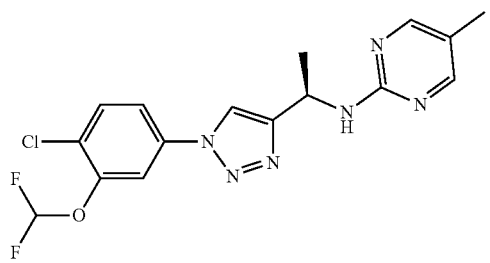 [SMILES: Cc1cnc(N[C@H](C)c2cn(-c3ccc(Cl)c(OC(F)F)c3)nn2)nc1]

The title compound was prepared in a manner analogous to Example 154 using (R)-1-(1-(4-chloro-3-(difluoromethoxy)phenyl)-1H-1,2,3-triazol-4-yl)ethan-1-amine (Intermediate 24) and 2-chloro-5-methylpyrimidine. MS (ESI): mass calcd. for $C_{16}H_{15}ClF_2N_6O$, 380.1; m/z found, 381.0 [M+H]$^+$. $^1$H NMR (500 MHz, CDCl$_3$) δ 8.17-8.11 (d, J=0.8 Hz, 2H), 7.87-7.82 (s, 1H), 7.69-7.65 (d, J=2.3 Hz, 1H), 7.61-7.51 (m, 2H), 6.78-6.45 (t, J=72.6 Hz, 1H), 5.46-5.36 (m, 2H), 2.17-2.10 (t, J=0.7 Hz, 3H), 1.77-1.68 (d, J=6.6 Hz, 3H).

Example 225: 5-Chloro-2-[[1-(4-chlorophenyl)triazol-4-yl]methoxy]pyrimidine

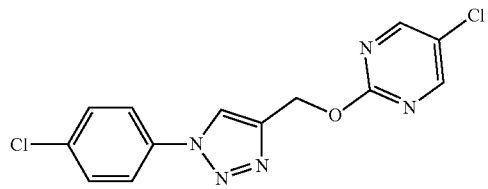 [SMILES: Clc1ccc(-n2cc(COc3ncc(Cl)cn3)nn2)cc1]

The title compound was prepared analogous to Example 155, using (1-(4-chlorophenyl)-1H-1,2,3-triazol-4-yl)methanol and 2,5-dichloropyrimidine. MS (ESI): mass calcd. for $C_{13}H_9Cl_{12}N_5O$, 321.0; m/z found, 322.0 [M+H]$^+$. $^1$H NMR (400 MHz, CDCl$_3$) δ 8.49 (s, 2H), 8.09 (s, 1H), 7.71-7.63 (m, 2H), 7.53-7.45 (m, 2H), 5.62 (d, J=0.7 Hz, 2H).

Example 226: 2-[[1-(4-Chlorophenyl)triazol-4-yl]methoxy]-5-(trifluoromethyl)pyrimidine

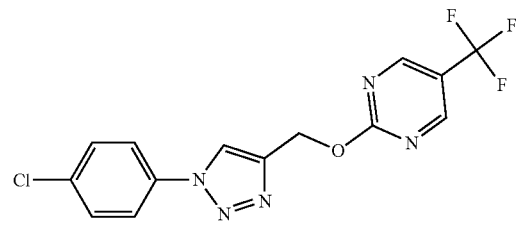 [SMILES: FC(F)(F)c1cnc(OCc2cn(-c3ccc(Cl)cc3)nn2)nc1]

The title compound was prepared analogous to Example 155, using (1-(4-chlorophenyl)-1H-1,2,3-triazol-4-yl)methanol and 2-chloro-5-trifluoromethylpyrimidine. MS (ESI): mass calcd. for $C_{14}H_9ClF_3N_5O$, 355.0; m/z found, 356.0 [M+H]$^+$. $^1$H NMR (500 MHz, CDCl$_3$) δ 8.82 (d, J=0.8 Hz, 2H), 8.11 (s, 1H), 7.71-7.66 (m, 2H), 7.54-7.49 (m, 2H), 5.73 (d, J=0.7 Hz, 2H).

Example 227: 2-[[1-(4-Chlorophenyl)triazol-4-yl]methoxy]-5-(difluoromethoxy)pyrimidine

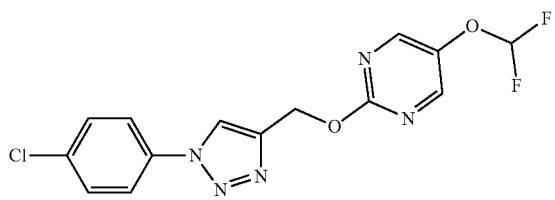 [SMILES: FC(F)Oc1cnc(OCc2cn(-c3ccc(Cl)cc3)nn2)nc1]

The title compound was prepared analogous to Example 155, using (1-(4-chlorophenyl)-1H-1,2,3-triazol-4-yl)methanol and 2-chloro-5-(difluoromethoxy)pyrimidine. MS (ESI): mass calcd. for $C_{14}H_{10}ClF_2N_5O_2$, 353.0; m/z found, 354.0 [M+H]$^+$. $^1$H NMR (500 MHz, CDCl$_3$) δ 8.46 (s, 2H), 8.12 (s, 1H), 7.73-7.68 (m, 2H), 7.55-7.50 (m, 2H), 6.55 (t, J=71.9 Hz, 1H), 5.67 (d, J=0.7 Hz, 2H).

Example 228: 2-[[1-(3-Fluorophenyl)triazol-4-yl]methoxy]pyrimidine

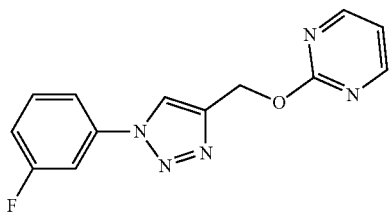 [SMILES: Fc1cccc(-n2cc(COc3ncccn3)nn2)c1]

The title compound was prepared in a manner analogous to Example 1 using (1-(3-fluorophenyl)-1H-1,2,3-triazol-4-yl)methanol (Intermediate 41) and 2-chloropyrimidine. MS (ESI): mass calcd. for $C_{13}H_{10}FN_5O$, 271.1; m/z found, 272.1 [M+H]$^+$. $^1$H NMR (500 MHz, DMSO-d$_6$) δ 8.98 (s, 1H), 8.66 (d, J=4.8 Hz, 2H), 7.87 (dt, J=10.0, 2.3 Hz, 1H), 7.82 (ddd, J=8.0, 2.0, 0.8 Hz, 1H), 7.66 (td, J=8.3, 6.3 Hz, 1H), 7.36 (tdd, J=8.6, 2.6, 0.9 Hz, 1H), 7.20 (t, J=4.8 Hz, 1H), 5.54 (d, J=0.6 Hz, 2H).

Example 229: 5-Fluoro-2-[[1-(3-fluorophenyl)triazol-4-yl]methoxy]pyrimidine

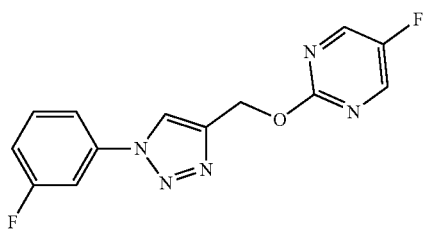 [SMILES: Fc1cnc(OCc2cn(-c3cccc(F)c3)nn2)nc1]

The title compound was prepared in a manner analogous to Example 1 using (1-(3-fluorophenyl)-1H-1,2,3-triazol-4-yl)methanol (Intermediate 41) and 2-chloro-5-fluoropyrimidine. MS (ESI): mass calcd. for $C_{13}H_9F_2N_5O$, 289.1; m/z found, 290.1 [M+H]$^+$. $^1$H NMR (500 MHz, DMSO-d$_6$) δ 8.97 (d, J=0.6 Hz, 1H), 8.75 (d, J=0.7 Hz, 2H), 7.86 (dt, J=10.0, 2.3 Hz, 1H), 7.82 (ddd, J=8.1, 2.1, 0.9 Hz, 1H), 7.66 (td, J=8.3, 6.3 Hz, 1H), 7.36 (tdd, J=8.5, 2.5, 0.9 Hz, 1H), 5.52 (d, J=0.6 Hz, 2H).

Example 230: 2-[[1-(3-Fluorophenyl)triazol-4-yl]methoxy]-5-methoxy-pyrimidine

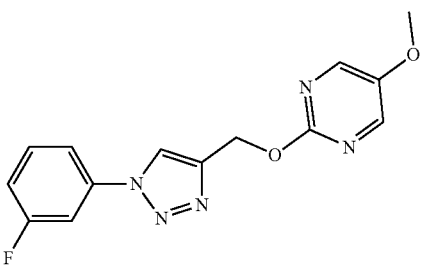 [SMILES: COc1cnc(OCc2cn(-c3cccc(F)c3)nn2)nc1]

The title compound was prepared in a manner analogous to Example 1 using (1-(3-fluorophenyl)-1H-1,2,3-triazol-4-yl)methanol (Intermediate 41) and 2-chloro-5-methoxypyrimidine. MS (ESI): mass calcd. for $C_{14}H_{12}FN_5O_2$, 301.1; m/z found, 302.1 [M+H]$^+$. $^1$H NMR (500 MHz, DMSO-d$_6$) δ 8.96 (d, J=0.6 Hz, 1H), 8.41 (s, 2H), 7.91-7.78 (m, 2H), 7.65 (td, J=8.2, 6.3 Hz, 1H), 7.36 (tdd, J=8.5, 2.5, 0.9 Hz, 1H), 5.47 (d, J=0.5 Hz, 2H), 3.86 (s, 3H).

Example 231: 5-Chloro-2-[[1-(3-fluorophenyl)triazol-4-yl]methoxy]pyrimidine

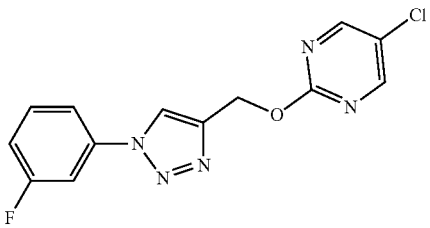 [SMILES: Fc1cccc(-n2cc(COc3ncc(Cl)cn3)nn2)c1]

The title compound was prepared in a manner analogous to Example 1 using (1-(3-fluorophenyl)-1H-1,2,3-triazol-4-yl)methanol (Intermediate 41) and 2,5-dichloropyrimidine. MS (ESI): mass calcd. for $C_{13}H_9ClFN_5O$, 305.0; m/z found, 306.0 [M+H]$^+$. $^1$H NMR (500 MHz, DMSO-d$_6$) δ 8.97 (d, J=0.7 Hz, 1H), 8.77 (s, 2H), 7.86 (dt, J=10.0, 2.3 Hz, 1H), 7.82 (ddd, J=8.1, 2.1, 0.9 Hz, 1H), 7.66 (td, J=8.3, 6.3 Hz, 1H), 7.36 (tdd, J=8.5, 2.5, 0.9 Hz, 1H), 5.55 (d, J=0.5 Hz, 2H).

Example 232: 2-[[1-(3-Fluorophenyl)triazol-4-yl]methoxy]-5-methyl-pyrimidine

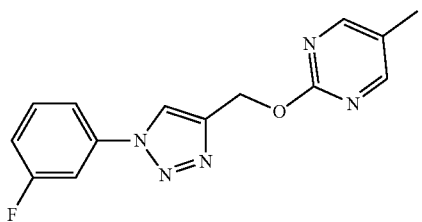 [SMILES: Cc1cnc(OCc2cn(-c3cccc(F)c3)nn2)nc1]

The title compound was prepared in a manner analogous to Example 1 using (1-(3-fluorophenyl)-1H-1,2,3-triazol-4-yl)methanol (Intermediate 41) and 2-chloro-5-methylpyrimidine. MS (ESI): mass calcd. for $C_{14}H_{12}FN_5O$, 285.1; m/z found, 286.1 [M+H]$^+$. $^1$H NMR (400 MHz, DMSO-d$_6$) δ 8.97 (s, 1H), 8.49 (d, J=0.9 Hz, 2H), 7.87 (dt, J=10.0, 2.3 Hz, 1H), 7.82 (ddd, J=8.1, 2.2, 0.9 Hz, 1H), 7.65 (td, J=8.2, 6.2 Hz, 1H), 7.36 (tdd, J=8.5, 2.5, 0.9 Hz, 1H), 5.50 (s, 2H), 2.21 (s, 3H).

Example 233: 5-Ethyl-2-[[1-(3-fluorophenyl)triazol-4-yl]methoxy]pyrimidine

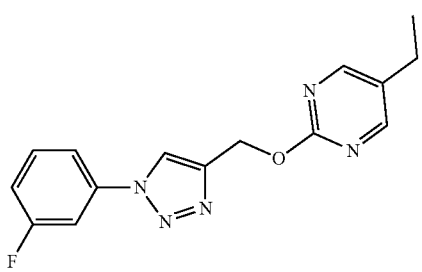 [SMILES: CCc1cnc(OCc2cn(-c3cccc(F)c3)nn2)nc1]

The title compound was prepared in a manner analogous to Example 1 using (1-(3-fluorophenyl)-1H-1,2,3-triazol-4-yl)methanol (Intermediate 41) and 2-chloro-5-ethylpyrimidine. MS (ESI): mass calcd. for $C_{15}H_{14}FN_5O$, 299.1; m/z found, 300.2 [M+H]$^+$. $^1$H NMR (400 MHz, DMSO-d$_6$) δ 8.97 (s, 1H), 8.53 (s, 2H), 7.87 (dt, J=10.0, 2.3 Hz, 1H), 7.82 (ddd, J=8.1, 2.0, 0.9 Hz, 1H), 7.65 (td, J=8.2, 6.2 Hz, 1H), 7.36 (tdd, J=8.5, 2.5, 0.9 Hz, 1H), 5.50 (s, 2H), 2.57 (q, J=7.6 Hz, 2H), 1.19 (t, J=7.6 Hz, 3H).

Example 234: 2-[[1-(3-Bromophenyl)triazol-4-yl]methoxy]-5-methyl-pyrimidine

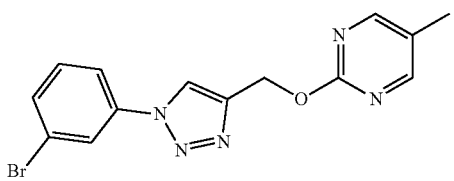 [SMILES: Cc1cnc(OCc2cn(-c3cccc(Br)c3)nn2)nc1]

The title compound was prepared in a manner analogous to Example 1 using (1-(3-bromophenyl)-1H-1,2,3-triazol-4-yl)methanol and 2-chloro-5-methylpyrimidine. MS (ESI): mass calcd. for $C_{14}H_{12}BrN_5O$, 345.0; m/z found, 348.0 [M+H]$^+$. $^1$H NMR (300 MHz, CDCl$_3$) δ 8.38 (s, 2H), 8.11 (s, 1H), 7.96-7.91 (m, 1H), 7.68 (dd, J=8.1, 1.0 Hz, 1H), 7.57 (dd, J=8.0, 0.5 Hz, 1H), 7.39 (t, J=8.1 Hz, 1H), 5.63 (s, 2H), 2.26 (s, 3H).

Example 235: 2-[[1-(3-Bromophenyl)triazol-4-yl]methoxy]-4-methyl-pyrimidine

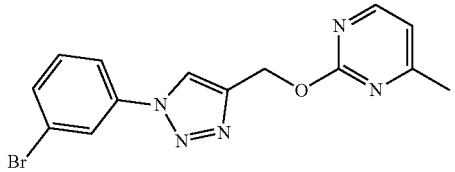 [SMILES: Cc1ccnc(OCc2cn(-c3cccc(Br)c3)nn2)n1]

The title compound was prepared in a manner analogous to Example 1 using (1-(3-bromophenyl)-1H-1,2,3-triazol-4-yl)methanol and 2-chloro-4-methylpyrimidine. MS (ESI): mass calcd. for $C_{14}H_{12}BrN_5O$, 345.0; m/z found, 347.9 [M+H]$^+$. $^1$H NMR (300 MHz, CDCl$_3$) δ 8.40 (d, J=5.0 Hz, 1H), 8.12 (s, 1H), 7.94 (s, 1H), 7.68 (d, J=8.0 Hz, 1H), 7.57 (d, J=8.1 Hz, 1H), 7.40 (t, J=8.1 Hz, 1H), 6.86 (d, J=5.0 Hz, 1H), 5.65 (s, 2H), 2.49 (s, 3H).

Example 236: 2-[[1-(o-Tolyl)triazol-4-yl]methoxy]pyrimidine

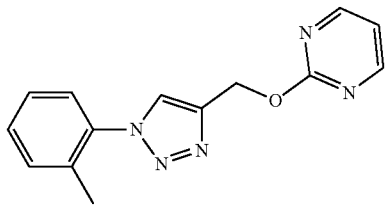 [SMILES: Cc1ccccc1-n1cc(COc2ncccn2)nn1]

The title compound was prepared in a manner analogous to Example 1 using (1-(2-methylphenyl)-1H-1,2,3-triazol-4-yl)methanol (Intermediate 38) and 2-chloropyrimidine. MS (ESI): mass calcd. for $C_{14}H_{13}N_5O$, 267.1; m/z found, 268.1 [M+H]$^+$. $^1$H NMR (500 MHz, DMSO-d$_6$) δ 8.66 (d, J=4.8 Hz, 2H), 8.60 (s, 1H), 7.52-7.39 (m, 4H), 7.20 (t, J=4.8 Hz, 1H), 5.53 (s, 2H), 2.15 (s, 3H).

Example 237: 5-Fluoro-2-[[1-(o-tolyl)triazol-4-yl]methoxy]pyrimidine

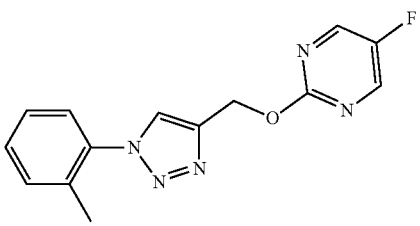 [SMILES: Cc1ccccc1-n1cc(COc2ncc(F)cn2)nn1]

The title compound was prepared in a manner analogous to Example 1 using (1-(2-methylphenyl)-1H-1,2,3-triazol- 4-yl)methanol (Intermediate 38) and 2-chloro-5-fluoropyrimidine. MS (ESI): mass calcd. for $C_{14}H_{12}FN_5O$, 285.1; m/z found, 286.1 [M+H]$^+$. $^1$H NMR (500 MHz, DMSO-d$_6$) δ 8.75 (d, J=0.7 Hz, 2H), 8.60 (s, 1H), 7.55-7.35 (m, 4H), 5.51 (s, 2H), 2.15 (s, 3H).

Example 238: 5-Methoxy-2-[[1-(o-tolyl)triazol-4-yl]methoxy]pyrimidine

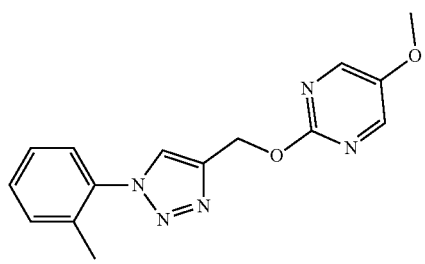 [SMILES: COc1cnc(OCc2cn(-c3ccccc3C)nn2)nc1]

The title compound was prepared in a manner analogous to Example 1 using (1-(2-methylphenyl)-1H-1,2,3-triazol-4-yl)methanol (Intermediate 38) and 2-chloro-5-methoxypyrimidine. MS (ESI): mass calcd. for $C_{15}H_{15}N_5O_2$, 297.1; m/z found, 298.1[M+H]$^+$. $^1$H NMR (500 MHz, DMSO-d$_6$) δ 8.57 (s, 1H), 8.41 (s, 2H), 7.59-7.37 (m, 4H), 5.46 (s, 2H), 3.86 (s, 3H), 2.15 (s, 3H).

Example 239: 5-Chloro-2-[[1-(o-tolyl)triazol-4-yl]methoxy]pyrimidine

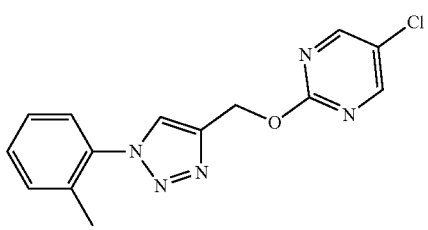 [SMILES: Cc1ccccc1-n1cc(COc2ncc(Cl)cn2)nn1]

The title compound was prepared in a manner analogous to Example 1 using (1-(2-methylphenyl)-1H-1,2,3-triazol-4-yl)methanol (Intermediate 38) and 2,5-dichloropyrimidine. MS (ESI): mass calcd. for $C_{14}H_{12}ClN_5O$, 301.1; m/z found, 302.1 [M+H]$^+$. $^1$H NMR (500 MHz, DMSO-d$_6$) δ 8.76 (s, 2H), 8.61 (s, 1H), 7.56-7.36 (m, 4H), 5.54 (s, 2H), 2.15 (s, 3H).

Example 240: 5-Methyl-2-[[1-(o-tolyl)triazol-4-yl]methoxy]pyrimidine

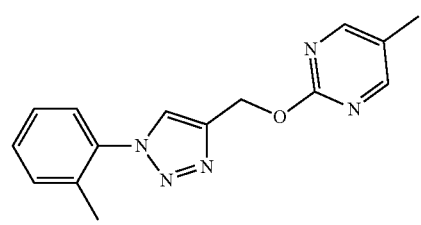 [SMILES: Cc1cnc(OCc2cn(-c3ccccc3C)nn2)nc1]

The title compound was prepared in a manner analogous to Example 1 using (1-(2-methylphenyl)-1H-1,2,3-triazol-4-yl)methanol (Intermediate 38) and 2-chloro-5-methylpyrimidine. MS (ESI): mass calcd. for $C_{15}H_{15}N_5O$, 281.1; m/z found, 282.2 [M+H]$^+$. $^1$H NMR (500 MHz, DMSO-d$_6$) δ 8.58 (s, 1H), 8.49 (d, J=0.8 Hz, 2H), 7.56-7.37 (m, 4H), 5.49 (s, 2H), 2.21 (d, J=0.8 Hz, 3H), 2.15 (s, 3H).

Example 241: 5-Ethyl-2-[[1-(o-tolyl)triazol-4-yl]methoxy]pyrimidine

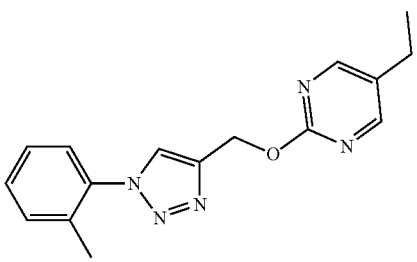 [SMILES: CCc1cnc(OCc2cn(-c3ccccc3C)nn2)nc1]

The title compound was prepared in a manner analogous to Example 1 using (1-(2-methylphenyl)-1H-1,2,3-triazol-4-yl)methanol (Intermediate 38) and 2-chloro-5-ethylpyrimidine. MS (ESI): mass calcd. for $C_{16}H_{17}N_5O$, 295.1; m/z found, 296.1[M+H]$^+$. $^1$H NMR (500 MHz, DMSO-d$_6$) δ 8.58 (s, 1H), 8.52 (d, J=0.6 Hz, 2H), 7.55-7.37 (m, 4H), 5.50 (s, 2H), 2.57 (q, J=7.6 Hz, 2H), 2.15 (s, 3H), 1.19 (t, J=7.6 Hz, 3H).

Example 242: 2-[[1-(m-Tolyl)triazol-4-yl]methoxy]pyrimidine

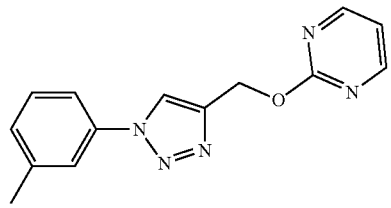 [SMILES: Cc1cccc(-n2cc(COc3ncccn3)nn2)c1]

The title compound was prepared in a manner analogous to Example 1 using (1-(m-Tolyl)-1H-1,2,3-triazol-4-yl)methanol (Intermediate 32) and 2-chloropyrimidine. MS (ESI): mass calcd. for $C_{14}H_{13}N_5O$, 267.1; m/z found, 268.1 [M+H]$^+$. $^1$H NMR (500 MHz, DMSO-d$_6$) δ 8.89 (s, 1H), 8.66 (d, J=4.7 Hz, 2H), 7.76 (td, J=1.8, 0.9 Hz, 1H), 7.70 (dt, J=7.9, 1.6 Hz, 1H), 7.48 (t, J=7.8 Hz, 1H), 7.32 (ddt, J=7.6, 1.7, 0.9 Hz, 1H), 7.20 (t, J=4.8 Hz, 1H), 5.52 (s, 2H), 2.42 (d, J=0.7 Hz, 3H)

Example 243: 5-Methyl-2-[[1-(m-tolyl)triazol-4-yl]methoxy]pyrimidine

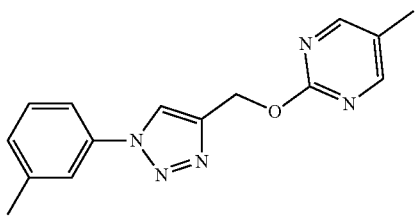 [SMILES: Cc1cnc(OCc2cn(-c3cccc(C)c3)nn2)nc1]

The title compound was prepared in a manner analogous to Example 1 using (1-(m-tolyl)-1H-1,2,3-triazol-4-yl)methanol (Intermediate 32) and 2-chloro-5-methylpyrimidine. MS (ESI): mass calcd. for $C_{15}H_{15}N_5O$, 281.1; m/z found, 282.2 [M+H]$^+$. $^1$H NMR (400 MHz, DMSO-d$_6$) δ 8.87 (s, 1H), 8.49 (d, J=0.9 Hz, 2H), 7.75 (d, J=1.9 Hz, 1H), 7.69 (dd, J=8.0, 2.2 Hz, 1H), 7.47 (t, J=7.8 Hz, 1H), 7.37-7.26 (m, 1H), 5.49 (s, 2H), 2.41 (s, 3H), 2.21 (s, 3H).

Example 244: 4-Methyl-2-[[1-(m-tolyl)triazol-4-yl]methoxy]pyrimidine

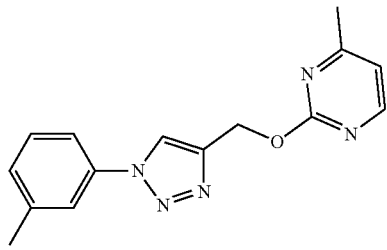 [SMILES: Cc1cccc(-n2cc(COc3nccc(C)n3)nn2)c1]

The title compound was prepared in a manner analogous to Example 1 using (1-(m-tolyl)-1H-1,2,3-triazol-4-yl)methanol (Intermediate 32) and 2-chloro-4-methylpyrimidine. MS (ESI): mass calcd. for $C_{15}H_{15}N_5O$, 281.1; m/z found, 282.2 [M+H]$^+$. $^1$H NMR (400 MHz, DMSO-d$_6$) δ 8.87 (s, 1H), 8.49 (d, J=5.0 Hz, 1H), 7.76 (d, J=2.1 Hz, 1H), 7.70 (dd, J=8.0, 2.1 Hz, 1H), 7.48 (t, J=7.8 Hz, 1H), 7.32 (d, J=7.6 Hz, 1H), 7.07 (d, J=4.9 Hz, 1H), 5.50 (s, 2H), 2.42 (d, J=5.7 Hz, 6H).

Example 245: 5-Ethyl-2-[[1-(m-tolyl)triazol-4-yl]methoxy]pyrimidine

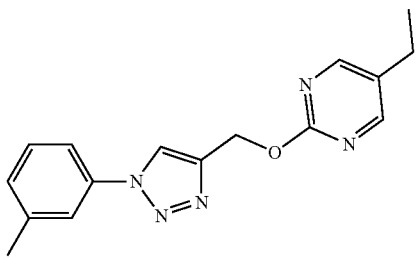 [SMILES: CCc1cnc(OCc2cn(-c3cccc(C)c3)nn2)nc1]

The title compound was prepared in a manner analogous to Example 1 using (1-(m-tolyl)-1H-1,2,3-triazol-4-yl)methanol (Intermediate 32) and 2-chloro-5-ethylpyrimidine. MS (ESI): mass calcd. for $C_{16}H_{17}N_5O$, 295.1; m/z found, 296.1[M+H]$^+$. $^1$H NMR (500 MHz, DMSO-d$_6$) δ 8.87 (s, 1H), 8.53 (d, J=0.6 Hz, 2H), 7.79-7.73 (m, 1H), 7.70 (ddt, J=8.2, 1.7, 0.8 Hz, 1H), 7.47 (t, J=7.9 Hz, 1H), 7.31 (ddt, J=7.7, 1.8, 0.9 Hz, 1H), 5.55-5.41 (m, 2H), 2.57 (q, J=7.6 Hz, 2H), 2.41 (s, 3H), 1.19 (t, J=7.6 Hz, 3H).

Example 246: 5-Chloro-2-[[1-(m-tolyl)triazol-4-yl]methoxy]pyrimidine

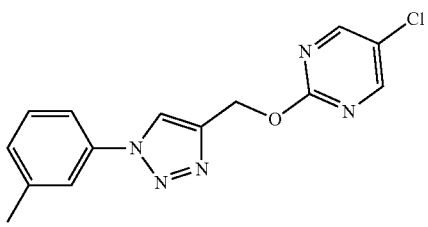 [SMILES: Cc1cccc(-n2cc(COc3ncc(Cl)cn3)nn2)c1]

The title compound was prepared in a manner analogous to Example 1 using (1-(m-tolyl)-1H-1,2,3-triazol-4-yl)methanol (Intermediate 32) and 2,5-dichloropyrimidine. MS (ESI): mass calcd. for $C_{14}H_{12}ClN_5O$, 301.1; m/z found, 302.1 [M+H]$^+$. $^1$H NMR (500 MHz, DMSO-d$_6$) δ 8.88 (s, 1H), 8.77 (s, 2H), 7.75 (dq, J=2.2, 1.1 Hz, 1H), 7.72-7.66 (m, 1H), 7.48 (t, J=7.8 Hz, 1H), 7.32 (ddt, J=7.6, 1.7, 0.8 Hz, 1H), 5.53 (d, J=0.6 Hz, 2H), 2.42 (d, J=0.7 Hz, 3H).

Example 247: 5-Fluoro-2-[[1-(m-tolyl)triazol-4-yl]methoxy]pyrimidine

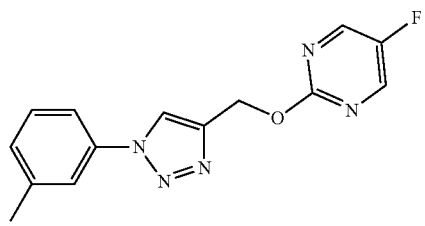 [SMILES: Cc1cccc(-n2cc(COc3ncc(F)cn3)nn2)c1]

The title compound was prepared in a manner analogous to Example 1 using (1-(m-tolyl)-1H-1,2,3-triazol-4-yl)methanol (Intermediate 32) and 2-chloro-5-fluoropyrimidine. MS (ESI): mass calcd. for $C_{14}H_{12}FN_5O$, 285.1; m/z found, 286.1 [M+H]$^+$. $^1$H NMR (500 MHz, DMSO-d$_6$) δ 8.88 (s, 1H), 8.75 (d, J=0.7 Hz, 2H), 7.75 (tq, J=1.5, 0.7 Hz, 1H), 7.69 (ddt, J=8.1, 2.3, 0.9 Hz, 1H), 7.48 (t, J=7.8 Hz, 1H), 7.32 (ddt, J=7.6, 1.8, 0.9 Hz, 1H), 5.51 (s, 2H), 2.42 (d, J=0.7 Hz, 3H)

Example 248: 5-Methoxy-2-[[1-(m-tolyl)triazol-4-yl]methoxy]pyrimidine

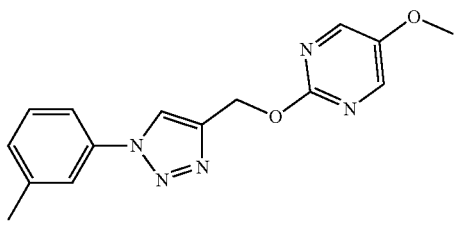 [SMILES: COc1cnc(OCc2cn(-c3cccc(C)c3)nn2)nc1]

The title compound was prepared in a manner analogous to Example 1 using (1-(m-tolyl)-1H-1,2,3-triazol-4-yl)methanol (Intermediate 32) and 2-chloro-5-methoxypyrimidine. MS (ESI): mass calcd. for $C_{15}H_{15}N_5O_2$, 297.1; m/z found, 298.2 [M+H]$^+$. $^1$H NMR (500 MHz, DMSO-d$_6$) δ 8.86 (s, 1H), 8.41 (s, 2H), 7.75 (d, J=1.9 Hz, 1H), 7.69 (dd, J=8.1, 2.2 Hz, 1H), 7.47 (t, J=7.8 Hz, 1H), 7.31 (ddt, J=7.6, 1.8, 0.9 Hz, 1H), 5.46 (s, 2H), 3.86 (s, 3H), 2.42 (s, 3H).

Example 249: 2-[2-[[1-(m-Tolyl)triazol-4-yl]methoxy]pyrimidin-5-yl]propan-2-ol

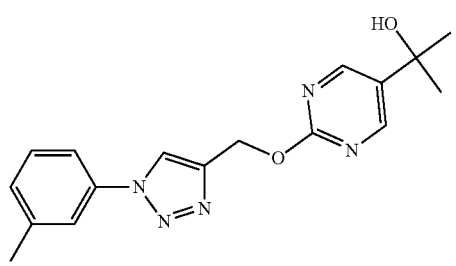 [SMILES: Cc1cccc(-n2cc(COc3ncc(C(C)(C)O)cn3)nn2)c1]

The title compound was prepared in a manner analogous to Example 1 using (1-(m-tolyl)-1H-1,2,3-triazol-4-yl)methanol (Intermediate 32) and 2-(2-chloropyrimidin-5-yl)propan-2-ol. MS (ESI): mass calcd. for $C_{17}H_{19}N_5O_2$, 325.2; m/z found, 326.3 [M+H]$^+$. $^1$H NMR (500 MHz, CD$_3$OD) δ 8.72 (d, J=3.0 Hz, 2H), 8.64 (d, J=2.9 Hz, 1H), 7.68 (d, J=2.0 Hz, 1H), 7.62 (dd, J=8.1, 2.2 Hz, 1H), 7.44 (t, J=7.8 Hz, 1H), 7.31 (d, J=7.7 Hz, 1H), 4.89 (d, J=2.8 Hz, 2H), 2.45 (s, 3H), 1.58 (d, J=3.2 Hz, 6H).

Example 250: 4-(Methoxymethyl)-2-[[1-(m-tolyl)triazol-4-yl]methoxy]pyrimidine

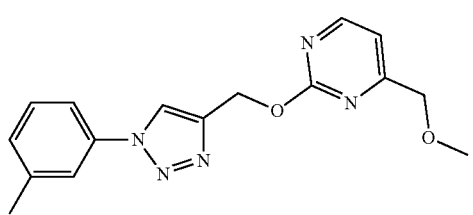 [SMILES: COCc1ccnc(OCc2cn(-c3cccc(C)c3)nn2)n1]

The title compound was prepared in a manner analogous to Example 1 using (1-(m-tolyl)-1H-1,2,3-triazol-4-yl)methanol (Intermediate 32) and 2-chloro-4-(methoxymethyl)pyrimidine. MS (ESI): mass calcd. for $C_{16}H_{17}N_5O_2$, 311.1; m/z found, 312.2 [M+H]$^+$. $^1$H NMR (500 MHz, CD$_3$OD) δ 8.62 (s, 1H), 8.56 (dd, J=5.1, 1.4 Hz, 1H), 7.65 (d, J=2.0 Hz, 1H), 7.60 (dd, J=8.1, 2.1 Hz, 1H), 7.42 (t, J=7.8 Hz, 1H), 7.29 (d, J=7.7 Hz, 1H), 7.20 (d, J=5.1 Hz, 1H), 5.59 (s, 2H), 4.50 (s, 2H), 3.48 (m, J=1.5 Hz, 3H), 2.43 (s, 3H).

Example 251: 4,5-Dimethyl-2-[[1-(m-tolyl)triazol-4-yl]methoxy]pyrimidine

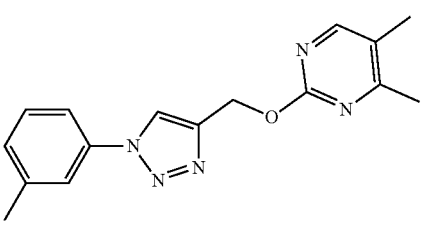 [SMILES: Cc1cccc(-n2cc(COc3ncc(C)c(C)n3)nn2)c1]

The title compound was prepared in a manner analogous to Example 1 using (1-(m-tolyl)-1H-1,2,3-triazol-4-yl)methanol (Intermediate 32) and 2-chloro-4,5-dimethylpyrimidine. MS (ESI): mass calcd. for $C_{16}H_{17}N_5O$, 295.1; m/z found, 296.1 [M+H]$^+$. $^1$H NMR (400 MHz, DMSO-d$_6$) δ 8.85 (s, 1H), 8.30 (d, J=1.0 Hz, 1H), 7.75 (d, J=2.1 Hz, 1H), 7.69 (d, J=8.1 Hz, 1H), 7.47 (t, J=7.8 Hz, 1H), 7.35-7.28 (m, 1H), 5.46 (s, 2H), 2.41 (s, 3H), 2.39 (s, 3H), 2.16 (s, 3H).

Example 252: 5-Fluoro-4-methyl-2-[[1-(m-tolyl)triazol-4-yl]methoxy]pyrimidine

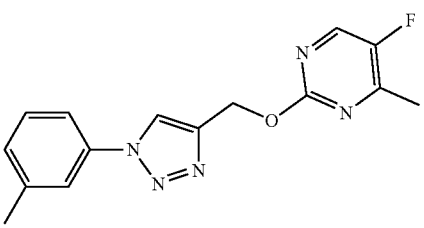 [SMILES: Cc1cccc(-n2cc(COc3ncc(F)c(C)n3)nn2)c1]

The title compound was prepared in a manner analogous to Example 1 using (1-(m-tolyl)-1H-1,2,3-triazol-4-yl)methanol (Intermediate 32) and 2-chloro-4-methyl-5-fluoropyrimidine. MS (ESI): mass calcd. for $C_{15}H_{14}FN_5O$, 299.1; m/z found, 300.2 [M+H]$^+$. $^1$H NMR (400 MHz, DMSO-d$_6$) δ 8.86 (s, 1H), 8.56 (d, J=1.5 Hz, 1H), 7.76 (d, J=2.1 Hz, 1H), 7.69 (dd, J=7.9, 2.2 Hz, 1H), 7.48 (td, J=7.8, 5.0 Hz, 1H), 7.32 (d, J=7.5 Hz, 1H), 5.48 (s, 2H), 2.44 (d, J=2.6 Hz, 3H), 2.42 (s, 3H)

Example 253: 5-Chloro-4-methyl-2-[[1-(m-tolyl)triazol-4-yl]methoxy]pyrimidine

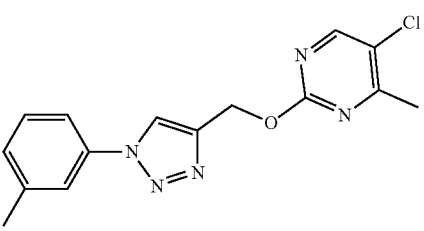 [SMILES: Cc1cccc(-n2cc(COc3ncc(Cl)c(C)n3)nn2)c1]

The title compound was prepared in a manner analogous to Example 1 using (1-(m-tolyl)-1H-1,2,3-triazol-4-yl)methanol (Intermediate 32) and 2,5-dichloro-4-methylpyrimidine. MS (ESI): mass calcd. for $C_{15}H_{14}ClN_5O$, 315.1; m/z found, 316.1 [M+H]$^+$. $^1$H NMR (500 MHz, DMSO-d$_6$) δ 8.88 (s, 1H), 8.63 (d, J=1.3 Hz, 1H), 7.76 (s, 1H), 7.69 (d, J=8.2 Hz, 1H), 7.48 (t, J=7.7 Hz, 1H), 7.32 (d, J=7.8 Hz, 1H), 5.51 (s, 2H), 2.43 (d, J=8.5 Hz, 6H).

Example 254: 5-Methyl-2-[[1-(m-tolyl)triazol-4-yl]methoxy]pyrimidin-4-amine

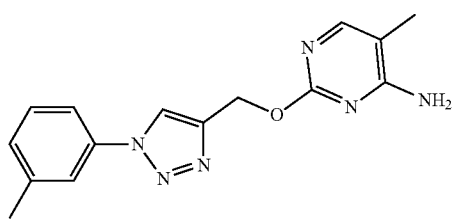 [SMILES: Cc1cccc(-n2cc(COc3ncc(C)c(N)n3)nn2)c1]

The title compound was prepared in a manner analogous to Example 1 using (1-(m-tolyl)-1H-1,2,3-triazol-4-yl)methanol (Intermediate 32) and 2-chloro-5-methylpyrimidin-4-amine. MS (ESI): mass calcd. for $C_{15}H_{16}N_6O$, 296.1; m/z found, 297.2 [M+H]$^+$. $^1$H NMR (500 MHz, DMSO-d$_6$) δ 8.84 (s, 1H), 7.78-7.72 (m, 2H), 7.69 (d, J=8.6 Hz, 1H), 7.47 (t, J=7.8 Hz, 1H), 7.37-7.25 (m, 1H), 6.76 (s, 2H), 5.33 (s, 2H), 2.41 (s, 3H), 1.92 (d, J=0.9 Hz, 3H).

Example 255: 1-[2-[[1-(m-Tolyl)triazol-4-yl]methoxy]pyrimidin-5-yl]ethanone

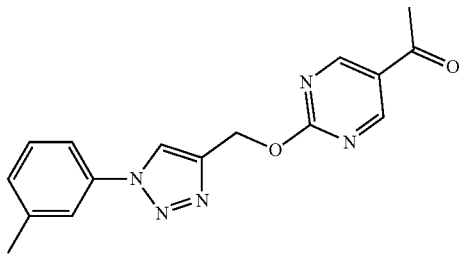 [SMILES: CC(=O)c1cnc(OCc2cn(-c3cccc(C)c3)nn2)nc1]

The title compound was prepared in a manner analogous to Example 1 using (1-(m-tolyl)-1H-1,2,3-triazol-4-yl)methanol (Intermediate 32) and 1-(2-chloropyrimidin-5-yl)ethan-1-one. MS (ESI): mass calcd. for $C_{16}H_{15}N_5O_2$, 309.1; m/z found, 310.1 [M+H]$^+$. $^1$H NMR (400 MHz, CD$_3$OD) δ 9.17 (s, 2H), 8.68 (s, 1H), 7.71 (s, 1H), 7.65 (d, J=8.2 Hz, 1H), 7.47 (t, J=7.9 Hz, 1H), 7.35 (d, J=7.6 Hz, 1H), 5.74 (s, 2H), 2.62 (d, J=3.2 Hz, 3H), 2.48 (s, 3H).

Example 256: 2-[[1-(p-Tolyl)triazol-4-yl]methoxy]pyrimidine

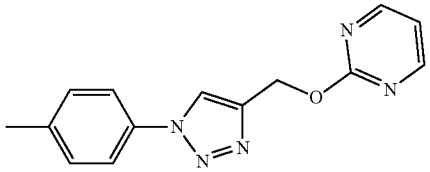 [SMILES: Cc1ccc(-n2cc(COc3ncccn3)nn2)cc1]

The title compound was prepared in a manner analogous to Example 1 using (1-(p-tolyl)-1H-1,2,3-triazol-4-yl)methanol (Intermediate 33) and 2-chloropyrimidine. MS (ESI): mass calcd. for $C_{14}H_{13}N_5O$, 267.1; m/z found, 268.1 [M+H]$^+$. $^1$H NMR (500 MHz, DMSO-d$_6$) δ 8.86 (s, 1H), 8.66 (d, J=4.8 Hz, 2H), 7.85-7.73 (m, 2H), 7.47-7.35 (m, 2H), 7.20 (t, J=4.8 Hz, 1H), 5.52 (s, 2H), 2.38 (s, 3H).

Example 257: 5-Fluoro-2-[[1-(p-tolyl)triazol-4-yl]methoxy]pyrimidine

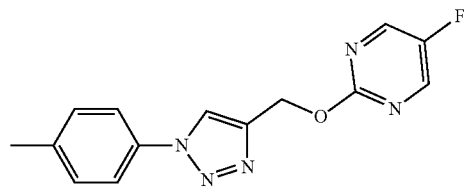 [SMILES: Cc1ccc(-n2cc(COc3ncc(F)cn3)nn2)cc1]

The title compound was prepared in a manner analogous to Example 1 using (1-(p-tolyl)-1H-1,2,3-triazol-4-yl)methanol (Intermediate 33) and 2-chloro-5-fluoropyrimidine. MS (ESI): mass calcd. for $C_{14}H_{12}FN_5O$, 285.1; m/z found, 286.1 [M+H]$^+$. $^1$H NMR (500 MHz, DMSO-d$_6$) δ 8.86 (s, 1H), 8.74 (d, J=0.7 Hz, 2H), 7.84-7.72 (m, 2H), 7.44-7.34 (m, 2H), 5.57-5.43 (m, 2H), 2.38 (s, 3H).

Example 258: 5-Methoxy-2-[[1-(p-tolyl)triazol-4-yl]methoxy]pyrimidine

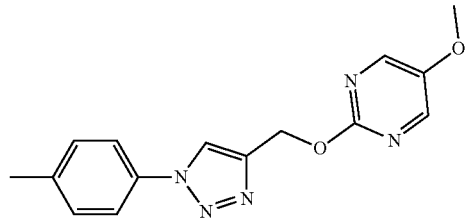 [SMILES: COc1cnc(OCc2cn(-c3ccc(C)cc3)nn2)nc1]

The title compound was prepared in a manner analogous to Example 1 using (1-(p-tolyl)-1H-1,2,3-triazol-4-yl)methanol (Intermediate 33) and 2-chloro-5-methoxypyrimidine. MS (ESI): mass calcd. for $C_{15}H_{15}N_5O_2$, 297.1; m/z found, 298.1 [M+H]$^+$. $^1$H NMR (500 MHz, DMSO-d$_6$) δ 8.84 (s, 1H), 8.41 (s, 2H), 7.88-7.72 (m, 2H), 7.46-7.30 (m, 2H), 5.45 (d, J=0.5 Hz, 2H), 3.86 (s, 3H), 2.38 (s, 3H).

Example 259: 5-Chloro-2-[[1-(p-tolyl)triazol-4-yl]methoxy]pyrimidine

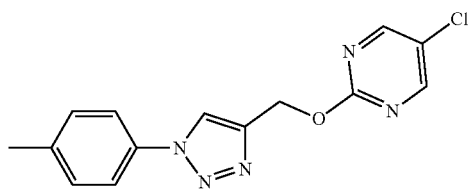 [SMILES: Cc1ccc(-n2cc(COc3ncc(Cl)cn3)nn2)cc1]

The title compound was prepared in a manner analogous to Example 1 using (1-(p-tolyl)-1H-1,2,3-triazol-4-yl)methanol (Intermediate 33) and 2,5-dichloropyrimidine. MS (ESI): mass calcd. for $C_{14}H_{12}ClN_5O$, 301.1; m/z found, 302.1 [M+H]$^+$. $^1$H NMR (500 MHz, DMSO-d$_6$) δ 8.86 (s, 1H), 8.76 (s, 2H), 7.84-7.69 (m, 2H), 7.44-7.29 (m, 2H), 5.53 (d, J=0.5 Hz, 2H), 2.38 (s, 3H).

Example 260: 5-Methyl-2-[[1-(p-tolyl)triazol-4-yl]methoxy]pyrimidine

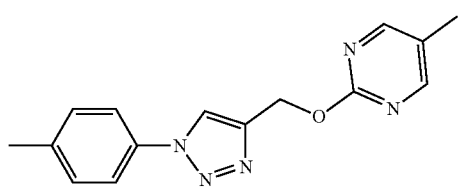

The title compound was prepared in a manner analogous to Example 1 using (1-(p-tolyl)-1H-1,2,3-triazol-4-yl)methanol (Intermediate 33) and 2-chloro-5-methylpyrimidine. MS (ESI): mass calcd. for $C_{15}H_{15}N_5O$, 281.1; m/z found, 282.2 [M+H]$^+$. $^1$H NMR (500 MHz, DMSO-d$_6$) δ 8.84 (d, J=0.7 Hz, 1H), 8.49 (q, J=0.7 Hz, 2H), 7.84-7.70 (m, 2H), 7.45-7.36 (m, 2H), 5.48 (d, J=0.5 Hz, 2H), 2.38 (s, 3H), 2.21 (d, J=0.8 Hz, 3H).

Example 261: 5-Ethyl-2-[[1-(p-tolyl)triazol-4-yl]methoxy]pyrimidine

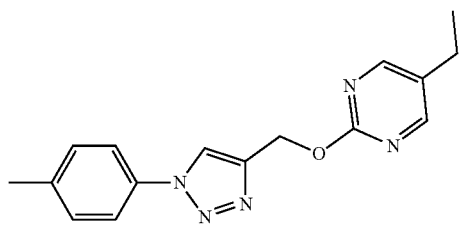 [SMILES: CCc1cnc(OCc2cn(-c3ccc(C)cc3)nn2)nc1]

The title compound was prepared in a manner analogous to Example 1 using (1-(p-tolyl)-1H-1,2,3-triazol-4-yl)methanol (Intermediate 33) and 2-chloro-5-ethylpyrimidine. MS (ESI): mass calcd. for $C_{15}H_{17}N_5O$, 295.1; m/z found, 296.1 [M+H]$^+$. $^1$H NMR (500 MHz, DMSO-d) δ 8.85 (s, 1H), 8.52 (d, J=0.6 Hz, 2H), 7.85-7.73 (m, 2H), 7.44-7.33 (m, 2H), 5.54-5.29 (m, 2H), 2.63-2.53 (m, 2H), 2.38 (s, 3H), 1.19 (t, J=7.6 Hz, 3H).

Example 262: 2-[[1-(3-Isopropylphenyl)triazol-4-yl]methoxy]pyrimidine

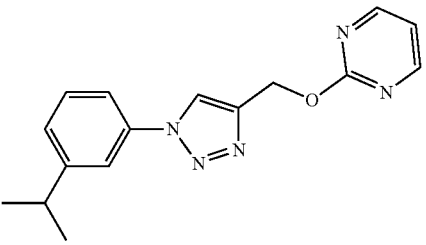 [SMILES: CC(C)c1cccc(-n2cc(COc3ncccn3)nn2)c1]

The title compound was prepared in a manner analogous to Example 1 using (1-(3-isopropylphenyl)-1H-1,2,3-triazol-4-yl)methanol (Intermediate 44) and 2-chloropyrimidine. MS (ESI): mass calcd. for $C_{16}H_{17}N_5O$, 295.1; m/z found, 296.1 [M+H]$^+$. $^1$H NMR (400 MHz, DMSO-d$_6$) δ 8.93 (s, 1H), 8.67 (d, J=4.8 Hz, 2H), 7.78 (t, J=2.0 Hz, 1H), 7.71 (ddd, J=8.1, 2.4, 1.1 Hz, 1H), 7.51 (t, J=7.9 Hz, 1H), 7.42-7.33 (m, 1H), 7.20 (t, J=4.8 Hz, 1H), 5.53 (s, 2H), 3.01 (p, J=7.0 Hz, 1H), 1.26 (d, J=6.9 Hz, 6H).

Example 263: 5-Fluoro-2-[[1-(3-isopropylphenyl)triazol-4-yl]methoxy]pyrimidine

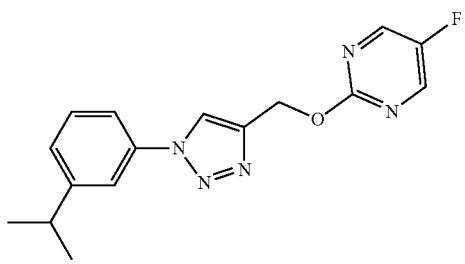 [SMILES: CC(C)c1cccc(-n2cc(COc3ncc(F)cn3)nn2)c1]

The title compound was prepared in a manner analogous to Example 1 using (1-(3-isopropylphenyl)-1H-1,2,3-triazol-4-yl)methanol (Intermediate 44) and 2-chloro-5-fluoropyrimidine. MS (ESI): mass calcd. for $C_{16}H_{16}FN_5O$, 313.1; m/z found, 314.1 [M+H]$^+$. $^1$H NMR (500 MHz, CD$_3$OD) δ 8.65 (s, 1H), 8.57 (s, 2H), 7.72 (t, J=2.1 Hz, 1H), 7.64 (ddd, J=8.0, 2.3, 1.1 Hz, 1H), 7.49 (t, J=7.9 Hz, 1H), 7.44-7.34 (m, 1H), 5.59 (s, 2H), 3.03 (p, J=6.9 Hz, 1H), 1.31 (d, J=6.9 Hz, 6H).

Example 264: 2-[[1-(3-Isopropylphenyl)triazol-4-yl]methoxy]-5-methoxy-pyrimidine

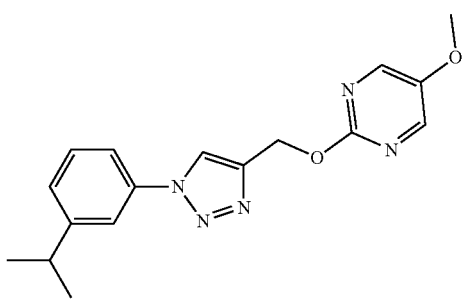 [SMILES: COc1cnc(OCc2cn(-c3cccc(C(C)C)c3)nn2)nc1]

The title compound was prepared in a manner analogous to Example 1 using (1-(3-isopropylphenyl)-1H-1,2,3-triazol-4-yl)methanol (Intermediate 44) and 2-chloro-5-methoxypyrimidine. MS (ESI): mass calcd. for $C_{17}H_9N_5O_2$, 325.2; m/z found, 326.1 [M+H]$^+$. $^1$H NMR (400 MHz, DMSO-$d_6$) δ 8.90 (s, 1H), 8.41 (s, 2H), 7.78 (t, J=2.0 Hz, 1H), 7.71 (ddd, J=8.0, 2.3, 1.1 Hz, 1H), 7.51 (t, J=7.9 Hz, 1H), 7.42-7.35 (m, 1H), 5.46 (s, 2H), 3.86 (s, 3H), 3.01 (p, J=6.9 Hz, 1H), 1.26 (d, J=6.9 Hz, 6H).

Example 265: 5-Chloro-2-[[1-(3-isopropylphenyl)triazol-4-yl]methoxy]pyrimidine

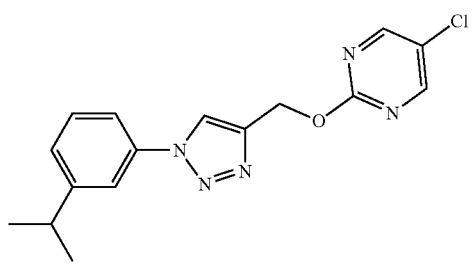 [SMILES: CC(C)c1cccc(-n2cc(COc3ncc(Cl)cn3)nn2)c1]

The title compound was prepared in a manner analogous to Example 1 using (1-(3-isopropylphenyl)-1H-1,2,3-triazol-4-yl)methanol (Intermediate 44) and 2,5-dichloropyrimidine. MS (ESI): mass calcd. for $C_{16}H_{16}ClN_5O$, 329.1; m/z found, 330.0 [M+H]$^+$. $^1$H NMR (400 MHz, DMSO-d) δ 8.92 (s, 1H), 8.77 (d, J=0.8 Hz, 2H), 7.77 (d, J=2.0 Hz, 1H), 7.74-7.66 (m, 1H), 7.51 (t, J=7.8 Hz, 1H), 7.39 (d, J=7.6 Hz, 1H), 5.54 (s, 2H), 3.00 (h, J=6.9 Hz, 1H), 1.31-1.14 (m, 6H).

Example 266: 2-[[1-(3-Isopropylphenyl)triazol-4-yl]methoxy]-5-methyl-pyrimidine

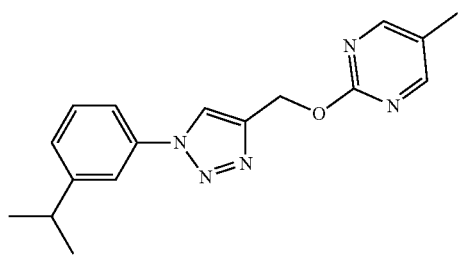 [SMILES: Cc1cnc(OCc2cn(-c3cccc(C(C)C)c3)nn2)nc1]

The title compound was prepared in a manner analogous to Example 1 using (1-(3-isopropylphenyl)-1H-1,2,3-triazol-4-yl)methanol (Intermediate 44) and 2-chloro-5-methylpyrimidine. MS (ESI): mass calcd. for $C_{17}H_{19}N_5O$, 309.2; m/z found, 310.2 [M+H]$^+$. $^1$H NMR (400 MHz, DMSO-$d_6$) δ 8.91 (s, 1H), 8.49 (s, 2H), 7.78 (t, J=2.0 Hz, 1H), 7.75-7.69 (m, 1H), 7.51 (t, J=7.8 Hz, 1H), 7.38 (d, J=7.7 Hz, 1H), 5.49 (s, 2H), 3.01 (p, J=6.7 Hz, 1H), 2.21 (s, 3H), 1.26 (d, J=6.9 Hz, 6H).

Example 267: 5-Ethyl-2-[[1-(3-isopropylphenyl)triazol-4-yl]methoxy]pyrimidine

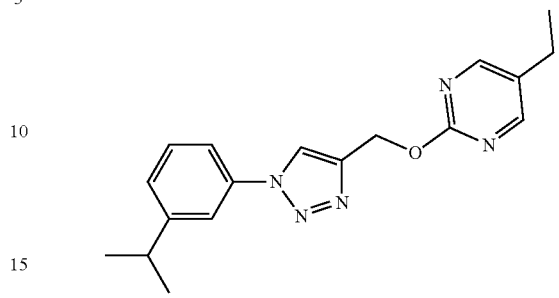

The title compound was prepared in a manner analogous to Example 1 using (1-(3-isopropylphenyl)-1H-1,2,3-triazol-4-yl)methanol (Intermediate 44) and 2-chloro-5-ethylpyrimidine. MS (ESI): mass calcd. for $C_{18}H_{21}N_5O$, 323.2; m/z found, 324.2 [M+H]$^+$. $^1$H NMR (400 MHz, DMSO-$d_6$) δ 8.92 (s, 1H), 8.53 (s, 2H), 7.78 (t, J=2.1 Hz, 1H), 7.75-7.69 (m, 1H), 7.51 (t, J=7.9 Hz, 1H), 7.43-7.36 (m, 1H), 5.50 (s, 2H), 3.02 (q, J=6.9 Hz, 1H), 2.57 (q, J=7.6 Hz, 2H), 1.26 (d, J=6.9 Hz, 6H), 1.19 (t, J=7.6 Hz, 3H)

Example 268: 2-[[1-[3-(Difluoromethyl)phenyl]triazol-4-yl]methoxy]-4-methyl-pyrimidine

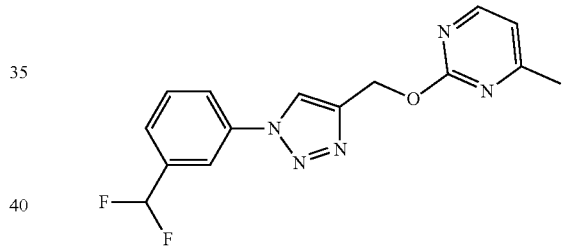

The title compound was prepared analogous to Example 155, using 2-chloro-4-methylpyrimidine. MS (ESI): mass calcd. for $C_{15}H_{13}F_2N_5O$, 317.1; m/z found, 318.0 [M+H]$^+$. $^1$H NMR (600 MHz, CDCl$_3$) δ 8.40 (d, J=4.9 Hz, 1H), 8.17 (s, 1H), 7.92-7.89 (m, 1H), 7.89-7.85 (m, 1H), 7.66-7.61 (m, 1H), 7.61-7.56 (m, 1H), 6.86 (d, J=5.0 Hz, 1H), 6.73 (t, J=56.2 Hz, 1H), 5.67 (d, J=0.8 Hz, 2H), 2.49 (s, 3H).

Example 269: 2-[[1-[3-(Difluoromethyl)phenyl]triazol-4-yl]methoxy]-5-fluoro-pyrimidine

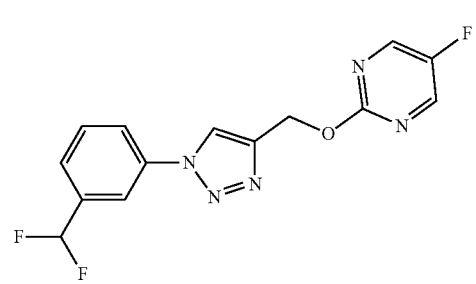 [SMILES: Fc1cnc(OCc2cn(-c3cccc(C(F)F)c3)nn2)nc1]

The title compound was prepared analogous to Example 155, using 2-chloro-5-fluoropyrimidine. MS (ESI): mass calcd. for $C_{14}H_{10}F_3N_5O$, 321.1; m/z found, 322.0 [M+H]$^+$. $^1$H NMR (600 MHz, CDCl$_3$) δ 8.43 (s, 2H), 8.18-8.15 (m, 1H), 7.93-7.85 (m, 2H), 7.67-7.57 (m, 2H), 6.73 (t, J=56.1 Hz, 1H), 5.65 (d, J=0.7 Hz, 2H).

Example 270: 2-[[1-[3-(Difluoromethyl)phenyl]triazol-4-yl]methoxy-4-isopropyl-pyrimidine

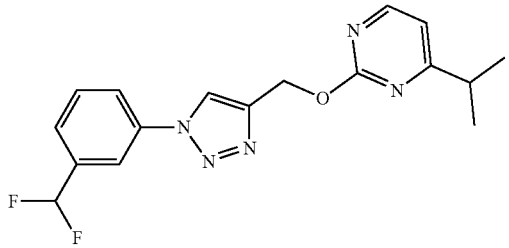 [SMILES: CC(C)c1ccnc(OCc2cn(-c3cccc(C(F)F)c3)nn2)n1]

The title compound was prepared analogous to Example 155, using 2-chloro-4-isopropylpyrimidine. MS (ESI): mass calcd. for $C_{17}H_{17}F_2N_5O$, 345.1; m/z found, 346.0 [M+H]$^+$. $^1$H NMR (500 MHz, CDCl$_3$) δ 8.43 (d, J=5.1 Hz, 1H), 8.18 (s, 1H), 7.92-7.89 (m, 1H), 7.88-7.84 (m, 1H), 7.65-7.60 (m, 1H), 7.59-7.55 (m, 1H), 6.86 (d, J=5.1 Hz, 1H), 6.72 (t, J=56.1 Hz, 1H), 5.66 (d, J=0.8 Hz, 2H), 2.96 (hept, J=6.9 Hz, 1H), 1.29 (d, J=6.9 Hz, 6H).

Example 271: 2-[[1-[3-(Difluoromethyl)phenyl]triazol-4-yl]methoxy]-4-(methoxymethyl)]pyrimidine

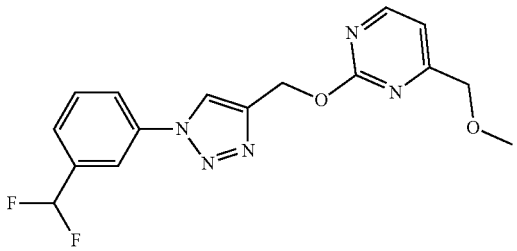 [SMILES: COCc1ccnc(OCc2cn(-c3cccc(C(F)F)c3)nn2)n1]

The title compound was prepared analogous to Example 155, using 2-chloro-4-(methoxymethyl)pyrimidine. MS (ESI): mass calcd. for $C_{16}H_{15}F_2N_5O_2$, 347.1; m/z found, 348.0 [M+H]$^+$. $^1$H NMR (400 MHz, CDCl$_3$) δ 8.54 (d, J=5.0 Hz, 1H), 8.20 (s, 1H), 7.93-7.84 (m, 2H), 7.67-7.56 (m, 2H), 7.15 (d, J=5.1 Hz, 1H), 6.72 (t, J=56.1 Hz, 1H), 5.66 (d, J=0.7 Hz, 2H), 4.50 (d, J=0.7 Hz, 2H), 3.49 (s, 3H).

Example 272: 2-[2-[[1-[3-(Difluoromethyl)phenyl]triazol-4-yl]methoxy]pyrimidin-5-yl]propan-2-ol

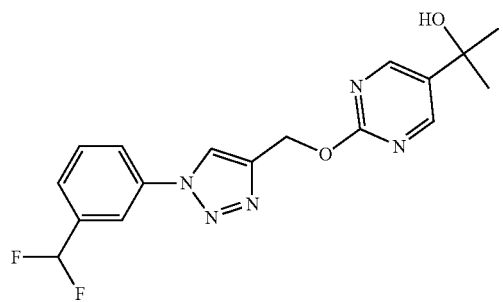 [SMILES: CC(C)(O)c1cnc(OCc2cn(-c3cccc(C(F)F)c3)nn2)nc1]

The title compound was prepared analogous to Example 155, using 2-(2-chloropyrimidin-5-yl)propan-2-ol. MS (ESI): mass calcd. for $C_{17}H_{17}F_2N_5O_2$, 361.1; m/z found, 362.1 [M+H]$^+$. $^1$H NMR (400 MHz, CDCl$_3$) δ 8.68 (s, 2H), 8.18 (s, 1H), 7.94-7.84 (m, 2H), 7.68-7.56 (m, 2H), 6.73 (t, J=56.1 Hz, 1H), 5.67 (d, J=0.7 Hz, 2H), 1.63 (s, 6H).

Example 273: 5-(Difluoromethyl)-2-[[1-[3-(difluoromethyl)phenyl]triazol-4-yl]methoxy]pyrimidine

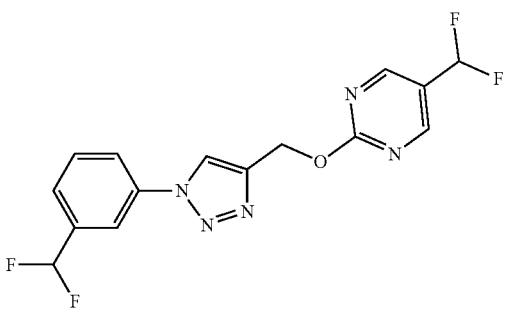 [SMILES: FC(F)c1cnc(OCc2cn(-c3cccc(C(F)F)c3)nn2)nc1]

The title compound was prepared analogous to Example 155, using 2-chloro-5-difluoromethylpyrimidine. MS (ESI): mass calcd. for $C_{15}H_{11}F_4N_5O$, 353.1; m/z found, 354.0 [M+H]$^+$. $^1$H NMR (400 MHz, CDCl$_3$) δ 8.72 (s, 2H), 8.18 (s, 1H), 7.94-7.85 (m, 2H), 7.69-7.57 (m, 2H), 6.89-6.57 (m, 2H), 5.73 (s, 2H).

Example 274: 4-(Difluoromethyl)-2-[[1-[3-(difluoromethyl)phenyl]triazol-4-yl]methoxy]pyrimidine

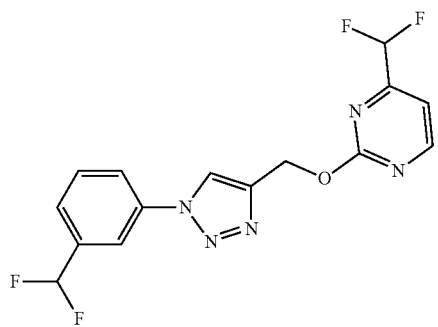 [SMILES: FC(F)c1cccc(-n2cc(COc3nccc(C(F)F)n3)nn2)c1]

The title compound was prepared analogous to Example 155, using 2-chloro-4-difluoromethylpyrimidine. MS (ESI): mass calcd. for $C_{15}H_{11}F_4N_5O$, 353.1; m/z found, 354.0 [M+H]$^+$. $^1$H NMR (400 MHz, CDCl$_3$) δ 8.76 (d, J=4.9 Hz, 1H), 8.21 (s, 1H), 7.94-7.84 (m, 2H), 7.63 (dt, J=16.0, 7.7 Hz, 2H), 7.30 (d, J=4.9 Hz, 1H), 6.88-6.34 (m, 2H), 5.71 (d, J=0.7 Hz, 2H)

Example 275: 2-[[1-[3-(Difluoromethyl)phenyl]triazol-4-yl]methoxy]-5-(trifluoromethyl)pyrimidine

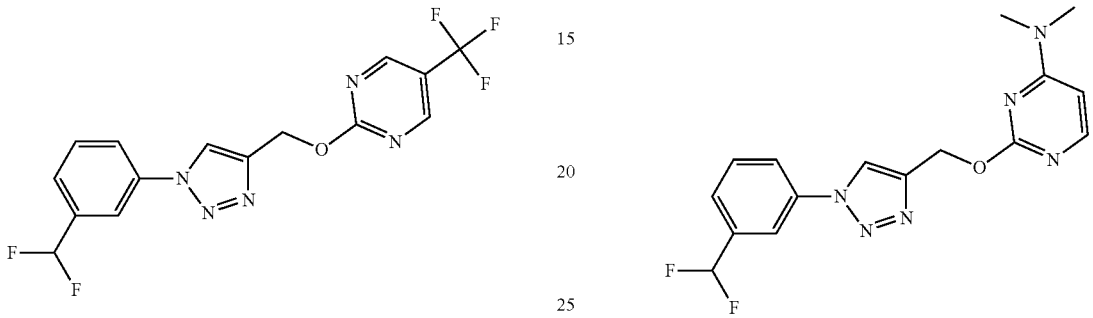

The title compound was prepared analogous to Example 155, using 2,-chloro-5-trifluoromethylpyrimidine. MS (ESI): mass calcd. for $C_{15}H_{10}F_8N_5O$, 371.1; m/z found, 372.0 [M+H]$^+$. $^1$H NMR (400 MHz, CDCl$_3$) δ 8.82 (d, J=0.8 Hz, 2H), 8.19 (s, 1H), 7.94-7.85 (m, 2H), 7.71-7.57 (m, 2H), 6.73 (t, J=56.1 Hz, 1H), 5.75 (s, 2H).

Example 276: 5-(Difluoromethoxy)-2-[[1-[3-(difluoromethyl)phenyl]triazol-4-yl]methoxy]pyrimidine

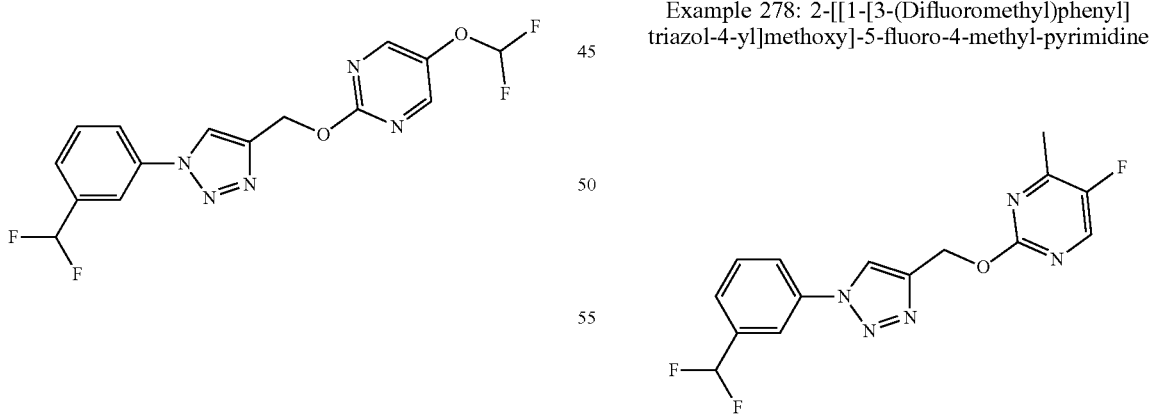

The title compound was prepared analogous to Example 155, using 2-chloro-5-difluoromethoxypyrimidine. MS (ESI): mass calcd. for $C_{15}H_{11}F_4N_5O_2$, 369.1; m/z found, 370.0 [M+H]$^+$. $^1$H NMR (400 MHz, CDCl$_3$) δ 8.48-8.43 (m, 2H), 8.21-8.14 (m, 1H), 7.96-7.84 (m, 2H), 7.69-7.57 (m, 2H), 6.89-6.34 (m, 2H), 5.67 (d, J=0.7 Hz, 2H).

Example 277: 2-[[1-[3-(Difluoromethyl)phenyl]triazol-4-yl]methoxy]-N,N-dimethyl-pyrimidin-4-amine The title compound was prepared analogous to Example 155, using 2-chloro-N,N-dimethylpyrimidin-4-amine. MS (ESI): mass calcd. for $C_{16}H_{16}F_2N_6O$, 346.1; m/z found, 347.1 [M+H]$^+$. $^1$H NMR (400 MHz, CDCl$_3$) δ 8.15 (s, 1H), 8.03 (d, J=6.1 Hz, 1H), 7.92-7.88 (m, 1H), 7.89-7.83 (m, 1H), 7.66-7.55 (m, 2H), 6.72 (t, J=56.1 Hz, 1H), 6.13 (d, J=6.1 Hz, 1H), 5.62 (d, J=0.8 Hz, 2H), 3.11 (s, 6H).

Example 278: 2-[[1-[3-(Difluoromethyl)phenyl]triazol-4-yl]methoxy]-5-fluoro-4-methyl-pyrimidine The title compound was prepared analogous to Example 155, using 2-chloro-5-fluoro-4-methylpyrimidine. MS (ESI): mass calcd. for $C_{15}H_{12}F_3N_5O$, 335.1; m/z found, 336.1 [M+H]$^+$. $^1$H NMR (400 MHz, CDCl$_3$) δ 8.26 (d, J=1.2 Hz, 1H), 8.16 (s, 1H), 7.93-7.85 (m, 2H), 7.67-7.57 (m, 2H), 6.73 (t, J=56.1 Hz, 1H), 5.62 (d, J=0.7 Hz, 2H), 2.49 (d, J=2.5 Hz, 3H).

Example 279: 5-Chloro-2-[[1-[3-(difluoromethyl)phenyl]triazol-4-yl]methoxy]-4-methyl-pyrimidine

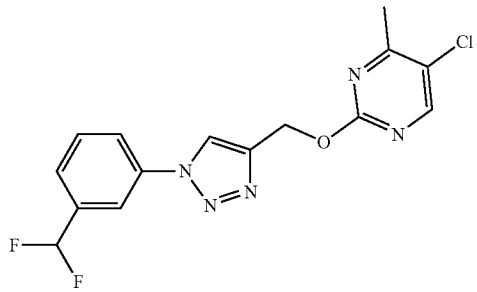 [SMILES: Cc1nc(OCc2cn(-c3cccc(C(F)F)c3)nn2)ncc1Cl]

The title compound was prepared analogous to Example 155, using 2,5-dichloro-4-methylpyrimidine. MS (ESI): mass calcd. for $C_{15}H_{12}ClF_2N_5O$, 351.1; m/z found, 352.1 [M+H]$^+$. $^1$H NMR (400 MHz, CDCl$_3$) δ 8.38 (s, 1H), 8.16 (s, 1H), 7.93-7.84 (m, 2H), 7.68-7.56 (m, 2H), 6.73 (t, J=56.1 Hz, 1H), 5.64 (d, J=0.7 Hz, 2H), 2.56 (s, 3H).

Example 280: 2-Chloro-4-[[1-[3-(difluoromethyl)phenyl]triazol-4-yl]methoxy]-5-methyl-pyrimidine

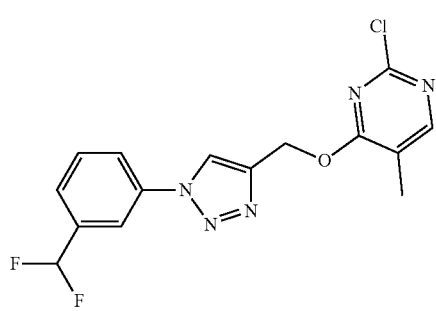 [SMILES: Cc1cnc(Cl)nc1OCc1cn(-c2cccc(C(F)F)c2)nn1]

The title compound was prepared analogous to Example 155, using 2,4-dichloro-5-methylpyrimidine. MS (ESI): mass calcd. for $C_{15}H_{12}ClF_2N_5O$, 351.1; m/z found, 352.0 [M+H]$^+$. $^1$H NMR (600 MHz, CDCl$_3$) δ 8.24-8.19 (m, 1H), 8.17-8.14 (m, 1H), 7.95-7.91 (m, 1H), 7.89-7.85 (m, 1H), 7.68-7.63 (m, 1H), 7.62-7.60 (m, 1H), 6.74 (t, J=56.1 Hz, 1H), 5.67 (d, J=0.5 Hz, 2H), 2.14 (d, J=0.9 Hz, 3H).

Example 281: 2-[[1-[3-(Difluoromethyl)phenyl]triazol-4-yl]methoxy]-N,N,5-trimethyl-pyrimidin-4-amine

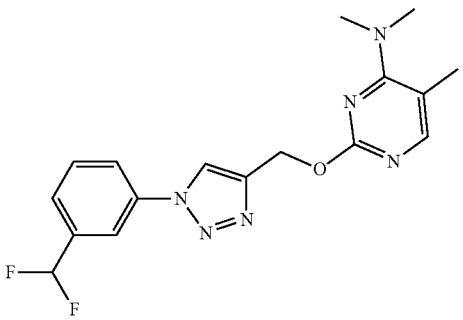 [SMILES: Cc1cnc(OCc2cn(-c3cccc(C(F)F)c3)nn2)nc1N(C)C]

The title compound was prepared analogous to Example 155, using 2-chloro-N,N,5-trimethylpyrimidin-4-amine. MS (ESI): mass calcd. for $C_{17}H_{15}F_2N_6O$, 360.2; m/z found, 361.0 [M+H]$^+$. $^1$H NMR (400 MHz, CDCl$_3$) δ 8.15 (s, 1H), 7.90 (s, 1H), 7.87-7.82 (m, 1H), 7.67-7.53 (m, 2H), 6.72 (t, J=56.1 Hz, 1H), 5.59 (s, 2H), 3.13 (s, 6H), 2.25 (s, 3H).

Example 282: 5-Cyclopropyl-2-[[1-[3-(difluoromethyl)phenyl]triazol-4-yl]methoxy]pyrimidine

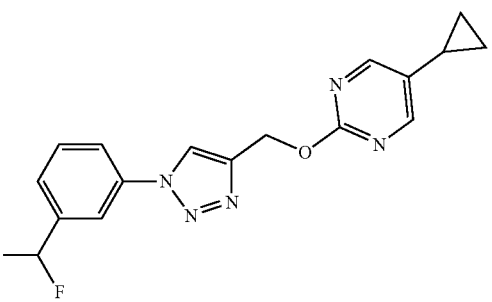

The title compound was prepared analogous to Example 155, using 2-chloro-5-cyclopropylpyrimidine. MS (ESI): mass calcd. for $C_{17}H_{15}F_2N_5O$, 343.1; m/z found, 344.1 [M+H]$^+$. $^1$H NMR (500 MHz, CDCl$_3$) δ 8.74 (d, J=1.4 Hz, 2H), 8.58 (s, 1H), 8.34-8.31 (m, 1H), 8.30-8.27 (m, 1H), 8.08-8.02 (m, 1H), 8.02-7.97 (m, 1H), 7.14 (t, J=56.1 Hz, 1H), 6.06 (s, 2H), 2.29-2.21 (m, 1H), 1.47-1.41 (m, 2H), 1.15-1.09 (m, 2H).

Example 283: 4-Cyclopropyl-2-[[1-[3-(difluoromethyl)phenyl]triazol-4-yl]methoxy]pyrimidine

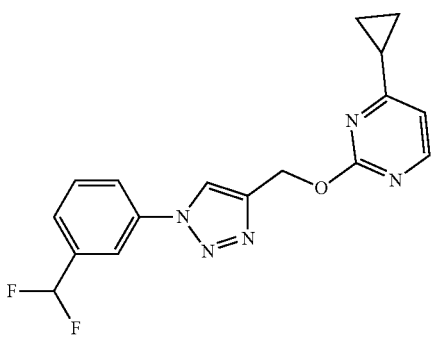 [SMILES: FC(F)c1cccc(-n2cc(COc3nccc(C4CC4)n3)nn2)c1]

The title compound was prepared analogous to Example 155, using 2-chloro-4-cyclopropylpyrimidine. MS (ESI): mass calcd. for $C_{17}H_{15}F_2N_5O$, 343.1; m/z found, 344.1 [M+H]$^+$. $^1$H NMR (500 MHz, CDCl$_3$) δ 8.31 (dd, J=5.1, 1.1 Hz, 1H), 8.15 (s, 1H), 7.92-7.89 (m, 1H), 7.88-7.84 (m, 1H), 7.66-7.61 (m, 1H), 7.60-7.57 (m, 1H), 6.86 (dd, J=5.2, 1.0 Hz, 1H), 6.72 (t, J=56.1 Hz, 1H), 5.61 (s, 2H), 1.96 (ttd, J=8.0, 4.7, 1.0 Hz, 1H), 1.22-1.17 (m, 2H), 1.10-1.06 (m, 2H)

Example 284: 2-[[1-[3-(Difluoromethyl)phenyl]triazol-4-yl]methoxy]-4-pyrrolidin-1-yl-pyrimidine

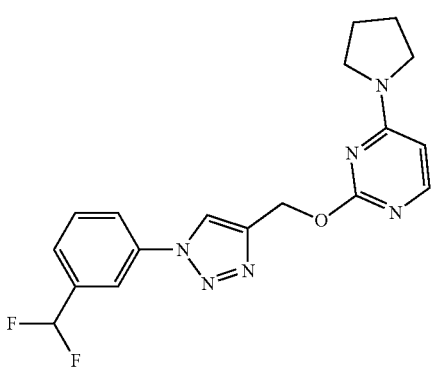 [SMILES: FC(F)c1cccc(-n2cc(COc3nccc(N4CCCC4)n3)nn2)c1]

The title compound was prepared analogous to Example 155, using 2-chloro-4-cyclopropylpyrimidine 2-chloro-4-(pyrrolidin-1-yl)pyrimidine. MS (ESI): mass calcd. for $C_{18}H_{18}F_2N_6O$, 372.2; m/z found, 373.0 [M+H]$^+$. $^1$H NMR (400 MHz, CDCl$_3$) δ 8.16 (s, 1H), 8.00 (s, 1H), 7.90 (s, 1H), 7.88-7.83 (m, 1H), 7.66-7.56 (m, 2H), 6.72 (t, J=56.1 Hz, 1H), 6.00 (d, J=5.9 Hz, 1H), 5.62 (s, 2H), 3.63 (s, 2H), 3.42-3.27 (m, 2H), 2.11-1.89 (m, 4H).

Example 285: 2-[[1-[3-(Difluoromethyl)phenyl]triazol-4-yl]methoxy]-4-(1-piperidyl)pyrimidine

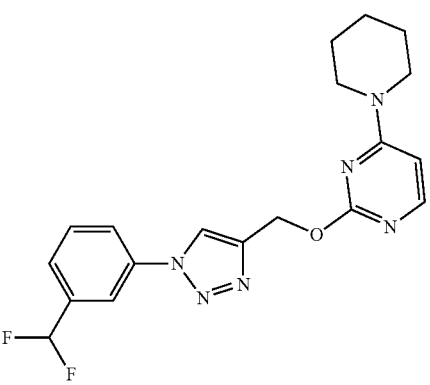 [SMILES: FC(F)c1cccc(-n2cc(COc3nccc(N4CCCCC4)n3)nn2)c1]

The title compound was prepared analogous to Example 155, using 2-chloro-4-(piperidin-1-yl)pyrimidine. MS (ESI): mass calcd. for $C_{19}H_{20}F_2N_6O$, 386.2; m/z found, 387.1 [M+H]$^+$. $^1$H NMR (400 MHz, CDCl$_3$) δ 8.15 (s, 1H), 8.01 (d, J=6.1 Hz, 1H), 7.90 (s, 1H), 7.89-7.83 (m, 1H), 7.67-7.54 (m, 2H), 6.72 (t, J=56.1 Hz, 1H), 6.19 (d, J=6.2 Hz, 1H), 5.59 (d, J=0.8 Hz, 2H), 3.71-3.56 (m, 4H), 1.75-1.56 (m, 6H).

Example 286: 5-Methyl-2-[[1-[3-(trifluoromethyl)phenyl]triazol-4-yl]methoxy]pyrimidine

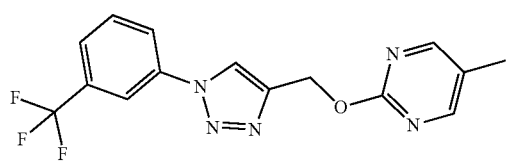 [SMILES: Cc1cnc(OCc2cn(-c3cccc(C(F)(F)F)c3)nn2)nc1]

The title compound was prepared in a manner analogous to Example 155 using (1-(3-(trifluoromethyl)phenyl)-1H-1,2,3-triazol-4-yl)methanol (Intermediate 30) and 2-chloro-5-methylpyrimidine. MS (ESI): mass calcd. for $C_{15}H_{12}F_3N_5O$, 335.1; m/z found, 335.9 [M+H]$^+$. $^1$H NMR (400 MHz, DMSO-d$_6$) δ 9.10 (s, 1H), 8.51-8.49 (m, 2H), 8.33-8.26 (m, 2H), 7.92-7.82 (m, 2H), 5.52 (s, 2H), 2.22 (t, J=0.8 Hz, 3H).

Example 287: 5-Ethyl-2-[[1-[3-(trifluoromethyl)phenyl]triazol-4-yl]methoxy]pyrimidine

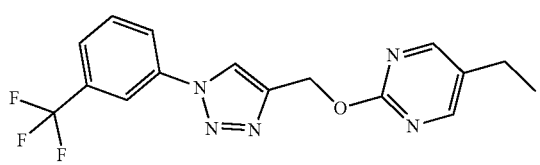 [SMILES: CCc1cnc(OCc2cn(-c3cccc(C(F)(F)F)c3)nn2)nc1]

The title compound was prepared in a manner analogous to Example 155 using (1-(3-(trifluoromethyl)phenyl)-1H-1,2,3-triazol-4-yl)methanol (Intermediate 30) and 2-chloro-5-ethylpyrimidine. MS (ESI): mass calcd. for $C_{16}H_{14}F_3N_5O$, 349.1; m/z found, 349.9 [M+H]$^+$. $^1$H NMR (500 MHz, DMSO-d$_6$) δ 9.10 (s, 1H), 8.54-8.52 (m, 2H), 8.32-8.30 (m, 1H), 8.30-8.26 (m, 1H), 7.90-7.83 (m, 2H), 5.52 (s, 2H), 2.58 (q, J=7.6 Hz, 2H), 1.19 (t, J=7.6 Hz, 3H).

Example 288: 5-Isopropyl-2-[[1-[3-(trifluoromethyl)phenyl]triazol-4-yl]methoxy]pyrimidine

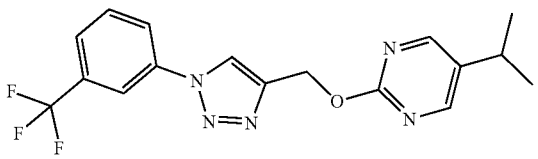 [SMILES: CC(C)c1cnc(OCc2cn(-c3cccc(C(F)(F)F)c3)nn2)nc1]

The title compound was prepared in a manner analogous to Example 155 using (1-(3-(trifluoromethyl)phenyl)-1H-1,2,3-triazol-4-yl)methanol (Intermediate 30) and 2-chloro-5-isopropylpyrimidine. MS (ESI): mass calcd. for C$_{17}$H$_{16}$F$_3$N$_5$O, 363.1; m/z found, 363.9 [M+H]$^+$. $^1$H NMR (500 MHz, DMSO-d$_6$) δ 9.10 (s, 1H), 8.58-8.56 (m, 2H), 8.32-8.30 (m, 1H), 8.30-8.26 (m, 1H), 7.91-7.82 (m, 2H), 5.53 (s, 2H), 2.98-2.87 (m, 1H), 1.24 (d, J=7.0 Hz, 6H).

Example 289: 5-(Difluoromethyl)-2-[[1-[3-(trifluoromethyl)phenyl]triazol-4-yl]methoxy]pyrimidine

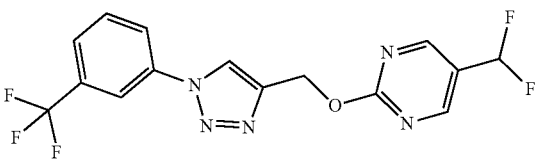 [SMILES: FC(F)c1cnc(OCc2cn(-c3cccc(C(F)(F)F)c3)nn2)nc1]

The title compound was prepared in a manner analogous to Example 155 using (1-(3-(trifluoromethyl)phenyl)-1H-1,2,3-triazol-4-yl)methanol (Intermediate 30) and 2-chloro-5-(difluoromethyl)pyrimidine. MS (ESI): mass calcd. for C$_{15}$H$_{10}$F$_8$N$_5$O, 371.1; m/z found, 371.9 [M+H]$^+$. $^1$H NMR (500 MHz, DMSO-d$_6$) δ 9.13 (s, 1H), 8.91-8.90 (m, 2H), 8.32-8.30 (m, 1H), 8.29-8.26 (m, 1H), 7.91-7.83 (m, 2H), 7.16 (t, J=55.0 Hz, 1H), 5.63 (s, 2H).

Example 290: 4,5-Dimethyl-2-[[1-[3-(trifluoromethyl)phenyl]triazol-4-yl]methoxy]pyrimidine

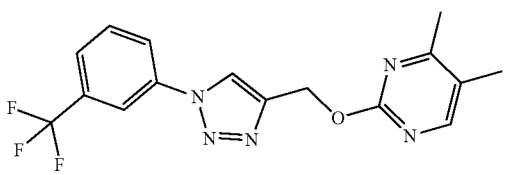 [SMILES: Cc1cnc(OCc2cn(-c3cccc(C(F)(F)F)c3)nn2)nc1C]

The title compound was prepared in a manner analogous to Example 155 using (1-(3-(trifluoromethyl)phenyl)-1H-1,2,3-triazol-4-yl)methanol (Intermediate 30) and 2-chloro-4,5-dimethylpyrimidine. MS (ESI): mass calcd. for C$_{16}$H$_{14}$F$_3$N$_5$O, 349.1; m/z found, 349.9 [M+H]$^+$. $^1$H NMR (500 MHz, DMSO-d$_6$) δ 9.08 (s, 1H), 8.33-8.25 (m, 3H), 7.90-7.82 (m, 2H), 5.50 (s, 2H), 2.39 (s, 3H), 2.16 (s, 3H).

Example 291: 5-Chloro-4-methyl-2-[[1-[3-(trifluoromethyl)phenyl]triazol-4-yl]methoxy]pyrimidine

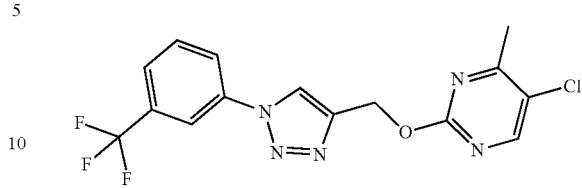

The title compound was prepared in a manner analogous to Example 155 using (1-(3-(trifluoromethyl)phenyl)-1H-1,2,3-triazol-4-yl)methanol (Intermediate 30) and 2,5-dichloro-4-methylpyrimidine. MS (ESI): mass calcd. for C$_{15}$H$_{11}$ClF$_3$N$_5$O, 369.1; m/z found, 369.9 [M+H]$^+$. $^1$H NMR (500 MHz, DMSO-d$_6$) δ 9.09 (s, 1H), 8.63 (s, 1H), 8.31-8.29 (m, 1H), 8.29-8.26 (m, 1H), 7.90-7.82 (m, 2H), 5.54 (s, 2H), 2.51 (s, 3H).

Example 292: 2-[[1-[3-(1,1-Difluoroethyl)phenyl]triazol-4-yl]methoxy]pyrimidine

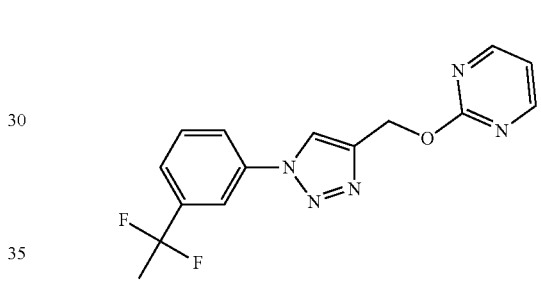

The title compound was prepared analogous to Example 155, using (1-(3-(1,1-difluoroethyl)phenyl)-1H-1,2,3-triazol-4-yl)methanol (Intermediate 64) and 2-chloropyrimidine. MS (ESI): mass calcd. for C$_{15}$H$_{13}$F$_2$N$_5$O, 317.1; m/z found, 318.0 [M+H]$^+$. $^1$H NMR (500 MHz, CDCl$_3$) δ 8.58 (d, J=4.8 Hz, 2H), 8.25-8.08 (m, 1H), 7.94-7.86 (m, 1H), 7.86-7.74 (m, 1H), 7.70-7.51 (m, 2H), 7.01 (t, J=4.8 Hz, 1H), 5.68 (d, J=0.7 Hz, 2H), 1.98 (t, J=18.2 Hz, 3H).

Example 293: 5-Bromo-2-[[1-[3-(1,1-difluoroethyl)phenyl]triazol-4-yl]methoxy]pyrimidine

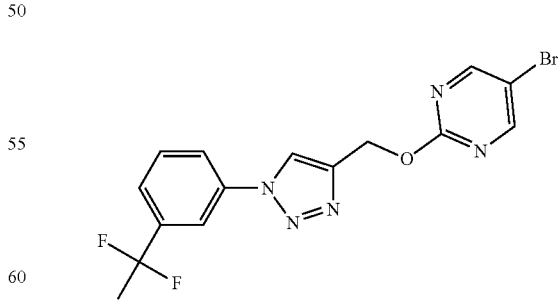

The title compound was prepared in a manner analogous to Example 153 using (1-(3-(1,1-difluoroethyl)phenyl)-1H-1,2,3-triazol-4-yl)methanol (Intermediate 64) and 5-bromo-2-chloropyrimidine, using ACN instead of DMF. MS (ESI): mass calcd. for C$_{15}$H$_{12}$BrF$_2$N$_5$O, 395.0; m/z found, 396.0

[M+H]⁺. ¹H NMR (400 MHz, CDCl₃) δ 8.62-8.55 (s, 2H), 8.19-8.13 (s, 1H), 7.92-7.85 (m, 1H), 7.85-7.78 (m, 1H), 7.64-7.57 (m, 2H), 5.69-5.61 (d, J=0.7 Hz, 2H), 2.19-1.78 (t, J=18.2 Hz, 3H).

Example 294: 5-Chloro-2-[[1-[3-(1,1-difluoroethyl)phenyl]triazol-4-yl]methoxy]pyrimidine

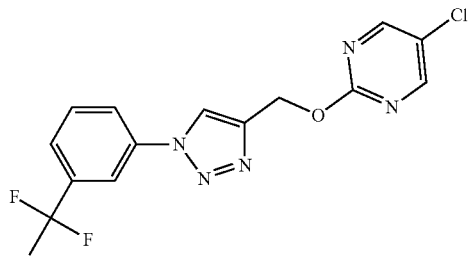 [SMILES: CC(F)(F)c1cccc(-n2cc(COc3ncc(Cl)cn3)nn2)c1]

The title compound was prepared analogous to Example 155, using (1-(3-(1,1-difluoroethyl)phenyl)-1H-1,2,3-triazol-4-yl)methanol (Intermediate 64) and 2,5-dichloropyrimidine. MS (ESI): mass calcd. for C₁₅H₁₂ClF₂N₅O, 351.1; m/z found, 352.0 [M+H]⁺. ¹H NMR (400 MHz, CDCl₃) δ 8.51 (s, 2H), 8.18-8.13 (m, 1H), 7.91-7.87 (m, 1H), 7.84-7.79 (m, 1H), 7.65-7.55 (m, 2H), 5.73-5.60 (m, 2H), 1.98 (t, J=18.2 Hz, 3H).

Example 295: 2-[[1-[3-(1,1-Difluoroethyl)phenyl]triazol-4-yl]methoxy]-5-fluoro-pyrimidine

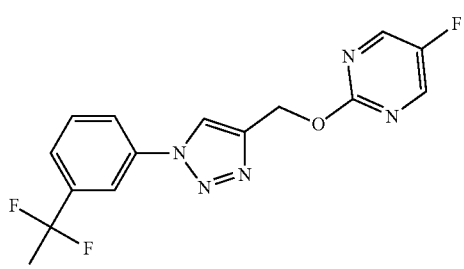 [SMILES: CC(F)(F)c1cccc(-n2cc(COc3ncc(F)cn3)nn2)c1]

The title compound was prepared analogous to Example 155, using (1-(3-(1,1-difluoroethyl)phenyl)-1H-1,2,3-triazol-4-yl)methanol (Intermediate 64) and 2-chloro-5-fluoropyrimidine. MS (ESI): mass calcd. for C₁₅H₁₂F₃N₅O, 335.1; m/z found, 336.0 [M+H]⁺. ¹H NMR (500 MHz, CDCl₃) δ 8.43 (s, 2H), 8.20-8.13 (m, 1H), 7.91-7.86 (m, 1H), 7.87-7.76 (m, 1H), 7.66-7.57 (m, 2H), 5.64 (d, J=0.7 Hz, 2H), 1.98 (t, J=18.2 Hz, 3H)

Example 296: 2-[[1-[3-(1,1-Difluoroethyl)phenyl]triazol-4-yl]methoxy]-4-methyl-pyrimidine

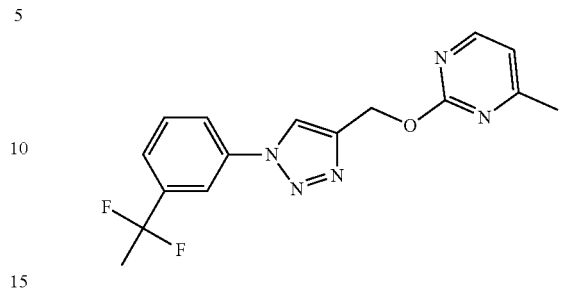

The title compound was prepared analogous to Example 155, using (1-(3-(1,1-difluoroethyl)phenyl)-1H-1,2,3-triazol-4-yl)methanol (Intermediate 64) and 2-chloro-4-methylpyrimidine. MS (ESI): mass calcd. for C₁₆H₁₅F₂N₅O, 331.1; m/z found, 332.1 [M+H]⁺. ¹H NMR (500 MHz, CDCl₃) δ 8.40 (d, J=5.0 Hz, 1H), 8.23-8.12 (m, 1H), 7.95-7.86 (m, 1H), 7.86-7.75 (m, 1H), 7.66-7.54 (m, 2H), 6.92-6.81 (m, 1H), 5.67 (d, J=0.8 Hz, 2H), 2.50 (s, 3H), 1.98 (t, J=18.2 Hz, 3H).

Example 297: 2-[[1-[3-(1,1-Difluoroethyl)phenyl]triazol-4-yl]methoxy]-5-methyl-pyrimidine

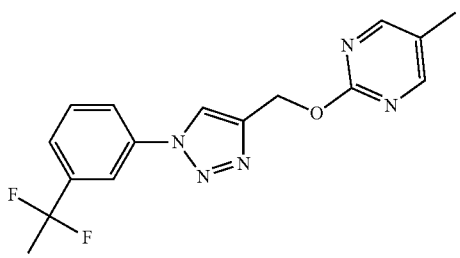 [SMILES: Cc1cnc(OCc2cn(-c3cccc(C(C)(F)F)c3)nn2)nc1]

The title compound was prepared analogous to Example 155, using (1-(3-(1,1-difluoroethyl)phenyl)-1H-1,2,3-triazol-4-yl)methanol (Intermediate 64) and 2-chloro-5-methylpyrimidine. MS (ESI): mass calcd. for C₁₆H₁₅F₂N₅O, 331.1; m/z found, 332.1 [M+H]⁺. ¹H NMR (400 MHz, CDCl₃) δ 8.48-8.30 (m, 2H), 8.16 (s, 1H), 7.95-7.84 (m, 1H), 7.85-7.75 (m, 1H), 7.68-7.52 (m, 2H), 5.64 (d, J=0.6 Hz, 2H), 2.26 (s, 3H), 1.97 (t, J=18.2 Hz, 3H).

Example 298: [2-[[1-[3-(1,1-Difluoroethyl)phenyl]triazol-4-yl]methoxy]pyrimidin-5-yl]methanol

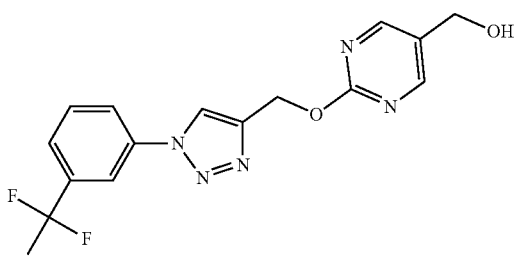 [SMILES: CC(F)(F)c1cccc(-n2cc(COc3ncc(CO)cn3)nn2)c1]

The title compound was prepared in a manner analogous to Example 159, Steps A-B using (1-(3-(1,1-difluoroethyl)phenyl)-1H-1,2,3-triazol-4-yl)methanol (Intermediate 64) and 5-(((tert-butyldimethylsilyl)oxy)methyl)-2-chloropyrimidine (Intermediate 53) in Step A. MS (ESI): mass calcd. for $C_{16}H_{15}F_2N_5O_2$, 347.1; m/z found, 348.0 [M+H]$^+$. $^1$H NMR (500 MHz, CDCl$_3$) δ 8.60-8.52 (s, 2H), 8.22-8.15 (s, 1H), 7.92-7.86 (m, 1H), 7.84-7.77 (m, 1H), 7.65-7.53 (m, 2H), 5.71-5.57 (m, 2H), 4.77-4.64 (s, 2H), 2.71-2.48 (s, 1H), 2.02-1.92 (t, J=18.2 Hz, 3H).

Example 299: [2-[[1-[3-(1,1-Difluoroethyl)phenyl]triazol-4-yl]methoxy]pyrimidin-4-yl]methanol

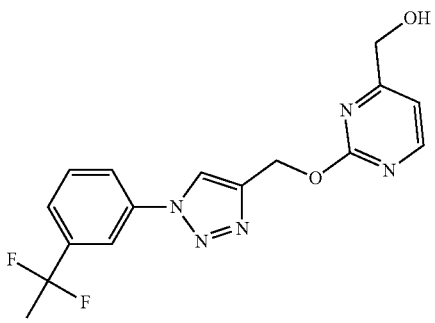 [SMILES: CC(F)(F)c1cccc(-n2cc(COc3nccc(CO)n3)nn2)c1]

The title compound was prepared in a manner analogous to Example 159, Steps A-B using (1-(3-(1,1-difluoroethyl)phenyl)-1H-1,2,3-triazol-4-yl)methanol (Intermediate 64) and 4-(((tert-butyldimethylsilyl)oxy)methyl)-2-chloropyrimidine (Intermediate 54) in Step A. MS (ESI): mass calcd. for $C_{16}H_{15}F_2N_5O_2$, 347.1; m/z found, 348.1 [M+H]$^+$. $^1$H NMR (500 MHz, CDCl$_3$) δ 8.56-8.48 (d, J=5.0 Hz, 1H), 8.23-8.15 (m, 1H), 7.93-7.85 (m, 1H), 7.86-7.76 (m, 1H), 7.65-7.54 (m, 2H), 7.07-6.96 (m, 1H), 5.71-5.64 (m, 2H), 4.78-4.68 (d, J=0.7 Hz, 2H), 2.02-1.92 (t, J=18.2 Hz, 3H).

Example 300: 2-[[1-[3-(1,1-Difluoroethyl)phenyl]triazol-4-yl]methoxy]-4-(methoxymethyl)pyrimidine

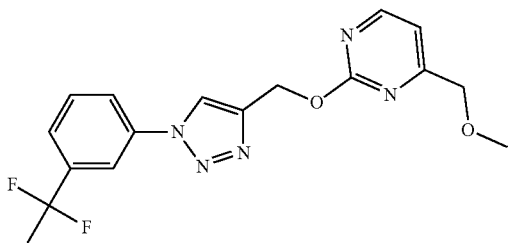 [SMILES: COCc1ccnc(OCc2cn(-c3cccc(C(C)(F)F)c3)nn2)n1]

The title compound was prepared analogous to Example 155, using (1-(3-(1,1-difluoroethyl)phenyl)-1H-1,2,3-triazol-4-yl)methanol (Intermediate 64) and 2-chloro-4-(methoxymethyl)pyrimidine. MS (ESI): mass calcd. for $C_{17}H_{17}F_2N_5O_2$, 361.1; m/z found, 362.1 [M+H]$^+$. $^1$H NMR (400 MHz, CDCl$_3$) δ 8.55 (d, J=5.0 Hz, 1H), 8.20 (t, J=0.7 Hz, 1H), 7.91-7.87 (m, 1H), 7.86-7.78 (m, 1H), 7.64-7.56 (m, 2H), 7.16 (dt, J=5.0, 0.8 Hz, 1H), 5.67 (d, J=0.7 Hz, 2H), 4.60-4.40 (m, 2H), 3.50 (s, 3H), 1.97 (t, J=18.2 Hz, 3H).

Example 301: 2-[2-[[1-[3-(1,1-Difluoroethyl)phenyl]triazol-4-yl]methoxy]pyrimidin-5-yl]propan-2-ol

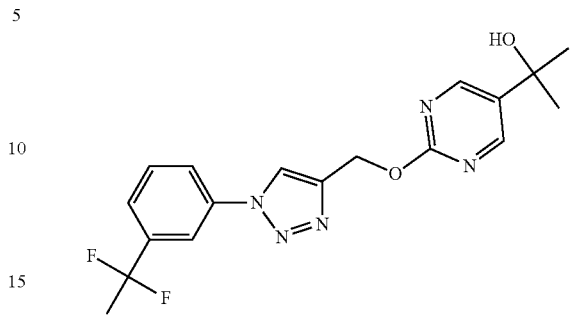

The title compound was prepared analogous to Example 155, using (1-(3-(1,1-difluoroethyl)phenyl)-1H-1,2,3-triazol-4-yl)methanol (Intermediate 64) and 2-(2-chloropyrimidin-5-yl)propan-2-ol. MS (ESI): mass calcd. for $C_{18}H_{19}F_2N_5O_2$, 375.2; m/z found, 376.0 [M+H]$^+$. $^1$H NMR (500 MHz, CDCl$_3$) δ 8.68 (s, 2H), 8.21-8.15 (m, 1H), 7.92-7.86 (m, 1H), 7.86-7.79 (m, 1H), 7.63-7.56 (m, 2H), 5.67 (d, J=0.7 Hz, 2H), 2.12-1.88 (m, 3H), 1.63 (s, 6H).

Example 302: 2-[[1-[3-(1,1-Difluoroethyl)phenyl]triazol-4-yl]methoxy]-5-(difluoromethyl)pyrimidine

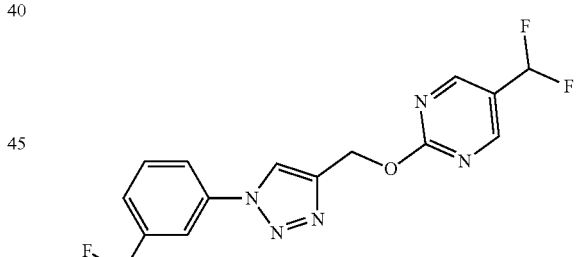

The title compound was prepared analogous to Example 155, using (1-(3-(1,1-difluoroethyl)phenyl)-1H-1,2,3-triazol-4-yl)methanol (Intermediate 64) and 2-chloro-5-(difluoromethyl)pyrimidine. MS (ESI): mass calcd. for $C_{16}H_{13}F_4N_5O$, 367.1; m/z found, 368.1 [M+H]$^+$. $^1$H NMR (400 MHz, CDCl$_3$) δ 8.77-8.66 (m, 2H), 8.25-8.11 (m, 1H), 7.96-7.87 (m, 1H), 7.87-7.77 (m, 1H), 7.66-7.55 (m, 2H), 6.73 (t, J=55.6 Hz, 1H), 5.73 (d, J=0.7 Hz, 2H), 1.98 (t, J=18.2 Hz, 3H).

Example 303: 2-[[1-[3-(1,1-Difluoroethyl)phenyl]triazol-4-yl]methoxy]-4-(difluoromethyl)pyrimidine

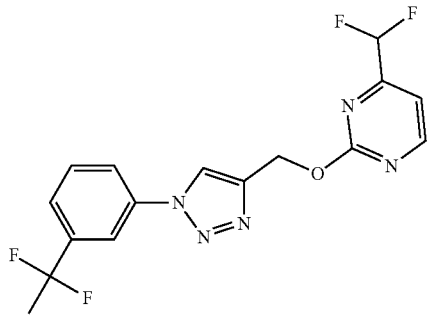 [SMILES: CC(F)(F)c1cccc(-n2cc(COc3nccc(C(F)F)n3)nn2)c1]

The title compound was prepared analogous to Example 155, using (1-(3-(1,1-difluoroethyl)phenyl)-1H-1,2,3-triazol-4-yl)methanol (Intermediate 64) and 2-chloro-4-(difluoromethyl)pyrimidine. MS (ESI): mass calcd. for $C_{16}H_{13}F_4N_5O$, 367.1; m/z found, 368.1 [M+H]$^+$. $^1$H NMR (500 MHz, CDCl$_3$) δ 8.76 (d, J=4.9 Hz, 1H), 8.25-8.16 (m, 1H), 7.92-7.86 (m, 1H), 7.86-7.77 (m, 1H), 7.67-7.56 (m, 2H), 7.34-7.28 (m, 1H), 6.65-6.37 (m, 1H), 5.71 (d, J=1.3 Hz, 2H), 2.09-1.85 (m, 3H).

Example 304: 2-[[1-[3-(1,1-Difluoroethyl)phenyl]triazol-4-yl]methoxy]-4-(trifluoromethyl)pyrimidine

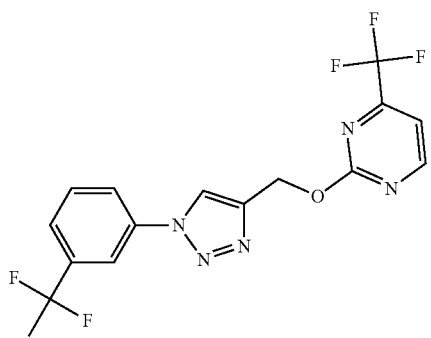 [SMILES: CC(F)(F)c1cccc(-n2cc(COc3nccc(C(F)(F)F)n3)nn2)c1]

The title compound was prepared analogous to Example 155, using (1-(3-(1,1-difluoroethyl)phenyl)-1H-1,2,3-triazol-4-yl)methanol (Intermediate 64) and 2-chloro-4-(trifluoromethyl)pyrimidine. MS (ESI): mass calcd. for $C_{16}H_{12}F_5N_5O$, 385.1; m/z found, 386.0 [M+H]$^+$. $^1$H NMR (400 MHz, CDCl$_3$) δ 8.83 (d, J=4.9 Hz, 1H), 8.22 (t, J=0.7 Hz, 1H), 7.89 (d, J=1.0 Hz, 1H), 7.86-7.75 (m, 1H), 7.65-7.57 (m, 2H), 7.34 (d, J=4.9 Hz, 1H), 5.73 (d, J=0.6 Hz, 2H), 1.98 (t, J=18.2 Hz, 3H).

Example 305: (R/S)-2-[2-[[1-[3-(1,1-Difluoroethyl)phenyl]triazol-4-yl]methoxy]pyrimidin-5-yl]-1,1,1-trifluoro-propan-2-ol

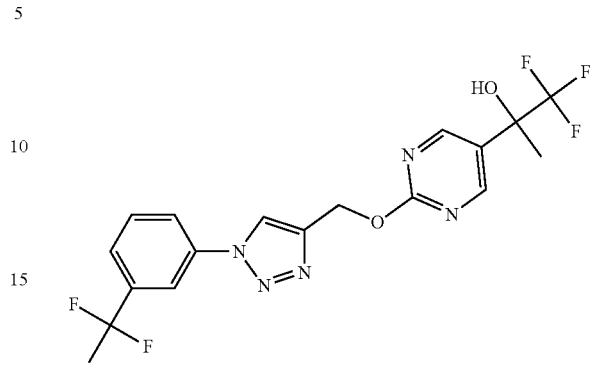

The title compound was prepared in a manner analogous to Example 153 using (1-(3-(1,1-difluoroethyl)phenyl)-1H-1,2,3-triazol-4-yl)methanol (Intermediate 64) and 2-(2-chloropyrimidin-5-yl)-1,1,1-trifluoropropan-2-ol, using ACN instead of DMF. MS (ESI): mass calcd. for $C_{18}H_{16}F_5N_5O_2$, 429.1; m/z found, 430.0 [M+H]$^+$. $^1$H NMR (500 MHz, CDCl$_3$) δ 8.78-8.72 (s, 2H), 8.21-8.16 (t, J=0.7 Hz, 1H), 7.92-7.86 (s, 1H), 7.85-7.78 (m, 1H), 7.65-7.56 (m, 2H), 5.72-5.65 (d, J=0.7 Hz, 2H), 2.70-2.59 (s, 1H), 2.04-1.92 (t, J=18.2 Hz, 3H), 1.86-1.81 (m, 3H).

Example 306: 2-[[1-[3-(1,1-Difluoroethyl)phenyl]triazol-4-yl]methoxy]-5-methoxy-pyrimidine

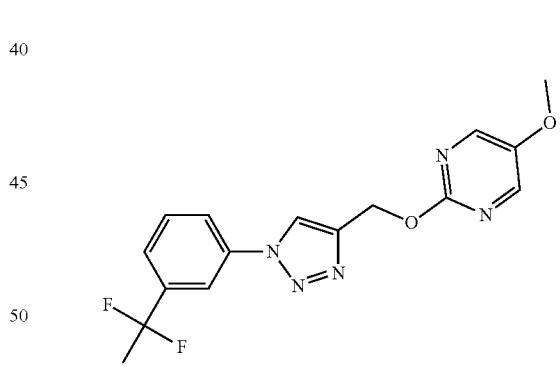

The title compound was prepared analogous to Example 155, using (1-(3-(1,1-difluoroethyl)phenyl)-1H-1,2,3-triazol-4-yl)methanol (Intermediate 64) and 2-chloro-5-methoxypyrimidine. MS (ESI): mass calcd. for $C_{16}H_{15}F_2N_5O_2$, 347.1; m/z found, 348.0 [M+H]$^+$. $^1$H NMR (500 MHz, CDCl$_3$) δ 8.24 (s, 2H), 8.20-8.11 (m, 1H), 7.93-7.87 (m, 1H), 7.84-7.77 (m, 1H), 7.67-7.53 (m, 2H), 5.62 (d, J=0.7 Hz, 2H), 3.88 (s, 3H), 1.97 (t, J=18.2 Hz, 3H).

Example 307: 2-[[1-[3-(1,1-Difluoroethyl)phenyl]triazol-4-yl]methoxy]-4-methoxy-pyrimidine

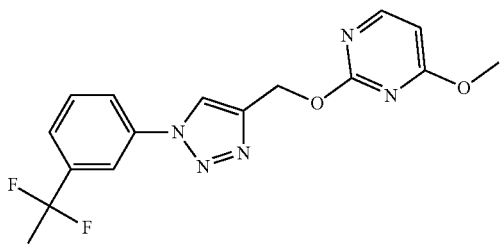 [SMILES: COc1ccnc(OCc2cn(-c3cccc(C(C)(F)F)c3)nn2)n1]

The title compound was prepared analogous to Example 155, using (1-(3-(1,1-difluoroethyl)phenyl)-1H-1,2,3-triazol-4-yl)methanol (Intermediate 64) and 2-chloro-4-methoxypyrimidine. MS (ESI): mass calcd. for $C_{16}H_{15}F_2N_5O_2$, 347.1; m/z found, 348.0 [M+H]+. $^1$H NMR (400 MHz, CDCl$_3$) δ 8.23 (d, J=5.7 Hz, 1H), 8.16 (t, J=0.7 Hz, 1H), 7.92-7.86 (m, 1H), 7.86-7.77 (m, 1H), 7.64-7.56 (m, 2H), 6.43 (d, J=5.8 Hz, 1H), 5.66 (d, J=0.7 Hz, 2H), 3.99 (s, 3H), 1.98 (t, J=18.2 Hz, 3H).

Example 308: 2-[[1-[3-(1,1-Difluoroethyl)phenyl]triazol-4-yl]methoxy]-5-(difluoromethoxy)pyrimidine

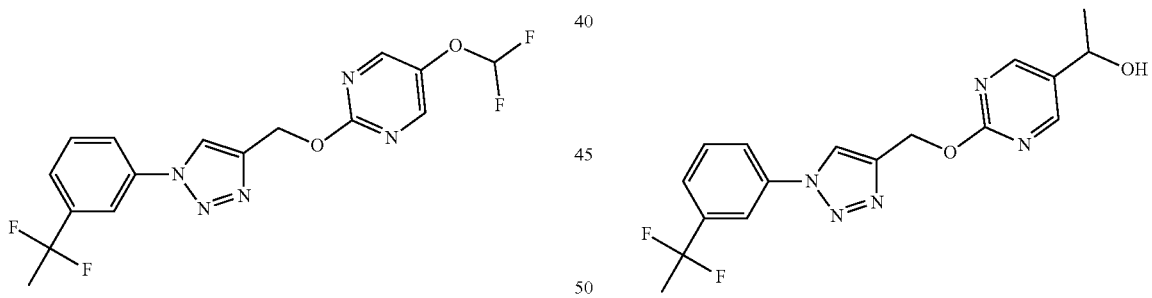

The title compound was prepared analogous to Example 155, using (1-(3-(1,1-difluoroethyl)phenyl)-1H-1,2,3-triazol-4-yl)methanol (Intermediate 64) and 2-chloro-5-(difluoromethoxy)pyrimidine. MS (ESI): mass calcd. for $C_{16}H_{13}F_4N_5O_2$, 383.1; m/z found, 384.0 [M+H]+. $^1$H NMR (400 MHz, CDCl$_3$) δ 8.45 (s, 2H), 8.17 (s, 1H), 7.93-7.87 (m, 1H), 7.87-7.76 (m, 1H), 7.68-7.55 (m, 2H), 6.53 (t, J=71.9 Hz, 1H), 5.67 (d, J=0.7 Hz, 2H), 1.98 (t, J=18.2 Hz, 3H).

Example 309: 1-[2-[[1-[3-(1,1-Difluoroethyl)phenyl]triazol-4-yl]methoxy]pyrimidin-5-yl]ethanone

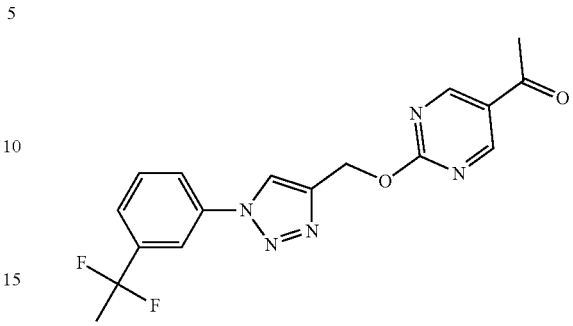

The title compound was prepared analogous to Example 155, using (1-(3-(1,1-difluoroethyl)phenyl)-1H-1,2,3-triazol-4-yl)methanol (Intermediate 64) and 1-(2-chloropyrimidin-5-yl)ethan-1-one. MS (ESI): mass calcd. for $C_{17}H_{15}F_2N_5O_2$, 359.1; m/z found, 360.1 [M+H]+. $^1$H NMR (400 MHz, CDCl$_3$) δ 9.16-9.05 (s, 2H), 8.24-8.16 (s, 1H), 7.93-7.88 (d, J=2.0 Hz, 1H), 7.86-7.78 (m, 1H), 7.66-7.57 (m, 2H), 5.83-5.73 (d, J=0.9 Hz, 2H), 2.67-2.55 (s, 3H), 2.06-1.90 (t, J=18.2 Hz, 3H).

Example 310: (R/S)-1-[2-[[1-[3-(1,1-Difluoroethyl)phenyl]triazol-4-yl]methoxy]pyrimidin-5-yl]ethanol The title compound was prepared in a manner analogous to Example 157 using 1-(2-((1-(3-(1,1-difluoroethyl)phenyl)-1H-1,2,3-triazol-4-yl)methoxy)pyrimidin-5-yl)ethan-1-one (Example 309). MS (ESI): mass calcd. for $C_{17}H_{17}F_2N_5O_2$, 361.1; m/z found, 362.1 [M+H]+. $^1$H NMR (500 MHz, CDCl$_3$) δ 8.64-8.52 (s, 2H), 8.26-8.10 (s, 1H), 7.93-7.85 (m, 1H), 7.84-7.77 (m, 1H), 7.66-7.54 (m, 2H), 5.72-5.57 (d, J=0.7 Hz, 2H), 5.03-4.88 (m, 1H), 2.23-2.10 (s, 1H), 2.07-1.88 (t, J=18.3 Hz, 3H), 1.61-1.52 (d, J=6.5 Hz, 3H).

Example 311: (R/S)-2-[[1-[3-(1,1-Difluoroethyl)phenyl]triazol-4-yl]methoxy]-5-(1-methoxyethyl)pyrimidine

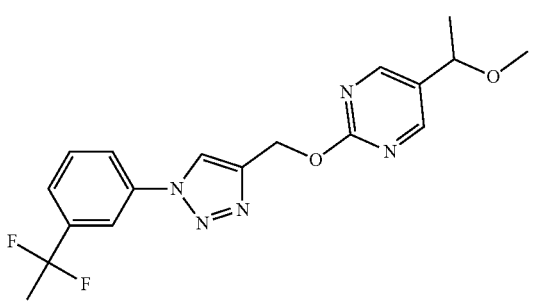 [SMILES: COC(C)c1cnc(OCc2cn(-c3cccc(C(C)(F)F)c3)nn2)nc1]

To a solution of 1-(2-((1-(3-(1,1-difluoroethyl)phenyl)-1H-1,2,3-triazol-4-yl)methoxy)pyrimidin-5-yl)ethan-1-ol (Example 310, 21 mg, 0.06 mmol) in ACN was added NaH (7 mg, 0.17 mmol) followed by iodomethane (82 mg, 0.58 mmol). The resulting suspension was stirred at rt for 2 h. The completed reaction was diluted with EtOAc and washed with water, brine and dried ($Na_2SO_4$), filtered, and concentrated under reduced pressure. Purification (FCC, $SiO_2$, 0-3% MeOH in DCM) afforded the titled compound (9.6 mg, 44%). MS (ESI): mass calcd. for $C_{18}H_{19}F_2N_5O_2$, 375.2; m/z found, 376.0 [M+H]$^+$. $^1$H NMR (400 MHz, CDCl$_3$) δ 8.57-8.48 (s, 2H), 8.24-8.15 (t, J=0.7 Hz, 1H), 7.92-7.86 (m, 1H), 7.86-7.78 (m, 1H), 7.67-7.53 (m, 2H), 5.72-5.64 (d, J=0.7 Hz, 2H), 4.40-4.29 (m, 1H), 3.35-3.21 (s, 3H), 2.08-1.88 (t, J=18.2 Hz, 3H), 1.54-1.43 (d, J=6.5 Hz, 3H).

Example 312: 5-Chloro-2-[[1-[3-(1,1-difluoroethyl)phenyl]triazol-4-yl]methoxy]-4-methyl-pyrimidine

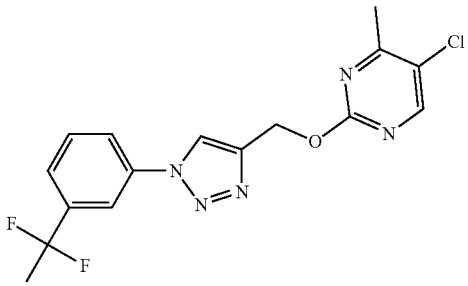 [SMILES: Cc1nc(OCc2cn(-c3cccc(C(C)(F)F)c3)nn2)ncc1Cl]

The title compound was prepared analogous to Example 155, using (1-(3-(1,1-difluoroethyl)phenyl)-1H-1,2,3-triazol-4-yl)methanol (Intermediate 64) and 2,5-dichloro-4-methylpyrimidine. MS (ESI): mass calcd. for $C_{16}H_{14}ClF_2N_5O$, 365.1; m/z found, 366.0 [M+H]$^+$. $^1$H NMR (400 MHz, CDCl$_3$) δ 8.39 (s, 1H), 8.17-8.14 (m, 1H), 7.90-7.87 (m, 1H), 7.84-7.79 (m, 1H), 7.62-7.57 (m, 2H), 5.64 (d, J=0.7 Hz, 2H), 2.57 (s, 3H), 1.98 (t, J=18.2 Hz, 3H).

Example 313: 2-[[1-[3-(1,1-Difluoroethyl)phenyl]triazol-4-yl]methoxy]-5-fluoro-4-methyl-pyrimidine

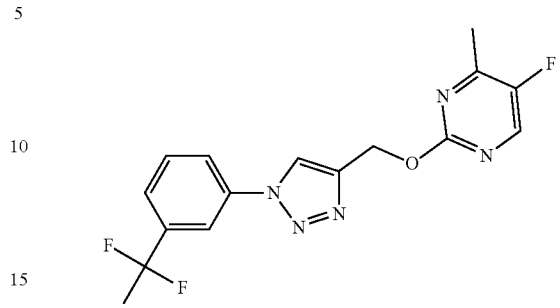

The title compound was prepared analogous to Example 155, using (1-(3-(1,1-difluoroethyl)phenyl)-1H-1,2,3-triazol-4-yl)methanol (Intermediate 64) and 2-chloro-5-fluoro-4-methylpyrimidine. MS (ESI): mass calcd. for $C_{16}H_{14}F_3N_5O$, 349.1; m/z found, 350.1 [M+H]$^+$. $^1$H NMR (400 MHz, CDCl$_3$) δ 8.26 (d, J=1.2 Hz, 1H), 8.16 (s, 1H), 7.89 (s, 1H), 7.86-7.77 (m, 1H), 7.68-7.53 (m, 2H), 5.62 (d, J=0.7 Hz, 2H), 2.50 (d, J=2.5 Hz, 3H), 1.98 (t, J=18.2 Hz, 3H).

Example 314: 2-[[1-[3-(1,1-Difluoroethyl)phenyl]triazol-4-yl]methoxy]-5-methyl-pyrimidin-4-amine

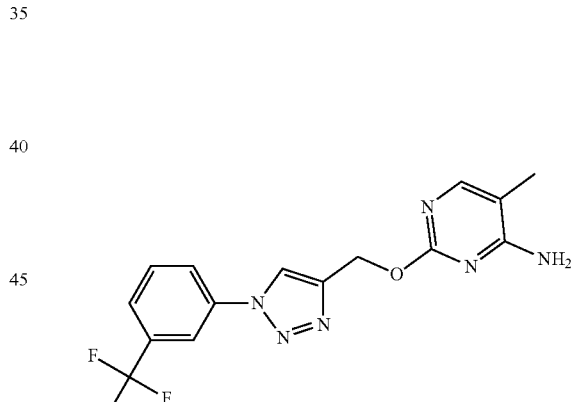

The title compound was prepared in a manner analogous to Example 153 using (1-(3-(1,1-difluoroethyl)phenyl)-1H-1,2,3-triazol-4-yl)methanol (Intermediate 64) and 2-chloro-5-methylpyrimidin-4-amine, using ACN instead of DMF. MS (ESI): mass calcd. for $C_{16}H_{16}F_2N_6O$, 346.1; m/z found, 347.1 [M+H]$^+$. $^1$H NMR (500 MHz, CDCl$_3$) δ 8.19-8.13 (s, 1H), 7.94-7.86 (m, 2H), 7.85-7.75 (m, 1H), 7.63-7.55 (m, 2H), 5.62-5.51 (s, 2H), 5.08-4.91 (s, 2H), 2.05-2.02 (s, 3H), 2.02-1.93 (t, J=18.2 Hz, 3H).

Example 315: 2-[[1-[3-(1,1-Difluoroethyl)phenyl]triazol-4-yl]methoxy]-5-fluoro-N-methyl-pyrimidin-4-amine

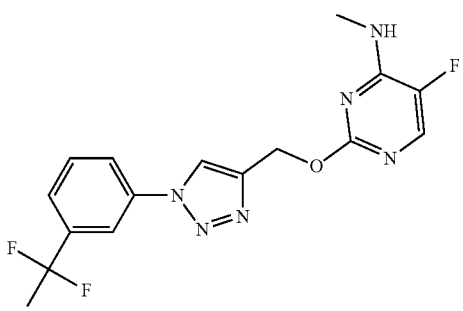 [SMILES: CNc1nc(OCc2cn(-c3cccc(C(C)(F)F)c3)nn2)ncc1F]

The title compound was prepared in a manner analogous to Example 163, Steps B-C using (1-(3-(1,1-difluoroethyl)phenyl)-1H-1,2,3-triazol-4-yl)methanol (Intermediate 64) and 2-chloro-5-fluoro-N-methyl-N-((2-(trimethylsilyl)ethoxy)methyl)pyrimidin-4-amine (Intermediate 59) in step A. MS (ESI): mass calcd. for $C_{16}H_{15}F_3N_6O$, 364.1; m/z found, 365.1 [M+H]$^+$. $^1$H NMR (400 MHz, CDCl$_3$) δ 8.17-8.12 (t, J=0.7 Hz, 1H), 7.92-7.86 (m, 1H), 7.85-7.77 (m, 2H), 7.64-7.56 (m, 2H), 5.61-5.55 (d, J=0.7 Hz, 2H), 5.15-5.10 (s, 1H), 3.11-3.05 (d, J=5.0 Hz, 3H), 2.00-1.90 (m, 3H).

Example 316: 2-[[1-[3-(1,1-Difluoroethyl)phenyl]triazol-4-yl]methoxy]pyrimidin-4-amine

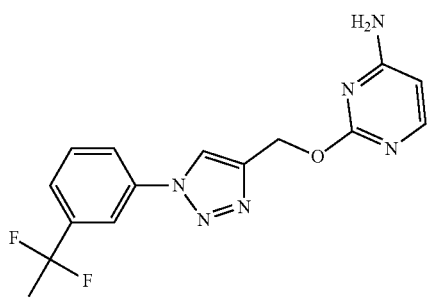 [SMILES: CC(F)(F)c1cccc(-n2cc(COc3nccc(N)n3)nn2)c1]

The title compound was prepared in a manner analogous to Example 153 using (1-(3-(1,1-difluoroethyl)phenyl)-1H-1,2,3-triazol-4-yl)methanol (Intermediate 64) and 2-chloro-pyrimidin-4-amine, using ACN instead of DMF. MS (ESI): mass calcd. for $C_{15}H_{14}F_2N_6O$, 332.1; m/z found, 333.1 [M+H]$^+$. $^1$H NMR (400 MHz, CDCl$_3$) δ 8.22-8.11 (t, J=0.7 Hz, 1H), 8.09-7.99 (d, J=5.7 Hz, 1H), 7.94-7.84 (m, 1H), 7.84-7.76 (m, 1H), 7.65-7.52 (m, 2H), 6.22-6.07 (d, J=5.7 Hz, 1H), 5.65-5.50 (d, J=0.8 Hz, 2H), 5.29-5.12 (s, 2H), 2.04-1.88 (t, J=18.2 Hz, 3H).

Example 317: 2-[[1-[3-(1,1-Difluoroethyl)phenyl]triazol-4-yl]methoxy]-N-methyl-pyrimidin-4-amine

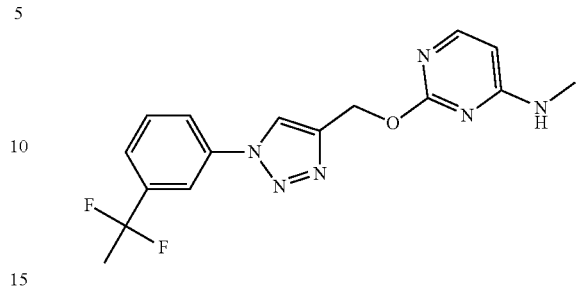

The title compound was prepared in a manner analogous to Example 163, Steps B-C using tert-butyl (2-chloropyrimidin-4-yl)(methyl)carbamate (Intermediate 55) and (1-(3-(1,1-difluoroethyl)phenyl)-1H-1,2,3-triazol-4-yl)methanol (Intermediate 64). MS (ESI): mass calcd. for $C_{16}H_{16}F_2N_6O$, 346.1; m/z found, 347.0 [M+H]$^+$. $^1$H NMR (500 MHz, CDCl$_3$) δ 8.18-8.13 (t, J=0.7 Hz, 1H), 8.07-7.98 (s, 1H), 7.92-7.86 (dt, J=3.0, 1.1 Hz, 1H), 7.85-7.78 (m, 1H), 7.63-7.55 (m, 2H), 6.07-6.02 (d, J=5.9 Hz, 1H), 5.64-5.58 (d, J=0.8 Hz, 2H), 5.09-4.83 (s, 1H), 3.08-2.85 (m, 3H), 2.12-1.82 (t, J=18.2 Hz, 3H).

Example 318: 2-[[1-[3-(1,1-Difluoroethyl)phenyl]triazol-4-yl]methoxy]-N,N-dimethyl-pyrimidin-4-amine

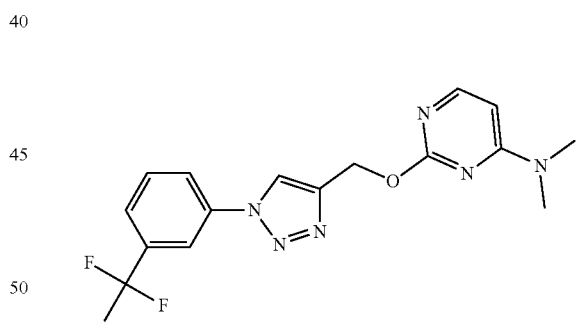

The title compound was prepared analogous to Example 155, using (1-(3-(1,1-difluoroethyl)phenyl)-1H-1,2,3-triazol-4-yl)methanol (Intermediate 64) and 2-chloro-N,N-dimethylpyrimidin-4-amine. MS (ESI): mass calcd. for $C_{17}H_{18}F_2N_6O$, 360.2; m/z found, 361.0 [M+H]$^+$. $^1$H NMR (500 MHz, CDCl$_3$) δ 8.19-8.12 (t, J=0.8 Hz, 1H), 8.06-8.00 (d, J=6.1 Hz, 1H), 7.94-7.87 (t, J=2.1 Hz, 1H), 7.84-7.77 (m, 1H), 7.63-7.55 (m, 2H), 6.16-6.09 (d, J=6.1 Hz, 1H), 5.64-5.59 (d, J=0.8 Hz, 2H), 3.25-2.97 (s, 6H), 2.08-1.90 (m, 3H).

Example 319: 5-Cyclopropyl-2-[[1-[3-(1,1-difluoroethyl)phenyl]triazol-4-yl]methoxy]pyrimidine

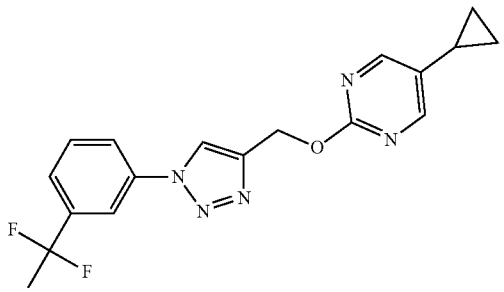 [SMILES: CC(F)(F)c1cccc(-n2cc(COc3ncc(C4CC4)cn3)nn2)c1]

The title compound was prepared analogous to Example 155, using (1-(3-(1,1-difluoroethyl)phenyl)-1H-1,2,3-triazol-4-yl)methanol (Intermediate 64) and 2-chloro-5-cyclopropylpyrimidine. MS (ESI): mass calcd. for $C_{18}H_{17}F_2N_5O$, 357.1; m/z found, 358.0 [M+H]$^+$. $^1$H NMR (400 MHz, CDCl$_3$) δ 8.32 (d, J=0.5 Hz, 2H), 8.17-8.15 (m, 1H), 7.90-7.87 (m, 1H), 7.81 (d, J=6.4 Hz, 1H), 7.63-7.57 (m, 2H), 5.64 (d, J=0.7 Hz, 2H), 1.97 (t, J=18.2 Hz, 3H), 1.89-1.77 (m, 1H), 1.07-0.98 (m, 2H), 0.75-0.64 (m, 2H).

Example 320: 5-(Azetidin-1-yl)-2-[[1-[3-(1,1-difluoroethyl)phenyl]triazol-4-yl]methoxy]pyrimidine

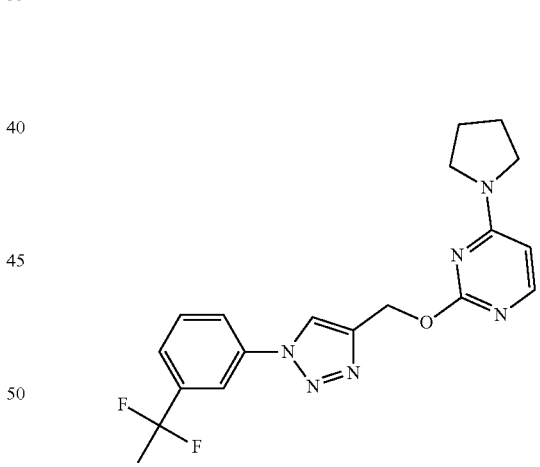

The title compound was prepared in a manner analogous to Example 165, Steps A-C, using 5-bromo-2-((1-(3-(1,1-difluoroethyl)phenyl)-1H-1,2,3-triazol-4-yl)methoxy)pyrimidine (Example 293) and azetidine in Step A. MS (ESI): mass calcd. for $C_{18}H_{18}F_2N_6O$, 372.2; m/z found, 373.1 [M+H]$^+$. $^1$H NMR (500 MHz, CDCl$_3$) δ 8.16-8.13 (t, J=0.7 Hz, 1H), 7.91-7.87 (m, 1H), 7.84-7.79 (s, 3H), 7.64-7.54 (m, 2H), 5.62-5.55 (d, J=0.8 Hz, 2H), 3.97-3.86 (t, J=7.2 Hz, 4H), 2.50-2.39 (m, 2H), 2.04-1.88 (t, J=18.2 Hz, 3H).

Example 321: 2-[[1-[3-(1,1-Difluoroethyl)phenyl]triazol-4-yl]methoxy]-5-(3-fluoroazetidin-1-yl)pyrimidine

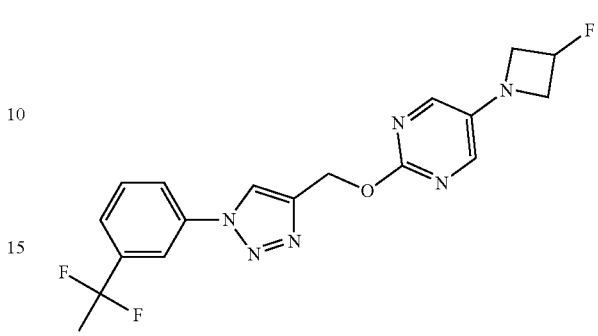

The title compound was prepared in a manner analogous to Example 165, Steps A-C, using 5-bromo-2-((1-(3-(1,1-difluoroethyl)phenyl)-1H-1,2,3-triazol-4-yl)methoxy)pyrimidine (Example 293) and 3-fluoroazetidine in Step A. MS (ESI): mass calcd. for $C_{18}H_{17}F_3N_6O$, 390.1; m/z found, 391.1 [M+H]$^+$. $^1$H NMR (500 MHz, CDCl$_3$) δ 8.17-8.12 (t, J=0.7 Hz, 1H), 7.91-7.86 (m, 3H), 7.85-7.77 (m, 1H), 7.64-7.55 (m, 2H), 5.62-5.56 (d, J=0.8 Hz, 2H), 5.56-5.34 (m, 1H), 4.29-4.18 (m, 2H), 4.06-3.94 (m, 2H), 2.04-1.91 (t, J=18.2 Hz, 3H).

Example 322: 2-[[1-[3-(1,1-Difluoroethyl)phenyl]triazol-4-yl]methoxy]-4-pyrrolidin-1-yl-pyrimidine The title compound was prepared in a manner analogous to Example 153 using (1-(3-(1,1-difluoroethyl)phenyl)-1H-1,2,3-triazol-4-yl)methanol (Intermediate 64) and 2-chloro-4-(pyrrolidin-1-yl)pyrimidine using ACN instead of DMF. MS (ESI): mass calcd. for $C_{19}H_{20}F_2N_6O$, 386.2; m/z found, 387.1 [M+H]$^+$. $^1$H NMR (400 MHz, CDCl$_3$) δ 8.17-8.14 (s, 1H), 8.02-7.98 (d, J=5.9 Hz, 1H), 7.91-7.87 (m, 1H), 7.84-7.77 (m, 1H), 7.62-7.55 (m, 2H), 6.06-5.95 (d, J=6.0 Hz, 1H), 5.68-5.55 (d, J=0.8 Hz, 2H), 3.76-3.54 (m, 2H), 3.47-3.27 (m, 2H), 2.10-1.88 (m, 7H).

Example 323: 2-[[1-[3-(Difluoromethoxy)phenyl]triazol-4-yl]methoxy]pyrimidine

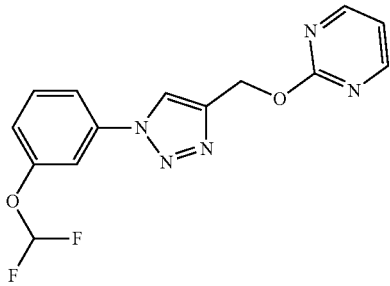 [SMILES: FC(F)Oc1cccc(-n2cc(COc3ncccn3)nn2)c1]

The title compound was prepared in a manner analogous to Example 1 using (1-(3-(difluoromethoxy)phenyl)-1H-1,2,3-triazol-4-yl)methanol (Intermediate 42) and 2-chloropyrimidine. MS (ESI): mass calcd. for $C_{14}H_{11}F_2N_5O_2$, 319.1; m/z found, 320.1 [M+H]$^+$. $^1$H NMR (400 MHz, DMSO-$d_6$) δ 8.99 (s, 1H), 8.66 (d, J=4.8 Hz, 2H), 7.86-7.76 (m, 2H), 7.66 (t, J=8.2 Hz, 1H), 7.48 (d, J=73.5 Hz, 1H), 7.31 (dd, J=7.9, 2.4 Hz, 1H), 7.24-7.14 (m, 1H), 5.54 (s, 2H).

Example 324: 2-[[1-[3-(Difluoromethoxy)phenyl]triazol-4-yl]methoxy]-5-fluoro-pyrimidine

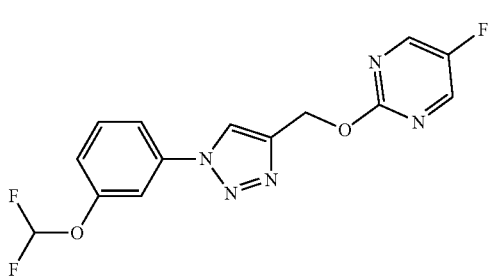 [SMILES: Fc1cnc(OCc2cn(-c3cccc(OC(F)F)c3)nn2)nc1]

The title compound was prepared in a manner analogous to Example 1 using (1-(3-(difluoromethoxy)phenyl)-1H-1,2,3-triazol-4-yl)methanol (Intermediate 42) and 2-chloro-5-fluoropyrimidine. MS (ESI): mass calcd. for $C_{14}H_{10}F_3N_5O_2$, 337.1; m/z found, 338.1 [M+H]$^+$. $^1$H NMR (400 MHz, DMSO-$d_6$) δ 8.98 (s, 1H), 8.75 (d, J=0.7 Hz, 2H), 7.82 (ddd, J=8.1, 2.1, 0.9 Hz, 1H), 7.79 (t, J=2.2 Hz, 1H), 7.66 (t, J=8.2 Hz, 1H), 7.60-7.17 (m, 2H), 5.52 (s, 2H).

Example 325: 2-[[1-[3-(Difluoromethoxy)phenyl]triazol-4-yl]methoxy]-5-methoxy-pyrimidine

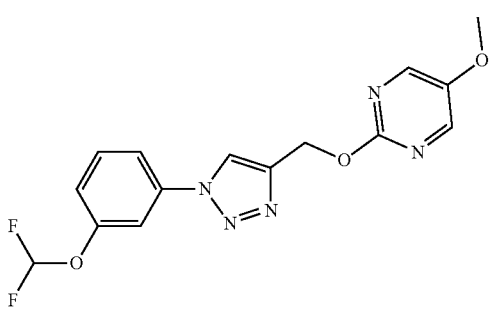 [SMILES: COc1cnc(OCc2cn(-c3cccc(OC(F)F)c3)nn2)nc1]

The title compound was prepared in a manner analogous to Example 1 using (1-(3-(difluoromethoxy)phenyl)-1H-1,2,3-triazol-4-yl)methanol (Intermediate 42) and 2-chloro-5-methoxypyrimidine. MS (ESI): mass calcd. for $C_{15}H_{13}F_2N_5O_3$, 349.1; m/z found, 350.1 [M+H]$^+$. $^1$H NMR (400 MHz, DMSO-$d_6$) δ 8.96 (s, 1H), 8.41 (s, 2H), 7.83 (dd, J=8.1, 2.2 Hz, 1H), 7.79 (t, J=2.2 Hz, 1H), 7.66 (t, J=8.2 Hz, 1H), 7.59-7.16 (m, 2H), 5.47 (s, 2H), 3.86 (s, 3H).

Example 326: 5-Chloro-2-[[1-[3-(difluoromethoxy)phenyl]triazol-4-yl]methoxy]pyrimidine

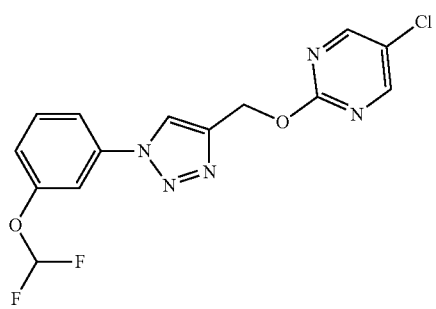 [SMILES: FC(F)Oc1cccc(-n2cc(COc3ncc(Cl)cn3)nn2)c1]

The title compound was prepared in a manner analogous to Example 1 using (1-(3-(difluoromethoxy)phenyl)-1H-1,2,3-triazol-4-yl)methanol (Intermediate 42) and 2,5-dichloropyrimidine. MS (ESI): mass calcd. for $C_{14}H_{10}ClF_2N_5O_2$, 353.0; m/z found, 354.0 [M+H]$^+$. $^1$H NMR (500 MHz, DMSO-$d_6$) δ 8.98 (s, 1H), 8.77 (s, 2H), 7.82 (ddd, J=8.1, 2.1, 0.9 Hz, 1H), 7.79 (t, J=2.2 Hz, 1H), 7.66 (t, J=8.2 Hz, 1H), 7.56-7.23 (m, 2H), 5.79-5.32 (m, 2H).

Example 327: 2-[[1-[3-(Difluoromethoxy)phenyl]triazol-4-yl]methoxy]-5-methyl-pyrimidine

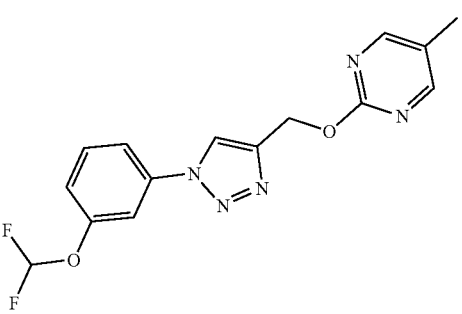 [SMILES: Cc1cnc(OCc2cn(-c3cccc(OC(F)F)c3)nn2)nc1]

The title compound was prepared in a manner analogous to Example 1 using (1-(3-(difluoromethoxy)phenyl)-1H-1,2,3-triazol-4-yl)methanol (Intermediate 42) and 2-chloro-5-methylpyrimidine. MS (ESI): mass calcd. for $C_{15}H_{13}F_2N_5O_2$, 333.1; m/z found, 334.1 [M+H]$^+$. $^1$H NMR (500 MHz, DMSO-$d_6$) δ 8.97 (s, 1H), 8.49 (d, J=0.8 Hz, 2H), 7.83 (ddd, J=8.1, 2.1, 0.9 Hz, 1H), 7.79 (t, J=2.2 Hz, 1H), 7.66 (t, J=8.2 Hz, 1H), 7.56-7.22 (m, 2H), 5.62-5.21 (m, 2H), 2.21 (d, J=0.8 Hz, 3H).

Example 328: 2-[[1-[3-(Difluoromethoxy)phenyl]
triazol-4-yl]methoxy]-5-ethyl-pyrimidine

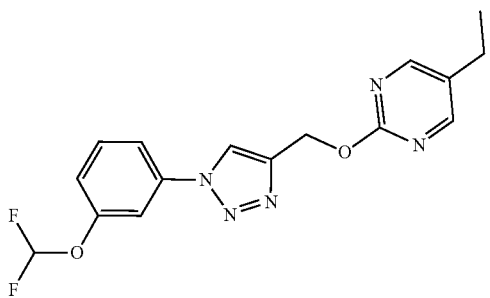 [SMILES: CCc1cnc(OCc2cn(-c3cccc(OC(F)F)c3)nn2)nc1]

The title compound was prepared in a manner analogous to Example 1 using (1-(3-(difluoromethoxy)phenyl)-1H-1,2,3-triazol-4-yl)methanol (Intermediate 42) and 2-chloro-5-ethylpyrimidine. MS (ESI): mass calcd. for $C_{16}H_{15}F_2N_5O_2$, 347.1; m/z found, 348.2 [M+H]$^+$. $^1$H NMR (500 MHz, DMSO-d$_6$) δ 8.98 (d, J=0.6 Hz, 1H), 8.53 (d, J=0.6 Hz, 2H), 7.83 (ddd, J=8.1, 2.1, 0.9 Hz, 1H), 7.79 (t, J=2.2 Hz, 1H), 7.66 (t, J=8.2 Hz, 1H), 7.55-7.19 (m, 2H), 5.67-5.35 (m, 2H), 2.62-2.54 (m, 2H), 1.19 (t, J=7.6 Hz, 3H).

Example 329: 2-[[1-[4-(Difluoromethoxy)phenyl]
triazol-4-yl]methoxy]pyrimidine

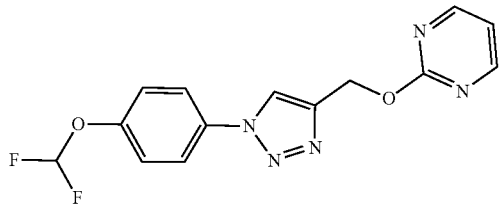 [SMILES: FC(F)Oc1ccc(-n2cc(COc3ncccn3)nn2)cc1]

The title compound was prepared in a manner analogous to Example 1 using (1-(4-(difluoromethoxy)phenyl)-1H-1,2,3-triazol-4-yl)methanol (Intermediate 43) and 2-chloropyrimidine. MS (ESI): mass calcd. for $C_{14}H_{11}F_2N_5O_2$, 319.1; m/z found, 320.1 [M+H]$^+$. $^1$H NMR (500 MHz, DMSO-d$_6$) δ 8.92 (d, J=0.6 Hz, 1H), 8.66 (d, J=4.8 Hz, 2H), 8.05-7.91 (m, 2H), 7.52-7.16 (m, 4H), 5.53 (d, J=0.5 Hz, 2H).

Example 330: 2-[[1-[4-(Difluoromethoxy)phenyl]
triazol-4-yl]methoxy]-5-fluoro-pyrimidine

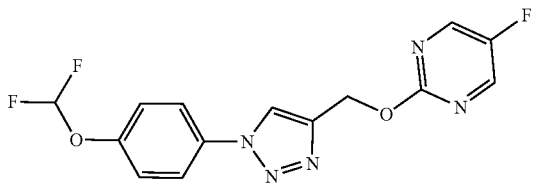 [SMILES: Fc1cnc(OCc2cn(-c3ccc(OC(F)F)cc3)nn2)nc1]

The title compound was prepared in a manner analogous to Example 1 using (1-(4-(difluoromethoxy)phenyl)-1H-1,2,3-triazol-4-yl)methanol (Intermediate 43) and 2-chloro-5-fluoropyrimidine. MS (ESI): mass calcd. for $C_{14}H_{10}F_3N_5O_2$, 337.1; 338.1 [M+H]$^+$. $^1$H NMR (500 MHz, DMSO-d$_6$) δ 8.91 (s, 1H), 8.75 (d, J=0.7 Hz, 2H), 8.01-7.92 (m, 2H), 7.52-7.17 (m, 3H), 5.52 (s, 2H).

Example 331: 2-[[1-[4-(Difluoromethoxy)phenyl]
triazol-4-yl]methoxy]-5-methoxy-pyrimidine

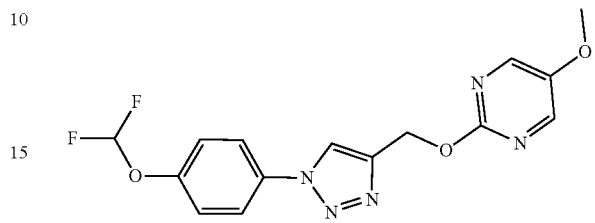

The title compound was prepared in a manner analogous to Example 1 using (1-(4-(difluoromethoxy)phenyl)-1H-1,2,3-triazol-4-yl)methanol (Intermediate 43) and 2-chloro-5-methoxypyrimidine. MS (ESI): mass calcd. for $C_{15}H_{13}F_2N_5O_3$, 349.1; m/z found, 350.1 [M+H]$^+$. $^1$H NMR (500 MHz, DMSO-d$_6$) δ 8.89 (s, 1H), 8.41 (s, 2H), 8.02-7.94 (m, 2H), 7.53-7.16 (m, 3H), 5.46 (d, J=0.6 Hz, 2H), 3.86 (s, 3H).

Example 332: 5-Chloro-2-[[1-[4-(difluoromethoxy)
phenyl]triazol-4-yl]methoxy]pyrimidine

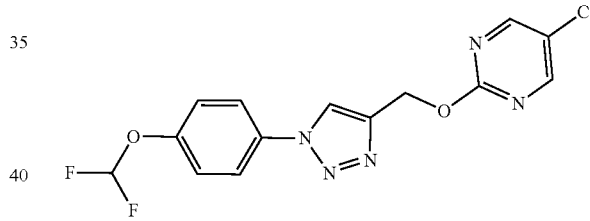

The title compound was prepared in a manner analogous to Example 1 using (1-(4-(difluoromethoxy)phenyl)-1H-1,2,3-triazol-4-yl)methanol (Intermediate 43) and 2,5-dichloropyrimidine. $^1$H NMR (500 MHz, DMSO-d$_6$) δ 8.91 (s, 1H), 8.77 (s, 2H), 8.01-7.93 (m, 2H), 7.53-7.16 (m, 3H), 5.59-5.49 (m, 2H).

Example 333: 2-[[1-[4-(Difluoromethoxy)phenyl]
triazol-4-yl]methoxy]-5-methyl-pyrimidine

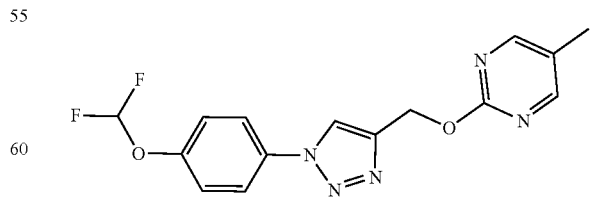

The title compound was prepared in a manner analogous to Example 1 using (1-(4-(difluoromethoxy)phenyl)-1H-1,2,3-triazol-4-yl)methanol (Intermediate 43) and 2-chloro-5-methylpyrimidine. $^1$H NMR (500 MHz, DMSO-d$_6$) δ 8.90

(s, 1H), 8.49 (d, J=0.8 Hz, 2H), 8.04-7.90 (m, 2H), 7.55-7.16 (m, 3H), 5.49 (s, 2H), 2.21 (d, J=0.8 Hz, 3H).

Example 334: 2-[[1-[4-(Difluoromethoxy)phenyl]triazol-4-yl]methoxy]-5-ethyl-pyrimidine

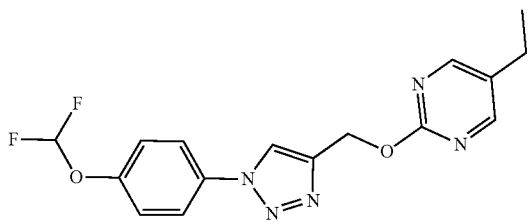 [SMILES: CCc1cnc(OCc2cn(-c3ccc(OC(F)F)cc3)nn2)nc1]

The title compound was prepared in a manner analogous to Example 1 using (1-(4-(difluoromethoxy)phenyl)-1H-1,2,3-triazol-4-yl)methanol (Intermediate 43) and 2-chloro-5-ethylpyrimidine. $^1$H NMR (500 MHz, DMSO-d$_6$) δ 8.90 (s, 1H), 8.53 (t, J=0.6 Hz, 2H), 8.01-7.88 (m, 2H), 7.54-7.16 (m, 3H), 5.50 (d, J=0.6 Hz, 2H), 2.57 (q, J=7.6 Hz, 2H), 1.19 (t, J=7.6 Hz, 3H).

Example 335: 2-[[1-[4-(Trifluoromethoxy)phenyl]triazol-4-yl]methoxy]pyrimidine

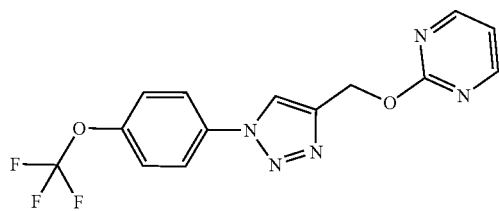 [SMILES: FC(F)(F)Oc1ccc(-n2cc(COc3ncccn3)nn2)cc1]

The title compound was prepared in a manner analogous to Example 1 using (1-(4-(trifluoromethoxy)phenyl)-1H-1,2,3-triazol-4-yl)methanol (Intermediate 34) and 2-chloropyrimidine. MS (ESI): mass calcd. for C$_{14}$H$_{10}$F$_3$N$_5$O$_2$, 337.1; m/z found, 338.1 [M+H]$^+$. $^1$H NMR (500 MHz, DMSO-d$_6$) δ 8.97 (s, 1H), 8.66 (d, J=4.8 Hz, 2H), 8.12-7.99 (m, 2H), 7.69-7.58 (m, 2H), 7.20 (t, J=4.8 Hz, 1H), 5.61-5.39 (m, 2H).

Example 336: 5-Fluoro-2-[[1-[4-(trifluoromethoxy)phenyl]triazol-4-yl]methoxy]pyrimidine

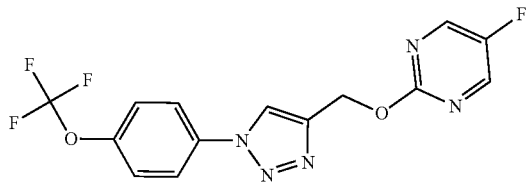 [SMILES: Fc1cnc(OCc2cn(-c3ccc(OC(F)(F)F)cc3)nn2)nc1]

The title compound was prepared in a manner analogous to Example 1 using (1-(4-(trifluoromethoxy)phenyl)-1H-1,2,3-triazol-4-yl)methanol (Intermediate 34) and 2-chloro-5-fluoropyrimidine. MS (ESI): mass calcd. for C$_{14}$H$_9$F$_4$N$_5$O$_2$, 355.1; m/z found, 356.0 [M+H]$^+$. $^1$H NMR (500 MHz, CD$_3$OD) δ 8.74 (s, 1H), 8.57 (s, 2H), 8.03-7.94 (m, 2H), 7.57-7.44 (m, 2H), 5.44 (s, 2H).

Example 337: 5-Methoxy-2-[[1-[4-(trifluoromethoxy)phenyl]triazol-4-yl]methoxy]pyrimidine

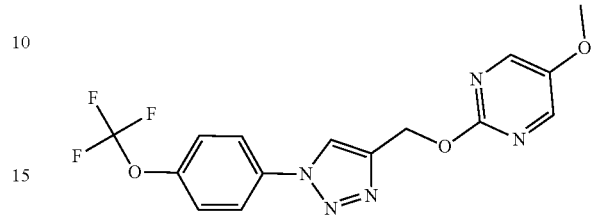

The title compound was prepared in a manner analogous to Example 1 using (1-(4-(trifluoromethoxy)phenyl)-1H-1,2,3-triazol-4-yl)methanol (Intermediate 34) and 2-chloro-5-methoxypyrimidine. MS (ESI): mass calcd. for C$_{15}$H$_{12}$F$_3$N$_5$O$_3$, 367.1; m/z found, 368.1 [M+H]$^+$. $^1$H NMR (500 MHz, DMSO-d$_6$) δ 8.94 (s, 1H), 8.41 (s, 2H), 8.11-8.00 (m, 2H), 7.68-7.54 (m, 2H), 5.51-5.43 (m, 2H), 3.86 (s, 3H).

Example 338: 5-Chloro-2-[[1-[4-(trifluoromethoxy)phenyl]triazol-4-yl]methoxy]pyrimidine

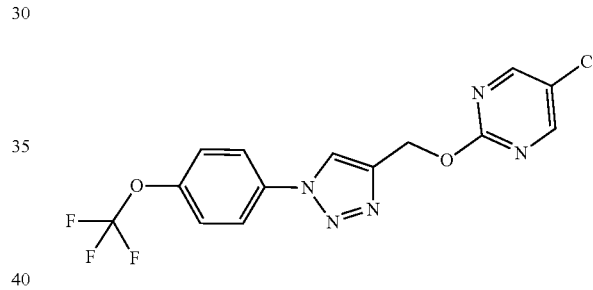

The title compound was prepared in a manner analogous to Example 1 using (1-(4-(trifluoromethoxy)phenyl)-1H-1,2,3-triazol-4-yl)methanol (Intermediate 34) and 2,5-dichloropyrimidine. MS (ESI): mass calcd. for C$_{14}$H$_9$ClF$_3$N$_5$O$_2$, 371.0; m/z found, 372.0 [M+H]$^+$. $^1$H NMR (500 MHz, DMSO-d$_6$) δ 8.96 (s, 1H), 8.77 (s, 2H), 8.10-8.01 (m, 2H), 7.67-7.55 (m, 2H), 5.55 (d, J=0.6 Hz, 2H).

Example 339: 5-Methyl-2-[[1-[4-(trifluoromethoxy)phenyl]triazol-4-yl]methoxy]pyrimidine

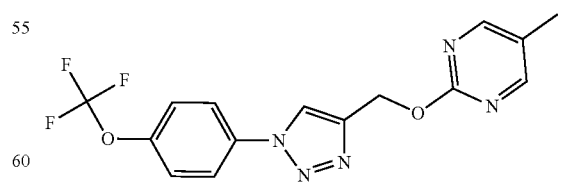

The title compound was prepared in a manner analogous to Example 1 using (1-(4-(trifluoromethoxy)phenyl)-1H-1,2,3-triazol-4-yl)methanol (Intermediate 34) and 2-chloro-5-methylpyrimidine. MS (ESI): mass calcd. for C$_{15}$H$_{12}$F$_3$N$_5$O$_2$, 351.1; m/z found, 352.1 [M+H]$^+$. $^1$H NMR (500 MHz, DMSO-d$_6$) δ 8.95 (s, 1H), 8.49 (d, J=0.7 Hz, 2H), 8.12-8.02 (m, 2H), 7.70-7.56 (m, 2H), 5.50 (s, 2H), 2.21 (t, J=0.8 Hz, 3H).

Example 340: 5-Ethyl-2-[[1-[4-(trifluoromethoxy) phenyl]triazol-4-yl]methoxy]pyrimidine

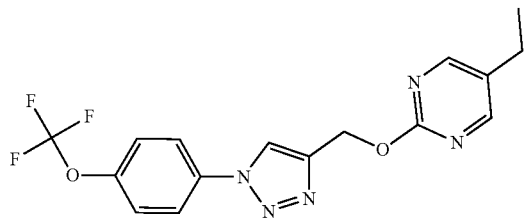 [SMILES: CCc1cnc(OCc2cn(-c3ccc(OC(F)(F)F)cc3)nn2)nc1]

The title compound was prepared in a manner analogous to Example 1 using (1-(4-(trifluoromethoxy)phenyl)-1H-1,2,3-triazol-4-yl)methanol (Intermediate 34) and 2-chloro-5-ethylpyrimidine. MS (ESI): mass calcd. for C$_{16}$H$_{14}$F$_3$N$_5$O$_2$, 365.1; m/z found, 366.2 [M+H]$^+$. $^1$H NMR (500 MHz, DMSO-d$_6$) δ 8.96 (s, 1H), 8.53 (s, 2H), 8.16-7.97 (m, 2H), 7.70-7.51 (m, 2H), 5.58-5.41 (m, 2H), 2.57 (q, 2H), 1.19 (t, J=7.6 Hz, 3H).

Example 341: 2-[[1-[3-(Trifluoromethoxy)phenyl] triazol-4-yl]methoxy]pyrimidine

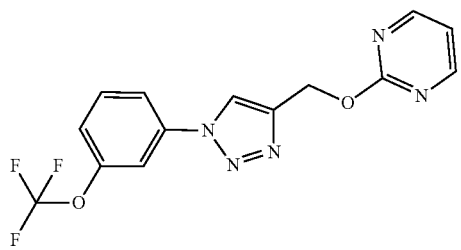 [SMILES: FC(F)(F)Oc1cccc(-n2cc(COc3ncccn3)nn2)c1]

The title compound was prepared in a manner analogous to Example 1 using (1-(3-(trifluoromethoxy)phenyl)-1H-1,2,3-triazol-4-yl)methanol (Intermediate 35) and 2-chloropyrimidine. $^1$H NMR (500 MHz, DMSO-d) δ 9.03 (s, 1H), 8.67 (d, J=4.8 Hz, 2H), 8.05-7.92 (m, 2H), 7.75 (t, J=8.2 Hz, 1H), 7.52 (d, J=8.3 Hz, 1H), 7.20 (t, J=4.8 Hz, 1H), 5.54 (s, 2H).

Example 342: 5-Methyl-2-[[1-[3-(trifluoromethoxy) phenyl]triazol-4-yl]methoxy]pyrimidine

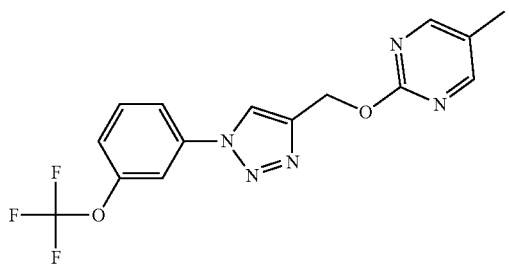 [SMILES: Cc1cnc(OCc2cn(-c3cccc(OC(F)(F)F)c3)nn2)nc1]

The title compound was prepared in a manner analogous to Example 1 using (1-(3-(trifluoromethoxy)phenyl)-1H-1,2,3-triazol-4-yl)methanol (Intermediate 35) and 2-chloro-5-methylpyrimidine. MS (ESI): mass calcd. for C$_{15}$H$_{12}$F$_3$N$_5$O$_2$, 351.1; m/z found, 352.1 [M+H]$^+$. $^1$H NMR (400 MHz, DMSO-d$_6$) δ 9.02 (s, 1H), 8.49 (d, J=0.8 Hz, 2H), 8.04-7.96 (m, 2H), 7.78-7.68 (m, 1H), 7.52 (ddt, J=8.3, 2.3, 1.2 Hz, 1H), 5.50 (s, 2H), 2.21 (d, J=0.8 Hz, 3H).

Example 343: 5-Methyl-2-[[1-[3-(trifluoromethoxy) phenyl]triazol-4-yl]methoxy]pyrimidin-4-amine

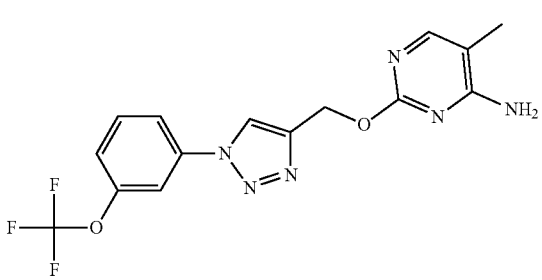 [SMILES: Cc1cnc(OCc2cn(-c3cccc(OC(F)(F)F)c3)nn2)nc1N]

The title compound was prepared in a manner analogous to Example 1 using (1-(3-(trifluoromethoxy)phenyl)-1H-1,2,3-triazol-4-yl)methanol (Intermediate 35) and 2-chloro-5-methylpyrimidin-4-amine. MS (ESI): mass calcd. for C$_{15}$H$_{13}$F$_3$N$_6$O$_2$, 366.1; m/z found, 367.1 [M+H]$^+$. $^1$H NMR (500 MHz, DMSO-d$_6$) δ 8.99 (s, 1H), 8.04-7.95 (m, 2H), 7.79-7.70 (m, 2H), 7.54-7.49 (m, 1H), 6.76 (s, 2H), 5.35 (s, 2H), 1.92 (d, J=0.9 Hz, 3H).

Example 344: 1-[2-[[1-[3-(Trifluoromethoxy)phenyl]triazol-4-yl]methoxy]pyrimidin-5-yl]ethanone

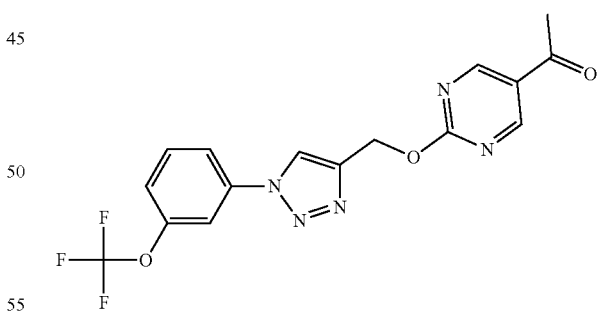

The title compound was prepared in a manner analogous to Example 1 using (1-(3-(trifluoromethoxy)phenyl)-1H-1,2,3-triazol-4-yl)methanol (Intermediate 35) and 1-(2-chloropyrimidin-5-yl)ethan-1-one. MS (ESI): mass calcd. for C$_{16}$H$_{12}$F$_3$N$_5$O$_3$, 379.1; m/z found, 380.1 [M+H]$^+$. $^1$H NMR (500 MHz, DMSO-d$_6$) δ 9.16 (s, 2H), 9.06 (s, 1H), 8.04-7.99 (m, 2H), 7.80-7.71 (m, 1H), 7.57-7.47 (m, 1H), 5.66 (s, 2H), 2.60 (s, 3H).

Example 345: 2-[2-[[1-[3-(Trifluoromethoxy)phenyl]triazol-4-yl]methoxy]pyrimidin-5-yl]propan-2-ol

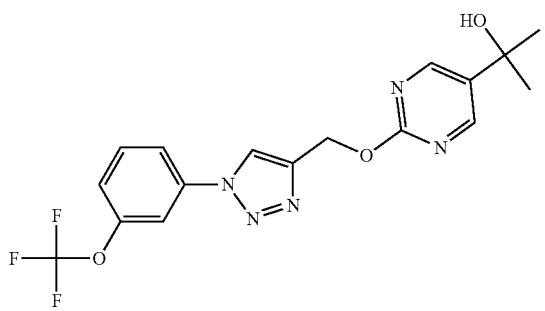 [SMILES: CC(C)(O)c1cnc(OCc2cn(-c3cccc(OC(F)(F)F)c3)nn2)nc1]

The title compound was prepared in a manner analogous to Example 1 using (1-(3-(trifluoromethoxy)phenyl)-1H-1,2,3-triazol-4-yl)methanol (Intermediate 35) and 2-(2-chloropyrimidin-5-yl)propan-2-ol. MS (ESI): mass calcd. for $C_{17}H_{16}F_3N_5O_3$, 395.1; m/z found, 396.1 [M+H]$^+$. $^1$H NMR (500 MHz, CD$_3$OD) δ 8.76 (s, 1H), 8.72 (s, 2H), 7.94-7.85 (m, 2H), 7.69 (t, J=8.2 Hz, 1H), 7.43 (ddt, J=8.3, 2.3, 1.1 Hz, 1H), 5.62 (s, 2H), 1.57 (s, 6H).

Example 346: 4-(Methoxymethyl)-2-[[1-[3-(trifluoromethoxy)phenyl]triazol-4-yl]methoxy]pyrimidine

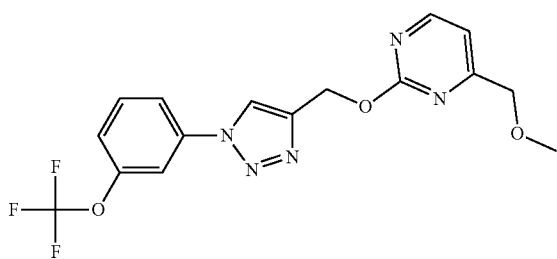 [SMILES: COCc1ccnc(OCc2cn(-c3cccc(OC(F)(F)F)c3)nn2)n1]

The title compound was prepared in a manner analogous to Example 1 using (1-(3-(trifluoromethoxy)phenyl)-1H-1,2,3-triazol-4-yl)methanol (Intermediate 35) and 2-chloro-4-(methoxymethyl)pyrimidine. MS (ESI): mass calcd. for $C_{16}H_{14}F_3N_5O_3$, 381.1; m/z found, 382.1 [M+H]$^+$. $^1$H NMR (400 MHz, CD$_3$OD) δ 8.84-8.72 (m, 1H), 8.59 (s, 1H), 7.90 (d, J=9.3 Hz, 2H), 7.71 (d, J=7.9 Hz, 1H), 7.45 (s, 1H), 7.23 (s, 1H), 5.63 (d, J=5.4 Hz, 2H), 4.68-4.42 (m, 2H), 3.62-3.44 (m, 3H).

Example 347: 4-Methyl-2-[[1-[3-(trifluoromethoxy)phenyl]triazol-4-yl]methoxy]pyrimidine

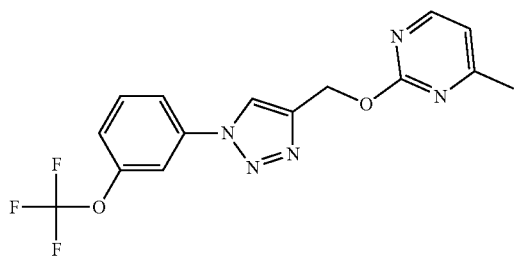 [SMILES: Cc1ccnc(OCc2cn(-c3cccc(OC(F)(F)F)c3)nn2)n1]

The title compound was prepared in a manner analogous to Example 1 using (1-(3-(trifluoromethoxy)phenyl)-1H-1,2,3-triazol-4-yl)methanol (Intermediate 35) and 2-chloro-4-methylpyrimidine. MS (ESI): mass calcd. for $C_{15}H_{12}F_3N_5O_2$, 351.1; m/z found, 352.1[M+H]$^+$. $^1$H NMR (500 MHz, DMSO-d$_6$) δ 9.02 (s, 1H), 8.49 (d, J=5.0 Hz, 1H), 8.07-7.98 (m, 2H), 7.75 (t, J=8.2 Hz, 1H), 7.58-7.51 (m, 1H), 7.08 (d, J=4.9 Hz, 1H), 5.52 (s, 2H), 2.43 (s, 3H).

Example 348: 5-Fluoro-2-[[1-[3-(trifluoromethoxy)phenyl]triazol-4-yl]methoxy]pyrimidine

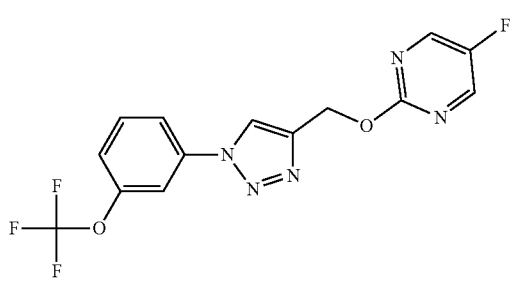 [SMILES: Fc1cnc(OCc2cn(-c3cccc(OC(F)(F)F)c3)nn2)nc1]

The title compound was prepared in a manner analogous to Example 1 using (1-(3-(trifluoromethoxy)phenyl)-1H-1,2,3-triazol-4-yl)methanol (Intermediate 35) and 2-chloro-5-fluoropyrimidine. MS (ESI): mass calcd. for $C_{14}H_9F_4N_5O_2$, 355.1; m/z found, 256.1 [M+H]$^+$. $^1$H NMR (500 MHz, DMSO-d$_6$) δ 9.03 (s, 1H), 8.75 (d, J=0.7 Hz, 2H), 8.05-7.96 (m, 2H), 7.80-7.71 (m, 1H), 7.53 (ddq, J=8.3, 2.2, 1.1 Hz, 1H), 5.53 (d, J=0.6 Hz, 2H)

Example 349: 5-Methoxy-2-[[1-[3-(trifluoromethoxy)phenyl]triazol-4-yl]methoxy]pyrimidine

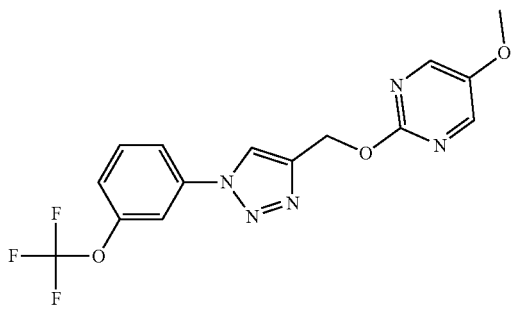 [SMILES: COc1cnc(OCc2cn(-c3cccc(OC(F)(F)F)c3)nn2)nc1]

The title compound was prepared in a manner analogous to Example 1 using (1-(3-(trifluoromethoxy)phenyl)-1H-1,2,3-triazol-4-yl)methanol (Intermediate 35) and 2-chloro-5-methoxypyrimidine. MS (ESI): mass calcd. for $C_{15}H_{12}F_3N_5O_3$, 367.1; m/z found, 368.1 [M+H]$^+$. $^1$H NMR (500 MHz, DMSO-d$_6$) δ 9.01 (s, 1H), 8.41 (s, 2H), 8.05-7.96 (m, 2H), 7.75 (t, J=8.2 Hz, 1H), 7.52 (d, J=8.2 Hz, 1H), 5.48 (s, 2H), 3.86 (s, 3H).

Example 350: 5-Chloro-2-[[1-[3-(trifluoromethoxy)phenyl]triazol-4-yl]methoxy]pyrimidine

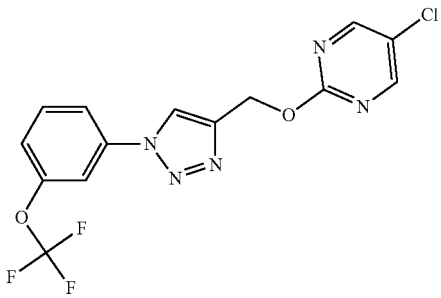 [SMILES: FC(F)(F)Oc1cccc(-n2cc(COc3ncc(Cl)cn3)nn2)c1]

The title compound was prepared in a manner analogous to Example 1 using (1-(3-(trifluoromethoxy)phenyl)-1H-1,2,3-triazol-4-yl)methanol (Intermediate 35) and 2,5-dichloropyrimidine. MS (ESI): mass calcd. for $C_{14}H_9ClF_3N_5O_2$, 371.0; m/z found, 372.0 [M+H]$^+$. $^1$H NMR (500 MHz, DMSO-d$_6$) δ 9.02 (s, 1H), 8.77 (s, 2H), 8.05-7.95 (m, 2H), 7.81-7.70 (m, 1H), 7.53 (ddt, J=8.3, 2.2, 1.1 Hz, 1H), 5.55 (s, 2H).

Example 351: 5-Ethyl-2-[[1-[3-(trifluoromethoxy)phenyl]triazol-4-yl]methoxy]pyrimidine

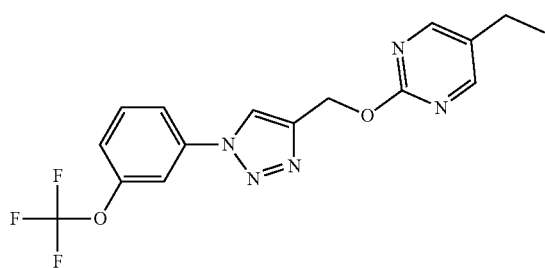 [SMILES: CCc1cnc(OCc2cn(-c3cccc(OC(F)(F)F)c3)nn2)nc1]

The title compound was prepared in a manner analogous to Example 1 using (1-(3-(trifluoromethoxy)phenyl)-1H-1,2,3-triazol-4-yl)methanol (Intermediate 35) and 2-chloro-5-ethylpyrimidine. MS (ESI): mass calcd. for $C_{16}H_{14}F_3N_5O_2$, 365.1; m/z found, 366.2 [M+H]$^+$. $^1$H NMR (500 MHz, DMSO-d$_6$) δ 9.03 (s, 1H), 8.53 (d, J=0.8 Hz, 2H), 8.08-7.91 (m, 2H), 7.80-7.69 (m, 1H), 7.52 (ddt, J=8.3, 2.2, 1.1 Hz, 1H), 5.52 (s, 2H), 2.58 (q, J=7.6 Hz, 2H), 1.19 (t, J=7.6 Hz, 3H).

Example 352: N-Methyl-2-[[1-[3-(trifluoromethoxy)phenyl]triazol-4-yl]methoxy]pyrimidin-4-amine

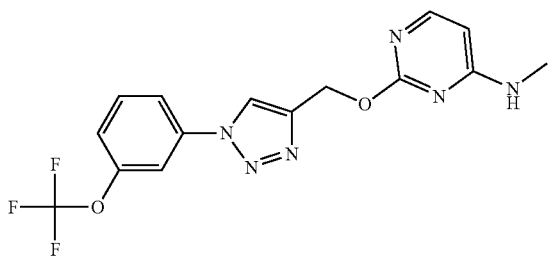 [SMILES: CNc1ccnc(OCc2cn(-c3cccc(OC(F)(F)F)c3)nn2)n1]

The title compound was prepared in a manner analogous to Example 163, Steps B-C, using tert-butyl (2-chloropyrimidin-4-yl)(methyl)carbamate (Intermediate 55) and (1-(3-(trifluoromethoxy)phenyl)-1H-1,2,3-triazol-4-yl)methanol (Intermediate 35). MS (ESI): mass calcd. for $C_{15}H_{13}F_3N_6O_2$, 366.1; m/z found, 367.4 [M+H]$^+$. $^1$H NMR (400 MHz, CD$_3$OD) δ 8.69 (s, 1H), 7.97-7.84 (m, 2H), 7.80 (s, 1H), 7.69 (dd, J=10.2, 6.3 Hz, 1H), 7.51-7.37 (m, 2H), 6.20-6.05 (m, 1H), 5.53 (s, 2H), 2.92 (s, 3H).

Example 353: 2-[[1-[3-(Trifluoromethoxy)phenyl]triazol-4-yl]methoxy]pyrimidin-4-amine

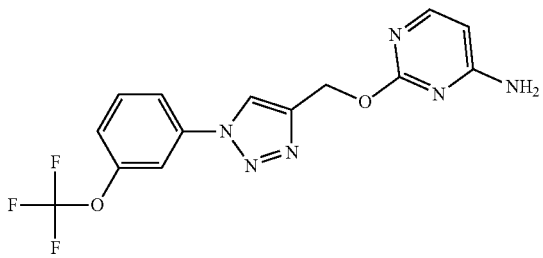 [SMILES: Nc1ccnc(OCc2cn(-c3cccc(OC(F)(F)F)c3)nn2)n1]

The title compound was prepared in a manner analogous to Example 153 using (1-(3-(trifluoromethoxy)phenyl)-1H-1,2,3-triazol-4-yl)methanol (Intermediate 35) and 2-chloropyrimidin-4-amine. MS (ESI): mass calcd. for $C_{14}H_{11}F_3N_6O_2$, 352.1; m/z found, 353.3[M+H]$^+$. $^1$H NMR (400 MHz, CD$_3$OD) δ 8.72 (s, 1H), 7.95-7.82 (m, 3H), 7.69 (dd, J=9.7, 6.9 Hz, 1H), 7.48-7.34 (m, 1H), 6.17 (d, J=5.9 Hz, 1H), 5.48 (d, J=3.7 Hz, 2H).

Example 354: 2-[[1-(2,2-Difluoro-1,3-benzodioxol-5-yl)triazol-4-yl]methoxy]-5-methyl-pyrimidine

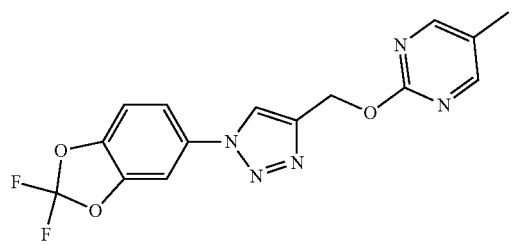 [SMILES: Cc1cnc(OCc2cn(-c3ccc4c(c3)OC(F)(F)O4)nn2)nc1]

The title compound was prepared in a manner analogous to Example 1 using (1-(2,2-difluorobenzo[d][1,3]dioxol-5-yl)-1H-1,2,3-triazol-4-yl)methanol (Intermediate 45) and 2-chloro-5-methylpyrimidine. MS (ESI): mass calcd. for $C_{15}H_{11}F_2N_5O_3$, 347.1; m/z found, 348.0 [M+H]$^+$. $^1$H NMR (400 MHz, DMSO-d$_6$) δ 8.88 (s, 1H), 8.49 (d, J=0.9 Hz, 2H), 8.08 (d, J=2.2 Hz, 1H), 7.79 (dd, J=8.8, 2.2 Hz, 1H), 7.65 (d, J=8.7 Hz, 1H), 5.49 (s, 2H), 2.21 (d, J=0.7 Hz, 3H).

Example 355: 2-[[1-(2,2-Difluoro-1,3-benzodioxol-5-yl)triazol-4-yl]methoxy]pyrimidine

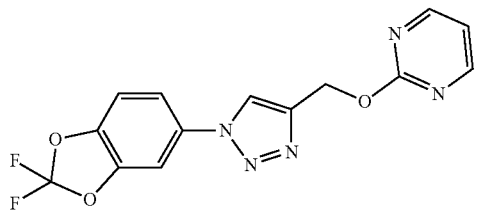 [SMILES: FC1(F)Oc2ccc(-n3cc(COc4ncccn4)nn3)cc2O1]

The title compound was prepared in a manner analogous to Example 1 using (1-(2,2-difluorobenzo[d][1,3]dioxol-5-yl)-1H-1,2,3-triazol-4-yl)methanol (Intermediate 45) and 2-chloropyrimidine. MS (ESI): mass calcd. for $C_{14}H_9F_2N_5O_3$, 333.1; m/z found, 334.1 [M+H]$^+$. $^1$H NMR (400 MHz, DMSO-d$_6$) δ 8.91 (s, 1H), 8.67 (d, J=4.8 Hz, 2H), 8.09 (d, J=2.2 Hz, 1H), 7.80 (dd, J=8.7, 2.2 Hz, 1H), 7.65 (d, J=8.7 Hz, 1H), 7.20 (t, J=4.8 Hz, 1H), 5.54 (s, 2H).

Example 356: 5-Chloro-2-[[1-(2,2-difluoro-1,3-benzodioxol-5-yl)triazol-4-yl]methoxy]pyrimidine

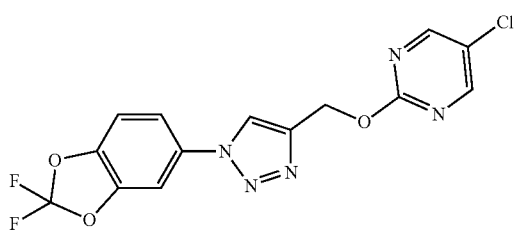 [SMILES: FC1(F)Oc2ccc(-n3cc(COc4ncc(Cl)cn4)nn3)cc2O1]

The title compound was prepared in a manner analogous to Example 1 using (1-(2,2-difluorobenzo[d][1,3]dioxol-5-yl)-1H-1,2,3-triazol-4-yl)methanol (Intermediate 45) and 2,5-dichloropyrimidine. MS (ESI): mass calcd. for $C_{14}H_8ClF_2N_5O_3$, 367.0; m/z found, 368.0 [M+H]$^+$. $^1$H NMR (400 MHz, DMSO-ds) δ 8.89 (s, 1H), 8.77 (s, 2H), 8.08 (d, J=2.2 Hz, 1H), 7.79 (dd, J=8.8, 2.2 Hz, 1H), 7.65 (d, J=8.8 Hz, 1H), 5.54 (s, 2H).

Example 357: 2-[[1-(2,2-Difluoro-1,3-benzodioxol-5-yl)triazol-4-yl]methoxy]-5-fluoro-4-methyl-pyrimidine

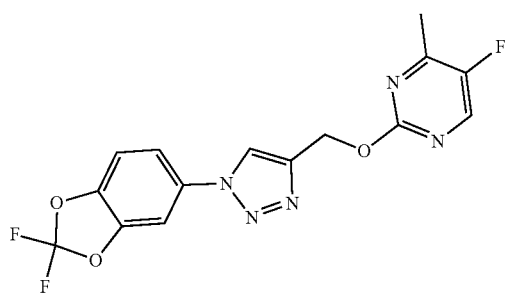 [SMILES: Cc1nc(OCc2cn(-c3ccc4c(c3)OC(F)(F)O4)nn2)ncc1F]

The title compound was prepared in a manner analogous to Example 1 using (1-(2,2-difluorobenzo[d][1,3]dioxol-5-yl)-1H-1,2,3-triazol-4-yl)methanol (Intermediate 45) and 2-chloro-5-fluoro-4-methylpyrimidine. MS (ESI): mass calcd. for $C_{15}H_{10}F_3N_5O_3$, 365.1; m/z found, 366.0 [M+H]$^+$. $^1$H NMR (400 MHz, DMSO-d$_6$) δ 8.88 (s, 1H), 8.56 (d, J=1.6 Hz, 1H), 8.08 (d, J=2.2 Hz, 1H), 7.79 (dd, J=8.7, 2.2 Hz, 1H), 7.65 (d, J=8.8 Hz, 1H), 5.49 (s, 2H), 2.44 (d, J=2.6 Hz, 3H).

Example 358: 2-[[1-(2,2-Difluoro-1,3-benzodioxol-5-yl)triazol-4-yl]methoxy]-5-fluoro-pyrimidine

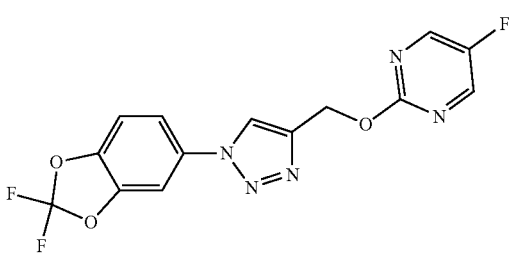 [SMILES: Fc1cnc(OCc2cn(-c3ccc4c(c3)OC(F)(F)O4)nn2)nc1]

The title compound was prepared in a manner analogous to Example 1 using (1-(2,2-difluorobenzo[d][1,3]dioxol-5-yl)-1H-1,2,3-triazol-4-yl)methanol (Intermediate 45) and 2-chloro-5-fluoropyrimidine. MS (ESI): mass calcd. for $C_{14}H_6F_3N_5O_3$, 351.1; m/z found, 352.1 [M+H]$^+$. $^1$H NMR (400 MHz, DMSO-d$_6$) δ 8.89 (s, 1H), 8.75 (d, J=0.6 Hz, 2H), 8.08 (d, J=2.2 Hz, 1H), 7.79 (dd, J=8.8, 2.2 Hz, 1H), 7.65 (d, J=8.7 Hz, 1H), 5.52 (s, 2H).

Example 359: 2-[[1-(2,2-Difluoro-1,3-benzodioxol-5-yl)triazol-4-yl]methoxy]-4,5-dimethyl-pyrimidine

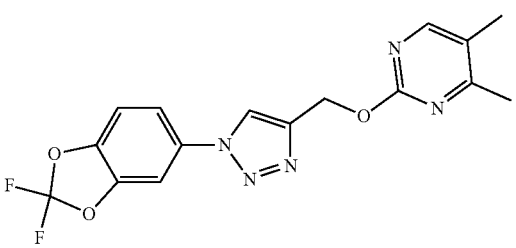 [SMILES: Cc1cnc(OCc2cn(-c3ccc4c(c3)OC(F)(F)O4)nn2)nc1C]

The title compound was prepared in a manner analogous to Example 1 using (1-(2,2-difluorobenzo[d][1,3]dioxol-5-yl)-1H-1,2,3-triazol-4-yl)methanol (Intermediate 45) and 2-chloro-4,5-dimethylpyrimidine. MS (ESI): mass calcd. for $C_{16}H_{13}F_2N_5O_3$, 361.1; m/z found, 362.1 [M+H]$^+$. $^1$H NMR (400 MHz, DMSO-d$_6$) δ 8.87 (s, 1H), 8.30 (s, 1H), 8.08 (d, J=2.2 Hz, 1H), 7.79 (dd, J=8.8, 2.2 Hz, 1H), 7.65 (d, J=8.7 Hz, 1H), 5.47 (s, 2H), 2.39 (s, 3H), 2.16 (s, 3H).

Example 360: 2-[[1-(3,5-Dimethylphenyl)triazol-4-yl]methoxy]pyrimidine

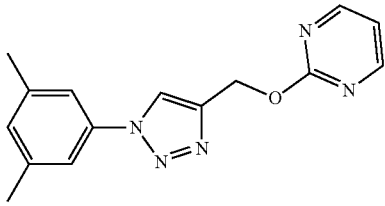 [SMILES: Cc1cc(C)cc(-n2cc(COc3ncccn3)nn2)c1]

The title compound was prepared in a manner analogous to Example 1 using (1-(3,5-dimethylphenyl)-1H-1,2,3-triazol-4-yl)methanol (Intermediate 36) and 2-chloropyrimidine. MS (ESI): mass calcd. for $C_{15}H_{15}N_5O$, 281.1; m/z found, 282.2 [M+H]$^+$. $^1$H NMR (500 MHz, DMSO-d$_6$) δ 8.85 (s, 1H), 8.66 (d, J=4.8 Hz, 2H), 7.59-7.44 (m, 2H), 7.20 (t, J=4.8 Hz, 1H), 7.13 (td, J=1.5, 0.8 Hz, 1H), 5.52 (s, 2H), 2.37 (d, J=0.8 Hz, 6H).

Example 361: 2-[[1-(3,5-Dimethylphenyl)triazol-4-yl]methoxy]-5-fluoro-pyrimidine

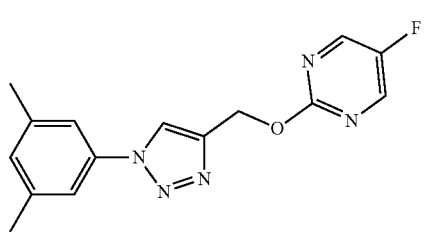 [SMILES: Cc1cc(C)cc(-n2cc(COc3ncc(F)cn3)nn2)c1]

The title compound was prepared in a manner analogous to Example 1 using (1-(3,5-dimethylphenyl)-1H-1,2,3-triazol-4-yl)methanol (Intermediate 36) and 2-chloro-5-fluoropyrimidine. MS (ESI): mass calcd. for $C_{15}H_{14}FN_5O$, 299.1; m/z found, 300.1 [M+H]$^+$. $^1$H NMR (500 MHz, DMSO-d$_6$) δ 8.84 (s, 1H), 8.75 (d, J=0.6 Hz, 2H), 7.54 (dt, J=1.4, 0.7 Hz, 2H), 7.14 (dq, J=1.8, 0.8 Hz, 1H), 5.50 (s, 2H), 2.37 (d, J=0.7 Hz, 6H).

Example 362: 2-[[1-(3,5-Dimethylphenyl)triazol-4-yl]methoxy]-5-methoxy-pyrimidine

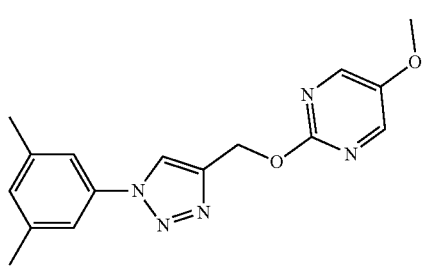 [SMILES: COc1cnc(OCc2cn(-c3cc(C)cc(C)c3)nn2)nc1]

The title compound was prepared in a manner analogous to Example 1 using (1-(3,5-dimethylphenyl)-1H-1,2,3-triazol-4-yl)methanol (Intermediate 36) and 2-chloro-5-methoxypyrimidine. MS (ESI): mass calcd. for $C_{16}H_{17}N_5O_2$, 311.1; m/z found, 312.2 [M+H]$^+$. $^1$H NMR (500 MHz, DMSO-d$_6$) δ 8.82 (s, 1H), 8.41 (s, 2H), 7.54 (dt, J=1.5, 0.7 Hz, 2H), 7.13 (tt, J=1.7, 0.8 Hz, 1H), 5.45 (d, J=0.6 Hz, 2H), 3.86 (s, 3H), 2.37 (d, J=0.7 Hz, 6H).

Example 363: 5-Chloro-2-[[1-(3,5-dimethylphenyl)triazol-4-yl]methoxy]pyrimidine

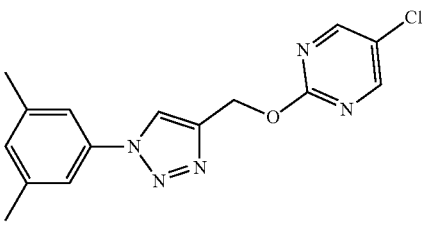 [SMILES: Cc1cc(C)cc(-n2cc(COc3ncc(Cl)cn3)nn2)c1]

The title compound was prepared in a manner analogous to Example 1 using (1-(3,5-dimethylphenyl)-1H-1,2,3-triazol-4-yl)methanol (Intermediate 36) and 2,5-dichloropyrimidine. MS (ESI): mass calcd. for $C_{15}H_{14}ClN_5O$, 315.1; m/z found, 316.1 [M+H]$^+$. $^1$H NMR (500 MHz, DMSO-d$_6$) δ 8.85 (s, 1H), 8.77 (s, 2H), 7.54 (dd, J=1.4, 0.8 Hz, 2H), 7.14 (tt, J=1.6, 0.8 Hz, 1H), 5.53 (d, J=0.5 Hz, 2H), 2.37 (q, J=0.7 Hz, 6H).

Example 364: 2-[[1-(3,5-Dimethylphenyl)triazol-4-yl]methoxy]-5-methyl-pyrimidine

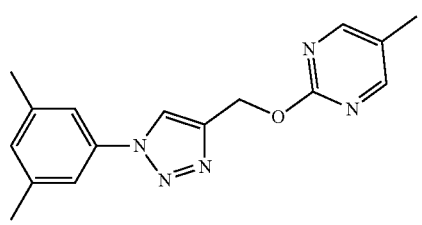 [SMILES: Cc1cnc(OCc2cn(-c3cc(C)cc(C)c3)nn2)nc1]

The title compound was prepared in a manner analogous to Example 1 using (1-(3,5-dimethylphenyl)-1H-1,2,3-triazol-4-yl)methanol (Intermediate 36) and 2-chloro-5-methylpyrimidine. MS (ESI): mass calcd. for $C_{16}H_{17}N_5O$, 295.1; m/z found, 296.1 [M+H]$^+$. $^1$H NMR (500 MHz, DMSO-d$_6$) δ 8.83 (s, 1H), 8.49 (d, J=0.8 Hz, 2H), 7.54 (dd, J=1.5, 0.8 Hz, 2H), 7.18-7.06 (m, 1H), 5.48 (s, 2H), 2.37 (d, J=0.7 Hz, 6H), 2.21 (t, J=0.7 Hz, 3H).

Example 365: 2-[[1-(3,5-Dimethylphenyl)triazol-4-yl]methoxy]-5-ethyl-pyrimidine

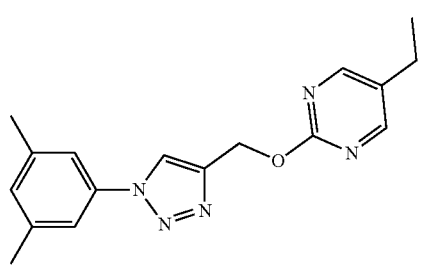 [SMILES: CCc1cnc(OCc2cn(-c3cc(C)cc(C)c3)nn2)nc1]

The title compound was prepared in a manner analogous to Example 1 using (1-(3,5-dimethylphenyl)-1H-1,2,3-triazol-4-yl)methanol (Intermediate 36) and 2-chloro-5-ethylpyrimidine. MS (ESI): mass calcd. for $C_{17}H_{19}N_5O$, 309.2; m/z found, 310.2 [M+H]$^+$. $^1$H NMR (500 MHz, DMSO-d$_6$) δ 8.84 (s, 1H), 8.53 (s, 2H), 7.54 (dt, J=1.5, 0.7 Hz, 2H), 7.13 (tt, J=1.6, 0.8 Hz, 1H), 5.49 (s, 2H), 2.57 (q, J=7.6 Hz, 2H), 1.19 (t, J=7.6 Hz, 3H).

Example 366: 2-[(1-Indan-5-yltriazol-4-yl)methoxy]-5-methyl-pyrimidine

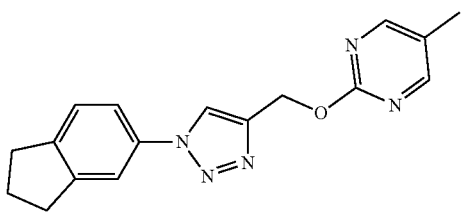 [SMILES: Cc1cnc(OCc2cn(-c3ccc4c(c3)CCC4)nn2)nc1]

The title compound was prepared in a manner analogous to Example 1 using (1-(2,3-dihydro-1H-inden-5-yl)-1H-1,2,3-triazol-4-yl)methanol (Intermediate 51) and 2-chloro-5-methylpyrimidine. MS (ESI): mass calcd. for $C_{17}H_{17}N_5O$, 307.1; m/z found, 308.1 [M+H]$^+$. $^1$H NMR (400 MHz, DMSO-d$_6$) δ 8.82 (s, 1H), 8.49 (d, J=0.9 Hz, 2H), 7.74 (d, J=2.0 Hz, 1H), 7.63 (dd, J=8.1, 2.2 Hz, 1H), 7.41 (d, J=8.1 Hz, 1H), 5.47 (s, 2H), 2.94 (dt, J=12.9, 7.4 Hz, 4H), 2.21 (s, 3H), 2.14-2.00 (m, 2H).

Example 367: 5-Chloro-2-[(1-indan-5-yltriazol-4-yl)methoxy]pyrimidine

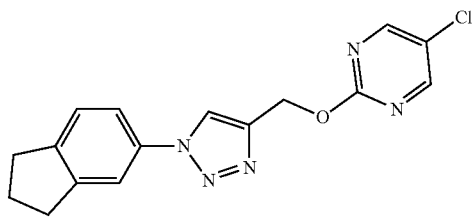 [SMILES: Clc1cnc(OCc2cn(-c3ccc4c(c3)CCC4)nn2)nc1]

The title compound was prepared in a manner analogous to Example 1 using (1-(2,3-dihydro-1H-inden-5-yl)-1H-1,2,3-triazol-4-yl)methanol (Intermediate 51) and 2,5-dichloropyrimidine. MS (ESI): mass calcd. for $C_{16}H_{14}ClN_5O$, 327.1; m/z found, 328.1 [M+H]$^+$. $^1$H NMR (400 MHz, DMSO-d$_6$) δ 8.83 (s, 1H), 8.76 (s, 2H), 7.74 (d, J=2.1 Hz, 1H), 7.63 (dd, J=8.1, 2.2 Hz, 1H), 7.41 (d, J=8.1 Hz, 1H), 5.52 (s, 2H), 2.94 (dt, J=12.6, 7.4 Hz, 4H), 2.08 (p, J=7.5 Hz, 2H).

Example 368: 2-[(1-Indan-5-yltriazol-4-yl)methoxy]-4-(methoxymethyl)pyrimidine

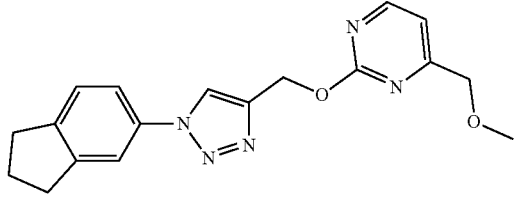 [SMILES: COCc1ccnc(OCc2cn(-c3ccc4c(c3)CCC4)nn2)n1]

The title compound was prepared in a manner analogous to Example 1 using (1-(2,3-dihydro-1H-inden-5-yl)-1H-1,2,3-triazol-4-yl)methanol (Intermediate 51) and 2-chloro-4-(methoxymethyl)pyrimidine. MS (ESI): mass calcd. for $C_{18}H_{19}N_5O_2$, 337.2; m/z found, 338.1 [M+H]$^+$. $^1$H NMR (400 MHz, DMSO-d$_6$) δ 8.82 (s, 1H), 8.64 (d, J=5.0 Hz, 1H), 7.74 (d, J=2.0 Hz, 1H), 7.63 (dd, J=8.1, 2.2 Hz, 1H), 7.42 (d, J=8.1 Hz, 1H), 7.20-7.16 (m, 1H), 5.50 (s, 2H), 4.47 (d, J=0.7 Hz, 2H), 3.40 (s, 3H), 2.94 (dt, J=14.1, 7.3 Hz, 4H), 2.14-2.03 (m, 2H).

Example 369: 2-[2-[(1-Indan-5-yltriazol-4-yl)methoxy]pyrimidin-5-yl]propan-2-ol

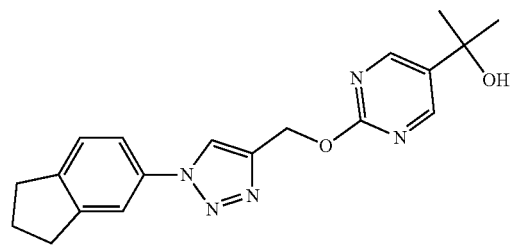 [SMILES: CC(C)(O)c1cnc(OCc2cn(-c3ccc4c(c3)CCC4)nn2)nc1]

The title compound was prepared in a manner analogous to Example 1 using (1-(2,3-dihydro-1H-inden-5-yl)-1H-1,2,3-triazol-4-yl)methanol (Intermediate 51) and 2-(2-chloropyrimidin-5-yl)propan-2-ol. MS (ESI): mass calcd. for $C_{19}H_{21}N_5O_2$, 351.2; m/z found, 352.2 [M+H]$^+$. $^1$H NMR (400 MHz, DMSO-d$_6$) δ 8.83 (s, 1H), 8.69 (s, 2H), 7.75 (d, J=2.0 Hz, 1H), 7.64 (dd, J=8.1, 2.3 Hz, 1H), 7.41 (d, J=8.1 Hz, 1H), 5.50 (s, 2H), 5.30 (s, 1H), 2.94 (dt, J=13.9, 7.5 Hz, 4H), 2.14-2.04 (m, 2H), 1.46 (s, 6H)

Example 370: 4-(Difluoromethyl)-2-[(1-indan-5-yltriazol-4-yl)methoxy]pyrimidine

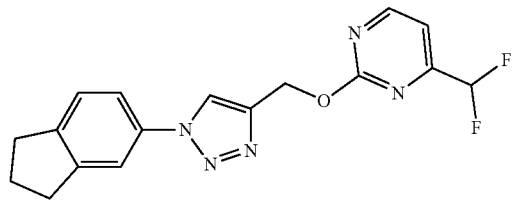 [SMILES: FC(F)c1ccnc(OCc2cn(-c3ccc4c(c3)CCC4)nn2)n1]

The title compound was prepared in a manner analogous to Example 1 using (1-(2,3-dihydro-1H-inden-5-yl)-1H-1,2,3-triazol-4-yl)methanol (Intermediate 51) and 2-chloro-4-

(difluoromethyl)pyrimidine. MS (ESI): mass calcd. for C$_{15}$H$_{15}$F$_2$N$_5$O, 343.1; m/z found, 344.1[M+H]$^+$. $^1$H NMR (500 MHz, DMSO-d$_6$) δ 8.90 (d, J=4.9 Hz, 1H), 8.84 (s, 1H), 7.74 (d, J=2.0 Hz, 1H), 7.63 (dt, J=8.1, 1.3 Hz, 1H), 7.46 (d, J=4.9 Hz, 1H), 7.42 (d, J=8.1 Hz, 1H), 6.96 (t, J=54.1 Hz, 1H), 5.57 (s, 2H), 2.94 (dt, J=15.3, 7.4 Hz, 4H), 2.08 (p, J=7.5 Hz, 2H).

Example 371: 5-Chloro-2-[(1-indan-5-yltriazol-4-yl)methoxy]-4-methyl-pyrimidine

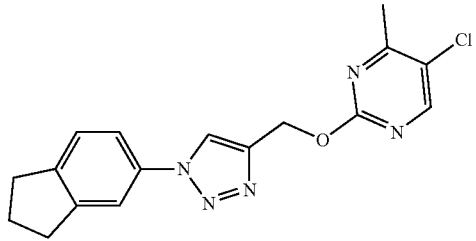 [SMILES: Cc1nc(OCc2cn(-c3ccc4c(c3)CCC4)nn2)ncc1Cl]

The title compound was prepared in a manner analogous to Example 1 using (1-(2,3-dihydro-1H-inden-5-yl)-1H-1,2,3-triazol-4-yl)methanol (Intermediate 51) and 2,5-dichloro-4-methylpyrimidine. MS (ESI): mass calcd. for C$_{17}$H$_{16}$ClN$_5$O, 341.1; m/z found, 342.0 [M+H]$^+$. $^1$H NMR (500 MHz, DMSO-d$_6$) δ 8.82 (s, 1H), 8.62 (s, 1H), 7.74 (d, J=2.0 Hz, 1H), 7.63 (dd, J=8.1, 2.1 Hz, 1H), 7.41 (d, J=8.1 Hz, 1H), 5.50 (s, 2H), 2.94 (dt, J=15.4, 7.4 Hz, 4H), 2.51 (s, 5H), 2.08 (p, J=7.5 Hz, 2H).

Example 372: 2-[[1-[4-Chloro-3-(difluoromethoxy)phenyl]triazol-4-yl]methoxy]-4,5-dimethyl-pyrimidine

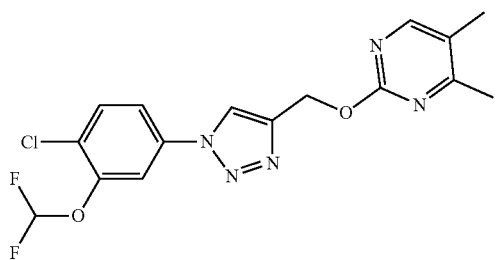 [SMILES: Cc1cnc(OCc2cn(-c3ccc(Cl)c(OC(F)F)c3)nn2)nc1C]

The title compound was prepared in a manner analogous to Example 1 using (1-(4-chloro-3-(difluoromethoxy)phenyl)-1H-1,2,3-triazol-4-yl)methanol and 2-chloro-4,5-dimethylpyrimidine. MS (ESI): mass calcd. for C$_{16}$H$_{14}$ClF$_2$N$_5$O$_2$, 381.1; m/z found, 382.1 [M+H]$^+$. $^1$H NMR (500 MHz, DMSO-d$_6$) δ 8.98 (s, 1H), 8.30 (d, J=0.8 Hz, 1H), 7.99 (dd, J=2.2, 0.7 Hz, 1H), 7.91-7.82 (m, 2H), 7.45 (t, J=72.8 Hz, 1H), 5.54-5.37 (m, 2H), 2.38 (s, 3H), 2.16 (s, 3H).

Example 373: 2-[[1-[4-Chloro-3-(difluoromethoxy)phenyl]triazol-4-yl]methoxy]-5-isopropyl-pyrimidine

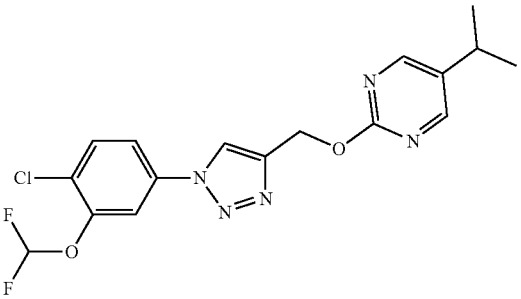 [SMILES: CC(C)c1cnc(OCc2cn(-c3ccc(Cl)c(OC(F)F)c3)nn2)nc1]

The title compound was prepared in a manner analogous to Example 1 using (1-(4-chloro-3-(difluoromethoxy)phenyl)-1H-1,2,3-triazol-4-yl)methanol and 2-chloro-5-isopropylpyrimidine. MS (ESI): mass calcd. for C$_{17}$H$_{16}$ClF$_2$N$_5$O$_2$, 395.1; m/z found, 396.2 [M+H]$^+$. $^1$H NMR (500 MHz, DMSO-d$_6$) δ 9.01 (s, 1H), 8.56 (s, 2H), 7.99 (d, J=2.2 Hz, 1H), 7.95-7.81 (m, 2H), 7.45 (t, J=72.8 Hz, 1H), 5.52 (s, 2H), 2.93 (p, J=7.0 Hz, 1H), 1.24 (d, J=6.9 Hz, 6H).

Example 374: 2-[(1R)-1-[1-[4-Chloro-3-(difluoromethoxy)phenyl]triazol-4-yl]ethoxy]pyrimidine

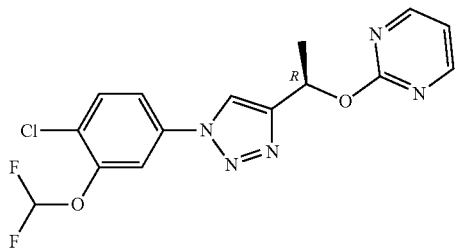

The title compound was prepared in a manner analogous to Example 1 using (R)-1-(1-(4-chloro-3-(difluoromethoxy)phenyl)-1H-1,2,3-triazol-4-yl)ethan-1-ol (Intermediate 22) and 2-chloropyrimidine. MS (ESI): mass calcd. for C$_{15}$H$_{12}$ClF$_2$N$_5$O$_2$, 367.1; m/z found, 368.1 [M+H]$^+$. $^1$H NMR (400 MHz, CD$_3$OD) δ 8.66 (d, J=3.4 Hz, 1H), 8.58 (d, J=4.7 Hz, 2H), 7.86 (d, J=4.1 Hz, 1H), 7.81-7.61 (m, 2H), 7.29-6.75 (m, 1H), 6.48 (dt, J=9.5, 4.6 Hz, 1H), 1.82 (dd, J=6.7, 3.4 Hz, 3H).

Example 375: 5-Chloro-2-[(1R)-1-[1-[4-chloro-3-(difluoromethoxy)phenyl]triazol-4-yl]ethoxy]pyrimidine

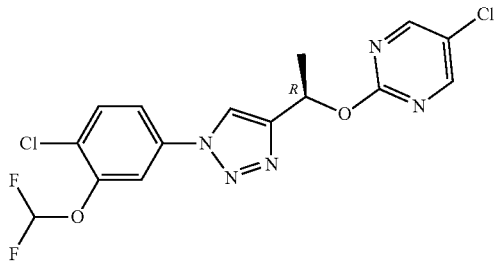

The title compound was prepared in a manner analogous to Example 1 using (R)-1-(1-(4-chloro-3-(difluoromethoxy)phenyl)-1H-1,2,3-triazol-4-yl)ethan-1-ol (Intermediate 22) and 2,5-dichloropyrimidine. MS (ESI): mass calcd. for $C_{15}H_{11}Cl_{12}F_2N_5O_2$, 401.0; m/z found, 402.0[M+H]$^+$. $^1$H NMR (500 MHz, CD$_3$OD) δ 8.67 (d, J=0.6 Hz, 1H), 8.58 (d, J=1.2 Hz, 2H), 7.86 (d, J=2.3 Hz, 1H), 7.82-7.66 (m, 2H), 7.02 (t, J=72.8 Hz, 1H), 6.41 (dt, J=7.1, 6.3 Hz, 1H), 1.83 (d, J=6.7 Hz, 3H).

Example 376: 2-[(1R)-1-[1-[4-Chloro-3-(difluoromethoxy)phenyl]triazol-4-yl]ethoxy]-5-methylpyrimidine The title compound was prepared in a manner analogous to Example 1 using (R)-1-(1-(4-chloro-3-(difluoromethoxy)phenyl)-1H-1,2,3-triazol-4-yl)ethan-1-ol (Intermediate 22) and 2-chloro-5-methylpyrimidine. MS (ESI): mass calcd. for $C_{15}H_{14}ClF_2N_5O_2$, 381.1; m/z found, 382.1 [M+H]$^+$. $^1$H NMR (500 MHz, DMSO-d$_6$) δ 8.96 (d, J=0.6 Hz, 1H), 8.46 (d, J=0.8 Hz, 2H), 7.97 (d, J=2.3 Hz, 1H), 7.91-7.80 (m, 2H), 7.43 (t, J=72.8 Hz, 1H), 6.34 (q, J=6.6 Hz, 1H), 2.19 (d, J=0.8 Hz, 3H), 1.73 (d, J=6.6 Hz, 3H).

Example 377: 2-[(1R)-1-[1-[4-Chloro-3-(difluoromethoxy)phenyl]triazol-4-yl]ethoxy]-5-methoxypyrimidine

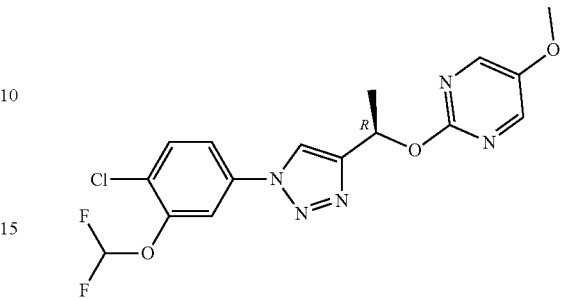

The title compound was prepared in a manner analogous to Example 1 using (R)-1-(1-(4-chloro-3-(difluoromethoxy)phenyl)-1H-1,2,3-triazol-4-yl)ethan-1-ol (Intermediate 22) and 2-chloro-5-methoxypyrimidine. MS (ESI): mass calcd. for $C_{16}H_{14}ClF_2N_5O_3$, 397.1; m/z found, 398.1 [M+H]$^+$. $^1$H NMR (500 MHz, CD$_3$OD) δ 8.64 (d, J=0.6 Hz, 1H), 8.30 (s, 2H), 7.86 (d, J=2.3 Hz, 1H), 7.80-7.65 (m, 2H), 7.02 (t, J=72.8 Hz, 1H), 6.36 (dt, J=6.8, 6.3 Hz, 1H), 3.88 (s, 3H), 1.80 (d, J=6.6 Hz, 3H).

Example 378: 2-[(1S)-1-[1-[4-Chloro-3-(difluoromethoxy)phenyl]triazol-4-yl]ethoxy]pyrimidine

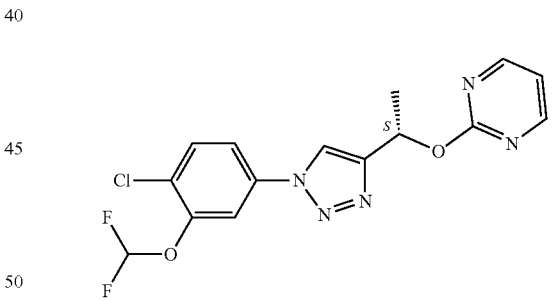

The title compound was prepared in a manner analogous to Example 1 using (S)-1-(1-(4-chloro-3-(difluoromethoxy)phenyl)-1H-1,2,3-triazol-4-yl)ethan-1-ol (Intermediate 23) (Intermediate 23) and 2-chloropyrimidine. MS (ESI): mass calcd. for $C_{15}H_{12}ClF_2N_5O_2$, 367.1; m/z found, 368.0 [M+H]$^+$. $^1$H NMR (500 MHz, DMSO-d$_6$) δ 8.99 (d, J=0.6 Hz, 1H), 8.63 (d, J=4.8 Hz, 2H), 7.98 (d, J=2.3 Hz, 1H), 7.92-7.80 (m, 2H), 7.43 (t, J=72.8 Hz, 1H), 7.16 (t, J=4.8 Hz, 1H), 6.39 (q, J=6.5 Hz, 1H), 1.75 (d, J=6.6 Hz, 3H).

Example 379: 5-Chloro-2-[(1S)-1-[1-[4-chloro-3-(difluoromethoxy)phenyl]triazol-4-yl]ethoxy]pyrimidine

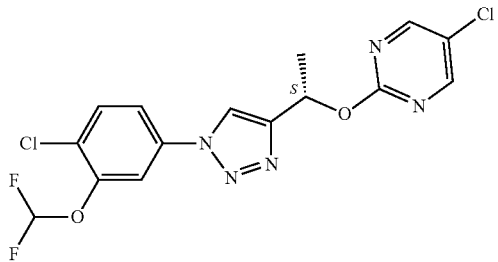

The title compound was prepared in a manner analogous to Example 1 using (S)-1-(1-(4-chloro-3-(difluoromethoxy)phenyl)-1H-1,2,3-triazol-4-yl)ethan-1-ol (Intermediate 23) and 2,5-dichloropyrimidine. MS (ESI): mass calcd. for $C_{15}H_1Cl_2F_2N_5O_2$, 401.0; m/z found, 402.0[M+H]⁺. ¹H NMR (400 MHz, CD₃OD) δ 8.67 (s, 1H), 8.59 (s, 2H), 7.87 (d, J=2.5 Hz, 1H), 7.80-7.65 (m, 2H), 7.02 (t, J=72.8 Hz, 1H), 6.41 (q, J=6.5 Hz, 1H), 1.90-1.72 (m, 3H).

Example 380: 2-[(1S)-1-[1-[4-Chloro-3-(difluoromethoxy)phenyl]triazol-4-yl]ethoxy]-5-methylpyrimidine

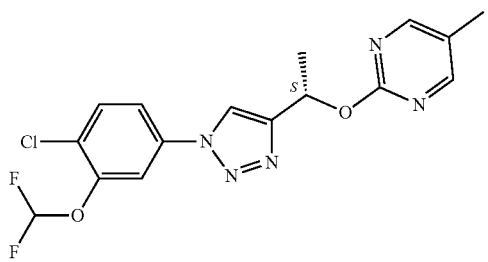

The title compound was prepared in a manner analogous to Example 1 using (S)-1-(1-(4-chloro-3-(difluoromethoxy)phenyl)-1H-1,2,3-triazol-4-yl)ethan-1-ol (Intermediate 23) and 2-chloro-5-methylpyrimidine. ¹H NMR (400 MHz, DMSO-d₆) δ 8.96 (s, 1H), 8.46 (d, J=0.8 Hz, 2H), 7.97 (d, J=2.1 Hz, 1H), 7.93-7.78 (m, 2H), 7.43 (t, J=72.8 Hz, 1H), 6.34 (q, J=6.6 Hz, 1H), 2.19 (d, J=0.7 Hz, 3H), 1.73 (d, J=6.6 Hz, 3H).

Example 381: 2-[(1S)-1-[1-[4-Chloro-3-(difluoromethoxy)phenyl]triazol-4-yl]ethoxy]-5-methoxypyrimidine

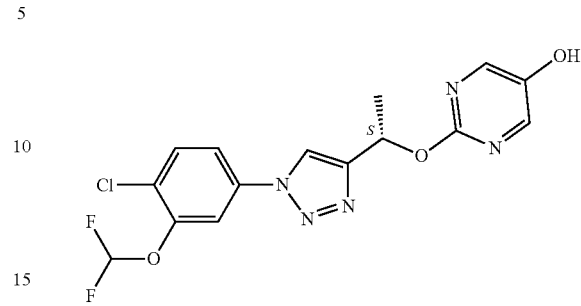

The title compound was prepared in a manner analogous to Example 1 using (S)-1-(1-(4-chloro-3-(difluoromethoxy)phenyl)-1H-1,2,3-triazol-4-yl)ethan-1-ol (Intermediate 23) and 2-chloro-5-methoxypyrimidine. MS (ESI): mass calcd. for $C_{16}H_{14}ClF_2N_5O_3$, 397.1; m/z found, 398.1 [M+H]⁺. ¹H NMR (400 MHz, CD₃OD) δ 8.64 (s, 1H), 8.30 (s, 2H), 7.80 (d, J=48.2 Hz, 3H), 7.02 (t, J=72.2 Hz, 1H), 6.36 (s, 1H), 3.88 (s, 3H), 1.81 (s, 3H).

Example 382: 2-[[1-[4-Chloro-3-(difluoromethoxy)phenyl]triazol-4-yl]methoxy]pyrimidin-4-amine

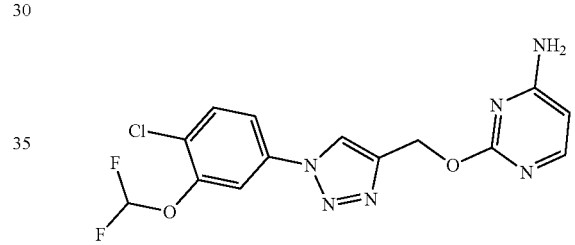

The title compound was prepared in a manner analogous to Example 155 using (1-(4-chloro-3-(difluoromethoxy)phenyl)-1H-1,2,3-triazol-4-yl)methanol (Intermediate 1) and 2-chloropyrimidin-4-amine. MS (ESI): mass calcd. for $C_{14}H_{11}ClF_2N_6O_2$, 368.1; m/z found, 369.1 [M+H]⁺. ¹H NMR (500 MHz, DMSO-d₆) δ 8.97-8.95 (m, 1H), 7.99-7.97 (m, 1H), 7.90 (d, J=5.8 Hz, 1H), 7.88-7.83 (m, 2H), 7.44 (t, J=72.8 Hz, 1H), 6.90 (s, 2H), 6.11 (d, J=5.8 Hz, 1H), 5.38 (s, 2H).

Example 383: [2-[[1-[4-Chloro-3-(difluoromethoxy)phenyl]triazol-4-yl]methoxy]pyrimidin-4-yl]methanol

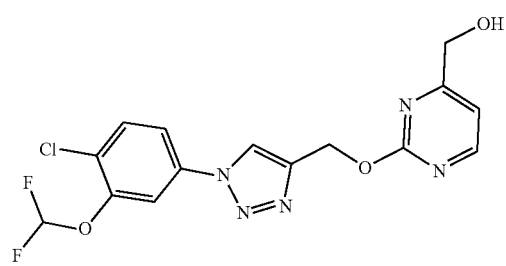 [SMILES: OCc1ccnc(OCc2cn(-c3ccc(Cl)c(OC(F)F)c3)nn2)n1]

Step A. 2-Chloro-4-(((2-(trimethylsilyl)ethoxy)methoxy)methyl)pyrimidine

The title compound was prepared in a manner analogous to Intermediate 59, using (2-chloropyrimidin-4-yl)methanol and (2-(chloromethoxy)ethyl)trimethylsilane. $^1$H NMR (400 MHz, DMSO-$d_6$) δ 8.77 (d, J=5.0 Hz, 1H), 7.60-7.55 (m, 1H), 4.77 (s, 2H), 4.65-4.62 (m, 2H), 3.64-3.56 (m, 2H), 0.87-0.80 (m, 2H), 0.00--0.03 (s, 9H).

Step B. [2-[[1-[4-Chloro-3-(difluoromethoxy)phenyl]triazol-4-yl]methoxy]pyrimidin-4-yl]methanol The title compound was prepared in a manner analogous to Example 163, Steps B-C, using (1-(4-chloro-3-(difluoromethoxy)phenyl)-1H-1,2,3-triazol-4-yl)methanol (Intermediate 1) and chloro-4-(((2-(trimethylsilyl)ethoxy)methoxy)methyl)pyrimidine and using THF instead of DMF in Step B. MS (ESI): mass calcd. for $C_{15}H_{12}ClF_2N_5O_3$, 383.1; m/z found, 384.1 [M+H]$^+$. $^1$H NMR (400 MHz, DMSO-$d_6$) δ 9.00 (s, 1H), 8.62 (d, J=5.0 Hz, 1H), 8.00-7.97 (m, 1H), 7.89-7.83 (m, 2H), 7.44 (t, J=72.8 Hz, 1H), 7.25-7.23 (m, 1H), 5.63 (t, J=5.7 Hz, 1H), 5.53 (s, 2H), 4.51 (d, J=5.3 Hz, 2H).

Example 384: 2-[[1-[4-Chloro-3-(difluoromethoxy)phenyl]triazol-4-yl]methoxy]-4-(methoxymethyl)pyrimidine

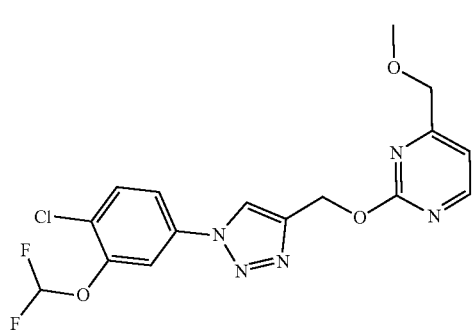 [SMILES: COCc1ccnc(OCc2cn(-c3ccc(Cl)c(OC(F)F)c3)nn2)n1]

The title compound was prepared in a manner analogous to Example 155 using 2-chloro-4-(methoxymethyl)pyrimidine and (1-(4-chloro-3-(difluoromethoxy)phenyl)-1H-1,2,3-triazol-4-yl)methanol (Intermediate 1). MS (ESI): mass calcd. for $C_{16}H_{14}ClF_2N_5O_3$, 397.1; m/z found, 398.1 [M+H]$^+$. $^1$H NMR (500 MHz, DMSO-$d_6$) δ 9.00-8.99 (m, 1H), 8.64 (d, J=5.0 Hz, 1H), 7.99-7.97 (m, 1H), 7.89-7.83 (m, 2H), 7.44 (t, J=72.8 Hz, 1H), 7.18 (dt, J=5.0, 0.7 Hz, 1H), 5.54 (s, 2H), 4.49-4.46 (m, 2H), 3.40 (s, 3H)

Example 385: 2-[2-[[1-[4-Chloro-3-(difluoromethoxy)phenyl]triazol-4-yl]methoxy]pyrimidin-5-yl]propan-2-ol

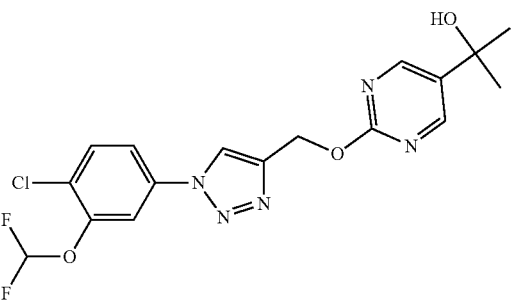 [SMILES: CC(C)(O)c1cnc(OCc2cn(-c3ccc(Cl)c(OC(F)F)c3)nn2)nc1]

The title compound was prepared in a manner analogous to Example 153 using (1-(3-(difluoromethoxy)-4-chlorophenyl)-1H-1,2,3-triazol-4-yl)methanol and 2-(2-chloropyrimidin-5-yl)propan-2-ol, using ACN instead of DMF. MS (ESI): mass calcd. for $C_{17}H_{16}ClF_2N_5O_3$, 411.1; m/z found, 412.0 [M+H]$^+$. $^1$H NMR (500 MHz, CDCl$_3$) δ 8.79-8.61 (s, 2H), 8.16-8.10 (s, 1H), 7.74-7.68 (d, J=2.2 Hz, 1H), 7.66-7.54 (m, 2H), 6.80-6.46 (t, J=72.5 Hz, 2H), 5.71-5.61 (s, 2H), 1.65-1.59 (s, 6H).

Example 386: 2-((1-(4-Chloro-3-(difluoromethoxy)phenyl)-1H-1,2,3-triazol-4-yl)methoxy)-4-isopropoxypyrimidine

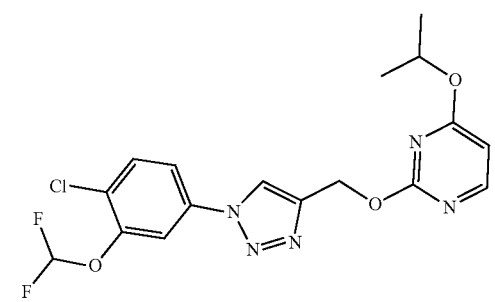 [SMILES: CC(C)Oc1ccnc(OCc2cn(-c3ccc(Cl)c(OC(F)F)c3)nn2)n1]

The title compound was prepared in a manner analogous to Example 155 using 2-chloro-4-isopropoxypyrimidine and (1-(4-chloro-3-(difluoromethoxy)phenyl)-1H-1,2,3-triazol-4-yl)methanol (Intermediate 1). MS (ESI): mass calcd. for $C_{17}H_{16}ClF_2N_5O_3$, 411.1; m/z found, 412.1 [M+H]$^+$. $^1$H NMR (400 MHz, DMSO-$d_6$) δ 9.00 (s, 1H), 8.31 (d, J=5.7 Hz, 1H), 8.01-7.97 (m, 1H), 7.90-7.83 (m, 2H), 7.44 (t, J=72.8 Hz, 1H), 6.53 (d, J=5.7 Hz, 1H), 5.51 (s, 2H), 5.33-5.25 (m, 1H), 1.29 (d, J=6.2 Hz, 6H).

Example 387: Methyl 2-((1-(4-chloro-3-(difluoromethoxy)phenyl)-1H-1,2,3-triazol-4-yl)methoxy)pyrimidine-4-carboxylate

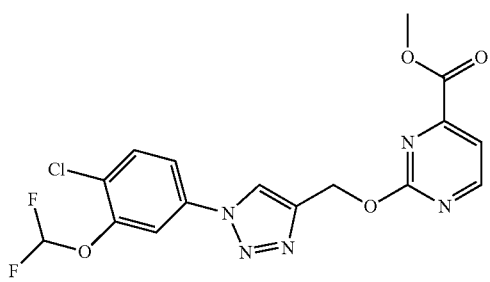 [SMILES: COC(=O)c1ccnc(OCc2cn(-c3ccc(Cl)c(OC(F)F)c3)nn2)n1]

The title compound was prepared in a manner analogous to Example 155 using methyl 2-chloropyrimidine-4-carboxylate and (1-(4-chloro-3-(difluoromethoxy)phenyl)-1H-1,2,3-triazol-4-yl)methanol (Intermediate 1). MS (ESI): mass calcd. for $C_{16}H_{12}ClF_2N_5O_4$, 411.1; m/z found, 412.1 [M+H]$^+$.

Example 388: 2-[[1-[4-Chloro-3-(difluoromethoxy)phenyl]triazol-4-yl]methoxy]-N-(2,2-difluoroethyl)-5-fluoro-pyrimidin-4-amine. as the Trifluoroacetic Acid Salt

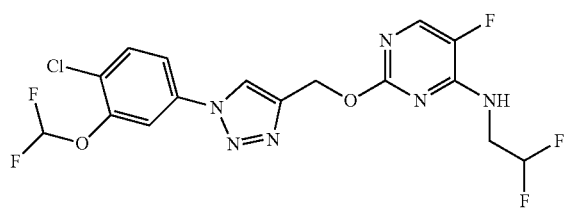 [SMILES: Fc1cnc(OCc2cn(-c3ccc(Cl)c(OC(F)F)c3)nn2)nc1NCC(F)F]

The title compound was prepared in a manner analogous to Example 163, Steps B-C using tert-butyl (2-chloro-5-fluoropyrimidin-4-yl)(2,2-difluoroethyl)carbamate (Intermediate 57) and (1-(4-chloro-3-(difluoromethoxy)phenyl)-1H-1,2,3-triazol-4-yl)methanol (Intermediate 1). MS (ESI): mass calcd. for $C_{16}H_{12}ClF_5N_6O_2$, 450.1; m/z found, 451.1 [M+H]$^+$. $^1$H NMR (400 MHz, DMSO-d$_6$) δ 8.97 (s, 1H), 8.19-8.12 (m, 1H), 8.07 (d, J=3.3 Hz, 1H), 8.00-7.97 (m, 1H), 7.90-7.82 (m, 2H), 7.44 (t, J=72.8 Hz, 1H), 6.33-5.99 (m, 1H), 5.42 (s, 2H).

Example 389: 2-[[1-[4-Chloro-3-(difluoromethoxy)phenyl]triazol-4-yl]methoxy]-5-fluoro-N-methyl-pyrimidin-4-amine. as the Trifluoroacetic Acid Salt

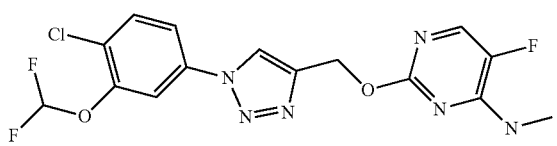 [SMILES: CNc1nc(OCc2cn(-c3ccc(Cl)c(OC(F)F)c3)nn2)ncc1F]

The title compound was prepared in a manner analogous to Example 163, Steps B-C, using (1-(4-chloro-3-(difluoromethoxy)phenyl)-1H-1,2,3-triazol-4-yl)methanol (Intermediate 1) and 2-chloro-5-fluoro-N-methyl-N-((2-(trimethylsilyl)ethoxy)methyl)pyrimidin-4-amine (Intermediate 59) in Step A. MS (ESI): mass calcd. for $C_{15}H_{12}ClF_3N_6O_2$, 400.1; m/z found, 401.1 [M+H]$^+$. $^1$H NMR (500 MHz, DMSO-d$_6$) δ 8.98 (s, 1H), 8.01-7.84 (m, 5H), 7.46 (t, J=72.8 Hz, 1H), 5.43 (s, 2H), 2.87 (d, J=4.6 Hz, 3H).

Example 390: 2-((1-(4-Chloro-3-(difluoromethoxy)phenyl)-1H-1,2,3-triazol-4-yl)methoxy)-5-fluoropyrimidin-4-amine

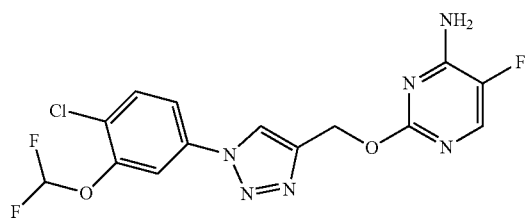 [SMILES: Nc1nc(OCc2cn(-c3ccc(Cl)c(OC(F)F)c3)nn2)ncc1F]

Step A. 4-Chloro-2-((1-(4-chloro-3-(difluoromethoxy)phenyl)-1H-1,2,3-triazol-4-yl)methoxy)-5-fluoropyrimidine The title compound was prepared in a manner analogous to Example 167 using 4-chloro-5-fluoro-2-(methylsulfonyl)pyrimidine and (1-(4-chloro-3-(difluoromethoxy)phenyl)-1H-1,2,3-triazol-4-yl)methanol (Intermediate 1) in Step B. MS (ESI): mass calcd. for $C_{14}H_8Cl_2F_3N_5O_2$, 405.0; m/z found, 406.0 [M+H]$^+$.

Step B. 2-((1-(4-Chloro-3-(difluoromethoxy)phenyl)-1H-1,2,3-triazol-4-yl)methoxy)-5-fluoropyrimidin-4-amine The title compound was prepared in a manner analogous to Example 167, Step C. MS (ESI): mass calcd. for $C_{14}H_{10}ClF_3N_6O_2$, 386.1; m/z found, 387.1 [M+H]$^+$. $^1$H NMR (400 MHz, DMSO-do) δ 8.96 (s, 1H), 8.00-7.96 (m, 2H), 7.89-7.83 (m, 2H), 7.44 (t, J=72.8 Hz, 1H), 7.34 (s, 2H), 5.36 (s, 2H).

Example 391: 5-(Azetidin-1-yl)-2-((1-(4-chloro-3-(difluoromethoxy)phenyl)-1H-1,2,3-triazol-4-yl)methoxy)pyrimidine

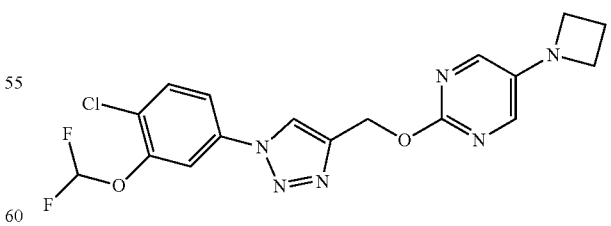

The title compound was prepared in a manner analogous to Example 165, Steps A-C using (1-(4-chloro-3-(difluoromethoxy)phenyl)-1H-1,2,3-triazol-4-yl)methanol (Intermediate 1) in Step C. MS (ESI): mass calcd. for $C_{17}H_{15}ClF_2N_5O_2$, 408.1; m/z found, 409.1 [M+H]$^+$. $^1$H NMR (400 MHz, DMSO-d$_6$) δ 8.98-8.96 (m, 1H), 8.00-7.97

(m, 1H), 7.92 (s, 2H), 7.89-7.83 (m, 2H), 7.45 (t, J=72.8 Hz, 1H), 5.45-5.41 (m, 2H), 3.84 (t, J=7.2 Hz, 4H), 2.39-2.29 (m, 2H).

Example 392: 2-((1-(4-Chloro-3-(difluoromethoxy)phenyl)-1H-1,2,3-triazol-4-yl)methoxy)-5-(3-fluoroazetidin-1-yl)pyrimidine

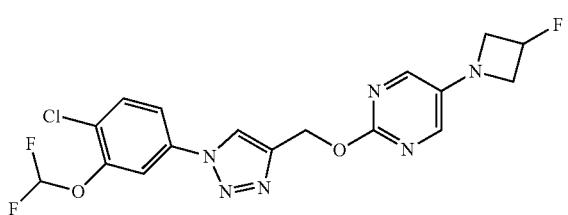 [SMILES: FC1CN(c2cnc(OCc3cn(-c4ccc(Cl)c(OC(F)F)c4)nn3)nc2)C1]

The title compound was prepared in a manner analogous to Example 165, Steps A-C using 3-fluoroazetidine in Step A and (1-(4-chloro-3-(difluoromethoxy)phenyl)-1H-1,2,3-triazol-4-yl)methanol (Intermediate 1) in Step C. MS (ESI): mass calcd. for $C_{17}H_{14}ClF_3N_6O_2$, 426.1; m/z found, 427.1 [M+H]$^+$. $^1$H NMR (400 MHz, DMSO-$d_6$) δ 8.97 (s, 1H), 8.03-7.96 (m, 3H), 7.90-7.82 (m, 2H), 7.44 (t, J=72.8 Hz, 1H), 5.60-5.38 (m, 3H), 4.25-4.14 (m, 2H), 4.00-3.88 (m, 2H).

Example 393: 2-((1-(4-Chloro-3-(difluoromethoxy)phenyl)-1H-1,2,3-triazol-4-yl)methoxy)-5-(3,3-difluoroazetidin-1-yl)pyrimidine

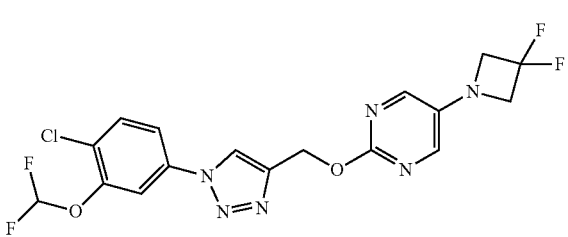 [SMILES: FC(F)Oc1cc(-n2cc(COc3ncc(N4CC(F)(F)C4)cn3)nn2)ccc1Cl]

The title compound was prepared in a manner analogous to Example 165, Steps A-C using 3,3-difluoroazetidine in Step A and (1-(4-chloro-3-(difluoromethoxy)phenyl)-1H-1,2,3-triazol-4-yl)methanol (Intermediate 1) in Step C. MS (ESI): mass calcd. for $C_{17}H_{13}ClF_4N_6O_2$, 444.1; m/z found, 445.1 [M+H]$^+$. $^1$H NMR (400 MHz, DMSO-$d_6$) δ 8.98 (s, 1H), 8.09 (s, 2H), 8.00-7.97 (m, 1H), 7.90-7.83 (m, 2H), 7.44 (t, J=72.8 Hz, 1H), 5.46 (s, 2H), 4.34 (t, J=12.3 Hz, 4H).

Example 394: 2-[[1-[4-Chloro-3-(difluoromethoxy)phenyl]triazol-4-yl]methoxy]-6-fluoro-pyridine

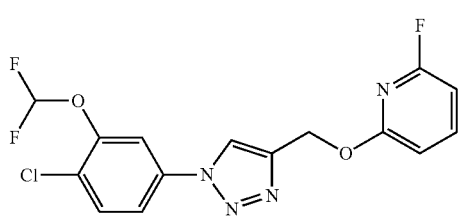 [SMILES: Fc1cccc(OCc2cn(-c3ccc(Cl)c(OC(F)F)c3)nn2)n1]

The title compound was prepared in a manner analogous to Example 155 using (1-(4-chloro-3-(difluoromethoxy)phenyl)-1H-1,2,3-triazol-4-yl)methanol (Intermediate 1) and 2,6-difluoropyridine. MS (ESI): mass calcd. for $C_{15}H_{10}ClF_3N_4O_2$, 370.0; m/z found, 371.0 [M+H]$^+$. $^1$H NMR (500 MHz, CD$_3$CN) δ 8.42 (s, 1H), 7.84 (q, J=8.1 Hz, 1H), 7.80-7.76 (m, 1H), 7.76-7.67 (m, 2H), 6.93 (t, J=73.0 Hz, 1H), 6.70 (ddd, J=53.8, 7.9, 2.0 Hz, 2H), 5.50 (s, 2H).

Example 395: 2-[[1-[3-(Difluoromethoxy)-4-fluorophenyl]triazol-4-yl]methoxy]-6-(trifluoromethyl)pyridine

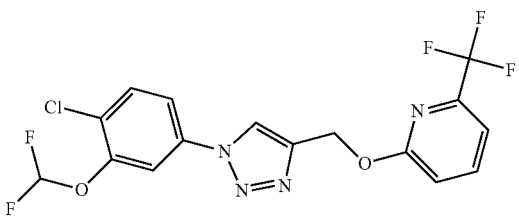 [SMILES: FC(F)Oc1cc(-n2cc(COc3cccc(C(F)(F)F)n3)nn2)ccc1Cl]

The title compound was prepared in a manner analogous to Example 155 using (1-(4-chloro-3-(difluoromethoxy)phenyl)-1H-1,2,3-triazol-4-yl)methanol (Intermediate 6) and 2-fluoro-6-(trifluoromethyl)pyridine. MS (ESI): mass calcd. for $C_{16}H_{10}F_6N_4O_2$, 404.1; m/z found, 404.9 [M+H]$^+$. $^1$H NMR (500 MHz, DMSO-$d_6$) δ 8.92 (s, 1H), 8.04-8.00 (m, 1H), 7.98 (dd, J=6.9, 2.6 Hz, 1H), 7.85 (ddd, J=9.0, 3.9, 2.6 Hz, 1H), 7.69 (dd, J=10.2, 9.0 Hz, 1H), 7.56-7.24 (m, 2H), 7.23-7.20 (m, 1H), 5.53 (s, 2H)

Example 396: 2-[[1-[3-(Difluoromethoxy)-4-fluorophenyl]triazol-4-yl]methoxy]-5-methyl-pyrazine

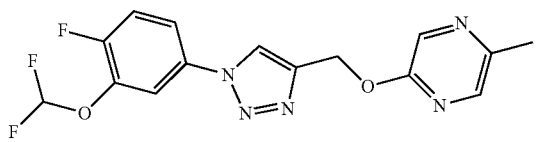 [SMILES: Cc1cnc(OCc2cn(-c3ccc(F)c(OC(F)F)c3)nn2)cn1]

The title compound was prepared in a manner analogous to Example 155 using (1-(4-chloro-3-(difluoromethoxy)phenyl)-1H-1,2,3-triazol-4-yl)methanol (Intermediate 6) and using 2-chloro-5-methylpyrazine. MS (ESI): mass calcd. for $C_{15}H_{12}F_3N_5O_2$, 351.1; m/z found, 351.9 [M+H]$^+$. $^1$H NMR (500 MHz, DMSO-$d_6$) δ 8.95 (s, 1H), 8.25 (d, J=1.4 Hz, 1H), 8.14-8.12 (m, 1H), 7.99 (dd, J=6.9, 2.6 Hz, 1H), 7.87 (ddd, J=9.0, 3.9, 2.6 Hz, 1H), 7.68 (dd, J=10.2, 9.0 Hz, 1H), 7.39 (t, J=72.8 Hz, 1H), 5.50 (s, 2H), 2.42 (s, 3H).

Example 397: 2-[[1-[3-(Difluoromethoxy)-4-fluorophenyl]triazol-4-yl]methoxy]-5-(2-thienyl)pyrazine

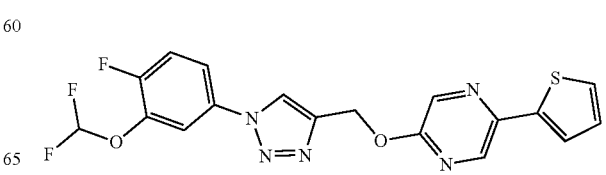

The title compound was prepared in a manner analogous to Example 155 using (1-(4-chloro-3-(difluoromethoxy)phenyl)-1H-1,2,3-triazol-4-yl)methanol (Intermediate 6) and using 2-chloro-5-(thiophen-2-yl)pyrazine. MS (ESI): mass calcd. for $C_{18}H_{12}F_3N_5O_2S$, 419.1; m/z found, 419.9 [M+H]$^+$. $^1$H NMR (500 MHz, DMSO-d$_6$) δ 8.97 (s, 1H), 8.83 (d, J=1.4 Hz, 1H), 8.34 (d, J=1.4 Hz, 1H), 8.00 (dd, J=6.9, 2.6 Hz, 1H), 7.87 (ddd, J=9.0, 3.9, 2.6 Hz, 1H), 7.79 (dd, J=3.6, 1.1 Hz, 1H), 7.69 (dd, J=10.2, 9.0 Hz, 1H), 7.65 (dd, J=5.1, 1.1 Hz, 1H), 7.39 (t, J=72.7 Hz, 1H), 7.19 (dd, J=5.1, 3.6 Hz, 1H), 5.58 (s, 2H).

Example 398: 5-Bromo-2-[[1-[3-(difluoromethyl)-4-fluoro-phenyl]triazol-4-yl]methoxy]pyrimidine

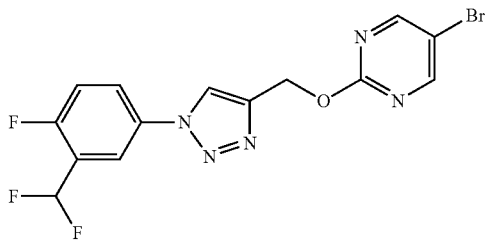 [SMILES: Fc1ccc(-n2cc(COc3ncc(Br)cn3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 5-bromo-2-chloropyrimidine. MS (ESI): mass calcd. for $C_{14}H_9BrF_3N_5O$, 399.0; m/z found, 399.9 [M+H]$^+$. $^1$H NMR (300 MHz, DMSO-de δ 9.00 (s, 1H), 8.82 (s, 2H), 8.18 (dd, J=12.7, 4.6 Hz, 2H), 7.66 (t, J=9.3 Hz, 1H), 7.31 (t, J=53.9 Hz, 1H), 5.54 (s, 2H).

Example 399: 2-[[1-[3-(Difluoromethyl)-4-fluoro-phenyl]triazol-4-yl]methoxy]-4-(methoxymethyl)pyrimidine

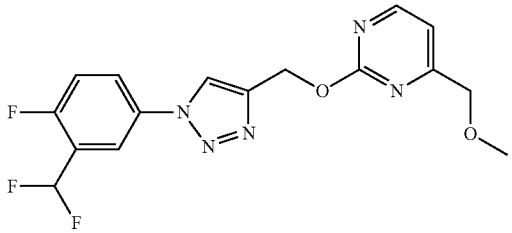 [SMILES: COCc1ccnc(OCc2cn(-c3ccc(F)c(C(F)F)c3)nn2)n1]

The title compound was prepared in a manner analogous to Example 155 using (1-(3-(difluoromethyl)-4-fluorophenyl)-1H-1,2,3-triazol-4-yl)methanol (Intermediate 9) and 2-chloro-4-(methoxymethyl)pyrimidine. MS (ESI): mass calcd. for $C_{16}H_{14}F_3N_5O_2$, 365.1; m/z found, 366.0 [M+H]$^+$. $^1$H NMR (400 MHz, CDCl$_3$) δ 8.55 (d, J=5.0 Hz, 1H), 8.17 (s, 1H), 7.98-7.85 (m, 2H), 7.33 (s, 1H), 7.16 (d, J=5.1 Hz, 1H), 7.10-6.79 (m, 1H), 5.66 (d, J=0.7 Hz, 2H), 4.50 (d, J=0.8 Hz, 2H), 3.50 (s, 3H).

Example 400: [2-[[1-[3-(Difluoromethyl)-4-fluoro-phenyl]triazol-4-yl]methoxy]pyrimidin-4-yl]methanol

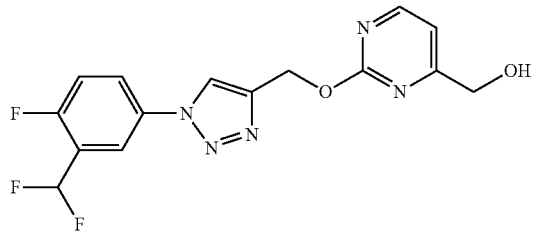 [SMILES: OCc1ccnc(OCc2cn(-c3ccc(F)c(C(F)F)c3)nn2)n1]

The title compound was prepared in a manner analogous to Example 159, Steps A-B using (1-(3-(difluoromethyl)-4-fluorophenyl)-1H-1,2,3-triazol-4-yl)methanol (Intermediate 9) and 4-(((tert-butyldimethylsilyl)oxy)methyl)-2-chloropyrimidine (Intermediate 54) in Step A. MS (ESI): mass calcd. for $C_{15}H_{12}F_3N_5O_2$, 351.1; m/z found, 352.0 [M+H]$^+$. $^1$H NMR (500 MHz, CDCl$_3$) δ 8.56-8.45 (d, J=5.0 Hz, 1H), 8.20-8.11 (s, 1H), 7.99-7.93 (dd, J=5.8, 2.7 Hz, 1H), 7.93-7.87 (ddd, J=8.1, 4.2, 2.9 Hz, 1H), 7.37-7.29 (tt, J=9.0, 1.1 Hz, 1H), 7.10-6.79 (m, 2H), 5.74-5.63 (m, 2H), 4.81-4.66 (m, 2H).

Example 401: 2-[2-[[1-[3-(Difluoromethyl)-4-fluoro-phenyl]triazol-4-yl]methoxy]pyrimidin-5-yl]propan-2-ol

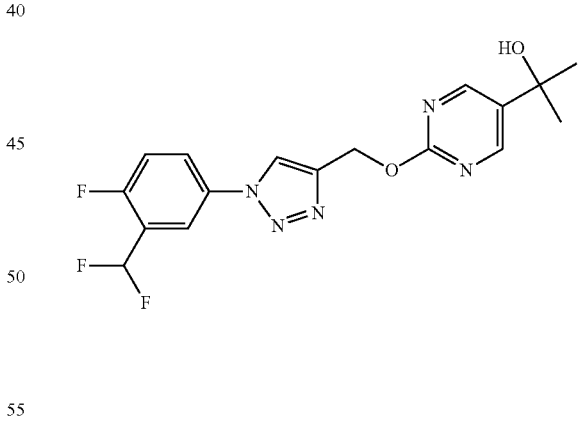

The title compound was prepared in a manner analogous to Example 155 using (1-(3-(difluoromethyl)-4-fluorophenyl)-1H-1,2,3-triazol-4-yl)methanol (Intermediate 9) and 2-(2-chloropyrimidin-5-yl)propan-2-ol. MS (ESI): mass calcd. for $C_{17}H_6F_3N_5O_2$, 379.1; m/z found, 380.1 [M+H]$^+$. $^1$H NMR (500 MHz, CDCl$_3$) δ 8.68 (s, 2H), 8.17-8.13 (m, 1H), 7.98-7.88 (m, 2H), 7.37-7.29 (m, 1H), 6.95 (t, J=54.6 Hz, 1H), 5.67 (d, J=0.7 Hz, 2H), 1.63 (s, 6H).

Example 402: 4-(Difluoromethyl)-2-[[1-[3-(difluoromethyl)-4-fluoro-phenyl]triazol-4-yl]methoxy]pyrimidine

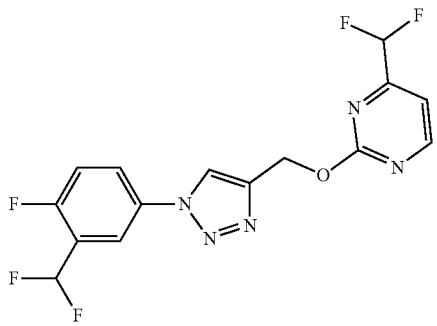 [SMILES: Fc1ccc(-n2cc(COc3nccc(C(F)F)n3)nn2)cc1C(F)F]

The title compound was prepared in a manner analogous to Example 155 using (1-(3-(difluoromethyl)-4-fluorophenyl)-1H-1,2,3-triazol-4-yl)methanol (Intermediate 9) and 2-chloro-4-(difluoromethyl)pyrimidine. MS (ESI): mass calcd. for $C_{15}H_{10}F_8N_5O$, 371.1; m/z found, 372.0 [M+H]$^+$. $^1$H NMR (500 MHz, CDCl$_3$) δ 8.79-8.74 (m, 1H), 8.20-8.15 (m, 1H), 7.97-7.93 (m, 1H), 7.93-7.87 (m, 1H), 7.38-7.28 (m, 2H), 7.09-6.83 (m, 1H), 6.63-6.37 (m, 1H), 5.75-5.68 (m, 2H).

Example 403: 2-[[1-[3-(Difluoromethyl)-4-fluorophenyl]triazol-4-yl]methoxy]-4-(trifluoromethyl)pyrimidine

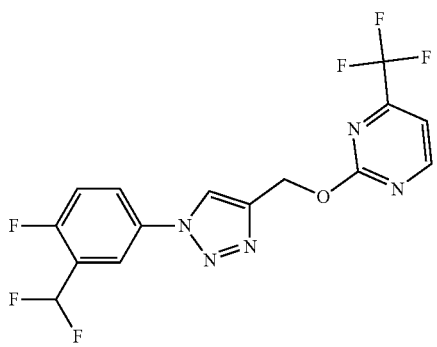 [SMILES: Fc1ccc(-n2cc(COc3nccc(C(F)(F)F)n3)nn2)cc1C(F)F]

The title compound was prepared in a manner analogous to Example 155 using (1-(3-(1,1-difluoromethyl)-4-fluorophenyl)-1H-1,2,3-triazol-4-yl)methanol and 2-chloro-4-trifluoromethylpyrimidine. MS (ESI): mass calcd. for $C_{15}H_9F_6N_5O$, 389.1; m/z found, 390.0 [M+H]$^+$. $^1$H NMR (500 MHz, CDCl$_3$) δ 8.83 (d, J=4.8 Hz, 1H), 8.19 (t, J=0.6 Hz, 1H), 7.98-7.85 (m, 2H), 7.39-7.30 (m, 2H), 6.95 (t, J=54.6 Hz, 1H), 5.72 (d, J=0.6 Hz, 2H).

Example 404: (R/S)-2-[2-[[1-[3-(Difluoromethyl)-4-fluoro-phenyl]triazol-4-yl]methoxy]pyrimidin-5-yl]-1,1,1-trifluoro-propan-2-ol

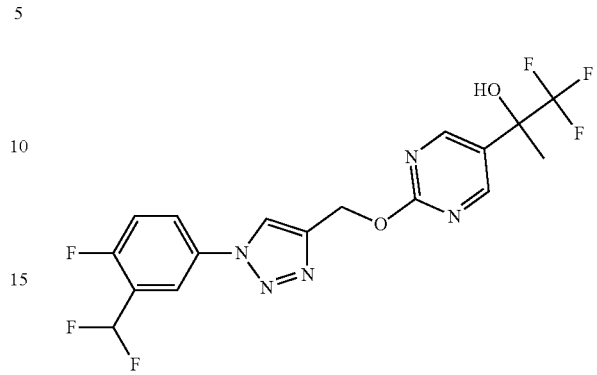

The title compound was prepared in a manner analogous to Example 153 using (1-(3-(difluoromethyl)-4-fluorophenyl)-1H-1,2,3-triazol-4-yl)methanol (Intermediate 9) and 2-(2-chloropyrimidin-5-yl)-1,1,1-trifluoropropan-2-ol, using ACN instead of DMF. MS (ESI): mass calcd. for $C_{17}H_{13}FN_5O_2$, 433.1; m/z found, 434.0 [M+H]$^+$. $^1$H NMR (500 MHz, CDCl$_3$) δ 8.78-8.71 (s, 2H), 8.16-8.12 (t, J=0.7 Hz, 1H), 7.98-7.93 (d, J=5.4 Hz, 1H), 7.93-7.87 (m, 1H), 7.38-7.29 (t, J=9.0 Hz, 1H), 7.08-6.79 (t, J=54.6 Hz, 1H), 5.73-5.67 (d, J=0.7 Hz, 2H), 2.59-2.51 (s, 1H), 1.87-1.80 (m, 3H).

Example 405: 5-(Difluoromethoxy)-2-[[1-[3-(difluoromethyl)-4-fluoro-phenyl]triazol-4-yl]methoxy]pyrimidine

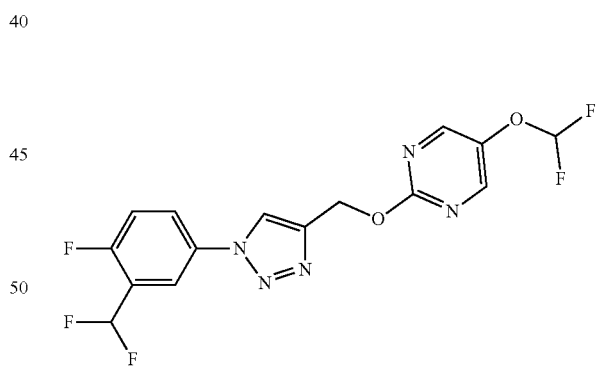

The title compound was prepared in a manner analogous to Example 155 using (1-(3-(difluoromethyl)-4-fluorophenyl)-1H-1,2,3-triazol-4-yl)methanol (Intermediate 9) and 2-chloro-5-(difluoromethoxy)pyrimidine. MS (ESI): mass calcd. for $C_{15}H_{10}F_8N_5O_2$, 387.1; m/z found, 388.0 [M+H]$^+$. $^1$H NMR (500 MHz, CDCl$_3$) δ 8.45 (t, J=0.8 Hz, 2H), 8.14 (t, J=0.7 Hz, 1H), 8.01-7.86 (m, 2H), 7.33 (t, J=9.0 Hz, 1H), 6.95 (t, J=54.6 Hz, 1H), 6.53 (t, J=71.9 Hz, 1H), 5.66 (d, J=0.7 Hz, 2H).

Example 406: 5-Chloro-2-[[1-[3-(difluoromethyl)-4-fluoro-phenyl]triazol-4-yl]methoxy]-4-methyl-pyrimidine

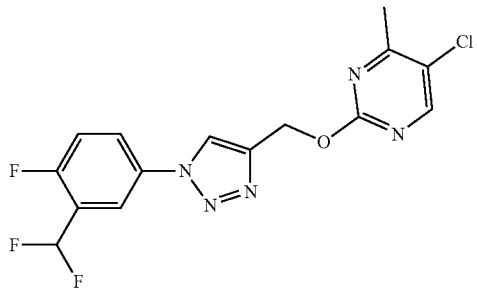 [SMILES: Cc1nc(OCc2cn(-c3ccc(F)c(C(F)F)c3)nn2)ncc1Cl]

The title compound was prepared in a manner analogous to Example 155 using (1-(3-(difluoromethyl)-4-fluorophenyl)-1H-1,2,3-triazol-4-yl)methanol (Intermediate 9) and 2,5-dichloro-4-methylpyrimidine. MS (ESI): mass calcd. for $C_{15}H_{11}ClF_3N_5O$, 369.1; m/z found, 370.0 [M+H]$^+$. $^1$H NMR (500 MHz, CDCl$_3$) δ 8.39 (s, 2H), 8.12 (s, 1H), 7.99-7.86 (m, 2H), 7.39-7.29 (m, 1H), 6.95 (t, J=54.6 Hz, 1H), 5.64 (d, J=0.7 Hz, 2H), 2.57 (s, 3H).

Example 407: 2-[[1-[3-(Difluoromethyl)-4-fluoro-phenyl]triazol-4-yl]methoxy]-5-fluoro-4-methyl-pyrimidine The title compound was prepared in a manner analogous to Example 155 using (1-(3-(difluoromethyl)-4-fluorophenyl)-1H-1,2,3-triazol-4-yl)methanol (Intermediate 9) and 2-chloro-5-fluoro-4-methylpyrimidine. MS (ESI): mass calcd. for $C_{15}H_{11}F_4N_5O$, 353.1; m/z found, 354.0 [M+H]$^+$. $^1$H NMR (400 MHz, CDCl$_3$) δ 8.26 (d, J=1.2 Hz, 1H), 8.12 (t, J=0.7 Hz, 1H), 7.97-7.87 (m, 2H), 7.33 (t, J=9.0 Hz, 1H), 6.95 (t, J=54.6 Hz, 1H), 5.62 (d, J=0.7 Hz, 2H), 2.50 (d, J=2.5 Hz, 3H).

Example 408: 2-[[1-[3-(Difluoromethyl)-4-fluoro-phenyl]triazol-4-yl]methoxy]-4,5-dimethyl-pyrimidine

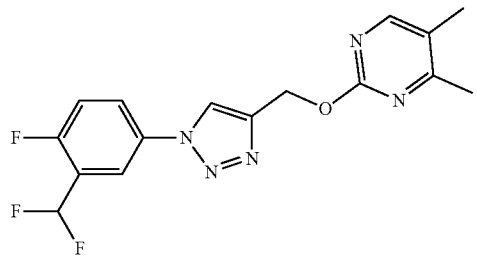 [SMILES: Cc1cnc(OCc2cn(-c3ccc(F)c(C(F)F)c3)nn2)nc1C]

The title compound was prepared in a manner analogous to Example 155 using (1-(3-(difluoromethyl)-4-fluorophenyl)-1H-1,2,3-triazol-4-yl)methanol (Intermediate 9) and 2-chloro-4,5-dimethylpyrimidine. MS (ESI): mass calcd. for $C_{16}H_{14}F_3N_5O$, 349.1; m/z found, 350.1 [M+H]$^+$. $^1$H NMR (400 MHz, CDCl$_3$) δ 8.21 (d, J=0.9 Hz, 1H), 8.13 (t, J=0.8 Hz, 1H), 7.98-7.85 (m, 2H), 7.32 (s, 1H), 6.95 (t, J=54.6 Hz, 1H), 5.66-5.59 (m, 2H), 2.45 (s, 3H), 2.20 (s, 3H)

Example 409: 2-[[1-[3-(Difluoromethyl)-4-fluoro-phenyl]triazol-4-yl]methoxy]-N-methyl-pyrimidine-5-carboxamide

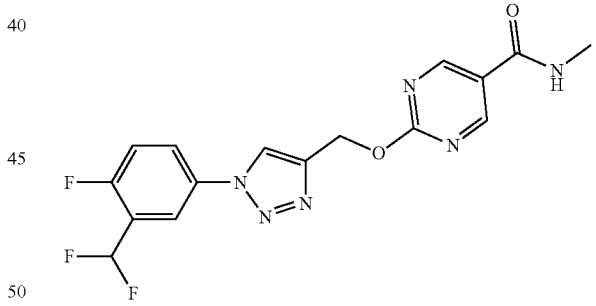

The title compound was prepared in a manner analogous to Example 153 using (1-(3-(difluoromethyl)-4-fluorophenyl)-1H-1,2,3-triazol-4-yl)methanol (Intermediate 9) and 2-chloro-N-methylpyrimidine-5-carboxamide, using ACN instead of DMF. MS (ESI): mass calcd. for $C_{16}H_{13}F_3N_6O_2$, 378.1; m/z found, 379.1 [M+H]$^+$. $^1$H NMR (500 MHz, CDCl$_3$) δ 9.05-8.95 (m, 2H), 8.42-8.34 (d, J=0.9 Hz, 1H), 8.05-8.00 (m, 1H), 8.00-7.91 (m, 1H), 7.40-7.35 (m, 1H), 7.12-6.85 (t, J=54.5 Hz, 1H), 5.76-5.66 (s, 2H), 3.03-2.87 (m, 3H).

Example 410: 2-[[1-[3-(Difluoromethyl)-4-fluorophenyl]triazol-4-yl]methoxy]-N,N-dimethyl-pyrimidine-4-carboxamide

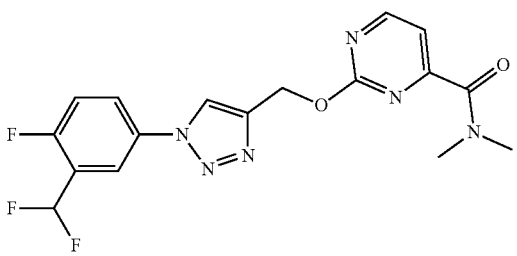 [SMILES: CN(C)C(=O)c1ccnc(OCc2cn(-c3ccc(F)c(C(F)F)c3)nn2)n1]

The title compound was prepared in a manner analogous to Example 162, Steps A-B, using dimethylamine in Step B. MS (ESI): mass calcd. for $C_{17}H_{15}F_3N_6O_2$, 392.1; m/z found, 393.0 [M+H]$^+$. $^1$H NMR (500 MHz, CDCl$_3$) δ 8.69 (d, J=4.9 Hz, 1H), 8.21 (s, 1H), 7.98 (dd, J=5.9, 2.6 Hz, 1H), 7.94-7.86 (m, 1H), 7.37-7.29 (m, 1H), 7.22 (d, J=4.9 Hz, 1H), 6.95 (t, J=54.6 Hz, 1H), 5.72-5.62 (m, 2H), 3.14 (s, 3H), 3.09 (s, 3H).

Example 411: 2-[[1-[3-(Difluoromethyl)-4-fluorophenyl]triazol-4-yl]methoxy]-4-methoxy-5-methyl-pyrimidine

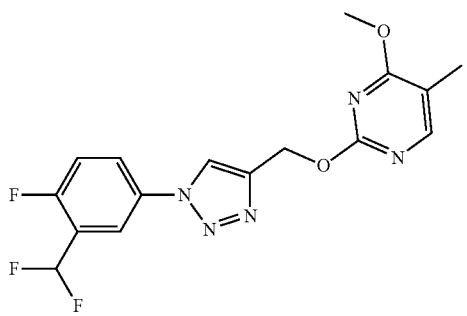 [SMILES: COc1nc(OCc2cn(-c3ccc(F)c(C(F)F)c3)nn2)ncc1C]

The title compound was prepared in a manner analogous to Example 153 using (1-(3-(difluoromethyl)-4-fluorophenyl)-1H-1,2,3-triazol-4-yl)methanol (Intermediate 9) and 2-chloro-4-methoxy-5-methylpyrimidine, using ACN instead of DMF. MS (ESI): mass calcd. for $C_{16}H_{14}F_3N_5O_2$, 365.1; m/z found, 366.1 [M+H]$^+$. $^1$H NMR (500 MHz, CDCl$_3$) δ 8.14-8.10 (s, 1H), 8.05-8.00 (d, J=1.2 Hz, 1H), 7.97-7.92 (dd, J=5.8, 2.6 Hz, 1H), 7.92-7.86 (m, 1H), 7.36-7.29 (m, 1H), 7.08-6.82 (t, J=54.6 Hz, 1H), 5.64-5.60 (d, J=0.6 Hz, 2H), 4.07-3.90 (s, 3H), 2.12-2.02 (m, 3H).

Example 412: 2-[[1-[3-(Difluoromethyl)-4-fluorophenyl]triazol-4-yl]methoxy]pyrimidin-4-amine

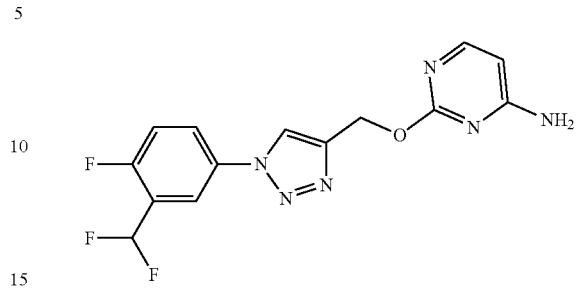

The title compound was prepared in a manner analogous to Example 153 using (1-(3-(difluoromethyl)-4-fluorophenyl)-1H-1,2,3-triazol-4-yl)methanol (Intermediate 9) and 2-chloropyrimidin-4-amine, using ACN instead of DMF. MS (ESI): mass calcd. for $C_{14}H_{11}F_3N_6O$, 336.1; m/z found, 337.0 [M+H]$^+$. $^1$H NMR (400 MHz, CDCl$_3$) δ 8.17-8.09 (s, 1H), 8.09-8.01 (m, 1H), 7.99-7.84 (m, 2H), 7.38-7.28 (m, 1H), 7.10-6.76 (t, J=54.6 Hz, 1H), 6.19-6.09 (m, 1H), 5.63-5.54 (m, 2H), 5.08-4.89 (s, 2H).

Example 413: 2-[[1-[3-(Difluoromethyl)-4-fluorophenyl]triazol-4-yl]methoxy]-N-methyl-pyrimidin-4-amine

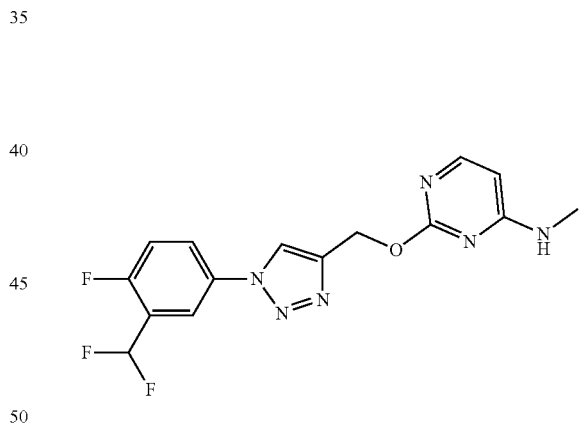

The title compound was prepared in a manner analogous to Example 163, Steps B-C using tert-butyl (2-chloropyrimidin-4-yl)(methyl)carbamate (Intermediate 55) and (1-(3-(difluoromethyl)-4-fluorophenyl)-1H-1,2,3-triazol-4-yl)methanol (Intermediate 9). MS (ESI): mass calcd. for $C_{15}H_{13}F_3N_6O$, 350.1; m/z found, 351.0 [M+H]$^+$. $^1$H NMR (500 MHz, CDCl$_3$) δ 8.14-8.10 (s, 1H), 8.07-7.98 (d, J=7.4 Hz, 1H), 7.98-7.92 (m, 1H), 7.93-7.85 (m, 1H), 7.36-7.28 (m, 1H), 7.07-6.81 (t, J=54.6 Hz, 1H), 6.08-6.02 (d, J=5.9 Hz, 1H), 5.64-5.55 (s, 2H), 5.14-4.91 (m, 1H), 3.04-2.86 (d, J=4.8 Hz, 3H).

Example 414: 2-[[1-[3-(Difluoromethyl)-4-fluorophenyl]triazol-4-yl]methoxy]-5-fluoro-N-methyl-pyrimidin-4-amine

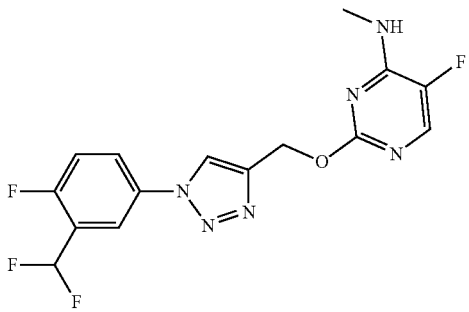 [SMILES: CNc1nc(OCc2cn(-c3ccc(F)c(C(F)F)c3)nn2)ncc1F]

The title compound was prepared in a manner analogous to 163, Steps B-C using (1-(3-(difluoromethyl)-4-fluorophenyl)-1H-1,2,3-triazol-4-yl)methanol (Intermediate 9) and 2-chloro-5-fluoro-N-methyl-N-((2-(trimethylsilyl)ethoxy)methyl)pyrimidin-4-amine (Intermediate 59) in Step A. MS (ESI): mass calcd. for $C_{15}H_{12}F_4N_6O$, 368.1; m/z found, 369.0 [M+H]+. $^1$H NMR (400 MHz, CDCl$_3$) δ 8.16-8.09 (d, J=0.8 Hz, 1H), 7.98-7.92 (m, 1H), 7.92-7.86 (m, 1H), 7.85-7.78 (m, 1H), 7.37-7.28 (m, 1H), 7.11-6.77 (t, J=54.6 Hz, 1H), 5.64-5.50 (m, 2H), 5.26-5.01 (s, 1H), 3.14-2.98 (m, 3H).

Example 415: 2-[[1-[3-(Difluoromethyl)-4-fluorophenyl]triazol-4-yl]methoxy]-N,N-dimethyl-pyrimidin-4-amine

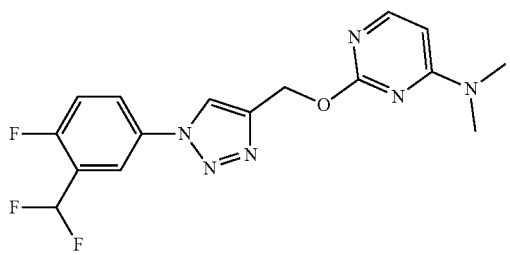 [SMILES: CN(C)c1ccnc(OCc2cn(-c3ccc(F)c(C(F)F)c3)nn2)n1]

The title compound was prepared in a manner analogous to Example 155 using (1-(3-(difluoromethyl)-4-fluorophenyl)-1H-1,2,3-triazol-4-yl)methanol (Intermediate 9) and 2-chloro-N,N-dimethylpyrimidin-4-amine. MS (ESI): mass calcd. for $C_{16}H_{15}F_3N_6O$, 364.1; m/z found, 365.1 [M+H]+. $^1$H NMR (500 MHz, CDCl$_3$) δ 8.14-8.09 (t, J=0.8 Hz, 1H), 8.06-8.01 (d, J=6.1 Hz, 1H), 7.97-7.92 (m, 1H), 7.92-7.86 (m, 1H), 7.35-7.28 (m, 1H), 7.08-6.81 (t, J=54.6 Hz, 1H), 6.16-6.08 (d, J=6.1 Hz, 1H), 5.64-5.58 (d, J=0.8 Hz, 2H), 3.21-3.04 (s, 6H).

Example 416: 2-((1-(3-(Difluoromethyl)-4-fluorophenyl)-1H-1,2,3-triazol-4-yl)methoxy)-5-(3-fluoroazetidin-1-yl)pyrimidine

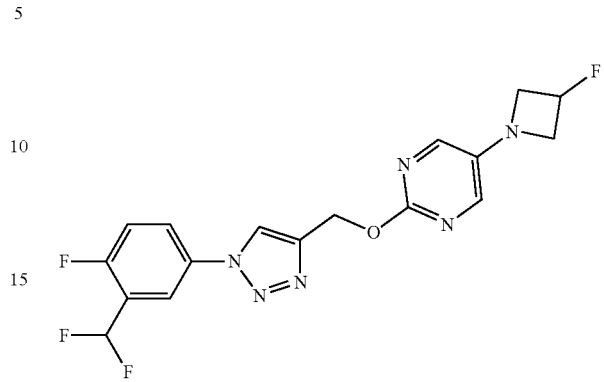

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and 3-fluoroazetidine hydrochloride. MS (ESI): mass calcd. for $C_{17}H_{14}F_4N_6O$, 394.3; m/z found, 395.1 [M+H]+. $^1$H NMR (400 MHz, CDCl$_3$) δ 8.18-8.15 (s, 1H), 8.00-7.97 (m, 1H), 7.97-7.92 (m, 1H), 7.92-7.89 (s, 2H), 7.40-7.33 (m, 1H), 7.14-6.84 (m, 1H), 5.67-5.61 (s, 2H), 5.60-5.39 (m, 1H), 4.34-4.22 (m, 2H), 4.11-3.98 (m, 2H).

Example 417: 5-(Azetidin-1-yl)-2-((1-(3-(difluoromethyl)-4-fluorophenyl)-1H-1,2,3-triazol-4-yl)methoxy)pyrimidine

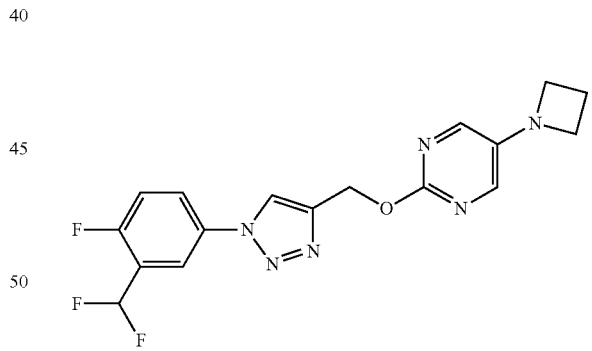

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and azetidine. MS (ESI): mass calcd. for $C_{17}H_{15}F_3N_6O$, 376.3; m/z found, 377.1 [M+H]+. $^1$H NMR (400 MHz, CDCl$_3$) δ 8.18-8.12 (s, 1H), 8.01-7.97 (m, 1H), 7.96-7.91 (m, 1H), 7.88-7.83 (s, 2H), 7.40-7.32 (m, 1H), 7.14-6.83 (t, J=54.6 Hz, 1H), 5.66-5.58 (s, 2H), 4.02-3.87 (m, 4H), 2.55-2.43 (m, 2H).

Example 418: 2-((1-(3-(Difluoromethyl)-4-fluorophenyl)-1H-1,2,3-triazol-4-yl)methoxy)-5-(3-methoxyazetidin-1-yl)pyrimidine

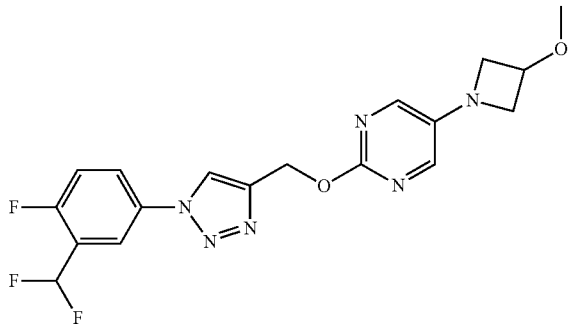 [SMILES: COC1CN(c2cnc(OCc3cn(-c4ccc(F)c(C(F)F)c4)nn3)nc2)C1]

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and 3-methoxyazetidine hydrochloride. MS (ESI): mass calcd. for $C_1H_{17}F_3N_6O_2$, 406.3; m/z found, 407.1 [M+H]$^+$. $^1$H NMR (500 MHz, CDCl$_3$) δ 8.12-8.09 (s, 1H), 7.97-7.92 (m, 1H), 7.92-7.87 (m, 1H), 7.86-7.81 (s, 2H), 7.35-7.29 (m, 1H), 7.07-6.81 (m, 1H), 5.62-5.56 (d, J=0.7 Hz, 2H), 4.43-4.36 (m, 1H), 4.19-4.11 (m, 2H), 3.79-3.68 (m, 2H), 3.37-3.31 (s, 3H).

Example 419: 5-(3,3-Difluoroazetidin-1-yl)-2-((1-(3-(difluoromethyl)-4-fluorophenyl)-1H-1,2,3-triazol-4-yl)methoxy)pyrimidine

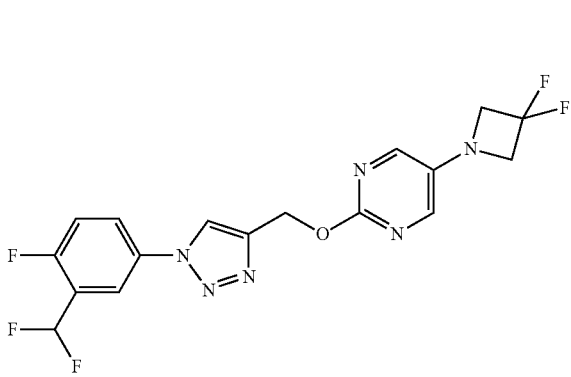 [SMILES: Fc1ccc(-n2cc(COc3ncc(N4CC(F)(F)C4)cn3)nn2)cc1C(F)F]

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and 3,3-difluoroazetidine hydrochloride. MS (ESI): mass calcd. for $C_{17}H_{13}F_8N_6O$, 412.3; m/z found, 413.1 [M+H]$^+$. $^1$H NMR (500 MHz, CDCl$_3$) δ 8.13-8.11 (s, 1H), 7.96-7.93 (m, 1H), 7.93-7.88 (s, 3H), 7.36-7.30 (m, 1H), 7.07-6.82 (m, 1H), 5.62-5.57 (d, J=0.8 Hz, 2H), 4.33-4.22 (m, 4H).

Example 420: 2-((1-(3-(Difluoromethyl)-4-fluorophenyl)-1H-1,2,3-triazol-4-yl)methoxy)-5-(3-fluoro-3-methylazetidin-1-yl)pyrimidine

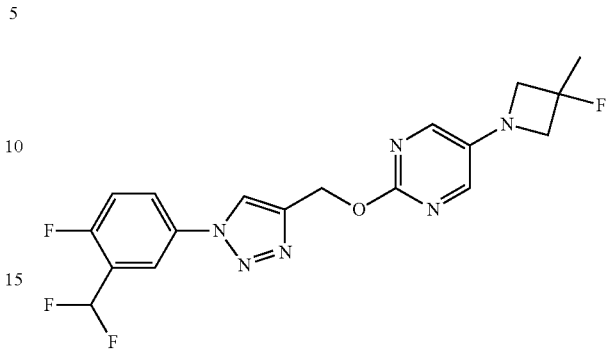

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and 3-fluoro-3-methylazetidine hydrochloride. MS (ESI): mass calcd. for $C_{18}H_{16}F_4N_6O$, 408.3; m/z found, 409.1 [M+H]$^+$. $^1$H NMR (500 MHz, CDCl$_3$) δ 8.13-8.10 (t, J=0.7 Hz, 1H), 7.96-7.92 (m, 1H), 7.92-7.88 (m, 1H), 7.88-7.85 (s, 2H), 7.35-7.29 (m, 1H), 7.06-6.83 (t, J=54.6 Hz, 1H), 5.62-5.56 (d, J=0.7 Hz, 2H), 4.06-3.98 (m, 2H), 3.98-3.89 (m, 2H), 1.76-1.67 (d, J=21.8 Hz, 3H).

Example 421: 2-((1-(3-(Difluoromethyl)-4-fluorophenyl)-1H-1,2,3-triazol-4-yl)methoxy)-5-(3-(difluoromethyl)azetidin-1-yl)pyrimidine

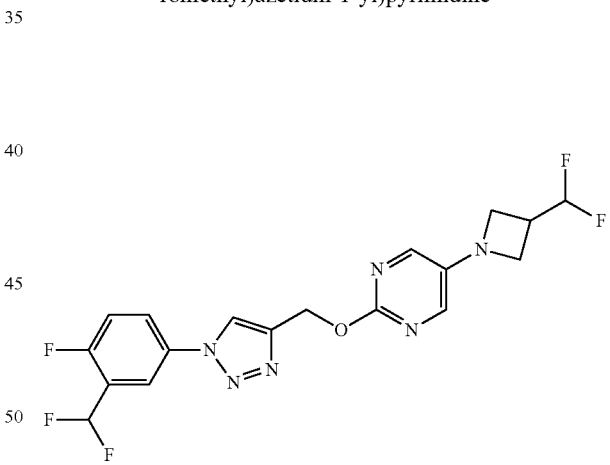

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and 3-(difluoromethyl)azetidine hydrochloride. MS (ESI): mass calcd. for $C_{18}H_{15}F_8N_6O$, 426.3; m/z found, 427.1 [M+H]$^+$. $^1$H NMR (500 MHz, CDCl$_3$) δ 8.13-8.09 (m, 1H), 7.96-7.93 (dd, J=5.8, 2.8 Hz, 1H), 7.92-7.87 (m, 1H), 7.87-7.83 (s, 2H), 7.35-7.29 (m, 1H), 7.07-6.83 (t, J=54.6 Hz, 1H), 6.20-5.94 (m, 1H), 5.61-5.56 (d, J=0.8 Hz, 2H), 4.07-4.00 (m, 2H), 3.94-3.89 (dd, J=7.6, 5.3 Hz, 2H), 3.26-3.14 (m, 1H).

Example 422: 2-((1-(3-(Difluoromethyl)-4-fluorophenyl)-1H-1,2,3-triazol-4-yl)methoxy)-5-(3,3-difluoropyrrolidin-1-yl)pyrimidine

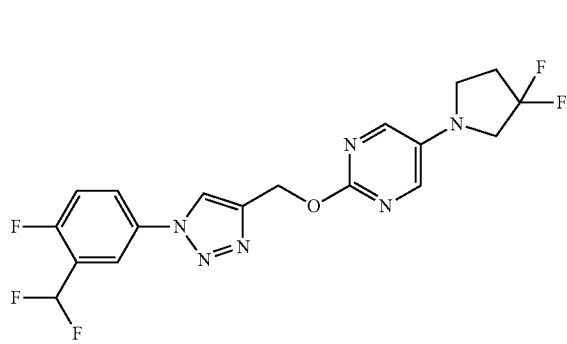 [SMILES: Fc1ccc(-n2cc(COc3ncc(N4CCC(F)(F)C4)cn3)nn2)cc1C(F)F]

The title compound was made in an analogous manner to Example 187 using 5-bromo-2-((1-(4-fluoro-3-(difluoromethyl)phenyl)-1H-1,2,3-triazol-4-yl)methoxy)pyrimidine (Example 398) and 3,3-difluoropyrrolidine hydrochloride. MS (ESI): mass calcd. for $C_{18}H_{15}F_8N_6O$, 426.3; m/z found, 427.1 [M+H]$^+$. $^1$H NMR (500 MHz, CDCl$_3$) δ 8.15-8.11 (d, J=0.8 Hz, 1H), 7.99-7.95 (m, 3H), 7.94-7.89 (m, 1H), 7.37-7.31 (m, 1H), 7.09-6.84 (m, 1H), 5.63-5.60 (s, 2H), 3.72-3.63 (m, 2H), 3.58-3.52 (m, 2H), 2.60-2.50 (m, 2H)

Example 423: 5-Cyclopropyl-2-[[1-[3-(difluoromethyl)-4-fluoro-phenyl]triazol-4-yl]methoxy]pyrimidine

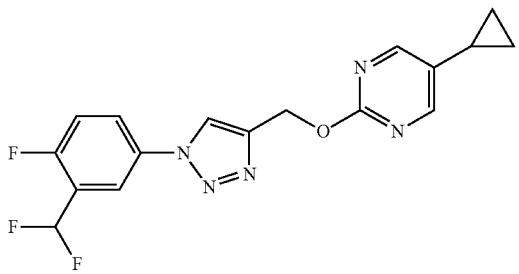 [SMILES: Fc1ccc(-n2cc(COc3ncc(C4CC4)cn3)nn2)cc1C(F)F]

The title compound was prepared in a manner analogous to Example 155 using (1-(3-(difluoromethyl)-4-fluorophenyl)-1H-1,2,3-triazol-4-yl)methanol (Intermediate 9) and 2-chloro-5-cyclopropylpyrimidine. MS (ESI): mass calcd. for $C_{17}H_{14}F_3N_5O$, 361.1; m/z found, 362.1 [M+H]$^+$. $^1$H NMR (400 MHz, CDCl$_3$) δ 8.32 (d, J=0.6 Hz, 2H), 8.12 (t, J=0.7 Hz, 1H), 7.96-7.87 (m, 2H), 7.32 (t, J=9.0 Hz, 1H), 6.95 (t, J=54.6 Hz, 1H), 5.63 (d, J=0.7 Hz, 2H), 1.88-1.78 (m, 1H), 1.07-0.99 (m, 2H), 0.75-0.64 (m, 2H).

Example 424: 2-[[1-[3-(Difluoromethyl)-4-fluorophenyl]triazol-4-yl]methoxy]-4-(2-furyl)pyrimidine

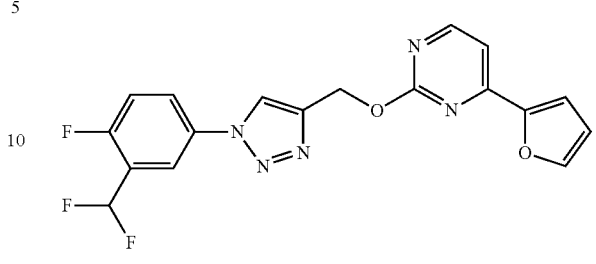

The title compound was prepared in a manner analogous to Example 153 using (1-(3-(difluoromethyl)-4-fluorophenyl)-1H-1,2,3-triazol-4-yl)methanol (Intermediate 9) and 2-chloro-4-(furan-2-yl)pyrimidine, using ACN instead of DMF. MS (ESI): mass calcd. for $C_{18}H_{12}F_3N_5O_2$, 387.1; m/z found, 388.1 [M+H]$^+$. $^1$H NMR (500 MHz, CDCl$_3$) δ 8.62-8.52 (d, J=5.1 Hz, 1H), 8.25-8.15 (s, 1H), 7.98-7.93 (m, 1H), 7.92-7.87 (m, 1H), 7.66-7.58 (m, 1H), 7.39-7.28 (m, 3H), 7.08-6.80 (t, J=54.6 Hz, 1H), 6.64-6.56 (m, 1H), 5.76-5.67 (s, 2H)

Example 425: 2-[[1-[3-(Difluoromethyl)-4-fluorophenyl]-5-iodo-triazol-4-yl]methoxy]-5-methyl-pyrimidine

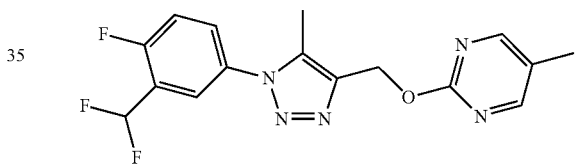

The title compound was prepared in a manner analogous to Example 155 using (1-(3-(difluoromethyl)-4-fluorophenyl)-5-iodo-1H-1,2,3-triazol-4-yl)methanol (Intermediate 27) and 2-chloro-5-methylpyrimidine. MS (ESI): mass calcd. for $C_{15}H_{11}F_3IN_5O$, 461.0; m/z found, 461.8 [M+H]$^+$. $^1$H NMR (400 MHz, DMSO-d$_6$) δ 8.51-8.49 (m, 2H), 7.99-7.91 (m, 2H), 7.75-7.67 (m, 1H), 7.33 (t, J=53.9 Hz, 1H), 5.44 (s, 2H), 2.22 (s, 3H).

Example 426: [3H]-2-((1-(3-(Difluoromethyl)-4-fluorophenyl)-1H-1,2,3-triazol-4-yl-5-t)methoxy)-5-methylpyrimidine

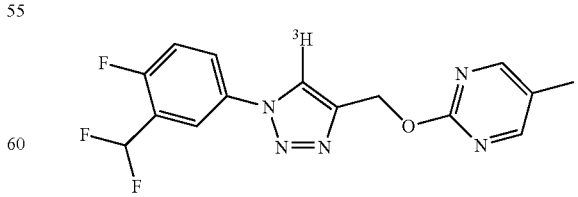

A solution of 2-((1-(3-(difluoromethyl)-4-fluorophenyl)-5-iodo-1H-1,2,3-triazol-4-yl)methoxy)-5-methylpyrimidine (Example 425, 5 mg, 0.01 mmol), Pd/C 10% (9 mg, 0.008 mmol), DMF (1 ml), DIPEA (0.018 mL, 0.1 mmol), and tritium gas (760 mm Hg) was stirred for 30 minutes. The resulting product was dissolved in ethanol and filtered. The labile tritium was removed by rotovap three times. Purification (HPLC-C-18 column using gradient A: 0.1% TFA, B: 100% CH$_3$CN, A to 100% B in 60 min., U.V. 250 nm, flow 6 ml/min) afforded the title compound.

Example 427: 3-Fluoro-2-[[1-[4-fluoro-3-(trifluoromethyl)phenyl]triazol-4-yl]methoxy]pyridine

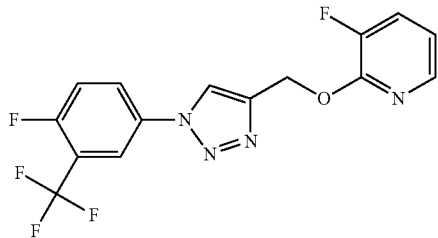 [SMILES: Fc1ccc(-n2cc(COc3ncccc3F)nn2)cc1C(F)(F)F]

The title compound was prepared analogous to Example 158 using 2-chloro-3-fluoropyridine. MS (ESI): mass calcd. for C$_{15}$H$_9$F$_8$N$_4$O, 356.1; m/z found, 357.0 [M+H]$^+$. $^1$H NMR (400 MHz, CDCl$_3$) δ 8.11 (s, 1H), 8.04-7.92 (m, 3H), 7.44-7.33 (m, 2H), 6.95-6.88 (m, 1H), 5.69 (d, J=0.7 Hz, 2H).

Example 428: 5-Chloro-2-[[1-[4-fluoro-3-(trifluoromethyl)phenyl]triazol-4-yl]methoxy]pyridine

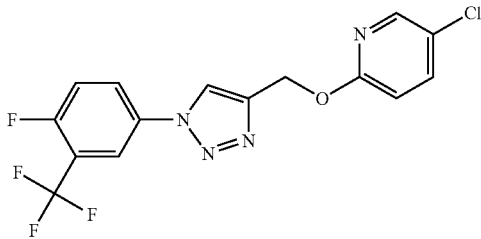 [SMILES: Fc1ccc(-n2cc(COc3ccc(Cl)cn3)nn2)cc1C(F)(F)F]

The title compound was prepared analogous to Example 158 using 2, 5-dichloropyridine. MS (ESI): mass calcd. for C$_{15}$H$_9$ClF$_4$N$_4$O, 372.0; m/z found, 373.0 [M+H]$^+$. $^1$H NMR (400 MHz, CDCl$_3$) δ 8.16-8.12 (m, 1H), 8.10-8.04 (m, 1H), 8.03-7.91 (m, 2H), 7.60-7.53 (m, 1H), 7.40 (t, J=9.1 Hz, 1H), 6.81-6.72 (m, 1H), 5.57 (d, J=0.6 Hz, 2H).

Example 429: 2-[[1-[4-Fluoro-3-(trifluoromethyl)phenyl]triazol-4-yl]methoxy]-4-methyl-pyridine

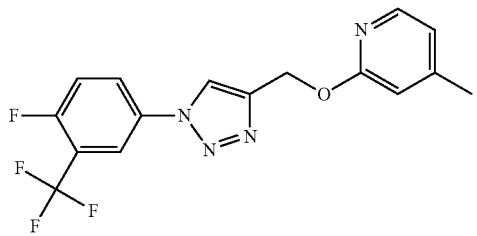 [SMILES: Cc1ccnc(OCc2cn(-c3ccc(F)c(C(F)(F)F)c3)nn2)c1]

The title compound was prepared analogous to Example 158 using 2-chloro-4-methylpyridine. MS (ESI): mass calcd. for C$_{16}$H$_{12}$F$_4$N$_4$O, 352.1; m/z found, 353.0 [M+H]$^+$. $^1$H NMR (500 MHz, CDCl$_3$) δ 8.08-8.03 (m, 2H), 8.00-7.97 (m, 1H), 7.97-7.92 (m, 1H), 7.39 (t, J=9.1 Hz, 1H), 6.75 (d, J=5.2 Hz, 1H), 6.62 (d, J=1.4 Hz, 1H), 5.59 (d, J=0.7 Hz, 2H), 2.31 (s, 3H).

Example 430: 2-[[1-[4-Fluoro-3-(trifluoromethyl)phenyl]triazol-4-yl]methoxy]-6-methyl-pyridine

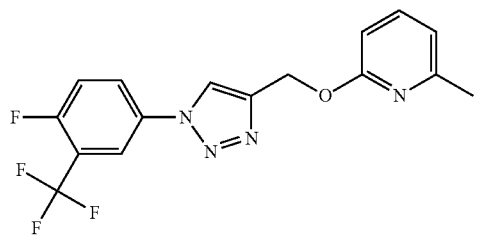

The title compound was prepared analogous to Example 158 using 2-chloro-6-methylpyridine. MS (ESI): mass calcd. for C$_{16}$H$_{12}$F$_4$N$_4$O, 352.1; m/z found, 353.1 [M+H]$^+$. $^1$H NMR (500 MHz, CDCl$_3$) δ 8.07 (t, J=0.7 Hz, 1H), 8.02-7.98 (m, 1H), 7.97-7.92 (m, 1H), 7.52-7.46 (m, 1H), 7.39 (t, J=9.1 Hz, 1H), 6.88-6.70 (m, 1H), 6.68-6.54 (m, 1H), 5.60 (d, J=0.7 Hz, 2H), 2.48 (t, J=0.7 Hz, 3H).

Example 431: 2-[[1-[4-Fluoro-3-(trifluoromethyl)phenyl]triazol-4-yl]methoxy]-5-methyl-pyridine

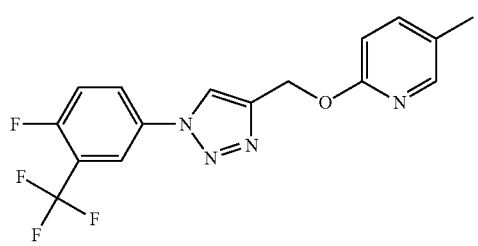 [SMILES: Cc1ccc(OCc2cn(-c3ccc(F)c(C(F)(F)F)c3)nn2)nc1]

The title compound was prepared analogous to Example 158 using 2-chloro-5-methylpyridine. MS (ESI): mass calcd. for C$_{16}$H$_{12}$F$_4$N$_4$O, 352.1; m/z found, 353.1 [M+H]$^+$. $^1$H NMR (500 MHz, CDCl$_3$) δ 8.09-8.05 (m, 1H), 8.03-7.97 (m, 2H), 7.98-7.93 (m, 1H), 7.45-7.36 (m, 2H), 6.72 (d, J=8.4 Hz, 1H), 5.69-5.48 (m, 2H), 2.26 (s, 3H).

Example 432: 2-[[1-[4-Fluoro-3-(trifluoromethyl)phenyl]triazol-4-yl]methoxy]-5-(trifluoromethyl)pyridine

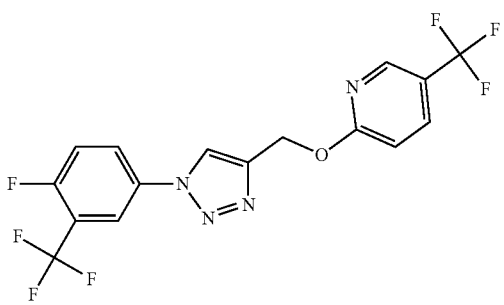 [SMILES: Fc1ccc(-n2cc(COc3ccc(C(F)(F)F)cn3)nn2)cc1C(F)(F)F]

The title compound was prepared analogous to Example 158 using 2-chloro-5-trifluoromethylpyridine. MS (ESI): mass calcd. for $C_{15}H_6F_7N_4O$, 406.1; m/z found, 407.1 [M+H]$^+$. $^1$H NMR (500 MHz, CDCl$_3$) δ 8.50 (d, J=1.3 Hz, 1H), 8.09 (t, J=0.6 Hz, 1H), 8.03-7.98 (m, 1H), 7.98-7.93 (m, 1H), 7.85-7.78 (m, 1H), 7.40 (t, J=9.1 Hz, 1H), 6.91-6.88 (m, 1H), 5.66 (d, J=0.6 Hz, 2H).

Example 433: 2-[6-[[1-[4-Fluoro-3-(trifluoromethyl)phenyl]triazol-4-yl]methoxy]-3-pyridyl]propan-2-ol

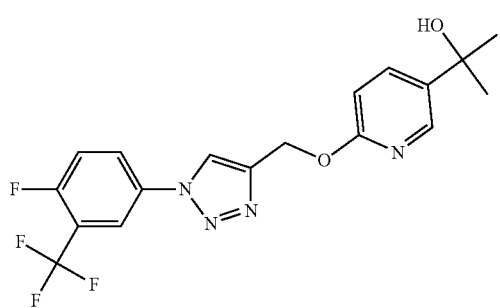 [SMILES: CC(C)(O)c1ccc(OCc2cn(-c3ccc(F)c(C(F)(F)F)c3)nn2)nc1]

The title compound was prepared analogous to Example 158 using 2-(6-chloropyridin-3-yl)propan-2-ol. MS (ESI): mass calcd. for $C_{18}H_{16}F_4N_4O_2$, 396.1; m/z found, 397.0 [M+H]$^+$. $^1$H NMR (500 MHz, CDCl$_3$) δ 8.34-8.27 (m, 1H), 8.10 (s, 1H), 8.03-7.98 (m, 1H), 7.98-7.93 (m, 1H), 7.80-7.72 (m, 1H), 7.39 (t, J=9.1 Hz, 1H), 6.78 (dd, J=8.6, 0.8 Hz, 1H), 5.59 (s, 2H), 1.60 (s, 6H).

Example 434: 2-[[1-[4-Fluoro-3-(trifluoromethyl)phenyl]triazol-4-yl]methoxy]pyrazine

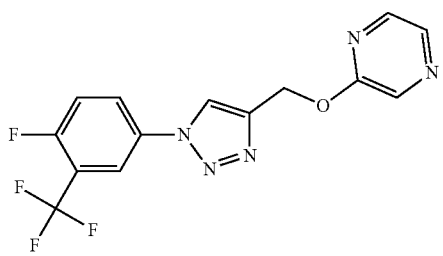 [SMILES: Fc1ccc(-n2cc(COc3cnccn3)nn2)cc1C(F)(F)F]

The title compound was prepared analogous to Example 155, using (1-(3-(trifluoromethyl)-4-fluorophenyl)-1H-1,2,3-triazol-4-yl)methanol and 2-chloropyrazine. MS (ESI): mass calcd. for $C_{14}H_9F_4N_5O$, 339.1; m/z found, 340.0 [M+H]$^+$. $^1$H NMR (400 MHz, CDCl$_3$) δ 8.38-8.27 (m, 1H), 8.30-8.07 (m, 2H), 8.07-7.93 (m, 2H), 7.41 (t, J=9.6 Hz, 1H), 7.26 (s, 1H), 5.62 (s, 2H).

Example 435: 2-[2-[[1-[4-Fluoro-3-(trifluoromethyl)phenyl]triazol-4-yl]methoxy]pyrimidin-5-yl]propan-2-ol

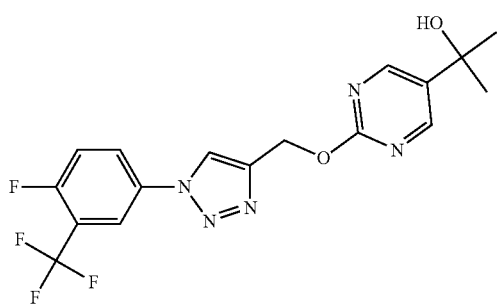 [SMILES: CC(C)(O)c1cnc(OCc2cn(-c3ccc(F)c(C(F)(F)F)c3)nn2)nc1]

The title compound was prepared analogous to Example 155, using (1-(3-(trifluoromethyl)-4-fluorophenyl)-1H-1,2,3-triazol-4-yl)methanol and 2-(2-chloropyrimidin-5-yl)propan-2-ol. MS (ESI): mass calcd. for $C_{17}H_{15}F_4N_5O_2$, 397.1; m/z found, 398.1 [M+H]$^+$. $^1$H NMR (400 MHz, CDCl$_3$) δ 8.68 (s, 2H), 8.15 (s, 1H), 7.99 (d, J=20.7 Hz, 2H), 7.50-7.28 (m, 1H), 5.82-5.58 (m, 2H), 1.78-1.44 (m, 6H).

Example 436: 2-[[1-[4-Fluoro-3-(trifluoromethyl)phenyl]triazol-4-yl]methoxy]-5-(1-methoxy-1-methyl-ethyl)pyrimidine

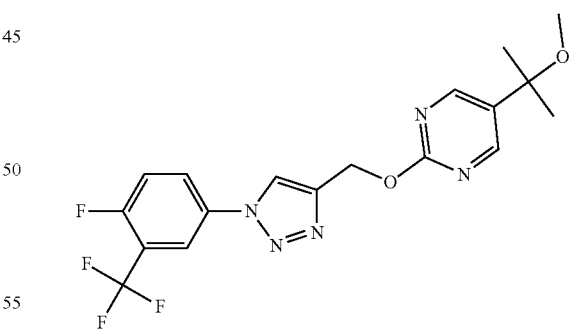

The title compound was prepared in a manner analogous to Example 311 using 2-(2-((1-(4-fluoro-3-(trifluoromethyl)phenyl)-1H-1,2,3-triazol-4-yl)methoxy)pyrimidin-5-yl)propan-2-ol (Example 435). MS (ESI): mass calcd. for $C_{17}H_{17}F_4N_5O_2$, 411.1; m/z found, 412.1 [M+H]$^+$. $^1$H NMR (500 MHz, CDCl$_3$) δ 8.64-8.53 (s, 2H), 8.20-8.13 (t, J=0.7 Hz, 1H), 8.03-7.99 (m, 1H), 7.98-7.94 (m, 1H), 7.46-7.36 (t, J=9.1 Hz, 1H), 5.72-5.63 (d, J=0.7 Hz, 2H), 3.16-3.08 (s, 3H), 1.59-1.51 (s, 6H).

Example 437: 2-[[1-[4-Fluoro-3-(trifluoromethyl)phenyl]triazol-4-yl]methoxy]-5-(methoxymethyl)pyrimidine

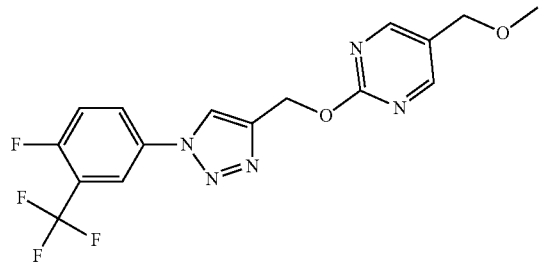 [SMILES: COCc1cnc(OCc2cn(-c3ccc(F)c(C(F)(F)F)c3)nn2)nc1]

The title compound was prepared in a manner analogous to Example 153 using (1-(4-fluoro-3-(trifluoromethyl)phenyl)-1H-1,2,3-triazol-4-yl)methanol (Intermediate 5) and 2-chloro-5-(methoxymethyl)pyrimidine, using ACN instead of DMF. MS (ESI): mass calcd. for $C_{16}H_{13}F_4N_5O_2$, 383.1; m/z found, 384.1 [M+H]$^+$. $^1$H NMR (500 MHz, CDCl$_3$) δ 8.60-8.48 (s, 2H), 8.21-8.10 (m, 1H), 8.02-7.98 (m, 1H), 7.98-7.92 (m, 1H), 7.46-7.35 (t, J=9.1 Hz, 1H), 5.74-5.61 (d, J=0.8 Hz, 2H), 4.50-4.33 (s, 2H), 3.49-3.36 (s, 3H).

Example 438: 2-[[1-[4-Fluoro-3-(trifluoromethyl)phenyl]triazol-4-yl]methoxy]-4-(methoxymethyl)pyrimidine

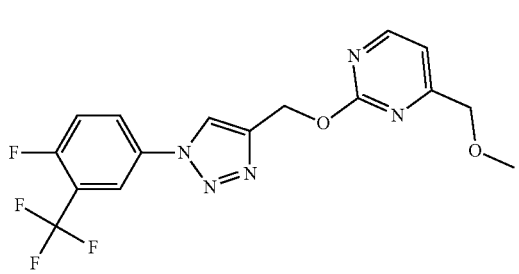 [SMILES: COCc1ccnc(OCc2cn(-c3ccc(F)c(C(F)(F)F)c3)nn2)n1]

The title compound was prepared analogous to Example 155, using (1-(4-fluoro-3-(trifluoromethyl)phenyl)-1H-1,2,3-triazol-4-yl)methanol (Intermediate 5) and 2-chloro-4-(methoxymethyl)pyrimidine. MS (ESI): mass calcd. for $C_{16}H_{13}F_4N_5O_2$, 383.1; m/z found, 384.0 [M+H]$^+$. $^1$H NMR (400 MHz, CDCl$_3$) δ 8.55 (d, J=5.0 Hz, 1H), 8.17 (t, J=0.8 Hz, 1H), 8.03-7.98 (m, 1H), 7.98-7.92 (m, 1H), 7.40 (t, J=9.2 Hz, 1H), 7.16 (dt, J=5.0, 0.7 Hz, 1H), 5.66 (d, J=0.7 Hz, 2H), 4.50 (d, J=0.7 Hz, 2H), 3.50 (s, 3H)

Example 439: 5-(Difluoromethyl)-2-[[1-[4-fluoro-3-(trifluoromethyl)phenyl]triazol-4-yl]methoxy]pyrimidine

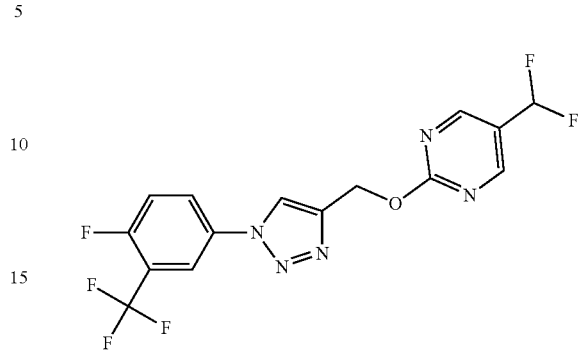

The title compound was prepared analogous to Example 155, using (1-(4-fluoro-3-(trifluoromethyl)phenyl)-1H-1,2,3-triazol-4-yl)methanol (Intermediate 5). MS (ESI): mass calcd. for $C_{15}H_9F_6N_5O$, 389.1; m/z found, 390.0 [M+H]$^+$. $^1$H NMR (500 MHz, CDCl$_3$) δ 8.72 (t, J=1.3 Hz, 2H), 8.15 (t, J=0.7 Hz, 1H), 8.04-7.98 (m, 1H), 7.99-7.92 (m, 1H), 7.41 (t, J=9.1 Hz, 1H), 6.73 (t, J=55.6 Hz, 1H), 5.72 (d, J=0.7 Hz, 2H).

Example 440: 4-(Difluoromethyl)-2-[[1-[4-fluoro-3-(trifluoromethyl)phenyl]triazol-4-yl]methoxy]pyrimidine

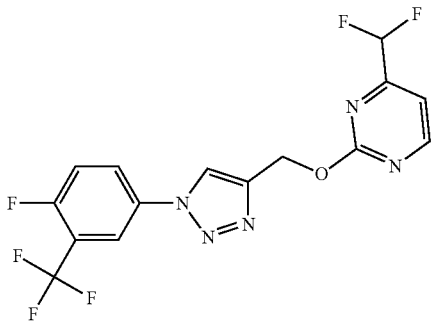 [SMILES: Fc1ccc(-n2cc(COc3nccc(C(F)F)n3)nn2)cc1C(F)(F)F]

The title compound was prepared analogous to Example 155, using (1-(4-fluoro-3-(trifluoromethyl)phenyl)-1H-1,2,3-triazol-4-yl)methanol (Intermediate 5) and 2-chloro-4-(difluoromethyl)pyrimidine. MS (ESI): mass calcd. for $C_{15}H_9F_6N_5O$, 389.1; m/z found, 390.0 [M+H]$^+$. $^1$H NMR (500 MHz, CDCl$_3$) δ 8.77 (d, J=5.0 Hz, 1H), 8.18 (s, 1H), 8.05-7.98 (m, 1H), 7.98-7.92 (m, 1H), 7.41 (t, J=9.0 Hz, 1H), 7.31 (d, J=5.0 Hz, 1H), 6.51 (t, J=54.7 Hz, 1H), 5.71 (d, J=0.9 Hz, 2H)

Example 441: (R/S)-1,1,1-Trifluoro-2-[2-[[1-[4-fluoro-3-(trifluoromethyl)phenyl]triazol-4-yl]methoxy]pyrimidin-5-yl]propan-2-ol

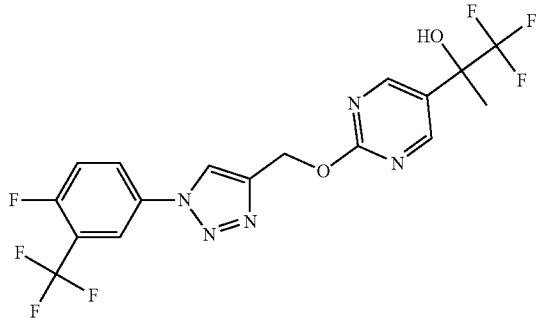 [SMILES: CC(O)(c1cnc(OCc2cn(-c3ccc(F)c(C(F)(F)F)c3)nn2)nc1)C(F)(F)F]

The title compound was prepared in a manner analogous to Example 153 using (1-(4-fluoro-3-(trifluoromethyl)phenyl)-1H-1,2,3-triazol-4-yl)methanol (Intermediate 5) and 2-(2-chloropyrimidin-5-yl)-1,1,1-trifluoropropan-2-ol, using ACN instead of DMF. MS (ESI): mass calcd. for $C_{17}H_{12}F_7N_5O_2$, 451.1; m/z found, 452.0 [M+H]$^+$. $^1$H NMR (500 MHz, CDCl$_3$) δ 8.78-8.73 (s, 2H), 8.18-8.11 (s, 1H), 8.05-7.98 (m, 1H), 7.98-7.92 (d, J=9.0 Hz, 1H), 7.45-7.37 (t, J=9.1 Hz, 1H), 5.73-5.66 (d, J=0.7 Hz, 2H), 2.68-2.60 (d, J=17.8 Hz, 1H), 1.85-1.81 (d, J=1.1 Hz, 3H).

Example 442: 2-[[1-[4-Fluoro-3-(trifluoromethyl)phenyl]triazol-4-yl]methoxy]-4-methoxy-pyrimidine

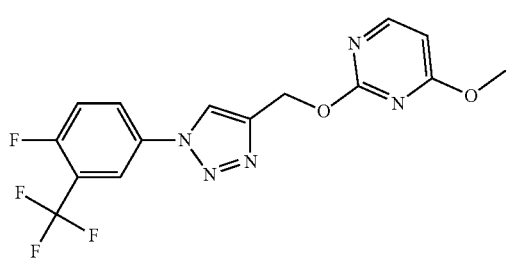 [SMILES: COc1ccnc(OCc2cn(-c3ccc(F)c(C(F)(F)F)c3)nn2)n1]

The title compound was prepared analogous to Example 155, using (1-(3-(trifluoromethyl)-4-fluorophenyl)-1H-1,2,3-triazol-4-yl)methanol (Intermediate 5) and 2-chloro-4-methoxypyrimidine. MS (ESI): mass calcd. for $C_{15}H_{11}F_4N_5O_2$, 369.1; m/z found, 370.0 [M+H]$^+$. $^1$H NMR (400 MHz, CDCl$_3$) δ 8.23 (d, J=5.7 Hz, 1H), 8.14 (s, 1H), 8.08-7.87 (m, 2H), 7.40 (t, J=9.1 Hz, 1H), 6.44 (d, J=5.9 Hz, 1H), 5.66 (s, 2H), 3.99 (s, 3H).

Example 443: 5-Ethoxy-2-[[1-[4-fluoro-3-(trifluoromethyl)phenyl]triazol-4-yl]methoxy]pyrimidine

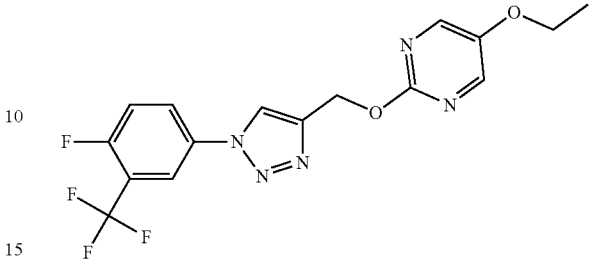

The title compound was prepared analogous to Example 155, using (1-(4-fluoro-3-(trifluoromethyl)phenyl)-1H-1,2,3-triazol-4-yl)methanol (Intermediate 5) and 2-chloro-5-ethoxypyrimidine. MS (ESI): mass calcd. for $C_{16}H_{13}F_4N_5O_2$, 383.1; m/z found, 384.0 [M+H]$^+$. $^1$H NMR (400 MHz, CDCl$_3$) δ 8.23 (s, 2H), 8.12 (s, 1H), 8.06-7.91 (m, 2H), 7.40 (t, J=9.2 Hz, 1H), 5.61 (d, J=0.7 Hz, 2H), 4.09 (q, J=7.0 Hz, 2H), 1.44 (t, J=6.9 Hz, 3H).

Example 444: 5-Chloro-2-[[1-[4-fluoro-3-(trifluoromethyl)phenyl]triazol-4-yl]methoxy]-4-methylpyrimidine

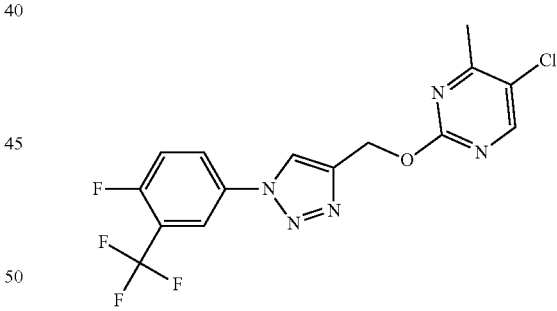

The title compound was prepared analogous to Example 155, using (1-(3-(trifluoromethyl)-4-fluorophenyl)-1H-1,2,3-triazol-4-yl)methanol (Intermediate 5) and 2,5 dichloro-4-methylpyrimidine. MS (ESI): mass calcd. for $C_{15}H_{10}ClF_4N_5O$, 387.1; m/z found, 388.0 [M+H]$^+$. $^1$H NMR (400 MHz, CDCl$_3$) δ 8.39 (s, 1H), 8.13 (s, 1H), 8.11-7.90 (m, 2H), 7.41 (t, J=9.1 Hz, 1H), 5.64 (d, J=3.5 Hz, 2H), 2.68-2.50 (m, 3H).

Example 445: 5-Fluoro-2-[[1-[4-fluoro-3-(trifluoromethyl)phenyl]triazol-4-yl]methoxy]-4-methylpyrimidine

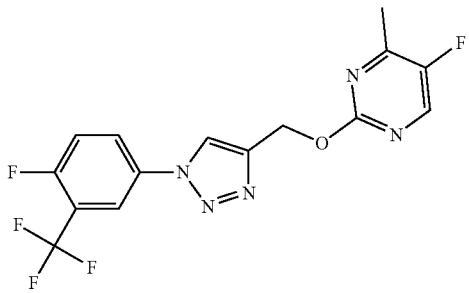 [SMILES: Cc1nc(OCc2cn(-c3ccc(F)c(C(F)(F)F)c3)nn2)ncc1F]

The title compound was prepared analogous to Example 155, using (1-(4-fluoro-3-(trifluoromethyl)phenyl)-1H-1,2,3-triazol-4-yl)methanol (Intermediate 5) and 2-chloro-5-fluoro-4-methylpyrimidine. MS (ESI): mass calcd. for $C_{15}H_{10}F_8N_5O$, 371.1; m/z found, 372.0 [M+H]$^+$. $^1$H NMR (400 MHz, CDCl$_3$) δ 8.26 (d, J=1.2 Hz, 1H), 8.12 (t, J=0.7 Hz, 1H), 8.06-7.90 (m, 2H), 7.40 (t, J=9.1 Hz, 1H), 5.62 (d, J=0.7 Hz, 2H), 2.50 (d, J=2.5 Hz, 3H).

Example 446: 2-[[1-[4-Fluoro-3-(trifluoromethyl)phenyl]triazol-4-yl]methoxy]-4,5-dimethyl-pyrimidine

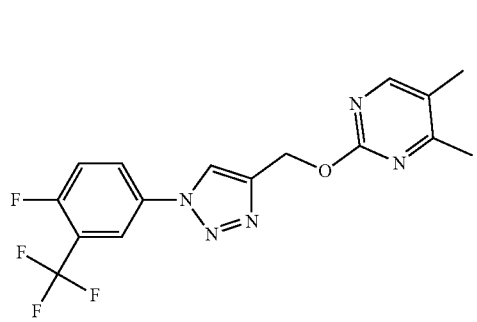 [SMILES: Cc1cnc(OCc2cn(-c3ccc(F)c(C(F)(F)F)c3)nn2)nc1C]

The title compound was prepared analogous to Example 155, using (1-(4-fluoro-3-(trifluoromethyl)phenyl)-1H-1,2,3-triazol-4-yl)methanol (Intermediate 5) and 2-chloro-4,5-dimethylpyrimidine. MS (ESI): mass calcd. for $C_{16}H_{13}F_4N_5O$, 367.1; m/z found, 368.1 [M+H]$^+$. $^1$H NMR (400 MHz, CDCl$_3$) δ 8.19-8.10 (m, 1H), 8.06-7.89 (m, 2H), 7.40 (t, J=9.1 Hz, 1H), 6.74 (s, 1H), 5.65 (d, J=0.8 Hz, 2H), 2.44 (d, J=0.5 Hz, 6H).

Example 447: 1-[2-[[1-[4-Fluoro-3-(trifluoromethyl)phenyl]triazol-4-yl]methoxy]pyrimidin-5-yl]ethanone

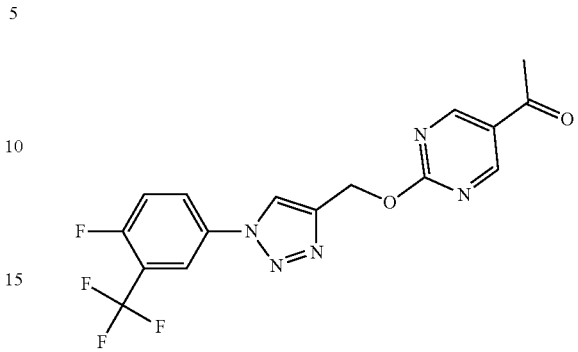

The title compound was prepared analogous to Example 155, using (1-(4-fluoro-3-(trifluoromethyl)phenyl)-1H-1,2,3-triazol-4-yl)methanol (Intermediate 5) and 1-(2-chloropyrimidin-5-yl)ethan-1-one. MS (ESI): mass calcd. for $C_{16}H_{11}F_4N_5O_2$, 381.1; m/z found, 382.0 [M+H]$^+$. $^1$H NMR (400 MHz, CDCl$_3$) δ 9.19-9.07 (d, J=1.8 Hz, 2H), 8.22-8.11 (s, 1H), 8.07-7.91 (m, 2H), 7.47-7.37 (t, J=9.1 Hz, 1H), 5.82-5.71 (s, 2H), 2.73-2.52 (s, 3H).

Example 448: (R/S)-1-[2-[[1-[4-Fluoro-3-(trifluoromethyl)phenyl]triazol-4-yl]methoxy]pyrimidin-5-yl]ethanol

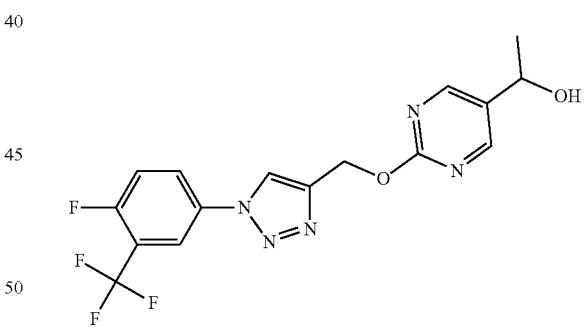

The title compound was prepared in a manner analogous to Example 157 using 1-(2-((1-(4-fluoro-3-(trifluoromethyl)phenyl)-1H-1,2,3-triazol-4-yl)methoxy)pyrimidin-5-yl)ethan-1-one (Example 447). MS (ESI): mass calcd. for $C_{16}H_{13}F_4N_5O_2$, 383.1; m/z found, 384.1 [M+H]$^+$. $^1$H NMR (500 MHz, CDCl$_3$) δ 8.62-8.53 (s, 2H), 8.19-8.13 (s, 1H), 8.04-7.99 (m, 1H), 7.99-7.92 (m, 1H), 7.44-7.35 (t, J=9.1 Hz, 1H), 5.69-5.59 (d, J=0.8 Hz, 2H), 5.02-4.88 (m, 1H), 2.41-2.17 (s, 1H), 1.62-1.49 (d, J=6.5 Hz, 3H).

Example 449: 2-[[1-[4-Fluoro-3-(trifluoromethyl)phenyl]triazol-4-yl]methoxy]-N-methyl-pyrimidin-4-amine

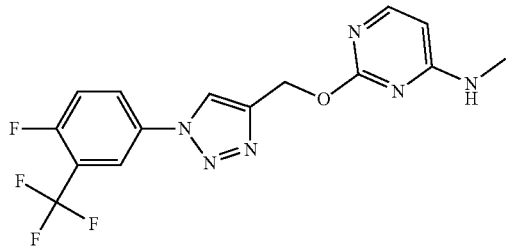 [SMILES: CNc1ccnc(OCc2cn(-c3ccc(F)c(C(F)(F)F)c3)nn2)n1]

The title compound was prepared in a manner analogous to Example 163, Steps B-C using tert-butyl (2-chloropyrimidin-4-yl)(methyl)carbamate (Intermediate 55) and (1-(4-fluoro-3-(trifluoromethyl)phenyl)-1H-1,2,3-triazol-4-yl)methanol (Intermediate 5). MS (ESI): mass calcd. for $C_{15}H_{12}F_4N_6O$, 368.1; m/z found, 369.0 [M+H]$^+$. $^1$H NMR (500 MHz, CDCl$_3$) δ 8.23-8.09 (s, 1H), 8.09-7.99 (m, 2H), 7.98-7.89 (dt, J=8.8, 3.4 Hz, 1H), 7.46-7.34 (t, J=9.2 Hz, 1H), 6.17-5.99 (d, J=6.0 Hz, 1H), 5.69-5.54 (s, 2H), 5.34-5.08 (s, 1H), 3.05-2.91 (d, J=4.4 Hz, 3H).

Example 450: 2-[[1-[4-Fluoro-3-(trifluoromethyl)phenyl]triazol-4-yl]methoxy]-N,N-dimethyl-pyrimidin-4-amine

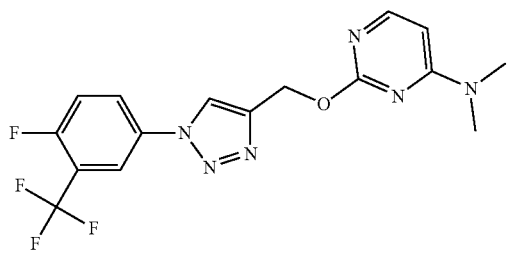 [SMILES: CN(C)c1ccnc(OCc2cn(-c3ccc(F)c(C(F)(F)F)c3)nn2)n1]

The title compound was prepared analogous to Example 155, using (1-(4-fluoro-3-(trifluoromethyl)phenyl)-1H-1,2,3-triazol-4-yl)methanol (Intermediate 5) and 2-chloro-N,N-dimethylpyrimidin-4-amine. MS (ESI): mass calcd. for $C_{16}H_{14}F_4N_5O$, 382.1; m/z found, 383.1 [M+H]$^+$. $^1$H NMR (400 MHz, CDCl$_3$) δ 8.17-8.12 (s, 1H), 8.08-7.98 (t, J=6.7 Hz, 2H), 7.98-7.90 (m, 1H), 7.44-7.33 (t, J=9.1 Hz, 1H), 6.17-6.10 (d, J=6.1 Hz, 1H), 5.64-5.58 (d, J=0.8 Hz, 2H), 3.19-3.06 (s, 6H).

Example 451: 5-Fluoro-2-[[1-[4-fluoro-3-(trifluoromethyl)phenyl]triazol-4-yl]methoxy]-N-methyl-pyrimidin-4-amine

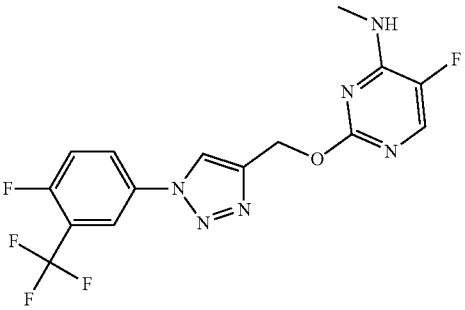 [SMILES: CNc1nc(OCc2cn(-c3ccc(F)c(C(F)(F)F)c3)nn2)ncc1F]

The title compound was prepared in a manner analogous to Example 163, Steps B-C using (1-(4-fluoro-3-(trifluoromethyl)phenyl)-1H-1,2,3-triazol-4-yl)methanol (Intermediate 5) and 2-chloro-5-fluoro-N-methyl-N-((2-(trimethylsilyl)ethoxy)methyl)pyrimidin-4-amine (Intermediate 59) in step A. MS (ESI): mass calcd. for $C_{15}H_{11}F_8N_6O$, 386.1; m/z found, 387.0 [M+H]$^+$. $^1$H NMR (400 MHz, CDCl$_3$) δ 8.17-8.10 (s, 1H), 8.06-7.98 (m, 1H), 7.98-7.89 (m, 1H), 7.85-7.78 (d, J=3.0 Hz, 1H), 7.46-7.34 (t, J=9.0 Hz, 1H), 5.62-5.54 (d, J=0.8 Hz, 2H), 5.20-5.04 (s, 1H), 3.20-2.96 (m, 3H).

Example 452: 2-[[1-[4-Fluoro-3-(trifluoromethyl)phenyl]triazol-4-yl]methoxy]-N-methyl-pyrimidine-5-carboxamide

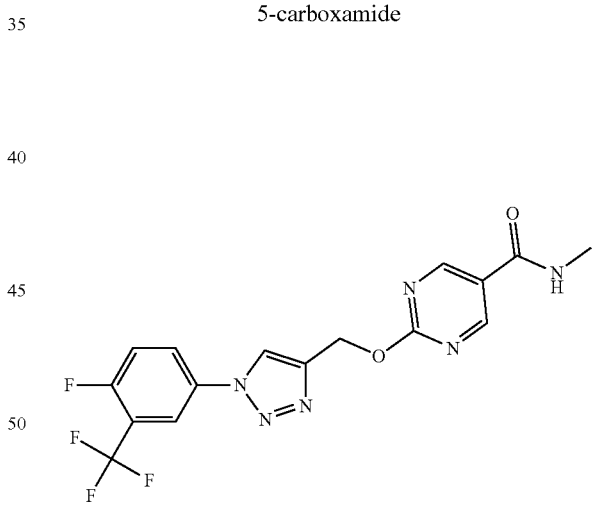

The title compound was prepared in a manner analogous to Example 153 using (1-(4-fluoro-3-(trifluoromethyl)phenyl)-1H-1,2,3-triazol-4-yl)methanol (Intermediate 5) and 2-chloro-N-methylpyrimidine-5-carboxamide, using ACN instead of DMF. MS (ESI): mass calcd. for $C_{16}H_{12}F_4N_6O_2$, 396.1; m/z found, 397.0 [M+H]$^+$. $^1$H NMR (400 MHz, CDCl$_3$) δ 9.00-8.98 (s, 2H), 8.44-8.38 (s, 1H), 8.12-8.07 (m, 1H), 8.07-8.00 (m, 1H), 7.49-7.41 (t, J=9.2 Hz, 1H), 5.77-5.67 (s, 2H), 3.03-2.90 (s, 3H).

Example 453: 5-Cyclopropyl-2-[[1-[4-fluoro-3-(trifluoromethyl)phenyl]triazol-4-yl]methoxy]pyrimidine

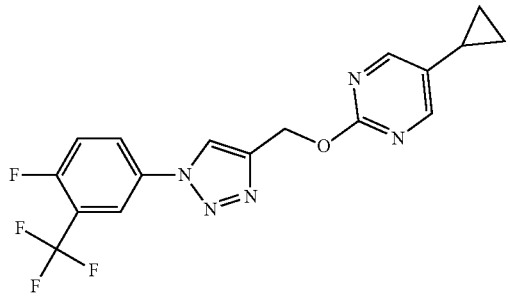 [SMILES: Fc1ccc(-n2cc(COc3ncc(C4CC4)cn3)nn2)cc1C(F)(F)F]

The title compound was prepared analogous to Example 155, using (1-(4-fluoro-3-(trifluoromethyl)phenyl)-1H-1,2,3-triazol-4-yl)methanol (Intermediate 5) and 2-chloro-5-cyclopropylpyrimidine. MS (ESI): mass calcd. for $C_{17}H_{13}F_4N_5O$, 379.1; m/z found, 380.0 [M+H]$^+$. $^1$H NMR (400 MHz, CDCl$_3$) δ 8.32 (d, J=0.6 Hz, 2H), 8.14-8.12 (m, 1H), 8.02-7.98 (m, 1H), 7.98-7.92 (m, 1H), 7.40 (t, J=9.1 Hz, 1H), 5.64 (d, J=0.7 Hz, 2H), 1.90-1.76 (m, 1H), 1.09-0.97 (m, 2H), 0.75-0.65 (m, 2H)

Example 454: 5-Bromo-2-((1-(4-fluoro-3-(trifluoromethyl)phenyl)-1H-1,2,3-triazol-4-yl)methoxy)pyrimidine

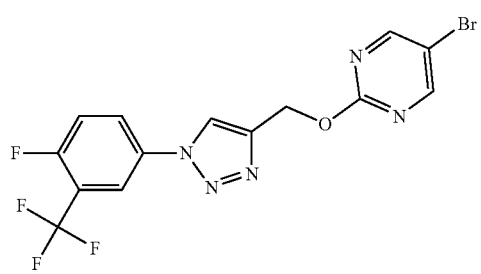 [SMILES: Fc1ccc(-n2cc(COc3ncc(Br)cn3)nn2)cc1C(F)(F)F]

The title compound was made analogous to Example 156, using (1-(4-fluoro-3-(trifluoromethyl)phenyl)-1H-1,2,3-triazol-4-yl)methanol (Intermediate 5) and 2,5-dibromopyrimidine. MS (ESI): mass calcd. for $C_{14}H_8BrF_4N_5O$, 418.3; m/z found, 419.1 [M+H]$^+$. $^1$H NMR (400 MHz, CDCl$_3$) b 8.67-8.61 (s, 2H), 8.20-8.15 (s, 1H), 8.07-8.02 (m, 1H), 8.02-7.96 (m, 1H), 7.48-7.40 (m, 1H), 5.72-5.65 (d, J=0.6 Hz, 2H).

Example 455: 2-((1-(4-Fluoro-3-(trifluoromethyl)phenyl)-1H-1,2,3-triazol-4-yl)methoxy)-5-(3-fluoroazetidin-1-yl)pyrimidine

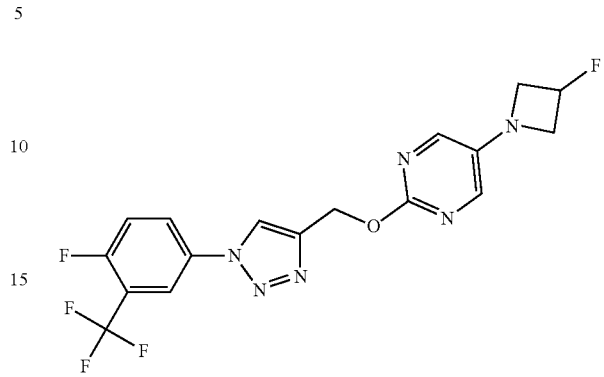

The title compound was made in an analogous manner to Example 187 using 5-bromo-2-((1-(4-fluoro-3-(trifluoromethyl)phenyl)-1H-1,2,3-triazol-4-yl)methoxy)pyrimidine (Example 454) and 3-fluoroazetidine hydrochloride. MS (ESI): mass calcd. for $C_{17}H_{13}F_5N_6O$, 412.3; m/z found, 413.1 [M+H]$^+$. $^1$H NMR (400 MHz, CDCl$_3$) δ 8.08-8.02 (s, 1H), 7.96-7.90 (m, 1H), 7.90-7.84 (m, 1H), 7.82-7.76 (s, 2H), 7.37-7.27 (m, 1H), 5.54-5.49 (m, 2H), 5.48-5.26 (m, 1H), 4.23-4.11 (m, 2H), 3.99-3.84 (m, 2H).

Example 456: 4-(2-((1-(4-Fluoro-3-(trifluoromethyl)phenyl)-1H-1,2,3-triazol-4-yl)methoxy)pyrimidin-5-yl)morpholine

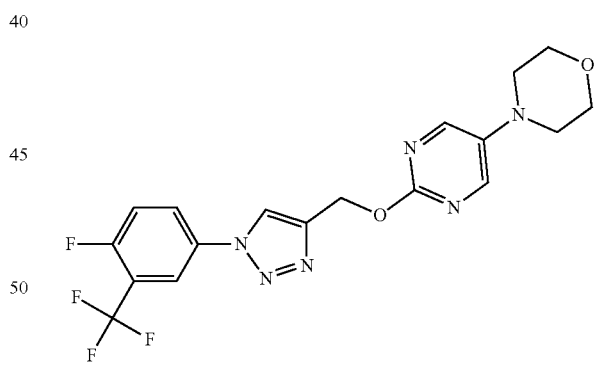

The title compound was made in an analogous manner to Example 187 using 5-bromo-2-((1-(4-fluoro-3-(trifluoromethyl)phenyl)-1H-1,2,3-triazol-4-yl)methoxy)pyrimidine (Example 454). MS (ESI): mass calcd. for $C_{18}H_{16}F_4N_6O_2$, 424.3; m/z found, 425.1 [M+H]$^+$. $^1$H NMR (400 MHz, CDCl$_3$) δ 8.19-8.13 (s, 2H), 8.07-8.04 (s, 1H), 7.95-7.91 (m, 1H), 7.91-7.85 (m, 1H), 7.36-7.29 (m, 1H), 5.57-5.51 (s, 2H), 3.85-3.76 (m, 4H), 3.08-3.00 (m, 4H).

Example 457: 5-(Azetidin-1-yl)-2-((1-(3-(trifluoromethyl)-4-fluorophenyl)-1H-1,2,3-triazol-4-yl)methoxy)-4-methylpyrimidine

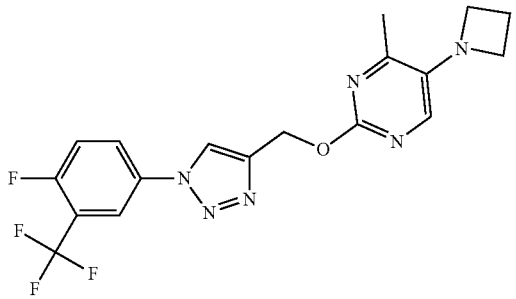 [SMILES: Cc1nc(OCc2cn(-c3ccc(F)c(C(F)(F)F)c3)nn2)ncc1N1CCC1]

The title compound was made in an analogous manner to Example 187 using 5-chloro-2-((1-(4-fluoro-3-(trifluoromethyl)phenyl)-1H-1,2,3-triazol-4-yl)methoxy)-4-methylpyrimidine (Example 444) and azetidine. MS (ESI): mass calcd. for $C_{18}H_{16}F_4N_6O$, 408.3; m/z found, 409.1 [M+H]$^+$. $^1$H NMR (400 MHz, CDCl$_3$) δ 8.18-8.15 (s, 1H), 8.06-8.02 (m, 1H), 8.01-7.96 (m, 1H), 7.76-7.72 (s, 1H), 7.47-7.40 (m, 1H), 5.66-5.59 (s, 2H), 3.96-3.88 (m, 4H), 2.44-2.42 (s, 3H), 2.42-2.36 (m, 2H).

Example 458: 2-((1-(3-(Trifluoromethyl)-4-fluorophenyl)-1H-1,2,3-triazol-4-yl)methoxy)-N-ethyl-4-methylpyrimidin-5-amine The title compound was made in an analogous manner to Example 187 using 5-chloro-2-((1-(4-fluoro-3-(trifluoromethyl)phenyl)-1H-1,2,3-triazol-4-yl)methoxy)-4-methylpyrimidine (Example 444) and ethylamine. MS (ESI): mass calcd. for $C_{17}H_{16}F_4N_6O$, 396.3; m/z found, 397.1 [M+H]$^+$. $^1$H NMR (400 MHz, CDCl$_3$) δ 8.19-8.15 (s, 1H), 8.07-8.02 (dd, J=5.8, 2.7 Hz, 1H), 8.01-7.95 (m, 1H), 7.86-7.84 (s, 1H), 7.47-7.39 (m, 1H), 5.65-5.59 (s, 2H), 3.26-3.17 (m, 2H), 3.16-3.08 (s, 1H), 2.42-2.38 (s, 3H), 1.39-1.33 (m, 3H).

Example 459: 2-((1-(3-(Trifluoromethyl)-4-fluorophenyl)-1H-1,2,3-triazol-4-yl)methoxy)-N-ethylpyrimidin-5-amine

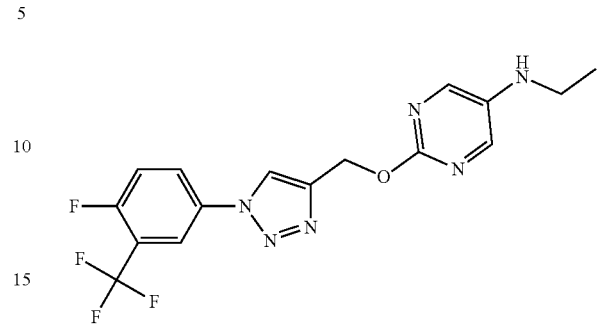

The title compound was made in an analogous manner to Example 187 using 5-bromo-2-((1-(4-fluoro-3-(trifluoromethyl)phenyl)-1H-1,2,3-triazol-4-yl)methoxy)pyrimidine (Example 454) and ethylamine. MS (ESI): mass calcd. for $C_{16}H_{14}F_4N_6O$, 382.3; m/z found, 383.1 [M+H]$^+$. $^1$H NMR (400 MHz, CDCl$_3$) δ 8.06-8.04 (s, 1H), 7.95-7.92 (m, 1H), 7.92-7.91 (s, 2H), 7.90-7.85 (m, 1H), 7.35-7.28 (m, 1H), 5.53-5.49 (s, 2H), 3.31-3.20 (s, 1H), 3.14-3.04 (m, 2H), 1.24-1.20 (m, 3H).

Example 460: 2-((1-(3-(Trifluoromethyl)-4-fluorophenyl)-1H-1,2,3-triazol-4-yl)methoxy)-5-(3-methoxyazetidin-1-yl)pyrimidine

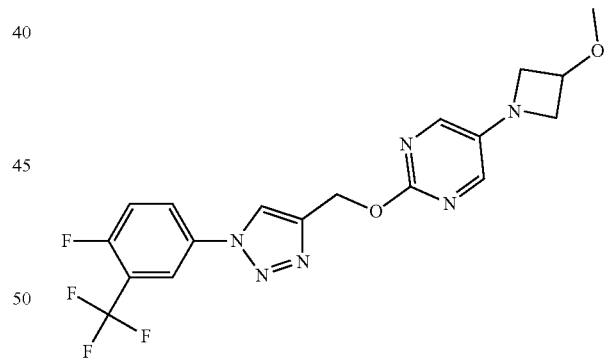

The title compound was made in an analogous manner to Example 187 using 5-bromo-2-((1-(4-fluoro-3-(trifluoromethyl)phenyl)-1H-1,2,3-triazol-4-yl)methoxy)pyrimidine (Example 454) and 3-methoxyazetidine hydrochloride. MS (ESI): mass calcd. for $C_{18}H_{16}F_4N_6O_2$, 424.3; m/z found, 425.1 [M+H]$^+$. $^1$H NMR (400 MHz, CDCl$_3$) δ 8.14-8.10 (s, 1H), 8.02-7.98 (m, 1H), 7.98-7.92 (m, 1H), 7.86-7.82 (s, 2H), 7.43-7.36 (m, 1H), 5.63-5.53 (s, 2H), 4.42-4.34 (m, 1H), 4.18-4.11 (m, 2H), 3.77-3.70 (m, 2H), 3.38-3.29 (s, 3H).

Example 461: 5-Chloro-2-[[1-[2-fluoro-3-(trifluoromethyl)phenyl]triazol-4-yl]methoxy]pyrimidine

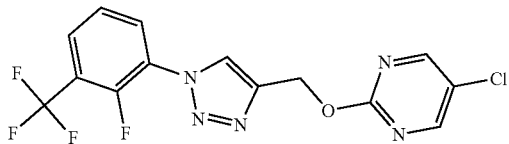 [SMILES: Fc1c(-n2cc(COc3ncc(Cl)cn3)nn2)cccc1C(F)(F)F]

The title compound was prepared in a manner analogous to Example 155 using 2,5-dichloropyrimidine and (1-(2-fluoro-3-(trifluoromethyl)phenyl)-1H-1,2,3-triazol-4-yl)methanol (Intermediate 28). MS (ESI): mass calcd. for $C_{14}H_8ClF_4N_5O$, 373.0; m/z found, 373.9 $[M+H]^+$. $^1H$ NMR (400 MHz, DMSO-$d_6$) δ 8.82 (d, J=2.1 Hz, 1H), 8.77 (s, 2H), 8.25-8.17 (m, 1H), 8.05-7.99 (m, 1H), 7.70-7.64 (m, 1H), 5.57 (s, 2H).

Example 462: 4-[[1-(4-Fluoro-3-methyl-phenyl)triazol-4-yl]methoxy]-6-methyl-pyrimidine

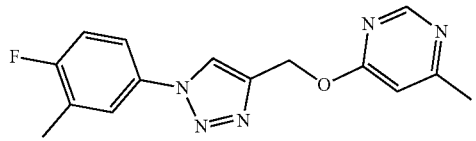 [SMILES: Cc1cc(OCc2cn(-c3ccc(F)c(C)c3)nn2)ncn1]

The title compound was prepared in a manner analogous to Example 155 using (1-(4-fluoro-3-methylphenyl)-1H-1,2,3-triazol-4-yl)methanol (Intermediate 40) and 4-chloro-6-methylpyrimidine. MS (ESI): mass calcd. for $C_{15}H_{14}FN_5O$, 299.1; m/z found, 300.0 $[M+H]^+$. $^1H$ NMR (400 MHz, DMSO-$d_6$) δ 8.85 (s, 1H), 8.72 (d, J=1.1 Hz, 1H), 7.90-7.86 (m, 1H), 7.78-7.72 (m, 1H), 7.38 (t, J=9.1 Hz, 1H), 6.88-6.86 (m, 1H), 5.55 (s, 2H), 2.39 (s, 3H), 2.34 (d, J=2.1 Hz, 3H).

Example 463: 5-Chloro-2-[[1-(3-fluoro-2-methylphenyl)triazol-4-yl]methoxy]pyrimidine

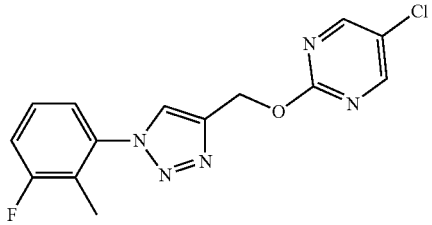 [SMILES: Cc1c(F)cccc1-n1cc(COc2ncc(Cl)cn2)nn1]

The title compound was prepared in a manner analogous to Example 1 using (1-(3-fluoro-2-methylphenyl)-1H-1,2,3-triazol-4-yl)methanol (Intermediate 49) and 2,5-dichloropyrimidine. MS (ESI): mass calcd. for $C_{14}H_{11}ClFN_5O$, 319.1; m/z found, 320.1 $[M+H]^+$. $^1H$ NMR (500 MHz, DMSO-$d_6$) δ 8.77 (s, 2H), 8.65 (s, 1H), 7.52-7.41 (m, 2H), 7.38-7.33 (m, 1H), 5.54 (s, 2H), 2.25-1.93 (m, 3H).

Example 464: 2-[[1-(3-Fluoro-2-methyl-phenyl)triazol-4-yl]methoxy]-5-methyl-pyrimidine

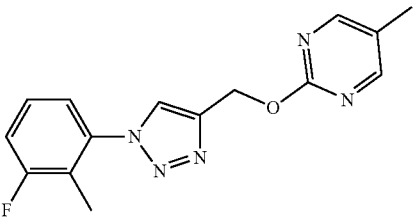 [SMILES: Cc1cnc(OCc2cn(-c3cccc(F)c3C)nn2)nc1]

The title compound was prepared in a manner analogous to Example 1 using (1-(3-fluoro-2-methylphenyl)-1H-1,2,3-triazol-4-yl)methanol (Intermediate 49) and 2-chloro-5-methylpyrimidine. MS (ESI): mass calcd. for $C_{15}H_{14}FN_5O$, 299.1; m/z found, 300.2 $[M+H]^+$. $^1H$ NMR (500 MHz, DMSO-$d_6$) δ 8.63 (s, 1H), 8.49 (d, J=0.8 Hz, 2H), 7.51-7.41 (m, 2H), 7.35 (dd, J=6.8, 1.9 Hz, 1H), 5.49 (s, 2H), 2.21 (d, J=0.8 Hz, 3H), 2.05 (d, J=2.2 Hz, 3H).

Example 465: 5-Fluoro-2-[[1-(3-fluoro-2-methylphenyl)triazol-4-yl]methoxy]-4-methyl-pyrimidine

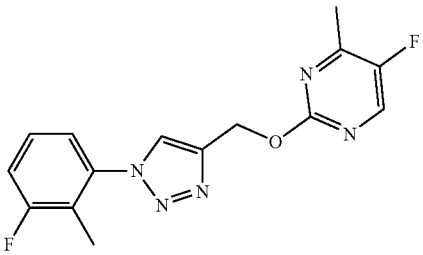 [SMILES: Cc1nc(OCc2cn(-c3cccc(F)c3C)nn2)ncc1F]

The title compound was prepared in a manner analogous to Example 1 using (1-(3-fluoro-2-methylphenyl)-1H-1,2,3-triazol-4-yl)methanol (Intermediate 49) and 2-chloro-5-fluoro-4-methylpyrimidine. MS (ESI): mass calcd. for $C_{15}H_{13}F_2N_5O$, 317.1; m/z found, 318.1 $[M+H]^+$. $^1H$ NMR (500 MHz, CD$_3$OD) δ 8.41-8.35 (m, 2H), 7.42 (td, J=8.2, 5.9 Hz, 1H), 7.32 (td, J=8.9, 8.3, 1.3 Hz, 1H), 7.26 (dd, J=7.9, 1.3 Hz, 1H), 5.58 (d, J=1.8 Hz, 2H), 2.48 (d, J=2.6 Hz, 3H), 2.09 (d, J=2.2 Hz, 3H).

Example 466: 2-[2-[[1-(3-Fluoro-2-methyl-phenyl)triazol-4-yl]methoxy]pyrimidin-5-yl]propan-2-ol

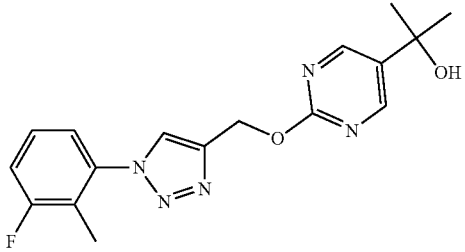 [SMILES: Cc1c(F)cccc1-n1cc(COc2ncc(C(C)(C)O)cn2)nn1]

The title compound was prepared in a manner analogous to Example 1 using (1-(3-fluoro-2-methylphenyl)-1H-1,2,3- triazol-4-yl)methanol (Intermediate 49) and 2-(2-chloropyrimidin-5-yl)propan-2-ol. MS (ESI): mass calcd. for C$_{17}$H$_{18}$FN$_5$O$_2$, 343.1; m/z found, 344.1 [M+H]$^+$. $^1$H NMR (500 MHz, DMSO-d$_6$) δ 8.69 (s, 2H), 8.65 (d, J=4.5 Hz, 1H), 7.53-7.42 (m, 2H), 7.36 (d, J=7.4 Hz, 1H), 5.52 (s, 2H), 5.32 (s, 1H), 2.07 (s, 3H), 1.47 (d, J=6.6 Hz, 6H).

Example 467: 2-[[1-(2-Fluoro-3-methyl-phenyl)triazol-4-yl]methoxy]-5-methyl-pyrimidine

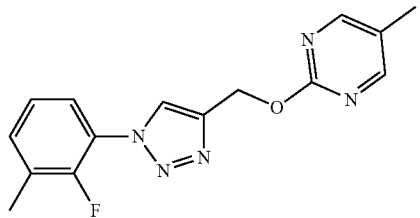 [SMILES: Cc1cnc(OCc2cn(-c3cccc(C)c3F)nn2)nc1]

The title compound was prepared in a manner analogous to Example 1 using (1-(2-fluoro-3-methylphenyl)-1H-1,2,3-triazol-4-yl)methanol (Intermediate 50) and 2-chloro-5-methylpyrimidine. MS (ESI): mass calcd. for C$_{15}$H$_{14}$FN$_5$O, 299.1; m/z found, 300.1[M+H]$^+$. $^1$H NMR (500 MHz, DMSO-d$_6$) δ 8.66 (d, J=2.0 Hz, 1H), 8.49 (t, J=0.7 Hz, 2H), 7.68-7.60 (m, 1H), 7.55-7.45 (m, 1H), 7.33 (t, J=7.8 Hz, 1H), 5.50 (s, 2H), 2.36 (d, J=2.3 Hz, 3H), 2.21 (t, J=0.7 Hz, 3H).

Example 468: 5-Chloro-2-[[1-(2-fluoro-3-methyl-phenyl)triazol-4-yl]methoxy]pyrimidine

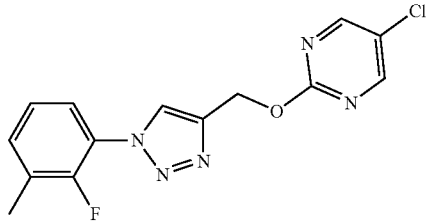 [SMILES: Cc1cccc(-n2cc(COc3ncc(Cl)cn3)nn2)c1F]

The title compound was prepared in a manner analogous to Example 1 using (1-(2-fluoro-3-methylphenyl)-1H-1,2,3-triazol-4-yl)methanol (Intermediate 50) and 2,5-dichloropyrimidine. MS (ESI): mass calcd. for C$_{14}$H$_{11}$ClFN$_5$O, 319.1; m/z found, 320.1 [M+H]$^+$. $^1$H NMR (500 MHz, DMSO-d$_6$) δ 8.77 (s, 2H), 8.69 (d, J=2.1 Hz, 1H), 7.63 (td, J=7.6, 1.8 Hz, 1H), 7.57-7.46 (m, 1H), 7.33 (td, J=7.8, 1.0 Hz, 1H), 5.55 (s, 2H), 2.36 (d, J=2.2 Hz, 3H).

Example 469: 2-[[1-(2-Fluoro-3-methyl-phenyl)triazol-4-yl]methoxy]-5-(trifluoromethyl)pyrimidine

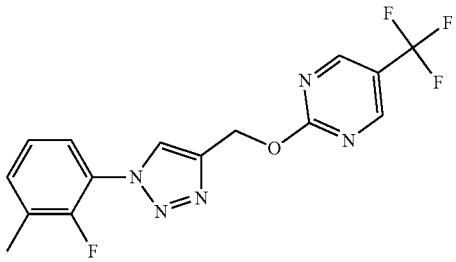 [SMILES: Cc1cccc(-n2cc(COc3ncc(C(F)(F)F)cn3)nn2)c1F]

The title compound was prepared in a manner analogous to Example 1 using (1-(2-fluoro-3-methylphenyl)-1H-1,2,3-triazol-4-yl)methanol (Intermediate 50) and 2-chloro-5-(trifluoromethyl)pyrimidine. MS (ESI): mass calcd. for C$_{15}$H$_{11}$F$_4$N$_5$O, 353.1; m/z found, 354.0 [M+H]$^+$. $^1$H NMR (500 MHz, DMSO-d$_6$) δ 9.12 (q, J=0.8 Hz, 2H), 8.73 (d, J=2.1 Hz, 1H), 7.68-7.60 (m, 1H), 7.51 (tdd, J=7.0, 1.8, 0.9 Hz, 1H), 7.33 (td, J=7.8, 1.0 Hz, 1H), 5.66 (s, 2H), 2.36 (d, J=2.1 Hz, 3H).

Example 470: 5-Chloro-2-[[1-(2-fluoro-3-methyl-phenyl)triazol-4-yl]methoxy]-4-methyl-pyrimidine

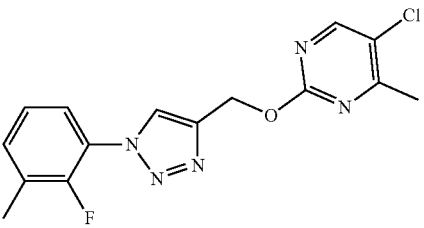 [SMILES: Cc1cccc(-n2cc(COc3ncc(Cl)c(C)n3)nn2)c1F]

The title compound was prepared in a manner analogous to Example 1 using (1-(2-fluoro-3-methylphenyl)-1H-1,2,3-triazol-4-yl)methanol (Intermediate 50) and 2,5-dichloro-4-methylpyrimidine. MS (ESI): mass calcd. for C$_{15}$H$_{13}$ClFN$_5$O, 333.1; m/z found, 334.1 [M+H]$^+$. $^1$H NMR (500 MHz, DMSO-d$_6$) δ 8.68 (d, J=2.1 Hz, 1H), 8.62 (d, J=1.5 Hz, 1H), 7.63 (t, J=7.5 Hz, 1H), 7.51 (t, J=7.3 Hz, 1H), 7.33 (t, J=7.8 Hz, 1H), 5.53 (d, J=1.5 Hz, 2H), 2.50 (m, 3H), 2.36 (d, J=2.1 Hz, 3H).

Example 471: 5-(Difluoromethoxy)-2-[[1-(2-fluoro-3-methyl-phenyl)triazol-4-yl]methoxy]pyrimidine

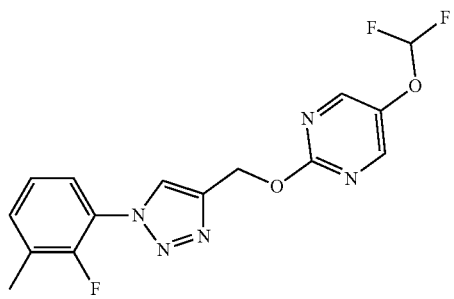 [SMILES: Cc1cccc(-n2cc(COc3ncc(OC(F)F)cn3)nn2)c1F]

The title compound was prepared in a manner analogous to Example 1 using (1-(2-fluoro-3-methylphenyl)-1H-1,2,3-triazol-4-yl)methanol (Intermediate 50) and 2-chloro-5-(difluoromethoxy)pyrimidine. MS (ESI): mass calcd. for $C_{15}H_{12}F_3N_5O_2$, 351.1; m/z found, 352.1 [M+H]$^+$. $^1$H NMR (400 MHz, DMSO-d$_6$) δ 8.70 (d, J=2.1 Hz, 1H), 8.65 (s, 2H), 7.68-7.59 (m, 1H), 7.55-7.47 (m, 1H), 7.45-7.03 (m, 2H), 5.54 (s, 2H), 2.36 (d, J=2.2 Hz, 3H).

Example 472: 2-[[1-(4-Fluoro-3-methyl-phenyl)triazol-4-yl]methoxy]pyrimidin-4-amine

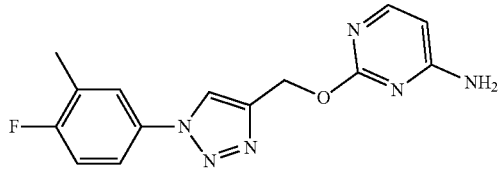 [SMILES: Cc1cc(-n2cc(COc3nccc(N)n3)nn2)ccc1F]

The title compound was prepared in a manner analogous to Example 1 using (1-(4-fluoro-3-methylphenyl)-1H-1,2,3-triazol-4-yl)methanol (Intermediate 40) and 2-chloropyrimidin-4-amine. MS (ESI): mass calcd. for $C_{14}H_{13}FN_6O$, 300.1; m/z found, 301.1 [M+H]$^+$. $^1$H NMR (500 MHz, DMSO-d$_6$) δ 8.82 (s, 1H), 7.89 (t, J=6.4 Hz, 2H), 7.75 (dt, J=7.6, 3.4 Hz, 1H), 7.38 (t, J=9.1 Hz, 1H), 6.92 (s, 2H), 6.11 (d, J=5.7 Hz, 1H), 5.35 (s, 2H), 2.33 (d, J=2.0 Hz, 3H).

Example 473: 2-[[1-(4-Fluoro-3-methyl-phenyl)triazol-4-yl]methoxy]pyrimidine

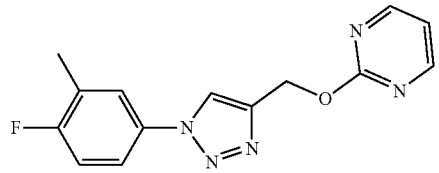 [SMILES: Cc1cc(-n2cc(COc3ncccn3)nn2)ccc1F]

The title compound was prepared in a manner analogous to Example 1 using (1-(4-fluoro-3-methylphenyl)-1H-1,2,3-triazol-4-yl)methanol and 2-chloropyrimidine. MS (ESI): mass calcd. for $C_{14}H_{12}FN_5O$, 285.1; m/z found, 286.1 [M+H]$^+$. $^1$H NMR (600 MHz, DMSO-d$_6$) δ 8.87 (s, 1H), 8.67 (d, J=4.8 Hz, 2H), 7.90 (ddd, J=6.7, 2.8, 0.9 Hz, 1H), 7.81-7.71 (m, 1H), 7.38 (t, J=9.1 Hz, 1H), 7.20 (t, J=4.8 Hz, 1H), 5.52 (s, 2H), 2.33 (d, J=2.0 Hz, 3H).

Example 474: 5-Fluoro-2-[[1-(4-fluoro-3-methyl-phenyl)triazol-4-yl]methoxy]pyrimidine

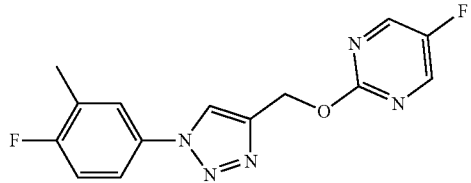 [SMILES: Cc1cc(-n2cc(COc3ncc(F)cn3)nn2)ccc1F]

The title compound was prepared in a manner analogous to Example 1 using (1-(4-fluoro-3-methylphenyl)-1H-1,2,3-triazol-4-yl)methanol (Intermediate 40) and 2-chloro-5-fluoropyrimidine. MS (ESI): mass calcd. for $C_{14}H_{11}F_2N_5O$, 303.1; m/z found, 304.1 [M+H]$^+$. $^1$H NMR (600 MHz, DMSO-d$_6$) δ 8.86 (s, 1H), 8.75 (d, J=0.6 Hz, 2H), 7.93-7.85 (m, 1H), 7.76 (dt, J=7.9, 3.6 Hz, 1H), 7.39 (t, J=9.1 Hz, 1H), 5.51 (s, 2H), 2.33 (d, J=2.1 Hz, 3H).

Example 475: 2-[[1-(4-Fluoro-3-methyl-phenyl)triazol-4-yl]methoxy]-5-methoxy-pyrimidine

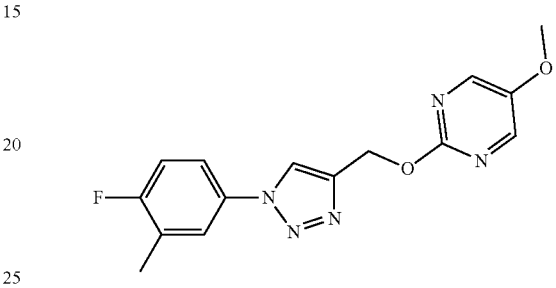

The title compound was prepared in a manner analogous to Example 1 using (1-(4-fluoro-3-methylphenyl)-1H-1,2,3-triazol-4-yl)methanol (Intermediate 40) and 2-chloro-5-methoxypyrimidine. MS (ESI): mass calcd. for $C_{15}H_{14}FN_5O_2$, 315.1; m/z found, 316.1 [M+H]$^+$. $^1$H NMR (600 MHz, DMSO-d$_6$) δ 8.84 (s, 1H), 8.41 (s, 2H), 7.89 (dd, J=6.6, 2.7 Hz, 1H), 7.76 (dt, J=8.4, 3.6 Hz, 1H), 7.38 (t, J=9.1 Hz, 1H), 5.45 (s, 2H), 3.86 (s, 3H), 2.33 (d, J=2.1 Hz, 3H).

Example 476: 5-Chloro-2-[[1-(4-fluoro-3-methyl-phenyl)triazol-4-yl]methoxy]pyrimidine

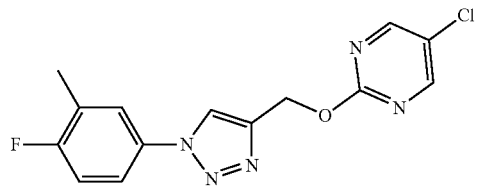 [SMILES: Cc1cc(-n2cc(COc3ncc(Cl)cn3)nn2)ccc1F]

The title compound was prepared in a manner analogous to Example 1 using (1-(4-fluoro-3-methylphenyl)-1H-1,2,3-triazol-4-yl)methanol (Intermediate 40) and 2,5-dichloropyrimidine. MS (ESI): mass calcd. for $C_{14}H_{11}ClFN_5O$, 319.1; m/z found, 320.0 [M+H]$^+$. $^1$H NMR (600 MHz, DMSO-d$_6$) δ 8.86 (s, 1H), 8.77 (s, 2H), 7.95-7.86 (m, 1H), 7.76 (dt, J=7.5, 3.6 Hz, 1H), 7.39 (t, J=9.1 Hz, 1H), 5.53 (s, 2H), 2.33 (d, J=2.0 Hz, 3H)

Example 477: 2-[[1-(4-Fluoro-3-methyl-phenyl)triazol-4-yl]methoxy]-5-methyl-pyrimidine

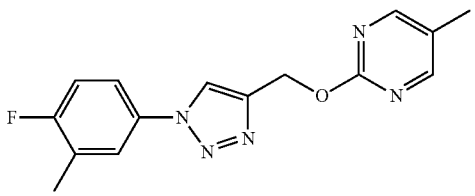 [SMILES: Cc1cnc(OCc2cn(-c3ccc(F)c(C)c3)nn2)nc1]

The title compound was prepared in a manner analogous to Example 1 using (1-(4-fluoro-3-methylphenyl)-1H-1,2,3-triazol-4-yl)methanol (Intermediate 40) and 2-chloro-5-methylpyrimidine. MS (ESI): mass calcd. for $C_{15}H_{14}FN_5O$, 299.1; m/z found, 300.2 [M+H]$^+$. $^1$H NMR (600 MHz, DMSO-d$_6$) δ 8.85 (s, 1H), 8.49 (d, J=0.8 Hz, 2H), 7.89 (ddd, J=6.6, 2.8, 0.9 Hz, 1H), 7.83-7.71 (m, 1H), 7.38 (t, J=9.1 Hz, 1H), 5.48 (s, 2H), 2.33 (d, J=2.0 Hz, 3H), 2.21 (t, J=0.8 Hz, 3H).

Example 478: 5-Ethyl-2-[[1-(4-fluoro-3-methyl-phenyl)triazol-4-yl]methoxy]pyrimidine

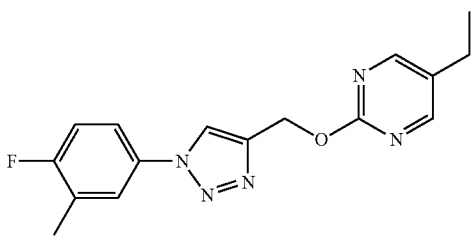 [SMILES: CCc1cnc(OCc2cn(-c3ccc(F)c(C)c3)nn2)nc1]

The title compound was prepared in a manner analogous to Example 1 using (1-(4-fluoro-3-methylphenyl)-1H-1,2,3-triazol-4-yl)methanol (Intermediate 40) and 2-chloro-5-ethylpyrimidine. MS (ESI): mass calcd. for $C_{16}H_{16}FN_5O$, 313.1; m/z found, 314.1 [M+H]$^+$. $^1$H NMR (600 MHz, DMSO-d$_6$) δ 8.86 (s, 1H), 8.53 (s, 2H), 7.90 (dd, J=6.8, 2.7 Hz, 1H), 7.76 (dt, J=8.2, 3.6 Hz, 1H), 7.38 (t, J=9.1 Hz, 1H), 5.49 (s, 2H), 2.57 (q, J=7.6 Hz, 2H), 2.33 (d, J=2.0 Hz, 3H), 1.19 (t, J=7.6 Hz, 3H).

Example 479: 2-[[1-(4-Fluoro-3-methyl-phenyl)triazol-4-yl]methoxy]-4-(methoxymethyl)pyrimidine

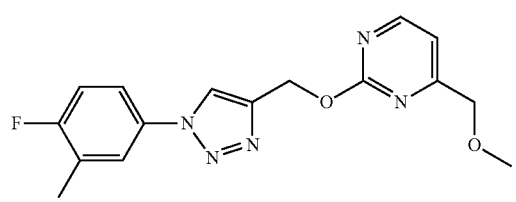 [SMILES: COCc1ccnc(OCc2cn(-c3ccc(F)c(C)c3)nn2)n1]

The title compound was prepared in a manner analogous to Example 1 using (1-(4-fluoro-3-methylphenyl)-1H-1,2,3-triazol-4-yl)methanol (Intermediate 40) and 2-chloro-4-(methoxymethyl)pyrimidine. MS (ESI): mass calcd. for $C_{16}H_{16}FN_5O_2$, 329.1; m/z found, 330.0[M+H]$^+$. $^1$H NMR (400 MHz, DMSO-d$_6$) δ 8.85 (s, 1H), 8.64 (d, J=5.0 Hz, 1H), 7.88 (ddd, J=6.5, 2.7, 0.9 Hz, 1H), 7.75 (ddd, J=8.9, 4.3, 3.0 Hz, 1H), 7.38 (t, J=9.1 Hz, 1H), 7.24-7.12 (m, 1H), 5.51 (s, 2H), 4.47 (d, J=0.7 Hz, 2H), 3.40 (s, 3H), 2.33 (d, J=2.1 Hz, 3H).

Example 480: 2-[[1-(4-Fluoro-3-methyl-phenyl)triazol-4-yl]methoxy]-4,5-dimethyl-pyrimidine

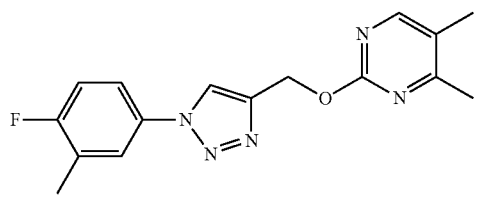 [SMILES: Cc1cc(-n2cc(COc3ncc(C)c(C)n3)nn2)ccc1F]

The title compound was prepared in a manner analogous to Example 1 using (1-(4-fluoro-3-methylphenyl)-1H-1,2,3-triazol-4-yl)methanol (Intermediate 40) and 2-chloro-4,5-dimethylpyrimidine. MS (ESI): mass calcd. for $C_{16}H_{16}FN_5O$, 313.1; m/z found, 314.1 [M+H]$^+$. $^1$H NMR (400 MHz, DMSO-d$_6$) δ 8.82 (s, 1H), 8.30 (s, 1H), 7.89 (dd, J=6.7, 2.9 Hz, 1H), 7.75 (dt, J=7.5, 3.5 Hz, 1H), 7.38 (t, J=9.1 Hz, 1H), 5.46 (s, 2H), 2.38 (s, 3H), 2.33 (d, J=2.0 Hz, 3H), 2.16 (s, 3H).

Example 481: 5-Fluoro-2-[[1-(4-fluoro-3-methyl-phenyl)triazol-4-yl]methoxy]-4-methyl-pyrimidine

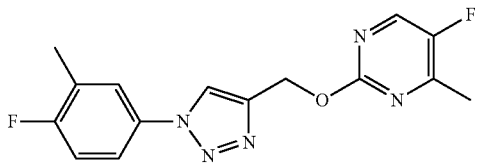 [SMILES: Cc1cc(-n2cc(COc3ncc(F)c(C)n3)nn2)ccc1F]

The title compound was prepared in a manner analogous to Example 1 using (1-(4-fluoro-3-methylphenyl)-1H-1,2,3-triazol-4-yl)methanol (Intermediate 40) and 2-chloro-5-fluoro-4-methylpyrimidine. MS (ESI): mass calcd. for $C_{15}H_{13}F_2N_5O$, 317.1; m/z found, 318.0 [M+H]$^+$. $^1$H NMR (400 MHz, DMSO-d$_6$) δ 8.84 (s, 1H), 8.56 (d, J=1.5 Hz, 1H), 7.88 (dd, J=6.8, 2.9 Hz, 1H), 7.75 (dt, J=8.1, 3.8 Hz, 1H), 7.38 (t, J=9.1 Hz, 1H), 5.48 (s, 2H), 2.44 (d, J=2.5 Hz, 3H), 2.33 (d, J=2.0 Hz, 3H).

Example 482: 5-Chloro-2-[[1-(4-fluoro-3-methyl-phenyl)triazol-4-yl]methoxy]-4-methyl-pyrimidine

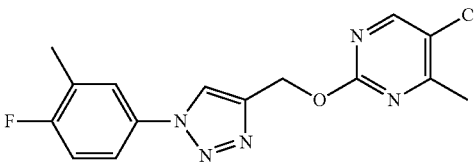

The title compound was prepared in a manner analogous to Example 1 using (1-(4-fluoro-3-methylphenyl)-1H-1,2,3- triazol-4-yl)methanol (Intermediate 40) and 2,5-dichloro-4-methylpyrimidine. MS (ESI): mass calcd. for $C_{15}H_{13}ClFN_5O$, 333.1; m/z found, 334.1 [M+H]$^+$. $^1$H NMR (400 MHz, DMSO-d$_6$) δ 8.84 (s, 1H), 8.62 (s, 1H), 7.88 (dd, J=6.8, 2.8 Hz, 1H), 7.75 (dt, J=8.9, 3.6 Hz, 1H), 7.38 (t, J=9.1 Hz, 1H), 5.51 (s, 2H), 2.51 (m, J=1.3 Hz, 3H), 2.33 (d, J=2.2 Hz, 3H).

Example 483: 5-(2-Fluoroethoxy)-2-[[1-(4-fluoro-3-methyl-phenyl)triazol-4-yl]methoxy]pyrimidine

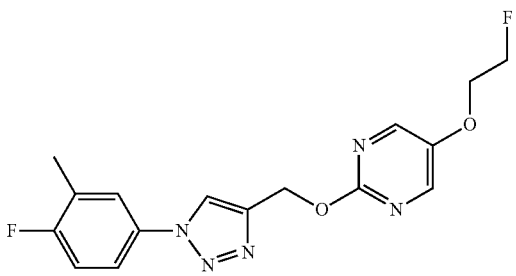 [SMILES: Cc1cc(-n2cc(COc3ncc(OCCF)cn3)nn2)ccc1F]

The title compound was prepared in a manner analogous to Example 192, Steps A-B, using (1-(4-fluoro-3-methyl-phenyl)-1H-1,2,3-triazol-4-yl)methanol (Intermediate 40) in Step B. MS (ESI): mass calcd. for $C_{16}H_{15}F_2N_5O_2$, 347.1; m/z found, 348.2 [M+H]$^+$. $^1$H NMR (400 MHz, CDCl$_3$) δ 8.29 (s, 2H), 8.05 (s, 1H), 7.64-7.53 (m, 1H), 7.51-7.42 (m, 1H), 7.14 (t, J=8.8 Hz, 1H), 5.60 (d, J=0.8 Hz, 2H), 4.88-4.76 (m, 1H), 4.76-4.65 (m, 1H), 4.36-4.27 (m, 1H), 4.27-4.18 (m, 1H), 2.36 (d, J=2.0 Hz, 3H).

Example 484: 2-[[1-(2-Fluoro-5-methyl-phenyl)triazol-4-yl]methoxy]-5-methyl-pyrimidine

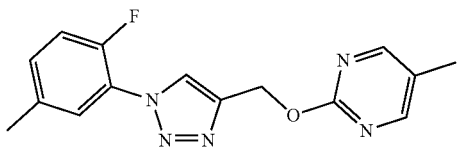

The title compound was prepared in a manner analogous to Example 155 using (1-(2-fluoro-5-methylphenyl)-1H-1,2,3-triazol-4-yl)methanol (Intermediate 29) and 2-chloro-5-methylpyrimidine. MS (ESI): mass calcd. for $C_{15}H_{14}FN_5O$, 299.1; m/z found, 300.0 [M+H]$^+$. $^1$H NMR (500 MHz, DMSO-d$_6$) δ 8.67 (d, J=2.0 Hz, 1H), 8.51-8.47 (m, 2H), 7.68-7.64 (m, 1H), 7.48-7.38 (m, 2H), 5.49 (s, 2H), 2.38 (s, 3H), 2.21 (t, J=0.8 Hz, 3H).

Example 485: 5-Chloro-2-[[1-(2-fluoro-5-methyl-phenyl)triazol-4-yl]methoxy]-4-methyl-pyrimidine

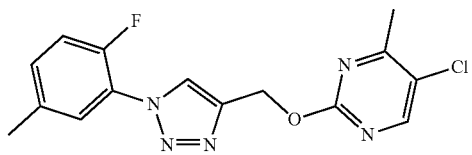 [SMILES: Cc1ccc(F)c(-n2cc(COc3ncc(Cl)c(C)n3)nn2)c1]

The title compound was prepared in a manner analogous to Example 155 using (1-(2-fluoro-5-methylphenyl)-1H-1,2,3-triazol-4-yl)methanol (Intermediate 29) and 2,5-dichloro-4-methylpyrimidine. MS (ESI): mass calcd. for $C_{15}H_{13}ClFN_5O$, 333.1; m/z found, 333.9 [M+H]$^+$. $^1$H NMR (500 MHz, DMSO-d6) δ 8.69 (d, J=2.0 Hz, 1H), 8.62 (s, 1H), 7.68-7.64 (m, 1H), 7.48-7.39 (m, 2H), 5.52 (s, 2H), 2.38 (s, 3H).

Example 486: 5-Fluoro-2-[[1-(2-fluoro-5-methyl-phenyl)triazol-4-yl]methoxy]-4-methyl-pyrimidine

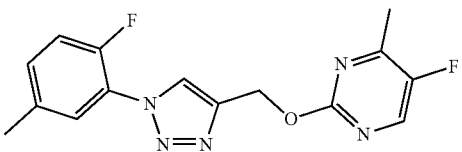 [SMILES: Cc1ccc(F)c(-n2cc(COc3ncc(F)c(C)n3)nn2)c1]

The title compound was prepared in a manner analogous to Example 155 using (1-(2-fluoro-5-methylphenyl)-1H-1,2,3-triazol-4-yl)methanol (Intermediate 29) and 2-chloro-5-fluoro-4-methylpyrimidine. MS (ESI): mass calcd. for $C_{15}H_{13}F_2N_5O$, 317.1; m/z found, 317.9 [M+H]$^+$. $^1$H NMR (500 MHz, DMSO-d$_6$) δ 8.68 (d, J=2.0 Hz, 1H), 8.57 (d, J=1.5 Hz, 1H), 7.68-7.64 (m, 1H), 7.48-7.38 (m, 2H), 5.49 (s, 2H), 2.44 (d, J=2.5 Hz, 3H), 2.38 (s, 3H).

Example 487: 5-Fluoro-2-[[1-(4-fluoro-2-methyl-phenyl)triazol-4-yl]methoxy]pyrimidine

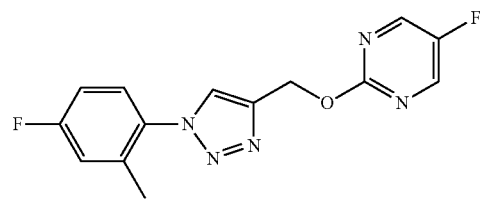 [SMILES: Cc1cc(F)ccc1-n1cc(COc2ncc(F)cn2)nn1]

The title compound was prepared in a manner analogous to Example 1 using (1-(4-fluoro-2-methylphenyl)-1H-1,2,3-triazol-4-yl)methanol (Intermediate 37) and 2-chloro-5-fluoropyrimidine. MS (ESI): mass calcd. for $C_{14}H_{11}F_2N_5O$, 303.1; m/z found, 304.1 [M+H]$^+$. $^1$H NMR (500 MHz, CD$_3$OD) δ 8.56 (d, J=0.6 Hz, 2H), 8.35 (d, J=0.5 Hz, 1H), 7.42 (dd, J=8.7, 5.2 Hz, 1H), 7.22 (ddd, J=9.3, 2.9, 0.9 Hz, 1H), 7.14 (dddd, J=8.7, 8.0, 2.9, 0.7 Hz, 1H), 5.60 (d, J=0.5 Hz, 2H), 2.16 (s, 3H).

Example 488: 2-[[1-(4-Fluoro-2-methyl-phenyl)triazol-4-yl]methoxy]-5-methoxy-pyrimidine

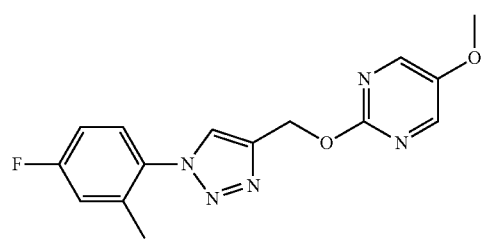 [SMILES: COc1cnc(OCc2cn(-c3ccc(F)cc3C)nn2)nc1]

The title compound was prepared in a manner analogous to Example 1 using (1-(4-fluoro-2-methylphenyl)-1H-1,2,3-triazol-4-yl)methanol (Intermediate 37) and 2-chloro-5-methoxypyrimidine. MS (ESI): mass calcd. for $C_{15}H_{14}FN_5O_2$, 315.1; m/z found, 316.1 [M+H]$^+$. $^1$H NMR (400 MHz, DMSO-d$_6$) δ 8.56 (s, 1H), 8.41 (s, 2H), 7.51 (dd, J=8.7, 5.4 Hz, 1H), 7.39 (dd, J=9.6, 2.9 Hz, 1H), 7.26 (td, J=8.5, 2.9 Hz, 1H), 5.46 (s, 2H), 3.86 (s, 3H), 2.13 (s, 3H).

Example 489: 5-Chloro-2-[[1-(4-fluoro-2-methyl-phenyl)triazol-4-yl]methoxy]pyrimidine

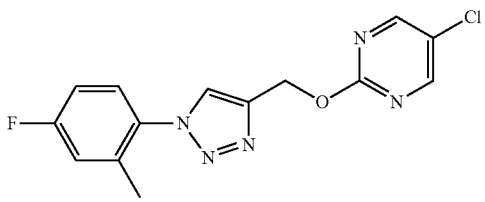 [SMILES: Cc1cc(F)ccc1-n1cc(COc2ncc(Cl)cn2)nn1]

The title compound was prepared in a manner analogous to Example 1 using (1-(4-fluoro-2-methylphenyl)-1H-1,2,3-triazol-4-yl)methanol (Intermediate 37) and 2,5-dichloropyrimidine. MS (ESI): mass calcd. for $C_{14}H_{11}ClFN_5O$, 319.1; m/z found, 320.0 [M+H]$^+$.

Example 490: 2-[[1-(4-Fluoro-2-methyl-phenyl)triazol-4-yl]methoxy]-5-methyl-pyrimidine

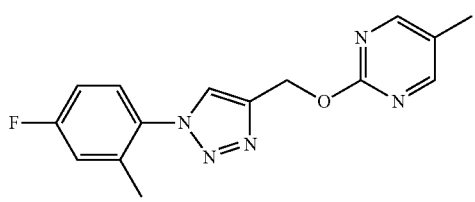 [SMILES: Cc1cnc(OCc2cn(-c3ccc(F)cc3C)nn2)nc1]

The title compound was prepared in a manner analogous to Example 1 using (1-(4-fluoro-2-methylphenyl)-1H-1,2,3-triazol-4-yl)methanol (Intermediate 37) and 2-chloro-5-methylpyrimidine. MS (ESI): mass calcd. for $C_{15}H_{14}FN_5O$, 299.1; m/z found, 300.2[M+H]$^+$. $^1$H NMR (500 MHz, CD$_3$OD) δ 8.43 (d, J=0.9 Hz, 2H), 8.34 (s, 1H), 7.41 (dd, J=8.7, 5.2 Hz, 1H), 7.20 (dd, J=9.5, 3.1 Hz, 1H), 7.12 (td, J=8.4, 2.9 Hz, 1H), 5.58 (s, 2H), 2.25 (d, J=0.8 Hz, 3H), 2.15 (s, 3H).

Example 491: 5-Ethyl-2-[[1-(4-fluoro-2-methyl-phenyl)triazol-4-yl]methoxy]pyrimidine

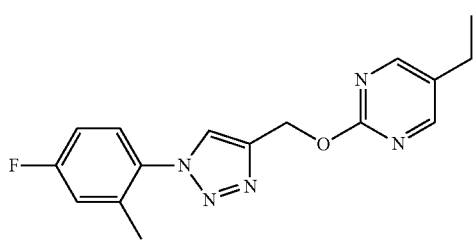 [SMILES: CCc1cnc(OCc2cn(-c3ccc(F)cc3C)nn2)nc1]

The title compound was prepared in a manner analogous to Example 1 using (1-(4-fluoro-2-methylphenyl)-1H-1,2,3-triazol-4-yl)methanol (Intermediate 37) and 2-chloro-5-ethylpyrimidine. MS (ESI): mass calcd. for $C_{16}H_{16}FN_5O$, 313.1; m/z found, 314.1 [M+H]$^+$. $^1$H NMR (500 MHz, CD$_3$OD) δ 8.45 (d, J=0.7 Hz, 2H), 8.35 (s, 1H), 7.41 (dd, J=8.7, 5.2 Hz, 1H), 7.20 (ddd, J=9.3, 2.9, 0.8 Hz, 1H), 7.12 (dddd, J=8.8, 8.0, 2.9, 0.7 Hz, 1H), 5.68-5.47 (m, 2H), 2.62 (q, J=7.6 Hz, 2H), 2.15 (s, 3H), 1.24 (t, J=7.6 Hz, 3H).

Example 492: 2-[[1-[3-(Difluoromethoxy)-4-fluorophenyl]triazol-4-yl]methoxy]-5-fluoro-pyrimidine

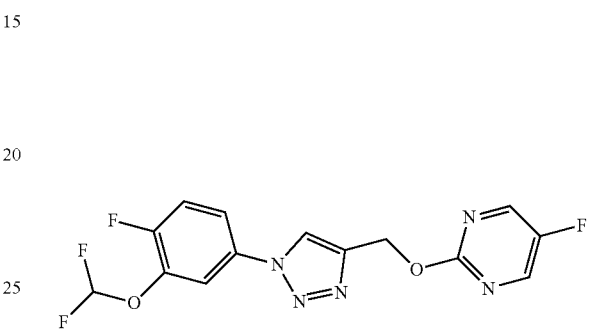

The title compound was prepared in a manner analogous to Example 155 using (1-(3-(difluoromethoxy)-4-fluorophenyl)-1H-1,2,3-triazol-4-yl)methanol (Intermediate 6) and 2-chloro-5-fluoropyrimidine. MS (ESI): mass calcd. for $C_{14}H_9F_4N_5O_2$, 355.1; m/z found, 355.9 [M+H]$^+$. $^1$H NMR (500 MHz, DMSO-d$_6$) δ 8.96 (s, 1H), 8.76-8.74 (m, 2H), 8.00 (dd, J=6.9, 2.6 Hz, 1H), 7.87 (ddd, J=9.0, 4.0, 2.7 Hz, 1H), 7.68 (dd, J=10.2, 9.0 Hz, 1H), 7.39 (t, J=72.8 Hz, 1H), 5.52 (s, 2H).

Example 493: 2-[[1-[3-(Difluoromethoxy)-4-fluorophenyl]triazol-4-yl]methoxy]-5-fluoro-4-methyl-pyrimidine

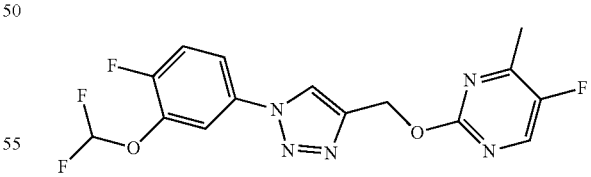

The title compound was prepared in a manner analogous to Example 155 using (1-(3-(difluoromethoxy)-4-fluorophenyl)-1H-1,2,3-triazol-4-yl)methanol (Intermediate 6) and 2-chloro-5-fluoro-4-methylpyrimidine. MS (ESI): mass calcd. for $C_{15}H_{11}F_4N_5O_2$, 369.1; m/z found, 369.9 [M+H]$^+$. $^1$H NMR (500 MHz, DMSO-d$_6$) δ 8.94 (s, 1H), 8.57 (d, J=1.5 Hz, 1H), 8.00 (dd, J=6.9, 2.6 Hz, 1H), 7.87 (ddd, J=9.0, 3.9, 2.7 Hz, 1H), 7.68 (dd, J=10.2, 9.0 Hz, 1H), 7.39 (t, J=72.8 Hz, 1H), 5.50 (s, 2H), 2.44 (d, J=2.6 Hz, 3H).

Example 494: 5-Bromo-2-[[1-[3-(difluoromethoxy)-4-fluoro-phenyl]triazol-4-yl]methoxy]pyrimidine

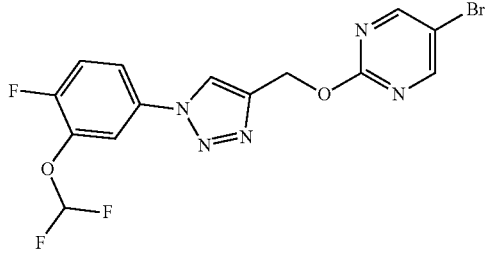 [SMILES: Fc1ccc(-n2cc(COc3ncc(Br)cn3)nn2)cc1OC(F)F]

The title compound was prepared in a manner analogous to Example 155 using (1-(3-(difluoromethoxy)-4-fluorophenyl)-1H-1,2,3-triazol-4-yl)methanol (Intermediate 6) and 5-bromo-2-chloropyrimidine. MS (ESI): mass calcd. for $C_{14}H_9BrF_3N_5O_2$, 415.0; m/z found, 416 [M+H]+. $^1$H NMR (300 MHz, DMSO-do δ 8.95 (s, 1H), 8.81 (s, 2H), 7.99 (dd, J=6.8, 2.1 Hz, 1H), 7.92-7.82 (m, 1H), 7.68 (t, J=9.6 Hz, 1H), 7.39 (t, J=72.8 Hz, 1H), 5.54 (s, 2H).

Example 495: 2-f[[1-[3-(Difluoromethoxy)-4-fluoro-phenyl]triazol-4-yl]methoxy]-4-ethyl-pyrimidine

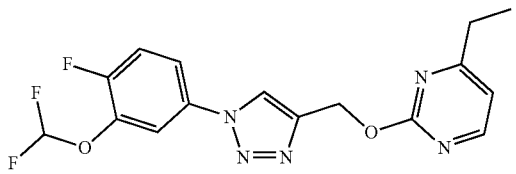 [SMILES: CCc1ccnc(OCc2cn(-c3ccc(F)c(OC(F)F)c3)nn2)n1]

The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-ethylpyrimidine. MS (ESI): mass calcd. for $C_{16}H_{14}F_3N_5O_2$, 365.1; m/z found, 365.9 [M+H]+. $^1$H NMR (400 MHz, DMSO-d$_6$) δ 8.95 (s, 1H), 8.51 (d, J=5.0 Hz, 1H), 8.00 (dd, J=6.9, 2.6 Hz, 1H), 7.88 (ddd, J=9.0, 4.0, 2.6 Hz, 1H), 7.68 (dd, J=10.2, 9.0 Hz, 1H), 7.39 (t, J=72.8 Hz, 1H), 7.08 (d, J=5.0 Hz, 1H), 5.52 (s, 2H), 2.71 (q, J=7.6 Hz, 2H), 1.22 (t, J=7.6 Hz, 3H).

Example 496: 2-[[1-[3-(Difluoromethoxy)-4-fluoro-phenyl]triazol-4-yl]methoxy]-4-isopropyl-pyrimidine

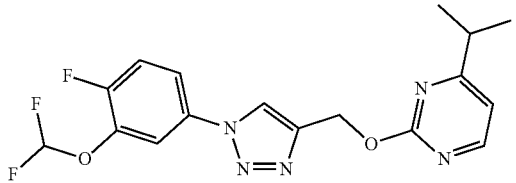

The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-isopropylpyrimidine. MS (ESI): mass calcd. for $C_{17}H_{16}F_3N_5O_2$, 379.1; m/z found, 379.9 [M+H]+. $^1$H NMR (400 MHz, DMSO-d$_6$) δ 8.95 (s, 1H), 8.53 (d, J=5.1 Hz, 1H), 8.00 (dd, J=6.9, 2.6 Hz, 1H), 7.88 (ddd, J=9.0, 3.9, 2.6 Hz, 1H), 7.68 (dd, J=10.2, 9.0 Hz, 1H), 7.39 (t, J=72.8 Hz, 1H), 7.10 (d, J=5.1 Hz, 1H), 5.52 (s, 2H), 2.95 (hept, J=7.0 Hz, 1H), 1.22 (d, J=6.9 Hz, 6H).

Example 497: 2-[[1-[3-(Difluoromethoxy)-4-fluoro-phenyl]triazol-4-yl]methoxy]-4-methoxy-pyrimidine. as the Trifluoroacetic Acid Salt

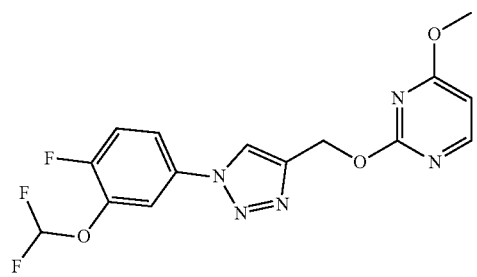 [SMILES: COc1ccnc(OCc2cn(-c3ccc(F)c(OC(F)F)c3)nn2)n1]

The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-methoxypyrimidine. MS (ESI): mass calcd. for $C_{15}H_{12}F_3N_5O_3$, 367.1; m/z found, 368.2 [M+H]+. $^1$H NMR (400 MHz, DMSO-d$_6$) δ 8.96 (s, 1H), 8.34 (d, J=5.7 Hz, 1H), 8.01 (dd, J=6.9, 2.6 Hz, 1H), 7.88 (ddd, J=9.0, 4.0, 2.6 Hz, 1H), 7.69 (dd, J=10.2, 9.0 Hz, 1H), 7.40 (t, J=72.7 Hz, 1H), 6.62 (d, J=5.7 Hz, 1H), 5.53 (s, 2H), 3.91 (s, 3H)

Example 498: [2-[[1-[3-(Difluoromethoxy)-4-fluoro-phenyl]triazol-4-yl]methoxy]pyrimidin-4-yl]methanol

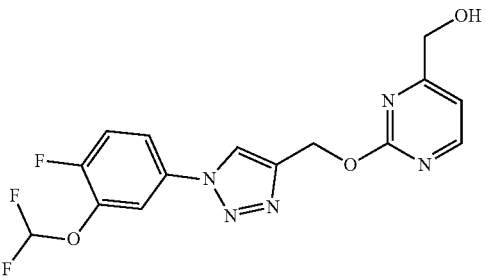 [SMILES: OCc1ccnc(OCc2cn(-c3ccc(F)c(OC(F)F)c3)nn2)n1]

The title compound was prepared in a manner analogous to Example 163, Steps B-C, using (1-(3-(difluoromethoxy)-4-fluorophenyl)-1H-1,2,3-triazol-4-yl)methanol (Intermediate 6) and 2-chloro-4-(((2-(trimethylsilyl)ethoxy)methoxy)methyl)pyrimidine (Example 383, product from Step A). MS (ESI): mass calcd. for $C_{15}H_{12}F_3N_5O_3$, 367.1; m/z found, 368.1 [M+H]+. $^1$H NMR (400 MHz, DMSO-d) δ 8.94 (s, 1H), 8.62 (d, J=5.0 Hz, 1H), 8.00 (dd, J=7.0, 2.6 Hz, 1H), 7.87 (ddd, J=9.0, 4.0, 2.6 Hz, 1H), 7.68 (dd, J=10.2, 9.0 Hz, 1H), 7.39 (t, J=72.8 Hz, 1H), 7.26-7.22 (m, 1H), 5.63 (t, J=5.8 Hz, 1H), 5.52 (s, 2H), 4.51 (d, J=5.7 Hz, 2H).

Example 499: 2-[[1-[3-(Difluoromethoxy)-4-fluorophenyl]triazol-4-yl]methoxy]-4-(methoxymethyl)pyrimidine

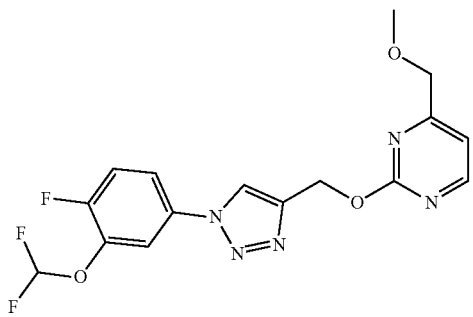 [SMILES: COCc1ccnc(OCc2cn(-c3ccc(F)c(OC(F)F)c3)nn2)n1]

The title compound was prepared in a manner analogous to Example 155 using (1-(3-(difluoromethoxy)-4-fluorophenyl)-1H-1,2,3-triazol-4-yl)methanol (Intermediate 6) and 2-chloro-4-(methoxymethyl)pyrimidine. MS (ESI): mass calcd. for $C_{16}H_{14}F_3N_5O_3$, 381.1; m/z found, 381.9 [M+H]$^+$. $^1$H NMR (400 MHz, DMSO-d$_6$) δ 8.95 (s, 1H), 8.64 (d, J=5.0 Hz, 1H), 8.00 (dd, J=6.9, 2.6 Hz, 1H), 7.90-7.84 (m, 1H), 7.69 (dd, J=10.2, 9.0 Hz, 1H), 7.40 (t, J=72.8 Hz, 1H), 7.20-7.17 (m, 1H), 5.53 (s, 2H), 4.48 (s, 2H), 3.41 (s, 3H)

Example 500: 2-[2-[[1-[3-(Difluoromethoxy)-4-fluoro-phenyl]triazol-4-yl]methoxy]pyrimidin-5-yl]propan-2-ol

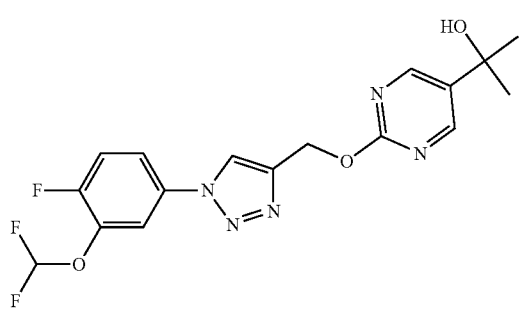 [SMILES: CC(C)(O)c1cnc(OCc2cn(-c3ccc(F)c(OC(F)F)c3)nn2)nc1]

The title compound was prepared in a manner analogous to Example 153 using (1-(3-(difluoromethoxy)-4-fluorophenyl)-1H-1,2,3-triazol-4-yl)methanol and 2-(2-chloropyrimidin-5-yl)propan-2-ol, using ACN instead of DMF. MS (ESI): mass calcd. for $C_{17}H_{16}F_3N_5O_3$, 395.1; m/z found, 396.0 [M+H]$^+$. $^1$H NMR (500 MHz, CDCl$_3$) δ 8.70-8.65 (s, 2H), 8.12-8.08 (t, J=0.7 Hz, 1H), 7.71-7.67 (dd, J=6.6, 2.6 Hz, 1H), 7.61-7.55 (m, 1H), 7.38-7.30 (t, J=9.2 Hz, 1H), 6.80-6.48 (t, J=72.6 Hz, 1H), 5.72-5.61 (d, J=0.7 Hz, 2H), 1.70-1.60 (s, 6H).

Example 501: 2-[[1-[3-(Difluoromethoxy)-4-fluorophenyl]triazol-4-yl]methoxy]pyrimidin-4-amine

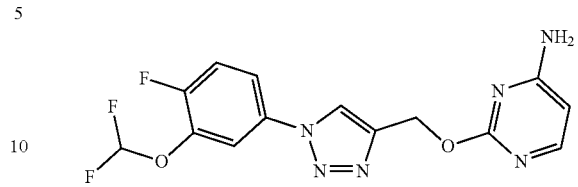

The title compound was prepared in a manner analogous to Example 155 using (1-(3-(difluoromethoxy)-4-fluorophenyl)-1H-1,2,3-triazol-4-yl)methanol (Intermediate 6) and 2-chloropyrimidin-4-amine. MS (ESI): mass calcd. for $C_{14}H_{11}F_3N_6O_2$, 352.1; m/z found, 352.9 [M+H]$^+$. $^1$H NMR (400 MHz, DMSO-d$_6$) δ 8.91 (s, 1H), 7.99 (dd, J=6.9, 2.6 Hz, 1H), 7.91-7.83 (m, 2H), 7.68 (dd, J=10.2, 9.0 Hz, 1H), 7.39 (t, J=72.8 Hz, 1H), 6.92 (s, 2H), 6.11 (d, J=5.7 Hz, 1H), 5.37 (s, 2H).

Example 502: 2-[[1-[3-(Difluoromethoxy)-4-fluorophenyl]triazol-4-yl]methoxy]pyrimidin-5-amine

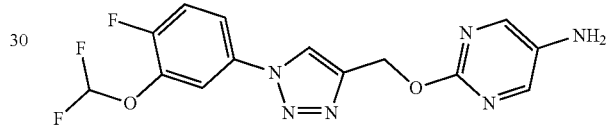

The title compound was prepared in a manner analogous to Example 155 using (1-(3-(difluoromethoxy)-4-fluorophenyl)-1H-1,2,3-triazol-4-yl)methanol (Intermediate 6) and 2-chloropyrimidin-5-amine. MS (ESI): mass calcd. for $C_{14}H_{11}F_3N_6O_2$, 352.1; m/z found, 352.9 [M+H]$^+$. $^1$H NMR (400 MHz, CD$_2$Cl$_2$) δ 8.17-8.01 (m, 3H), 7.73-7.67 (m, 1H), 7.62-7.55 (m, 1H), 7.40-7.32 (m, 1H), 6.68 (t, J=72.8 Hz, 1H), 5.50 (s, 2H).

Example 503: 2-[[1-[3-(Difluoromethoxy)-4-fluorophenyl]triazol-4-yl]methoxy]-N-methyl-pyrimidin-4-amine

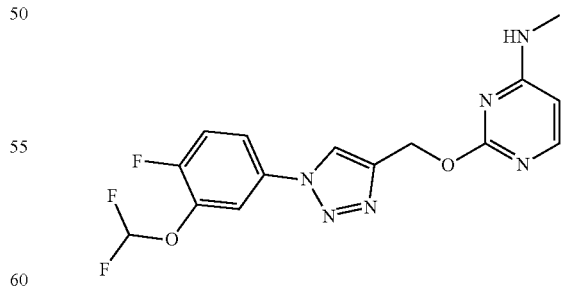

The title compound was prepared in a manner analogous to Example 163, Steps B-C using tert-butyl (2-chloropyrimidin-4-yl)(methyl)carbamate (Intermediate 55) and (1-(3-(difluoromethoxy)-4-fluorophenyl)-1H-1,2,3-triazol-4-yl)methanol (Intermediate 6) in Step A. MS (ESI): mass calcd. for $C_{15}H_{13}F_3N_6O_2$, 366.1; m/z found, 366.9 [M+H]$^+$.

¹H NMR (500 MHz, DMSO-d₆) δ 8.90 (s, 1H), 8.00 (dd, J=7.0, 2.6 Hz, 1H), 7.89-7.79 (m, 2H), 7.67 (dd, J=10.2, 9.0 Hz, 1H), 7.55-7.22 (m, 2H), 6.14 (d, J=5.9 Hz, 1H), 5.40 (s, 2H), 2.81-2.74 (m, 3H).

Example 504: 2-((1-(3-(Difluoromethoxy)-4-fluorophenyl)-1H-1,2,3-triazol-4-yl)methoxy)-N-ethylpyrimidin-4-amine

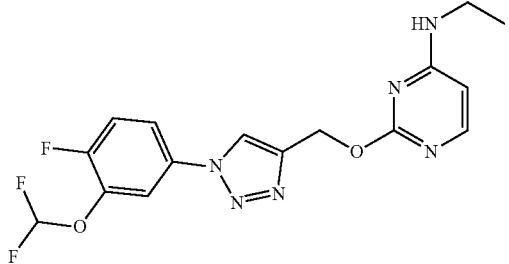 [SMILES: CCNc1ccnc(OCc2cn(-c3ccc(F)c(OC(F)F)c3)nn2)n1]

The title compound was prepared in a manner analogous to Example 163 Steps B-C, using (1-(3-(difluoromethoxy)-4-fluorophenyl)-1H-1,2,3-triazol-4-yl)methanol (Intermediate 6) and 2-chloro-N-ethyl-N-((2-(trimethylsilyl)ethoxy)methyl)pyrimidin-4-amine (Intermediate 60) in Step A. MS (ESI): mass calcd. for $C_{16}H_{15}F_3N_6O_2$, 380.1; m/z found, 381.2 [M+H]⁺. ¹H NMR (400 MHz, DMSO-d₆) δ 8.91 (s, 1H), 8.00 (dd, J=6.9, 2.6 Hz, 1H), 7.90-7.80 (m, 2H), 7.68 (dd, J=10.2, 9.0 Hz, 1H), 7.59-7.20 (m, 2H), 6.13 (d, J=5.9 Hz, 1H), 5.39 (s, 2H), 1.11 (t, J=7.2 Hz, 3H).

Example 505: 2-[[1-[3-(Difluoromethoxy)-4-fluorophenyl]triazol-4-yl]methoxy]-N,N-dimethyl-pyrimidin-4-amine

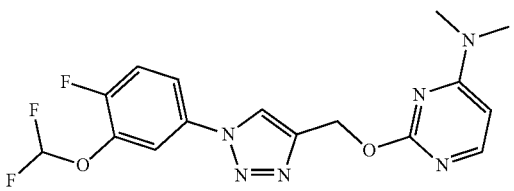 [SMILES: CN(C)c1ccnc(OCc2cn(-c3ccc(F)c(OC(F)F)c3)nn2)n1]

The title compound was prepared in a manner analogous to Example 155 using (1-(3-(difluoromethoxy)-4-fluorophenyl)-1H-1,2,3-triazol-4-yl)methanol (Intermediate 6) and 2-chloro-N,N-dimethylpyrimidin-4-amine. MS (ESI): mass calcd. for $C_{16}H_{15}F_3N_5O_2$, 380.1; m/z found, 380.9 [M+H]⁺. ¹H NMR (400 MHz, DMSO-d₆) δ 8.91 (s, 1H), 8.03-7.98 (m, 2H), 7.88 (ddd, J=9.0, 4.0, 2.6 Hz, 1H), 7.68 (dd, J=10.2, 9.0 Hz, 1H), 7.39 (t, J=72.8 Hz, 1H), 6.36 (d, J=6.1 Hz, 1H), 5.43 (s, 2H), 3.05 (s, 6H).

Example 506: 2-[[1-[3-(Difluoromethoxy)-4-fluorophenyl]triazol-4-yl]methoxy]-4-phenyl-pyrimidine

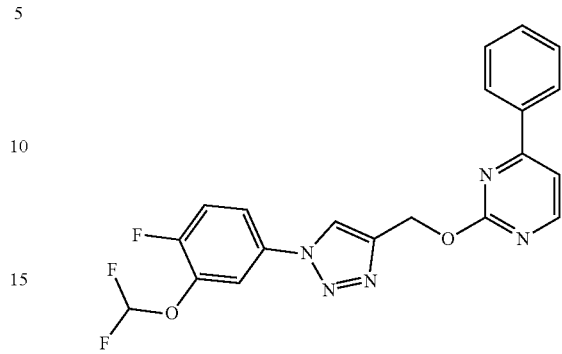

The title compound was prepared in a manner analogous to Example 155 using (1-(3-(difluoromethoxy)-4-fluorophenyl)-1H-1,2,3-triazol-4-yl)methanol (Intermediate 6) and (1-(3-(difluoromethoxy)-4-fluorophenyl)-1H-1,2,3-triazol-4-yl)methanol (Intermediate 6) and 2-chloro-4-phenylpyrimidine. MS (ESI): mass calcd. for $C_{20}H_{14}F_3N_5O_2$, 413.1; m/z found, 413.9 [M+H]⁺. ¹H NMR (500 MHz, DMSO-d₆) δ 9.00 (s, 1H), 8.72 (d, J=5.2 Hz, 1H), 8.25-8.21 (m, 2H), 8.01 (dd, J=6.9, 2.6 Hz, 1H), 7.88 (ddd, J=9.0, 4.0, 2.7 Hz, 1H), 7.78 (d, J=5.2 Hz, 1H), 7.68 (dd, J=10.2, 9.0 Hz, 1H), 7.61-7.23 (m, 4H), 5.65 (s, 2H).

Example 507: 2-[[1-[3-(Difluoromethoxy)-4-fluorophenyl]triazol-4-yl]methoxy]-5-(3-fluoroazetidin-1-yl)pyrimidine

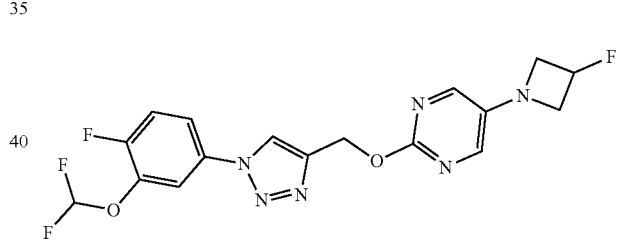

The title compound was prepared in a manner analogous to Example 165 using 3-fluoroazetidine hydrochloride in Step A. MS (ESI): mass calcd. for $C_{17}H_{14}F_4N_4O_2$, 410.1; m/z found, 411.2 [M+H]⁺. ¹H NMR (400 MHz, DMSO-d₆) δ 8.92 (s, 1H), 8.02-7.98 (m, 3H), 7.87 (ddd, J=9.0, 4.0, 2.7 Hz, 1H), 7.68 (dd, J=10.2, 9.0 Hz, 1H), 7.39 (t, J=72.8 Hz, 1H), 5.59-5.38 (m, 3H), 4.26-4.14 (m, 2H), 4.00-3.88 (m, 2H).

Example 508: 5-(3,3-Difluoroazetidin-1-yl)-2-[[1-[3-(difluoromethoxy)-4-fluoro-phenyl]triazol-4-yl]methoxy]pyrimidine

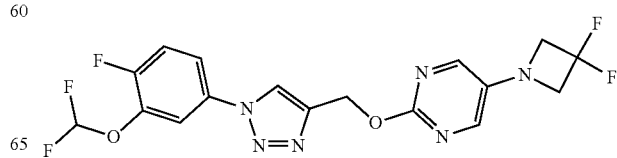

The title compound was prepared in a manner analogous to Example 165 using 3,3-difluoroazetidine hydrochloride in Step A. MS (ESI): mass calcd. for $C_{17}H_{13}F_8N_6O_2$, 428.1; m/z found, 429.2 [M+H]$^+$. $^1$H NMR (400 MHz, DMSO-d$_6$) δ 8.93 (s, 1H), 8.08 (s, 2H), 8.00 (dd, J=6.9, 2.6 Hz, 1H), 7.87 (ddd, J=9.0, 4.0, 2.7 Hz, 1H), 7.68 (dd, J=10.2, 9.0 Hz, 1H), 7.39 (t, J=72.8 Hz, 1H), 5.45 (s, 2H), 4.34 (t, J=12.3 Hz, 4H)

Example 509: 4-(Azetidin-1-yl)-2-[[1-[3-(difluoromethoxy)-4-fluoro-phenyl]triazol-4-yl]methoxy]pyrimidine

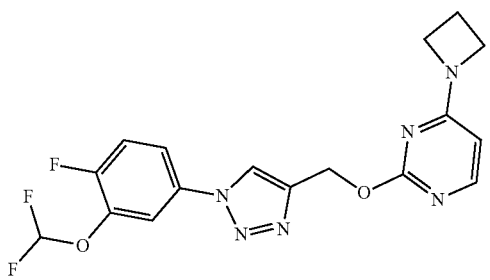 [SMILES: Fc1ccc(-n2cc(COc3nccc(N4CCC4)n3)nn2)cc1OC(F)F]

The title compound was prepared in a manner analogous to Example 166 using azetidine in Step A. MS (ESI): mass calcd. for $C_{17}H_{15}F_3N_6O_2$, 392.1; m/z found, 392.9 [M+H]$^+$. $^1$H NMR (500 MHz, DMSO-d) δ 8.89 (s, 1H), 8.02-7.98 (m, 2H), 7.87 (ddd, J=9.0, 3.9, 2.7 Hz, 1H), 7.67 (dd, J=10.2, 9.0 Hz, 1H), 7.39 (t, J=72.8 Hz, 1H), 6.04 (d, J=5.8 Hz, 1H), 5.40 (s, 2H), 4.02 (t, J=7.6 Hz, 4H), 2.39-2.31 (m, 2H).

Example 510: 2-[[1-[3-(Difluoromethoxy)-4-fluoro-phenyl]triazol-4-yl]methoxy]-4-(3-fluoroazetidin-1-yl)pyrimidine

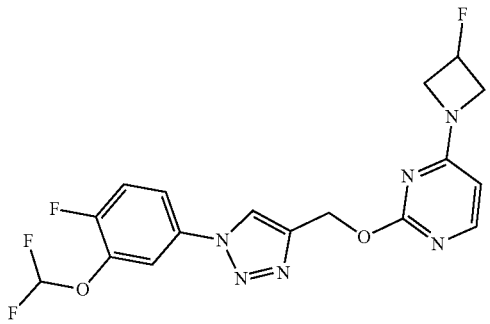 [SMILES: Fc1ccc(-n2cc(COc3nccc(N4CC(F)C4)n3)nn2)cc1OC(F)F]

The title compound was prepared in a manner analogous to Example 166 using 3-fluoroazetidine hydrochloride in Step A. MS (ESI): mass calcd. for $C_{17}H_{14}F_4N_6O_2$, 410.1; m/z found, 410.9 [M+H]$^+$. $^1$H NMR (500 MHz, DMSO-d$_6$) δ 8.90 (s, 1H), 8.06 (d, J=5.8 Hz, 1H), 8.00 (dd, J=6.9, 2.6 Hz, 1H), 7.87 (ddd, J=9.0, 4.0, 2.7 Hz, 1H), 7.67 (dd, J=10.2, 9.0 Hz, 1H), 7.39 (t, J=72.8 Hz, 1H), 6.16 (d, J=5.8 Hz, 1H), 5.60-5.41 (m, 3H), 4.41-4.31 (m, 2H), 4.14-4.04 (m, 2H).

Example 511: 4-(3,3-Difluoroazetidin-1-yl)-2-[[1-[3-(difluoromethoxy)-4-fluoro-phenyl]triazol-4-yl]methoxy]pyrimidine

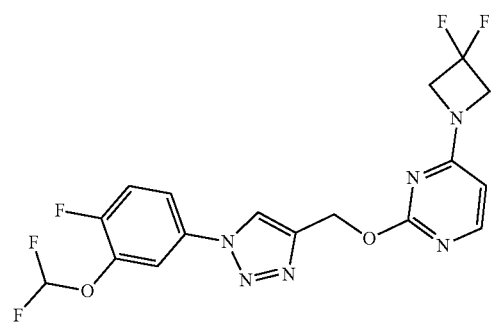 [SMILES: Fc1ccc(-n2cc(COc3nccc(N4CC(F)(F)C4)n3)nn2)cc1OC(F)F]

The title compound was prepared in a manner analogous to Example 166 using 3,3-difluoroazetidine hydrochloride in Step A. MS (ESI): mass calcd. for $C_{17}H_{13}F_8N_5O_2$, 428.1; m/z found, 428.9 [M+H]$^+$. $^1$H NMR (400 MHz, DMSO-d$_6$) δ 8.92 (s, 1H), 8.15 (d, J=5.7 Hz, 1H), 8.02-7.98 (m, 1H), 7.90-7.85 (m, 1H), 7.68 (dd, J=10.2, 9.0 Hz, 1H), 7.39 (t, J=72.8 Hz, 1H), 6.28 (d, J=5.8 Hz, 1H), 5.45 (s, 2H), 4.49 (t, J=12.4 Hz, 4H).

Example 512: (R)-2-[[1-[3-(Difluoromethoxy)-4-fluoro-phenyl]triazol-4-yl]methoxy]-4-[(3R)-3-fluoropyrrolidin-1-yl]pyrimidine

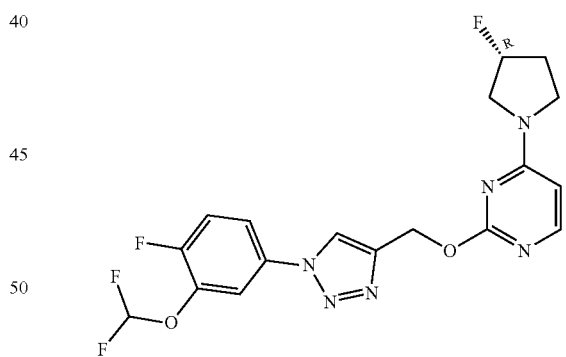

The title compound was prepared in a manner analogous to Example 166 using (R)-3-fluoropyrrolidine hydrochloride in Step A. MS (ESI): mass calcd. for $C_{18}H_{16}F_4N_6O_2$, 424.1; m/z found, 424.9 [M+H]$^+$. $^1$H NMR (500 MHz, DMSO-d$_6$) δ 8.91 (s, 1H), 8.04 (d, J=5.9 Hz, 1H), 8.00 (dd, J=6.9, 2.6 Hz, 1H), 7.87 (ddd, J=9.0, 4.0, 2.7 Hz, 1H), 7.67 (dd, J=10.2, 9.0 Hz, 1H), 7.39 (t, J=72.8 Hz, 1H), 6.30-6.19 (m, 1H), 5.55-5.34 (m, 3H), 3.95-3.36 (m, 4H), 2.35-2.02 (m, 2H).

Example 513: 5-Chloro-2-[[1-[3-(difluoromethoxy)-4-fluoro-phenyl]triazol-4-yl]methoxy]-4-methyl-pyrimidine

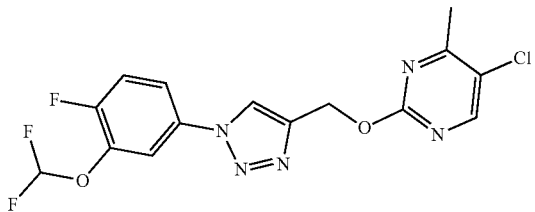 [SMILES: Cc1nc(OCc2cn(-c3ccc(F)c(OC(F)F)c3)nn2)ncc1Cl]

The title compound was prepared in a manner analogous to Example 155 using (1-(3-(difluoromethoxy)-4-fluorophenyl)-1H-1,2,3-triazol-4-yl)methanol (Intermediate 6) and 2,5-dichloro-4-methylpyrimidine. MS (ESI): mass calcd. for $C_{15}H_{11}ClF_3N_5O_2$, 385.1; m/z found, 385.9 [M+H]$^+$. $^1$H NMR (500 MHz, DMSO-d$_6$) δ 8.94 (s, 1H), 8.62 (s, 1H), 8.01-7.97 (m, 1H), 7.90-7.84 (m, 1H), 7.72-7.64 (m, 1H), 7.39 (t, J=72.8 Hz, 1H), 5.53 (s, 2H).

Example 514: 2-[[1-[3-(Difluoromethoxy)-4-fluoro-phenyl]triazol-4-yl]methoxy]-5-methyl-pyrimidin-4-amine. as the Trifluoroacetic Acid Salt

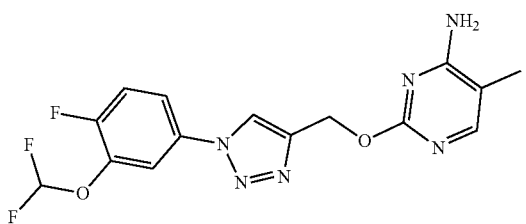 [SMILES: Cc1cnc(OCc2cn(-c3ccc(F)c(OC(F)F)c3)nn2)nc1N]

The title compound was prepared in a manner analogous to Example 155 using (1-(3-(difluoromethoxy)-4-fluorophenyl)-1H-1,2,3-triazol-4-yl)methanol (Intermediate 6) and 2-chloro-5-methylpyrimidin-4-amine. MS (ESI): mass calcd. for $C_{15}H_{13}F_3N_6O_2$, 366.1; m/z found, 366.9 [M+H]$^+$. $^1$H NMR (400 MHz, DMSO-d$_6$) δ 9.03 (s, 1H), 7.99-7.95 (m, 1H), 7.95-7.92 (m, 1H), 7.88-7.82 (m, 1H), 7.72 (dd, J=10.2, 9.0 Hz, 1H), 7.39 (t, J=72.7 Hz, 1H), 5.59 (s, 2H), 2.02-1.97 (m, 3H).

Example 515: 2-[[1-[3-(Difluoromethoxy)-4-fluoro-phenyl]triazol-4-yl]methoxy]-N,5-dimethyl-pyrimidin-4-amine

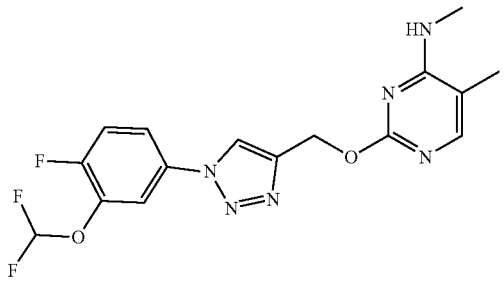 [SMILES: CNc1nc(OCc2cn(-c3ccc(F)c(OC(F)F)c3)nn2)ncc1C]

The title compound was prepared in a manner analogous to Example 163, Steps B-C using tert-butyl (2-chloro-5-methylpyrimidin-4-yl)(methyl)carbamate (Intermediate 56) and (1-(3-(difluoromethoxy)-4-fluorophenyl)-1H-1,2,3-triazol-4-yl)methanol (Intermediate 6) in Step A. MS (ESI): mass calcd. for $C_{16}H_{15}F_3N_6O_2$, 380.1; m/z found, 381.2 [M+H]$^+$. $^1$H NMR (500 MHz, DMSO-d$_6$) δ 8.95 (s, 1H), 7.99 (dd, J=6.9, 2.7 Hz, 1H), 7.87 (ddd, J=9.0, 3.9, 2.6 Hz, 1H), 7.84-7.82 (m, 1H), 7.69 (dd, J=10.2, 9.0 Hz, 1H), 7.39 (t, J=72.7 Hz, 1H), 5.63 (s, 2H), 3.01 (d, J=4.5 Hz, 3H), 2.00-1.97 (m, 3H).

Example 516: 2-[[1-[3-(Difluoromethoxy)-4-fluoro-phenyl]triazol-4-yl]methoxy]-N,N,5-trimethyl-pyrimidin-4-amine

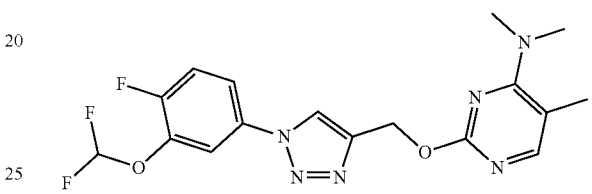

The title compound was prepared in a manner analogous to Example 155 using (1-(3-(difluoromethoxy)-4-fluorophenyl)-1H-1,2,3-triazol-4-yl)methanol (Intermediate 6) and 2-chloro-N,N,5-trimethylpyrimidin-4-amine. MS (ESI): mass calcd. for $C_{17}H_{17}F_3N_6O_2$, 394.1; m/z found, 395.0 [M+H]$^+$. $^1$H NMR (400 MHz, DMSO-d$_6$) δ 8.90 (s, 1H), 8.00 (dd, J=6.9, 2.7 Hz, 1H), 7.87 (ddd, J=9.0, 4.0, 2.6 Hz, 1H), 7.84-7.82 (m, 1H), 7.67 (dd, J=10.2, 9.0 Hz, 1H), 7.39 (t, J=72.8 Hz, 1H), 5.40 (s, 2H), 3.07 (s, 6H), 2.22 (d, J=0.9 Hz, 3H).

Example 517: N-(2,2-Difluoroethyl)-2-[[1-[3-(difluoromethoxy)-4-fluoro-phenyl]triazol-4-yl]methoxy]-5-fluoro-pyrimidin-4-amine. as the Trifluoroacetic Acid Salt

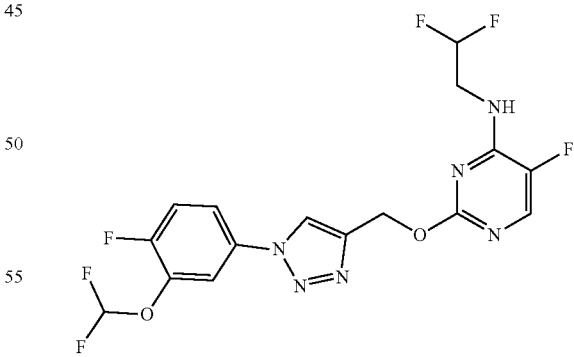

The title compound was prepared in a manner analogous to Example 163, Steps B-C using tert-butyl (2-chloro-5-fluoropyrimidin-4-yl)(2,2-difluoroethyl)carbamate (Intermediate 57) and (1-(3-(difluoromethoxy)-4-fluorophenyl)-1H-1,2,3-triazol-4-yl)methanol (Intermediate 6) in Step A. MS (ESI): mass calcd. for $C_{16}H_{12}F_8N_6O_2$, 434.1; m/z found, 435.2 [M+H]$^+$. $^1$H NMR (400 MHz, DMSO-d$_6$) δ 8.92 (s, 1H), 8.19-8.12 (m, 1H), 8.07 (d, J=3.3 Hz, 1H), 8.00 (dd, J=6.9, 2.6 Hz, 1H), 7.88 (ddd, J=9.0, 3.9, 2.6 Hz, 1H), 7.69 (dd, J=10.2, 9.0 Hz, 1H), 7.40 (t, J=72.8 Hz, 1H), 6.34-6.00 (m, 1H), 5.42 (s, 2H).

Example 518: 2-[[1-[3-(Difluoromethoxy)-4-fluorophenyl]triazol-4-yl]methoxy]-5-fluoro-N-methyl-pyrimidin-4-amine. as the Trifluoroacetic Acid Salt

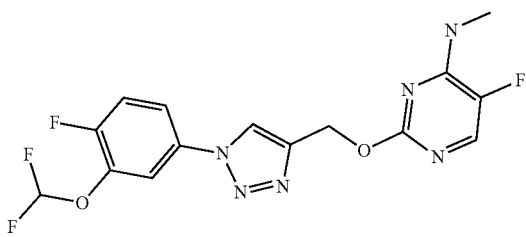 [SMILES: CNc1nc(OCc2cn(-c3ccc(F)c(OC(F)F)c3)nn2)ncc1F]

The title compound was prepared in a manner analogous to Example 163, Steps B-C, using (1-(3-(difluoromethoxy)-4-fluorophenyl)-1H-1,2,3-triazol-4-yl)methanol (Intermediate 6) and 2-chloro-5-fluoro-N-methyl-N-((2-(trimethylsilyl)ethoxy)methyl)pyrimidin-4-amine (Intermediate 59) in Step A. MS (ESI): mass calcd. for $C_{15}H_{12}F_4N_6O_2$, 384.1; m/z found, 385.1 [M+H]$^+$. $^1$H NMR (500 MHz, DMSO-d$_6$) δ 8.91 (s, 1H), 8.01-7.97 (m, 2H), 7.94-7.85 (m, 2H), 7.68 (dd, J=10.2, 9.0 Hz, 1H), 7.39 (t, J=72.8 Hz, 1H), 5.43 (s, 2H), 2.87 (d, J=4.6 Hz, 3H).

Example 519: N-Cyclopropyl-2-((1-(3-(difluoromethoxy)-4-fluorophenyl)-1H-1,2,3-triazol-4-yl)methoxy)-5-fluoropyrimidin-4-amine

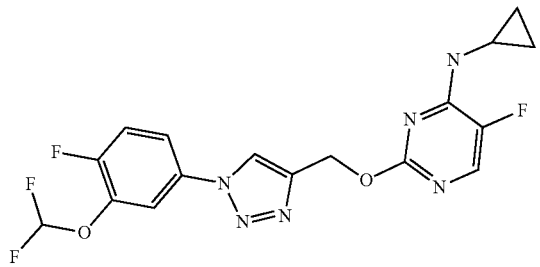 [SMILES: Fc1ccc(-n2cc(COc3ncc(F)c(NC4CC4)n3)nn2)cc1OC(F)F]

The title compound was prepared in a manner analogous to Example 167 using 4-chloro-2-((1-(3-(difluoromethoxy)-4-fluorophenyl)-1H-1,2,3-triazol-4-yl)methoxy)-5-fluoropyrimidine and cyclopropylamine in Step C. MS (ESI): mass calcd. for $C_{17}H_{14}F_4N_6O_2$, 411.1; m/z found, 410.1 [M+H]$^+$. $^1$H NMR (400 MHz, DMSO-d$_6$) δ 8.91 (s, 1H), 8.00 (dd, J=6.9, 2.6 Hz, 1H), 7.95 (d, J=3.5 Hz, 1H), 7.90-7.84 (m, 2H), 7.68 (dd, J=10.2, 9.0 Hz, 1H), 7.39 (t, J=72.8 Hz, 1H), 5.40 (s, 2H), 2.85-2.75 (m, 1H), 0.74-0.67 (m, 2H), 0.60-0.53 (m, 2H).

Example 520: 1-(2-((1-(3-(Difluoromethoxy)-4-fluorophenyl)-1H-1,2,3-triazol-4-yl)methoxy)pyrimidin-4-yl)-N-methylmethanamine

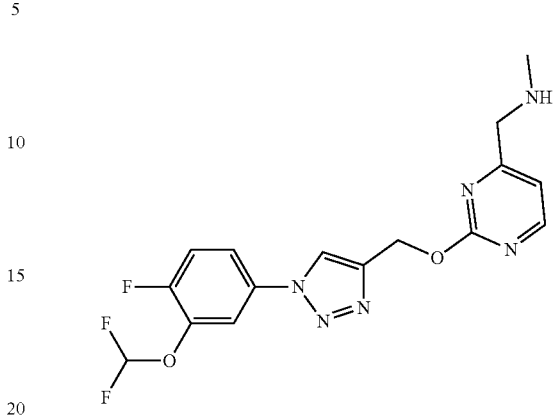

The title compound was prepared in a manner analogous to Example 163, Steps B-C, using tert-butyl methyl((2-(methylsulfonyl)pyrimidin-4-yl)methyl)carbamate (Intermediate 61) and (1-(3-(difluoromethoxy)-4-fluorophenyl)-1H-1,2,3-triazol-4-yl)methanol (Intermediate 6). MS (ESI): mass calcd. for $C_{16}H_{15}F_3N_6O_2$, 380.1; m/z found, 381.1 [M+H]$^+$. $^1$H NMR (500 MHz, DMSO-d$_6$) δ 8.97 (s, 1H), 8.57 (d, J=5.0 Hz, 1H), 8.00 (dd, J=6.9, 2.6 Hz, 1H), 7.87 (ddd, J=9.0, 4.0, 2.6 Hz, 1H), 7.68 (dd, J=10.2, 9.0 Hz, 1H), 7.39 (t, J=72.8 Hz, 1H), 7.21 (d, J=5.0 Hz, 1H), 5.52 (s, 2H), 3.69 (s, 2H), 2.29 (s, 3H).

Example 521: 2-[[1-[3-(Difluoromethoxy)-4-methyl-phenyl]triazol-4-yl]methoxy]-5-methyl-pyrimidin-4-amine

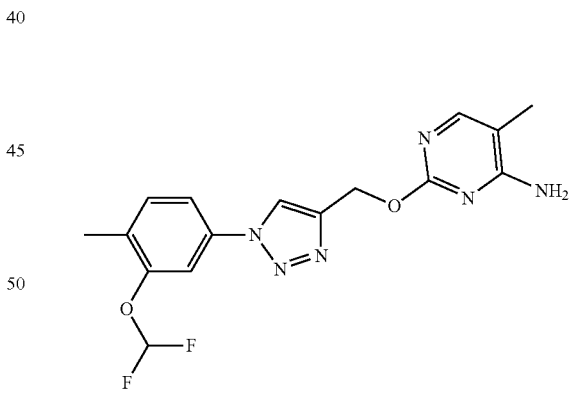

The title compound was prepared in a manner analogous to Example 1 using (1-(3-(difluoromethoxy)-4-methylphenyl)-1H-1,2,3-triazol-4-yl)methanol (Intermediate 52) and 2-chloro-4-amino-5-methylpyrimidine. MS (ESI): mass calcd. for $C_{16}H_{16}F_2N_6O_2$, 362.1; m/z found, 363.2[M+H]$^+$. $^1$H NMR (400 MHz, DMSO-d$_6$) δ 8.88 (s, 1H), 7.93-7.66 (m, 2H), 7.61-7.10 (m, 3H), 6.76 (s, 2H), 5.35 (s, 2H), 2.29 (s, 3H), 1.92 (s, 3H).

Example 522: 1-[2-[[1-[3-(Difluoromethoxy)-4-methyl-phenyl]triazol-4-yl]methoxy]pyrimidin-5-yl]ethanone

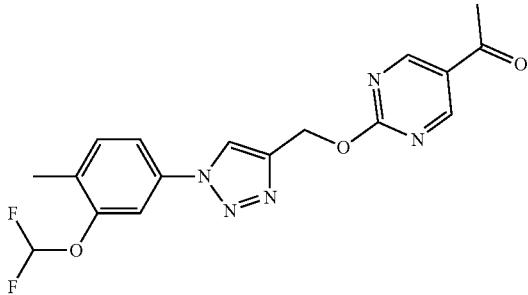 [SMILES: CC(=O)c1cnc(OCc2cn(-c3ccc(C)c(OC(F)F)c3)nn2)nc1]

The title compound was prepared in a manner analogous to Example 1 using (1-(3-(difluoromethoxy)-4-methylphenyl)-1H-1,2,3-triazol-4-yl)methanol (Intermediate 52) and 1-(2-chloropyrimidin-5-yl)ethan-1-one. MS (ESI): mass calcd. for $C_{17}H_{15}F_2N_5O_3$, 375.1; m/z found, 376.1 [M+H]$^+$. $^1$H NMR (400 MHz, DMSO-d$_6$) δ 9.15 (s, 2H), 8.97 (s, 1H), 7.79-7.67 (m, 2H), 7.60-7.13 (m, 2H), 5.65 (s, 2H), 2.59 (s, 3H), 2.30 (s, 3H).

Example 523: 2-[[1-[3-(Difluoromethoxy)-4-methyl-phenyl]triazol-4-yl]methoxy]-4-methyl-pyrimidine

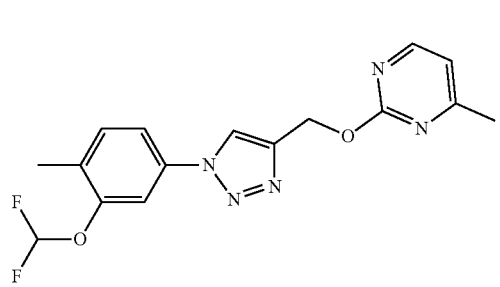 [SMILES: Cc1ccnc(OCc2cn(-c3ccc(C)c(OC(F)F)c3)nn2)n1]

The title compound was prepared in a manner analogous to Example 1 using (1-(3-(difluoromethoxy)-4-methylphenyl)-1H-1,2,3-triazol-4-yl)methanol (Intermediate 52) and 2-chloro-4-methylpyrimidine. MS (ESI): mass calcd. for $C_{16}H_{15}F_2N_5O_2$, 347.1; m/z found, 348.0 [M+H]$^+$. $^1$H NMR (400 MHz, DMSO-d$_6$) δ 8.92 (s, 1H), 8.49 (d, J=4.8 Hz, 1H), 7.80-7.67 (m, 2H), 7.57-7.14 (m, 2H), 7.07 (d, J=5.1 Hz, 1H), 5.51 (s, 2H), 2.43 (s, 3H), 2.30 (s, 3H).

Example 524: 2-[[1-[3-(Difluoromethoxy)-4-methyl-phenyl]triazol-4-yl]methoxy]-5-methyl-pyrimidine

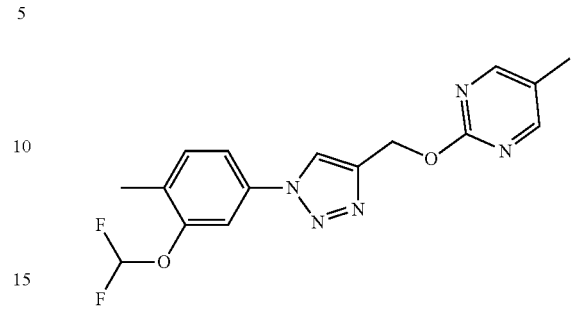

The title compound was prepared in a manner analogous to Example 1 using (1-(3-(difluoromethoxy)-4-methylphenyl)-1H-1,2,3-triazol-4-yl)methanol (Intermediate 52) and 2-chloro-5-methylpyrimidine. MS (ESI): mass calcd. for $C_{16}H_{15}F_2N_5O_2$, 347.1; m/z found, 348.0 [M+H]$^+$. $^1$H NMR (400 MHz, DMSO-d$_6$) δ 8.93 (d, J=2.7 Hz, 1H), 8.50 (d, J=7.9 Hz, 2H), 7.84-7.68 (m, 2H), 7.61-7.10 (m, 2H), 5.50 (d, J=2.5 Hz, 2H), 2.30 (s, 2H), 2.21 (s, 2H).

Example 525: 5-Bromo-2-[[1-[3-(difluoromethoxy)-4-methyl-phenyl]triazol-4-yl]methoxy]pyrimidine

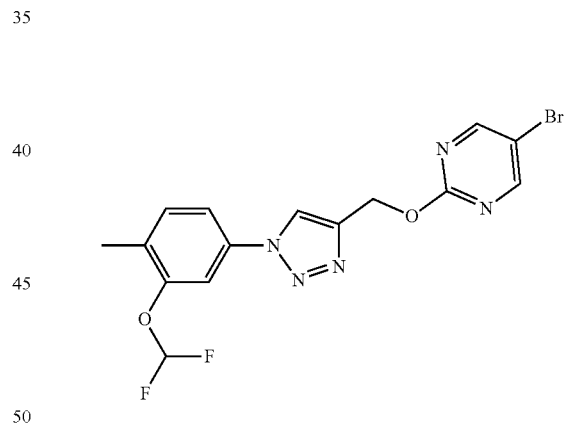

The title compound was prepared in a manner analogous to Example 1 using (1-(3-(difluoromethoxy)-4-methylphenyl)-1H-1,2,3-triazol-4-yl)methanol (Intermediate 52) and 2-chloro-5-bromopyrimidine. MS (ESI): mass calcd. for $C_{15}H_{12}BrF_2N_5O_2$, 411.0; m/z found, 412.1 [M+H]$^+$. $^1$H NMR (400 MHz, CD$_3$OD) δ 8.71 (s, 2H), 8.68 (s, 1H), 7.69 (d, J=2.1 Hz, 1H), 7.65 (dd, J=8.2, 2.2 Hz, 1H), 7.50 (d, J=8.2 Hz, 1H), 6.97 (t, J=73.6 Hz, 1H), 5.62 (s, 2H), 2.37 (s, 3H)

Example 526: 2-[2-[[1-[3-(Difluoromethoxy)-4-methyl-phenyl]triazol-4-yl]methoxy]pyrimidin-5-yl]propan-2-ol

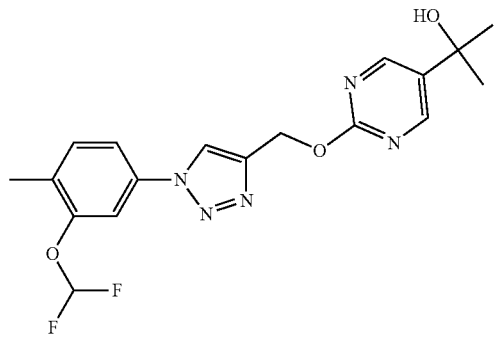 [SMILES: Cc1ccc(-n2cc(COc3ncc(C(C)(C)O)cn3)nn2)cc1OC(F)F]

The title compound was prepared in a manner analogous to Example 1 using (1-(3-(difluoromethoxy)-4-methylphenyl)-1H-1,2,3-triazol-4-yl)methanol (Intermediate 52) and 2-(2-chloropyrimidin-5-yl)propan-2-ol. MS (ESI): mass calcd. for $C_{18}H_{19}F_2N_5O_3$, 391.1; m/z found, 392.1 $[M+H]^+$.

Example 527: 2-[[1-[3-(Difluoromethoxy)-4-methyl-phenyl]triazol-4-yl]methoxy]-4-(methoxymethyl)pyrimidine

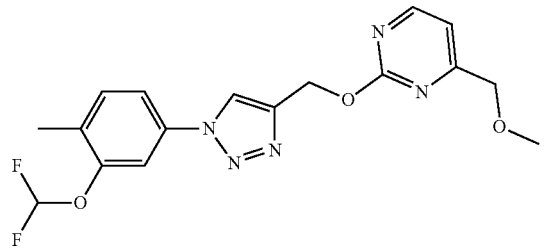 [SMILES: COCc1ccnc(OCc2cn(-c3ccc(C)c(OC(F)F)c3)nn2)n1]

The title compound was prepared in a manner analogous to Example 1 using (1-(3-(difluoromethoxy)-4-methylphenyl)-1H-1,2,3-triazol-4-yl)methanol (Intermediate 52) and 2-chloro-4-(methoxymethyl)pyrimidine. MS (ESI): mass calcd. for $C_{17}H_{17}F_2N_5O_3$, 377.1; m/z found, 378.2 $[M+H]^+$. $^1$H NMR (400 MHz, CD$_3$OD) δ 8.67 (s, 1H), 8.59 (d, J=5.1 Hz, 1H), 7.71-7.57 (m, 2H), 7.49 (d, J=8.3 Hz, 1H), 7.23 (d, J=5.1 Hz, 1H), 6.98 (t, J=73.7 Hz, 1H), 5.62 (s, 2H), 4.53 (s, 2H), 3.50 (s, 3H), 2.37 (s, 3H).

Example 528: 2-[[1-[3-(Difluoromethyl)phenyl]-5-methyl-triazol-4-yl]methoxy]-4,5-dimethyl-pyrimidine

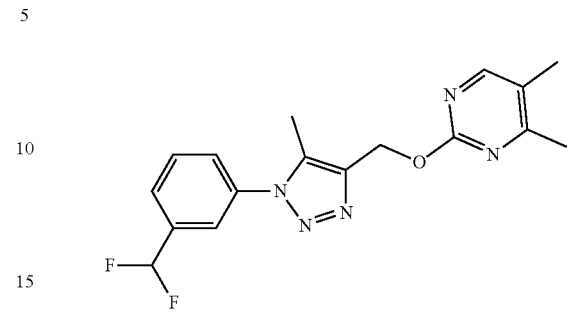

The title compound was prepared in a manner analogous to Example 172, Steps A through D, using 2-chloro-4,5-dimethylpyrimidine in Step D. MS (ESI): mass calcd. for $C_{17}H_{17}F_2N_5O$, 345.1; m/z found, 346.0 $[M+H]^+$. $^1$H NMR (400 MHz, CDCl$_3$) δ 8.19 (d, J=0.9 Hz, 1H), 7.71-7.56 (m, 4H), 6.73 (t, J=56.1 Hz, 1H), 5.57 (s, 2H), 2.44 (s, 3H), 2.43 (s, 3H), 2.19 (s, 3H).

Example 529: 5-Chloro-2-[[1-[3-(difluoromethyl)phenyl]-5-methyl-triazol-4-yl]methoxy]pyrimidine

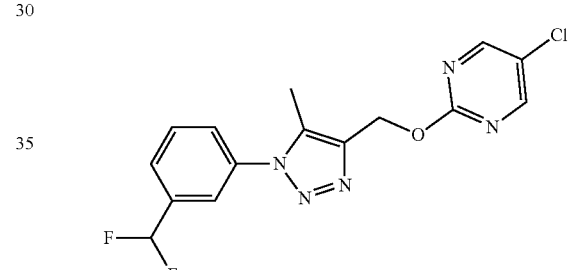

The title compound was prepared in a manner analogous to Example 172, Steps A through D, using 2,5-dichloropyrimidine in Step D. MS (ESI): mass calcd. for $C_{15}H_{12}ClF_2N_5O$, 351.1; m/z found, 352.0 $[M+H]^+$. $^1$H NMR (400 MHz, CDCl$_3$) δ 8.50 (s, 2H), 7.72-7.54 (m, 4H), 6.73 (t, J=56.1 Hz, 1H), 5.59 (s, 2H), 2.45 (s, 3H).

Example 530: 2-[[1-[4-Chloro-3-(1,1-difluoroethyl)phenyl]triazol-4-yl]methoxy]-5-methyl-pyrimidine

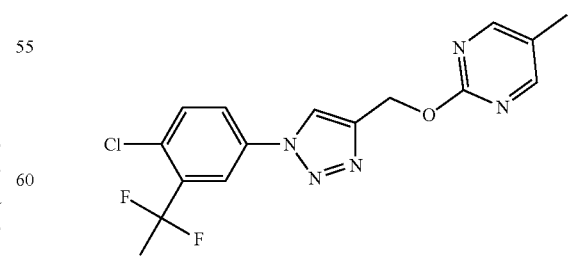

The title compound was prepared in a manner analogous to Example 155 using (1-(4-chloro-3-(1,1-difluoroethyl)phenyl)-1H-1,2,3-triazol-4-yl)methanol (Intermediate 63)

and 2-chloro-5-methylpyrimidine. MS (ESI): mass calcd. for $C_{16}H_{14}ClF_2N_5O$, 365.1; m/z found, 366.0 [M+H]$^+$. $^1$H NMR (400 MHz, CDCl$_3$) δ 8.38 (d, J=0.8 Hz, 2H), 8.20-8.09 (m, 1H), 7.97 (d, J=2.6 Hz, 1H), 7.84-7.76 (m, 1H), 7.65-7.58 (m, 1H), 5.64 (d, J=0.7 Hz, 2H), 2.26 (t, J=0.7 Hz, 3H), 2.09 (t, J=18.5 Hz, 3H).

Example 531: 2-[[1-[4-Chloro-3-(1,1-difluoroethyl)phenyl]triazol-4-yl]methoxy]-4-methyl-pyrimidine

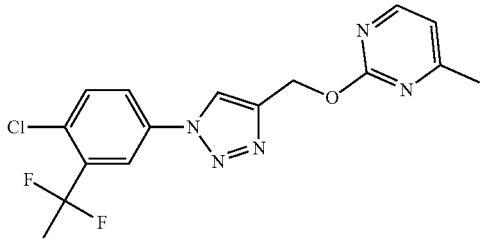 [SMILES: Cc1ccnc(OCc2cn(-c3ccc(Cl)c(C(C)(F)F)c3)nn2)n1]

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-4-methylpyrimidine. MS (ESI): mass calcd. for $C_{16}H_{14}ClF_2N_5O$, 365.1; m/z found, 366.0 [M+H]$^+$. $^1$H NMR (400 MHz, CDCl$_3$) δ 8.40 (d, J=5.0 Hz, 1H), 8.16 (s, 1H), 7.97 (d, J=2.6 Hz, 1H), 7.85-7.74 (m, 1H), 7.61 (d, J=8.6 Hz, 1H), 6.92-6.80 (m, 1H), 5.66 (d, J=0.7 Hz, 2H), 2.56-2.43 (m, 3H), 2.18-1.97 (m, 3H).

Example 532: 2-[2-[[1-[4-Chloro-3-(1,1-difluoroethyl)phenyl]triazol-4-yl]methoxy]pyrimidin-5-yl]propan-2-ol

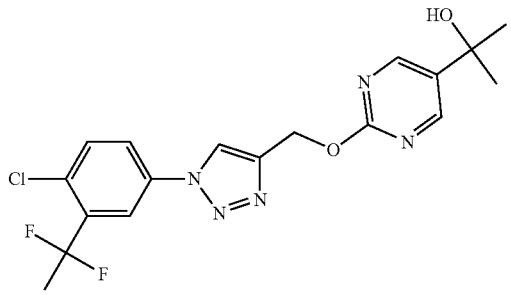 [SMILES: CC(C)(O)c1cnc(OCc2cn(-c3ccc(Cl)c(C(C)(F)F)c3)nn2)nc1]

The title compound was prepared in a manner analogous to Example 155 using (1-(4-chloro-3-(1,1-difluoroethyl)phenyl)-1H-1,2,3-triazol-4-yl)methanol (Intermediate 63) and 2-(2-chloropyrimidin-5-yl)propan-2-ol. MS (ESI): mass calcd. for $C_{18}H_{18}ClF_2N_5O_2$, 409.1; m/z found, 410.1 [M+H]$^+$. $^1$H NMR (500 MHz, CDCl$_3$) δ 8.68 (d, J=1.4 Hz, 2H), 8.20-8.13 (m, 1H), 7.98 (d, J=2.5 Hz, 1H), 7.84-7.74 (m, 1H), 7.61 (d, J=8.6 Hz, 1H), 5.67 (t, J=0.9 Hz, 2H), 2.20-1.99 (m, 3H), 1.70-1.59 (m, 6H).

Example 533: [2-[[1-[4-Chloro-3-(1,1-difluoroethyl)phenyl]triazol-4-yl]methoxy]pyrimidin-5-yl]methanol

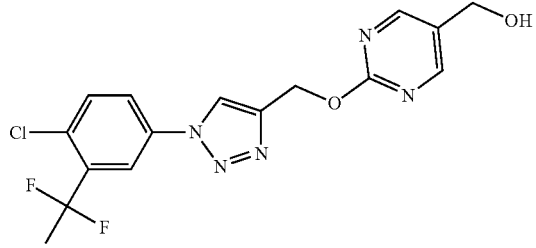 [SMILES: CC(F)(F)c1cc(-n2cc(COc3ncc(CO)cn3)nn2)ccc1Cl]

The title compound was prepared in a manner analogous to Example 159, Steps A-B using (1-(4-chloro-3-(1,1-difluoroethyl)phenyl)-1H-1,2,3-triazol-4-yl)methanol (Intermediate 63) and 5-(((tert-butyldimethylsilyl)oxy)methyl)-2-chloropyrimidine (Intermediate 53) in Step A. MS (ESI): mass calcd. for $C_{16}H_{14}ClF_2N_5O_2$, 381.1; m/z found, 382.0 [M+H]$^+$. $^1$H NMR (500 MHz, CDCl$_3$) δ 8.60-8.54 (s, 2H), 8.18-8.12 (t, J=0.7 Hz, 1H), 8.00-7.94 (d, J=2.6 Hz, 1H), 7.83-7.75 (m, 1H), 7.65-7.57 (m, 1H), 5.70-5.63 (d, J=0.7 Hz, 2H), 4.75-4.66 (m, 2H), 2.16-2.03 (t, J=18.5 Hz, 3H), 1.90-1.57 (s, 1H).

Example 534: 2-[[1-[4-Chloro-3-(1,1-difluoroethyl)phenyl]triazol-4-yl]methoxy]-4-(methoxymethyl)pyrimidine

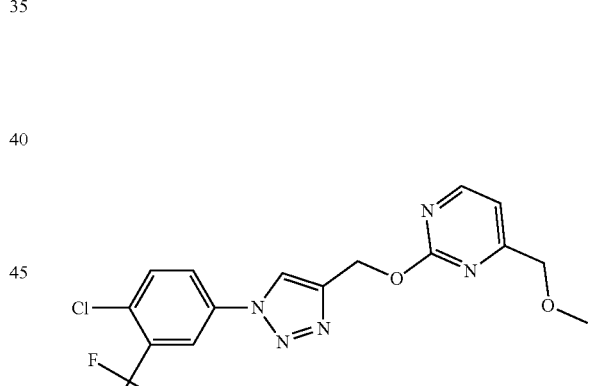

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-4-(methoxymethyl)pyrimidine. MS (ESI): mass calcd. for $C_{17}H_{16}ClF_2N_5O_2$, 395.1; m/z found, 396.0 [M+H]$^+$. $^1$H NMR (400 MHz, CDCl$_3$) δ 8.55 (d, J=5.0 Hz, 1H), 8.18 (t, J=0.7 Hz, 1H), 7.97 (d, J=2.6 Hz, 1H), 7.82-7.76 (m, 1H), 7.61 (d, J=8.6 Hz, 1H), 7.16 (d, J=5.0 Hz, 1H), 5.66 (d, J=0.7 Hz, 2H), 4.50 (d, J=0.7 Hz, 2H), 3.50 (s, 3H), 2.29-1.90 (m, 3H)

Example 535: 2-[[1-[4-Chloro-3-(1,1-difluoroethyl) phenyl]triazol-4-yl]methoxy]-5-(difluoromethyl) pyrimidine

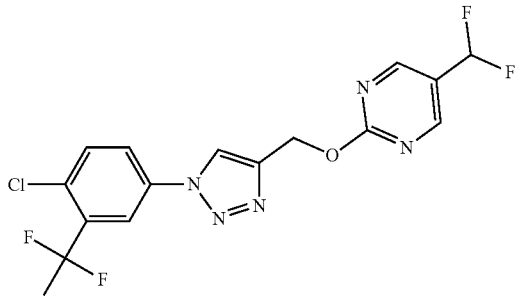 [SMILES: CC(F)(F)c1cc(-n2cc(COc3ncc(C(F)F)cn3)nn2)ccc1Cl]

The title compound was prepared in a manner analogous to Example 155 using (1-(4-chloro-3-(1,1-difluoroethyl) phenyl)-1H-1,2,3-triazol-4-yl)methanol (Intermediate 63) and 2-chloro-4-difluoromethylpyrimidine. MS (ESI): mass calcd. for $C_{15}H_{12}ClF_4N_5O$, 401.1; m/z found, 402.0 [M+H]$^+$. $^1$H NMR (400 MHz, CDCl$_3$) δ 8.75-8.68 (m, 2H), 8.16 (s, 1H), 7.97 (d, J=2.7 Hz, 1H), 7.84-7.76 (m, 1H), 7.62 (d, J=8.6 Hz, 1H), 6.73 (t, J=55.6 Hz, 1H), 5.72 (d, J=0.7 Hz, 2H), 2.09 (t, J=18.5 Hz, 3H).

Example 536: 2-[[1-[4-Chloro-3-(1,1-difluoroethyl) phenyl]triazol-4-yl]methoxy]-4-(difluoromethyl) pyrimidine

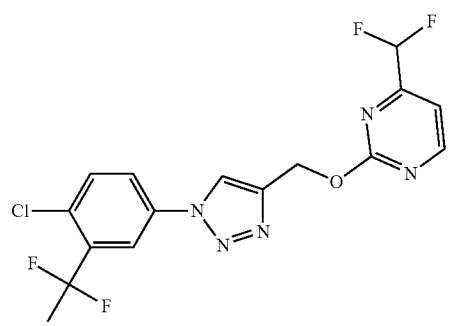 [SMILES: CC(F)(F)c1cc(-n2cc(COc3nccc(C(F)F)n3)nn2)ccc1Cl]

The title compound was prepared in a manner analogous to Example 155 using (1-(4-chloro-3-(1,1-difluoroethyl) phenyl)-1H-1,2,3-triazol-4-yl)methanol (Intermediate 63) and 2-chloro-4-(difluoromethyl)pyrimidine. MS (ESI): mass calcd. for $C_{16}H_{12}ClF_4N_5O$, 401.1; m/z found, 402.0 [M+H]$^+$. $^1$H NMR (500 MHz, CDCl$_3$) δ 8.76 (d, J=4.9 Hz, 1H), 8.19 (s, 1H), 8.07-7.93 (m, 1H), 7.87-7.74 (m, 1H), 7.62 (d, J=8.7 Hz, 1H), 7.31 (d, J=5.0 Hz, 1H), 6.51 (t, J=54.7 Hz, 1H), 5.71 (s, 2H), 2.20-1.99 (m, 3H)

Example 537: 2-[[1-[4-Chloro-3-(1,1-difluoroethyl) phenyl]triazol-4-yl]methoxy]-5-(trifluoromethyl) pyrimidine

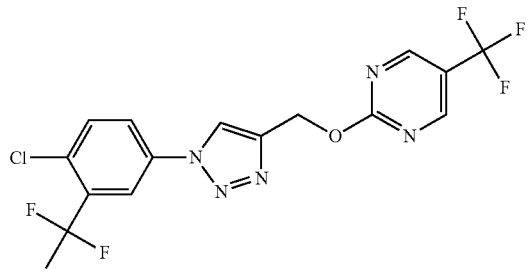 [SMILES: CC(F)(F)c1cc(-n2cc(COc3ncc(C(F)(F)F)cn3)nn2)ccc1Cl]

The title compound was prepared in a manner analogous to Example 155 using (1-(4-chloro-3-(1,1-difluoroethyl) phenyl)-1H-1,2,3-triazol-4-yl)methanol (Intermediate 63) and 2-chloro-5-trifluoromethylpyrimidine. MS (ESI): mass calcd. for $C_{16}H_{11}ClF_5N_5O$, 419.1; m/z found, 420.0 [M+H]$^+$. $^1$H NMR (400 MHz, CDCl$_3$) δ 8.89-8.76 (m, 2H), 8.23-8.08 (m, 1H), 7.97 (d, J=2.6 Hz, 1H), 7.85-7.75 (m, 1H), 7.70-7.57 (m, 1H), 5.74 (d, J=0.7 Hz, 2H), 2.09 (t, J=18.5 Hz, 3H).

Example 538: 2-[[1-[4-Chloro-3-(1,1-difluoroethyl) phenyl]triazol-4-yl]methoxy]-4-(trifluoromethyl) pyrimidine

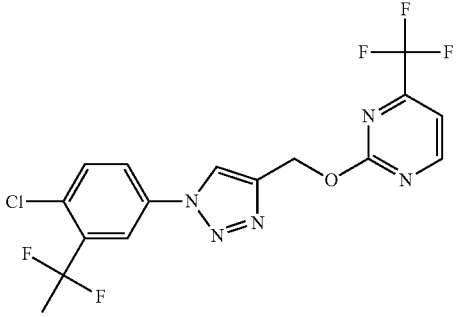 [SMILES: CC(F)(F)c1cc(-n2cc(COc3nccc(C(F)(F)F)n3)nn2)ccc1Cl]

The title compound was prepared in a manner analogous to Example 155 using (1-(4-chloro-3-(1,1-difluoroethyl) phenyl)-1H-1,2,3-triazol-4-yl)methanol (Intermediate 63) and 2-chloro-4-trifluoromethylpyrimidine. MS (ESI): mass calcd. for $C_{16}H_{11}ClF_5N_5O$, 419.1; m/z found, 420.0 [M+H]$^+$. $^1$H NMR (400 MHz, CDCl$_3$) δ 8.83 (d, J=4.8 Hz, 1H), 8.21 (s, 1H), 7.97 (d, J=2.6 Hz, 1H), 7.79 (dd, J=8.6, 2.6 Hz, 1H), 7.62 (d, J=8.6 Hz, 1H), 7.34 (d, J=4.9 Hz, 1H), 5.72 (d, J=0.7 Hz, 2H), 2.09 (t, J=18.5 Hz, 3H).

Example 539: (R/S)-2-[2-[[1-[4-Chloro-3-(1,1-difluoroethyl)phenyl]triazol-4-yl]methoxy]pyrimidin-5-yl]-1,1,1-trifluoro-propan-2-ol

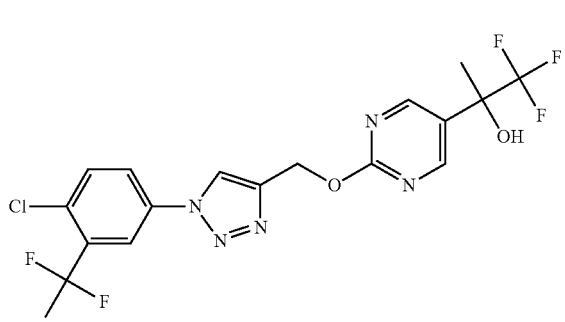 [SMILES: CC(F)(F)c1cc(-n2cc(COc3ncc(C(C)(O)C(F)(F)F)cn3)nn2)ccc1Cl]

The title compound was prepared in a manner analogous to Example 153 using (1-(4-chloro-3-(1,1-difluoroethyl)phenyl)-1H-1,2,3-triazol-4-yl)methanol (Intermediate 63) and 2-(2-chloropyrimidin-5-yl)-1,1,1-trifluoropropan-2-ol, using ACN instead of DMF. MS (ESI): mass calcd. for $C_{18}H_{15}ClF_5N_5O_2$, 463.1; m/z found, 464.0 [M+H]$^+$. $^1$H NMR (500 MHz, CDCl$_3$) δ 8.77-8.71 (s, 2H), 8.20-8.13 (s, 1H), 8.01-7.95 (d, J=2.6 Hz, 1H), 7.83-7.75 (m, 1H), 7.64-7.58 (d, J=8.6 Hz, 1H), 5.72-5.65 (d, J=0.8 Hz, 2H), 2.16-2.03 (t, J=18.5 Hz, 3H), 1.87-1.78 (m, 3H).

Example 540: [2-[[1-[4-Chloro-3-(1,1-difluoroethyl)phenyl]triazol-4-yl]methoxy]pyrimidin-4-yl]methanol

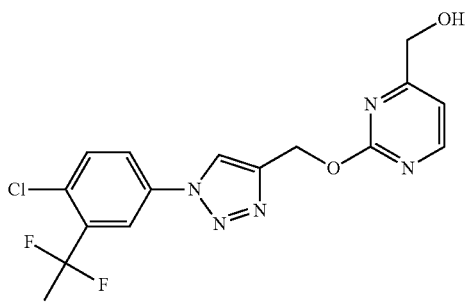 [SMILES: CC(F)(F)c1cc(-n2cc(COc3nccc(CO)n3)nn2)ccc1Cl]

The title compound was prepared in a manner analogous to Example 159, Steps A-B using (1-(4-chloro-3-(1,1-difluoroethyl)phenyl)-1H-1,2,3-triazol-4-yl)methanol (Intermediate 63) and 4-(((tert-butyldimethylsilyl)oxy)methyl)-2-chloropyrimidine (Intermediate 54) in Step A. MS (ESI): mass calcd. for $C_{16}H_{14}ClF_2N_5O_2$, 381.1; m/z found, 382.0 [M+H]$^+$. $^1$H NMR (500 MHz, CDCl$_3$) δ 8.55-8.48 (d, J=5.0 Hz, 1H), 8.21-8.12 (s, 1H), 8.00-7.95 (d, J=2.6 Hz, 1H), 7.84-7.75 (m, 1H), 7.65-7.57 (d, J=8.6 Hz, 1H), 7.07-6.98 (d, J=5.0 Hz, 1H), 5.73-5.62 (d, J=0.7 Hz, 2H), 4.80-4.68 (d, J=0.7 Hz, 2H), 2.18-1.99 (m, 3H)

Example 541: 2-[[1-[4-Chloro-3-(1,1-difluoroethyl)phenyl]triazol-4-yl]methoxy]-4-methoxy-pyrimidine

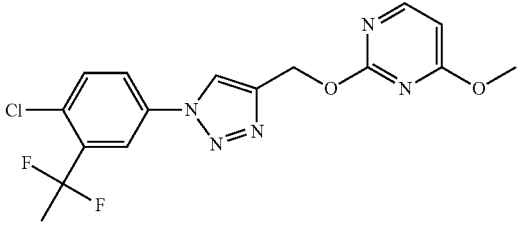 [SMILES: COc1ccnc(OCc2cn(-c3ccc(Cl)c(C(C)(F)F)c3)nn2)n1]

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-4-methoxypyrimidine. MS (ESI): mass calcd. for $C_{16}H_{14}ClF_2N_5O_2$, 381.1; m/z found, 382.0 [M+H]$^+$. $^1$H NMR (400 MHz, CDCl$_3$) δ 8.23 (d, J=5.7 Hz, 1H), 8.15 (s, 1H), 7.97 (d, J=2.6 Hz, 1H), 7.86-7.73 (m, 1H), 7.61 (d, J=8.6 Hz, 1H), 6.43 (d, J=5.7 Hz, 1H), 5.65 (d, J=0.7 Hz, 2H), 3.99 (s, 3H), 2.20-1.99 (m, 3H).

Example 542: 2-[[1-[4-Chloro-3-(1,1-difluoroethyl)phenyl]triazol-4-yl]methoxy]-5-(difluoromethoxy)pyrimidine

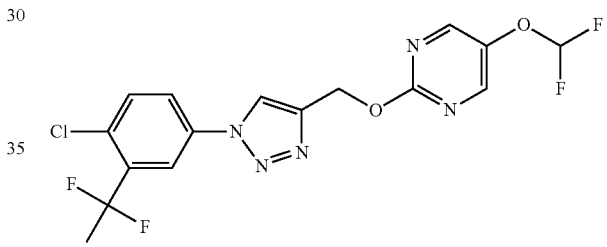

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-5-difluoromethoxypyrimidine. MS (ESI): mass calcd. for $C_{15}H_{12}ClF_4N_5O_2$, 417.1; m/z found, 418.0 [M+H]$^+$. $^1$H NMR (400 MHz, CDCl$_3$) δ 8.53-8.41 (m, 2H), 8.15 (s, 1H), 7.98 (d, J=2.6 Hz, 1H), 7.80 (dd, J=8.6, 2.6 Hz, 1H), 7.62 (d, J=8.6 Hz, 1H), 6.53 (t, J=71.9 Hz, 1H), 5.66 (d, J=0.7 Hz, 2H), 2.09 (t, J=18.5 Hz, 3H).

Example 543: 5-Chloro-2-[[1-[4-chloro-3-(1,1-difluoroethyl)phenyl]triazol-4-yl]methoxy]-4-methyl-pyrimidine

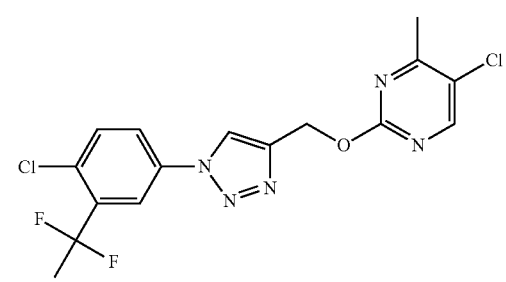 [SMILES: Cc1nc(OCc2cn(-c3ccc(Cl)c(C(C)(F)F)c3)nn2)ncc1Cl]

The title compound was prepared in a manner analogous to Example 155 using (1-(4-chloro-3-(1,1-difluoroethyl)phenyl)-1H-1,2,3-triazol-4-yl)methanol (Intermediate 63) and 2,5-dichloro-4-methylpyrimidine. MS (ESI): mass calcd. for $C_{16}H_{13}Cl_2F_2N_5O$, 399.0; m/z found, 400.0 [M+H]$^+$. $^1$H NMR (400 MHz, CDCl$_3$) δ 8.39 (s, 1H), 8.14 (s, 1H), 7.97 (d, J=2.6 Hz, 1H), 7.79 (dd, J=8.6, 2.6 Hz, 1H), 7.61 (d, J=8.6 Hz, 1H), 5.69-5.57 (m, 2H), 2.57 (s, 3H), 2.09 (t, J=18.5 Hz, 3H).

Example 544: 2-[[1-[4-Chloro-3-(1,1-difluoroethyl)phenyl]triazol-4-yl]methoxy]-5-fluoro-4-methyl-pyrimidine

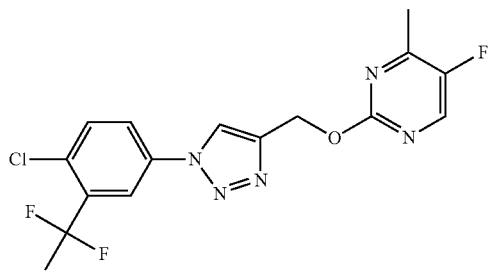 [SMILES: Cc1nc(OCc2cn(-c3ccc(Cl)c(C(C)(F)F)c3)nn2)ncc1F]

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-5-fluoro-4-methylpyrimidine. MS (ESI): mass calcd. for $C_{16}H_{13}ClF_3N_5O$, 383.1; m/z found, 384.0 [M+H]$^+$. $^1$H NMR (400 MHz, CDCl$_3$) δ 8.26 (d, J=1.2 Hz, 1H), 8.14 (t, J=0.7 Hz, 1H), 7.97 (d, J=2.6 Hz, 1H), 7.86-7.75 (m, 1H), 7.61 (d, J=8.6 Hz, 1H), 5.62 (d, J=0.7 Hz, 2H), 2.50 (d, J=2.5 Hz, 3H), 2.09 (t, J=18.5 Hz, 3H).

Example 545: 2-[[1-[4-Chloro-3-(1,1-difluoroethyl)phenyl]triazol-4-yl]methoxy]-4,5-dimethyl-pyrimidine

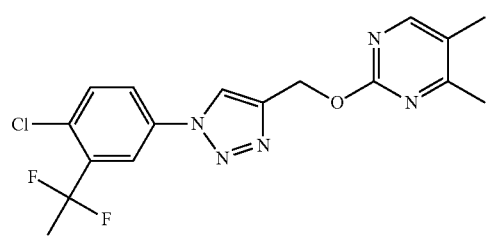 [SMILES: Cc1cnc(OCc2cn(-c3ccc(Cl)c(C(C)(F)F)c3)nn2)nc1C]

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-4,5-dimethylpyrimidine. MS (ESI): mass calcd. for $C_{17}H_{16}ClF_2N_5O$, 379.1; m/z found, 380.1 [M+H]$^+$. $^1$H NMR (400 MHz, CDCl$_3$) δ 8.20 (d, J=0.9 Hz, 1H), 8.15 (s, 1H), 7.97 (d, J=2.6 Hz, 1H), 7.79 (dd, J=8.6, 2.6 Hz, 1H), 7.61 (d, J=8.6 Hz, 1H), 5.63 (d, J=0.8 Hz, 2H), 2.44 (s, 3H), 2.20 (s, 3H), 2.09 (t, J=18.5 Hz, 3H).

Example 546: 2-[[1-[4-Chloro-3-(1,1-difluoroethyl)phenyl]triazol-4-yl]methoxy]-4,6-dimethyl-pyrimidine

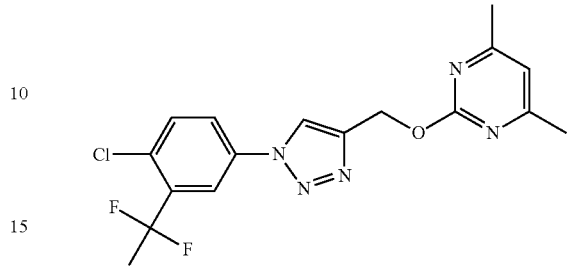

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-4,6-dimethylpyrimidine. MS (ESI): mass calcd. for $C_{17}H_{16}ClF_2N_5O$, 379.1; m/z found, 380.1 [M+H]$^+$. $^1$H NMR (400 MHz, CDCl$_3$) δ 8.16 (t, J=0.8 Hz, 1H), 7.97 (d, J=2.6 Hz, 1H), 7.79 (dd, J=8.6, 2.6 Hz, 1H), 7.61 (d, J=8.7 Hz, 1H), 6.73 (s, 1H), 5.65 (d, J=0.8 Hz, 2H), 2.52-2.31 (m, 6H), 2.09 (t, J=18.5 Hz, 3H).

Example 547: 2-[[1-[4-Chloro-3-(1,1-difluoroethyl)phenyl]triazol-4-yl]methoxy]pyrimidin-4-amine

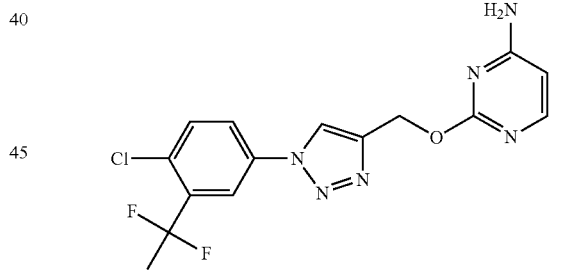

The title compound was prepared in a manner analogous to Example 153 using (1-(4-chloro-3-(1,1-difluoroethyl)phenyl)-1H-1,2,3-triazol-4-yl)methanol (Intermediate 63) and 2-chloropyrimidin-4-amine, using ACN instead of DMF. MS (ESI): mass calcd. for $C_{15}H_{13}ClF_2N_6O$, 366.1; m/z found, 367.0 [M+H]$^+$. $^1$H NMR (400 MHz, CDCl$_3$) δ 8.21-8.11 (t, J=0.8 Hz, 1H), 8.11-8.02 (d, J=5.7 Hz, 1H), 8.00-7.95 (d, J=2.6 Hz, 1H), 7.86-7.72 (m, 1H), 7.66-7.54 (d, J=8.6 Hz, 1H), 6.25-6.00 (d, J=5.7 Hz, 1H), 5.70-5.44 (d, J=0.7 Hz, 2H), 5.20-4.99 (s, 2H), 2.21-1.96 (t, J=18.5 Hz, 3H).

Example 548: 2-[[1-[4-Chloro-3-(1,1-difluoroethyl)phenyl]triazol-4-yl]methoxy]-N-methyl-pyrimidin-4-amine

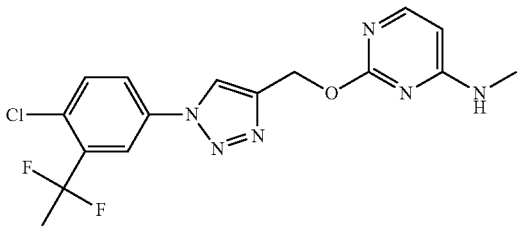 [SMILES: CNc1ccnc(OCc2cn(-c3ccc(Cl)c(C(C)(F)F)c3)nn2)n1]

The title compound was prepared in a manner analogous to Example 163, Steps B-C using tert-butyl (2-chloropyrimidin-4-yl)(methyl)carbamate (Intermediate 55) and (1-(4-chloro-3-(1,1-difluoroethyl)phenyl)-1H-1,2,3-triazol-4-yl)methanol (Intermediate 63). MS (ESI): mass calcd. for $C_{16}H_{15}ClF_2N_6O$, 380.1; m/z found, 381.0 [M+H]$^+$. $^1$H NMR (500 MHz, CDCl$_3$) δ 8.20-8.16 (s, 1H), 8.07-7.96 (m, 2H), 7.82-7.76 (m, 1H), 7.64-7.57 (d, J=8.6 Hz, 1H), 6.10-6.07 (d, J=5.9 Hz, 1H), 5.67-5.57 (s, 2H), 5.40-5.26 (s, 1H), 3.05-2.91 (s, 3H), 2.18-2.00 (t, J=18.5 Hz, 3H).

Example 549: 2-[[1-[4-Chloro-3-(1,1-difluoroethyl)phenyl]triazol-4-yl]methoxy]-5-fluoro-N-methyl-pyrimidin-4-amine

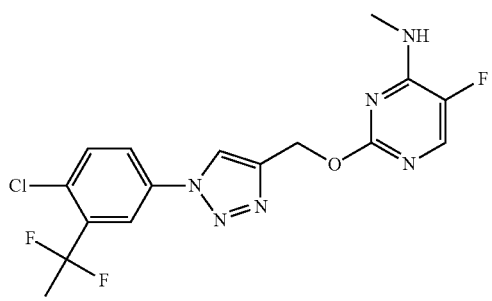 [SMILES: CNc1nc(OCc2cn(-c3ccc(Cl)c(C(C)(F)F)c3)nn2)ncc1F]

The title compound was prepared in a manner analogous to Example 163, Steps B-C using (1-(4-chloro-3-(1,1-difluoroethyl)phenyl)-1H-1,2,3-triazol-4-yl)methanol (Intermediate 63) and 2-chloro-5-fluoro-N-methyl-N-((2-(trimethylsilyl)ethoxy)methyl)pyrimidin-4-amine (Intermediate 59) in step A. MS (ESI): mass calcd. for $C_{15}H_{14}ClF_3N_6O$, 398.1; m/z found, 399.0 [M+H]$^+$. $^1$H NMR (400 MHz, CDCl$_3$) δ 8.16-8.11 (s, 1H), 8.01-7.94 (d, J=2.6 Hz, 1H), 7.86-7.73 (m, 2H), 7.66-7.56 (d, J=8.6 Hz, 1H), 5.63-5.51 (s, 2H), 5.19-5.03 (s, 1H), 3.15-3.04 (d, J=5.0 Hz, 3H), 2.21-1.97 (m, 3H).

Example 550: 1-[2-[[1-[4-Chloro-3-(1,1-difluoroethyl)phenyl]triazol-4-yl]methoxy]pyrimidin-5-yl]ethanone

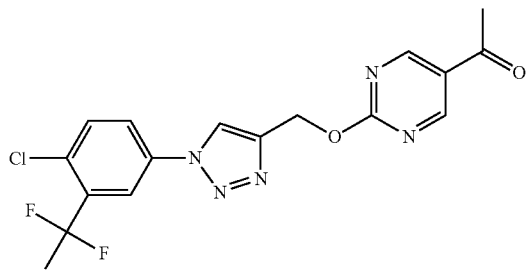 [SMILES: CC(=O)c1cnc(OCc2cn(-c3ccc(Cl)c(C(C)(F)F)c3)nn2)nc1]

The title compound was prepared in a manner analogous to Example 155 using (1-(4-chloro-3-(1,1-difluoroethyl)phenyl)-1H-1,2,3-triazol-4-yl)methanol (Intermediate 63) and 1-(2-chloropyrimidin-5-yl)ethan-1-one. MS (ESI): mass calcd. for $C_{17}H_{14}ClF_2N_5O_2$, 393.1; m/z found, 394.0 [M+H]$^+$. $^1$H NMR (400 MHz, CDCl$_3$) δ 9.18-9.05 (m, 2H), 8.25-8.14 (s, 1H), 8.04-7.92 (m, 1H), 7.88-7.75 (m, 1H), 7.70-7.58 (m, 1H), 5.83-5.70 (m, 2H), 2.69-2.57 (m, 3H), 2.23-2.00 (m, 3H).

Example 551: (R/S)-1-[2-[[1-[4-Chloro-3-(1,1-difluoroethyl)phenyl]triazol-4-yl]methoxy]pyrimidin-5-yl]ethanol

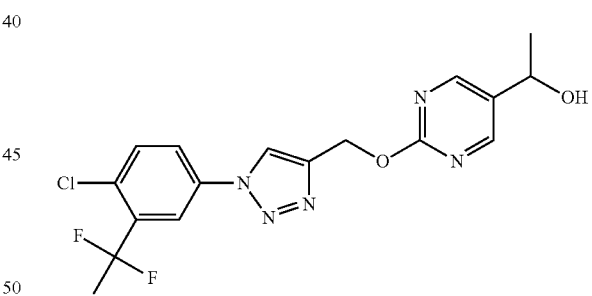

The title compound was prepared in a manner analogous to Example 157 using 1-(2-((1-(4-chloro-3-(1,1-difluoroethyl)phenyl)-1H-1,2,3-triazol-4-yl)methoxy)pyrimidin-5-yl)ethan-1-one (Example 550). MS (ESI): mass calcd. for $C_{17}H_{16}ClF_2N_5O_2$, 395.1; m/z found, 396.0 [M+H]$^+$. $^1$H NMR (400 MHz, CDCl$_3$) δ 8.62-8.55 (d, J=0.6 Hz, 2H), 8.18-8.14 (t, J=0.7 Hz, 1H), 8.00-7.96 (d, J=2.6 Hz, 1H), 7.83-7.76 (m, 1H), 7.65-7.57 (d, J=8.6 Hz, 1H), 5.71-5.62 (d, J=0.8 Hz, 2H), 5.03-4.92 (q, J=6.5 Hz, 1H), 2.20-2.01 (t, J=18.4 Hz, 3H), 1.62-1.50 (d, J=6.5 Hz, 3H).

Example 552: 2-[[1-[4-Chloro-3-(1,1-difluoroethyl)phenyl]triazol-4-yl]methoxy]-5-cyclopropyl-pyrimidine

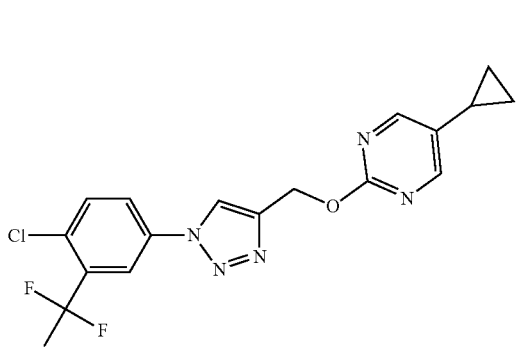 [SMILES: CC(F)(F)c1cc(-n2cc(COc3ncc(C4CC4)cn3)nn2)ccc1Cl]

The title compound was prepared in a manner analogous to Example 155 using (1-(4-chloro-3-(1,1-difluoroethyl)phenyl)-1H-1,2,3-triazol-4-yl)methanol (Intermediate 63) and 2-chloro-5-cyclopropylpyrimidine. MS (ESI): mass calcd. for $C_{18}H_{16}ClF_2N_5O$, 391.1; m/z found, 392.1 [M+H]$^+$. $^1$H NMR (400 MHz, CDCl$_3$) δ 8.32 (d, J=0.5 Hz, 2H), 8.14 (t, J=0.7 Hz, 1H), 7.97 (d, J=2.6 Hz, 1H), 7.83-7.77 (m, 1H), 7.61 (d, J=8.6 Hz, 1H), 5.63 (d, J=0.7 Hz, 2H), 2.09 (t, J=18.5 Hz, 3H), 1.88-1.78 (m, 1H), 1.07-0.98 (m, 2H), 0.74-0.67 (m, 2H)

Example 553: 2-[[1-[4-Chloro-3-(1,1-difluoroethyl)phenyl]triazol-4-yl]methoxy]-4-pyrrolidin-1-yl-pyrimidine

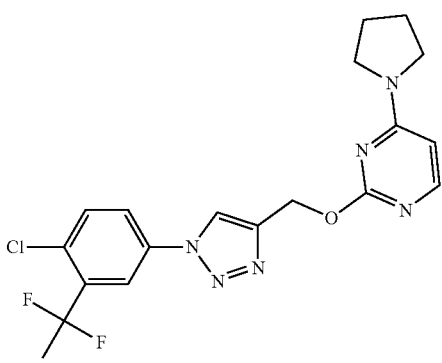 [SMILES: CC(F)(F)c1cc(-n2cc(COc3nccc(N4CCCC4)n3)nn2)ccc1Cl]

The title compound was prepared in a manner analogous to Example 153 using (1-(4-chloro-3-(1,1-difluoroethyl)phenyl)-1H-1,2,3-triazol-4-yl)methanol (Intermediate 63) and 2-chloro-4-(pyrrolidin-1-yl)pyrimidine, using ACN instead of DMF. MS (ESI): mass calcd. for $C_{19}H_{19}ClF_2N_6O$, 420.1; m/z found, 421.0 [M+H]$^+$. $^1$H NMR (400 MHz, CDCl$_3$) δ 8.16-8.11 (t, J=0.7 Hz, 1H), 8.02-7.98 (d, J=5.9 Hz, 1H), 7.98-7.96 (d, J=2.6 Hz, 1H), 7.82-7.74 (dd, J=8.6, 2.7 Hz, 1H), 7.64-7.55 (d, J=8.6 Hz, 1H), 6.03-5.97 (d, J=5.9 Hz, 1H), 5.63-5.57 (d, J=0.8 Hz, 2H), 3.72-3.53 (m, 2H), 3.43-3.26 (m, 2H), 2.17-1.92 (m, 7H).

Example 554: 2-[[1-[3-(1,1-Difluoroethyl)-4-fluorophenyl]triazol-4-yl]methoxy]pyridine

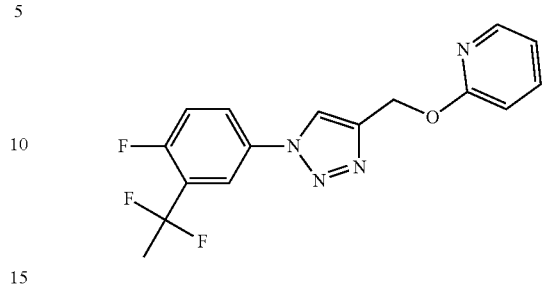

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloropyridine. MS (ESI): mass calcd. for $C_{16}H_{13}F_3N_4O$, 334.1; m/z found, 335.1 [M+H]$^+$. $^1$H NMR (400 MHz, CDCl$_3$) δ 8.29-8.12 (m, 1H), 8.13-7.99 (m, 1H), 7.96-7.80 (m, 2H), 7.68-7.53 (m, 1H), 7.42-7.22 (m, 1H), 7.05-6.70 (m, 2H), 5.72-5.50 (m, 2H), 2.23-1.82 (m, 3H)

Example 555: 2-[[1-[3-(1,1-Difluoroethyl)-4-fluorophenyl]triazol-4-yl]methoxy]-3-fluoro-pyridine

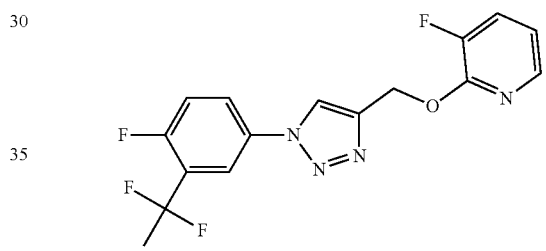

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloro-3-fluoropyridine. MS (ESI): mass calcd. for $C_{16}H_{12}F_4N_4O$, 352.1; m/z found, 353.1 [M+H]$^+$. $^1$H NMR (400 MHz, CDCl$_3$) δ 8.11 (s, 1H), 8.02-7.96 (m, 1H), 7.95-7.87 (m, 1H), 7.88-7.81 (m, 1H), 7.43-7.26 (m, 2H), 6.98-6.87 (m, 1H), 5.68 (d, J=2.0 Hz, 2H), 2.05 (t, J=18.4, 1.6 Hz, 3H).

Example 556: 2-[[1-[3-(1,1-Difluoroethyl)-4-fluorophenyl]triazol-4-yl]methoxy]-6-methyl-pyridine

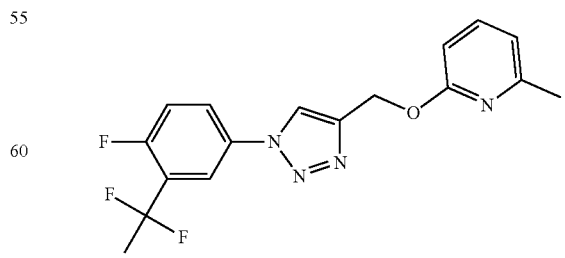

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloro-6-methylpyridine. MS (ESI): mass calcd. for $C_{17}H_{15}F_3N_4O$, 348.1; m/z found, 349.1 [M+H]$^+$. $^1$H NMR (400 MHz, CDCl$_3$) δ 8.09-8.03 (m, 1H), 7.93-7.85 (m, 1H), 7.86-7.78 (m, 1H), 7.54-7.41 (m, 1H), 7.36-7.26 (m, 1H), 6.81-6.73 (m, 1H), 6.64-6.51 (m, 1H), 5.59 (d, J=0.7 Hz, 2H), 2.48 (t, J=0.6 Hz, 3H), 2.05 (td, J=18.6, 1.2 Hz, 3H).

Example 557: 2-[[1-[3-(1,1-Difluoroethyl)-4-fluorophenyl]triazol-4-yl]methoxy]-4-methyl-pyridine

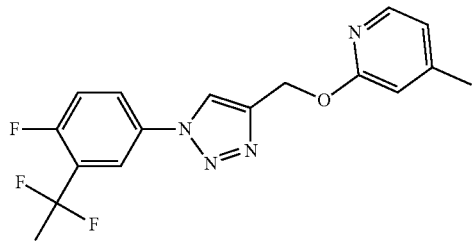 [SMILES: Cc1ccnc(OCc2cn(-c3ccc(F)c(C(C)(F)F)c3)nn2)c1]

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloro-4-methylpyridine. MS (ESI): mass calcd. for $C_{17}H_{15}F_3N_4O$, 348.1; m/z found, 349.0 [M+H]$^+$. $^1$H NMR (400 MHz, CDCl$_3$) δ 8.15-8.01 (m, 1H), 7.97-7.76 (m, 2H), 7.39-7.22 (m, 2H), 6.83-6.58 (m, 2H), 5.68-5.49 (m, 2H), 2.31 (s, 3H), 2.20-1.90 (m, 3H).

Example 558: 2-[[1-[3-(1,1-Difluoroethyl)-4-fluorophenyl]triazol-4-yl]methoxy]-5-methyl-pyridine

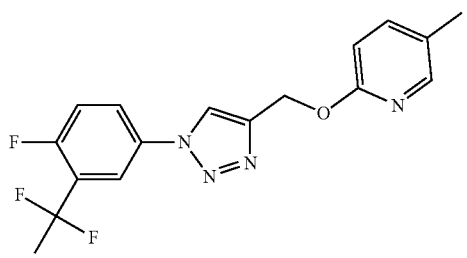 [SMILES: Cc1ccc(OCc2cn(-c3ccc(F)c(C(C)(F)F)c3)nn2)nc1]

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloro-5-methylpyridine. MS (ESI): mass calcd. for $C_{17}H_{15}F_3N_4O$, 348.1; m/z found, 349.0 [M+H]$^+$. $^1$H NMR (400 MHz, CDCl$_3$) δ 8.13-8.04 (m, 1H), 8.05-7.96 (m, 1H), 7.96-7.75 (m, 2H), 7.49-7.35 (m, 1H), 7.36-7.21 (m, 1H), 6.81-6.63 (m, 1H), 5.57 (d, J=4.0 Hz, 2H), 2.27 (d, J=3.6 Hz, 3H), 2.05 (t, 3H).

Example 559: 2-[[1-[3-(1,1-Difluoroethyl)-4-fluorophenyl]triazol-4-yl]methoxy]-5-(trifluoromethyl)pyridine

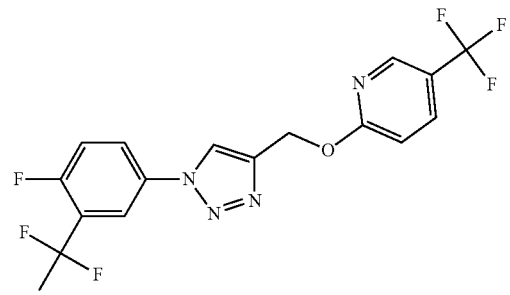 [SMILES: CC(F)(F)c1cc(-n2cc(COc3ccc(C(F)(F)F)cn3)nn2)ccc1F]

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloro-5-trifluoromethylpyridine. MS (ESI): mass calcd. for $C_{17}H_{12}F_6N_4O$, 402.1; m/z found, 403.0 [M+H]$^+$. $^1$H NMR (400 MHz, CDCl$_3$) δ 8.60-8.39 (m, 1H), 8.23-8.02 (m, 1H), 8.01-7.74 (m, 2H), 7.43-7.22 (m, 2H), 7.03-6.84 (m, 1H), 5.65 (s, 2H), 2.05 (t, J=18.4 Hz, 3H).

Example 560: 6-[[1-[3-(1,1-Difluoroethyl)-4-fluorophenyl]triazol-4-yl]methoxy]-2,3-dimethyl-pyridine

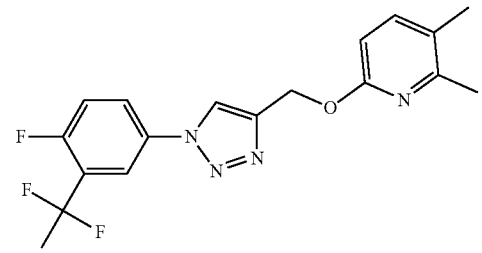 [SMILES: Cc1ccc(OCc2cn(-c3ccc(F)c(C(C)(F)F)c3)nn2)nc1C]

The title compound was prepared in a manner analogous to Example 158 using (1-(3-(1,1-difluoroethyl)-4-fluorophenyl)-1H-1,2,3-triazol-4-yl)methanol (Intermediate 11) and 2-chloro-5,6-dimethylpyridine. MS (ESI): mass calcd. for $C_{18}H_{17}F_3N_4O$, 362.1; m/z found, 363.1 [M+H]$^+$. $^1$H NMR (400 MHz, CDCl$_3$) δ 8.06 (s, 1H), 7.98-7.76 (m, 2H), 7.42-7.26 (m, 2H), 6.64-6.51 (m, 1H), 5.57 (d, J=2.5 Hz, 2H), 2.43 (s, 3H), 2.20 (s, 3H), 2.03 (t, 3H).

Example 561: 3-[[1-[3-(1,1-Difluoroethyl)-4-fluorophenyl]triazol-4-yl]methoxy]-2-methoxy-pyridine

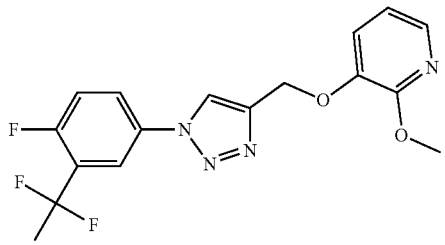 [SMILES: COc1ncccc1OCc1cn(-c2ccc(F)c(C(C)(F)F)c2)nn1]

The title compound was prepared in a manner analogous to Example 153, using 4-(chloromethyl)-1-(3-(1,1-difluoroethyl)-4-fluorophenyl)-1H-1,2,3-triazole (Intermediate 20, product from Step A) and 2-methoxypyridin-3-ol (24 mg, 0.189 mmol) and stirred at rt overnight. MS (ESI): mass calcd. for $C_{17}H_{15}F_3N_4O_2$, 364.1; m/z found, 365.1 $[M+H]^+$. $^1$H NMR (500 MHz, CDCl$_3$) δ 8.09 (t, J=0.7 Hz, 1H), 7.92-7.88 (m, 1H), 7.86-7.80 (m, 1H), 7.81-7.77 (m, 1H), 7.34-7.28 (m, 2H), 6.91-6.78 (m, 1H), 5.46-5.28 (m, 2H), 4.03 (s, 3H), 2.05 (t, J=18.6, 1.2 Hz, 3H).

Example 562: 2-[[1-[3-(1,1-Difluoroethyl)-4-fluorophenyl]triazol-4-yl]methoxy]-5-(difluoromethyl)pyrimidine

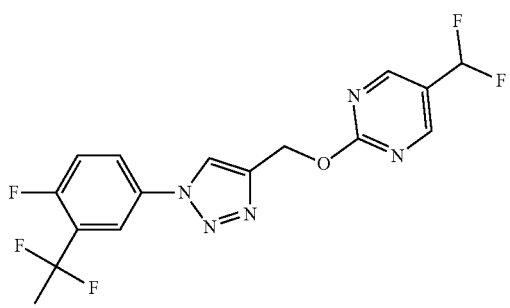 [SMILES: CC(F)(F)c1cc(-n2cc(COc3ncc(C(F)F)cn3)nn2)ccc1F]

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-5-(difluoromethyl)pyrimidine. MS (ESI): mass calcd. for $C_{16}H_{12}F_8N_5O$, 385.1; m/z found, 386.1 $[M+H]^+$. $^1$H NMR (500 MHz, CDCl$_3$) δ 8.76-8.67 (m, 2H), 8.13 (s, 1H), 7.94-7.87 (m, 1H), 7.87-7.81 (m, 1H), 7.32 (t, J=9.4 Hz, 1H), 6.73 (t, J=55.6 Hz, 1H), 5.78-5.68 (m, 2H), 2.12-1.96 (m, 3H).

Example 563: 2-[[1-[3-(1,1-Difluoroethyl)-4-fluorophenyl]triazol-4-yl]methoxy]-4-(difluoromethyl)pyrimidine

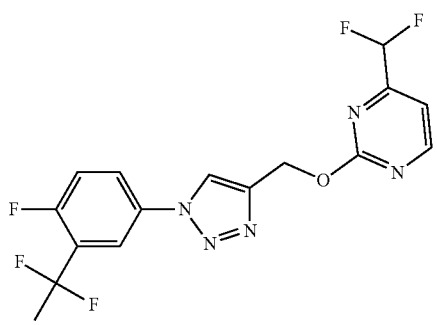 [SMILES: CC(F)(F)c1cc(-n2cc(COc3nccc(C(F)F)n3)nn2)ccc1F]

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-4-(difluoromethyl)pyrimidine. MS (ESI): mass calcd. for $C_{16}H_{12}F_5N_5O$, 385.1; m/z found, 386.1 $[M+H]^+$. $^1$H NMR (500 MHz, CDCl$_3$) δ 8.76 (d, J=4.9 Hz, 1H), 8.16 (t, J=0.7 Hz, 1H), 7.93-7.87 (m, 1H), 7.87-7.79 (m, 1H), 7.36-7.28 (m, 2H), 6.50 (t, J=54.7 Hz, 1H), 5.70 (d, J=0.7 Hz, 2H), 2.05 (td, J=18.6, 1.1 Hz, 3H)

Example 564: 2-[[1-[3-(1,1-Difluoroethyl)-4-fluorophenyl]triazol-4-yl]methoxy]-4-(trifluoromethyl)pyrimidine

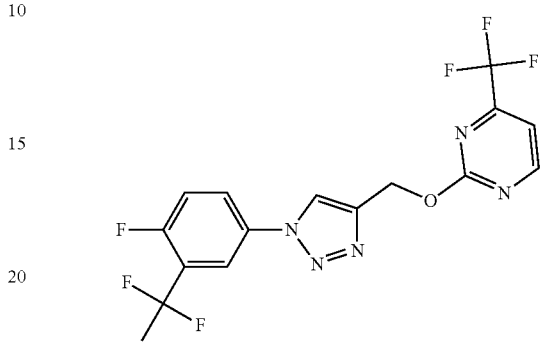

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-3-trifluoromethylpyrimidine. MS (ESI): mass calcd. for $C_{16}H_{11}F_6N_5O$, 403.1; m/z found, 404.0 $[M+H]^+$. $^1$H NMR (400 MHz, CDCl$_3$) δ 8.83 (d, J=4.8 Hz, 1H), 8.18 (s, 1H), 7.95-7.86 (m, 1H), 7.87-7.78 (m, 1H), 7.38-7.28 (m, 2H), 5.78-5.66 (m, 2H), 2.05 (t, J=18.6, 1.2 Hz, 3H).

Example 565: (R/S)-2-[2-[[1-[3-(1,1-Difluoroethyl)-4-fluoro-phenyl]triazol-4-yl]methoxy]pyrimidin-5-yl]-1,1,1-trifluoro-propan-2-ol

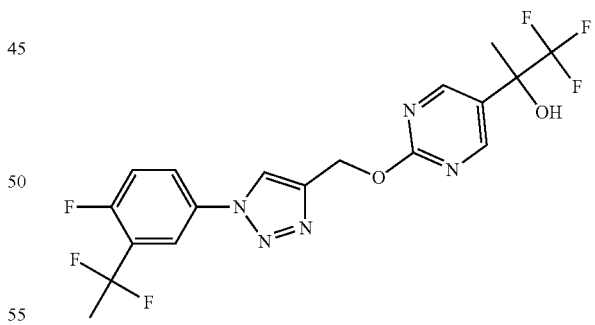

The title compound was prepared in a manner analogous to Example 153 using (1-(3-(1,1-difluoroethyl)-4-fluorophenyl)-1H-1,2,3-triazol-4-yl)methanol (Intermediate 11) and 2-(2-chloropyrimidin-5-yl)-1,1,1-trifluoropropan-2-ol, using ACN instead of DMF. MS (ESI): mass calcd. for $C_{18}H_{15}F_6N_5O_2$, 447.1; m/z found, 448.0 $[M+H]^+$. $^1$H NMR (500 MHz, CDCl$_3$) δ 8.79-8.70 (s, 2H), 8.17-8.08 (t, J=0.7 Hz, 1H), 7.94-7.88 (m, 1H), 7.88-7.78 (m, 1H), 7.35-7.27 (m, 1H), 5.74-5.65 (d, J=0.7 Hz, 2H), 2.77-2.56 (s, 1H), 2.11-1.99 (m, 3H), 1.86-1.79 (m, 3H)

Example 566: 2-[2-[[1-[3-(1,1-Difluoroethyl)-4-fluoro-phenyl]triazol-4-yl]methoxy]pyrimidin-5-yl]propan-2-ol

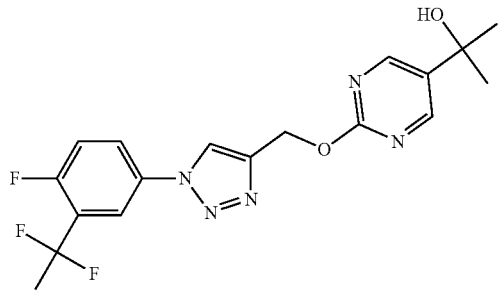 [SMILES: CC(C)(O)c1cnc(OCc2cn(-c3ccc(F)c(C(C)(F)F)c3)nn2)nc1]

The title compound was prepared in a manner analogous to Example 155 using (1-(3-(1,1-difluoroethyl)-4-fluorophenyl)-1H-1,2,3-triazol-4-yl)methanol (Intermediate 11) and 2-(2-chloropyrimidin-5-yl)propan-2-ol. MS (ESI): mass calcd. for $C_{18}H_{18}F_3N_5O_2$, 393.1; m/z found, 394.0 [M+H]$^+$. $^1$H NMR (500 MHz, CDCl$_3$) δ 8.68 (s, 2H), 8.13 (s, 1H), 7.95-7.79 (m, 2H), 7.37-7.27 (m, 1H), 5.67 (d, J=0.7 Hz, 2H), 2.15-1.97 (m, 3H), 1.63 (s, 6H).

Example 567: 2-[[1-[3-(1,1-Difluoroethyl)-4-fluoro-phenyl]triazol-4-yl]methoxy]-5-(1-methoxy-1-methyl-ethyl)pyrimidine

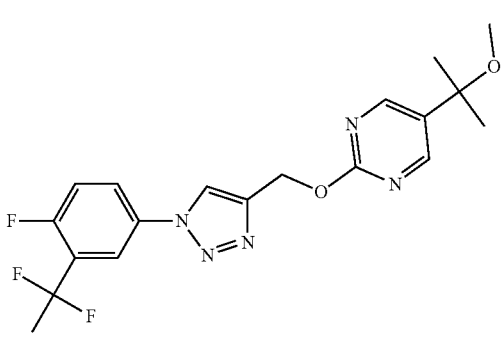 [SMILES: COC(C)(C)c1cnc(OCc2cn(-c3ccc(F)c(C(C)(F)F)c3)nn2)nc1]

The title compound was prepared in a manner analogous to Example 311 using 2-(2-((1-(3-(1,1-difluoroethyl)-4-fluorophenyl)-1H-1,2,3-triazol-4-yl)methoxy)pyrimidin-5-yl)propan-2-ol (Example 566). MS (ESI): mass calcd. for $C_{19}H_{20}F_3N_5O_2$, 407.2; m/z found, 408.1 [M+H]$^+$. $^1$H NMR (500 MHz, CDCl$_3$) δ 8.62-8.56 (s, 2H), 8.16-8.09 (t, J=0.7 Hz, 1H), 7.93-7.87 (m, 1H), 7.87-7.80 (m, 1H), 7.35-7.28 (m, 1H), 5.72-5.63 (d, J=0.7 Hz, 2H), 3.18-3.09 (s, 3H), 2.14-1.97 (m, 3H), 1.56-1.55 (s, 6H)

Example 568: [2-[[1-[3-(1,1-Difluoroethyl)-4-fluoro-phenyl]triazol-4-yl]methoxy]pyrimidin-4-yl]methanol

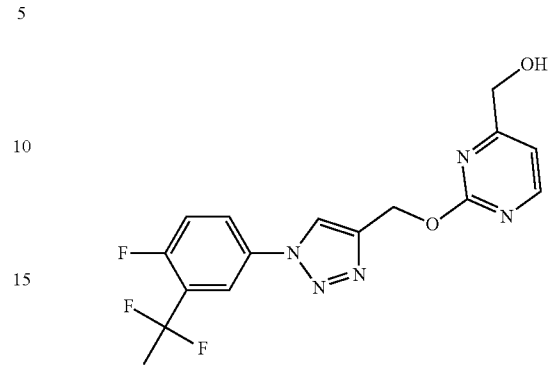

The title compound was prepared in a manner analogous to Example 159, Steps A-B using (1-(3-(1,1-difluoroethyl)-4-fluorophenyl)-1H-1,2,3-triazol-4-yl)methanol (Intermediate 11) and 4-(((tert-butyldimethylsilyl)oxy)methyl)-2-chloropyrimidine (Intermediate 54) in Step A. MS (ESI): mass calcd. for $C_{16}H_{14}F_3N_5O_2$, 365.1; m/z found, 366.1 [M+H]$^+$. $^1$H NMR (500 MHz, CDCl$_3$) δ 8.60-8.43 (d, J=5.0 Hz, 1H), 8.19-8.11 (s, 1H), 7.95-7.87 (dd, J=6.2, 2.7 Hz, 1H), 7.87-7.76 (m, 1H), 7.34-7.28 (m, 1H), 7.07-6.94 (d, J=5.0 Hz, 1H), 5.74-5.62 (d, J=0.7 Hz, 2H), 4.84-4.67 (d, J=0.8 Hz, 2H), 2.15-1.92 (m, 3H).

Example 569: 2-[[1-[3-(1,1-Difluoroethyl)-4-fluoro-phenyl]triazol-4-yl]methoxy]-5-(methoxymethyl)pyrimidine

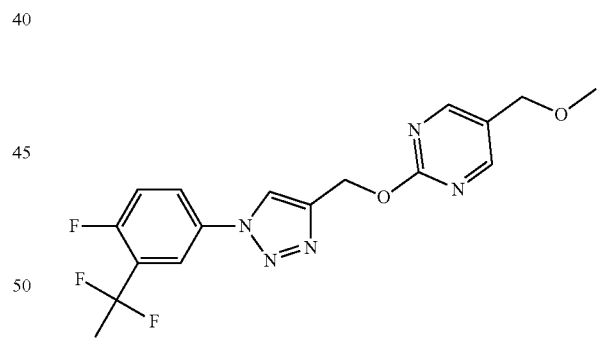

The title compound was prepared in a manner analogous to Example 153 using (1-(3-(1,1-difluoroethyl)-4-fluorophenyl)-1H-1,2,3-triazol-4-yl)methanol (Intermediate 11) and 2-chloro-5-(methoxymethyl)pyrimidine, using ACN instead of DMF. MS (ESI): mass calcd. for $C_{17}H_{16}F_3N_5O_2$, 379.1; m/z found, 380.1 [M+H]$^+$. $^1$H NMR (500 MHz, CDCl$_3$) δ 8.56-8.52 (s, 2H), 8.14-8.09 (t, J=0.7 Hz, 1H), 7.92-7.87 (m, 1H), 7.87-7.78 (m, 1H), 7.35-7.27 (m, 1H), 5.70-5.64 (d, J=0.7 Hz, 2H), 4.45-4.37 (s, 2H), 3.45-3.39 (s, 3H), 2.12-1.97 (m, 3H)

Example 570: 2-[[1-[3-(1,1-Difluoroethyl)-4-fluorophenyl]triazol-4-yl]methoxy]-4-(methoxymethyl)pyrimidine

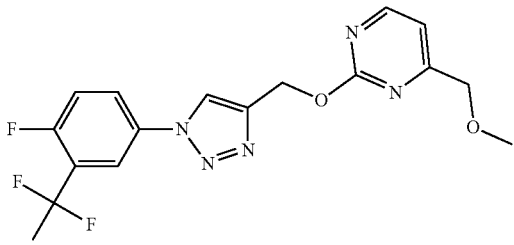 [SMILES: COCc1ccnc(OCc2cn(-c3ccc(F)c(C(C)(F)F)c3)nn2)n1]

The title compound was prepared in a manner analogous to Example 155 using (1-(3-(1,1-difluoroethyl)phenyl)-1H-1,2,3-triazol-4-yl)methanol and 2-chloro-4-(methoxymethyl)pyrimidine. MS (ESI): mass calcd. for $C_{17}H_{16}F_3N_5O_2$, 379.1; m/z found, 380.1 [M+H]$^+$. $^1$H NMR (400 MHz, CDCl$_3$) δ 8.55 (d, J=5.0 Hz, 1H), 8.15 (t, J=0.8 Hz, 1H), 7.92-7.86 (m, 1H), 7.86-7.80 (m, 1H), 7.31 (t, J=10.0, 8.8 Hz, 1H), 7.16 (d, J=5.1 Hz, 1H), 5.66 (d, J=0.7 Hz, 2H), 4.50 (d, J=0.7 Hz, 2H), 3.50 (s, 3H), 2.05 (t, J=18.6, 1.2 Hz, 3H).

Example 571: [2-[[1-[3-(1,1-difluoroethyl)-4-fluorophenyl]triazol-4-yl]methoxy]pyrimidin-5-yl]methanol

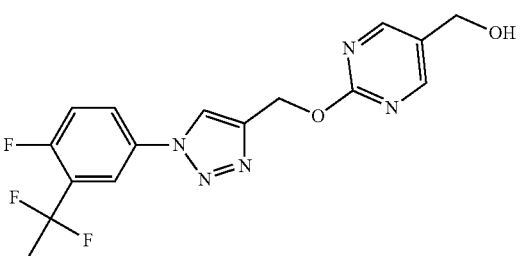 [SMILES: CC(F)(F)c1cc(-n2cc(COc3ncc(CO)cn3)nn2)ccc1F]

The title compound was prepared in a manner analogous to Example 159, Steps A-B using (1-(3-(1,1-difluoroethyl)-4-fluorophenyl)-1H-1,2,3-triazol-4-yl)methanol (Intermediate 11) and 5-(((tert-butyldimethylsilyl)oxy)methyl)-2-chloropyrimidine (Intermediate 53) in Step A. MS (ESI): mass calcd. for $C_{16}H_{14}F_3N_5O_2$, 365.1; m/z found, 366.1 [M+H]$^+$. $^1$H NMR (500 MHz, CDCl$_3$) δ 8.61-8.56 (s, 2H), 8.15-8.10 (t, J=0.7 Hz, 1H), 7.93-7.86 (m, 1H), 7.86-7.81 (m, 1H), 7.34-7.27 (m, 1H), 5.70-5.65 (d, J=0.7 Hz, 2H), 4.75-4.67 (m, 2H), 2.16-1.95 (m, 3H)

Example 572: 2-[[1-[3-(1,1-Difluoroethyl)-4-fluorophenyl]triazol-4-yl]methoxy]-5-(difluoromethoxy)pyrimidine

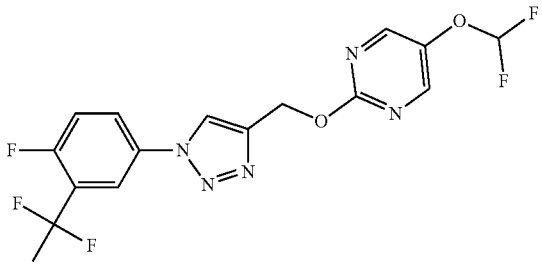 [SMILES: CC(F)(F)c1cc(-n2cc(COc3ncc(OC(F)F)cn3)nn2)ccc1F]

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-5-(difluoromethoxy)pyrimidine. MS (ESI): mass calcd. for $C_{16}H_{12}F_5N_5O_2$, 401.1; m/z found, 402.0 [M+H]$^+$. $^1$H NMR (500 MHz, CDCl$_3$) δ 8.45 (s, 2H), 8.12 (s, 1H), 7.92-7.88 (m, 1H), 7.87-7.80 (m, 1H), 7.31 (t, J=9.4 Hz, 1H), 6.53 (t, J=71.9 Hz, 1H), 5.66 (d, J=0.7 Hz, 2H), 2.05 (t, J=18.6, 1.2 Hz, 3H).

Example 573: 2-[[1-[3-(1,1-Difluoroethyl)-4-fluorophenyl]triazol-4-yl]methoxy]-4,5-dimethyl-pyrimidine The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-4,5-dimethylpyrimidine. MS (ESI): mass calcd. for $C_{17}H_{16}F_3N_5O$, 363.1; m/z found, 364.0 [M+H]$^+$. $^1$H NMR (500 MHz, CDCl$_3$) δ 8.20 (d, J=1.0 Hz, 1H), 8.12 (d, J=0.7 Hz, 1H), 7.91-7.87 (m, 1H), 7.86-7.80 (m, 1H), 7.30 (t, J=9.4 Hz, 1H), 5.73-5.55 (m, 2H), 2.44 (s, 3H), 2.20 (s, 3H), 2.05 (td, J=18.5, 1.2 Hz, 3H).

Example 574: 5-Chloro-2-[[1-[3-(1,1-difluoroethyl)-4-fluoro-phenyl]triazol-4-yl]methoxy]-4-methyl-pyrimidine

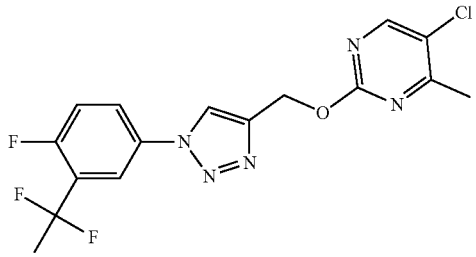 [SMILES: Cc1nc(OCc2cn(-c3ccc(F)c(C(C)(F)F)c3)nn2)ncc1Cl]

The title compound was prepared in a manner analogous to Example 155 using (1-(3-(1,1-difluoroethyl)-4-fluorophenyl)-1H-1,2,3-triazol-4-yl)methanol (Intermediate 11) and 2,5-dichloro-4-methylpyrimidine. MS (ESI): mass calcd. for $C_{16}H_{13}ClF_3N_5O$, 383.1; m/z found, 384.0 [M+H]$^+$. $^1$H NMR (500 MHz, CDCl$_3$) δ 8.39 (s, 1H), 8.15-8.07 (m, 1H), 7.89 (dd, J=6.2, 2.7 Hz, 1H), 7.87-7.80 (m, 1H), 7.31 (t, J=9.4 Hz, 1H), 5.73-5.56 (m, 2H), 2.68-2.52 (m, 3H), 2.15-1.91 (m, 3H).

Example 575: 2-[[1-[3-(1,1-Difluoroethyl)-4-fluoro-phenyl]triazol-4-yl]methoxy]-5-fluoro-4-methyl-pyrimidine

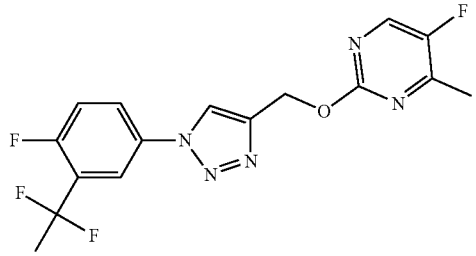

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-5-fluoro-4-methylpyrimidine. MS (ESI): mass calcd. for $C_{16}H_{13}F_4N_5O$, 367.1; m/z found, 368.1 [M+H]$^+$. $^1$H NMR (400 MHz, CDCl$_3$) δ 8.26 (d, J=1.2 Hz, 1H), 8.11 (t, J=0.7 Hz, 1H), 7.94-7.86 (m, 1H), 7.86-7.78 (m, 1H), 7.31 (t, J=9.4 Hz, 1H), 5.62 (d, J=0.8 Hz, 2H), 2.49 (d, J=2.5 Hz, 3H), 2.05 (td, J=18.7, 1.2 Hz, 3H).

Example 576: 2-[[1-[3-(1,1-Difluoroethyl)-4-fluoro-phenyl]triazol-4-yl]methoxy]-5-methyl-pyrimidin-4-amine

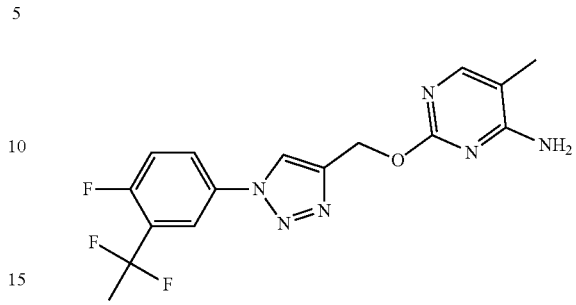

The title compound was prepared in a manner analogous to Example 153 using (1-(3-(I, 1-difluoroethyl)-4-fluoro-phenyl)-1H-1,2,3-triazol-4-yl)methanol (Intermediate 11) and 2-chloro-5-methylpyrimidin-4-amine, using ACN instead of DMF. MS (ESI): mass calcd. for $C_{16}H_{15}F_3N_6O$, 364.1; m/z found, 365.1 [M+H]$^+$. $^1$H NMR (400 MHz, CDCl$_3$) δ 8.16-8.05 (m, 1H), 7.93-7.87 (m, 1H), 7.86-7.80 (m, 1H), 7.37-7.27 (m, 2H), 5.56 (d, J=0.8 Hz, 2H), 4.98-4.81 (m, 2H), 2.15-1.94 (m, 6H).

Example 577: 2-[[1-[3-(1,1-Difluoroethyl)-4-fluoro-phenyl]triazol-4-yl]methoxy]-N,5-dimethyl-pyrimidin-4-amine

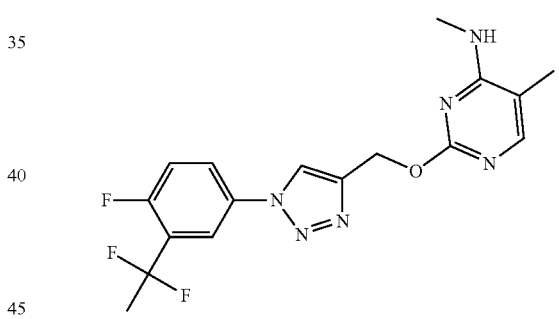

Step A: tert-Butyl (2-((1-(3-(1,1-difluoroethyl)-4-fluorophenyl)-1H-1,2,3-triazol-4-yl)methoxy)pyrimidin-4-yl)(methyl)carbamate The title compound was prepared in a manner analogous to Example 153 using (1-(3-(1,1-difluoroethyl)-4-fluorophenyl)-1H-1,2,3-triazol-4-yl)methanol (Intermediate 11) and tert-butyl (2-chloro-5-methylpyrimidin-4-yl)(methyl)carbamate, using ACN instead of DMF. MS (ESI): mass calcd. for $C_{22}H_{25}F_3N_6O_5$, 478.2; m/z found, 479.1 [M+H]$^+$.

Step B: tert-Butyl (2-((1-(3-(1,1-difluoroethyl)-4-fluorophenyl)-1H-1,2,3-triazol-4-yl)methoxy)pyrimidin-4-yl)(methyl)carbamate To a vial with tert-butyl (2-((1-(3-(1,1-difluoroethyl)-4-fluorophenyl)-1H-1,2,3-triazol-4-yl)methoxy)-5-methylpyrimidin-4-yl)(methyl)carbamate in DCM (3 mL) was added TFA (0.5 mL). The reaction mixture was stirred at rt overnight. The completed reaction was concentrated under reduced pressure. Purification (FCC, SiO$_2$, eluting with 0-3% 2M NH$_3$ in MeOH in DCM) afforded the title compound (17.9 mg, 41%) over the two step process. MS (ESI): mass calcd. for C$_{17}$H$_{17}$F$_3$N$_6$O, 378.1; m/z found, 379.0 [M+H]$^+$. $^1$H NMR (500 MHz, CDCl$_3$) δ 8.14-8.08 (t, J=0.8 Hz, 1H), 7.92-7.87 (m, 1H), 7.85-7.79 (m, 1H), 7.79-7.76 (d, J=1.1 Hz, 1H), 7.34-7.27 (m, 1H), 5.64-5.56 (d, J=0.7 Hz, 2H), 4.75-4.59 (s, 1H), 3.13-3.03 (d, J=4.8 Hz, 3H), 2.10-1.99 (m, 3H), 1.99-1.95 (d, J=1.0 Hz, 3H).

Example 578: 2-[[1-[3-(1,1-Difluoroethyl)-4-fluorophenyl]triazol-4-yl]methoxy]-5-fluoro-N-methyl-pyrimidin-4-amine

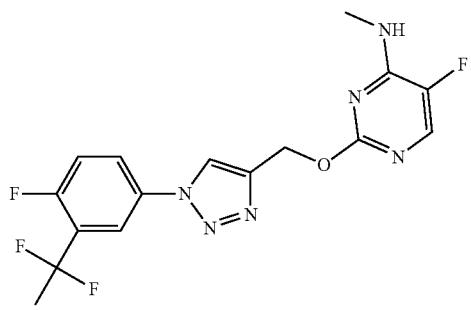 [SMILES: CNc1nc(OCc2cn(-c3ccc(F)c(C(C)(F)F)c3)nn2)ncc1F]

The title compound was prepared in a manner analogous to Example 163, Steps B-C using (1-(3-(1,1-difluoroethyl)-4-fluorophenyl)-1H-1,2,3-triazol-4-yl)methanol (Intermediate 11) and 2-chloro-5-fluoro-N-methyl-N-((2-(trimethylsilyl)ethoxy)methyl)pyrimidin-4-amine (Intermediate 59) in Step A. MS (ESI): mass calcd. for C$_{16}$H$_{14}$F$_4$N$_6$O, 382.1; m/z found, 383.0 [M+H]$^+$. $^1$H NMR (400 MHz, CDCl$_3$) δ 8.14-8.07 (d, J=2.4 Hz, 1H), 7.95-7.87 (m, 1H), 7.86-7.78 (m, 2H), 7.36-7.22 (m, 1H), 5.61-5.52 (d, J=2.4 Hz, 2H), 5.22-5.08 (s, 1H), 3.16-3.02 (m, 3H), 2.17-1.90 (m, 3H).

Example 579: 2-[[1-[3-(1,1-Difluoroethyl)-4-fluorophenyl]triazol-4-yl]methoxy]-N,N,5-trimethyl-pyrimidin-4-amine

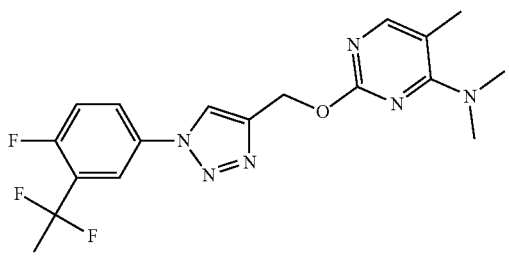 [SMILES: Cc1cnc(OCc2cn(-c3ccc(F)c(C(C)(F)F)c3)nn2)nc1N(C)C]

The title compound was prepared in a manner analogous to Example 153 using (1-(3-(1,1-difluoroethyl)-4-fluorophenyl)-1H-1,2,3-triazol-4-yl)methanol (Intermediate 11) and 2-chloro-N,N,5-trimethylpyrimidin-4-amine, using ACN instead of DMF. MS (ESI): mass calcd. for C$_{18}$H$_{19}$F$_3$N$_5$O, 392.2; m/z found, 393.1 [M+H]$^+$. $^1$H NMR (400 MHz, CDCl$_3$) δ 8.10 (s, 1H), 7.92-7.87 (m, 1H), 7.86-7.79 (m, 2H), 7.33-7.27 (m, 1H), 5.58 (s, 2H), 3.13 (s, 6H), 2.25 (s, 3H), 2.13-1.96 (m, 3H).

Example 580: 2-[[1-[3-(1,1-Difluoroethyl)-4-fluorophenyl]triazol-4-yl]methoxy]pyrimidin-4-amine

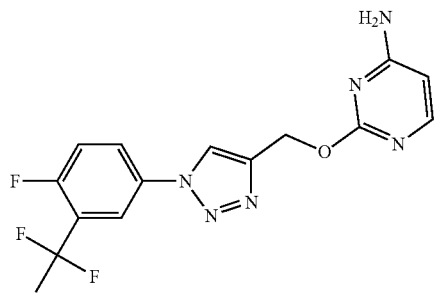 [SMILES: CC(F)(F)c1cc(-n2cc(COc3nccc(N)n3)nn2)ccc1F]

The title compound was prepared in a manner analogous to Example 153 using (1-(3-(1,1-difluoroethyl)-4-fluorophenyl)-1H-1,2,3-triazol-4-yl)methanol (Intermediate 11) and 2-chloropyrimidin-4-amine, using ACN instead of DMF. MS (ESI): mass calcd. for C$_{15}$H$_{13}$F$_3$N$_5$O, 350.1; m/z found, 351.0 [M+H]$^+$. $^1$H NMR (400 MHz, CDCl$_3$) δ 8.26-7.99 (m, 2H), 7.99-7.68 (m, 2H), 7.49-7.03 (m, 1H), 6.36-5.98 (m, 1H), 5.75-5.49 (d, J=3.0 Hz, 2H), 5.20-4.89 (s, 2H), 2.28-1.91 (m, 3H).

Example 581: 2-[[1-[3-(1,1-Difluoroethyl)-4-fluorophenyl]triazol-4-yl]methoxy]-N-methyl-pyrimidin-4-amine

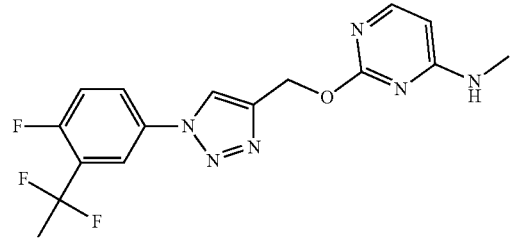 [SMILES: CNc1ccnc(OCc2cn(-c3ccc(F)c(C(C)(F)F)c3)nn2)n1]

The title compound was prepared in a manner analogous to Example 163, Steps B-C using tert-butyl (2-chloropyrimidin-4-yl)(methyl)carbamate (Intermediate 55) and (1-(3-(1,1-difluoroethyl)-4-fluorophenyl)-1H-1,2,3-triazol-4-yl)methanol (Intermediate 11). MS (ESI): mass calcd. for C$_{16}$H$_{15}$F$_3$N$_5$O, 364.1; m/z found, 365.1 [M+H]$^+$. $^1$H NMR (500 MHz, CDCl$_3$) δ 8.17-8.05 (s, 1H), 8.09-7.95 (s, 1H), 7.96-7.87 (m, 1H), 7.87-7.76 (m, 1H), 7.38-7.27 (m, 1H), 6.15-5.98 (d, J=5.7 Hz, 1H), 5.71-5.51 (s, 2H), 5.27-4.95 (s, 1H), 3.05-2.86 (d, J=4.8 Hz, 3H), 2.12-1.93 (m, 3H).

Example 582: 2-[[1-[3-(1,1-Difluoroethyl)-4-fluoro-phenyl]triazol-4-yl]methoxy]-N,N-dimethyl-pyrimidin-4-amine

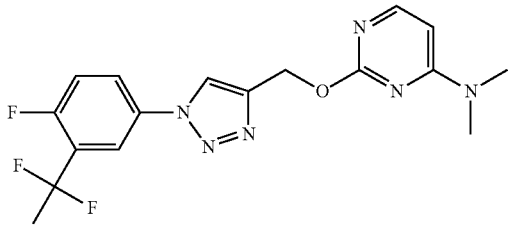 [SMILES: CN(C)c1ccnc(OCc2cn(-c3ccc(F)c(C(C)(F)F)c3)nn2)n1]

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-N,N-dimethylpyrimidin-4-amine. MS (ESI): mass calcd. for $C_{17}H_{17}F_3N_6O$, 378.1; m/z found, 379.0 [M+H]$^+$. $^1$H NMR (400 MHz, CDCl$_3$) δ 8.15-8.08 (t, J=0.8 Hz, 1H), 8.07-7.98 (d, J=6.0 Hz, 1H), 7.94-7.86 (m, 1H), 7.86-7.78 (m, 1H), 7.34-7.26 (m, 1H), 6.18-6.08 (d, J=6.1 Hz, 1H), 5.66-5.54 (d, J=0.7 Hz, 2H), 3.22-3.03 (s, 6H), 2.15-1.95 (m, 3H).

Example 583: 2-[[1-[3-(1,1-Difluoroethyl)-4-fluoro-phenyl]triazol-4-yl]methoxy]pyrimidine-5-carbonitrile The title compound was prepared in a manner analogous to Example 153 using (1-(3-(1,1-difluoroethyl)-4-fluorophenyl)-1H-1,2,3-triazol-4-yl)methanol (Intermediate 11) and 2-chloro-5-cyanopyrimidine, using ACN instead of DMF, employing microwave heating at 140° C. for 90 min. MS (ESI): mass calcd. for $C_{16}H_{11}F_3N_6O$, 360.1; m/z found, 361.0 [M+H]$^+$. $^1$H NMR (400 MHz, CDCl$_3$) δ 8.85 (s, 2H), 8.16-8.09 (m, 1H), 7.92-7.86 (m, 1H), 7.86-7.81 (m, 1H), 7.38-7.29 (m, 1H), 5.74 (d, J=0.6 Hz, 2H), 2.17-1.91 (m, 3H).

Example 584: 2-[[1-[3-(1,1-Difluoroethyl)-4-fluoro-phenyl]triazol-4-yl]methoxy]-5-methylsulfonyl-pyrimidine

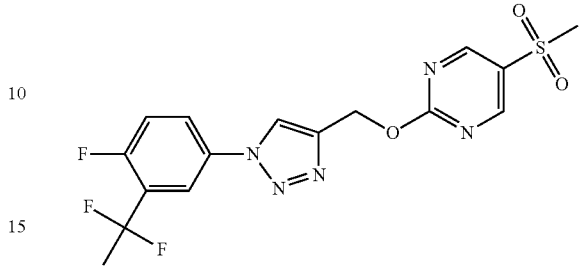

The title compound was prepared in a manner analogous to Example 153 using (1-(3-(1, i-difluoroethyl)-4-fluorophenyl)-1H-1,2,3-triazol-4-yl)methanol (Intermediate 11) and 2-chloro-5-(methylsulfonyl)pyrimidine, using ACN instead of DMF. MS (ESI): mass calcd. for $C_{16}H_{14}F_3N_5O_3S$, 413.1; m/z found, 414.0 [M+H]$^+$. $^1$H NMR (400 MHz, CDCl$_3$) δ 9.05 (s, 2H), 8.21-8.05 (m, 1H), 7.92-7.88 (m, 1H), 7.87-7.81 (m, 1H), 7.33 (t, J=9.3 Hz, 1H), 5.84-5.68 (m, 2H), 3.15 (s, 3H), 2.18-1.92 (m, 3H).

Example 585: 1-[2-[[1-[3-(1,1-Difluoroethyl)-4-fluoro-phenyl]triazol-4-yl]methoxy]pyrimidin-5-yl]ethanone

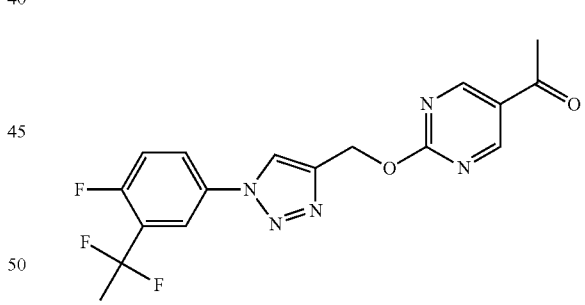

The title compound was prepared in a manner analogous to Example 155 using (1-(3-(1,1-difluoroethyl)-4-fluorophenyl)-1H-1,2,3-triazol-4-yl)methanol (Intermediate 11) and 1-(2-chloropyrimidin-5-yl)ethan-1-one. MS (ESI): mass calcd. for $C_{17}H_{14}F_3N_5O_2$, 377.1; m/z found, 378.0 [M+H]$^+$. $^1$H NMR (400 MHz, CDCl$_3$) δ 9.15-9.06 (s, 2H), 8.19-8.10 (s, 1H), 7.94-7.87 (m, 1H), 7.87-7.80 (m, 1H), 7.38-7.28 (m, 1H), 5.81-5.71 (m, 2H), 2.65-2.55 (s, 3H), 2.16-1.94 (m, 3H)

Example 586: (R/S)-1-[2-[[1-[3-(1,1-Difluoroethyl)-4-fluoro-phenyl]triazol-4-yl]methoxy]pyrimidin-5-yl]ethanol

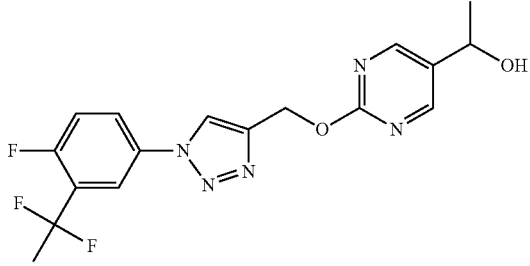 [SMILES: CC(O)c1cnc(OCc2cn(-c3ccc(F)c(C(C)(F)F)c3)nn2)nc1]

The title compound was prepared in a manner analogous to Example 157 using 1-(2-((1-(3-(1,1-difluoroethyl)-4-fluorophenyl)-1H-1,2,3-triazol-4-yl)methoxy)pyrimidin-5-yl)ethan-1-one (Example 585). MS (ESI): mass calcd. for $C_{17}H_{11}F_3N_5O_2$, 379.1; m/z found, 380.1 [M+H]$^+$. $^1$H NMR (400 MHz, CDCl$_3$) δ 8.61-8.52 (s, 2H), 8.17-8.10 (s, 1H), 7.93-7.86 (m, 1H), 7.86-7.79 (m, 1H), 7.35-7.28 (m, 1H), 5.69-5.60 (d, J=0.7 Hz, 2H), 5.03-4.92 (m, 1H), 2.12-1.97 (m, 3H), 1.61-1.50 (d, J=6.5 Hz, 3H).

Example 587: 5-Cyclopropyl-2-[[1-[3-(1,1-difluoroethyl)-4-fluoro-phenyl]triazol-4-yl]methoxy]pyrimidine

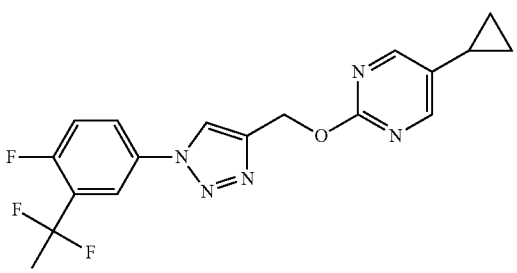 [SMILES: CC(F)(F)c1cc(-n2cc(COc3ncc(C4CC4)cn3)nn2)ccc1F]

The title compound was prepared in a manner analogous to Example 155 using (1-(3-(1,1-difluoroethyl)-4-fluorophenyl)-1H-1,2,3-triazol-4-yl)methanol (Intermediate 11) and 2-chloro-5-cyclopropylpyrimidine. MS (ESI): mass calcd. for $C_{18}H_{16}F_3N_5O$, 375.1; m/z found, 376.0 [M+H]$^+$. $^1$H NMR (400 MHz, CDCl$_3$) δ 8.34-8.29 (m, 2H), 8.13-8.08 (m, 1H), 7.92-7.86 (m, 1H), 7.86-7.79 (m, 1H), 7.34-7.27 (m, 1H), 5.63 (d, J=0.7 Hz, 2H), 2.16-1.94 (m, 3H), 1.91-1.74 (m, 1H), 1.09-0.97 (m, 2H), 0.78-0.63 (m, 2H)

Example 588: 5-(Azetidin-1-yl)-2-[[1-[3-(1,1-difluoroethyl)-4-fluoro-phenyl]triazol-4-yl]methoxy]pyrimidine

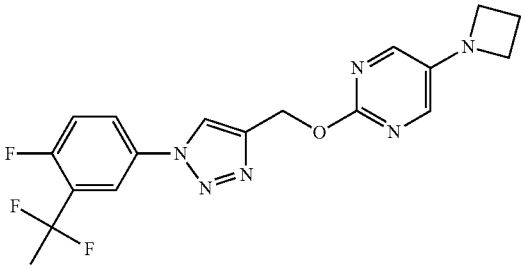 [SMILES: CC(F)(F)c1cc(-n2cc(COc3ncc(N4CCC4)cn3)nn2)ccc1F]

The title compound was prepared in a manner analogous to Example 165, Step A, using 5-bromo-2-[[1-[3-(1,1-difluoroethyl)-4-fluoro-phenyl]triazol-4-yl]methoxy]pyrimidine (Example 183) and azetidine. MS (ESI): mass calcd. for $C_{18}H_{17}F_3N_6O$, 390.1; m/z found, 391.0 [M+H]$^+$. $^1$H NMR (400 MHz, CDCl$_3$) δ 8.12-8.07 (t, J=0.7 Hz, 1H), 7.93-7.87 (m, 1H), 7.87-7.78 (s, 3H), 7.35-7.27 (m, 1H), 5.62-5.54 (d, J=0.7 Hz, 2H), 3.98-3.86 (t, J=7.2 Hz, 4H), 2.53-2.39 (m, 2H), 2.16-1.97 (m, 3H).

Example 589: 2-((1-(3-(1,1-Difluoroethyl)-4-fluorophenyl)-1H-1,2,3-triazol-4-yl)methoxy)-5-(3-fluoroazetidin-1-yl)pyrimidine

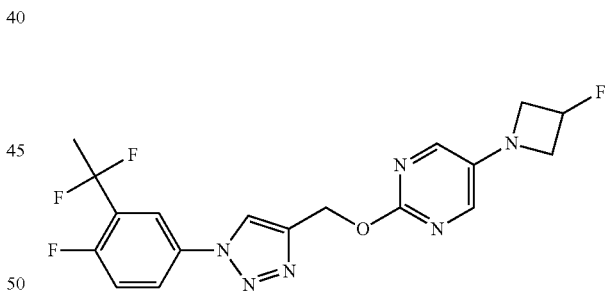

The title compound was made in an analogous manner to Example 187 using 3-fluoroazetidine hydrochloride. MS (ESI): mass calcd. for $C_{18}H_{16}F_4N_6O$, 408.3; m/z found, 409.1 [M+H]$^+$. $^1$H NMR (400 MHz, CDCl$_3$) δ 8.05-8.02 (s, 1H), 7.84-7.80 (m, 1H), 7.80-7.79 (s, 2H), 7.78-7.73 (m, 1H), 7.26-7.20 (m, 1H), 5.54-5.49 (s, 2H), 5.49-5.28 (m, 1H), 4.23-4.11 (m, 2H), 3.98-3.86 (m, 2H), 2.05-1.91 (m, 3H).

Example 590: 2-((1-(3-(1,1-Difluoroethyl)-4-fluoro-phenyl)-1H-1,2,3-triazol-4-yl)methoxy)-N,N-dimethylpyrimidin-5-amine

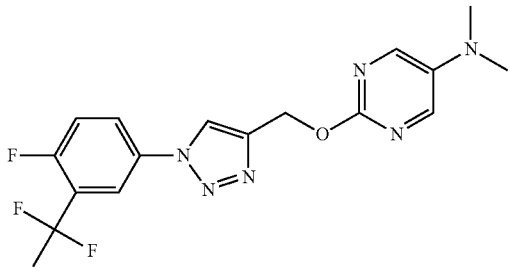 [SMILES: CN(C)c1cnc(OCc2cn(-c3ccc(F)c(C(C)(F)F)c3)nn2)nc1]

The title compound was made in an analogous manner to Example 187 using dimethylamine hydrochloride. MS (ESI): mass calcd. for $C_{17}H_{17}F_3N_6O$, 378.3; m/z found, 379.1 [M+H]$^+$. $^1$H NMR (400 MHz, CDCl$_3$) δ 8.05-8.03 (m, 1H), 8.03-8.01 (s, 2H), 7.84-7.80 (dd, J=6.3, 2.7 Hz, 1H), 7.78-7.73 (m, 1H), 7.26-7.20 (m, 1H), 5.53-5.50 (d, J=0.7 Hz, 2H), 2.89-2.83 (s, 6H), 2.05-1.90 (m, 3H).

Example 591: 2-[[1-[3-(1,1-Difluoroethyl)-4-fluoro-phenyl]triazol-4-yl]methoxy]-4-pyrrolidin-1-yl-pyrimidine

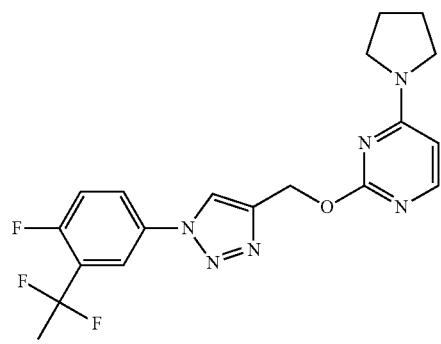 [SMILES: CC(F)(F)c1cc(-n2cc(COc3nccc(N4CCCC4)n3)nn2)ccc1F]

The title compound was prepared in a manner analogous to Example 153 using (1-(3-(1,1-difluoroethyl)-4-fluorophe-nyl)-1H-1,2,3-triazol-4-yl)methanol (Intermediate 11) and 2-chloro-4-(pyrrolidin-1-yl)pyrimidine, using ACN instead of DMF. MS (ESI): mass calcd. for $C_{19}H_{19}F_3N_6O$, 404.2; m/z found, 405.1 [M+H]$^+$. $^1$H NMR (400 MHz, CDCl$_3$) δ 8.12-8.08 (t, J=0.8 Hz, 1H), 8.02-7.96 (m, 1H), 7.91-7.86 (m, 1H), 7.84-7.79 (m, 1H), 7.33-7.27 (m, 1H), 6.04-5.96 (d, J=6.0 Hz, 1H), 5.65-5.57 (d, J=0.8 Hz, 2H), 3.80-3.22 (d, J=110.6 Hz, 4H), 2.13-1.94 (m, 7H).

Example 592: 2-[[1-[3-(1,1-Difluoroethyl)-4-fluoro-phenyl]triazol-4-yl]methoxy]-4-(1-piperidyl)pyrimi-dine

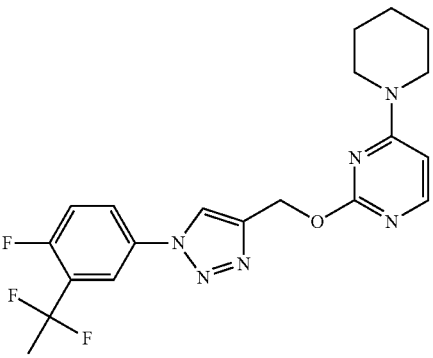 [SMILES: CC(F)(F)c1cc(-n2cc(COc3nccc(N4CCCCC4)n3)nn2)ccc1F]

The title compound was prepared in a manner analogous to Example 153 using (1-(3-(1,1-difluoroethyl)-4-fluorophe-nyl)-1H-1,2,3-triazol-4-yl)methanol (Intermediate 11) and 2-chloro-4-(piperidin-1-yl)pyrimidine, using ACN instead of DMF. MS (ESI): mass calcd. for $C_{20}H_{21}F_3N_6O$, 418.2; m/z found, 419.1 [M+H]$^+$. $^1$H NMR (500 MHz, CDCl$_3$) δ 8.15-8.07 (s, 1H), 8.07-7.97 (d, J=6.1 Hz, 1H), 7.95-7.86 (m, 1H), 7.86-7.78 (m, 1H), 7.34-7.27 (m, 1H), 6.22-6.15 (d, J=6.2 Hz, 1H), 5.61-5.54 (d, J=0.8 Hz, 2H), 3.73-3.53 (s, 4H), 2.13-1.98 (m, 3H), 1.75-1.65 (m, 2H), 1.65-1.56 (m, 4H).

Example 593: 2-[[1-[3-(1,1-Difluoroethyl)-4-fluoro-phenyl]-5-methyl-triazol-4-yl]methoxy]-5-ethyl-pyrimidine

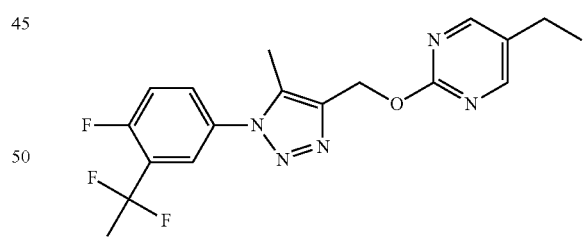

The title compound was prepared in a manner analogous to Example 173, Steps A through F, using 2-chloro-5-ethylpyrimidine in Step F. MS (ESI): mass calcd. for $C_{18}H_{18}F_3N_5O$, 377.1; m/z found, 378.1 [M+H]$^+$. $^1$H NMR (500 MHz, CDCl$_3$) δ 8.39 (s, 2H), 7.66 (dd, J=6.3, 2.6 Hz, 1H), 7.57-7.51 (m, 1H), 7.32 (t, J=9.3 Hz, 1H), 5.57 (s, 2H), 2.60 (q, J=7.6 Hz, 2H), 2.42 (s, 3H), 2.04 (td, J=18.6, 1.1 Hz, 3H), 1.25 (t, J=7.6 Hz, 3H).

Example 594: 5-Cyclopropyl-2-[[1-[3-(1,1-difluoro-ethyl)-4-fluoro-phenyl]-5-methyl-triazol-4-yl]methoxy]pyrimidine

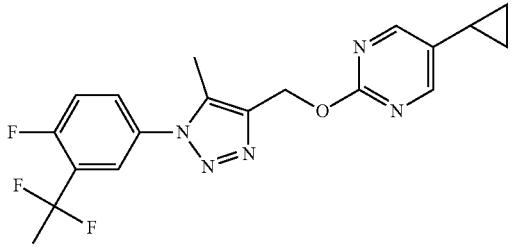 [SMILES: Cc1c(COc2ncc(C3CC3)cn2)nnn1-c1ccc(F)c(C(C)(F)F)c1]

The title compound was prepared in a manner analogous to Example 173, Steps A through F, using 2-chloro-5-cyclopropylpyrimidine in Step F. MS (ESI): mass calcd. for $C_{19}H_{18}F_3N_5O$, 389.1; m/z found, 390.1 [M+H]$^+$. $^1$H NMR (500 MHz, CDCl$_3$) δ 8.30 (s, 2H), 7.66 (dd, J=6.3, 2.6 Hz, 1H), 7.55-7.51 (m, 1H), 7.34-7.29 (m, 1H), 5.56 (s, 2H), 2.41 (s, 3H), 2.04 (td, J=18.6, 1.1 Hz, 3H), 1.82 (tt, J=8.5, 5.1 Hz, 1H), 1.04-0.97 (m, 2H), 0.73-0.63 (m, 2H).

Example 595: 2-[[1-[3-(1,1-Difluoroethyl)-4-fluoro-phenyl]-5-methyl-triazol-4-yl]methoxy]-4,5-dimethyl-pyrimidine

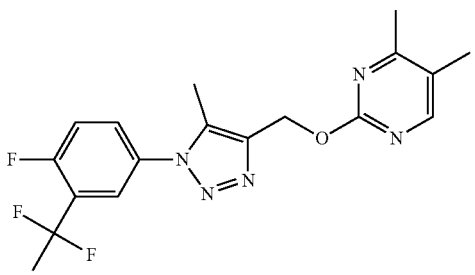 [SMILES: Cc1cnc(OCc2nnn(-c3ccc(F)c(C(C)(F)F)c3)c2C)nc1C]

The title compound was prepared in a manner analogous to Example 173, Steps A through F, using 2-chloro-4,5-dimethylpyrimidine in Step F. MS (ESI): mass calcd. for $C_{18}H_{18}F_3N_5O$, 377.1; m/z found, 378.0 [M+H]$^+$. $^1$H NMR (500 MHz, CDCl$_3$) δ 8.19 (s, 1H), 7.66 (dd, J=6.4, 2.6 Hz, 1H), 7.53 (ddd, J=8.6, 4.1, 2.8 Hz, 1H), 7.35-7.29 (m, 1H), 5.56 (s, 2H), 2.45-2.40 (m, 6H), 2.19 (s, 3H), 2.04 (td, J=18.6, 1.2 Hz, 3H).

Example 596: 5-Chloro-2-[[1-[3-(1,1-difluoroethyl)-4-fluoro-phenyl]-5-methyl-triazol-4-yl]methoxy]-4-methyl-pyrimidine

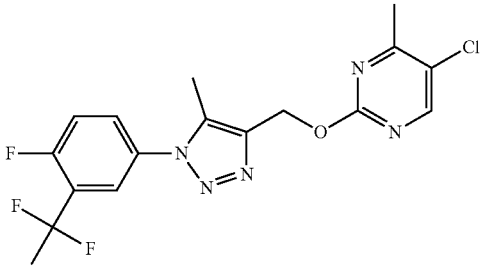 [SMILES: Cc1nc(OCc2nnn(-c3ccc(F)c(C(C)(F)F)c3)c2C)ncc1Cl]

The title compound was prepared in a manner analogous to Example 173, Steps A through F, using 2,5-dichloro-4-methylpyrimidine in Step F. MS (ESI): mass calcd. for $C_{17}H_{15}ClF_3N_5O$, 397.1; m/z found 398.0 [M+H]$^+$. $^1$H NMR (500 MHz, CDCl$_3$) δ 8.37 (s, 1H), 7.66 (dd, J=6.3, 2.6 Hz, 1H), 7.53 (ddd, J=8.6, 4.1, 2.7 Hz, 1H), 7.33 (t, J=9.3 Hz, 1H), 5.56 (s, 2H), 2.55 (s, 3H), 2.42 (s, 3H), 2.04 (td, J=18.6, 1.2 Hz, 3H).

Example 597: 2-[[1-(3,4-Difluorophenyl)triazol-4-yl]methoxy]pyrimidine

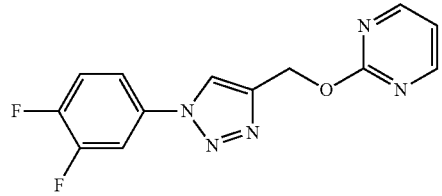 [SMILES: Fc1ccc(-n2cc(COc3ncccn3)nn2)cc1F]

The title compound was prepared in a manner analogous to Example 1 using (1-(3,4-difluorophenyl)-1H-1,2,3-triazol-4-yl)methanol (Intermediate 39) and 2-chloropyrimidine. MS (ESI): mass calcd. for $C_{13}H_9F_2N_5O$, 289.1; m/z found, 290.1 [M+H]$^+$. $^1$H NMR (500 MHz, DMSO-d$_6$) δ 8.94 (d, J=0.6 Hz, 1H), 8.66 (d, J=4.8 Hz, 2H), 8.13 (ddd, J=11.4, 7.0, 2.7 Hz, 1H), 7.83 (dddd, J=9.0, 4.1, 2.6, 1.6 Hz, 1H), 7.71 (dt, J=10.4, 8.8 Hz, 1H), 7.20 (t, J=4.8 Hz, 1H), 5.53 (d, J=0.6 Hz, 2H).

Example 598: 2-[[1-(3,4-Difluorophenyl)triazol-4-yl]methoxy]-5-fluoro-pyrimidine

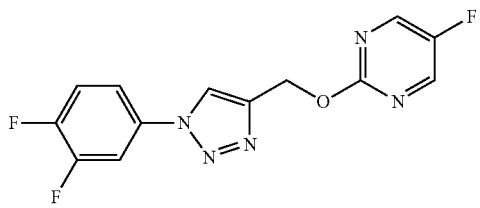 [SMILES: Fc1cnc(OCc2cn(-c3ccc(F)c(F)c3)nn2)nc1]

The title compound was prepared in a manner analogous to Example 1 using (1-(3,4-difluorophenyl)-1H-1,2,3-triazol-4-yl)methanol (Intermediate 39) and 2-chloro-5-fluoropyrimidine. MS (ESI): mass calcd. for $C_{13}H_6F_3N_5O$, 307.1; m/z found, 308.0 [M+H]. $^1$H NMR (500 MHz, DMSO-$d_6$) δ 8.93 (s, 1H), 8.75 (d, J=0.6 Hz, 2H), 8.13 (ddd, J=11.5, 7.0, 2.7 Hz, 1H), 7.83 (dt, J=8.3, 2.9 Hz, 1H), 7.71 (dt, J=10.4, 8.8 Hz, 1H), 5.52 (s, 2H).

Example 599: 2-[[1-(3,4-Difluorophenyl)triazol-4-yl]methoxy]-5-methoxy-pyrimidine

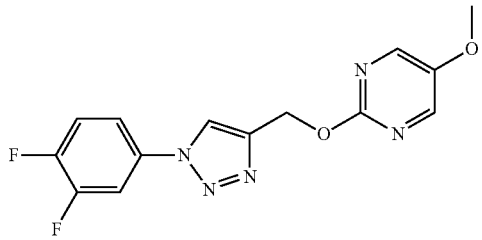 [SMILES: COc1cnc(OCc2cn(-c3ccc(F)c(F)c3)nn2)nc1]

The title compound was prepared in a manner analogous to Example 1 using (1-(3,4-difluorophenyl)-1H-1,2,3-triazol-4-yl)methanol (Intermediate 39) and 2-chloro-5-methoxypyrimidine. MS (ESI): mass calcd. for $C_{14}H_{11}F_2N_5O_2$, 319.1; m/z found, 320.1 [M+H]$^+$. $^1$H NMR (500 MHz, DMSO-$d_6$) δ 8.92 (s, 1H), 8.41 (s, 2H), 8.13 (ddd, J=11.4, 7.0, 2.6 Hz, 1H), 7.83 (dddd, J=9.0, 4.1, 2.6, 1.6 Hz, 1H), 7.71 (dt, J=10.4, 8.8 Hz, 1H), 5.47 (d, J=0.6 Hz, 2H), 3.86 (s, 3H).

Example 600: 5-Chloro-2-[[1-(3,4-difluorophenyl)triazol-4-yl]methoxy]pyrimidine

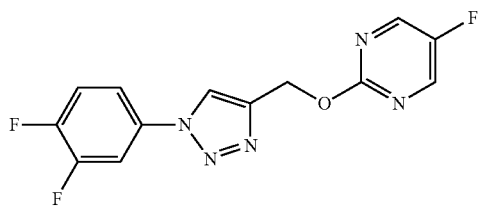 [SMILES: Fc1cnc(OCc2cn(-c3ccc(F)c(F)c3)nn2)nc1]

The title compound was prepared in a manner analogous to Example 1 using (1-(3,4-difluorophenyl)-1H-1,2,3-triazol-4-yl)methanol (Intermediate 39) and 2,5-dichloropyrimidine. MS (ESI): mass calcd. for $C_{13}H_8ClF_2N_5O$, 323.0; m/z found, 324.0 [M+H]$^+$. $^1$H NMR (500 MHz, DMSO-$d_6$) δ 8.93 (s, 1H), 8.77 (s, 2H), 8.13 (ddd, J=11.5, 7.0, 2.7 Hz, 1H), 7.83 (dtt, J=8.1, 2.6, 1.5 Hz, 1H), 7.71 (dt, J=10.4, 8.8 Hz, 1H), 5.54 (d, J=0.5 Hz, 2H)

Example 601: 2-[[1-(3,4-Difluorophenyl)triazol-4-yl]methoxy]-5-methyl-pyrimidine

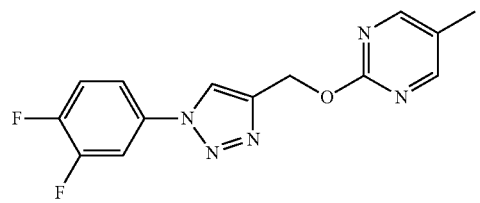 [SMILES: Cc1cnc(OCc2cn(-c3ccc(F)c(F)c3)nn2)nc1]

The title compound was prepared in a manner analogous to Example 1 using (1-(3,4-difluorophenyl)-1H-1,2,3-triazol-4-yl)methanol (Intermediate 39) and 2-chloro-5-methylpyrimidine. MS (ESI): mass calcd. for $C_{14}H_{11}F_2N_5O$, 303.1; m/z found, 304.1 [M+H]$^+$. $^1$H NMR (500 MHz, DMSO-$d_6$) δ 8.93 (d, J=0.6 Hz, 1H), 8.49 (d, J=0.8 Hz, 2H), 8.13 (ddd, J=11.5, 7.0, 2.7 Hz, 1H), 7.83 (dddd, J=9.1, 4.1, 2.6, 1.6 Hz, 1H), 7.71 (dt, J=10.3, 8.8 Hz, 1H), 5.49 (d, J=0.6 Hz, 2H), 2.21 (d, J=0.8 Hz, 3H).

Example 602: 2-[[1-(3,4-Difluorophenyl)triazol-4-yl]methoxy]-5-ethyl-pyrimidine

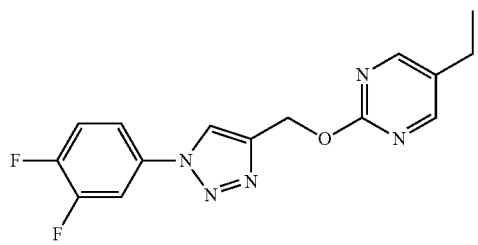 [SMILES: CCc1cnc(OCc2cn(-c3ccc(F)c(F)c3)nn2)nc1]

The title compound was prepared in a manner analogous to Example 1 using (1-(3,4-difluorophenyl)-1H-1,2,3-triazol-4-yl)methanol (Intermediate 39) and 2-chloro-5-ethyl-pyrimidine. MS (ESI): mass calcd. for $C_{15}H_{13}F_2N_5O$, 317.1; m/z found, 318.2 [M+H]$^+$. $^1$H NMR (500 MHz, DMSO-$d_6$) δ 8.93 (s, 1H), 8.52 (d, J=0.6 Hz, 2H), 8.13 (ddd, J=11.5, 7.1, 2.7 Hz, 1H), 7.87-7.80 (m, 1H), 7.71 (dt, J=10.4, 8.8 Hz, 1H), 5.50 (d, J=0.6 Hz, 2H), 2.62-2.54 (m, 2H), 1.19 (t, J=7.6 Hz, 3H).

Example 603: 2-[[1-(2,5-Difluorophenyl)triazol-4-yl]methoxy]-5-methyl-pyrimidine

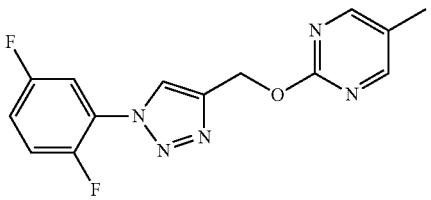 [SMILES: Cc1cnc(OCc2cn(-c3cc(F)ccc3F)nn2)nc1]

The title compound was prepared in a manner analogous to Example 1 using (1-(2,5-difluorophenyl)-1H-1,2,3-triazol-4-yl)methanol (Intermediate 47) and 2-chloro-5-methylpyrimidine. MS (ESI): mass calcd. for $C_{14}H_{11}F_2N_5O$, 303.1; m/z found, 304.1 [M+H]$^+$. $^1$H NMR (500 MHz, DMSO-$d_6$) δ 8.73 (s, 1H), 8.49 (d, J=1.0 Hz, 2H), 7.85 (s, 1H), 7.66 (td, J=9.9, 4.9 Hz, 1H), 7.51 (s, 1H), 5.50 (s, 2H), 2.21 (d, J=0.9 Hz, 3H).

Example 604: 2-[2-[[1-(2,5-Difluorophenyl)triazol-4-yl]methoxy]pyrimidin-5-yl]propan-2-ol

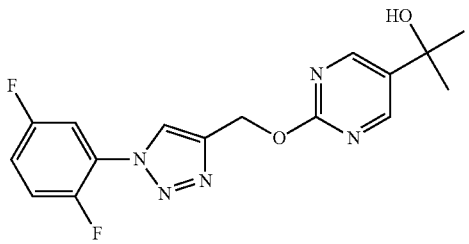 [SMILES: CC(C)(O)c1cnc(OCc2cn(-c3cc(F)ccc3F)nn2)nc1]

The title compound was prepared in a manner analogous to Example 1 using (1-(2,5-difluorophenyl)-1H-1,2,3-triazol-4-yl)methanol (Intermediate 47) and 2-(2-chloropyrimidin-5-yl)propan-2-ol. MS (ESI): mass calcd. for $C_{16}H_{15}F_2N_5O_2$, 347.1; m/z found, 348.0 [M+H]$^+$. $^1$H NMR (500 MHz, DMSO-d$_6$) δ 8.73 (s, 1H), 8.69 (d, J=1.1 Hz, 1H), 7.92-7.81 (m, 1H), 7.66 (td, J=9.7, 4.6 Hz, 1H), 7.52 (d, J=8.5 Hz, 1H), 5.53 (s, 2H), 5.32 (s, 1H), 1.47 (s, 6H).

Example 605: 5-Chloro-2-[[1-(2,3-difluorophenyl)triazol-4-yl]methoxy]pyrimidine

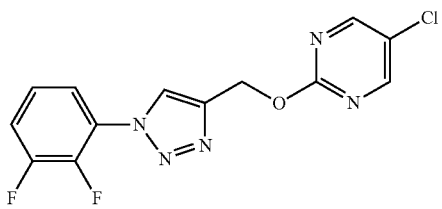 [SMILES: Fc1cccc(-n2cc(COc3ncc(Cl)cn3)nn2)c1F]

The title compound was prepared in a manner analogous to Example 1 using (1-(2,3-difluorophenyl)-1H-1,2,3-triazol-4-yl)methanol (Intermediate 48) and 2,5-dichloropyrimidine. MS (ESI): mass calcd. for $C_{13}H_8ClF_2N_5O$, 323.0; m/z found, 324.0 [M+H]$^+$. $^1$H NMR (500 MHz, DMSO-d$_6$) δ 8.86-8.66 (m, 2H), 7.71 (s, 2H), 7.48 (s, 1H), 5.56 (d, J=1.5 Hz, 2H).

Example 606: 2-[[1-(2,3-Difluorophenyl)triazol-4-yl]methoxy]-5-fluoro-pyrimidine

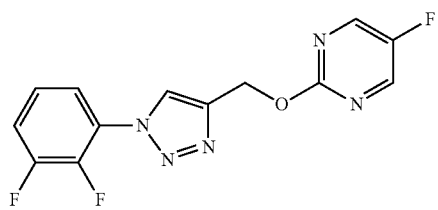 [SMILES: Fc1cnc(OCc2cn(-c3cccc(F)c3F)nn2)nc1]

The title compound was prepared in a manner analogous to Example 1 using (1-(2,3-difluorophenyl)-1H-1,2,3-triazol-4-yl)methanol (Intermediate 48) and 2-chloro-5-fluoropyrimidine. MS (ESI): mass calcd. for $C_{13}H_8F_3N_5O$, 307.1; m/z found, 308.0 [M+H]$^+$. $^1$H NMR (400 MHz, DMSO-d$_6$) δ 8.83-8.70 (m, 3H), 7.69 (dddd, J=11.8, 8.9, 5.5, 1.6 Hz, 2H), 7.54-7.42 (m, 1H), 5.54 (s, 2H).

Example 607: 2-[[1-(2,3-Difluorophenyl)triazol-4-yl]methoxy]pyrimidine

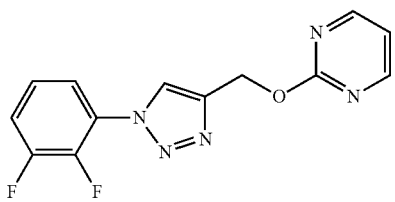 [SMILES: Fc1cccc(-n2cc(COc3ncccn3)nn2)c1F]

The title compound was prepared in a manner analogous to Example 1 using (1-(2,3-difluorophenyl)-1H-1,2,3-triazol-4-yl)methanol (Intermediate 48) and 2-chloropyrimidine. MS (ESI): mass calcd. for $C_{13}H_9F_2N_5O$, 289.1; m/z found, 290.1 [M+H]$^+$. $^1$H NMR (400 MHz, DMSO-d$_6$) δ 8.77 (d, J=2.0 Hz, 1H), 8.66 (d, J=4.8 Hz, 2H), 7.76-7.64 (m, 2H), 7.53-7.43 (m, 1H), 7.20 (t, J=4.8 Hz, 1H), 5.55 (s, 2H).

Example 608: 2-[2-[[1-(2,3-Difluorophenyl)triazol-4-yl]methoxy]pyrimidin-5-yl]propan-2-ol

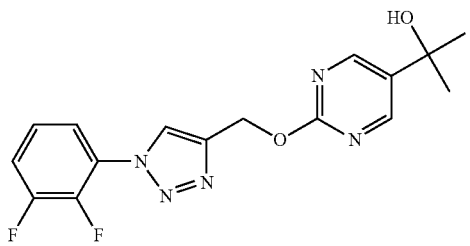 [SMILES: CC(C)(O)c1cnc(OCc2cn(-c3cccc(F)c3F)nn2)nc1]

The title compound was prepared in a manner analogous to Example 1 using (1-(2,3-difluorophenyl)-1H-1,2,3-triazol-4-yl)methanol (Intermediate 48) and 2-(2-chloropyrimidin-5-yl)propan-2-ol. MS (ESI): mass calcd. for $C_{16}H_{15}F_2N_5O_2$, 347.1; m/z found, 348.2 [M+H]$^+$. $^1$H NMR (400 MHz, CD$_3$OD) δ 8.70 (s, 2H), 8.58 (d, J=2.4 Hz, 1H), 7.68 (ddt, J=8.1, 6.3, 1.8 Hz, 1H), 7.49 (dddd, J=10.1, 8.8, 7.3, 1.7 Hz, 1H), 7.40 (tdd, J=8.4, 5.2, 2.0 Hz, 1H), 5.63 (d, J=2.5 Hz, 2H), 1.56 (d, J=2.7 Hz, 6H).

Example 609: 2-[[1-(2,3-Difluorophenyl)triazol-4-yl]methoxy]-5-fluoro-4-methyl-pyrimidine

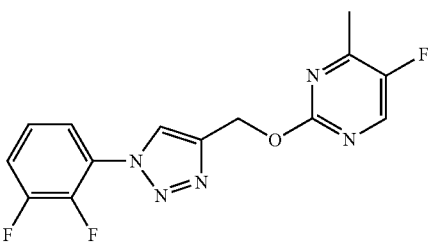 [SMILES: Cc1nc(OCc2cn(-c3cccc(F)c3F)nn2)ncc1F]

The title compound was prepared in a manner analogous to Example 1 using (1-(2,3-difluorophenyl)-1H-1,2,3-triazol-4-yl)methanol (Intermediate 48) and 2-chloro-5-fluoro-4-methylpyrimidine. MS (ESI): mass calcd. for $C_{14}H_{10}F_3N_5O$, 321.1; m/z found, 322.1 [M+H]$^+$. $^1$H NMR (400 MHz, DMSO-d$_6$) δ 8.92-8.50 (m, 2H), 7.79-7.63 (m, 2H), 7.48 (s, 1H), 5.49 (d, J=12.0 Hz, 2H), 2.37 (s, 3H).

Example 610: 2-[[1-(3-Chloro-2-fluoro-phenyl)triazol-4-yl]methoxy]-5-methyl-pyrimidine

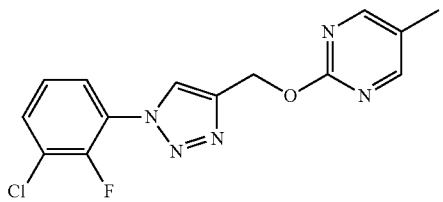 [SMILES: Cc1cnc(OCc2cn(-c3cccc(Cl)c3F)nn2)nc1]

The title compound was prepared in a manner analogous to Example 1 using (1-(3-chloro-2-fluorophenyl)-1H-1,2,3-triazol-4-yl)methanol (Intermediate 46) and 2-chloro-5-methylpyrimidine. MS (ESI): mass calcd. for $C_{14}H_{11}ClFN_5O$, 319.1; m/z found, 320.0 [M+H]$^+$. $^1$H NMR (500 MHz, CD$_3$OD) δ 8.55 (d, J=2.5 Hz, 1H), 8.45 (t, J=0.8 Hz, 2H), 7.81 (ddd, J=8.2, 6.6, 1.6 Hz, 1H), 7.69 (ddd, J=8.3, 6.8, 1.6 Hz, 1H), 7.40 (td, J=8.2, 1.6 Hz, 1H), 5.60 (d, J=0.6 Hz, 2H), 2.27 (t, J=0.8 Hz, 3H).

Example 611: 2-[[1-(3-Chloro-2-fluoro-phenyl)triazol-4-yl]methoxy]pyrimidine

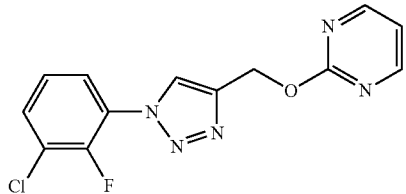 [SMILES: Fc1c(Cl)cccc1-n1cc(COc2ncccn2)nn1]

The title compound was prepared in a manner analogous to Example 1 using (1-(3-chloro-2-fluorophenyl)-1H-1,2,3-triazol-4-yl)methanol (Intermediate 46) and 2-chloropyrimidine. MS (ESI): mass calcd. for $C_{13}H_9ClFN_5O$, 305.0; m/z found, 306.0 [M+H]$^+$. $^1$H NMR (500 MHz, DMSO-d$_6$) δ 8.78 (d, J=2.3 Hz, 1H), 8.67 (dd, J=4.8, 1.6 Hz, 2H), 7.92-7.79 (m, 2H), 7.57-7.43 (m, 1H), 7.28-7.15 (m, 1H), 5.55 (d, J=1.5 Hz, 2H).

Example 612: 5-Chloro-2-[[1-(3-chloro-2-fluorophenyl)triazol-4-yl]methoxy]pyrimidine

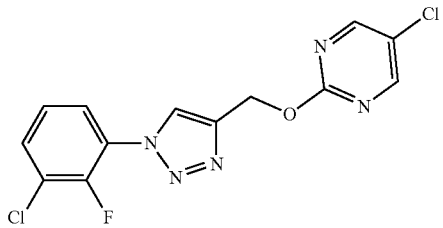 [SMILES: Fc1c(Cl)cccc1-n1cc(COc2ncc(Cl)cn2)nn1]

The title compound was prepared in a manner analogous to Example 1 using (1-(3-chloro-2-fluorophenyl)-1H-1,2,3-triazol-4-yl)methanol (Intermediate 46) and 2,5-dichloropyrimidine. MS (ESI): mass calcd. for $C_{13}H_8Cl_{12}FN_5O$, 339.0; m/z found, 341.0 [M+H]$^+$. $^1$H NMR (500 MHz, DMSO-d$_6$) δ 8.78 (d, J=5.8 Hz, 2H), 7.84 (q, J=8.0, 7.6 Hz, 3H), 7.58-7.40 (m, 1H), 5.56 (s, 2H)

Example 613: 2-[[1-(3-Chloro-2-fluoro-phenyl)triazol-4-yl]methoxy]-5-fluoro-4-methyl-pyrimidine

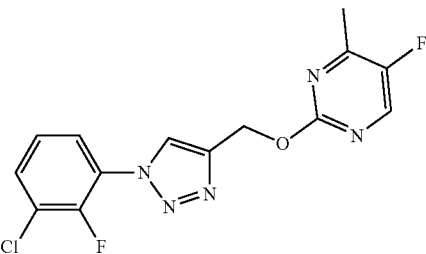 [SMILES: Cc1nc(OCc2cn(-c3cccc(Cl)c3F)nn2)ncc1F]

The title compound was prepared in a manner analogous to Example 1 using (1-(3-chloro-2-fluorophenyl)-1H-1,2,3-triazol-4-yl)methanol (Intermediate 46) and 2-chloro-5-fluoro-4-methylpyrimidine. MS (ESI): mass calcd. for $C_{14}H_{10}ClF_2N_5O$, 337.1; m/z found, 338.0 [M+H]$^+$. $^1$H NMR (500 MHz, DMSO-d$_6$) δ 8.76 (d, J=2.2 Hz, 1H), 8.57 (d, J=1.6 Hz, 1H), 7.84 (dt, J=7.9, 6.4 Hz, 2H), 7.53-7.45 (m, 1H), 5.51 (s, 2H), 2.44 (d, J=2.6 Hz, 3H).

Example 614: 2-[[1-(3-Chloro-2-fluoro-phenyl)triazol-4-yl]methoxy]-5-fluoro-pyrimidine

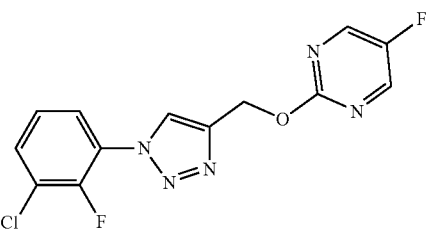 [SMILES: Fc1cnc(OCc2cn(-c3cccc(Cl)c3F)nn2)nc1]

The title compound was prepared in a manner analogous to Example 1 using (1-(3-chloro-2-fluorophenyl)-1H-1,2,3-triazol-4-yl)methanol (Intermediate 46) and 2-chloro-5-fluoropyrimidine. MS (ESI): mass calcd. for $C_{13}H_8ClF_2N_5O$, 323.0; m/z found, 324.0 [M+H]$^+$. $^1$H NMR (500 MHz, CD$_3$OD) δ 8.57 (d, J=4.1 Hz, 3H), 7.81 (ddd, J=8.2, 6.6, 1.7 Hz, 1H), 7.69 (ddd, J=8.4, 6.7, 1.6 Hz, 1H), 7.41 (td, J=8.2, 1.7 Hz, 1H), 5.61 (s, 2H).

Example 615: 2-[2-[[1-(3-Chloro-2-fluoro-phenyl)triazol-4-yl]methoxy]pyrimidin-5-yl]propan-2-ol

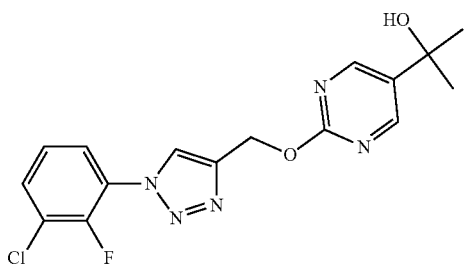 [SMILES: CC(C)(O)c1cnc(OCc2cn(-c3cccc(Cl)c3F)nn2)nc1]

The title compound was prepared in a manner analogous to Example 1 using (1-(3-chloro-2-fluorophenyl)-1H-1,2,3-triazol-4-yl)methanol (Intermediate 46) and 2-(2-chloropyrimidin-5-yl)propan-2-ol. MS (ESI): mass calcd. for $C_{16}H_{15}ClFN_5O_2$, 363.1; m/z found, 364.1 [M+H]$^+$. $^1$H NMR (500 MHz, DMSO-$d_6$) δ 8.77 (d, J=2.1 Hz, 1H), 8.69 (s, 2H), 7.84 (dddd, J=11.7, 8.3, 6.8, 1.6 Hz, 2H), 7.48 (td, J=8.2, 1.5 Hz, 1H), 5.53 (s, 2H), 5.32 (s, 1H), 1.46 (s, 6H).

Example 616: [2-[[1-(3-Bromo-4-fluoro-phenyl)triazol-4-yl]methoxy]pyrimidin-5-yl]methanol

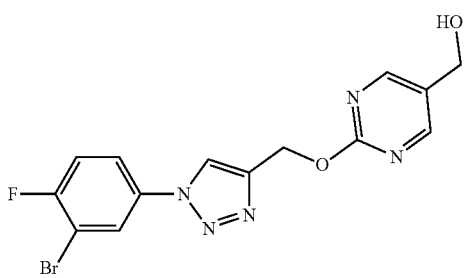 [SMILES: OCc1cnc(OCc2cn(-c3ccc(F)c(Br)c3)nn2)nc1]

The title compound was prepared analogous to Example 160, steps A-B, using (1-(3-bromo-4-fluorophenyl)-1H-1,2,3-triazol-4-yl)methanol (Intermediate 14) in step A. MS (ESI): mass calcd. for $C_{14}H_{11}BrFN_5O_2$, 379.0; m/z found, 380.0 [M+H]$^+$. $^1$H NMR (500 MHz, CDCl$_3$) δ 8.55 (s, 2H), 8.09 (s, 1H), 7.98 (dd, J=5.8, 2.6 Hz, 1H), 7.66 (ddd, J=8.9, 4.0, 2.7 Hz, 1H), 7.29-7.25 (m, 1H), 5.64 (d, J=0.7 Hz, 2H), 4.69 (s, 2H).

Example 617: [2-[[1-(3-Bromo-4-fluoro-phenyl)triazol-4-yl]methoxy]pyrimidin-4-yl]methanol

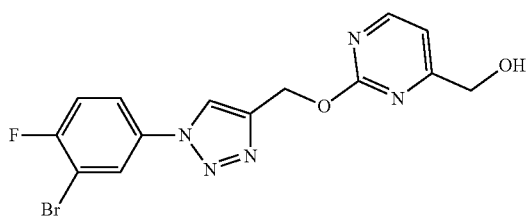 [SMILES: OCc1ccnc(OCc2cn(-c3ccc(F)c(Br)c3)nn2)n1]

The title compound was prepared analogous to Example 159, steps A-B, using (1-(3-bromo-4-fluorophenyl)-1H-1,2,3-triazol-4-yl)methanol (Intermediate 14) in step A. MS (ESI): mass calcd. for $C_{14}H_{11}BrFN_5O_2$, 379.0; m/z found, 380.0 [M+H]$^+$. $^1$H NMR (500 MHz, CDCl$_3$) δ 8.51 (d, J=5.0 Hz, 1H), 8.09 (s, 1H), 7.98 (dd, J=5.8, 2.7 Hz, 1H), 7.66 (ddd, J=8.8, 4.0, 2.6 Hz, 1H), 7.29-7.26 (m, 1H), 7.02 (d, J=5.0 Hz, 1H), 5.66 (d, J=0.7 Hz, 2H), 4.75-4.70 (m, 2H), 3.25 (s, 1H).

Example 618: 2-[[1-(3-Bromo-4-fluoro-phenyl)triazol-4-yl]methoxy]-5-(2-fluoroethoxy)pyrimidine

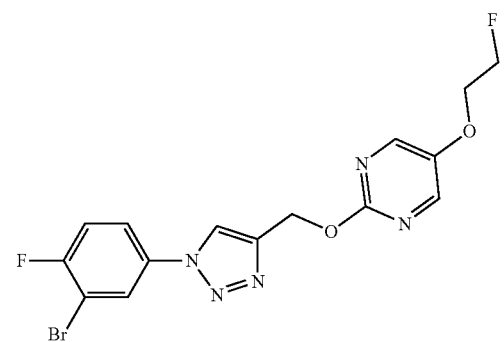 [SMILES: FCCOc1cnc(OCc2cn(-c3ccc(F)c(Br)c3)nn2)nc1]

The title compound was prepared in a manner analogous to Example 192, Steps A-B, using 1-(3-bromo-4-fluorophenyl)-1H-1,2,3-triazol-4-yl)methanol (Intermediate 14) in Step B. MS (ESI): mass calcd. for $C_{15}H_{12}BrF_2N_5O_2$, 411.0; m/z found, 412.0 [M+H]$^+$. $^1$H NMR (400 MHz, CD$_3$OD) δ 8.37 (s, 1H), 8.32 (s, 2H), 8.09 (dd, J=5.8, 2.7 Hz, 1H), 7.78 (ddd, J=8.9, 4.2, 2.7 Hz, 1H), 7.35 (dd, J=8.9, 7.9 Hz, 1H), 5.59 (s, 2H), 4.86-4.79 (m, 1H), 4.75-4.68 (m, 1H), 4.38-4.32 (m, 1H), 4.31-4.25 (m, 1H).

Example 619: 2-[[1-(3-Chloro-4-fluoro-phenyl)triazol-4-yl]methoxy]pyrimidine

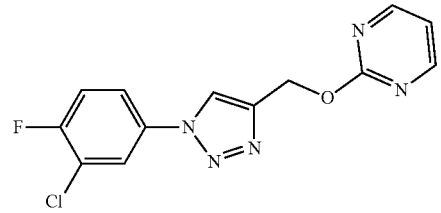 [SMILES: Fc1ccc(-n2cc(COc3ncccn3)nn2)cc1Cl]

The title compound was prepared analogous to Example 155, using (1-(3-chloro-4-fluorophenyl)-1H-1,2,3-triazol-4-yl)methanol and 2-chloropyrimidine. MS (ESI): mass calcd. for $C_{13}H_9ClFN_5O$, 305.0; m/z found, 306.0 [M+H]$^+$. $^1$H NMR (500 MHz, CDCl$_3$) δ 8.57 (d, J=4.7 Hz, 2H), 8.11-8.06 (m, 1H), 7.84 (dd, J=6.2, 2.7 Hz, 1H), 7.62 (ddd, J=8.9, 4.0, 2.7 Hz, 1H), 7.31 (t, J=8.6 Hz, 1H), 7.00 (t, J=4.8 Hz, 1H), 5.66 (d, J=0.7 Hz, 2H).

Example 620: 2-[[1-(3-Chloro-4-fluoro-phenyl)triazol-4-yl]methoxy]-5-methyl-pyrimidine

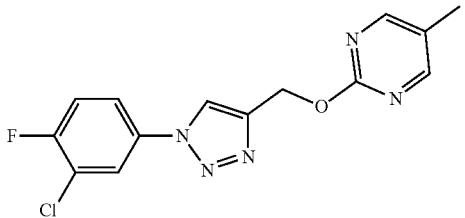 [SMILES: Cc1cnc(OCc2cn(-c3ccc(F)c(Cl)c3)nn2)nc1]

The title compound was prepared analogous to Example 155, using (1-(3-chloro-4-fluorophenyl)-1H-1,2,3-triazol-4-yl)methanol and 2-chloro-5-methylpyrimidine. MS (ESI): mass calcd. for $C_{14}H_{11}ClFN_5O$, 319.1; m/z found, 320.0 [M+H]$^+$. $^1$H NMR (500 MHz, CDCl$_3$) δ 8.38 (d, J=0.7 Hz, 2H), 8.07 (s, 1H), 7.84 (dd, J=6.3, 2.7 Hz, 1H), 7.61 (ddd, J=8.9, 4.0, 2.7 Hz, 1H), 7.30 (t, J=8.6 Hz, 1H), 5.63 (d, J=0.7 Hz, 2H), 2.26 (s, 3H).

Example 621: 2-[[1-(3-Chloro-4-fluoro-phenyl)triazol-4-yl]methoxy]-5-ethyl-pyrimidine

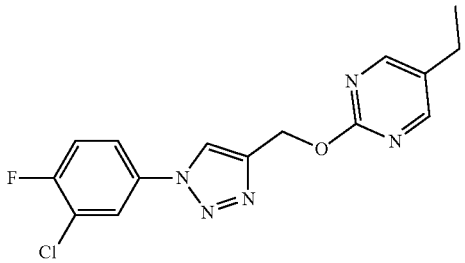 [SMILES: CCc1cnc(OCc2cn(-c3ccc(F)c(Cl)c3)nn2)nc1]

The title compound was prepared analogous to Example 155, using (1-(3-chloro-4-fluorophenyl)-1H-1,2,3-triazol-4-yl)methanol and 2-chloro-5-ethylpyrimidine. MS (ESI): mass calcd. for $C_{15}H_{13}ClFN_5O$, 333.1; m/z found, 334.0 [M+H]$^+$. $^1$H NMR (500 MHz, CDCl$_3$) δ 8.39 (s, 2H), 8.08 (s, 1H), 7.84 (dd, J=6.2, 2.7 Hz, 1H), 7.61 (ddd, J=8.9, 4.0, 2.7 Hz, 1H), 7.30 (t, J=8.6 Hz, 1H), 5.63 (s, 2H), 2.60 (q, J=7.6 Hz, 2H), 1.26 (t, J=7.6 Hz, 3H).

Example 622: 2-[[1-(3-Chloro-4-fluoro-phenyl)triazol-4-yl]methoxy]-4-(methoxymethyl)pyrimidine

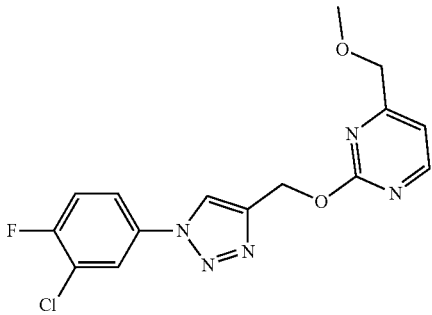 [SMILES: COCc1ccnc(OCc2cn(-c3ccc(F)c(Cl)c3)nn2)n1]

The title compound was prepared analogous to Example 155, using (1-(3-chloro-4-fluorophenyl)-1H-1,2,3-triazol-4-yl)methanol and 2-chloro-4-(methoxymethyl)pyrimidine. MS (ESI): mass calcd. for $C_{15}H_{13}ClFN_5O_2$, 349.1; m/z found, 350.0 [M+H]$^+$. $^1$H NMR (500 MHz, CDCl$_3$) δ 8.54 (d, J=5.0 Hz, 1H), 8.11 (s, 1H), 7.84 (dd, J=6.2, 2.7 Hz, 1H), 7.61 (ddd, J=8.9, 3.9, 2.7 Hz, 1H), 7.30 (t, J=8.6 Hz, 1H), 7.15 (d, J=5.0 Hz, 1H), 5.65 (s, 2H), 4.50 (s, 2H), 3.50 (s, 3H).

Example 623: 2-[[1-[4-Chloro-3-(difluoromethyl)phenyl]triazol-4-yl]methoxy]-4-isopropyl-pyrimidine

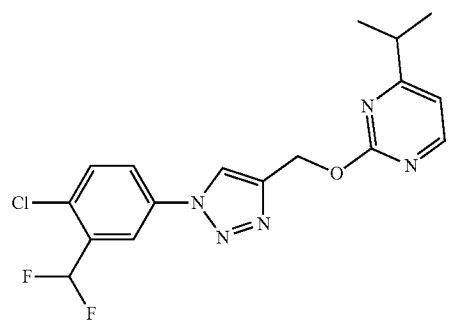

The title compound was prepared analogous to Example 155, using (1-(4-chloro-3-(difluoromethyl)phenyl)-1H-1,2,3-triazol-4-yl)methanol (Intermediate 8) and 2-chloro-4-isopropylpyrimidine. MS (ESI): mass calcd. for $C_{17}H_{16}ClF_2N_5O$, 379.1; m/z found, 380.1 [M+H]$^+$. $^1$H NMR (500 MHz, CDCl$_3$) δ 8.43 (d, J=5.1 Hz, 1H), 8.18 (s, 1H), 8.00 (d, J=2.6 Hz, 1H), 7.89-7.86 (m, 1H), 7.62-7.57 (m, 1H), 7.11-6.85 (m, 2H), 5.66 (s, 2H), 2.97 (hept, J=6.9 Hz, 1H), 1.30 (d, J=6.9 Hz, 6H).

Example 624: [2-[[1-[4-Chloro-3-(difluoromethyl)phenyl]triazol-4-yl]methoxy]pyrimidin-5-yl]methanol

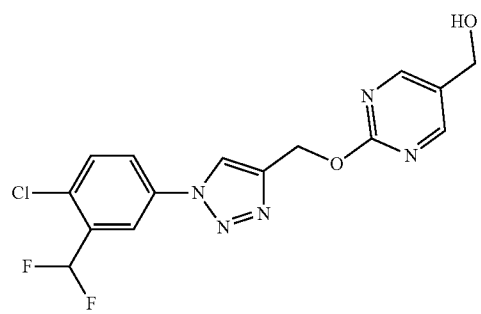 [SMILES: OCc1cnc(OCc2cn(-c3ccc(Cl)c(C(F)F)c3)nn2)nc1]

The title compound was prepared analogous to Example 160, steps A-B, using (1-(4-chloro-3-(difluoromethyl)phenyl)-1H-1,2,3-triazol-4-yl)methanol (Intermediate 8) in step A. MS (ESI): mass calcd. for $C_{15}H_{12}ClF_2N_5O_2$, 367.1; m/z found, 368.0 [M+H]$^+$. $^1$H NMR (500 MHz, CDCl$_3$) δ 8.58 (s, 2H), 8.17 (s, 1H), 8.01 (d, J=2.6 Hz, 1H), 7.89 (dd, J=8.7, 2.6 Hz, 1H), 7.66-7.56 (m, 1H), 6.99 (t, J=54.5 Hz, 1H), 5.68 (d, J=0.7 Hz, 2H), 4.71 (d, J=5.6 Hz, 2H), 1.78 (t, J=5.5 Hz, 1H).

Example 625: [2-[[1-[4-Chloro-3-(difluoromethyl)phenyl]triazol-4-yl]methoxy]pyrimidin-4-yl]methanol

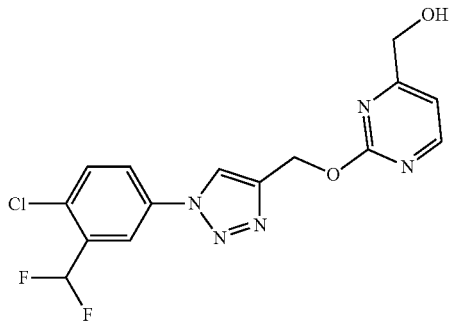 [SMILES: OCc1ccnc(OCc2cn(-c3ccc(Cl)c(C(F)F)c3)nn2)n1]

The title compound was prepared analogous to Example 159, Steps A-B, using (1-(4-chloro-3-(difluoromethyl)phenyl)-1H-1,2,3-triazol-4-yl)methanol (Intermediate 8) in Step A. MS (ESI): mass calcd. for $C_5H_{12}ClF_2N_5O_2$, 367.1; m/z found, 368.0 [M+H]$^+$. $^1$H NMR (500 MHz, CDCl$_3$) δ 8.51 (d, J=5.0 Hz, 1H), 8.19 (s, 1H), 8.00 (d, J=2.6 Hz, 1H), 7.92-7.83 (m, 1H), 7.64-7.56 (m, 1H), 7.11-6.85 (m, 2H), 5.67 (s, 2H), 4.72 (s, 2H).

Example 626: 2-[2-[[1-[4-Chloro-3-(difluoromethyl)phenyl]triazol-4-yl]methoxy]pyrimidin-5-yl]propan-2-ol

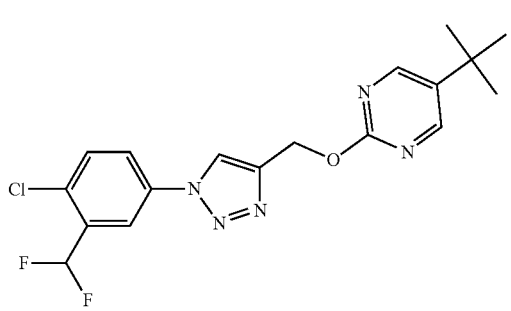 [SMILES: CC(C)(C)c1cnc(OCc2cn(-c3ccc(Cl)c(C(F)F)c3)nn2)nc1]

The title compound was prepared analogous to Example 155, using (1-(4-chloro-3-(difluoromethyl)phenyl)-1H-1,2,3-triazol-4-yl)methanol (Intermediate 8) and 2-(2-chloropyrimidin-5-yl)propan-2-ol. MS (ESI): mass calcd. for $C_{17}H_{16}ClF_2N_5O_2$, 395.1; m/z found, 396.0 [M+H]$^+$. $^1$H NMR (400 MHz, CDCl$_3$) δ 8.66 (s, 2H), 8.19 (s, 1H), 8.01 (d, J=2.6 Hz, 1H), 7.88 (dd, J=8.7, 2.6 Hz, 1H), 7.60 (dd, J=8.6, 1.2 Hz, 1H), 6.98 (t, J=54.5 Hz, 1H), 5.65-5.63 (m, 2H), 1.61 (s, 6H).

Example 627: 2-[[1-[4-Chloro-3-(difluoromethyl)phenyl]triazol-4-yl]methoxy]-4-(methoxymethyl)pyrimidine

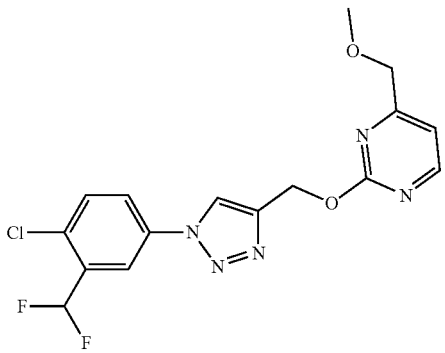 [SMILES: COCc1ccnc(OCc2cn(-c3ccc(Cl)c(C(F)F)c3)nn2)n1]

The title compound was prepared analogous to Example 155, using (1-(4-chloro-3-(difluoromethyl)phenyl)-1H-1,2,3-triazol-4-yl)methanol (Intermediate 8) and 2-chloro-4-(methoxymethyl)pyrimidine. MS (ESI): mass calcd. for $C_{16}H_{14}ClF_2N_5O_2$, 381.1; m/z found, 382.0 [M+H]$^+$. $^1$H NMR (400 MHz, CDCl$_3$) δ 8.55 (d, J=5.0 Hz, 1H), 8.21 (s, 1H), 8.00 (d, J=2.6 Hz, 1H), 7.91-7.86 (m, 1H), 7.63-7.58 (m, 1H), 7.15 (d, J=5.0 Hz, 1H), 6.99 (t, J=54.5 Hz, 1H), 5.66 (s, 2H), 4.50 (s, 2H), 3.50 (s, 3H).

Example 628: 2-[[1-[4-Chloro-3-(difluoromethyl)phenyl]triazol-4-yl]methoxy]-4-(difluoromethyl)pyrimidine

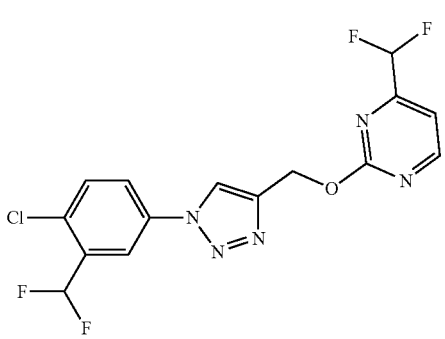 [SMILES: FC(F)c1ccnc(OCc2cn(-c3ccc(Cl)c(C(F)F)c3)nn2)n1]

The title compound was prepared analogous to Example 155, using (1-(4-chloro-3-(difluoromethyl)phenyl)-1H-1,2,3-triazol-4-yl)methanol (Intermediate 8) and 2-chloro-4-difluoromethylpyrimidine. MS (ESI): mass calcd. for $C_{15}H_{10}ClF_4N_5O$, 387.1; m/z found, 388.0 [M+H]$^+$. $^1$H NMR (400 MHz, CDCl$_3$) δ 8.76 (d, J=4.9 Hz, 1H), 8.20 (s, 1H), 8.01 (d, J=2.6 Hz, 1H), 7.91-7.85 (m, 1H), 7.64-7.57 (m, 1H), 7.30 (d, J=4.9 Hz, 1H), 6.99 (t, J=54.5 Hz, 1H), 6.50 (t, J=54.7 Hz, 1H), 5.71 (d, J=0.6 Hz, 2H).

Example 629: 2-[[1-[4-Chloro-3-(difluoromethyl)phenyl]triazol-4-yl]methoxy]-N,N-dimethyl-pyrimidin-4-amine

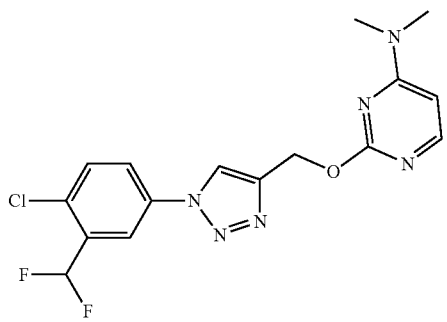 [SMILES: CN(C)c1ccnc(OCc2cn(-c3ccc(Cl)c(C(F)F)c3)nn2)n1]

The title compound was prepared analogous to Example 155, using (1-(4-chloro-3-(difluoromethyl)phenyl)-1H-1,2,3-triazol-4-yl)methanol (Intermediate 8) and 2-chloro-N,N-dimethylpyrimidin-4-amine. MS (ESI): mass calcd. for $C_{16}H_{15}ClF_2N_6O$, 380.1; m/z found, 381.0 [M+H]$^+$. $^1$H NMR (400 MHz, CDCl$_3$) δ 8.15 (s, 1H), 8.06-7.98 (m, 2H), 7.91-7.82 (m, 1H), 7.60 (dt, J=8.7, 1.2 Hz, 1H), 6.99 (t, J=54.6 Hz, 1H), 6.13 (d, J=6.1 Hz, 1H), 5.61 (d, J=0.8 Hz, 2H), 3.11 (s, 6H).

Example 630: 2-[[1-[4-Chloro-3-(difluoromethyl)phenyl]triazol-4-yl]methoxy]-5-cyclopropyl-pyrimidine

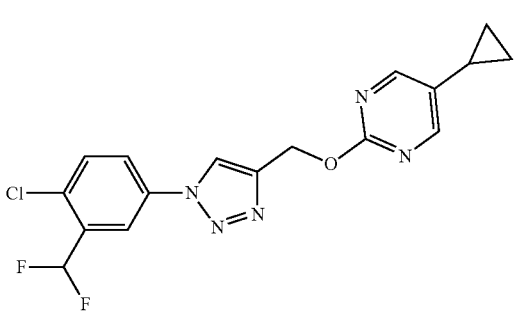 [SMILES: FC(F)c1cc(-n2cc(COc3ncc(C4CC4)cn3)nn2)ccc1Cl]

The title compound was prepared analogous to Example 155, using (1-(4-chloro-3-(difluoromethyl)phenyl)-1H-1,2,3-triazol-4-yl)methanol (Intermediate 8) and 2-chloro-5-cyclopropylpyrimidine. MS (ESI): mass calcd. for $C_{17}H_{14}ClF_2N_5O$, 377.1; m/z found, 378.0 [M+H]$^+$. $^1$H NMR (500 MHz, CDCl$_3$) δ 8.32 (s, 2H), 8.16 (s, 1H), 8.00 (d, J=2.6 Hz, 1H), 7.91-7.87 (m, 1H), 7.64-7.58 (m, 1H), 6.99 (t, J=54.5 Hz, 1H), 5.64 (s, 2H), 1.83 (tt, J=8.4, 5.1 Hz, 1H), 1.02 (ddd, J=8.3, 6.4, 4.8 Hz, 2H), 0.70 (ddd, J=7.3, 5.7, 4.4 Hz, 2H).

Example 631: 2-[[1-[4-Chloro-3-(difluoromethyl)phenyl]triazol-4-yl]methoxy]-4-cyclopropyl-pyrimidine

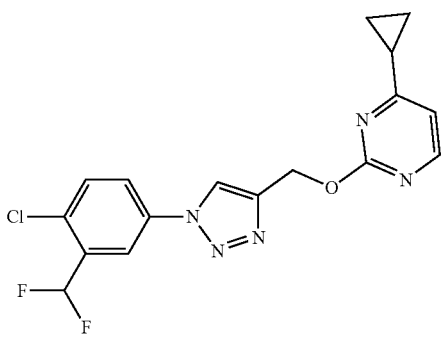 [SMILES: FC(F)c1cc(-n2cc(COc3nccc(C4CC4)n3)nn2)ccc1Cl]

The title compound was prepared analogous to Example 155, using (1-(4-chloro-3-(difluoromethyl)phenyl)-1H-1,2,3-triazol-4-yl)methanol (Intermediate 8) and 2-chloro-4-cyclopropylpyrimidine. MS (ESI): mass calcd. for $C_{17}H_{14}ClF_2N_5O$, 377.1; m/z found, 378.0 [M+H]$^+$. $^1$H NMR (500 MHz, CDCl$_3$) δ 8.32-8.29 (m, 1H), 8.16-8.12 (m, 1H), 8.02-7.98 (m, 1H), 7.89-7.84 (m, 1H), 7.60 (dd, J=8.5, 1.2 Hz, 1H), 7.10-6.84 (m, 2H), 5.60 (s, 2H), 2.00-1.90 (m, 1H), 1.22-1.16 (m, 2H), 1.08 (ddd, J=6.7, 3.0, 1.6 Hz, 2H).

Example 632: 2-[[1-[4-chloro-3-(difluoromethyl)phenyl]triazol-4-yl]methoxy]-5-methyl-pyrimidin-4-amine The title compound was prepared in a manner analogous to Example 161, using (1-(4-chloro-3-(difluoromethyl)phenyl)-1H-1,2,3-triazol-4-yl)methanol (Intermediate 8). (ESI): mass calcd. for $C_{15}H_{13}ClF_2N_6O$, 366.1; m/z found, 366.9 [M+H]$^+$. $^1$H NMR (500 MHz, CDCl$_3$) δ 8.15 (d, J=1.2 Hz, 1H), 8.00 (d, J=2.6 Hz, 1H), 7.92-7.84 (m, 2H), 7.62-7.56 (m, 1H), 6.98 (t, J=54.6 Hz, 1H), 5.60-5.54 (m, 2H), 4.91 (s, 2H), 2.07-2.01 (m, 3H).

Example 633: 2-[[1-[4-Chloro-3-(difluoromethyl)phenyl]triazol-4-yl]methoxy]-N,N,5-trimethyl-pyrimidin-4-amine

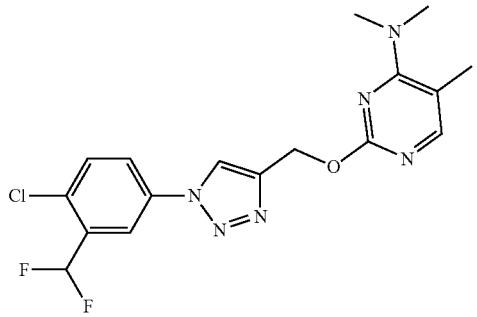 [SMILES: Cc1cnc(OCc2cn(-c3ccc(Cl)c(C(F)F)c3)nn2)nc1N(C)C]

The title compound was prepared analogous to Example 155, using (1-(4-chloro-3-(difluoromethyl)phenyl)-1H-1,2,3-triazol-4-yl)methanol (Intermediate 8) and 2-chloro-N,N,5-trimethylpyrimidin-4-amine. MS (ESI): mass calcd. for $C_{17}H_{17}ClF_2N_5O$, 394.1; m/z found, 395.1 [M+H]$^+$. $^1$H NMR (400 MHz, CDCl$_3$) δ 8.14 (s, 1H), 8.04-7.97 (m, 1H), 7.90-7.80 (m, 2H), 7.62-7.56 (m, 1H), 6.99 (t, J=54.6 Hz, 1H), 5.59 (s, 2H), 3.13 (s, 6H), 2.25 (s, 3H).

Example 634: 2-[[1-[4-Chloro-3-(difluoromethyl)phenyl]triazol-4-yl]methoxy]-4-pyrrolidin-1-yl-pyrimidine

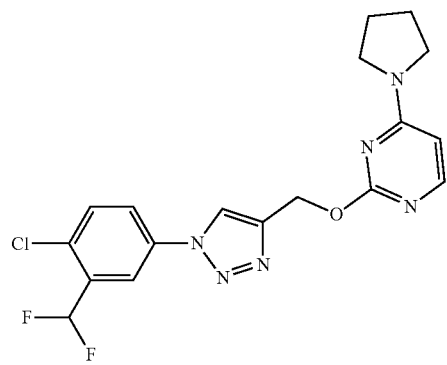 [SMILES: FC(F)c1cc(-n2cc(COc3nccc(N4CCCC4)n3)nn2)ccc1Cl]

The title compound was prepared analogous to Example 155, using (1-(4-chloro-3-(difluoromethyl)phenyl)-1H-1,2,3-triazol-4-yl)methanol (Intermediate 8) and 2-chloro-4-(pyrrolidin-1-yl)pyrimidine. MS (ESI): mass calcd. for $C_{18}H_{17}ClF_2N_6O$, 406.1; m/z found, 407.0 [M+H]$^+$. $^1$H NMR (400 MHz, CDCl$_3$) δ 8.15 (s, 1H), 7.90-7.84 (m, 1H), 7.60 (dt, J=8.6, 1.2 Hz, 1H), 6.99 (t, J=54.6 Hz, 1H), 6.00 (d, J=6.0 Hz, 1H), 5.61 (d, J=0.8 Hz, 2H), 3.62 (s, 2H), 3.35 (s, 2H), 2.00 (s, 4H).

Example 635: 2-[[1-[4-Chloro-3-(difluoromethyl)phenyl]triazol-4-yl]methoxy]-4-(1-piperidyl)pyrimidine

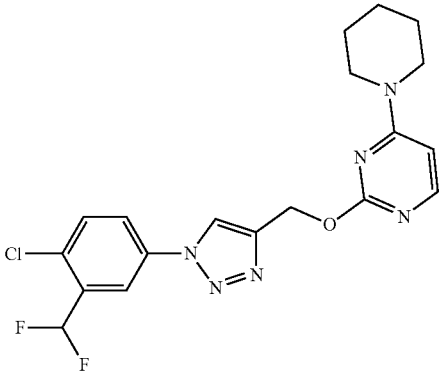 [SMILES: FC(F)c1cc(-n2cc(COc3nccc(N4CCCCC4)n3)nn2)ccc1Cl]

The title compound was prepared analogous to Example 155, using (1-(4-chloro-3-(difluoromethyl)phenyl)-1H-1,2,3-triazol-4-yl)methanol (Intermediate 8) and 2-chloro-4-(piperidin-1-yl)pyrimidine. MS (ESI): mass calcd. for $C_{19}H_{19}ClF_2N_6O$, 420.1; m/z found, 421.0 [M+H]$^+$. $^1$H NMR (400 MHz, CDCl$_3$) δ 8.15 (s, 1H), 8.06-7.96 (m, 2H), 7.91-7.80 (m, 1H), 7.68-7.52 (m, 1H), 6.98 (t, J=54.6 Hz, 1H), 6.19 (d, J=6.1 Hz, 1H), 5.58 (s, 2H), 3.73-3.48 (m, 4H), 1.73-1.56 (m, 6H).

Example 636: 2-[[1-[4-Chloro-3-(difluoromethyl)phenyl]triazol-4-yl]methoxy]-5-(2-fluoroethoxy)pyrimidine

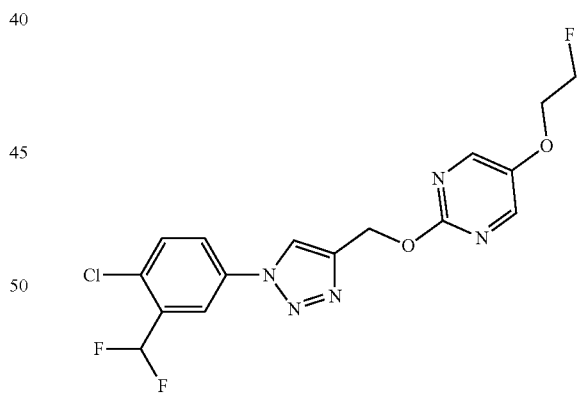

The title compound was prepared in a manner analogous to Example 192, Steps A-B, using (1-(4-chloro-3-(difluoromethyl)phenyl)-1H-1,2,3-triazol-4-yl)methanol (Intermediate 8) in Step B. MS (ESI): mass calcd. for $C_{16}H_{13}ClF_3N_5O_2$, 399.1; m/z found, 400.1 [M+H]$^+$. $^1$H NMR (400 MHz, CDCl$_3$) δ 8.29 (s, 2H), 8.16 (s, 1H), 8.01 (d, J=2.5 Hz, 1H), 7.89 (dd, J=8.7, 2.7 Hz, 1H), 7.61 (d, J=8.7 Hz, 1H), 6.99 (t, J=54.5 Hz, 1H), 5.62 (d, J=0.7 Hz, 2H), 4.90-4.77 (m, 1H), 4.76-4.66 (m, 1H), 4.37-4.27 (m, 1H), 4.27-4.18 (m, 1H). $^{19}$F NMR (376 MHz, CDCl$_3$) δ −115.87 (s), −116.02 (s).

Example 637: 2-[[1-[4-Chloro-3-(difluoromethyl)phenyl]triazol-4-yl]methoxy]-5-(3-fluoropropyl)pyrimidine

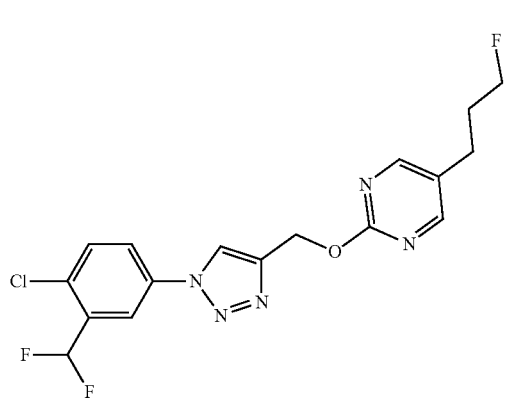 [SMILES: FCCCc1cnc(OCc2cn(-c3ccc(Cl)c(C(F)F)c3)nn2)nc1]

The title compound was prepared in a manner analogous to Example 196, Steps A-G, using (1-(4-chloro-3-(difluoromethyl)phenyl)-1H-1,2,3-triazol-4-yl)methanol (Intermediate 8) in step G. MS (ESI): mass calcd. for $C_{17}H_{15}ClF_3N_5O$, 397.1; m/z found, 398.1 [M+H]$^+$. $^1$H NMR (400 MHz, CDCl$_3$) δ 8.42 (s, 2H), 8.18 (s, 1H), 8.01 (d, J=2.7 Hz, 1H), 7.92-7.86 (m, 1H), 7.61 (d, J=8.7 Hz, 1H), 6.99 (t, J=54.5 Hz, 1H), 5.65 (d, J=0.7 Hz, 1H), 4.55 (t, J=5.7 Hz, 0H), 4.43 (t, J=5.7 Hz, 0H), 2.78-2.63 (m, 1H), 2.10-1.92 (m, 1H)

Example 638: 2-((1-(4-(Azetidin-1-yl)-3-(difluoromethyl)phenyl)-1H-1,2,3-triazol-4-yl)methoxy)-5-methylpyrimidine

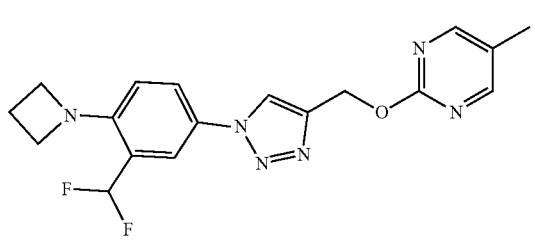 [SMILES: Cc1cnc(OCc2cn(-c3ccc(N4CCC4)c(C(F)F)c3)nn2)nc1]

Made in an analogous manner to Example 188 using 2-((1-(3-(difluoromethyl)-4-fluorophenyl)-1H-1,2,3-triazol-4-yl)methoxy)-5-methylpyrimidine (Example 51). MS (ESI): mass calcd. for $C_{18}H_{18}F_2N_7O$, 372.3; m/z found, 373.1 [M+H]$^+$. $^1$H NMR (500 MHz, CDCl$_3$) δ 8.41-8.34 (d, J=0.9 Hz, 2H), 8.05-8.00 (s, 1H), 7.74-7.70 (d, J=2.5 Hz, 1H), 7.67-7.62 (m, 1H), 6.91-6.64 (m, 1H), 6.58-6.51 (d, J=8.8 Hz, 1H), 5.64-5.58 (d, J=0.6 Hz, 2H), 4.15-4.07 (m, 4H), 2.45-2.35 (m, 2H), 2.29-2.21 (m, 3H).

Example 639: 2-[[1-(2,4-Difluoro-3-methyl-phenyl)triazol-4-yl]methoxy]-5-isopropyl-pyrimidine

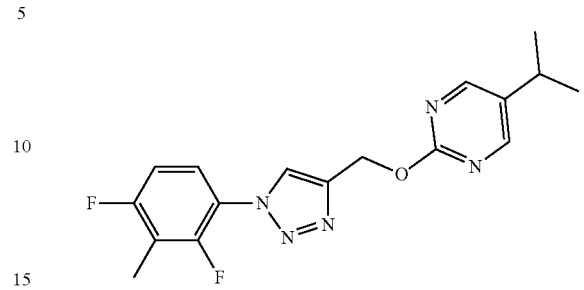

The title compound was prepared analogous to Example 155, using (1-(2,4-difluoro-3-methylphenyl)-1H-1,2,3-triazol-4-yl)methanol (Intermediate 10) and 2-chloro-5-isopropylpyrimidine. MS (ESI): mass calcd. for $C_{17}H_{17}F_2N_5O$, 345.1; m/z found, 346.0 [M+H]$^+$. $^1$H NMR (400 MHz, CDCl$_3$) δ 8.42 (s, 2H), 8.14 (d, J=2.8 Hz, 1H), 7.74-7.65 (m, 1H), 7.02 (td, J=8.8, 1.8 Hz, 1H), 5.65 (d, J=0.7 Hz, 2H), 2.91 (hept, J=6.8 Hz, 1H), 2.30 (t, J=2.0 Hz, 3H), 1.29 (d, J=7.0 Hz, 6H).

Example 640: 2-[[1-(2,4-Difluoro-3-methyl-phenyl)triazol-4-yl]methoxy]-4-isopropyl-pyrimidine

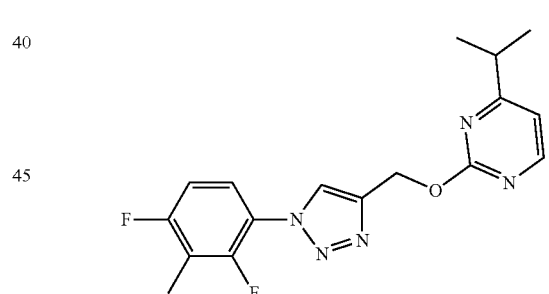

The title compound was prepared analogous to Example 155, using (1-(2,4-difluoro-3-methylphenyl)-1H-1,2,3-triazol-4-yl)methanol (Intermediate 10) and 2-chloro-4-isopropylpyrimidine. MS (ESI): mass calcd. for $C_{17}H_{17}F_2N_5O$, 345.1; m/z found, 346.0 [M+H]$^+$. $^1$H NMR (500 MHz, CDCl$_3$) δ 8.42 (d, J=5.1 Hz, 1H), 8.13 (d, J=2.9 Hz, 1H), 7.71-7.64 (m, 1H), 7.04-6.97 (m, 1H), 6.85 (d, J=5.1 Hz, 1H), 5.66 (d, J=0.7 Hz, 2H), 2.95 (hept, J=6.9 Hz, 1H), 2.28 (t, J=2.0 Hz, 3H), 1.28 (d, J=6.9 Hz, 6H).

Example 641: 5-(Difluoromethyl)-2-[[1-(2,4-difluoro-3-methyl-phenyl)triazol-4-yl]methoxy]pyrimidine

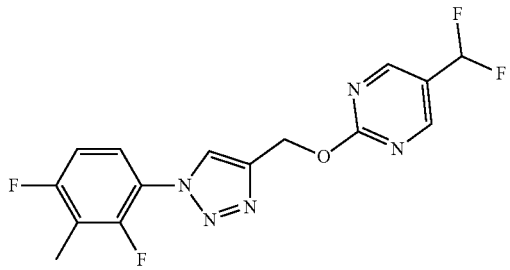 [SMILES: Cc1c(F)ccc(-n2cc(COc3ncc(C(F)F)cn3)nn2)c1F]

The title compound was prepared analogous to Example 155, using (1-(2,4-difluoro-3-methylphenyl)-1H-1,2,3-triazol-4-yl)methanol (Intermediate 10) and 2-chloro-5-difluoromethylpyrimidine. MS (ESI): mass calcd. for $C_{15}H_{11}F_4N_5O$, 353.1; m/z found, 354.0 [M+H]$^+$. $^1$H NMR (400 MHz, CDCl$_3$) δ 8.71 (t, J=1.2 Hz, 2H), 8.15 (d, J=2.8 Hz, 1H), 7.74-7.66 (m, 1H), 7.03 (td, J=8.6, 1.8 Hz, 1H), 6.72 (t, J=55.6 Hz, 1H), 5.72 (s, 2H), 2.30 (t, J=2.1 Hz, 3H).

Example 642: 4-(Difluoromethyl)-2-[[1-(2,4-difluoro-3-methyl-phenyl)triazol-4-yl]methoxy]pyrimidine

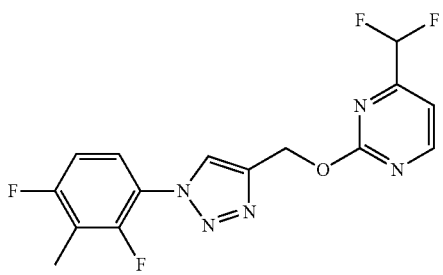 [SMILES: Cc1c(F)ccc(-n2cc(COc3nccc(C(F)F)n3)nn2)c1F]

The title compound was prepared analogous to Example 155, using (1-(2,4-difluoro-3-methylphenyl)-1H-1,2,3-triazol-4-yl)methanol (Intermediate 10) and 2-chloro-4-difluoromethylpyrimidine. MS (ESI): mass calcd. for $C_{15}H_{11}F_4N_5O$, 353.1; m/z found, 354.0 [M+H]$^+$. $^1$H NMR (400 MHz, CDCl$_3$) δ 8.75 (d, J=4.9 Hz, 1H), 8.16 (d, J=2.8 Hz, 1H), 7.75-7.64 (m, 1H), 7.29 (d, J=4.9 Hz, 1H), 7.10-6.96 (m, 1H), 6.49 (t, J=54.7 Hz, 1H), 5.71 (s, 2H), 2.30 (t, J=2.1 Hz, 3H).

Example 643: 2-[[1-(2,4-Difluoro-3-methyl-phenyl)triazol-4-yl]methoxy]-5-(trifluoromethyl)pyrimidine

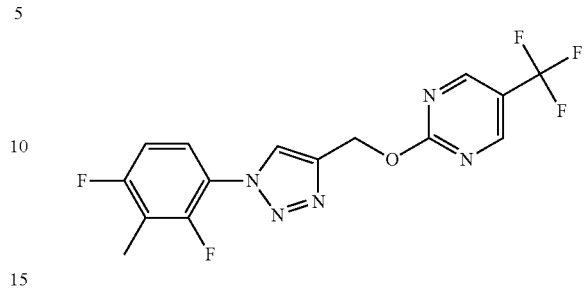

The title compound was prepared analogous to Example 155, using (1-(2,4-difluoro-3-methylphenyl)-1H-1,2,3-triazol-4-yl)methanol (Intermediate 10) and 2-chloro-5-trifluoromethylpyrimidine. MS (ESI): mass calcd. for $C_{15}H_{10}F_5N_5O$, 371.1; m/z found, 372.0 [M+H]$^+$. $^1$H NMR (400 MHz, CDCl$_3$) δ 8.81 (d, J=0.9 Hz, 2H), 8.16 (d, J=2.8 Hz, 1H), 7.70 (td, J=8.7, 5.6 Hz, 1H), 7.03 (td, J=8.7, 1.8 Hz, 1H), 5.74 (s, 2H), 2.30 (t, J=2.1 Hz, 3H).

Example 644: 2-[2-[[1-(2,4-Difluoro-3-methyl-phenyl)triazol-4-yl]methoxy]pyrimidin-5-yl]propan-2-ol

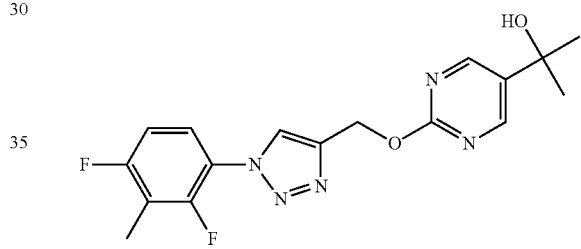

The title compound was prepared analogous to Example 155, using (1-(2,4-difluoro-3-methylphenyl)-1H-1,2,3-triazol-4-yl)methanol (Intermediate 10) and 2-(2-chloropyrimidin-5-yl)propan-2-ol. MS (ESI): mass calcd. for $C_{17}H_{17}F_2N_5O_{52}$, 361.1; m/z found, 362.1 [M+H]$^+$. $^1$H NMR (400 MHz, CDCl$_3$) δ 8.67 (s, 2H), 8.14 (d, J=2.8 Hz, 1H), 7.69 (td, J=8.6, 5.7 Hz, 1H), 7.02 (td, J=8.7, 1.9 Hz, 1H), 5.67 (s, 2H), 2.30 (s, 3H), 1.62 (s, 6H).

Example 645: 2-[[1-(2,4-Difluoro-3-methyl-phenyl)triazol-4-yl]methoxy]-4-(methoxymethyl)pyrimidine

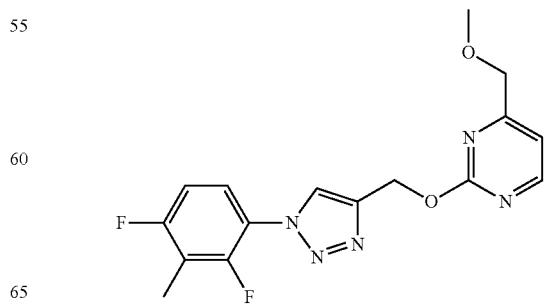

The title compound was prepared analogous to Example 155, using (1-(2,4-difluoro-3-methylphenyl)-1H-1,2,3-triazol-4-yl)methanol (Intermediate 10) and 2-chloro-4-(methoxymethyl)pyrimidine. MS (ESI): mass calcd. for $C_{15}H_{15}F_2N_5O_2$, 347.1; m/z found, 348.0 [M+H]$^+$. $^1$H NMR (400 MHz, CDCl$_3$) δ 8.54 (d, J=5.0 Hz, 1H), 8.14 (d, J=2.8 Hz, 1H), 7.68 (dddd, J=9.1, 8.4, 5.7, 0.8 Hz, 1H), 7.14 (dt, J=5.0, 0.7 Hz, 1H), 7.01 (td, J=8.7, 1.8 Hz, 1H), 5.65 (d, J=0.7 Hz, 2H), 4.49 (d, J=0.7 Hz, 2H), 3.49 (s, 3H), 2.29 (t, J=2.1 Hz, 3H).

Example 646: 5-(Difluoromethoxy)-2-[[1-(2,4-difluoro-3-methyl-phenyl)triazol-4-yl]methoxy]pyrimidine

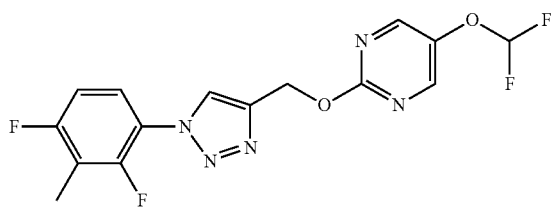 [SMILES: Cc1c(F)ccc(-n2cc(COc3ncc(OC(F)F)cn3)nn2)c1F]

The title compound was prepared analogous to Example 155, using (1-(2,4-difluoro-3-methylphenyl)-1H-1,2,3-triazol-4-yl)methanol (Intermediate 10) and 2-chloro-5-(difluoromethoxy)pyrimidine. MS (ESI): mass calcd. for $C_{15}H_{11}F_4N_5O_2$, 369.1; m/z found, 370.1 [M+H]$^+$. $^1$H NMR (400 MHz, CDCl$_3$) δ 8.44 (s, 2H), 8.14 (d, J=2.7 Hz, 1H), 7.74-7.65 (m, 1H), 7.02 (td, J=8.7, 1.8 Hz, 1H), 6.52 (t, J=71.9 Hz, 1H), 5.66 (d, J=0.6 Hz, 2H), 2.30 (t, J=2.1 Hz, 3H).

Example 647: 5-Cyclopropyl-2-[[1-(2,4-difluoro-3-methyl-phenyl)triazol-4-yl]methoxy]pyrimidine

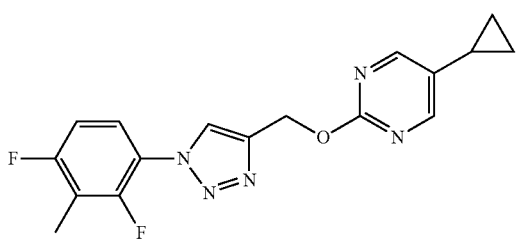 [SMILES: Cc1c(F)ccc(-n2cc(COc3ncc(C4CC4)cn3)nn2)c1F]

The title compound was prepared analogous to Example 155, using (1-(2,4-difluoro-3-methylphenyl)-1H-1,2,3-triazol-4-yl)methanol (Intermediate 10) and 2-chloro-5-cyclopropylpyrimidine. MS (ESI): mass calcd. for $C_{17}H_{15}F_2N_5O$, 343.1; m/z found, 344.1 [M+H]$^+$. $^1$H NMR (500 MHz, CDCl$_3$) δ 8.31 (s, 2H), 8.12 (d, J=2.8 Hz, 1H), 7.68 (td, J=8.7, 5.7 Hz, 1H), 7.01 (td, J=8.7, 1.8 Hz, 1H), 5.63 (s, 2H), 2.29 (t, J=2.0 Hz, 3H), 1.82 (tt, J=8.4, 5.1 Hz, 1H), 1.01 (ddd, J=8.4, 6.4, 4.9 Hz, 2H), 0.72-0.66 (m, 2H).

Example 648: 4-Cyclopropyl-2-[[1-(2,4-difluoro-3-methyl-phenyl)triazol-4-yl]methoxy]pyrimidine

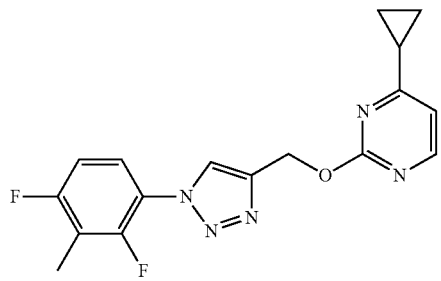 [SMILES: Cc1c(F)ccc(-n2cc(COc3nccc(C4CC4)n3)nn2)c1F]

The title compound was prepared analogous to Example 155, using (1-(2,4-difluoro-3-methylphenyl)-1H-1,2,3-triazol-4-yl)methanol (Intermediate 10) and 2-chloro-4-cyclopropylpyrimidine. MS (ESI): mass calcd. for $C_{17}H_{15}F_2N_5O$, 343.1; m/z found, 344.1 [M+H]$^+$. $^1$H NMR (500 MHz, CDCl$_3$) δ 8.29 (d, J=5.1 Hz, 1H), 8.10 (d, J=2.7 Hz, 1H), 7.68 (td, J=8.7, 5.7 Hz, 1H), 7.01 (td, J=8.7, 1.8 Hz, 1H), 6.85 (d, J=5.1 Hz, 1H), 5.60 (s, 2H), 2.29 (t, J=2.1 Hz, 3H), 1.94 (tt, J=8.1, 4.6 Hz, 1H), 1.22-1.16 (m, 2H), 1.10-1.03 (m, 2H).

Example 649: 2-[[1-(2,4-Difluoro-3-methyl-phenyl)triazol-4-yl]methoxy]-5-fluoro-4-methyl-pyrimidine

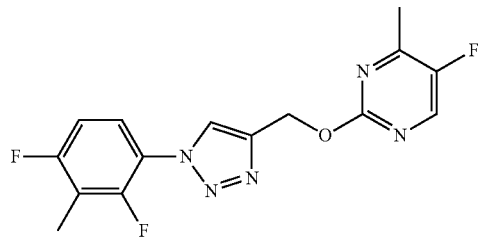 [SMILES: Cc1nc(OCc2cn(-c3ccc(F)c(C)c3F)nn2)ncc1F]

The title compound was prepared analogous to Example 155, using (1-(2,4-difluoro-3-methylphenyl)-1H-1,2,3-triazol-4-yl)methanol (Intermediate 10) and 2-chloro-5-fluoro-4-methylpyrimidine. MS (ESI): mass calcd. for $C_{15}H_{12}F_3N_5O$, 335.1; m/z found, 336.0 [M+H]$^+$. $^1$H NMR (400 MHz, CDCl$_3$) δ 8.25 (d, J=1.2 Hz, 1H), 8.13 (d, J=2.7 Hz, 1H), 7.76-7.64 (m, 1H), 7.06-6.95 (m, 1H), 5.67-5.57 (m, 2H), 2.49 (d, J=2.5 Hz, 3H), 2.30 (t, J=2.0 Hz, 3H).

Example 650: 5-Chloro-2-[[1-(2,4-difluoro-3-methyl-phenyl)triazol-4-yl]methoxy]-4-methyl-pyrimidine

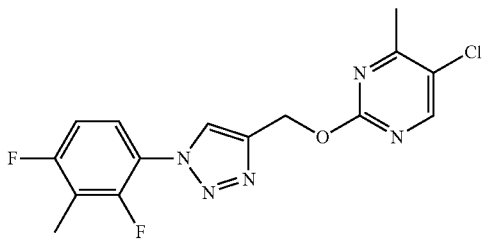 [SMILES: Cc1nc(OCc2cn(-c3ccc(F)c(C)c3F)nn2)ncc1Cl]

The title compound was prepared analogous to Example 155, using (1-(2,4-difluoro-3-methylphenyl)-1H-1,2,3-triazol-4-yl)methanol (Intermediate 10) and 2,5-dichloro-4-methylpyrimidine. MS (ESI): mass calcd. for $C_{15}H_{12}ClF_2N_5O$, 351.1; m/z found, 352.0 [M+H]$^+$. $^1$H NMR (400 MHz, CDCl$_3$) δ 8.38 (s, 1H), 8.13 (d, J=2.6 Hz, 1H), 7.76-7.63 (m, 1H), 7.06-6.99 (m, 1H), 5.66-5.60 (m, 2H), 2.56 (s, 3H), 2.30 (t, J=2.0 Hz, 3H).

Example 651: 2-[[1-(2,4-Difluoro-3-methyl-phenyl)triazol-4-yl]methoxy]-5-methyl-pyrimidin-4-amine

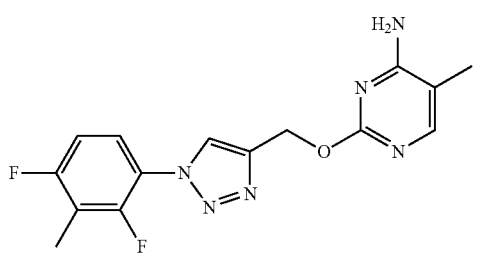 [SMILES: Cc1cnc(OCc2cn(-c3ccc(F)c(C)c3F)nn2)nc1N]

The title compound was prepared in a manner analogous to Example 161, using (1-(2,4-difluoro-3-methylphenyl)-1H-1,2,3-triazol-4-yl)methanol (Intermediate 10). MS (ESI): mass calcd. for $C_{15}H_{14}F_2N_6O$, 332.1; m/z found, 333.1 [M+H]$^+$. $^1$H NMR (500 MHz, CD$_3$OD) δ 8.46 (d, J=2.3 Hz, 1H), 7.72 (s, 1H), 7.65 (td, J=8.6, 5.6 Hz, 1H), 7.15 (td, J=8.8, 1.8 Hz, 1H), 5.46 (s, 2H), 2.30 (t, J=2.0 Hz, 3H), 1.99 (s, 3H).

Example 652: 2-[[1-[3-(Difluoromethyl)-2,4-difluoro-phenyl]triazol-4-yl]methoxy]-5-(trifluoromethyl)pyrimidine

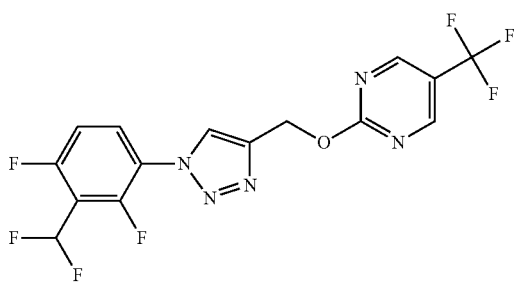 [SMILES: Fc1ccc(-n2cc(COc3ncc(C(F)(F)F)cn3)nn2)c(F)c1C(F)F]

Step A. 1-(3-(Difluoromethyl)-2,4-difluorophenyl)-1H-1,2,3-triazol-4-yl)methanol The title compound was prepared in a manner analogous to Intermediate 5 using 3-(difluoromethyl)-2,4-difluoroaniline in step A, and 1-azido-3-(difluoromethyl)-2,4-difluorobenzene and a reaction temperature of 60° C. in step B.

Step B. 2-[[1-[3-(Difluoromethyl)-2,4-difluoro-phenyl]triazol-4-yl]methoxy]-5-(trifluoromethyl)pyrimidine The title compound was prepared analogous to Example 155, using (1-(3-(difluoromethyl)-2,4-difluorophenyl)-1H-1,2,3-triazol-4-yl)methanol and 2-chloro-5-trifluoromethyl-pyrimidine. MS (ESI): mass calcd. for $C_{15}H_6F_7N_5O$, 407.1; m/z found, 408.0 [M+H]$^+$. $^1$H NMR (500 MHz, CDCl$_3$) δ 8.82 (s, 2H), 8.22 (d, J=2.7 Hz, 1H), 8.14-8.05 (m, 1H), 7.24-7.16 (m, 1H), 7.00 (t, J=52.9 Hz, 1H), 5.74 (s, 2H).

Example 653: 5-Chloro-2-[[1-(2,4-difluoro-5-methyl-phenyl)triazol-4-yl]methoxy]pyrimidine

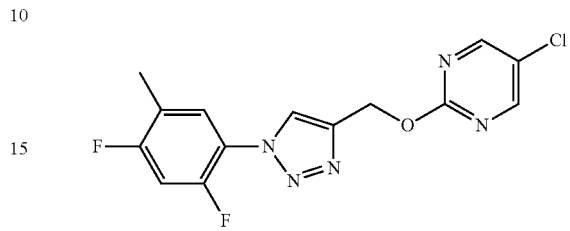

The title compound was prepared analogous to Example 155, using (1-(2,4-difluoro-5-methylphenyl)-1H-1,2,3-triazol-4-yl)methanol (Intermediate 13) and 2,5-dichloropyrimidine. MS (ESI): mass calcd. for $C_{14}H_{10}ClF_2N_5O$, 337.1; m/z found, 338.0 [M+H]$^+$. $^1$H NMR (500 MHz, CDCl$_3$) δ 8.49 (s, 2H), 8.14 (d, J=2.5 Hz, 1H), 7.77 (t, J=8.0 Hz, 1H), 7.00 (t, J=9.7 Hz, 1H), 5.63 (s, 2H), 2.32 (s, 3H).

Example 654: 2-[[1-(2,4-Difluoro-5-methyl-phenyl)triazol-4-yl]methoxy]-5-methyl-pyrimidine

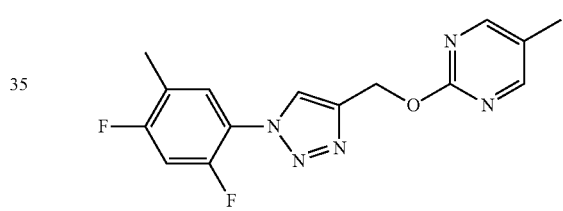

The title compound was prepared analogous to Example 155, using (1-(2,4-difluoro-5-methylphenyl)-1H-1,2,3-triazol-4-yl)methanol (Intermediate 13) and 2-chloro-5-methylpyrimidine. MS (ESI): mass calcd. for $C_{15}H_{13}F_2N_5O$, 317.1; m/z found, 318.1 [M+H]$^+$. $^1$H NMR (500 MHz, CDCl$_3$) δ 8.37 (s, 2H), 8.14 (d, J=2.7 Hz, 1H), 7.77 (t, J=8.0 Hz, 1H), 6.99 (dd, J=10.6, 8.9 Hz, 1H), 5.63 (s, 2H), 2.32 (s, 3H), 2.25 (s, 3H).

Example 655: 2-[[1-(2,4-Difluoro-5-methyl-phenyl)triazol-4-yl]methoxy]-5-ethyl-pyrimidine

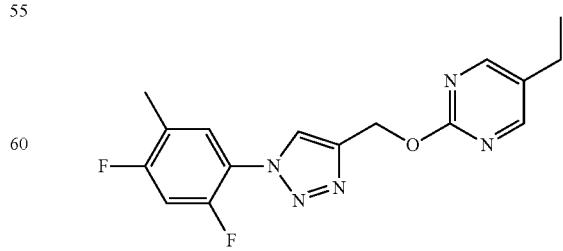

The title compound was prepared analogous to Example 155, using (1-(2,4-difluoro-5-methylphenyl)-1H-1,2,3-triazol-4-yl)methanol (Intermediate 13) and 2-chloro-5-ethyl-pyrimidine. MS (ESI): mass calcd. for $C_{16}H_{15}F_2N_5O$, 331.1; m/z found, 332.1 $[M+H]^+$. $^1H$ NMR (500 MHz, $CDCl_3$) δ 8.38 (s, 2H), 8.14 (d, J=2.8 Hz, 1H), 7.80-7.74 (m, 1H), 6.98 (dd, J=10.6, 8.9 Hz, 1H), 5.63 (d, J=0.6 Hz, 2H), 2.59 (q, J=7.6 Hz, 2H), 2.36-2.25 (m, 3H), 1.25 (t, J=7.6 Hz, 3H).

Example 656: 5-(Difluoromethyl)-2-[[1-(2,4-difluoro-5-methyl-phenyl)triazol-4-yl]methoxy]pyrimidine

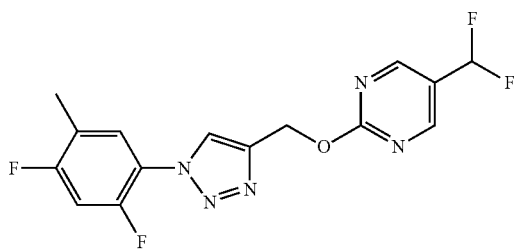 [SMILES: Cc1cc(-n2cc(COc3ncc(C(F)F)cn3)nn2)c(F)cc1F]

The title compound was prepared analogous to Example 155, using (1-(2,4-difluoro-5-methylphenyl)-1H-1,2,3-triazol-4-yl)methanol (Intermediate 13) and 2-chloro-5-difluoromethylpyrimidine. MS (ESI): mass calcd. for $C_{15}H_{11}F_4N_5O$, 353.1; m/z found, 354.0 $[M+H]^+$. $^1H$ NMR (500 MHz, $CDCl_3$) δ 8.70 (s, 2H), 8.16 (d, J=2.7 Hz, 1H), 7.77 (t, J=7.5 Hz, 1H), 7.00 (dd, J=10.7, 8.9 Hz, 1H), 6.72 (t, J=55.6 Hz, 1H), 5.71 (d, J=0.7 Hz, 2H), 2.37-2.26 (m, 3H).

Example 657: 5-Chloro-2-[[1-(2,4-difluoro-5-methyl-phenyl)triazol-4-yl]methoxy]-4-methyl-pyrimidine

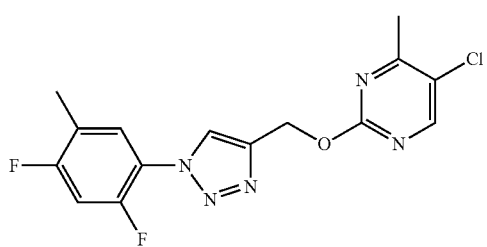 [SMILES: Cc1cc(-n2cc(COc3ncc(Cl)c(C)n3)nn2)c(F)cc1F]

The title compound was prepared analogous to Example 155, using (1-(2,4-difluoro-5-methylphenyl)-1H-1,2,3-triazol-4-yl)methanol (Intermediate 13) and 2,5-dichloro-4-methylpyrimidine. MS (ESI): mass calcd. for $C_{15}H_{12}ClF_2N_5O$, 351.1; m/z found, 352.0 $[M+H]^+$. $^1H$ NMR (500 MHz, $CDCl_3$) δ 8.36 (s, 1H), 8.14 (d, J=2.7 Hz, 1H), 7.82-7.70 (m, 1H), 6.99 (dd, J=10.6, 8.9 Hz, 1H), 5.62 (s, 2H), 2.55 (s, 3H), 2.33-2.29 (m, 3H).

Example 658: 5-Cyclopropyl-2-[[1-(2,4-difluoro-5-methyl-phenyl)triazol-4-yl]methoxy]pyrimidine

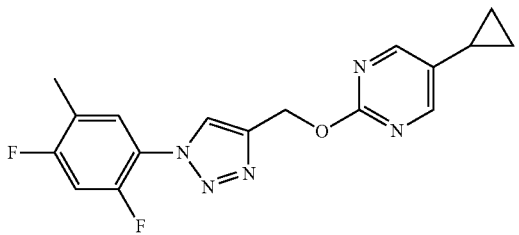 [SMILES: Cc1cc(-n2cc(COc3ncc(C4CC4)cn3)nn2)c(F)cc1F]

The title compound was prepared analogous to Example 155, using (1-(2,4-difluoro-5-methylphenyl)-1H-1,2,3-triazol-4-yl)methanol (Intermediate 13) and 2-chloro-5-cyclopropylpyrimidine. MS (ESI): mass calcd. for $C_{17}H_{15}F_2N_5O$, 343.1; m/z found, 344.1 $[M+H]^+$. $^1H$ NMR (500 MHz, $CDCl_3$) δ 8.31 (s, 2H), 8.14 (d, J=2.7 Hz, 1H), 7.77 (t, J=7.8 Hz, 1H), 6.99 (dd, J=10.6, 8.9 Hz, 1H), 5.63 (s, 2H), 2.33-2.31 (m, 3H), 1.82 (tt, J=8.5, 5.2 Hz, 1H), 1.04-0.99 (m, 2H), 0.69 (dt, J=6.4, 4.9 Hz, 2H)

Example 659: 5-Chloro-2-[[1-(6-methyl-2-pyridyl)triazol-4-yl]methoxy]pyrimidine

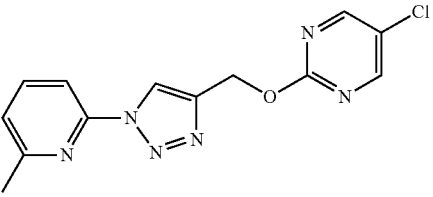 [SMILES: Cc1cccc(-n2cc(COc3ncc(Cl)cn3)nn2)n1]

The title compound was prepared in a manner analogous to Example 174, steps A-C, using 2,5-dichloropyrimidine in step C. MS (ESI): mass calcd. for $C_{13}H_{11}ClN_6O$, 302.1; m/z found, 303.0 $[M+H]^+$. $^1H$ NMR (500 MHz, $CDCl_3$) δ 8.71 (s, 1H), 8.49 (s, 2H), 7.96 (d, J=8.1 Hz, 1H), 7.77 (t, J=7.8 Hz, 1H), 7.18 (d, J=7.6 Hz, 1H), 5.64 (d, J=0.7 Hz, 2H), 2.57 (s, 3H).

Example 660: 5-Ethyl-2-[[1-(6-methyl-2-pyridyl)triazol-4-yl]methoxy]pyrimidine

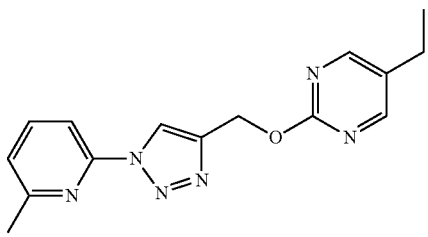 [SMILES: CCc1cnc(OCc2cn(-c3cccc(C)n3)nn2)nc1]

The title compound was prepared in a manner analogous to Example 174, steps A-C, using 2-chloro-5-ethylpyrimidine in step C. MS (ESI): mass calcd. for $C_{15}H_{16}N_6O$, 296.1; m/z found, 297.1 $[M+H]^+$. $^1H$ NMR (400 MHz, $CDCl_3$) δ 8.71 (s, 1H), 8.39 (d, J=0.6 Hz, 2H), 7.96 (d, J=8.1 Hz, 1H), 7.76 (t, J=7.8 Hz, 1H), 7.17 (d, J=7.5 Hz, 1H), 5.64 (d, J=0.7 Hz, 2H), 2.65-2.53 (m, 5H), 1.25 (t, J=7.6 Hz, 3H).

Example 661: 5-Chloro-4-methyl-2-[[1-(6-methyl-2-pyridyl)triazol-4-yl]methoxy]pyrimidine

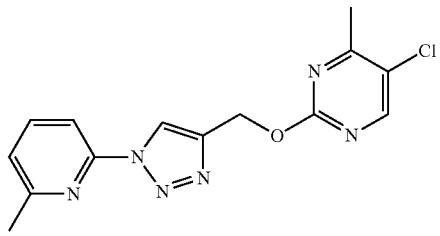 [SMILES: Cc1cccc(-n2cc(COc3ncc(Cl)c(C)n3)nn2)n1]

The title compound was prepared in a manner analogous to Example 174, Steps A-C, using 2,5-dichloro-4-methyl-pyrimidine in Step C. MS (ESI): mass calcd. for $C_{14}H_{13}ClN_6O$, 316.1; m/z found, 317.1 [M+H]$^+$. $^1$H NMR (500 MHz, CDCl$_3$) δ 8.71 (s, 1H), 8.38 (s, 1H), 7.97 (d, J=8.1 Hz, 1H), 7.77 (t, J=7.8 Hz, 1H), 7.18 (d, J=7.3 Hz, 1H), 5.63 (d, J=0.7 Hz, 2H), 2.57 (s, 3H), 2.56 (s, 3H).

Example 662: 5-Methyl-2-[[1-(4-methyl-2-pyridyl)triazol-4-yl]methoxy]pyrimidine

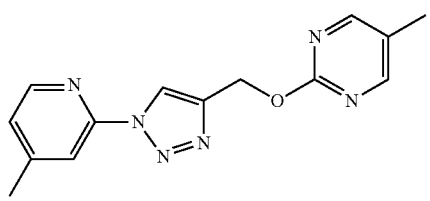 [SMILES: Cc1cnc(OCc2cn(-c3cc(C)ccn3)nn2)nc1]

The title compound was prepared analogous to Example 174, steps A-C, using 4-methylpyridine N-oxide in Step A, 7-methyltetrazolo[1,5-a]pyridine in Step B, and (1-(4-methylpyridin-2-yl)-1H-1,2,3-triazol-4-yl)methanol in Step C. MS (ESI): mass calcd. for $C_{14}H_{14}N_6O$, 282.1; m/z found, 283.0 [M+H]$^+$. $^1$H NMR (500 MHz, CDCl$_3$) δ 8.66 (s, 1H), 8.37 (s, 2H), 8.32 (d, J=5.0 Hz, 1H), 8.04-7.98 (m, 1H), 7.17-7.12 (m, 1H), 5.63 (s, 2H), 2.47 (s, 3H), 2.24 (s, 3H).

Example 663: 5-Ethyl-2-[[1-(4-methyl-2-pyridyl)triazol-4-yl]methoxy]pyrimidine

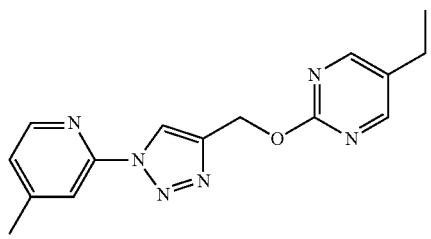 [SMILES: CCc1cnc(OCc2cn(-c3cc(C)ccn3)nn2)nc1]

The title compound was prepared analogous to Example 174, Steps A-C, using 4-methylpyridine N-oxide in Step A, 7-methyltetrazolo[1,5-a]pyridine in Step B, and (1-(4-methylpyridin-2-yl)-1H-1,2,3-triazol-4-yl)methanol and 2-chloro-5-ethylpyrimidine in Step C. MS (ESI): mass calcd. for $C_{15}H_{16}N_6O$, 296.1; m/z found, 297.1 [M+H]$^+$. $^1$H NMR (500 MHz, CDCl$_3$) δ 8.69-8.64 (m, 1H), 8.40-8.37 (m, 2H), 8.33 (d, J=5.0 Hz, 1H), 8.04-8.01 (m, 1H), 7.17-7.12 (m, 1H), 5.67-5.60 (m, 2H), 2.59 (q, J=7.4 Hz, 2H), 2.47 (s, 3H), 1.25 (t, J=7.6 Hz, 3H)

Example 664: 5-Ethyl-2-[[1-(2-methyl-4-pyridyl)triazol-4-yl]methoxy]pyrimidine

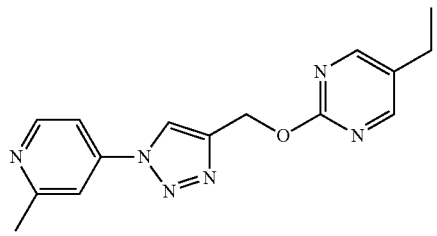 [SMILES: CCc1cnc(OCc2cn(-c3ccnc(C)c3)nn2)nc1]

The title compound was prepared analogous to Example 175, steps A-C, using 2-chloro-5-ethylpyrimidine in step C. MS (ESI): mass calcd. for $C_{15}H_{16}N_6O$, 296.1; m/z found, 297.1 [M+H]$^+$. $^1$H NMR (400 MHz, CDCl$_3$) δ 8.65 (d, J=5.5 Hz, 1H), 8.40 (s, 2H), 8.21 (s, 1H), 7.61 (d, J=2.1 Hz, 1H), 7.51-7.47 (m, 1H), 5.65 (s, 2H), 2.67 (s, 3H), 2.61 (q, J=7.6 Hz, 2H), 1.27 (t, J=7.6 Hz, 3H).

Example 665: 2-[[1-(2-Bromo-4-pyridyl)triazol-4-yl]methoxy]-5-ethyl-pyrimidine

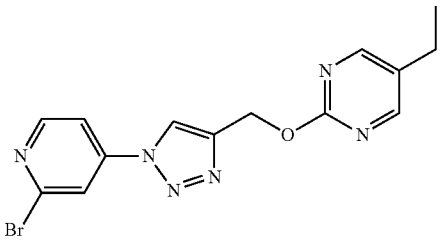 [SMILES: CCc1cnc(OCc2cn(-c3ccnc(Br)c3)nn2)nc1]

The title compound was prepared analogous to Example 177, steps A-C, using 2-chloro-5-ethylpyrimidine in step C. MS (ESI): mass calcd. for $C_{14}H_{13}BrN_6O$, 360.0; m/z found, 361.0 [M+H]$^+$. $^1$H NMR (400 MHz, CD$_3$OD) δ 8.88 (s, 1H), 8.53 (d, J=5.5 Hz, 1H), 8.48 (s, 2H), 8.24 (d, J=2.0 Hz, 1H), 8.01 (dd, J=5.5, 2.1 Hz, 1H), 5.61 (s, 2H), 2.64 (q, J=7.7 Hz, 2H), 1.26 (t, J=7.6 Hz, 3H).

Example 666: 5-Methyl-2-[[1-[2-(trifluoromethyl)-4-pyridyl]triazol-4-yl]methoxy]pyrimidine

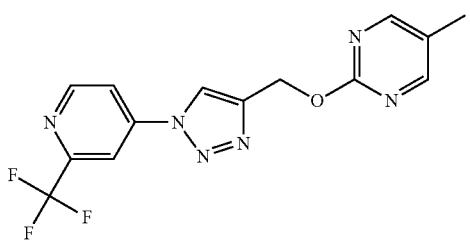 [SMILES: Cc1cnc(OCc2cn(-c3ccnc(C(F)(F)F)c3)nn2)nc1]

The title compound was prepared in a manner analogous to Example 177, steps A-C, using 4-amino-2-(trifluoromethyl)pyridine in step A, 4-azido-2-(trifluoromethyl)pyridine in step B, and (1-(2-(trifluoromethyl)pyridin-4-yl)-1H-1,2,3-triazol-4-yl)methanol in step C. MS (ESI): mass calcd. for $C_{14}H_{11}F_3N_6O$, 336.1; m/z found, 337.1 [M+H]$^+$. $^1$H NMR (500 MHz, CDCl$_3$) δ 8.90 (d, J=5.4 Hz, 1H), 8.39 (d, J=0.8 Hz, 2H), 8.30-8.28 (m, 1H), 8.12 (d, J=2.1 Hz, 1H), 7.92 (dd, J=5.4, 2.0 Hz, 1H), 5.66 (d, J=0.8 Hz, 2H), 2.27 (s, 3H).

Example 667: 5-Ethyl-2-[[1-[2-(trifluoromethyl)-4-pyridyl]triazol-4-yl]methoxy]pyrimidine

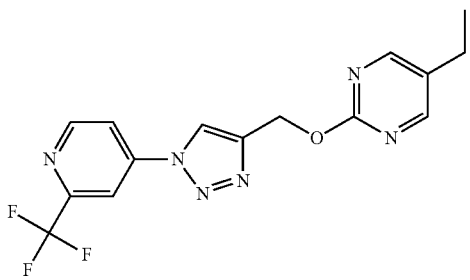 [SMILES: CCc1cnc(OCc2cn(-c3ccnc(C(F)(F)F)c3)nn2)nc1]

The title compound was prepared in a manner analogous to Example 177, Steps A-C, using 4-amino-2-(trifluoromethyl)pyridine in step A, 4-azido-2-(trifluoromethyl)pyridine in step B, and (1-(2-(trifluoromethyl)pyridin-4-yl)-1H-1,2,3-triazol-4-yl)methanol and 2-chloro-5-ethylpyrimidine in step C. MS (ESI): mass calcd. for $C_{15}H_{13}F_3N_6O$, 350.1; m/z found, 351.1 [M+H]$^+$. $^1$H NMR (500 MHz, CDCl$_3$) δ 8.90 (d, J=5.4 Hz, 1H), 8.42-8.39 (m, 2H), 8.30 (t, J=0.7 Hz, 1H), 8.13 (d, J=2.0 Hz, 1H), 7.92 (dd, J=5.4, 2.1 Hz, 1H), 5.67 (d, J=0.8 Hz, 2H), 2.62 (q, J=7.7 Hz, 2H), 1.27 (t, J=7.6 Hz, 3H).

Example 668: 5-Fluoro-4-methyl-2-((1-(5-(trifluoromethyl)thiophen-2-yl)-1H-1,2,3-triazol-4-yl)methoxy)pyrimidine

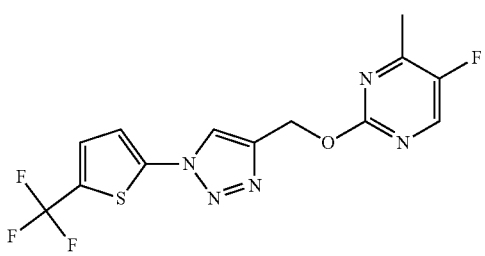 [SMILES: Cc1nc(OCc2cn(-c3ccc(C(F)(F)F)s3)nn2)ncc1F]

The title compound was prepared in a manner analogous to Example 155 using (1-(5-(trifluoromethyl)thiophen-2-yl)-1H-1,2,3-triazol-4-yl)methanol and 2-chloro-5-fluoro-4-methylpyrimidine. MS (ESI): mass calcd. for $C_{13}H_9F_4N_5OS$, 359.3; m/z found, 360.1 [M+H]$^+$. $^1$H NMR (500 MHz, CDCl$_3$) δ 8.28-8.23 (s, 1H), 8.11-8.05 (s, 1H), 7.42-7.37 (m, 1H), 7.19-7.15 (m, 1H), 5.62-5.57 (s, 2H), 2.53-2.45 (d, J=2.4 Hz, 3H).

Example 669: 5-Methoxy-2-((1-(5-(trifluoromethyl)thiophen-2-yl)-1H-1,2,3-triazol-4-yl)methoxy)pyrimidine

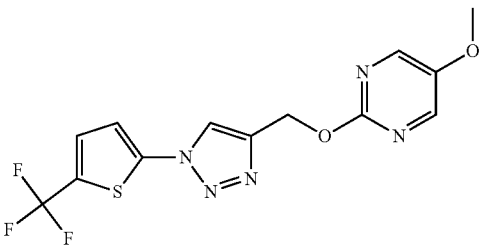 [SMILES: COc1cnc(OCc2cn(-c3ccc(C(F)(F)F)s3)nn2)nc1]

The title compound was prepared in a manner analogous to Example 155 using (1-(5-(trifluoromethyl)thiophen-2-yl)-1H-1,2,3-triazol-4-yl)methanol and 2-chloro-5-methoxypyrimidine. MS (ESI): mass calcd. for $C_{13}H_{10}F_3N_5O_2S$, 357.3; m/z found, 358.1 [M+H]$^+$. $^1$H NMR (500 MHz, CDCl$_3$) δ 8.26-8.22 (s, 2H), 8.09-8.06 (d, J=0.9 Hz, 1H), 7.40-7.37 (m, 1H), 7.19-7.15 (m, 1H), 5.62-5.56 (s, 2H), 3.91-3.85 (m, 3H).

Example 670: 5-(Trifluoromethyl)-2-((1-(5-(trifluoromethyl)thiophen-2-yl)-1H-1,2,3-triazol-4-yl)methoxy)pyrimidine

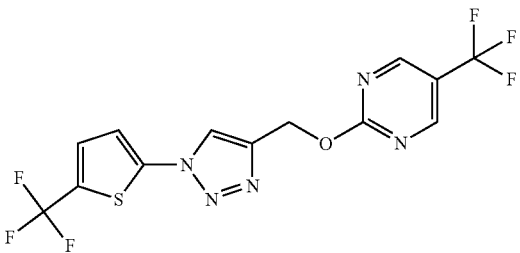 [SMILES: FC(F)(F)c1cnc(OCc2cn(-c3ccc(C(F)(F)F)s3)nn2)nc1]

The title compound was prepared in a manner analogous to Example 155 using (1-(5-(trifluoromethyl)thiophen-2-yl)-1H-1,2,3-triazol-4-yl)methanol and 2-chloro-5-(trifluoromethyl)pyrimidine. MS (ESI): mass calcd. for $C_{13}H_{17}F_6N_5OS$, 395.3; m/z found, 396.1 [M+H]$^+$. $^1$H NMR (400 MHz, CDCl$_3$) δ 8.85-8.80 (d, J=0.9 Hz, 2H), 8.12-8.09 (m, 1H), 7.42-7.38 (m, 1H), 7.22-7.17 (m, 1H), 5.74-5.70 (d, J=0.7 Hz, 2H).

Example 671: 2-((1-(3-(Difluoromethoxy)-4-fluorophenyl)-1H-1,2,3-triazol-4-yl)methoxy)-N-(oxetan-3-yl)pyrimidin-4-amine

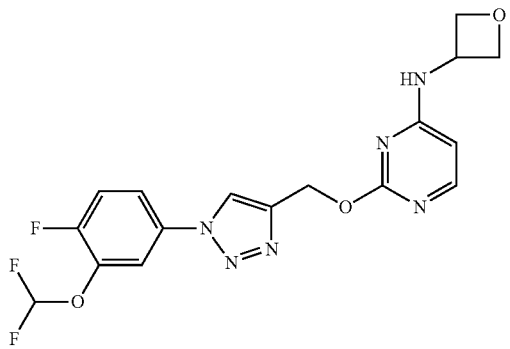 [SMILES: Fc1ccc(-n2cc(COc3nccc(NC4COC4)n3)nn2)cc1OC(F)F]

The title compound was prepared in a manner analogous to Example 159, using (1-(3-(difluoromethoxy)-4-fluorophenyl)-1H-1,2,3-triazol-4-yl)methanol and 2-chloro-N-(oxetan-3-yl)-N-((2-(trimethylsilyl)ethoxy)methyl)pyrimidin-4-amine (Intermediate 62) in Step A. MS (ESI): mass calcd. for $C_{17}H_{15}F_3N_6O_3$, 408.1; m/z found, 409.2 [M+H]$^+$. $^1$H NMR (500 MHz, DMSO-$d_6$) δ 8.91 (s, 1H), 8.26-8.17 (m, 1H), 8.00 (dd, J=7.0, 2.6 Hz, 1H), 7.97-7.91 (m, 1H), 7.87 (ddd, J=8.9, 3.9, 2.6 Hz, 1H), 7.68 (dd, J=10.2, 9.0 Hz, 1H), 7.40 (t, J=72.8 Hz, 1H), 6.24-6.16 (m, 1H), 5.38 (s, 2H), 5.00-4.86 (m, 1H), 4.79 (t, J=6.7 Hz, 2H), 4.45 (t, J=6.1 Hz, 2H).

Examples 672-689, 693-698, 700-716 may be prepared in a manner analogous to the previously described examples.

Example 672: 5-(Azetidin-1-yl)-2-((1-(3-(difluoromethoxy)-4-fluorophenyl)-1H-1,2,3-triazol-4-yl)methoxy)pyridine

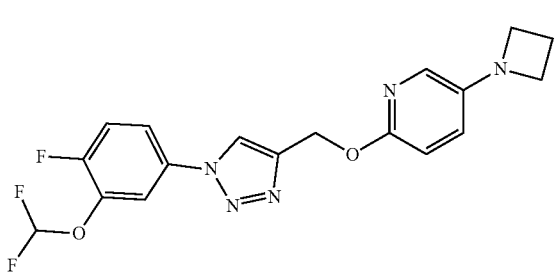 [SMILES: Fc1ccc(-n2cc(COc3ccc(N4CCC4)cn3)nn2)cc1OC(F)F]

MS (ESI): mass calcd. for $C_{18}H_{16}F_3N_5O_2$, 391.1

Example 673: 2-((1-(3-(Difluoromethoxy)-4-fluorophenyl)-1H-1,2,3-triazol-4-yl)methoxy)-5-(3-fluoroazetidin-1-yl)pyridine

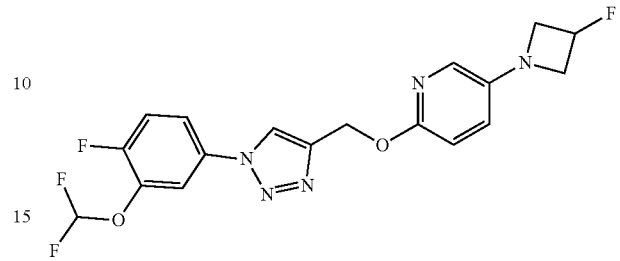

MS (ESI): mass calcd. for $C_{18}H_{15}F_4N_5O_2$, 409.1

Example 674: 5-(3,3-Difluoroazetidin-1-yl)-2-((1-(3-(difluoromethoxy)-4-fluorophenyl)-1H-1,2,3-triazol-4-yl)methoxy)pyridine

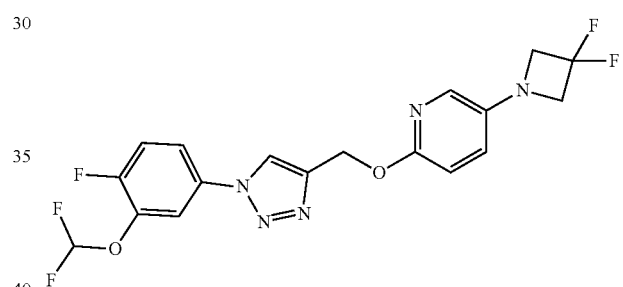

MS (ESI): mass calcd. for $C_{18}H_{14}F_5N_5O_2$, 427.1

Example 675: 2-(Azetidin-1-yl)-6-((1-(3-(difluoromethoxy)-4-fluorophenyl)-1H-1,2,3-triazol-4-yl)methoxy)pyridine

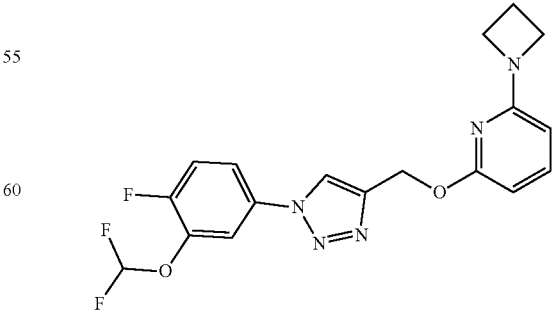

MS (ESI): mass calcd. for $C_{18}H_{16}F_3N_5O_2$, 391.1

Example 676: 2-((1-(3-(Difluoromethoxy)-4-fluorophenyl)-1H-1,2,3-triazol-4-yl)methoxy)-6-(3-fluoroazetidin-1-yl)pyridine

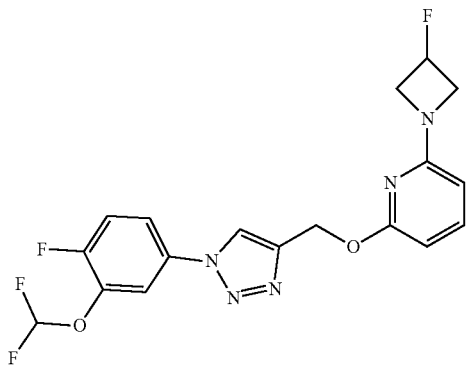 [SMILES: Fc1ccc(-n2cc(COc3cccc(N4CC(F)C4)n3)nn2)cc1OC(F)F]

MS (ESI): mass calcd. for $C_{18}H_{15}F_4N_5O_2$, 409.1

Example 677: 2-(3,3-Difluoroazetidin-1-yl)-6-((1-(3-(difluoromethoxy)-4-fluorophenyl)-1H-1,2,3-triazol-4-yl)methoxy)pyridine

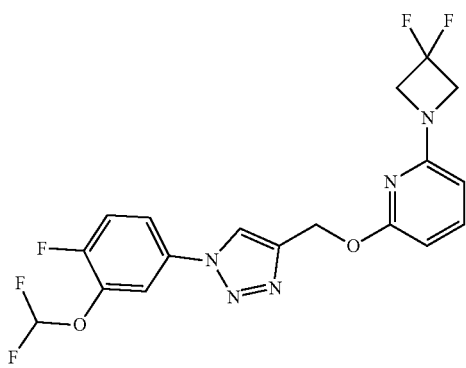 [SMILES: Fc1ccc(-n2cc(COc3cccc(N4CC(F)(F)C4)n3)nn2)cc1OC(F)F]

MS (ESI): mass calcd. for $C_{18}H_{14}F_5N_5O_2$, 427.1

Example 678: 4-(Azetidin-1-yl)-2-((1-(3-(difluoromethoxy)-4-fluorophenyl)-1H-1,2,3-triazol-4-yl)methoxy)pyridine

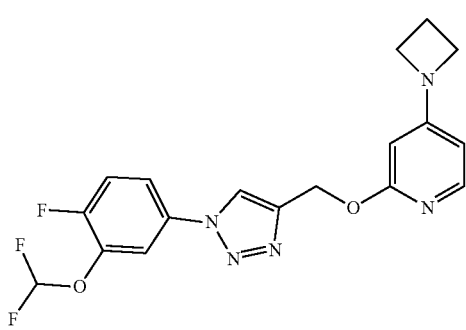 [SMILES: Fc1ccc(-n2cc(COc3cc(N4CCC4)ccn3)nn2)cc1OC(F)F]

Example 679: 2-((1-(3-(Difluoromethoxy)-4-fluorophenyl)-1H-1,2,3-triazol-4-yl)methoxy)-4-(3-fluoroazetidin-1-yl)pyridine

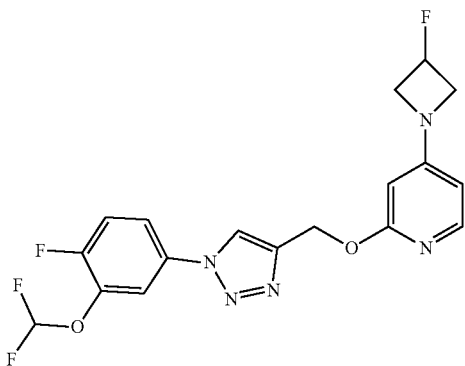 [SMILES: Fc1ccc(-n2cc(COc3cc(N4CC(F)C4)ccn3)nn2)cc1OC(F)F]

MS (ESI): mass calcd. for $C_{18}H_{15}F_4N_5O_2$, 409.1

Example 680: 4-(3,3-Difluoroazetidin-1-yl)-2-((1-(3-(difluoromethoxy)-4-fluorophenyl)-1H-1,2,3-triazol-4-yl)methoxy)pyridine

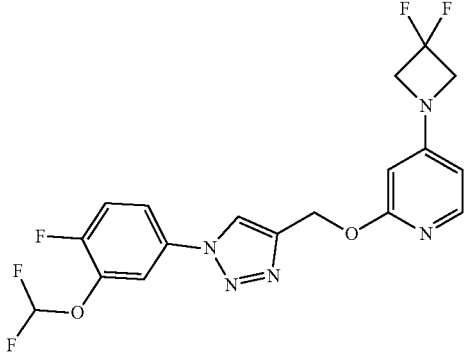 [SMILES: Fc1ccc(-n2cc(COc3cc(N4CC(F)(F)C4)ccn3)nn2)cc1OC(F)F]

MS (ESI): mass calcd. for $C_{18}H_{14}F_5N_5O_2$, 427.1

Example 681: 2-((1-(3-(Difluoromethoxy)-4-fluorophenyl)-1H-1,2,3-triazol-4-yl)methoxy)-4-(1H-pyrrol-2-yl)pyrimidine

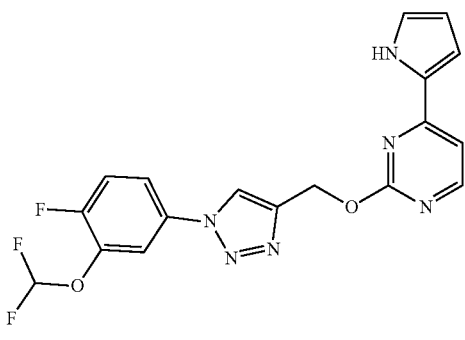 [SMILES: Fc1ccc(-n2cc(COc3nccc(-c4ccc[nH]4)n3)nn2)cc1OC(F)F]

MS (ESI): mass calcd. for $C_{18}H_{13}F_3N_6O_2$, 402.1

Example 682: 2-((1-(3-(Difluoromethoxy)-4-fluorophenyl)-1H-1,2,3-triazol-4-yl)methoxy)-4-(1H-pyrazol-5-yl)pyrimidine

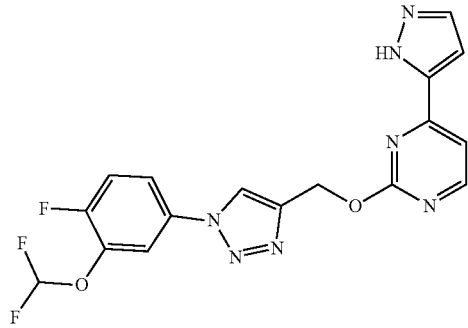 [SMILES: Fc1ccc(-n2cc(COc3nccc(-c4ccn[nH]4)n3)nn2)cc1OC(F)F]

MS (ESI): mass calcd. for $C_{17}H_{12}F_3N_7O_2$, 403.1

Example 683: 2-((1-(3-(Difluoromethoxy)-4-fluorophenyl-1H-1,2,3-triazol-4-yl)methoxy)-5-(1H-pyrrol-2-yl)pyrimidine

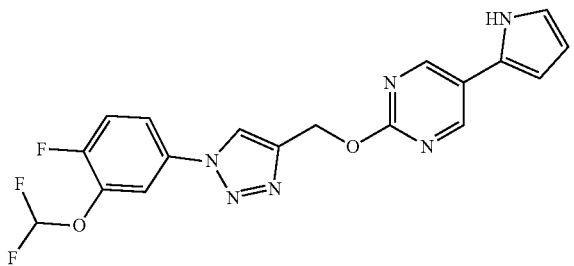 [SMILES: Fc1ccc(-n2cc(COc3ncc(-c4ccc[nH]4)cn3)nn2)cc1OC(F)F]

MS (ESI): mass calcd. for $C_{18}H_{13}F_3N_6O_2$, 402.1

Example 684: 2-((1-(3-(Difluoromethoxy)-4-fluorophenyl-1H-1,2,3-triazol-4-yl)methoxy)-5-(1H-pyrazol-5-yl)pyrimidine

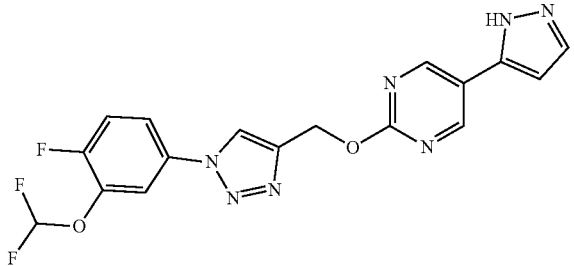 [SMILES: Fc1ccc(-n2cc(COc3ncc(-c4ccn[nH]4)cn3)nn2)cc1OC(F)F]

MS (ESI): mass calcd. for $C_{17}H_{12}F_3N_7O_2$, 403.1

Example 685: 2-((1-(3-(Difluoromethoxy)-4-fluorophenyl)-1H-1,2,3-triazol-4-yl)methoxy)-N-ethyl-5-fluoropyrimidin-4-amine

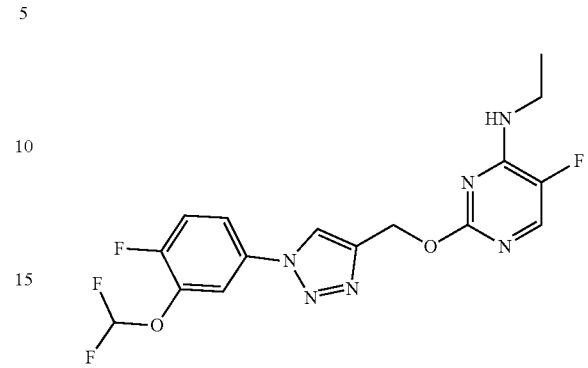

MS (ESI): mass calcd. for $C_{16}H_{14}F_4N_6O_2$, 398.1

Example 686: 2-((1-(3-Difluoromethoxy)-4-fluorophenyl)-1H-1,2,3-triazol-4-yl)methoxy)-5-fluoro-N-(oxetan-3-yl)pyrimidin-4-amine

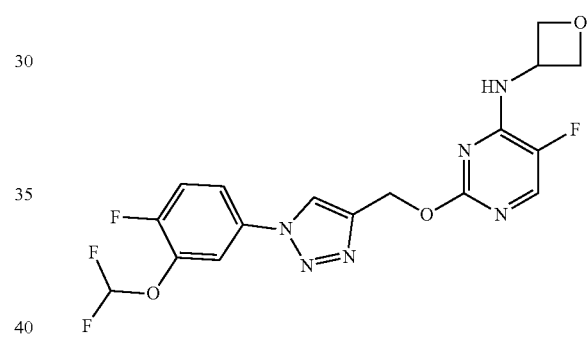

MS (ESI): mass calcd. for $C_{17}H_{14}F_4N_6O_3$, 426.1

Example 687: N-(3,3-Difluorocyclobutyl)-2-((1-(3-(difluoromethoxy)-4-fluorophenyl)-1H-1,2,3-triazol-4-yl)methoxy)-5-fluoropyrimidin-4-amine

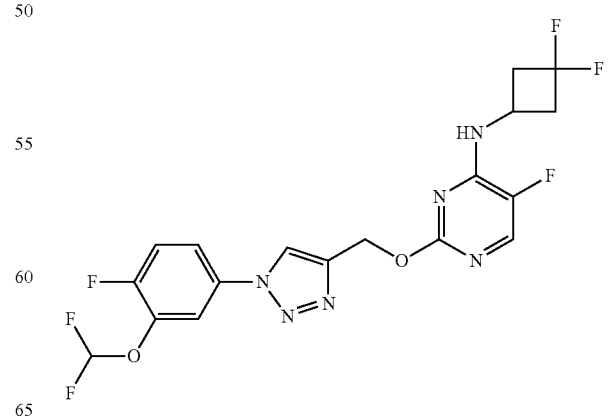

MS (ESI): mass calcd. for $C_{18}H_{14}F_6N_6O_2$, 460.1

Example 688: N-Cyclopropyl-2-((1-(3-(difluoromethyl)-4-fluorophenyl)-1H-1,2,3-triazol-4-yl)methoxy)pyrimidin-4-amine

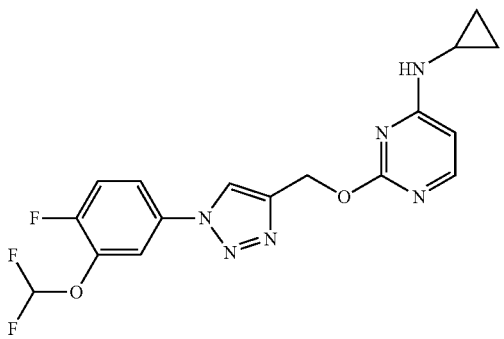 [SMILES: Fc1ccc(-n2cc(COc3nccc(NC4CC4)n3)nn2)cc1OC(F)F]

MS (ESI): mass calcd. for $C_{17}H_{15}F_3N_6O_2$, 392.1

Example 689: N-(3,3-Difluorocyclobutyl)-2-((1-(3-(difluoromethoxy)-4-fluorophenyl)-1H-1,2,3-triazol-4-yl)methoxy)pyrimidin-4-amine

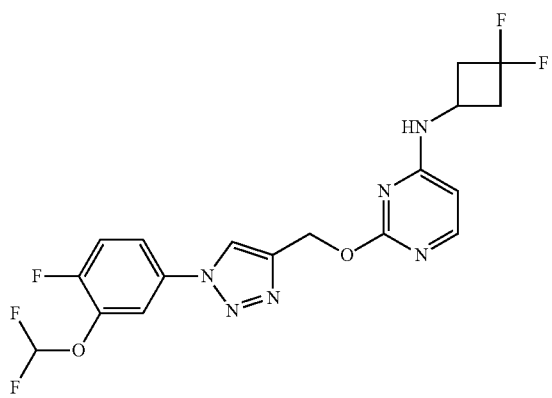 [SMILES: Fc1ccc(-n2cc(COc3nccc(NC4CC(F)(F)C4)n3)nn2)cc1OC(F)F]

MS (ESI): mass calcd. for $C_{18}H_{15}F_8N_6O_2$, 442.1

Example 690: N-Cyclopropyl-2-((1-(3-(difluoromethyl)-4-fluorophenyl)-1H-1,2,3-triazol-4-yl)methoxy)pyrimidin-4-amine

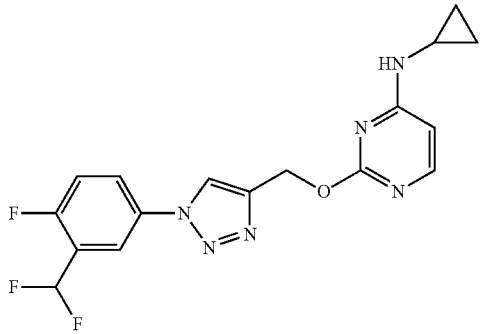 [SMILES: Fc1ccc(-n2cc(COc3nccc(NC4CC4)n3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 2-chloro-N-cyclopropylpyrimidine-4-amine. MS (ESI): mass calcd. for $C_{17}H_{15}F_3N_6O$, 376.1; m/z found, 377.1 [M+H]$^+$. $^1$H NMR (500 MHz, CDCl$_3$) δ 8.16-8.09 (m, 2H), 7.96-7.92 (m, 1H), 7.92-7.86 (m, 1H), 7.35-7.29 (m, 1H), 7.08-6.79 (t, J=54.6 Hz, 1H), 6.44-6.33 (s, 1H), 5.59-5.53 (d, J=0.8 Hz, 2H), 5.43-5.32 (s, 1H), 2.66-2.51 (s, 1H), 0.93-0.76 (m, 2H), 0.66-0.54 (m, 2H).

Example 691: N-Ethyl-2-((1-(3-(difluoromethyl)-4-fluorophenyl)-1H-1,2,3-triazol-4-yl)methoxy)pyrimidin-4-amine

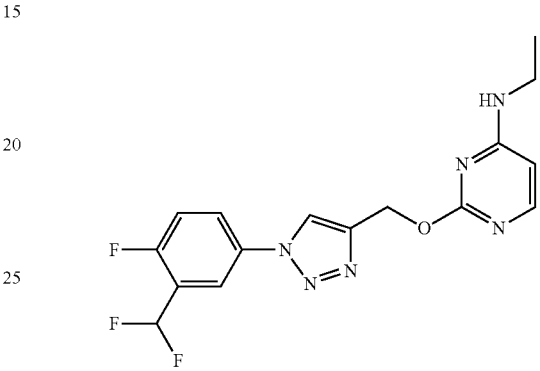

The title compound was prepared in a manner analogous to Example 171, Steps A-B, (1-(3-(difluoromethyl)-4-fluorophenyl)-1H-1,2,3-triazol-4-yl)methanol (Intermediate 9) and 2-chloro-N-ethyl-N-((2-(trimethylsilyl)ethoxy)methyl)pyrimidin-4-amine (Intermediate 60) in Step A. MS (ESI): mass calcd. for $C_{18}H_{21}F_3N_6O$, 394.2; m/z found, 365.1 [M+H]$^+$. $^1$H NMR (500 MHz, CDCl$_3$) δ 8.15-8.10 (s, 1H), 8.09-7.97 (d, J=11.8 Hz, 1H), 7.97-7.92 (d, J=5.5 Hz, 1H), 7.92-7.87 (s, 1H), 7.36-7.28 (t, J=9.0 Hz, 1H), 7.08-6.82 (t, J=54.6 Hz, 1H), 6.07-5.99 (d, J=5.8 Hz, 1H), 5.63-5.54 (s, 2H), 5.00-4.81 (s, 1H), 3.48-3.29 (m, 2H), 1.30-1.22 (t, J=7.1 Hz, 3H).

Example 692: 2-((1-(3-(Difluoromethyl)-4-fluorophenyl)-1H-1,2,3-triazol-4-yl)methoxy)-4-(2-methyl-1H-imidazol-1-yl)pyrimidine

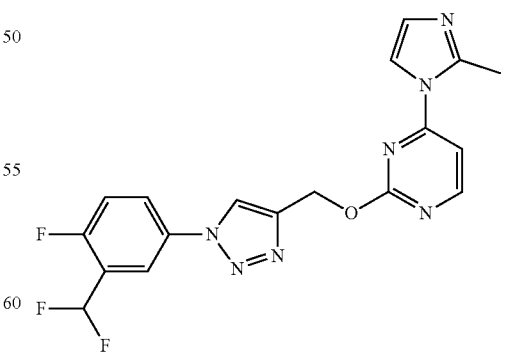

The title compound was prepared in a manner analogous to Example 1 using (1-(3-(difluoromethyl)-4-fluorophenyl)-1H-1,2,3-triazol-4-yl)methanol (Intermediate 9) and 2-chloro-4-(2-methyl-1H-imidazol-1-yl)pyrimidine. MS (ESI): mass calcd. for $C_{18}H_{14}F_3N_7O$, 401.1; m/z found, 402.1 [M+H]+. $^1$H NMR (500 MHz, CDCl$_3$) δ 8.48-8.42 (d, J=5.7 Hz, 1H), 8.12-8.06 (s, 1H), 7.97-7.93 (d, J=5.3 Hz, 1H), 7.93-7.88 (m, 2H), 7.39-7.30 (t, J=8.9 Hz, 1H), 7.09-6.83 (m, 2H), 6.78-6.61 (m, 1H), 5.78-5.62 (s, 2H), 2.96-2.80 (s, 3H).

Example 693: 2-((1-(3-(Difluoromethyl)-4-fluorophenyl)-1H-1,2,3-triazol-4-yl)methoxy)-5-(2-methyl-1H-imidazol-1-yl)pyrimidine

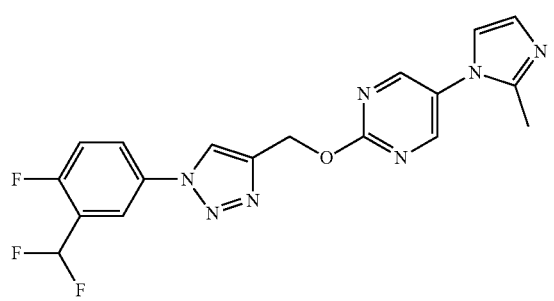 [SMILES: Cc1nccn1-c1cnc(OCc2cn(-c3ccc(F)c(C(F)F)c3)nn2)nc1]

MS (ESI): mass calcd. for $C_{18}H_{14}F_3N_7O$, 401.1

Example 694: 2-((1-(3-(Difluoromethyl)-4-fluorophenyl)-1H-1,2,3-triazol-4-yl)methoxy)-5-(1H-pyrazol-5-yl)pyrimidine

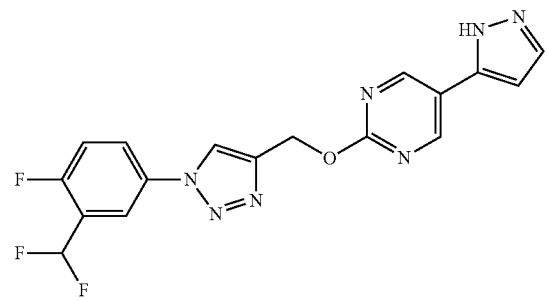 [SMILES: Fc1ccc(-n2cc(COc3ncc(-c4ccn[nH]4)cn3)nn2)cc1C(F)F]

MS (ESI): mass calcd. for $C_{17}H_{12}F_3N_7O$, 387.1

Example 695: 2-((1-(3-(Difluoromethyl)-4-fluorophenyl)-1H-1,2,3-triazol-4-yl)methoxy)-4-(1H-pyrazol-5-yl)pyrimidine

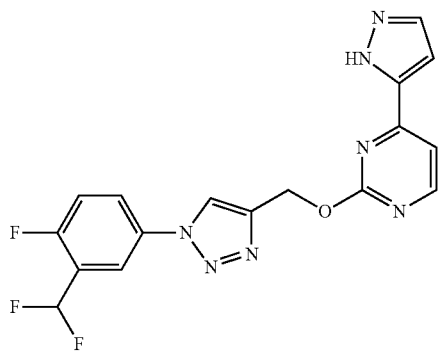 [SMILES: Fc1ccc(-n2cc(COc3nccc(-c4ccn[nH]4)n3)nn2)cc1C(F)F]

MS (ESI): mass calcd. for $C_{17}H_{12}F_3N_7O$, 387.1

Example 696: 4(1,1-Difluoroethyl)-2-((1-(3-(difluoromethyl)-4-fluorophenyl)-1H-1,2,3-triazol-4-yl)methoxy)pyrimidine

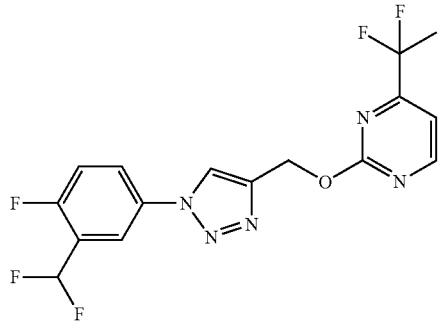 [SMILES: CC(F)(F)c1ccnc(OCc2cn(-c3ccc(F)c(C(F)F)c3)nn2)n1]

MS (ESI): mass calcd. for $C_{16}H_{12}F_5N_5O$, 385.1

Example 697: 4-((Difluoromethoxy)methyl)-2-((1-(3-(difluoromethyl)-4-fluorophenyl)-1H-1,2,3-triazol-4-yl)methoxy)pyrimidine

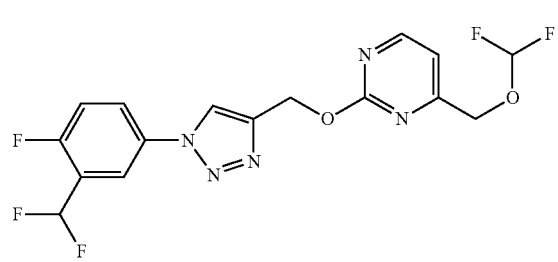 [SMILES: Fc1ccc(-n2cc(COc3nccc(COC(F)F)n3)nn2)cc1C(F)F]

MS (ESI): mass calcd. for $C_{16}H_{12}F_5N_5O_2$, 401.1

Example 698: 2-((1-(3-(Difluoromethyl)-4-fluorophenyl)-1H-1,2,3-triazol-4-yl)methoxy)-5-(1H-pyrazol-1-yl)pyrimidine

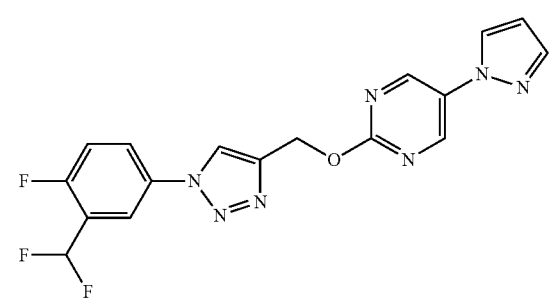 [SMILES: Fc1ccc(-n2cc(COc3ncc(-n4cccn4)cn3)nn2)cc1C(F)F]

MS (ESI): mass calcd. for $C_{17}H_{12}F_3N_7O$, 387.1

Example 699: 2-((1-(3-(Difluoromethyl)-4-fluorophenyl)-1H-1,2,3-triazol-4-yl)methoxy)-4-(1H-pyrazol-1-yl)pyrimidine

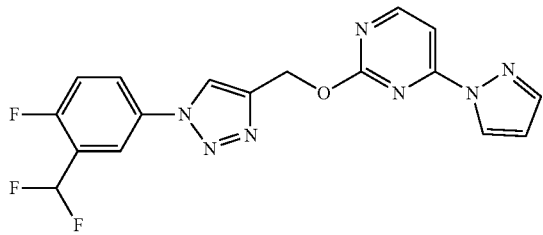 [SMILES: Fc1ccc(-n2cc(COc3nccc(-n4cccn4)n3)nn2)cc1C(F)F]

The title compound was prepared in a manner analogous to Example 1 using (1-(3-(difluoromethyl)-4-fluorophenyl)-1H-1,2,3-triazol-4-yl)methanol (Intermediate 9) and 2-chloro-4-(pyrazol-1-yl)pyrimidine. MS (ESI): mass calcd. for $C_{17}H_{12}F_3N_7O$, 387.1; m/z found, 388.0 [M+H]$^+$. $^1$H NMR (500 MHz, CDCl$_3$) δ 8.66-8.60 (m, 1H), 8.60-8.54 (d, J=5.5 Hz, 1H), 8.21-8.13 (s, 1H), 8.00-7.93 (m, 1H), 7.93-7.85 (m, 1H), 7.84-7.77 (m, 1H), 7.65-7.56 (d, J=5.5 Hz, 1H), 7.37-7.30 (m, 1H), 7.10-6.81 (t, J=54.6 Hz, 1H), 6.56-6.47 (m, 1H), 5.76-5.67 (m, 2H).

Example 700: (E)-1-(2-((1-(3-(Difluoromethyl)-4-fluorophenyl)-1H-1,2,3-triazol-4-yl)methoxy)pyrimidin-5-yl)ethan-1-one oxime

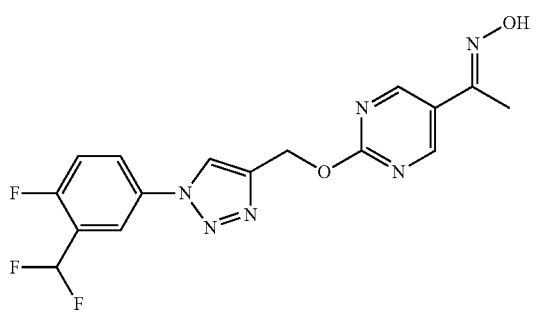 [SMILES: C/C(=N\O)c1cnc(OCc2cn(-c3ccc(F)c(C(F)F)c3)nn2)nc1]

MS (ESI): mass calcd. for $C_{16}H_{13}F_3N_8O_2$, 378.1

Example 701: 5-(1,1-Difluoroethyl)-2-((1-(3-(difluoromethyl)-4-fluorophenyl)-1H-1,2,3-triazol-4-yl)methoxy)pyrimidine

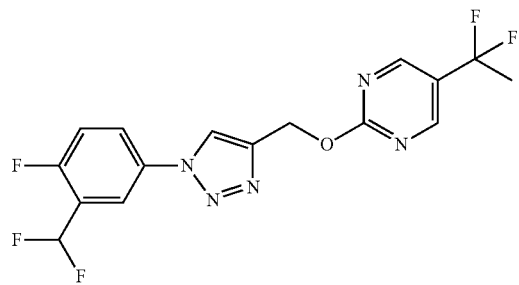 [SMILES: CC(F)(F)c1cnc(OCc2cn(-c3ccc(F)c(C(F)F)c3)nn2)nc1]

MS (ESI): mass calcd. for $C_{16}H_{12}F_5N_5O$, 385.1

Example 702: (Z)-1-(2-((1-(3-(Difluoromethyl)-4-fluorophenyl)-1H-1,2,3-triazol-4-yl)methoxy)pyrimidin-4-yl)ethan-1-one oxime

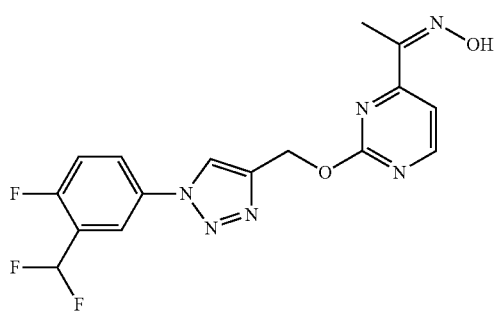 [SMILES: C/C(=N/O)c1ccnc(OCc2cn(-c3ccc(F)c(C(F)F)c3)nn2)n1]

MS (ESI): mass calcd. for $C_{16}H_{13}F_3N_6O_2$, 378.1

Example 703: (2-((1-(3-(Difluoromethoxy)-4-fluorophenyl)-1H-1,2,3-triazol-4-yl)methoxy)-5-fluoropyrimidin-4-yl)methanol

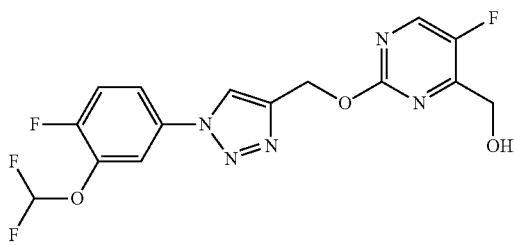 [SMILES: OCc1nc(OCc2cn(-c3ccc(F)c(OC(F)F)c3)nn2)ncc1F]

MS (ESI): mass calcd. for $C_{15}H_{11}F_4N_5O_3$, 385.1

Example 704: 2-((1-(3-(Difluoromethoxy)-4-fluorophenyl-1H-1,2,3-triazol-4-yl)methoxy)-4-((difluoromethoxy)methyl)-5-fluoropyrimidine

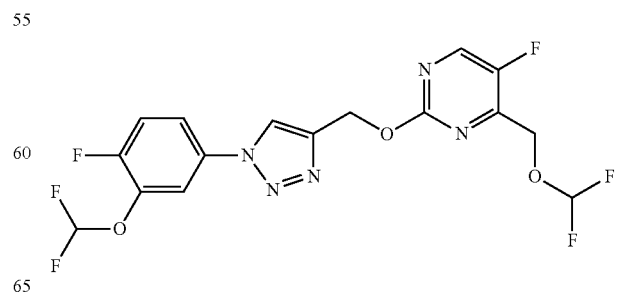

MS (ESI): mass calcd. for $C_{16}H_{11}F_6N_5O_3$, 435.1

Example 705: 2-((1-(3-(Difluoromethoxy)-4-fluorophenyl)-1H-1,2,3-triazol-4-yl)methoxy)-4-((difluoromethoxy)methyl)pyrimidine

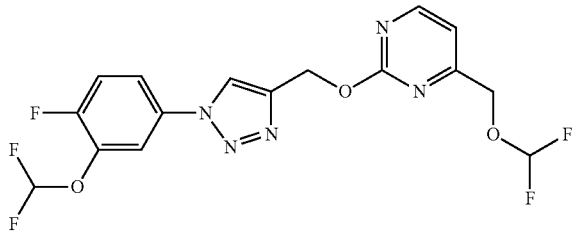 [SMILES: Fc1ccc(-n2cc(COc3nccc(COC(F)F)n3)nn2)cc1OC(F)F]

MS (ESI): mass calcd. for $C_{16}H_{12}F_5N_5O_3$, 417.1

Example 706: 2-((1-(3-(Difluoromethoxy)-4-fluorophenyl)-1H-1,2,3-triazol-4-yl)methoxy)-5-fluoro-4-((trifluoromethoxy)methyl)pyrimidine

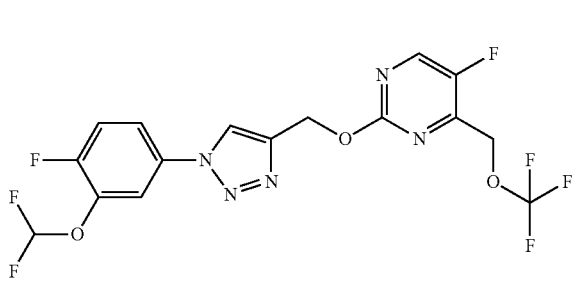 [SMILES: Fc1ccc(-n2cc(COc3ncc(F)c(COC(F)(F)F)n3)nn2)cc1OC(F)F]

MS (ESI): mass calcd. for $C_{10}H_{10}F_7N_5O_3$, 453.1

Example 707: 2-((1-(3-(Difluoromethoxy)-4-fluorophenyl)-1H-1,2,3-triazol-4-yl)methoxy)-4-((trifluoromethoxy)methyl)pyrimidine

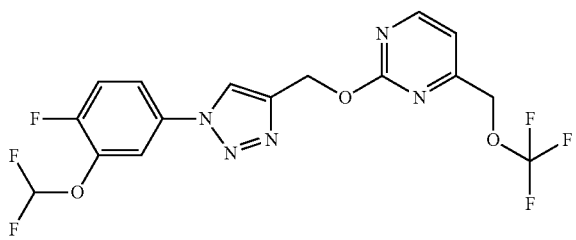 [SMILES: Fc1ccc(-n2cc(COc3nccc(COC(F)(F)F)n3)nn2)cc1OC(F)F]

MS (ESI): mass calcd. for $C_{16}H_{11}F_6N_5O_3$, 435.1

Example 708: 2-((1-(3-(Difluoromethoxy)-4-fluorophenyl)-1H-1,2,3-triazol-4-yl)methoxy)-4-(methoxymethyl-d2)pyrimidine

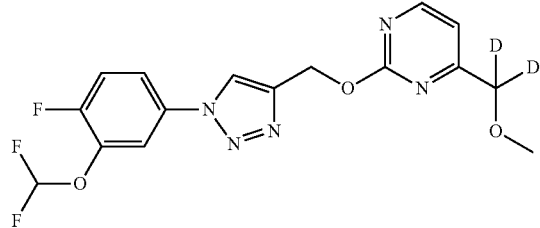 [SMILES: [2H]C([2H])(OC)c1ccnc(OCc2cn(-c3ccc(F)c(OC(F)F)c3)nn2)n1]

MS (ESI): mass calcd. for $C_{16}H_{12}D_2F_3N_5O_3$, 383.1

Example 709: 2-((1-(3-(Difluoromethoxy)-4-fluorophenyl)-1H-1,2,3-triazol-4-yl)methoxy)-4-((methoxy-d3)methyl-d2)pyrimidine

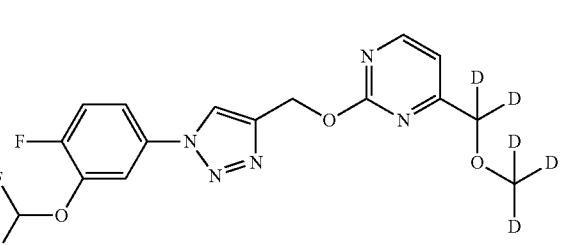

MS (ESI): mass calcd. for $C_{16}H_9D_5F_3N_5O_3$, 386.1

Example 710: 2-((1-(3-(Difluoromethoxy)-4-fluorophenyl)-1H-1,2,3-triazol-4-yl)methoxy)-4-((methoxy-d3)methyl)pyrimidine

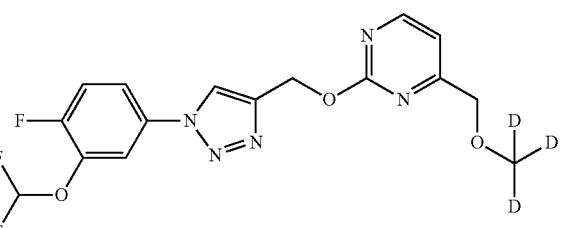

MS (ESI): mass calcd. for $C_{16}H_{11}D_3F_3N_5O_3$, 384.1

Example 711: 2-((1-(3-(Difluoromethoxy)-4-fluorophenyl)-1H-1,2,3-triazol-4-yl)methoxy)-4-(ethoxymethyl)pyrimidine

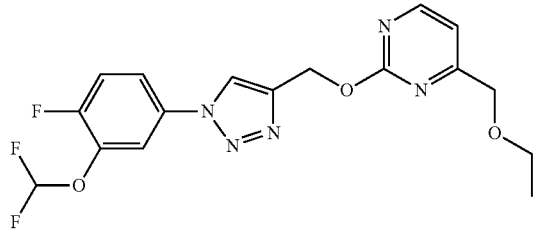 [SMILES: CCOCc1ccnc(OCc2cn(-c3ccc(F)c(OC(F)F)c3)nn2)n1]

MS (ESI): mass calcd. for $C_{17}H_{16}F_3N_5O_3$, 395.1

Example 712: 2-((1-(3-(Difluoromethoxy)-4-fluorophenyl-1H-1,2,3-triazol-4-yl)methoxy)-4-(1-methoxyethyl)pyrimidine

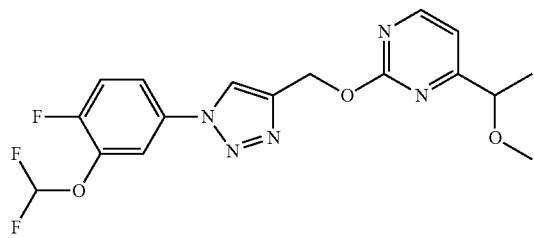 [SMILES: COC(C)c1ccnc(OCc2cn(-c3ccc(F)c(OC(F)F)c3)nn2)n1]

MS (ESI): mass calcd. for $C_{17}H_{16}F_3N_5O_3$, 395.1

Example 713: 1-(2-((1-(3-(Difluoromethoxy)-4-fluorophenyl)-1H-1,2,3-triazol-4-yl)methoxy)pyrimidin-4-yl)ethan-1-ol

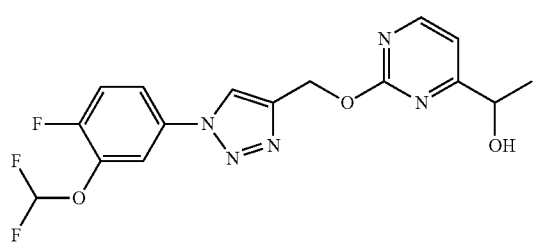 [SMILES: CC(C)(O)c1ccnc(OCc2cn(-c3ccc(F)c(OC(F)F)c3)nn2)n1]

MS (ESI): mass calcd. for $C_{16}H_{14}F_3N_5O_3$, 381.1

Example 714: 2-((1-(3-(Difluoromethoxy)-4-fluorophenyl)-1H-1,2,3-triazol-4-yl)methoxy)-4-(2-methoxypropan-2-yl)pyrimidine

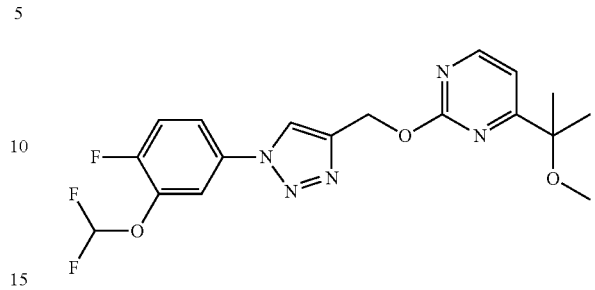

MS (ESI): mass calcd. for $C_{18}H_{18}F_3N_5O_3$, 409.1

Example 715: 2-(2-((1-(3-(Difluoromethoxy)-4-fluorophenyl)-1H-1,2,3-triazol-4-yl)methoxy)pyrimidin-4-yl)propan-2-ol

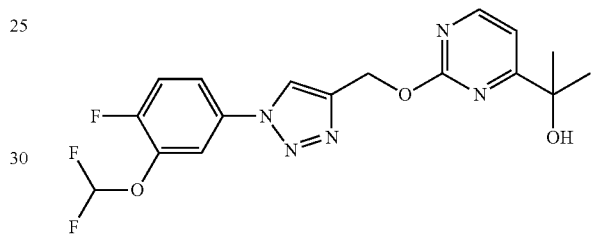

MS (ESI): mass calcd. for $C_{17}H_{16}F_3N_5O_3$, 395.1

Example 716: 4-((2,2-Difluoroethoxy)methyl)-2-((1-(3-(difluoromethoxy)-4-fluorophenyl)-1H-1,2,3-triazol-4-yl)methoxy)pyrimidine

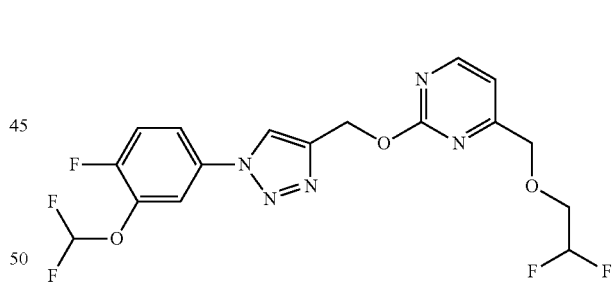

MS (ESI): mass calcd. for $C_{17}H_{14}F_5N_5O_3$, 431.1

Biological Assays

Effects of Test Articles on Cloned Human NR1/NR2B Ion Channels Expressed in Mammalian Cells NMDA receptors are ion channels that are highly permeable to $Ca^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular $Ca^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 149 mM NaCl, 4 mM KCl, 2 mM $CaCl_2$, and 1.5 mM $MgCl_2$, 10 mM HEPES and 5 mM D-glucose; pH 7.4. After 1 h incubation at the room temperature, the dye is washed away with the assay buffer (149 mM NaCl (standard assay) or 150 mM (HTS assay), 4 mM KCl (standard assay) or 3 mM (HTS assay), 2 mM $CaCl_2$, 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to $\sim EC_{80}$ (standard assay) or $EC_{40}$ (HTS assay) is used to maximize the assay's signal window or the ability to detect NMDA receptor antagonists and negative allosteric modulators, respectively. A saturating concentration (10 µM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

TABLE 5

| Ex #. | Compound Name | NR2B $IC_{50}$ (µM) standard assay |
|---|---|---|
| 1 | 2-((1-(4-Chloro-3-(difluoromethyl)phenyl)-1H-1,2,3-triazol-4-yl)methoxy)pyrimidine; | 0.049 |
| 2 | N-[[1-[4-Chloro-3-(difluoromethoxy)phenyl]triazol-4-yl]methyl]pyridin-2-amine; | 0.213 |
| 3 | N-[[1-[4-Fluoro-3-(trifluoromethyl)phenyl]triazol-4-yl]methyl]pyrimidin-2-amine; | 2.800 |
| 4 | 2-[[1-[3-(Difluoromethoxy)-4-fluoro-phenyl]triazol-4-yl]methoxy]pyridine; | 0.392 |
| 5 | 3-[[1-[4-Chloro-3-(difluoromethoxy)phenyl]triazol-4-yl]methoxy]pyridine; | 0.333 |
| 6 | N-((1-(3-(Difluoromethyl)phenyl)-1H-1,2,3-triazol-4-yl)methyl)pyrimidin-2-amine; | 10.573 |
| 7 | N-[[1-[3-(Difluoromethoxy)-4-fluoro-phenyl]triazol-4-yl]methyl]-1-methyl-imidazol-2-amine; | 1.870 |
| 8 | 2-[[1-[3-(Difluoromethoxy)-4-fluoro-phenyl]triazol-4-yl]methoxy]-6-methyl-pyridine; | 0.022 |
| 9 | 2-[[1-(3-Bromo-4-fluoro-phenyl)triazol-4-yl]methoxy]pyrimidine; | 0.020 |
| 10 | 2-[[1-[4-Chloro-3-(difluoromethoxy)phenyl]triazol-4-yl]methoxy]pyrimidine; | 0.010 |
| 11 | 2-[[1-[4-Chloro-3-(difluoromethyl)phenyl]triazol-4-yl]methoxy]pyridine; | 1.200 |
| 12 | 4-[[1-[4-Chloro-3-(difluoromethoxy)phenyl]triazol-4-yl]methoxy]pyrimidine; | 2.230 |
| 13 | 4-[[1-[4-Chloro-3-(difluoromethoxy)phenyl]triazol-4-yl]methoxy]pyrimidine; | 0.879 |
| 14 | 3-[[144-Chloro-3-(difluoromethoxy)phenyl]triazol-4-yl]methoxy]pyridazine; | 0.401 |
| 15 | 2-[[1-(4-Chloro-3-methoxy-phenyl)triazol-4-yl]methoxy]pyrimidine; | 0.699 |
| 16 | 2-[[1-(3-Bromo-4-fluoro-phenyl)triazol-4-yl]methoxy]-5-methyl-pyrimidine; | 0.001 |
| 17 | 2-[[1-(3-Bromo-4-fluoro-phenyl)triazol-4-yl]methoxy]-4-methyl-pyrimidine; | 0.010 |
| 18 | 2-[[1-(3-Bromo-4-fluoro-phenyl)triazol-4-yl]methoxy]-4,6-dimethyl-pyrimidine; | 0.082 |
| 19 | 2-[[1-(3-Bromo-4-fluoro-phenyl)triazol-4-yl]methoxy]-5-fluoro-pyrimidine; | 0.056 |
| 20 | 2-[[1-(4-Fluoro-3-methoxy-phenyl)triazol-4-yl]methoxy]pyrimidine; | 1.000 |
| 21 | 2-[[1-[4-Chloro-3-(difluoromethoxy)phenyl]triazol-4-yl]methoxy]-4-methyl-pyrimidine; | 0.002 |
| 22 | 2-[[1-[4-Chloro-3-(difluoromethoxy)phenyl]triazol-4-yl]methoxy]-5-methyl-pyrimidine; | 0.002 |
| 23 | 2-[[1-[4-Chloro-3-(difluoromethoxy)phenyl]triazol-4-yl]methoxy]pyrazine; | 0.456 |
| 24 | N-[[1-[3-(Difluoromethyl)-4-fluoro-phenyl]triazol-4-yl]methyl]pyrimidin-2-amine; | 0.824 |
| 25 | 2-[[1-[3-(Difluoromethyl)-4-fluoro-phenyl]triazol-4-yl]methoxy]pyrimidine; | 0.050 |
| 26 | 2-[[1-[4-Chloro-3-(difluoromethoxy)phenyl]triazol-4-yl]methoxy]-5-methoxy-pyrimidine; | 0.003 |
| 27 | 2-[[1-[4-Chloro-3-(difluoromethoxy)phenyl]triazol-4-yl]methoxy]-5-ethyl-pyrimidine; | 0.009 |
| 28 | 5-Chloro-2-[[1-[4-chloro-3-(difluoromethoxy)phenyl]triazol-4-yl]methoxy]pyrimidine; | 0.002 |
| 29 | 2-[[1-[4-Chloro-3-(difluoromethoxy)phenyl]triazol-4-yl]methoxy]-4-methoxy-pyrimidine; | 0.011 |
| 30 | 2-[[1-[4-Chloro-3-(difluoromethyl)phenyl]triazol-4-yl]methoxy]-4-methyl-pyrimidine; | 0.004 |
| 31 | 2-[[1-[4-Chloro-3-(difluoromethyl)phenyl]triazol-4-yl]methoxy]-5-methyl-pyrimidine; | 0.001 |
| 32 | 2-[[1-[4-Chloro-3-(difluoromethyl)phenyl]triazol-4-yl]methoxy]-5-ethyl-pyrimidine; | 0.002 |
| 33 | 2-[[1-[3-(Difluoromethoxy)-4-fluoro-phenyl]triazol-4-yl]methoxy]pyrimidine; | 0.018 |
| 34 | 2-[[1-[4-Chloro-3-(difluoromethoxy)phenyl]triazol-4-yl]methoxy]-5-methyl-pyrazine; | 0.159 |
| 35 | 2-[[1-[4-Chloro-3-(difluoromethoxy)phenyl]triazol-4-yl]methoxy]-5-(difluoromethoxy)pyrimidine; | 0.006 |
| 36 | N-[[1-[3-(Difluoromethoxy)-4-fluoro-phenyl]triazol-4-yl]methyl]pyrimidin-2-amine; | 0.351 |
| 37 | 5-Chloro-2[[1-(2,4-difluoro-3-methyl-phenyl)triazol-4-yl]methoxy]pyrimidine; | 0.053 |
| 38 | 2-[[1-(2,4-Difluoro-3-methyl-phenyl)triazol-4-yl]methoxy]-5-methyl-pyrimidine; | 0.027 |
| 39 | 2-[[1-(2,4-Difluoro-3-methyl-phenyl)triazol-4-yl]methoxy]-5-ethyl-pyrimidine; | 0.015 |
| 40 | 2-[[1-(3-Bromo-4-fluoro-phenyl)triazol-4-yl]methoxy]-5-ethyl-pyrimidine; | 0.001 |
| 41 | 2-[[1-(3-Bromo-4-fluoro-phenyl)triazol-4-yl]methoxy]-5-methoxy-pyrimidine; | 0.000 |
| 42 | 2-[[1-(3-Bromo-4-fluoro-phenyl)triazol-4-yl]methoxy]-5-chloro-pyrimidine; | 0.003 |
| 43 | 2-[[1-(3-Bromo-4-fluoro-phenyl)triazol-4-yl]methoxy]-5-isopropyl-pyrimidine; | 0.005 |
| 44 | 2-[[1-(3-Bromo-4-fluoro-phenyl)triazol-4-yl]methoxy]-5-(trifluoromethyl)pyrimidine; | 0.005 |
| 45 | 2-[[1-[4-Chloro-3-(difluoromethyl)phenyl]triazol-4-yl]methoxy]-5-(trifluoromethyl)pyrimidine; | 0.004 |
| 46 | 2-[[1-[4-Chloro-3-(difluoromethyl)phenyl]triazol-4-yl]methoxy]-5-methoxy-pyrimidine; | 0.001 |
| 47 | 5-Chloro-2-[[1-[4-chloro-3-(difluoromethyl)phenyl]triazol-4-yl]methoxy]pyrimidine; | 0.003 |
| 48 | 2-[[1-[4-Chloro-3-(difluoromethyl)phenyl]triazol-4-yl]methoxy]-5-isopropyl-pyrimidine; | 0.008 |
| 49 | 5-Chloro-2-[[1-[3-(difluoromethy)-4-fluoro-phenyl]triazol-4-yl]methoxy]pyrimidine; | 0.003 |
| 50 | 2-[[1-[3-(Difluoromethyl)-4-fluoro-phenyl]triazol-4-yl]methoxy]-5-(trifluoromethyl)pyrimidine; | 0.007 |
| 51 | 2-[[1-[3-(Difluoromethyl)-4-fluoro-phenyl]triazol-4-yl]methoxy]-5-methyl-pyrimidine; | 0.001 |
| 52 | 2-[[1-[3-(Difluoromethyl)-4-fluoro-phenyl]triazol-4-yl]methoxy]-4-methyl-pyrimidine; | 0.008 |
| 53 | (R/S)-2-[1-[1-[4-Chloro-3-(difluoromethoxy)pheny]triazol-4-yl]ethoxy]pyrimidine; | 0.026 |
| 54 | (R*)-2-[1-[1-[4-Chloro-3-(difluoromethoxy)phenyl]triazol-4-yl]ethoxy]pyrimidine; | 4.640 |
| 55 | (S*)-2-[1-[1-[4-Chloro-3-(difluoromethoxy)phenyl]triazol-4-yl]ethoxy]pyrimidine; | 0.008 |
| 56 | (R/S)-2-[1-[1-[4-Chloro-3-(difluoromethoxy)phenyl]triazol-4-yl]ethoxy]-5-methyl-pyrimidine; | 0.028 |

TABLE 5-continued

| Ex #. | Compound Name | NR2B IC$_{50}$ (μM) standard assay |
|---|---|---|
| 57 | (R*)-2-[1-[1-[4-Chloro-3-(difluoromethoxy)phenyl]triazol-4-yl]ethoxy]-5-methyl-pyrimidine; | 0.338 |
| 58 | (S*)-2-[1-[1-[4-Chloro-3-(difluoromethoxy)phenyl]triazol-4-yl]ethoxy]-5-methyl-pyrimidine; | 0.007 |
| 59 | (R/S)-2-[1-[1-[4-Chloro-3-(difluoromethoxy)phenyl]triazol-4-yl]ethoxy]-4-methyl-pyrimidine; | 0.040 |
| 60 | (R/S)-5-Chloro-2-[1-[1-[4-chloro-3-(difluoromethoxy)phenyl]triazol-4-yl]ethoxy]pyrimidine; | 0.032 |
| 61 | 5-Chloro-2-[[1-[3-(difluoromethoxy)-4-fluoro-phenyl]triazol-4-yl]methoxy]pyrimidine; | 0.003 |
| 62 | 2-[[1-[3-(Difluoromethoxy)-4-fluoro-phenyl]triazol-4-yl]methoxy]-5-(trifluoromethyl)pyrimidine; | 0.007 |
| 63 | 2-[[1-[3-(Difluoromethoxy)-4-fluoro-phenyl]triazol-4-yl]methoxy]-5-methyl-pyrimidine; | 0.003 |
| 64 | 2-[[1-[3-(Difluoromethoxy)-4-fluoro-phenyl]triazol-4-yl]methoxy]-4-methyl-pyrimidine; | 0.007 |
| 65 | 2-[[1-[3-(Difluoromethyl)-4-fluoro-phenyl]triazol-4-yl]methoxy]-5-(trifluoromethyl)pyridine; | 0.056 |
| 66 | 2-[[1-[4-Chloro-3-(difluoromethyl)phenyl]triazol-4-yl]methoxy]-5-fluoro-pyrimidine; | 0.052 |
| 67 | 2-[[1-[3-(1,1-Difluoroethyl)-4-fluoro-phenyl]triazol-4-yl]methoxy]-5-ethyl-pyrimidine; | 0.015 |
| 68 | 2-[[1-[3-(1,1-Difluoroethyl)-4-fluoro-phenyl]triazol-4-yl]methoxy]-5-methoxy-pyrimidine; | 0.007 |
| 69 | 5-Chloro-2[[1-[3-(1,1-difluoroethyl)-4-fluoro-phenyl]triazol-4-yl]methoxy]pyrimidine; | 0.009 |
| 70 | 2-[[1-[3-(1,1-Difluoroethyl)-4-fluoro-phenyl]triazol-4-yl]methoxy]-5-isopropyl-pyrimidine; | 0.044 |
| 71 | 2-[[1-[3-(1,1-Difluoroethyl)-4-fluoro-phenyl]triazol-4-yl]methoxy]-5-(trifluoromethyl)pyrimidine; | 0.040 |
| 72 | 5-Ethyl-2-[[1-[4-fluoro-3-(trifluoromethyl)phenyl]triazol-4-yl]methoxy]pyrimidine; | 0.010 |
| 73 | 2-[[1-[4-Fluoro-3-(trifluoromethyl)phenyl]triazol-4-yl]methoxy]-5-methoxy-pyrimidine; | 0.008 |
| 74 | 5-Chloro-2-[[1-[4-fluoro-3-(trifluoromethyl)phenyl]triazol-4-yl]methoxy]pyrimidine; | 0.016 |
| 75 | 2-[[1-[4-Fluoro-3-(trifluoromethy)phenyl]triazol-4-yl]methoxy]-5-isopropyl-pyrimidine; | 0.026 |
| 76 | 2-[[1-[4-Fluoro-3-(trifluoromethyl)phenyl]triazol-4-yl]methoxy]-5-(trifluoromethyl)pyrimidine; | 0.035 |
| 77 | 2-[[1-[3-(1,1-Difluoroethyl)-4-fluoro-phenyl]triazol-4-yl]methoxy]-5-methyl-pyrimidin; | 0.004 |
| 78 | 2-[[1-[3-(1,1-Difluoroethyl)-4-fluoro-phenyl]triazol-4-yl]methoxy]pyrimidine; | 0.060 |
| 79 | 2-[[1-[3-(1,1-Difluoroethyl)-4-fluoro-phenyl]triazol-4-yl]methoxy]-4-methyl-pyrimidine; | 0.007 |
| 80 | 2-[[1-[3-(1,1-Difluoroethyl)-4-fluoro-phenyl]triazol-4-yl]methoxy]-5-fluoro-pyrimidine; | 0.032 |
| 81 | 5-Chloro-2-[[1-[4-fluoro-3-(trifluoromethyl)phenyl]triazol-4-yl]methoxy]-5-methyl-pyrimidine; | 0.003 |
| 82 | 2-[[1-[4-Fluoro-3-(trifluoromethyl)phenyl]triazol-4-yl]methoxy]pyrimidine; | 0.126 |
| 83 | 2-[[1-[4-Fluoro-3-(trifluoromethyl)phenyl]triazol-4-yl]methoxy]-4-methyl-pyrimidine; | 0.020 |
| 84 | 5-Fuoro-2-[[1-[4-fluoro-3-(trifluoromethyl)phenyl]triazol-4-yl]methoxy]pyrimidine; | 0.072 |
| 85 | 2-[[1-[3-Bromo-4-fluoro-phenyl)triazol-4-yl]methoxy]-4,5-dimethyl-pyrimidine; | 0.003 |
| 86 | 2-[[1-[4-Chloro-3-(difluoromethoxy)phenyl]triazol-4-yl]methoxy]-4,5-dimethyl-pyrimidine; | 0.004 |
| 87 | 2-[[1-(4-Chloro-3-methoxy-phenyl)triazol-4-yl]methoxy]-5-methoxy-pyrimidine; | 0.012 |
| 88 | 2-[[1-(4-Chloro-3-methoxy-phenyl)triazol-4-yl]methoxy]-5-methyl-pyrimidine; | 0.019 |
| 89 | 2-[[1-[3-(Difluoromethyl)phenyl]triazol-4-yl]methoxy]-5-methyl-pyrimidine; | 0.011 |
| 90 | 2-[[1-[3-(Difluoromethyl)phenyl]triazol-4-yl]methoxy]-5-methoxy-pyrimidine; | 0.012 |
| 91 | 2-[[1-[3-(Difluoromethyl)phenyl]triazol-4-yl]methoxy]-5-ethyl-pyrimidine; | 0.004 |
| 92 | 5-Chloro-2[[1-[3-(difluoromethyl)phenyl]triazol-4-yl]methoxy]pyrimidine; | 0.019 |
| 93 | 2-[[1-[3-(Difluoromethyl)phenyl]triazol-4-yl]methoxy]pyrimidine; | 0.493 |
| 94 | 2-[[1-[(5-Bromo-6-methyl-2-pyridyl)triazol-4-yl]methoxy]-5-methyl-pyrimidine; | 2.910 |
| 95 | 2-[[1-[4-Chloro-3-(difluoromethoxy)phenyl]triazol-4-yl]methoxy]-5-fluoro-pyrimidine; | 0.023 |
| 96 | 2-[[1-[4-Chloro-3-(difluoromethoxy)phenyl]triazol-4-yl]methoxy]-5-(difluoromethyl)pyrimidine; | 0.008 |
| 97 | N-[[1-[4-Chloro-3-(difluoromethoxy)phenyl]triazol-4-yl]methyl]oxazol-2-amine; | 0.106 |
| 98 | N-[[1-[4-Chloro-3-(difluoromethoxy)phenyl]triazol-4-yl]methyl]pyrimidin-2-amine; | 0.331 |
| 99 | N-[[1-[3-(Difluoromethyl)-4-fluoro-phenyl]triazol-4-yl]methyl]-1-methyl-pyrazol-4-amine; | 5.050 |
| 100 | N-[[1-[3-(Difluoromethyl)-4-fluoro-phenyl]triazol-4-yl]methyl]-1-methyl-pyrazol-3-amine; | 0.894 |
| 101 | N-[[1-[3-(Difluoromethoxy)-4-fluoro-phenyl]triazol-4-yl]methyl]-1-methyl-pyrazol-3-amine; | 0.374 |
| 102 | N-[[1-[3-(Difluoromethoxy)-4-fluoro-phenyl]triazol-4-yl]methyl]-1-methyl-pyrazol-4-amine; | 3.250 |
| 103 | 3-[[1-[4-Chloro-3-(difluoromethoxy)phenyl]triazol-4-yl]methoxy]-2-methoxy-pyridine; | 0.064 |
| 104 | 5-[[1-[4-Chloro-3-(difluoromethoxy)phenyl]triazol-4-yl]methoxy]-2-methyl-pyridine; | 0.729 |
| 105 | 3-Chloro-2-[[1-[4-chloro-3-(difluoromethoxy)phenyl]triazol-4-yl]methoxy]pyridine; | 0.059 |
| 106 | 5-Chloro-2-[[1-[4-chloro-3-(difluoromethoxy)phenyl]triazol-4-yl]methoxy]-3-methoxy-pyridine; | 0.276 |
| 107 | 2-[[1-[4-Chloro-3-(difluoromethoxy)phenyl]triazol-4-yl]methoxy]-3-fluoro-pyridine; | 0.119 |
| 108 | 2-[[1-[4-Chloro-3-(difluoromethoxy)phenyl]triazol-4-yl]methoxy]-3-methoxy-pyridine; | 0.114 |
| 109 | N-[[1-[4-Chloro-3-(difluoromethyl)phenyl]triazol-4-yl]methyl]pyrimidin-2-amine; | 1.260 |
| 110 | N-[[1-[4-Chloro-3-(difluoromethyl)phenyl]triazol-4-yl]methyl]pyrimidin-4-amine; | 7.570 |
| 111 | 2-[[1-[3-(Difluoromethyl)-4-fluoro-phenyl]triazol-4-yl]methoxy]pyridine; | 0.684 |
| 112 | 5-Chloro-2-[[1-[3-(difluoromethyl)-4-fluoro-phenyl]triazol-4-yl]methoxy]pyridine; | 0.056 |
| 113 | 2-[[1-[3-(Difluoromethyl)-4-fluoro-phenyl]triazol-4-yl]methoxy]-6-methyl-pyridine; | 0.038 |
| 114 | 2-[[1-[3-(Difluoromethyl)-4-fluoro-phenyl]triazol-4-yl]methoxy]-5-methyl-pyridine; | 0.021 |
| 115 | 2-[[1-[3-(Difluoromethyl)-4-fluoro-phenyl]triazol-4-yl]methoxy]-4-methyl-pyridine; | 0.170 |
| 116 | 2-[[1-[3-(Difluoromethoxy)-4-fluoro-phenyl]triazol-4-yl]methoxy]-4-methyl-pyridine; | 0.102 |
| 117 | 5-Chloro-2-[[1-[3-(difluoromethoxy)-4-fluoro-phenyl]triazol-4-yl]methoxy]pyridine; | 0.073 |
| 118 | 2-[[1-[3-(Difluoromethoxy)-4-fluoro-phenyl]triazol-4-yl]methoxy]-5-methyl-pyridine; | 0.026 |
| 119 | 2-[[1-[3-(Difluoromethoxy)-4-fluoro-phenyl]triazol-4-yl]methoxy]-5-(trifluoromethyl)pyridine; | 0.114 |
| 120 | 5-Methyl-2-((1-(5-(trifluoromethyl)thiophen-2-yl)-1H-1,2,3-triazol-4-yl)methoxy)pyrimidine; | 0.005 |
| 121 | 5-Methyl-2-((1-(4-(trifluoromethyl)thiophen-2-yl)-1H-1,2,3-triazol-4-yl)methoxy)pyrimidine; | NT |
| 122 | 2-((1-(3-(Difluorometthy)-2-fluorophenyl)-1H-1,2,3-triazol-4-yl)methoxy)-5-methylpyrimidine; | NT |
| 123 | 2-((1-(4-Chlorophenyl)-1H-1,2,3-triazol-4-yl)methoxy)-5-methylpyrimidine; | NT |
| 124 | 2-((1-(4-Chloro-3-(oxetan-3-yl)phenyl)-1H-1,2,3-triazol-4-yl)methoxy)-5-methylpyrimidine; | NT |
| 125 | 2-((1-(4-Chloro-3-(difluoromethyl)phenyl)-5-fluoro-1H-1,2,3-triazol-4-yl)methoxy)-5-methylpyrimidine; | NT |
| 126 | 2-((1-(4-Chloro-3-(difluoromethyl)phenyl)-5-(trifluoromethyl)-1H-1,2,3-triazol-4-yl)methoxy)-5-methylpyrimidine; | NT |
| 127 | 2-((1-(4-Chloro-3-(difluoromethyl)phenyl)-5-methyl-1H-1,2,3-triazol-4-yl)methoxy)-5-methylpyrimidine; | NT |

TABLE 5-continued

| Ex # | Compound Name | NR2B IC$_{50}$ (μM) standard assay |
|---|---|---|
| 128 | 2-((1-(4-Chloro-3-(difluoromethyl)phenyl)-1H-1,2,3-triazol-4-yl)methoxy)-5-methylthiazole; | NT |
| 129 | 1-(4-Chloro-3-(difluoromethyl)phenyl)-4-(((5-methyl-1H-imidazol-2-yl)oxy)methyl)-1H-1,2,3-triazole; | NT |
| 130 | 2-((1-(4-Chloro-3-(difluoromethoxy)phenyl)-1H-1,2,3-triazol-4-yl)methoxy)-5-methylpyridine; | NT |
| 131 | 2-((1-(4-Chloro-3-(difluoromethoxy)phenyl)-1H-1,2,3-triazol-4-yl)methoxy)-6-methylpyridine; | NT |
| 132 | 6-((1-(4-Chloro-3-(difluoromethoxy)phenyl)-1H-1,2,3-triazol-4-yl)methoxy)-2,3-dimethylpyridine; | NT |
| 133 | 2-((1-(4-Chloro-3-(difluoromethoxy)phenyl)-1H-1,2,3-triazol-4-yl)methoxy)-6-methylpyrazine; | NT |
| 134 | 5-((1-(4-Chloro-3-(difluoromethoxy)phenyl)-1H-1,2,3-triazol-4-yl)methoxy)-2,3-dimethylpyrazine; | NT |
| 135 | 5-((1-(4-Chloro-3-(difluoromethoxy)phenyl)-1H-1,2,3-triazol-4-yl)methoxy)-2-methylpyrimidine; | NT |
| 136 | 6-((1-(4-Chloro-3-(difluoromethoxy)phenyl)-1H-1,2,3-triazol-4-yl)methoxy)-3,4-dimethylpyridazine; | NT |
| 137 | 3-((1-(4-Chloro-3-(difluoromethoxy)phenyl)-1H-1,2,3-triazol-4-yl)methoxy)-6-(trifluoromethyl)pyridazine; | NT |
| 138 | 3-((1-(4-Chloro-3-(difluoromethoxy)phenyl)-1H-1,2,3-triazol-4-yl)methoxy)-6-methoxypyridazine; | NT |
| 139 | 4-((1-(4-Chloro-3-(difluoromethoxy)phenyl)-1H-1,2,3-triazol-4-yl)methoxy)-2-methylpyrimidine; | NT |
| 140 | 4-((1-(4-Chloro-3-(difluoromethoxy)phenyl)-1H-1,2,3-triazol-4-yl)methoxy)-2-(trifluoromethyl)pyrimidine; | NT |
| 141 | 4-((1-(4-Chloro-3-(difluoromethoxy)phenyl)-1H-1,2,3-triazol-4-yl)methoxy)-2-methoxypyrimidine; | NT |
| 142 | 2-((1-(5-Chloro-6-(trifluoromethyl)pyridin-2-yl)-1H-1,2,3-triazol-4-yl)methoxy)-5-methylpyrimidine; | NT |
| 143 | 2-((1-(2-(Difluoromethyl)pyridin-4-yl)-1H-1,2,3-triazol-4-yl)methoxy)-5-methylpyrimidine; | NT |
| 144 | N-((1-(4-Chloro-3-(difluoromethoxy)phenyl)-1H-1,2,3-triazol-4-yl)methyl)-5-methylpyrimidin-2-amine; | NT |
| 145 | N-((1-(4-Chloro-3-(difluoromethoxy)phenyl)-1H-1,2,3-triazol-4-yl)methyl)-4,5-dimethylpyrimidin-2-amine; | NT |
| 146 | 3-((1-(4-Chloro-3-(yl)difluoromethoxy)phenyl)-1H-1,2,3-triazol-4-yl)methoxy)-4-methoxypyridine; | NT |
| 147 | 4-Chloro-3-((1-(4-chloro-3-(difluoromethoxy)phenyl)-1H-1,2,3-triazol-4-yl)methoxy)pyridine; | NT |
| 148 | 4-((1-(3-(Difluoromethoxy)phenyl)-1H-1,2,3-triazol-4-yl)methoxy)-5-methoxypyrimidine; | NT |
| 149 | 2-((1-(3-(Difluoromethyl)phenyl)-5-methyl-1H-1,2,3-triazol-4-yl)methoxy)-5-methylpyrimidine; | 0.952 |
| 150 | 5-Methyl-2-((1-(5-(trifluoromethyl)pyridin-2-yl)-1H-1,2,3-triazol-4-yl)methoxy)pyrimidine; | NT |
| 151 | 2-((1-(5-Bromo-6-fluoropyridin-3-yl)-1H-1,2,3-triazol-4-yl)methoxy)-5-methylpyrimidine; | NT |
| 152 | 5-Methyl-2-((1-(pyridin-4-yl)-1H-1,2,3-triazol-4-yl)methoxy)pyrimidine; | NT |
| 153 | 5-Chloro-N-[[1-[3-(difluoromethyl)phenyl]triazol-4-yl]methyl]pyrimidin-2-amine; | 0.216 |
| 154 | N-[[1-[4-Chloro-3-(difluoromethyl)phenyl]triazol-4-yl]methyl]-5-methyl-pyrimidin-2-amine; | 0.030 |
| 155 | 2-[[1-[3-(Difluoromethyl)phenyl]triazol-4-yl]methoxy]-4,5-dimethyl-pyrimidine; | 0.006 |
| 156 | 1-[2-[[1-[3-(Difluoromethyl)-4-fluoro-phenyl]triazol-4-yl]methoxy]pyrimidin-5-yl]ethanone; | 0.005 |
| 157 | (R/S)-1-[2-[[1-[3-(Difluoromethyl)-4-fluoro-phenyl]triazol-4-yl]methoxy]pyrimidin-5-yl]ethanol; | 0.018 |
| 158 | 2-[[1-[4-Fluoro-3-(trifluoromethyl)phenyl]triazol-4-yl]methoxy]pyridine; | 3.040 |
| 159 | [2-[[1-[3-(Difluoromethyl)phenyl]triazol-4-yl]methoxy]pyrimidin-4-yl]methanol; | 0.408 |
| 160 | [2-[[1-[3-(Difluoromethyl)phenyl]triazol-4-yl]methoxy]pyrimidin-5-yl]methanol; | 0.173 |
| 161 | 2-[[1-[3-(Difluoromethyl)phenyl]triazol-4-yl]methoxy]-5-methyl-pyrimidin-4-amine; | 0.055 |
| 162 | 2-[[1-[3-(Difluoromethyl)-4-fluoro-phenyl]triazol-4-yl]methoxy]-N-methyl-pyrimidine-4-carboxamide; | >2.99 |
| 163 | (R/S) 1-[2-[[1-[3-(Difluoromethoxy)-4-fluoro-phenyl]triazol-4-yl]methoxy]pyrimidin-4-yl]ethanamine; | 1.400 |
| 164 | 5-Chloro-2-[[1-(4-fluorophenyl)triazol-4-yl]methoxy]pyrimidine; | 0.371 |
| 165 | 5-(Azetidin-1-yl)-2-[[1-[3-(difluoromethoxy)-4-fluoro-phenyl]triazol-4-yl]methoxy]pyrimidine; | 0.016 |
| 166 | 2-[[1-[3-(Difluoromethoxy)-4-fluoro-phenyl]triazol-4-yl]methoxy]-4-(3,3-difluoropyrrolidin-1-yl)pyrimidine; | 0.144 |
| 167 | 2-((1-(3-(Difluoromethoxy)-4-fluorophenyl)-1H-1,2,3-triazol-4-yl)methoxy)-5-fluoropyrimidin-4-amine; | 0.013 |
| 168 | 2-[[1-[3-(Difluoromethoxy)-4-fluoro-phenyl]triazol-4-yl]methoxy]-4-pyrrolidin-1-yl-pyrimidine; | 0.008 |
| 169 | 2-[[1-[3-(Difluoromethoxy)-4-fluoro-phenyl]triazol-4-yl]methoxy]-4-(1-piperidyl)pyrimidine; | 0.031 |
| 170 | 4-[2-[[1-[3-(Difluoromethoxy)-4-fluoro-phenyl]triazol-4-yl]methoxy]pyrimidin-4-yl]morpholine; | 0.260 |
| 171 | 2-[[1-[4-Chloro-3-(difluoromethoxy)phenyl]triazol-4-yl]methoxy]-N-methyl-pyrimidin-4-amine; | 0.006 |
| 172 | 2-[[1-[3-(Difluoromethyl)phenyl]-5-methyl-triazol-4-yl]methoxy]-5-methoxy-pyrimidine; | 0.468 |
| 173 | 2[[1-[3-(1,1-Difluoroethyl)-4-fluoro-phenyl]-5-methyl-triazol-4-yl]methoxy]-5-methyl-pyrimidine; | 0.465 |
| 174 | 5-Methyl-2[[1-[(6-methyl-2-pyridyl)triazol-4-yl]methoxy]pyrimidine; | >2.99 |
| 175 | 5-Methyl-2-[[1-(2-methyl-4-pyridyl)triazol-4-yl]methoxy]pyrimidine; | 0.655 |
| 176 | 5-Methyl-2-[[1-(5-methyl-3-pyridyl)triazol-4-yl]methoxy]pyrimidine; | 0.929 |
| 177 | 2-[[1-(2-Bromo-4-pyridyl)triazol-4-yl]methoxy]-5-methyl-pyrimidine; | 0.172 |
| 178 | 2-[2-[[1-(3-Cyclobutyl-4-fluoro-phenyl)triazol-4-yl]methoxy]pyrimidin-5-yl]propan-2-ol; | 0.349 |
| 179 | 2-[2-[[1-(4-Fluoro-3-isopropyl-phenyl)triazol-4-yl]methoxy]pyrimidin-5-yl]propan-2-ol; | 0.029 |
| 180 | 2-[2-[[1-(3-Cyclopropyl-4-fluoro-phenyl)triazol-4-yl]methoxy]pyrimidin-5-yl]propan-2-ol; | 0.133 |
| 181 | 2-[2-[[1-(4-Fluoro-3-methyl-phenyl)triazol-4-yl]methoxy]pyrimidin-5-yl]propan-2-ol; | 0.097 |
| 182 | 2-[2-[[1-(3-Ethyl-4-fluoro-phenyl)triazol-4-yl]methoxy]pyrimidin-5-yl]propan-2-ol; | 0.027 |
| 183 | 5-Bromo-2-[[1-[3-(1,1-difluoroethyl)-4-fluoro-phenyl]triazol-4-yl]methoxy]pyrimidine; | 0.009 |
| 184 | 2-[[1-[3-(1,1-Difluoroethyl)-4-fluoro-phenyl]triazol-4-yl]methoxy]-5-(1-methylpyrazol-3-yl)pyrimidine; | 0.309 |
| 185 | 2-[[1-[3-(1,1-Difluoroethyl)-4-fluoro-phenyl]triazol-4-yl]methoxy]-5-(1H-pyrazol-4-yl)pyrimidine; | 0.166 |
| 186 | 2-[[1-[3-(1,1-Difluoroethyl)-4-fluoro-phenyl]triazol-4-yl]methoxy]-4-(1H-pyrazol-4-yl)pyrimidine; | 1.360 |
| 187 | 4-(2-((1-(3-(1,1-Difluoroethyl)-4-fluorophenyl)-1H-1,2,3-triazol-4-yl)methoxy)pyrimidin-5-yl)morpholine; | 0.088 |
| 188 | 2-((1-(4-(Azetidin-1-yl)-3-(difluoromethyl)phenyl)-1H-1,2,3-triazol-4-yl)methoxy)-5-methylpyrimidine; | 4.580 |
| 189 | 2-[[1-[4-Chloro-3-(difluoromethoxy)phenyl]triazol-4-yl]methoxy]-5-fluoro-pyrazine; | 1.460 |
| 190 | 4-Chloro-2-[[1-[4-chloro-3-(difluoromethoxy)phenyl]triazol-4-yl]methoxy]pyrimidine; | 0.026 |
| 191 | 2-[[1-[4-Chloro-3-(difluoromethoxy)phenyl]triazol-4-yl]methoxy]-4-fluoro-pyrimidine; | 0.023 |
| 192 | 2-[[1-[4-Chloro-3-(difluoromethoxy)phenyl]triazol-4-yl]methoxy]-5-(2-fluoroethoxy)pyrimidine; | 0.030 |
| 193 | 2-[[1-[4-Chloro-3-(2-fluoroethoxy)phenyl]triazol-4-yl]methoxy]-5-methoxy-pyrimdine; | 0.089 |
| 194 | 2-[[1-[4-Fluoro-3-(3-fluoropropyl)phenyl]triazol-4-yl]methoxy]-5-methoxy-pyrimidine; | 0.061 |
| 195 | 2-[[1-[3-(3-Chloropropyl)-4-fluoro-phenyl]triazol-4-yl]methoxy]-5-methoxy-pyrimidine; | 0.136 |
| 196 | 2-[[1-[4-Chloro-3-(difluoromethoxy)phenyl]triazol-4-yl]methoxy]-5-(3-fluoropropyl)pyrimidine; | 0.024 |
| 197 | N-[[1-[3-(Difluoromethyl)phenyl]triazol-4-yl]methyl]-5-fluoro-pyrimidin-2-amine; | 0.652 |
| 198 | N-[[1-(4-Fluoro-3-methyl-phenyl)triazol-4-yl]methyl]-5-methyl-pyrimidin-2-amine; | 0.147 |
| 199 | 5-Chloro-N-[[1-(4-fluoro-3-methyl-phenyl)triazol-4-yl]methyl]-4-methyl-pyrimidin-2-amine; | 0.051 |
| 200 | 5-Chloro-N-[[1-[4-chloro-3-(difluoromethyl)phenyl]triazol-4-yl]methyl]pyrimidin-2-amine; | 0.131 |

TABLE 5-continued

| Ex #. | Compound Name | NR2B IC$_{50}$ (μM) standard assay |
|---|---|---|
| 201 | N-[[1-[4-Chloro-3-(difluoromethyl)phenyl]triazol-4-yl]methyl]-4-methyl-pyrimidin-2-amine; | 0.100 |
| 202 | N-[[1-[4-Chloro-3-(difluoromethyl)phenyl]triazol-4-yl]methyl]-5-ethyl-pyrimidin-2-amine; | 0.044 |
| 203 | N-[[1-[4-Chloro-3-(difluoromethyl)phenyl]triazol-4-yl]methyl]-5-methoxy-pyrimidin-2-amine; | 0.030 |
| 204 | N-[[1-[4-Chloro-3-(difluoromethyl)phenyl]triazol-4-yl]methyl]-5-(difluoromethyl)pyrimidin-2-amine; | 0.240 |
| 205 | N-[[1-[4-Chloro-3-(difluoromethyl)phenyl]triazol-4-yl]methyl]-5-(trifluoromethyl)pyrimidin-2-amine; | 0.616 |
| 206 | N-[[1-[3-(1,1-Difluoroethyl)-4-fluoro-phenyl]triazol-4-yl]methyl]-5-methyl-pyrimidin-2-amine; | 0.219 |
| 207 | N-[[1-[3-(1,1-Difluoroethyl)-4-fluoro-phenyl]triazol-4-yl]methyl]-5-ethyl-pyrimidin-2-amine; | 0.128 |
| 208 | N-[[1-[3-(1,1-Difluoroethyl)-4-fluoro-phenyl]triazol-4-yl]methyl]-5-isopropyl-pyrimidin-2-amine; | 0.581 |
| 209 | 5-Cyclopropyl-N-[[1-[3-(1,1-difluoroethyl)-4-fluoro-phenyl]triazol-4-yl]methyl]pyrimidin-2-amine; | 0.104 |
| 210 | N-[[1-[3-(1,1-Difluoroethyl)-4-fluoro-phenyl]triazol-4-yl]methyl]-4,5-dimethyl-pyrimidin-2-amine; | 0.050 |
| 211 | N-[[1-[3-(Difluoromethyl)-4-fluoro-phenyl]triazol-4-yl]methyl]-5-methyl-pyrimidin-2-amine; | 0.049 |
| 212 | 5-Chloro-N-[[1-[3-(difluoromethyl)-4-fluoro-phenyl]triazol-4-yl]methyl]pyrimidin-2-amine; | 0.074 |
| 213 | N-[[1-[3-(Difluoromethyl)-4-fluoro-phenyl]triazol-4-yl]methyl]-5-(trifluoromethyl)pyrimidin-2-amine; | 0.108 |
| 214 | 2-[2-[[1-[3-(Difluoromethyl)-4-fluoro-phenyl]triazol-4-yl]methylamino]pyrimidin-5-yl]propan-2-ol; | 0.654 |
| 215 | N-((1-(3-(Difluoromethyl)-4-fluorophenyl)-1H-1,2,3-triazol-4-yl)methyl)pyridin-2-amine; | 0.986 |
| 216 | N-((1-(3-(Difluoromethyl)-4-fluorophenyl)-1H-1,2,3-triazol-4-yl)methyl)-5-ethylpyrimidin-2-amine; | 0.026 |
| 217 | N-((1-(3-(Difluoromethyl)-4-fluorophenyl)-1H-1,2,3-triazol-4-yl)methyl)-4,5-dimethylpyrimidin-2-amine; | 0.012 |
| 218 | 5-Chloro-N-((1-(3-(difluoromethyl)-4-fluorophenyl)-1H-1,2,3-triazol-4-yl)methyl)-4-methylpyrimidin-2-amine; | 0.011 |
| 219 | N-((1-(3-(Difluoromethyl)-4-fluorophenyl)-1H-1,2,3-triazol-4-yl)methyl)-1-methyl-1H-pyrazol-5-amine; | >10 |
| 220 | N-((1-(3-(Difluoromethyl)-4-fluorophenyl)-1H-1,2,3-triazol-4-yl)methyl)-1-methyl-1H-imidazol-2-amine; | 3.650 |
| 221 | N-((1-(3-(Difluoromethoxy)-4-fluorophenyl)-1H-1,2,3-triazol-4-yl)methyl)pyridin-2-amine; | 0.724 |
| 222 | N-((1-(3-(Difluoromethoxy)-4-fluorophenyl)-1H-1,2,3-triazol-4-yl)methyl)-5-methylpyrimidin-2-amine; | 0.064 |
| 223 | N-((1-(3-(Difluoromethoxy)-4-fluorophenyl)-1H-1,2,3-triazol-4-yl)methyl)-1-methyl-1H-pyrazol-5-amine, and | 11.801 |
| 224 | N-[(1R)-1-[1-[4-Chloro-3-(difluoromethoxy)phenyl]triazol-4-yl]ethyl]-5-methyl-pyrimidin-2-amine; | 0.121 |
| 225 | 5-Chloro-2[[1-(4-chlorophenyl)triazol-4-yl]methoxy]pyrimidine; | 0.070 |
| 226 | 2-[[1-(4-Chlorophenyl)triazol-4-yl]methoxy-5-(trifluoromethyl)pyrimidine; | 0.155 |
| 227 | 2-[[1-(4-Chlorophenyl)triazol-4-yl]methoxy-5-(difluoromethoxy)pyrimidine; | 0.151 |
| 228 | 2-[[1-(3-Chlorophenyl)triazol-4-yl]methoxy]pyrimidine; | 5.649 |
| 229 | 5-Fluoro-2[[1-(3-fluorophenyl)triazol-4-yl]methoxy]pyrimidine; | 2.980 |
| 230 | 2-[[1-(3-Fluorophenyl)triazol-4-yl]methoxy]-5-methoxy-pyrimidine; | 0.275 |
| 231 | 5-Chloro-2-[[1-(3-fluorophenyl)triazol-4-yl]methoxy]pyrimidine; | 0.389 |
| 232 | 2-[[1-(3-Fluorophenyl)triazol-4-yl]methoxy]-5-methyl-pyrimidine; | 0.205 |
| 233 | 5-Ethyl-2-[[1-(3-fluorophenyl)triazol-4-yl]methoxy]pyrimidine; | 0.075 |
| 234 | 2[[1-(3-Bromophenyl)triazol-4-yl]methoxy]-5-methyl-pyrimidine; | 0.022 |
| 235 | 2-[[1-(3-Bromophenyl)triazol-4-yl]methoxy]-4-methyl-pyrimidine; | NT |
| 236 | 2-[[1-(o-Tolyl)triazol-4-yl]methoxy]pyrimidine; | >10 |
| 237 | 5-Fluoro-2[[1-(o-tolyl)triazol-4-yl]methoxy]pyrimidine; | 16.600 |
| 238 | 5-Methoxy-2[[1-(o-tolyl)triazol-4-yl]methoxy]pyridine; | 5.990 |
| 239 | 5-Chloro-2[[1-(o-tolyl)triazol-4-yl]methoxy]pyrimidine; | 4.800 |
| 240 | 5-Methyl-2[[1-(o-tolyl)triazol-4-yl]methoxy]pyrimidine; | 5.580 |
| 241 | 5-Ethyl-2-[[1-(o-tolyl)triazol-4-yl]methoxy]pyrimidine; | 1.460 |
| 242 | 2-[[1-(m-Tolyl)triazol-4-yl]methoxy]pyrimidine; | 0.647 |
| 243 | 5-Methyl-2-[[1-(m-tolyl)triazol-4-yl]methoxy]pyrimidine; | 0.014 |
| 244 | 4-Methyl-2-[[1-(m-tolyl)triazol-4-yl]methoxy]pyrimidine; | 0.191 |
| 245 | 5-Ethyl-2-[[1-(m-tolyl)triazol-4-yl]methoxy]pyrimidine; | 0.010 |
| 246 | 5-Chloro-2-[[1-(m-tolyl)triazol-4-yl]methoxy]pyrimidine; | 0.033 |
| 247 | 5-Fluoro-24[1-(m-tolyl)triazol-4-yl]methoxy]pyrimidine; | 0.340 |
| 248 | 5-Methoxy-2-[[1-(m-tolyl)triazol-4-yl]methoxy]pyrimidine; | 0.009 |
| 249 | 2-[2-[[1-(m-Tolyl)triazol-4-yl]methoxy]pyrimidin-5-yl]propan-2-ol; | 0.289 |
| 250 | 4-(Methoxymethyl)-2-[[1-(m-tolyl)triazol-4-yl]methoxy]pyrimidine; | 0.249 |
| 251 | 4,5-Dimethyl-2-[[1-(m-tolyl)triazol-4-yl]methoxy]pyrimidine; | 0.002 |
| 252 | 5-Fluoro-4-methyl-2-[[1-tolyl)triazol-4-yl]methoxy]pyrimidine; | 0.065 |
| 253 | 5-Chloro-4-methyl-2-[[1-(m-tolyl)triazol-4-yl]methoxy]pyrimidine; | 0.007 |
| 254 | 5-Methyl-2-[[1-(m-tolyl)triazol-4-yl]methoxy]pyrimidin-4-amine; | 0.151 |
| 255 | 1-[2-[[1-(m-Tolyl)triazol-4-yl]methoxy]pyrimidin-5-yl]ethanone; | 0.224 |
| 256 | 2-[[1-(p-Tolyl)triazol-4-yl]methoxy]pyrimidine; | 4.420 |
| 257 | 5-Fluoro-2-[[1-(p-tolyl)triazol-4-yl]methoxy]pyrimidine; | 2.690 |
| 258 | 5-Methoxy-2-[[1-(p-tolyl)triazol-4-yl]methoxy]pyrimidine; | 0.225 |
| 259 | 5-Chloro-2-[[1-(p-tolyl)triazol-4-yl]methoxy]pyrimidine; | 0.711 |
| 260 | 5-Methyl-2-[[1-(p-tolyl)triazol-4-yl]methoxy]pyrimidine; | 0.271 |
| 261 | 5-Ethyl-2-[[1-(p-tolyl)triazol-4-yl]methoxy]pyrimidine; | 0.093 |
| 262 | 2-[[1-(3-Isopropylphenyl)triazol-4-yl]methoxy]pyrimidine; | 0.358 |
| 263 | 5-Fluoro-2[[1-(3-isopropylphenyl)triazol-4-yl]methoxy]pyrimidine; | 0.227 |
| 264 | 2-[[1-(3-Isopropylphenyl)triazol-4-yl]methoxy]-5-methoxy-pyrimidine; | 0.006 |
| 265 | 5-Chloro-2-[[1-(3-isopropylphenyl)triazol-4-yl]methoxy]pyrimidine; | 0.016 |
| 266 | 2-[[1-(3-Isopropylphenyl)triazol-4-yl]methoxy]-5-methyl-pyrimidine; | 0.010 |
| 267 | 5-Ethyl-2-[[1-(3-isopropylphenyl)triazol-4-yl]methoxy]pyrimidine; | 0.012 |
| 268 | 2-[[1-[3-(Difluoromethyl)phenyl]triazol-4-yl]methoxy]-4-methyl-pyrimidine; | 0.134 |
| 269 | 2-[[1-[3-(Difluoromethyl)phenyl]triazol-4-yl]methoxy]-5-fluoro-pyrimidine; | 0.325 |
| 270 | 2-[[1-[3-(Difluoromethyl)phenyl]triazol-4-yl]methoxy]-4-isopropyl-pyrimidine; | 0.617 |
| 271 | 2[[1-[3-(Difluoromethyl)phenyl]triazol-4-yl]methoxy]-4-(methoxymethyl)pyrimidine; | 0.360 |
| 272 | 2-[2-[[1-[3-(Difluoromethyl)phenyl]triazol-4-yl]methoxy]pyrimidin-5-yl]propan-2-ol; | 0.173 |
| 273 | 5-(Difluoromethyl)-2-[[1-[3-(difluoromethyl)phenyl]triazol-4-yl]methoxy]pyridine; | 0.027 |
| 274 | 4-(Difluoromethyl)-2-[[1-[3-(difluoromethyl)phenyl]triazol-4-yl]methoxy]pyrimidine; | 0.813 |
| 275 | 2-[[1-[3-(Difluoromethyl)phenyl]triazol-4-yl]methoxy-5-(trifluoromethyl)pyrimidine; | 0.025 |
| 276 | 5-(Difluoromethoxy)-2-[[1-[3-(difluoromethyl)phenyl]triazol-4-yl]methoxy]pyrimidine; | 0.031 |
| 277 | 2-[[1-[3-(Difluoromethyl)phenyl]triazol-4-yl]methoxy]-N,N-dimethyl-pyrimidin-4-amine; | 0.041 |

TABLE 5-continued

| Ex # | Compound Name | NR2B IC$_{50}$ (μM) standard assay |
|---|---|---|
| 278 | 2-[[1-[3-(Difluoromethyl)phenyl]triazol-4-yl]methoxy]-5-fluoro-4-methyl-pyrimidine; | 0.042 |
| 279 | 5-Chloro-2-[[1-[3-(difluoromethyl)phenyl]triazol-4-yl]methoxy]-4-methyl-pyrimidine; | 0.003 |
| 280 | 2-Chloro-4-[[1-[3-(difluoromethyl)phenyl]triazol-4-yl]methoxy]-5-methyl-pyrimidine; | 0.173 |
| 281 | 2-[[1-[3-(Difluoromethyl)phenyl]triazol-4-yl]methoxy]-N,N,5-trimethyl-pyrimidin-4-amine; | 0.130 |
| 282 | 5-Cyclopropyl-2-[[1-[3-(difluoromethyl)phenyl]triazol-4-yl]methoxy]pyrimidine; | 0.011 |
| 283 | 4-Cyclopropyl-2-[[1[3-(difluoromethyl)phenyl]triazol-4-yl]methoxy]pyrimidine; | 0.169 |
| 284 | 2-[[1-[3-(Difluoromethyl)phenyl]triazol-4-yl]methoxy]-4-pyrrolidin-1-yl-pyrimidine; | 0.094 |
| 285 | 2-[[1-[3-(Difluoromethyl)phenyl]triazol-4-yl]methoxy]-4-(1-piperidyl)pyrimidine; | 0.299 |
| 286 | 5-Methyl-2-[[1-[3-(trifluoromethyl)phenyl]triazol-4-yl]methoxy]pyrimidine; | 0.012 |
| 287 | 5-Ethyl-2-[[1-[3-(trifluoromethyl)phenyl]triazol-4-yl]methoxy]pyrimidine; | 0.005 |
| 288 | 5-Isopropyl-2-[[1-[3-(trifluoromethyl)phenyl]triazol-4-yl]methoxy]pyrimidine; | 0.040 |
| 289 | 5-(Difluoromethyl)-2-[[1-[3-(trifluoromethyl)phenyl]triazol-4-yl]methoxy]pyrimidine; | 0.037 |
| 290 | 4,5-Dimethyl-2-[[1-[3-(trifluoromethyl)phenyl]triazol-4-yl]methoxy]pyrimidine; | 0.007 |
| 291 | 5-Chloro-4-methyl-2-[[1-[3-(trifluoromethyl)phenyl]triazol-4-yl]methoxy]pyridine; | 0.009 |
| 292 | 2-[[1-[3-(1,1-Difluoroethyl)phenyl]triazol-4-yl]methoxy]pyrimidine; | 0.105 |
| 293 | 5-Bromo-2-[[1-[3-(1,1-difluoroethyl)phenyl]triazol-4-yl]methoxy]pyrimidine; | 0.039 |
| 294 | 5-Chloro-2-[[1-[3-(1,1-difluoroethyl)phenyl]triazol-4-yl]methoxy]pyridine; | 0.003 |
| 295 | 2-[[1-[3-(1,1-Difluoroethyl)phenyl]triazol-4-yl]methoxy]-5-fluoro-pyrimidine; | 0.061 |
| 296 | 2-[[1-[3-(1,1-Difluoroethyl)phenyl]triazol-4-yl]methoxy]-4-methyl-pyrimidine; | 0.012 |
| 297 | 2-[[1-[3-(1,1-Difluoroethyl)phenyl]triazol-4-yl]methoxy]-5-methyl-pyrimidine; | 0.005 |
| 298 | [2-[[1-[3-(1,1-Difluoroethyl)phenyl]triazol-4-yl]methoxy]pyrimidin-5-yl]methanol; | 0.034 |
| 299 | [2-[[1-[3-(1,1-Difluoroethyl)phenyl]triazol-4-yl]methoxy]pyrimidin-4-yl]methanol; | 0.049 |
| 300 | 2-[[1-[3-(1,1-Difluoroethyl)phenyl]triazol-4-yl]methoxy]-4-(methoxymethyl)pyrimidine; | 0.008 |
| 301 | 2-2-[[1-[3-(1,1-Difluoroethyl)phenyl]triazol-4-yl]methoxy]pyrimidin-5-yl]propan-2-ol; | 0.119 |
| 302 | 2-[[1-[3-(1,1-Difluoroethyl)phenyl]triazol-4-yl]methoxy]-5-(difluoromethyl)pyrimidine; | 0.002 |
| 303 | 2-[[1-[3-(1,1-Difluoroethyl)phenyl]triazol-4-yl]methoxy]-4-(difluoromethyl)pyrimidine; | 0.085 |
| 304 | 2-[[1-[3-(1,1-Difluoroethyl)phenyl]triazol-4-yl]methoxy]-4-(trifluoromethyl)pyrimidine; | 0.711 |
| 305 | (R/S)-2-2-[[1-[3-(1,1-Difluoroethyl)phenyl]triazol-4-yl]methoxy]pyrimidin-5-yl]-1,1,1-trifluoro-propan-2-ol; | 0.496 |
| 306 | 2-[[1-[3-(1,1-Difluoroethyl)phenyl]triazol-4-yl]methoxy]-5-methoxy-pyrimidine; | 0.003 |
| 307 | 2-[[1-[3-(1,1-Difluoroethyl)phenyl]triazol-4-yl]methoxy]-4-methoxy-pyrimidine; | 0.033 |
| 308 | 2-[[1-[3-(1,1-Difluoroethyl)phenyl]triazol-4-yl]methoxy]-5-(difluoromethoxy)pyrimidine; | 0.003 |
| 309 | 1-[2-[[1-[3-(1,1-Difluoroethyl)phenyl]triazol-4-yl]methoxy]pyrimidin-5-yl]ethanone; | 0.010 |
| 310 | (R/S)-1-[2-[[1-[3-(1,1-Difluoroethyl)phenyl]triazol-4-yl]methoxy]pyrimidin-5-yl]ethanol; | 0.037 |
| 311 | (R/S)-2-[[1-[3-(1,1-Difluoroethyl)phenyl]triazol-4-yl]methoxy]-5-(1-methoxyethyl)pyrimidine; | 1.580 |
| 312 | 5-Chloro-2-[[1-[3-(1,1-difluoroethyl)phenyl]triazol-4-yl]methoxy]-4-methyl-pyrimidine; | 0.004 |
| 313 | 2-[[1-[3-(1,1-Difluoroethyl)phenyl]triazol-4-yl]methoxy]-5-fluoro-4-methyl-pyrimidine; | 0.005 |
| 314 | 2-[[1-[3-(1,1-Difluoroethyl)phenyl]triazol-4-yl]methoxy]-5-methyl-pyrimidin-4-amine; | 0.006 |
| 315 | 2-[[1-[3-(1,1-Difluoroethyl)phenyl]triazol-4-yl]methoxy]-5-fluoro-N-methyl-pyrimidin-4-amine; | 0.158 |
| 316 | 2-[[1-[3-(1,1-Difluoroethyl)phenyl]triazol-4-yl]methoxy]pyrimidin-4-amine; | 0.183 |
| 317 | 2-[[1-[3-(1,1-Difluoroethyl)phenyl]triazol-4-yl]methoxyl-N-methyl-pyrimidin-4-amine; | 0.026 |
| 318 | 2-[[1-[3-(1,1-Difluoroethyl)phenyl]triazol-4-yl]methoxy]-N,N-dimethyl-pyrimidin-4-amine; | 0.026 |
| 319 | 5-Cyclopropyl-2-[[1-[3-(1,1-difluoroethyl)phenyl]triazol-4-yl]methoxy]pyrimidine; | 0.015 |
| 320 | 5-(Azetidin-1-yl)-2-[[1-[3-(1,1-difluoroethyl)phenyl]triazol-4-yl]methoxy]pyrimidine; | 0.061 |
| 321 | 2-[[1-[3-(1,1-Difluoroethyl)phenyl]triazol-4-yl]methoxy]-5-(3-fluoroazetidin-1-yl)pyrimidine; | 0.104 |
| 322 | 2-[[1-[3-(1,1-Difluoroethyl)phenyl]triazol-4-yl]methoxy]-4-pyrrolidin-1-yl-pyrimidine; | 0.011 |
| 323 | 2-[[1-[3-(Difluoromethoxy)phenyl]triazol-4-yl]methoxy]pyrimidine; | 0.788 |
| 324 | 2-[[1-[3-(Difluoromethoxy)phenyl]triazol-4-yl]methoxy]-5-fluoro-pyrimidine; | 0.494 |
| 325 | 2-[[1-[3-(Difluoromethoxy)phenyl]triazol-4-yl]methoxy]-5-methoxy-pyrimidine; | 0.027 |
| 326 | 5-Chloro-2-[[1-[3-(difluoromethoxy)phenyl]triazol-4-yl]methoxy]pyrimidine; | 0.069 |
| 327 | 2-[[1-[3-(Difluoromethoxy)phenyl]triazol-4-yl]methoxy]-5-methyl-pyrimidine; | 0.015 |
| 328 | 2-[[1-[3-(Difluoromethoxy)phenyl]triazol-4-yl]methoxy]-5-ethyl-pyrimidine; | 0.029 |
| 329 | 2-[[1-[4-(Difluoromethoxy)phenyl]triazol-4-yl]methoxy]pyridine; | 0.854 |
| 330 | 2-[[1-[4-(Difluoromethoxy)phenyl]triazol-4-yl]methoxy]-5-fluoro-pyrimidine; | 0.752 |
| 331 | 2-[[1-[4-(Difluoromethoxy)phenyl]triazol-4-yl]methoxy]-5-methoxy-pyrimidine; | 0.098 |
| 332 | 5-Chloro-2-[[1-[4-(difluoromethoxy)phenyl]triazol-4-yl]methoxy]pyrimidine; | 0.200 |
| 333 | 2-[[1-[4-(Difluoromethoxy)phenyl]triazol-4-yl]methoxy]-5-methyl-pyrimidine; | 0.087 |
| 334 | 2-[[1-[4-(Difluoromethoxy)phenyl]triazol-4-yl]methoxy]-5-ethyl-pyrimidine; | 0.051 |
| 335 | 2-[[1-[4-(Trifluoromethoxy)phenyl]triazol-4-yl]methoxy]pyrimidine; | 3.120 |
| 336 | 5-Fluoro-2-[[1-[4-(trifluoromethoxy)phenyl]triazol-4-yl]methoxy]pyrimidine; | 11.301 |
| 337 | 5-Methoxy-2-[[1-[4-(trifluoromethoxy)phenyl]triazol-4-yl]methoxy]pyrimidine; | >10 |
| 338 | 5-Chloro-2-[[1-[4-(trifluoromethoxy)phenyl]triazol-4-yl]methoxy]pyrimidine; | 9.049 |
| 339 | 5-Methyl-2-[[1-[4-(trifluoromethoxy)phenyl]triazol-4-yl]methoxy]pyrimidine; | 1.130 |
| 340 | 5-Ethyl-2-[[1-[4-(trifluoromethoxy)phenyl]triazol-4-yl]methoxy]pyridine; | 0.794 |
| 341 | 2-[[1-[3-(Trifluoromethoxy)phenyl]triazol-4-yl]methoxy]pyridine; | 0.538 |
| 342 | 5-Methyl-2-[[1-[3-(trifluoromethoxy)phenyl]triazol-4-yl]methoxy]pyrimidine; | 0.017 |
| 343 | 5-Methyl-2-[[1-[3-(trifluoromethoxy)phenyl]triazol-4-yl]methoxy]pyrimidin-4-amine; | 0.040 |
| 344 | 1-[2-[[1-[3-(Trifluoromethoxy)phenyl]triazol-4-yl]methoxy]pyrimidin-5-yl]ethanone; | 0.062 |
| 345 | 2-[2-[[1-[3-(Trifluoromethoxy)phenyl]triazol-4-yl]methoxy]pyrimidin-5-yl]propan-2-ol; | 0.284 |
| 346 | 4-(Methoxymethyl)-2-[[1-[3-(trifluoromethoxy)phenyl]triazol-4-yl]methoxy]pyrimidine; | 0.202 |
| 347 | 4-Methyl-2-[[1-[3-(trifluoromethoxy)phenyl]triazol-4-yl]methoxy]pyrimidine; | 0.137 |
| 348 | 5-Fluoro-2-[[1-[3-(trifluoromethoxy)phenyl]triazol-4-yl]methoxy]pyrimidine; | 0.447 |
| 349 | 5-Methoxy-2-[[1-[3-(trifluoromethoxy)phenyl]triazol-4-yl]methoxy]pyrimidine; | 0.013 |

TABLE 5-continued

| Ex # | Compound Name | NR2B IC$_{50}$ (μM) standard assay |
|---|---|---|
| 350 | 5-Chloro-2-[[1-[3-(trifluoromethoxy)phenyl]triazol-4-yl]methoxy]pyrimidine; | 0.050 |
| 351 | 5-Ethyl-2-[[1-[3-(trifluoromethoxy)phenyl]triazol-4-yl]methoxy]pyrimidine; | 0.015 |
| 352 | N-Methyl-2-[[1-[3-(trifluoromethoxy)phenyl]triazol-4-yl]methoxy]pyrimidin-4-amine; | 0.068 |
| 353 | 2-[[1-[3-(Trifluoromethoxy)phenyl]triazol-4-yl]methoxy]pyrimidin-4-amine; | 0.525 |
| 354 | 2-[[1-(2,2-Difluoro-1,3-benzodioxol-5-yl)triazol-4-yl]methoxy]-5-methyl-pyrimidine; | 0.073 |
| 355 | 2-[[1-(2,2-Difluoro-1,3-benzodioxol-5-yl)triazol-4-yl]methoxy]pyrimidine; | 0.238 |
| 356 | 5-Chloro-2-[[1-(2,2-difluoro-1,3-benzodioxol-5-yl)triazol-4-yl]methoxy]pyrimidine; | 0.185 |
| 357 | 2-[[1-(2,2-Difluoro-1,3-benzodioxol-5-yl)triazol-4-yl]methoxy]-5-fluoro-4-methyl-pyrimidine; | 0.350 |
| 358 | 2-[[1-(2,2-Difluoro-1,3-benzodioxol-5-yl)triazol-4-yl]methoxy]-5-fluoro-pyrimidine; | 0.726 |
| 359 | 2-[[1-(2,2-Difluoro-1,3-benzodioxol-5-yl)triazol-4-yl]methoxy]-4,5-dimethyl-pyrimidine; | 0.009 |
| 360 | 2-[1-(3,5-Dimethylphenyl)triazol-4-yl]methoxy]pyrimidine; | 0.791 |
| 361 | 2-[[1-(3,5-Dimethylphenyl)triazol-4-yl]methoxy]-5-fluoro-pyrimidine; | 0.587 |
| 362 | 2-[[1-(3,5-Dimethylphenyl)triazol-4-yl]methoxy]-5-methoxy-pyrimidine; | 0.032 |
| 363 | 5-Chloro-2-[[1-(3,5-dimethylphenyl)triazol-4-yl]methoxy]pyrimidine; | 0.118 |
| 364 | 2-[[1-(3,5-Dimethylphenyl)triazol-4-yl]methoxy]-5-methyl-pyrimidine; | 0.027 |
| 365 | 2-[[1-(3,5-Dimethylphenyl)triazol-4-yl]methoxy]-5-ethyl-pyrimidine; | 0.022 |
| 366 | 2-[(1-Indan-5-yltriazol-4-yl)methoxy]-5-methyl-pyrimidine; | 0.020 |
| 367 | 5-Chloro-2-[(1-indan-5-yltriazol-4-yl)methoxy]pyrimidine; | 0.053 |
| 368 | 2-[(1-Indan-5-yltriazol-4-yl)methoxy]-4-(methoxymethyl)pyrimidine; | 0.114 |
| 369 | 2-[2-[(1-Indan-5-yltriazol-4-yl)methoxy]pyrimidin-5-yl]propan-2-ol; | 0.175 |
| 370 | 4-(Difluoromethyl)-2-[(1-indan-5-yltriazol-4-yl)methoxy]pyrimidine; | 0.397 |
| 371 | 5-Chloro-2-[(1-indan-5-yltriazol-4-yl)methoxy]-4-methyl-pyrimidine; | 0.039 |
| 372 | 2-[[1-[4-Chloro-3-(difluoromethoxy)phenyl]triazol-4-yl]methoxy]-4,5-dimethyl-pyrimidine; | 0.008 |
| 373 | 2-[[1-[4-Chloro-3-(difluoromethoxy)phenyl]triazol-4-yl]methoxy]-5-isopropyl-pyrimidine; | 0.010 |
| 374 | 2-[(1R)-1-[1-[4-Chloro-3-(difluoromethoxy)phenyl]triazol-4-yl]ethoxy]pyrimidine; | 0.011 |
| 375 | 5-Chloro-2-[(1R)-1-[1-[4-chloro-3-(difluoromethoxy)phenyl]triazol-4-yl]ethoxy]pyrimidine; | 0.010 |
| 376 | 2-[(1R)-1-[1-[4-Chloro-3-(difluoromethoxy)phenyl]triazol-4-yl]ethoxy]-5-methyl-pyrimidine; | 0.011 |
| 377 | 2-[(1R)-1-[1-[4-Chloro-3-(difluoromethoxy)phenyl]triazol-4-yl]ethoxy]-5-methoxy-pyrimidine; | 0.010 |
| 378 | 2-[(1S)-1-[1-[4-Chloro-3-(difluoromethoxy)phenyl]triazol-4-yl]ethoxy]pyrimidine; | 2.300 |
| 379 | 5-Chloro-2-[(1S)-1-[1-[4-chloro-3-(difluoromethoxy)phenyl]triazol-4-yl]ethoxy]pyrimidine; | 0.575 |
| 380 | 2-[(1S)-1-[1-[4-Chloro-3-(difluoromethoxy)phenyl]triazol-4-yl]ethoxy]-5-methyl-pyrimidine; | 0.237 |
| 381 | 2-[(1S)-1-[1-[4-Chloro-3-(difluoromethoxy)phenyl]triazol-4-yl]ethoxy]-5-methoxy-pyrimidine; | 0.196 |
| 382 | 2-[[1-[4-Chloro-3-(difluoromethoxy)phenyl]triazol-4-yl]methoxy]pyrimidin-4-amine; | 0.021 |
| 383 | [2-[[1-[4-Chloro-3-(difluoromethoxy)phenyl]triazol-4-yl]methoxy]pyrimidin-4-yl]methanol; | 0.008 |
| 384 | 2-[[1-[4-Chloro-3-(difluoromethoxy)phenyl]triazol-4-yl]methoxy]-4-(methoxymethyl)pyrimidine; | 0.018 |
| 385 | 2-[2-[[1-[4-Chloro-3-(difluoromethoxy)phenyl]triazol-4-yl]methoxy]pyrimidin-5-yl]propan-2-ol; | 0.028 |
| 386 | 2-((1-(4-Chloro-3-(difluoromethoxy)phenyl)-1H-1,2,3-triazol-4-yl)methoxy)-4-isopropoxypyrimidine; | 0.504 |
| 387 | Methyl 2-((1-(4-chloro-3-(difluoromethoxy)phenyl)-1H-1,2,3-triazol-4-yl)methoxy)pyrimidine-4-carboxylate; | 0.068 |
| 388 | 2-[[1-[4-Chloro-3-(difluoromethoxy)phenyl]triazol-4-yl]methoxy]-N-(2,2-difluoroethyl)-5-fluoro-pyrimidin-4-amine; | 0.842 |
| 389 | 2-[[1-[4-Chloro-3-(difluoromethoxy)phenyl]triazol-4-yl]methoxy]-5-fluoro-N-methyl-pyrimidin-4-amine; | 0.033 |
| 390 | 2-((1-(4-Chloro-3-(difluoromethoxy)phenyl)-1H-1,2,3-triazol-4-yl)methoxy)-5-fluoropyrimidin-4-amine; | 0.006 |
| 391 | 5-(Azetidin-1-yl)-2-((1-(4-chloro-3-(difluoromethoxy)phenyl)-1H-1,2,3-triazol-4-yl)methoxy)pyrimidine; | 0.022 |
| 392 | 2-((1-(4-Chloro-3-(difluoromethoxy)phenyl)-1H-1,2,3-triazol-4-yl)methoxy)-5-(3-fluoroazetidin-1-yl)pyrimidine; | 0.017 |
| 393 | 2-((1-(4-Chloro-3-(difluoromethoxy)phenyl)-1H-1,2,3-triazol-4-yl)methoxy)-5-(3,3-difluoroazetidin-1-yl)pyrimidine; | 0.037 |
| 394 | 2-[[1-[4-Chloro-3-(difluoromethoxy)phenyl]triazol-4-yl]methoxy]-6-fluoro-pyridine; | 0.437 |
| 395 | 2-[[1-[3-(Difluoromethoxy)-4-fluoro-phenyl]triazol-4-yl]methoxy]-6-(trifluoromethyl)pyridine; | 0.919 |
| 396 | 2-[[1-[3-(Difluoromethoxy)-4-fluoro-phenyl]triazol-4-yl]methoxy]-5-methyl-pyrazine; | 0.647 |
| 397 | 2-[[1-[3-(Difluoromethoxy)-4-fluoro-phenyl]triazol-4-yl]methoxy]-5-(2-thienyl)pyrazine; | 10.700 |
| 398 | 5-Bromo-2-[[1-[3-(difluoromethyl)-4-fluoro-phenyl]triazol-4-yl]methoxy]pyrimidine; | 0.003 |
| 399 | 2-[[1-[3-(Difluoromethyl)-4-fluoro-phenyl]triazol-4-yl]methoxy]-4-(methoxymethyl)pyrimidine; | 0.023 |
| 400 | [2-[[1-[3-(Difluoromethyl)-4-fluoro-phenyl]triazol-4-yl]methoxy]pyrimidin-4-yl]methanol; | 0.036 |
| 401 | 2-[2-[[1-[3-(Difluoromethyl)-4-fluoro-phenyl]triazol-4-yl]methoxy]pyrimidin-5-yl]propan-2-ol; | 0.017 |
| 402 | 4-(Difluoromethyl)-2-[[1-[3-(difluoromethyl)-4-fluoro-phenyl]triazol-4-yl]methoxy]pyrimidine; | 0.051 |
| 403 | 2-[[1-[3-(Difluoromethyl)-4-fluoro-phenyl]triazol-4-yl]methoxy]-4-(trifluoromethyl)pyrimidine; | 0.199 |
| 404 | (R/S)-2-[2-[[1-[3-(Difluoromethyl)-4-fluoro-phenyl]triazol-4-yl]methoxy]pyrimidin-5-yl]-1,1,1-trifluoro-propan-2-ol; | 0.482 |
| 405 | 5-(Difluoromethoxy)-2-[[1-[3-(difluoromethyl)-4-fluoro-phenyl]triazol-4-yl]methoxy]pyrimidine; | 0.003 |
| 406 | 5-Chloro-2-[[1-[3-(difluoromethyl)-4-fluoro-phenyl]triazol-4-yl]methoxy]-4-methyl-pyrimidine; | 0.001 |
| 407 | 2-[[1-[3-(Difluoromethyl)-4-fluoro-phenyl]triazol-4-yl]methoxy]-5-fluoro-4-methyl-pyrimidine; | 0.001 |
| 408 | 2-[[1-[3-(Difluoromethyl)-4-fluoro-phenyl]triazol-4-yl]methoxy]-4,5-dimethyl-pyrimidine; | 0.002 |
| 409 | 2-[[1-[3-(Difluoromethyl)-4-fluoro-phenyl]triazol-4-yl]methoxy]-N-methyl-pyrimidine-5-carboxamide; | 0.149 |
| 410 | 2-[[1-[3-(Difluoromethyl)-4-fluoro-phenyl]triazol-4-yl]methoxy]-N,N-dimethyl-pyrimidine-4-carboxamde; | >2.99 |
| 411 | 2-[[1-[3-(Difluoromethyl)-4-fluoro-phenyl]triazol-4-yl]methoxy]-4-methoxy-5-methyl-pyrimidine; | 0.021 |
| 412 | 2-[[1-[3-(Difluoromethyl)-4-fluoro-phenyl]triazol-4-yl]methoxy]pyrimidin-4-amine; | 0.124 |
| 413 | 2-[[1-[3-(Difluoromethyl)-4-fluoro-phenyl]triazol-4-yl]methoxy]-N-methyl-pyrimidin-4-amine; | 0.015 |
| 414 | 2-[[1-[3-(Difluoromethyl)-4-fluoro-phenyl]triazol-4-yl]methoxy]-5-fluoro-N-methyl-pyrimidin-4-amine; | 0.122 |
| 415 | 2-[[1-[3-(Difluoromethyl)-4-fluoro-phenyl]triazol-4-yl]methoxy]-N,N-dimethyl-pyrimidin-4-amine; | 0.008 |
| 416 | 2-((1-(3-(Difluoromethyl)-4-fluorophenyl)-1H-1,2,3-triazol-4-yl)methoxy)-5-(3-fluoroazetidin-1-yl)pyrimidine; | 0.010 |
| 417 | 5-(Azetidin-1-yl)-2-((1-(3-(difluoromethyl)-4-fluorophenyl)-1H-1,2,3-triazol-4-yl)methoxy)pyrimidine; | 0.006 |

TABLE 5-continued

| Ex #. | Compound Name | NR2B IC$_{50}$ (μM) standard assay |
|---|---|---|
| 418 | 2-((1-(3-(Difluoromethyl)-4-fluorophenyl)-1H-1,2,3-triazol-4-yl)methoxy)-5-(3-methoxyazetidin-1-yl)pyrimidine; | 0.271 |
| 419 | 5-(3,3-Difluoroazetidin-1-yl)-2-((1-(3-(difluoromethyl)-4-fluorophenyl)-1H-1,2,3-triazol-4-yl)methoxy)pyrimidine; | 0.029 |
| 420 | 2-((1-(3-(Difluoromethyl)-4-fluorophenyl)-1H-1,2,3-triazol-4-yl)methoxy)-5-(3-fluoro-3-methylazetidin-1-yl)pyrimidine; | 0.260 |
| 421 | 2-((1-(3-(Difluoromethyl)-4-fluorophenyl)-1H-1,2,3-triazol-4-yl)methoxy)-5-(3-(difluoromethyl)azetidin-1-yl)pyrimidine; | 0.227 |
| 422 | 2-((1-(3-(Difluoromethyl)-4-fluorophenyl)-1H-1,2,3-triazol-4-yl)methoxy)-5-(3,3-difluoropyrrolidin-1-yl)pyrimidine; | 0.068 |
| 423 | 5-Cyclopropyl-2-[[1[3-(difluoromethyl)-4-fluoro-phenyl]triazol-4-yl]methoxy]pyrimidine; | 0.005 |
| 424 | 2-[[1-[3-(Difluoromethyl)-4-fluoro-phenyl]triazol-4-yl]methoxy]-4-(2-furyl)pyrimidine; | 0.141 |
| 425 | 2-[[1-[3-(Difluoromethyl)-4-fluoro-phenyl]-5-iodo-triazol-4-yl]methoxy]-5-methyl-pyrimidine; | 0.394 |
| 426 | [3H]-2-((1-(3-(Difluoromethyl)-4-fluorophenyl)-1H-1,2,3-triazol-4-yl-5-t)methoxy)-5-methylpyrimidine; | |
| 427 | 3-Fluoro-2-[[1-[4-fluoro-3-(trifluoromethyl)phenyl]triazol-4-yl]methoxy]pyridine; | 0.897 |
| 428 | 5-Chloro-2-[[1-[4-fluoro-3-(trifluoromethyl)phenyl]triazol-4-yl]methoxy]pyridine; | 0.796 |
| 429 | 2-[[1-[4-Fluoro-3-(trifluoromethyl)phenyl]triazol-4-yl]methoxy]-4-methyl-pyridine; | 0.665 |
| 430 | 2-[[1-[4-Fluoro-3-(trifluoromethyl)phenyl]triazol-4-yl]methoxy]-6-methyl-pyridine; | 0.110 |
| 431 | 2-[[1-[4-Fluoro-3-(trifluoromethyl)phenyl]triazol-4-yl]methoxy]-5-methyl-pyridine; | 0.101 |
| 432 | 2-[[1-[4-Fluoro-3-(trifluoromethyl)phenyl]triazol-4-yl]methoxy]-5-(trifluoromethyl)pyridine; | 0.528 |
| 433 | 2-[6-[[1[4-Fluoro-3-(trifluoromethyl)phenyl]triazol-4-yl]methoxy]-3-pyridyl]propan-2-ol; | 1.114 |
| 434 | 2-[[1-[4-Fluoro-3-(trifluoromethyl)phenyl]triazol-4-yl]methoxy]pyrazine; | 6.390 |
| 435 | 2-[2-[[1-[4-Fluoro-3-(trifluoromethyl)phenyl]triazol-4-yl]methoxy]pyrimidin-5-yl]propan-2-ol; | 0.098 |
| 436 | 2-[[1-[4-Fluoro-3-(trifluoromethyl)phenyl]triazol-4-yl]methoxy]-5-(1-methoxy-1-methyl-ethyl)pyrimidine; | 3.260 |
| 437 | 2-[[1-[4-Fluoro-3-(trifluoromethyl)phenyl]triazol-4-yl]methoxy]-5-(methoxymethyl)pyrimidine; | 0.071 |
| 438 | 2-[[1-[4-Fluoro-3-(trifluoromethyl)phenyl]triazol-4-yl]methoxy]-4-(methoxymethyl)pyrimidine; | 0.094 |
| 439 | 5-(Difluoromethyl)-2-[[1-[4-fluoro-3-(trifluoromethyl)phenyl]triazol-4-yl]methoxy]pyrimidine; | 0.013 |
| 440 | 4-(Difluoromethyl)-2-[[1-[4-fluoro-3-(trifluoromethyl)phenyl]triazol-4-yl]methoxy]pyrimidine; | 0.098 |
| 441 | (R/S)-1,1,1-Trifluoro-2-[2-[[1-[4-fluoro-3-(trifluoromethyl)phenyl]triazol-4-yl]methoxy]pyrimidin-5-yl]propan-2-ol; | 0.412 |
| 442 | 2-[[1-[4-Fluoro-3-(trifluoromethyl)phenyl]triazol-4-yl]methoxy]-4-methoxy-pyrimidine; | 0.072 |
| 443 | 5-Ethoxy-2-[[1-[4-fluoro-3-(trifluoromethyl)phenyl]triazol-4-yl]methoxy]pyrimidine; | 0.004 |
| 444 | 5-Chloro-2-[[1-[4-fluoro-3-(trifluoromethyl)phenyl]triazol-4-yl]methoxy]-4-methyl-pyrimidine; | 0.013 |
| 445 | 5-Fluoro-2-[[1-[4-fluoro-3-(trifluoromethyl)phenyl]triazol-4-yl]methoxy]-4-methyl-pyrimidine; | 0.006 |
| 446 | 2-[[1-[4-Fluoro-3-(trifluoromethyl)phenyl]triazol-4-yl]methoxy]-4,5-dimethyl-pyrimidine; | 0.001 |
| 447 | 1-[2-[[1-[4-Fluoro-3-(trifluoromethyl)phenyl]triazol-4-yl]methoxy]pyrimidin-5-yl]ethanone; | 0.014 |
| 448 | (R/S)-1-[2-[[1-[4-Fluoro-3-(trifluoromethyl)phenyl]triazol-4-yl]methoxy]pyrimidin-5-yl]ethanol; | 0.031 |
| 449 | 2-[[1-[4-Fluoro-3-(trifluoromethyl)phenyl]triazol-4-yl]methoxy]-N-methyl-pyrimidin-4-amine; | 0.034 |
| 450 | 2-[[1-[4-Fluoro-3-(trifluoromethyl)phenyl]triazol-4-yl]methoxy]-N,N-dimethyl-pyrimidin-4-amine; | 0.030 |
| 451 | 5-Fluoro-2-[[1-[4-fluoro-3-(trifluoromethyl)phenyl]triazol-4-yl]methoxy]-N-methyl-pyrimidin-4-amine; | 0.298 |
| 452 | 2-[[1-[4-Fluoro-3-(trifluoromethyl)phenyl]triazol-4-yl]methoxy]-N-methyl-pyrimidine-5-carboxamide; | 0.218 |
| 453 | 5-Cyclopropyl-2-[[1-[4-fluoro-3-(trifluoromethyl)phenyl]triazol-4-yl]methoxy]pyrimidine; | 0.022 |
| 454 | 5-Bromo-2-((1-(4-fluoro-3-(trifluoromethyl)phenyl)-1H-1,2,3-triazol-4-yl)methoxy)pyrimidine; | 0.013 |
| 455 | 2-((1-(4-Fluoro-3-(trifluoromethyl)phenyl)-1H-1,2,3-triazol-4-yl)methoxy)-5-(3-fluoroazetidin-1-yl)pyrimidine; | 0.034 |
| 456 | 4-(2-((1-(4-Fluoro-3-(trifluoromethyl)phenyl)-1H-1,2,3-triazol-4-yl)methoxy)pyrimidin-5-yl)morpholine; | 0.500 |
| 457 | 5-(Azetidin-1-yl)-2-((1-(3-(trifluoromethyl)-4-fluorophenyl)-1H-1,2,3-triazol-4-yl)methoxy)-4-methylpyrimidine; | 0.296 |
| 458 | 2-((1-(3-(Trifluoromethyl)-4-fluorophenyl)-1H-1,2,3-triazol-4-yl)methoxy)-N-ethyl-4-methylpyrimidin-5-amine; | 0.439 |
| 459 | 2-((1-(3-(Trifluoromethyl)-4-fluorophenyl)-1H-1,2,3-triazol-4-yl)methoxy)-N-ethylpyrimidin-5-amine; | 0.126 |
| 460 | 2-((1-(3-(Trifluoromethyl)-4-fluorophenyl)-1H-1,2,3-triazol-4-yl)methoxy)-5-(3-methoxyazetidin-1-yl)pyrimidine; | 0.726 |
| 461 | 5-Chloro-2-[[1-[2-fluoro-3-(trifluoromethyl)phenyl]triazol-4-yl]methoxy]pyrimidine; | 0.070 |
| 462 | 4-[[1-(4-Fluoro-3-methyl-phenyl)triazol-4-yl]methoxy]-6-methyl-pyrimidine; | 3.030 |
| 463 | 5-Chloro-2-[[1-(3-fluoro-2-methyl-phenyl)triazol-4-yl]methoxy]pyrimidine; | 0.647 |
| 464 | 2-[[1-(3-Fluoro-2-methyl-phenyl)triazol-4-yl]methoxy]-5-methyl-pyrimidine; | 0.515 |
| 465 | 5-Fluoro-2-[[1-(3-fluoro-2-methyl-phenyl)triazol-4-yl]methoxy]-4-methyl-pyrimidine; | 3.720 |
| 466 | 2-[2-[[1-(3-Fluoro-2-methyl-phenyl)triazol-4-yl]methoxy]pyrimidin-5-yl]propan-2-ol; | 7.010 |
| 467 | 2-[[1-(2-Fluoro-3-methyl-phenyl)triazol-4-yl]methoxy]-5-methyl-pyrimidine; | 0.711 |
| 468 | 5-Chloro-2-[[1-(2-fluoro-3-methyl-phenyl)triazol-4-yl]methoxy]pyrimidine; | 1.250 |
| 469 | 2-[[1-(2-Fluoro-3-methyl-phenyl)triazol-4-yl]methoxy]-5-(trifluoromethyl)pyrimidine; | 1.058 |
| 470 | 5-Chloro-2-[[1-(2-fluoro-3-methyl-phenyl)triazol-4-yl]methoxy]-4-methyl-pyrimidine; | 0.659 |
| 471 | 5-(Difluoromethoxy)-2-[[1-(2-fluoro-3-methyl-phenyl)triazol-4-yl]methoxy]pyrimidine; | 1.729 |
| 472 | 2-[[1-(4-Fluoro-3-methyl-phenyl)triazol-4-yl]methoxy]pyrimidin-4-amine; | 0.149 |
| 473 | 2-[[1-(4-Fluoro-3-methyl-phenyl)triazol-4-yl]methoxy]pyrimidine; | 0.072 |
| 474 | 5-Fluoro-2-[[1-(4-fluoro-3-methyl-phenyl)triazol-4-yl]methoxy]pyrimidine; | 0.022 |
| 475 | 2-[[1-(4-Fluoro-3-methyl-phenyl)triazol-4-yl]methoxy]-5-methoxy-pyrimidine; | 0.001 |
| 476 | 5-Chloro-2-[[1-(4-fluoro-3-methyl-phenyl)triazol-4-yl]methoxy]pyrimidine; | 0.002 |
| 477 | 2-[[1-(4-Fluoro-3-methyl-phenyl)triazol-4-yl]methoxy]-5-methyl-pyrimidine; | 0.001 |
| 478 | 5-Ethyl-2-[[1-(4-fluoro-3-methyl-phenyl)triazol-4-yl]methoxy]pyrimidine; | 0.001 |
| 479 | 2-[[1-(4-Fluoro-3-methyl-phenyl)triazol-4-yl]methoxy]-4-(methoxymethyl)pyrimidine; | 0.036 |
| 480 | 2-[[1-(4-Fluoro-3-methyl-phenyl)triazol-4-yl]methoxy]-4,5-dimethyl-pyrimidine; | 0.001 |
| 481 | 5-Fluoro-2-[[1-(4-fluoro-3-methyl-phenyl)triazol-4-yl]methoxy]-4-methyl-pyrimidine; | 0.002 |
| 482 | 5-Chloro-2-[[1-(4-fluoro-3-methyl-phenyl)triazol-4-yl]methoxy]-4-methyl-pyrimidine; | 0.001 |
| 483 | 5-(2-Fluoroethoxy)-2-[[1-(4-fluoro-3-methyl-phenyl)triazol-4-yl]methoxy]pyrimidine; | 0.007 |

TABLE 5-continued

| Ex #. | Compound Name | NR2B IC$_{50}$ (µM) standard assay |
|---|---|---|
| 484 | 2-[[1-(2-Fluoro-5-methyl-phenyl)triazol-4-yl]methoxy]-5-methyl-pyrimidine; | 1.000 |
| 485 | 5-Chloro-2-[[1-(2-fluoro-5-methyl-phenyl)triazol-4-yl]methoxy]-4-methyl-pyrimidine; | 1.010 |
| 486 | 5-Fluoro-2-[[1-(2-fluoro-5-methyl-phenyl)triazol-4-yl]methoxy]-4-methyl-pyrimidine; | >2.99 |
| 487 | 5-Fluoro-2-[[1-(4-fluoro-2-methyl-phenyl)triazol-4-yl]methoxy]pyridine; | 16.199 |
| 488 | 2-[[1-(4-Fluoro-2-methyl-phenyl)triazol-4-yl]methoxy]-5-methoxy-pyrimidine; | 2.650 |
| 489 | 5-Chloro-2-[[1-(4-fluoro-2-methyl-phenyl)triazol-4-yl]methoxy]pyrimidine; | 4.420 |
| 490 | 2-[[1-(4-Fluoro-2-methyl-phenyl)triazol-4-yl]methoxy]-5-methyl-pyrimidine; | 2.440 |
| 491 | 5-Ethyl-2-[[1-(4-fluoro-2-methyl-phenyl)triazol-4-yl]methoxy]pyrimidine; | 1.170 |
| 492 | 2-[[1-[3-(Difluoromethoxy)-4-fluoro-phenyl]triazol-4-yl]methoxy]-5-fluoro-pyrimidine; | 0.026 |
| 493 | 2-[[1-[3-(Difluoromethoxy)-4-fluoro-phenyl]triazol-4-yl]methoxy]-5-fluoro-4-methyl-pyrimidine; | 0.004 |
| 494 | 5-Bromo-2-[[1-[3-(difluoromethoxy)-4-fluoro-phenyl]triazol-4-yl]methoxy]pyrimidine; | 0.003 |
| 495 | 2-[[1-[3-(Difluoromethoxy)-4-fluoro-phenyl]triazol-4-yl]methoxy]-4-ethyl-pyrimidine; | 0.010 |
| 496 | 2[[1-[3-(Difluoromethoxy)-4-fluoro-phenyl]triazol-4-yl]methoxy]-4-isopropyl-pyrimidine; | 0.114 |
| 497 | 2-[[1-[3-(Difluoromethoxy)-4-fluoro-phenyl]triazol-4-yl]methoxy]-4-methoxy-pyrimidine; | 0.028 |
| 498 | [2-[[1-[3-(Difluoromethoxy)-4-fluoro-phenyl]triazol-4-yl]methoxy]pyrimidin-4-yl]methanol; | 0.019 |
| 499 | 2-[[1-[3-(Difluoromethoxy)-4-fluoro-phenyl]triazol-4-yl]methoxy]-4-(methoxymethyl)pyrimidine; | 0.016 |
| 500 | 2-[2-[[1-[3-(Difluoromethoxy)-4-fluoro-phenyl]triazol-4-yl]methoxy]pyrimidin-5-yl]propan-2-ol; | 0.068 |
| 501 | 2-[[1-[3-(Difluoromethoxy)-4-fluoro-phenyl]triazol-4-yl]methoxy]pyrimidin-4-amine; | 0.052 |
| 502 | 2-[[1-[3-(Difluoromethoxy)-4-fluoro-phenyl]triazol-4-yl]methoxy]pyrimidin-5-amine; | 0.136 |
| 503 | 2-[[1-[3-(Difluoromethoxy)-4-fluoro-phenyl]triazol-4-yl]methoxyl-N-methyl-pyrimidin-4-amine; | 0.008 |
| 504 | 2-((1-(3-(Difluoromethoxy)-4-fluorophenyl)-1H-1,2,3-triazol-4-yl)methoxy)-N-ethylpyrimidin-4-amine; | 0.007 |
| 505 | 2-[[1-[3-(Difluoromethoxy)-4-fluoro-phenyl]triazol-4-yl]methoxy]-N,N-dimethyl-pyrimidin-4-amine; | 0.007 |
| 506 | 2-[[1-[3-(Difluoromethoxy)-4-fluoro-phenyl]triazol-4-yl]methoxy]-4-phenyl-pyrimidine; | 9.750 |
| 507 | 2-[[1-[3-(Difluoromethoxy)-4-fluoro-phenyl]triazol-4-yl]methoxy]-5-(3-fluoroazetidin-1-yl)pyrimidine; | 0.008 |
| 508 | 5-(3,3-Difluoroazetidin-1-yl)-2[[1-[3-(difluoromethoxy)-4-fluoro-phenyl]triazol-4-yl]methoxy]pyrimidine; | 0.019 |
| 509 | 4-(Azetidin-1-yl)-2-[[1-[3-(difluoromethoxy)-4-fluoro-phenyl]triazol-4-yl]methoxy]pyrimidine; | 0.003 |
| 510 | 2-[[1-[3-(Difluoromethoxy)-4-fluoro-phenyl]triazol-4-yl]methoxy]-4-(3-fluoroazetidin-1-yl)pyrimidine; | 0.025 |
| 511 | 4-(3,3-Difluoroazetidin-1-yl)-2-[[1-[3-(difluoromethoxy)-4-fluoro-phenyl]triazol-4-yl]methoxy]pyrimidine; | 0.041 |
| 512 | (R)-2-[[1-[3-(Difluoromethoxy)-4-fluoro-phenyl]triazol-4-yl]methoxy]-4-[(3R)-3-fluoropyrrolidin-1-yl]pyrimidine; | 0.308 |
| 513 | 5-Chloro-2-[[1-[3-(difluoromethoxy)-4-fluoro-phenyl]triazol-4-yl]methoxy]-4-methyl-pyrimidine; | 0.004 |
| 514 | 2-[[1-[3-(Difluoromethoxy)-4-fluoro-phenyl]triazol-4-yl]methoxy]-5-methyl-pyrimidin-4-amine; | 0.005 |
| 515 | 2-[[1-[3-(Difluoromethoxy)-4-fluoro-phenyl]triazol-4-yl]methoxy]-N,5-dimethyl-pyrimidin-4-amine; | 0.099 |
| 516 | 2-[[1-[3-(Difluoromethoxy)-4-fluoro-phenyl]triazol-4-yl]methoxy]-N,N,5-trimethyl-pyrimidin-4-amine; | 0.017 |
| 517 | N-(2,2-Difluoroethyl)-2-[[1-[3-(difluoromethoxy)-4-fluoro-phenyl]triazol-4-yl]methoxy]-5-fluoro-pyrimidin-4-amine; | 0.912 |
| 518 | 2-[[1-[3-(Difluoromethoxy)-4-fluoro-phenyl]triazol-4-yl]methoxy]-5-fluoro-N-methyl-pyrimidin-4-amine; | 0.092 |
| 519 | N-Cyclopropyl-2-((1-(3-(difluoromethoxy)-4-fluorophenyl)-1H-1,2,3-triazol-4-yl)methoxy)-5-fluoropyrimidin-4-amine; | 0.204 |
| 520 | 1-(2-((1-(3-(Difluoromethoxy)-4-fluorophenyl)-1H-1,2,3-triazol-4-yl)methoxy)pyrimidin-4-yl)-N-methylmethanamine; | 0.672 |
| 521 | 2-[[1-[3-(Difluoromethoxy)-4-methyl-phenyl]triazol-4-yl]methoxy]-5-methyl-pyrimidin-4-amine; | 0.021 |
| 522 | 1-[2-[[1-[3-(Difluoromethoxy)-4-methyl-phenyl]triazol-4-yl]methoxy]pyrimidin-5-yl]ethanone; | 0.093 |
| 523 | 2-[[1-[3-(Difluoromethoxy)-4-methyl-phenyl]triazol-4-yl]methoxy]-4-methyl-pyrimidine; | 0.114 |
| 524 | 2-[[1-[3-(Difluoromethoxy)-4-methyl-phenyl]triazol-4-yl]methoxy]-5-methyl-pyrimidine; | 0.028 |
| 525 | 5-Bromo-2[[1-[3-(difluoromethoxy)-4-methyl-phenyl]triazol-4-yl]methoxy]pyrimidine; | 0.040 |
| 526 | 2-[2-[[1-[3-(Difluoromethoxy)-4-methyl-phenyl]triazol-4-yl]methoxy]pyrimidin-5-yl]propan-2-ol; | 0.425 |
| 527 | 2-[[1-[3-(Difluoromethoxy)-4-methyl-phenyl]triazol-4-yl]methoxy]-4-(methoxymethyl)pyrimidine; | 0.132 |
| 528 | 2-[[1-[3-(Difluoromethyl)phenyl]-5-methyl-triazol-4-yl]methoxy]-4,5-dimethyl-pyrimidine; | 0.752 |
| 529 | 5-Chloro-2-[[1-[3-(difluoromethyl)phenyl]-5-methyl-triazol-4-yl]methoxy]pyrimidine; | 1.320 |
| 530 | 2-[[1-[4-Chloro-3-(1,1-difluoroethyl)phenyl]triazol-4-yl]methoxy]-5-methyl-pyrimidine; | 0.005 |
| 531 | 2-[[1-[4-Chloro-3-(1,1-difluoroethyl)phenyl]triazol-4-yl]methoxy]-4-methyl-pyrimidine; | 0.017 |
| 532 | 2-[2-[[1-[4-Chloro-3-(1,1-difluoroethyl)phenyl]triazol-4-yl]methoxy]pyrimidin-5-yl]propan-2-ol; | 0.081 |
| 533 | [2-[[1-[4-Chloro-3-(1,1-difluoroethyl)phenyl]triazol-4-yl]methoxy]pyrimidin-5-yl]methanol; | 0.017 |
| 534 | 2-[[1-[4-Chloro-3-(1,1-difluoroethyl)phenyl]triazol-4-yl]methoxy]-4-(methoxymethyl)pyrimidine; | 0.003 |
| 535 | 2-[[1-[4-Chloro-3-(1,1-difluoroethyl)phenyl]triazol-4-yl]methoxy]-5-(difluoromethyl)pyrimidine; | 0.009 |
| 536 | 2-[[1-[4-Chloro-3-(1,1-difluoroethyl)phenyl]triazol-4-yl]methoxy]-4-(difluoromethyl)pyrimidine; | 0.067 |
| 537 | 2-[[1-[4-Chloro-3-(1,1-difluoroethyl)phenyl]triazol-4-yl]methoxy]-5-(trifluoromethyl)pyrimidine; | 0.016 |
| 538 | 2-[[1-[4-Chloro-3-(1,1-difluoroethyl)phenyl]triazol-4-yl]methoxy]-4-(trifluoromethyl)pyrimidine; | 0.318 |
| 539 | (R/S)-2-[2-[[1-[4-Chloro-3-(1,1-difluoroethyl)phenyl]triazol-4-yl]methoxy]pyrimidin-5-yl]-1,1,1-trifluoro-propan-2-ol; | 0.450 |
| 540 | [2-[[1-[4-Chloro-3-(1,1-difluoroethyl)phenyl]triazol-4-yl]methoxy]pyrimidin-4-yl]methanol; | 0.019 |
| 541 | 2-[[1-[4-Chloro-3-(1,1-difluoroethyl)phenyl]triazol-4-yl]methoxy]-4-methoxy-pyrimidine; | 0.012 |
| 542 | 2-[[1-[4-Chloro-3-(1,1-difluoroethyl)phenyl]triazol-4-yl]methoxy]-5-(difluoromethoxy)pyrimidine; | 0.012 |
| 543 | 5-Chloro-2-[[1-[4-chloro-3-(1,1-difluoroethyl)phenyl]triazol-4-yl]methoxy]-4-methyl-pyrimidine; | 0.015 |
| 544 | 2-[[1-[4-Chloro-3-(1,1-difluoroethyl)phenyl]triazol-4-yl]methoxy]-5-fluoro-4-methyl-pyrimidine; | 0.015 |
| 545 | 2-[[1-[4-Chloro-3-(1,1-difluoroethyl)phenyl]triazol-4-yl]methoxy]-4,5-dimethyl-pyrimidine; | 0.006 |
| 546 | 2-[[1-[4-Chloro-3-(1,1-difluoroethyl)phenyl]triazol-4-yl]methoxy]-4,6-dimethyl-pyrimidine; | 0.024 |
| 547 | 2-[[1-[4-Chloro-3-(1,1-difluoroethyl)phenyl]triazol-4-yl]methoxy]pyrimidin-4-amine; | 0.033 |
| 548 | 2-[[1-[4-Chloro-3-(1,1-difluoroethyl)phenyl]triazol-4-yl]methoxy]-N-methyl-pyrimidin-4-amine; | 0.055 |
| 549 | 2-[[1-[4-Chloro-3-(1,1-difluoroethyl)phenyl]triazol-4-yl]methoxy]-5-fluoro-N-methyl-pyrimidin-4-amine; | 0.094 |
| 550 | 1-[2-[[1-[4-Chloro-3-(1,1-difluoroethyl)phenyl]triazol-4-yl]methoxy]pyrimidin-5-yl]ethanone; | 0.016 |
| 551 | (R/S)-1-[2-[[1-[4-Chloro-3-(1,1-difluoroethyl)phenyl]triazol-4-yl]methoxy]pyrimidin-5-yl]ethanol; | 0.014 |
| 552 | 2-[[1-[4-Chloro-3-(1,1-difluoroethyl)phenyl]triazol-4-yl]methoxy]-5-cyclopropyl-pyrimidine; | 0.086 |

TABLE 5-continued

| Ex #. | Compound Name | NR2B IC$_{50}$ (µM) standard assay |
|---|---|---|
| 553 | 2-[[1-[4-Chloro-3-(1,1-difluoroethyl)phenyl]triazol-4-yl]methoxy]-4-pyrrolidin-1-yl-pyrimidine; | 0.043 |
| 554 | 2-[[1-[3-(1,1-Difluoroethyl)-4-fluoro-phenyl]triazol-4-yl]methoxy]pyridine; | 1.640 |
| 555 | 2-[[1-[3-[1,1-Difluoroethyl)-4-fluoro-phenyl]triazol-4-yl]methoxy]-3-fluoro-pyridine; | 0.265 |
| 556 | 2-[[1-[3-[1,1-Difluoroethyl)-4-fluoro-phenyl]triazol-4-yl]methoxy]-6-methyl-pyridine; | 0.098 |
| 557 | 2-[[1-[3-[1,1-Difluoroethyl)-4-fluoro-phenyl]triazol-4-yl]methoxy]-4-methyl-pyridine; | 0.246 |
| 558 | 2-[[1-[3-[1,1-Difluoroethyl)-4-fluoro-phenyl]triazol-4-yl]methoxy]-5-methyl-pyridine; | 0.125 |
| 559 | 2-[[1-[3-[1,1-Difluoroethyl)-4-fluoro-phenyl]triazol-4-yl]methoxy]-5-(trifluoromethyl)pyridine; | 0.812 |
| 560 | 6-[[1-[3-(1,1-Difluoroethyl)-4-fluoro-phenyl]triazol-4-yl]methoxy]-2,3-dimethyl-pyridine; | 0.052 |
| 561 | 3-[[1-[3-(1,1-Difluoroethyl)-4-fluoro-phenyl]triazol-4-yl]methoxy]-2-methoxy-pyridine; | 0.476 |
| 562 | 2-[[1-[3-(1,1-Difluoroethyl)-4-fluoro-phenyl]triazol-4-yl]methoxy]-5-(difluoromethyl)pyrimidine; | 0.014 |
| 563 | 2-[[1-[3-(1,1-Difluoroethyl)-4-fluoro-phenyl]triazol-4-yl]methoxy]-4-(difluoromethyl)pyrimidine; | 0.048 |
| 564 | 2-[[1-[3-(1,1-Difluoroethyl)-4-fluoro-phenyl]triazol-4-yl]methoxy]-4-(trifluoromethyl)pyrimidine; | 0.272 |
| 565 | (R/S)-2-[2-[1-[3-(1,1-Difluoroethyl)-4-fluoro-phenyl]triazol-4-yl]methoxy]pyrimidin-5-yl]-1,1,1-trifluoro-propan-2-ol; | 0.308 |
| 566 | 2-[2-[[1-[3-(1,1-Difluoroethyl)-4-fluoro-phenyl]triazol-4-yl]methoxy]pyrimidin-5-yl]propan-2-ol; | 0.008 |
| 567 | 2-[[1-[3-(1,1-Difluoroethyl)-4-fluoro-phenyl]triazol-4-yl]methoxy]-5-(1-methoxy-1-methyl-ethyl)pyrimidine; | 4.630 |
| 568 | [2-[[1-[3-(1,1-Difluoroethyl)-4-fluoro-phenyl]triazol-4-yl]methoxy]pyrimidin-4-yl]methanol; | 0.025 |
| 569 | 2-[[1-[3-(1,1-Difluoroethyl)-4-fluoro-phenyl]triazol-4-yl]methoxy]-5-(methoxymethyl)pyrimidine; | 0.089 |
| 570 | 2-[[1-[3-(1,1-Difluoroethyl)-4-fluoro-phenyl]triazol-4-yl]methoxy]-4-(methoxymethyl)pyrimidine; | 0.011 |
| 571 | [2-[[1-[3-(1,1-difluoroethyl)-4-fluoro-phenyl]triazol-4-yl]methoxy]pyrimidin-5-yl]methanol; | 0.021 |
| 572 | 2-[[1-[3-(1,1-Difluoroethyl)-4-fluoro-phenyl]triazol-4-yl]methoxy]-5-(difluoromethoxy)pyrimidine; | 0.025 |
| 573 | 2-[[1-[3-(1,1-Difluoroethyl)-4-fluoro-phenyl]triazol-4-yl]methoxy]-4,5-dimethyl-pyrimidine; | 0.019 |
| 574 | 5-Chloro-2-[[1-[3-(1,1-difluoroethyl)-4-fluoro-phenyl]triazol-4-yl]methoxy]-4-methyl-pyrimidine; | 0.010 |
| 575 | 2-[[1-[3-(1,1-Difluoroethyl)-4-fluoro-phenyl]triazol-4-yl]methoxy]-5-fluoro-4-methyl-pyrimidine; | 0.006 |
| 576 | 2-[[1-[3-(1,1-Difluoroethyl)-4-fluoro-phenyl]triazol-4-yl]methoxy]-5-methyl-pyrimidin-4-amine; | 0.017 |
| 577 | 2-[[1-[3-(1,1-Difluoroethyl)-4-fluoro-phenyl]triazol-4-yl]methoxy]-N,5-dimethyl-pyrimidin-4-amine; | 0.128 |
| 578 | 2-[[1-[3-(1,1-Difluoroethyl)-4-fluoro-phenyl]triazol-4-yl]methoxy]-5-fluoro-N-methyl-pyrimidin-4-amine; | 0.140 |
| 579 | 2-[[1-[3-(1,1-Difluoroethyl)-4-fluoro-phenyl]triazol-4-yl]methoxy]-N,N,5-trimethyl-pyrimidin-4-amine; | 0.087 |
| 580 | 2-[[1-[3-(1,1-Difluoroethyl)-4-fluoro-phenyl]triazol-4-yl]methoxy]pyrimidin-4-amine; | 0.088 |
| 581 | 2-[[1-3-(1,1-Difluoroethyl)-4-fluoro-phenyl]triazol-4-yl]methoxy]-N-methyl-pyrimidin-4-amine; | 0.033 |
| 582 | 2-[[1-3-(1,1-Difluoroethyl)-4-fluoro-phenyl]triazol-4-yl]methoxy]-N,N-dimethyl-pyrimidin-4-amine; | 0.028 |
| 583 | 2-[[1-[3-(1,1-Difluoroethyl)-4-fluoro-phenyl]triazol-4-yl]methoxy]pyrimidine-5-carbonitrile; | 0.067 |
| 584 | 2-[[1-[3-(1,1-Difluoroethyl)-4-fluoro-phenyl]triazol-4-yl]methoxy]-5-methylsulfonyl-pyrimidine; | 0.199 |
| 585 | 1-[2-[[1-[3-(1,1-Difluoroethyl)-4-fluoro-phenyl]triazol-4-yl]methoxy]pyrimidin-5-yl]ethanone; | 0.011 |
| 586 | (R/S)-1-[2-[[1-[3-(1,1-Difluoroethyl)-4-fluoro-phenyl]triazol-4-yl]methoxy]pyrimidin-5-yl]ethanol; | 0.014 |
| 587 | 5-Cyclopropyl-2-[[1-[3-(1,1-difluoroethyl)-4-fluoro-phenyl]triazol-4-yl]methoxy]pyrimidine; | 0.041 |
| 588 | 5-(Azetidin-1-yl)-2-[[1-[3-(1,1-difluoroethyl)-4-fluoro-phenyl]triazol-4-yl]methoxy]pyrimidine; | 0.034 |
| 589 | 2-((1-(3-(1,1-Difluoroethyl)-4-fluorophenyl)-1H-1,2,3-triazol-4-yl)methoxy)-5-(3-fluoroazetidin-1-yl)pyrimidine; | 0.013 |
| 590 | 2-((1-(3-(1,1-Difluoroethyl)-4-fluorophenyl)-1H-1,2,3-triazol-4-yl)methoxy)-N,N-dimethylpyrimidin-5-amine; | 0.039 |
| 591 | 2-[[1-[3-(1,1-Difluoroethyl)-4-fluoro-phenyl]triazol-4-yl]methoxy]-4-pyrrolidin-1-yl-pyrimidine; | 0.016 |
| 592 | 2-[[1-[3-(1,1-Difluoroethyl)-4-fluoro-phenyl]triazol-4-yl]methoxy]-4-(1-piperidyl)pyrimidine; | 0.271 |
| 593 | 2-[[1-[3-(1,1-Difluoroethyl)-4-fluoro-phenyl]-5-methyl-triazol-4-yl]methoxy]-5-ethyl-pyrimidine; | 0.486 |
| 594 | 5-Cyclopropyl-2-[[1-[3-(1,1-difluoroethyl)-4-fluoro-phenyl]-5-methyl-triazol-4-yl]methoxy]pyrimidine; | 0.171 |
| 595 | 2-[[1-[3-(1,1-Difluoroethyl)-4-fluoro-phenyl]-5-methyl-triazol-4-yl]methoxy]-4,5-dimethyl-pyrimidine; | 0.706 |
| 596 | 5-Chloro-2-[[1-[3-(1,1-difluoroethyl)-4-fluoro-phenyl]-5-methyl-triazol-4-yl]methoxy]-4-methyl-pyrimidine; | 0.601 |
| 597 | 2-[[1-(3,4-Difluorophenyl)triazol-4-yl]methoxy]pyrimidine; | 2.100 |
| 598 | 2-[[1-(3,4-Difluorophenyl)triazol-4-yl]methoxy]-5-fluoro-pyrimidine; | 1.450 |
| 599 | 2-[[1-(3,4-Difluorophenyl)triazol-4-yl]methoxy]-5-methoxy-pyrimidine; | 0.034 |
| 600 | 5-Chloro-2-[[1-(3,4-difluorophenyl)triazol-4-yl]methoxy]pyridine; | 0.238 |
| 601 | 2-[[1-(3,4-Difluorophenyl)triazol-4-yl]methoxy]-5-methyl-pyrimidine; | 0.048 |
| 602 | 2-[[1-(3,4-Difluorophenyl)triazol-4-yl]methoxy]-5-ethyl-pyrimidine; | 0.023 |
| 603 | 2-[[1-(2,5-Difluorophenyl)triazol-4-yl]methoxy]-5-methyl-pyrimidine; | 10.430 |
| 604 | 2-[2-[[1-(2,5-Difluoropheny)triazol-4-yl]methoxy]pyrimidin-5-yl]propan-2-ol; | 79.708 |
| 605 | 5-Chloro-2-[[1-(2,3-difluorophenyl)triazol-4-yl]methoxy]pyridine; | 4.360 |
| 606 | 2-[[1-(2,3-Difluorophenyl)triazol-4-yl]methoxy]-5-fluoro-pyrimidine; | 17.499 |
| 607 | 2-[[1-(2,3-Difluorophenyl)triazol-4-yl]methoxy]pyrimidine; | 3.425 |
| 608 | 2-[2-[[1-(2,3-Difluoropheny])triazol-4-yl]methoxy]pyrimidin-5-yl]propan-2-ol; | >10 |
| 609 | 2-[[1-(2,3-Difluorophenyl)triazol-4-yl]methoxy]-5-fluoro-4-methyl-pyrimidine; | 15,900 |
| 610 | 2-[[1-(3-Chloro-2-fluoro-phenyl)triazol-4-yl]methoxy]-5-methyl-pyrimidine; | 1.034 |
| 611 | 2-[[1-(3-Chloro-2-fluoro-phenyl)triazol-4-yl]methoxy]pyrimidine; | >10 |
| 612 | 5-Chloro-2-[[1-(3-chloro-2-fluoro-phenyl)triazol-4-yl]methoxy]pyrimidine; | 1.737 |
| 613 | 2-[[1-(3-Chloro-2-fluoro-phenyl)triazol-4-yl]methoxy]-5-fluoro-4-methyl-pyrimidine; | 1.441 |
| 614 | 2-[[1-(3-Chloro-2-fluoro-phenyl)triazol-4-yl]methoxy]-5-fluoro-pyrimidine; | 4.032 |
| 615 | 2-[2-[[1-(3-Chloro-2-fluoro-phenyl)triazol-4-yl]methoxy]pyrimidin-5-yl]propan-2-ol; | 4.658 |
| 616 | [2-[[1-(3-Bromo-4-fluoro-phenyl)triazol-4-yl]methoxy]pyrimidin-5-yl]methanol; | 0.030 |
| 617 | [2-[[1-(3-Bromo-4-fluoro-phenyl)triazol-4-yl]methoxy]pyrimidin-4-yl]methanol; | 0.041 |
| 618 | 2-[[1-(3-Bromo-4-fluoro-phenyl)triazol-4yl]methoxy]-5-(2-fluoroethoxy)pyrimidine; | 0.006 |
| 619 | 2-[[1-(3-Chloro-4-fluoro-phenyl)triazol-4-yl]methoxy]pyrimidine; | 0.217 |
| 620 | 2-[[1-(3-Chloro-4-fluoro-phenyl)triazol-4-yl]methoxy]-5-methyl-pyrimidine; | 0.008 |
| 621 | 2-[[1-(3-Chloro-4-fluoro-phenyl)triazol-4-yl]methoxy]-5-ethyl-pyrimidine; | 0.003 |
| 622 | 2-[[1-(3-Chloro-4-fluoro-phenyl)triazol-4-yl]methoxy]-4-(methoxymethyl)pyrimidine; | 0.066 |
| 623 | 2-[[1-[4-Chloro-3-(difluoromethyl)phenyl]triazol-4-yl]methoxy]-4-isopropyl-pyrimidine; | 0.129 |
| 624 | [2-[[1-[4-Chloro-3-(difluoromethyl)phenyl]triazol-4-yl]methoxy]pyrimidin-5-yl]methanol; | 0.020 |

TABLE 5-continued

| Ex #. | Compound Name | NR2B IC$_{50}$ (µM) standard assay |
|---|---|---|
| 625 | [2-[[1-[4-Chloro-3-(difluoromethyl)phenyl]triazol-4-yl]methoxy]pyrimidin-4-yl]methanol; | 0.017 |
| 626 | 2-[2-[[1-[4-Chloro-3-(difluoromethyl)phenyl]triazol-4-yl]methoxy]pyrimidin-5-yl]propan-2-ol; | 0.067 |
| 627 | 2-[[1-[4-Chloro-3-(difluoromethyl)phenyl]triazol-4-yl]methoxy]-4-(methoxymethyl)pyrimidine; | 0.038 |
| 628 | 2-[[1-[4-Chloro-3-(difluoromethyl)phenyl]triazol-4-yl]methoxy]-4-(difluoromethyl)pyrimidine; | 0.042 |
| 629 | 2-[[1-[4-Chloro-3-(difluoromethyl)phenyl]triazol-4-yl]methoxy]-N,N-dimethyl-pyrimidin-4-amine; | 0.007 |
| 630 | 2-[[1-[4-Chloro-3-(difluoromethyl)phenyl]triazol-4-yl]methoxy]-5-cyclopropyl-pyrimidine; | 0.013 |
| 631 | 2-[[1-[4-Chloro-3-(difluoromethyl)phenyl]triazol-4-yl]methoxy]-4-cyclopropyl-pyrimidine; | 0.042 |
| 632 | 2-[[1-[4-chloro-3-(difluoromethyl)phenyl]triazol-4-yl]methoxy]-5-methyl-pyrimidin-4-amine; | 0.004 |
| 633 | 2-[[1-[4-Chloro-3-(duoromethyl)phenyl]triazol-4-yl]methoxy]-N,N,5-trimethyl-pyrimidin-4-amine; | 0.057 |
| 634 | 2-[[1-[4-Chloro-3-(difluoromethyl)phenyl]triazol-4-yl]methoxy]-4-pyrrolidin-1-yl-pyrimidine; | 0.012 |
| 635 | 2-[[1-[4-Chloro-3-(difluoromethyl)phenyl]triazol-4-yl]methoxy]-4-(1-piperidyl)pyrimidine; | 0.169 |
| 636 | 2-[[1-[4-Chloro-3-(difluoromethyl)phenyl]triazol-4-yl]methoxy]-5-(2-fluoroethoxy)pyrimidine; | 0.010 |
| 637 | 2-[[1-[4-Chloro-3-(difluoromethyl)phenyl]triazol-4-yl]methoxy]-5-(3-fluoropropyl)pyrimidine; | 0.011 |
| 638 | 2-((1-(4-(Azetidin-1-yl)-3-(difluoromethyl)phenyl)-1H-1,2,3-triazol-4-yl)methoxy)-5-methylpyrimidine; | 0.511 |
| 639 | 2-[[1-(2,4-Difluoro-3-methyl-phenyl)triazol-4-yl]methoxy]-5-isopropyl-pyrimidine; | 0.052 |
| 640 | 2-[[1-(2,4-Difluoro-3-methyl-phenyl)triazol-4-yl]methoxy]-4-isopropyl-pyrimidine; | 1.980 |
| 641 | 5-(Difluoromethyl)-2-[[1-(2,4-difluoro-3-methyl-phenyl)triazol-4-yl]methoxy]pyrimidine; | 0.111 |
| 642 | 4-(Difluoromethyl)-2-[[1-(2,4-difluoro-3-methyl-phenyl)triazol-4-yl]methoxy]pyrimidine; | 2.210 |
| 643 | 2-[[1-(2,4-Difluoro-3-methyl-phenyl)triazol-4-yl]methoxy]-5-(trifluoromethyl)pyrimidine; | 0.200 |
| 644 | 2-[2-[[1-(2,4-Difluoro-3-methyl-phenyl)triazol-4-yl]methoxy]pyrimidin-5-yl]propan-2-ol; | 0.967 |
| 645 | 2-[[1-(2,4-Difluoro-3-methyl-phenyl)triazol-4-yl]methoxy]-4-(methoxymethyl)pyrimidine; | 0.799 |
| 646 | 5-(Difluoromethoxy)-2-[[1-(2,4-difluoro-3-methyl-phenyl)triazol-4-yl]methoxy]pyrimidine; | 0.099 |
| 647 | 5-Cyclopropyl-2-[[1-(2,4-difluoro-3-methyl-phenyl)triazol-4-yl]methoxy]pyrimidine; | 0.034 |
| 648 | 4-Cyclopropyl-2-[[1-(2,4-difluoro-3-methyl-phenyl)triazol-4-yl]methoxy]pyrimidine; | 0.592 |
| 649 | 2-[[1-(2,4-Difluoro-3-methyl-phenyl)triazol-4-yl]methoxy]-5-fluoro-4-methyl-pyrimidine; | 0.152 |
| 650 | 5-Chloro-2-[[1-(2,4-difluoro-3-methyl-phenyl)triazol-4-yl]methoxy]-4-methyl-pyrimidine; | 0.005 |
| 651 | 2-[[1-(2,4-Difluoro-3-methyl-phenyl)triazol-4-yl]methoxy]-5-methyl-pyrimidin-4-amine; | 0.262 |
| 652 | 2-[[1-[3-(Difluoromethyl)-2,4-difluoro-phenyl]triazol-4-yl]methoxy]-5-(trifluoromethyl)pyrimidine; | 0.112 |
| 653 | 5-Chloro-2-[[1-(2,4-difluoro-5-methyl-phenyl)triazol-4-yl]methoxy]pyrimidine; | 1.490 |
| 654 | 2-[[1-(2,4-Difluoro-5-methyl-phenyl)triazol-4-yl]methoxy]-5-methyl-pyrimidine; | 0.979 |
| 655 | 2-[[1-(2,4-Difluoro-5-methyl-phenyl)triazol-4-yl]methoxy]-5-ethyl-pyrimidine; | 0.507 |
| 656 | 5-(Difluoromethyl)-2-[[1-(2,4-difluoro-5-methyl-phenyl)triazol-4-yl]methoxy]pyrimidine; | 1.510 |
| 657 | 5-Chloro-2[[1-(2,4-difluoro-5-methyl-phenyl)triazol-4-yl]methoxy]-4-methyl-pyrimidine; | 0.781 |
| 658 | 5-Cyclopropyl-2-[[1-(2,4-difluoro-5-methyl-phenyl)triazol-4-yl]methoxy]pyrimidine; | 0.424 |
| 659 | 5-Chloro-2[[1-(6-methyl-2-pyridyl)triazol-4-yl]methoxy]pyrimidine; | >2.99 |
| 660 | 5-Ethyl-2-[[1-(6-methyl-2-pyridyl)triazol-4-yl]methoxy]pyrimidine; | >2.99 |
| 661 | 5-Chloro-4-methyl-2-[[1-(6-methyl-2-pyridyl)triazol-4-yl]methoxy]pyrimidine; | >2.99 |
| 662 | 5-Methyl-2-[[1-(4-methyl-2-pyridyl)triazol-4-yl]methoxy]pyrimidine; | >2.99 |
| 663 | 5-Ethyl-2-[[1-(4-methyl-2-pyridyl)triazol-4-yl]methoxy]pyrimidine; | 2.450 |
| 664 | 5-Ethyl-2-[[1-(2-methyl-4-pyridyl)triazol-4-yl]methoxy]pyrimidine; | 0.169 |
| 665 | 2-[[1-(2-Bromo-4-pyridyl)triazol-4-yl]methoxy]-5-ethyl-pyrimidine; | 0.261 |
| 666 | 5-Methyl-2-[[1-[2-(trifluoromethyl)-4-pyridyl]triazol-4-yl]methoxy]pyrimidine; | 0.668 |
| 667 | 5-Ethyl-2-[[1-[2-(trifluoromethyl)-4-pyridyl]triazol-4-yl]methoxy]pyrimidine; | 0.184 |
| 668 | 5-Fluoro-4-methyl-2-((1-(5-(trifluoromethyl)thiophen-2-yl)-1H-1,2,3-triazol-4-yl)methoxy)pyrimidine; | 0.008 |
| 669 | 5-Methoxy-2-((1-(5-(trifluoromethyl)thiophen-2-yl)-1H-1,2,3-triazol-4-yl)methoxy)pyrimidine; | 0.004 |
| 670 | 5-(Trifluoromethyl)-2-((1-(5-(trifluoromethyl)thiophen-2-yl)-1H-1,2,3-triazol-4-yl)methoxy)pyrimidine; | 0.063 |
| 671 | 2-((1-(3-(Difluoromethoxy)-4-fluorophenyl)-1H-1,2,3-triazol-4-yl)methoxy)-N-(oxetan-3-yl)pyrimidin-4-amine; | 0.126 |
| 672 | 5-(Azetidin-1-yl)-2-((1-(3-(difluoromethoxy)-4-fluorophenyl)-1H-1,2,3-triazol-4-yl)methoxy)pyridine; | NT |
| 673 | 2-((1-(3-(Difluoromethoxy)-4-fluorophenyl)-1H-1,2,3-triazol-4-yl)methoxy)-5-(3-fluoroazetidin-1-yl)pyridine; | NT |
| 674 | 5-(3,3-Difluoroazetidin-1-yl)-2-((1-(3-(difluoromethoxy)-4-fluorophenyl)-1H-1,2,3-triazol-4-yl)methoxy)pyridine; | NT |
| 675 | 2-(Azetidin-1-yl)-6-((1-(3-(difluoromethoxy)-4-fluorophenyl)-1H-1,2,3-triazol-4-yl)methoxy)pyridine; | NT |
| 676 | 2-((1-(3-(Difluoromethoxy)-4-fluorophenyl)-1H-1,2,3-triazol-4-yl)methoxy)-6-(3-fluoroazetidin-1-yl)pyridine; | NT |
| 677 | 2-3,3-Difluoroazetidin-1-yl)-6-((1-(3-(difluoromethoxy)-4-fluorophenyl)-1H-1,2,3-triazol-4-yl)methoxy)pyridine; | NT |
| 678 | 4-(Azetidin-1-yl)-2-((1-(3-(difluoromethoxy)-4-fluorophenyl)-1H-1,2,3-triazol-4-yl)methoxy)pyridine; | NT |
| 679 | 2-((1-(3-(Difluoromethoxy)-4-fluorophenyl)-1H-1,2,3-triazol-4-yl)methoxy)-4-(3-fluoroazetidin-1-yl)pyridine; | NT |
| 680 | 4-(3,3-Difluoroazetidin-1-yl)-2-((1-(3-(difluoromethoxy)-4-fluorophenyl)-1H-1,2,3-triazol-4-yl)methoxy)pyridine; | NT |
| 681 | 2-((1-(3-(Difluoromethoxy)-4-fluorophenyl)-1H-1,2,3-triazol-4-yl)methoxy)-4-(1H-pyrrol-2-yl)pyrimidine; | 0.681 |
| 682 | 2-((1-(3-(Difluoromethoxy)-4-fluorophenyl)-1H-1,2,3-triazol-4-yl)methoxy)-4-(1H-pyrazol-5-yl)pyrimidine; | NT |
| 683 | 2-((1-(3-(Difluoromethoxy)-4-fluorophenyl)-1H-1,2,3-triazol-4-yl)methoxy)-5-(1H-pyrrol-2-yl)pyrimidine; | NT |
| 684 | 2-((1-(3-(Difluoromethoxy)-4-fluorophenyl)-1H-1,2,3-triazol-4-yl)methoxy)-5-(1H-pyrazol-5-yl)pyrimidine; | NT |
| 685 | 2-((1-(3-(Difluoromethoxy)-4-fluorophenyl)-1H-1,2,3-triazol-4-yl)methoxy)-N-ethyl-5-fluoropyrimidin-4-amine; | NT |
| 686 | 2-((1-(3-(Difluoromethoxy)-4-fluorophenyl)-1H-1,2,3-triazol-4-yl)methoxy)-5-fluoro-N-(oxetan-3-yl)pyrimidin-4-amine; | NT |
| 687 | N-(3,3-Difluorocyclobutyl)-2-((1-(3-(difluoromethoxy)-4-fluorophenyl)-1H-1,2,3-triazol-4-yl)methoxy)-5-fluoropyrimidin-4-amine; | NT |
| 688 | N-Cyclopropyl-2-((1-(3-(difluoromethoxy)-4-fluorophenyl)-1H-1,2,3-triazol-4-yl)methoxy)pyrimidin-4-amine; | NT |
| 689 | N-(3,3-Difluorocyclobutyl)-2-((1-(3-(difluoromethoxy)-4-fluorophenyl)-1H-1,2,3-triazol-4-yl)methoxy)pyrimidin-4-amine; | NT |
| 690 | N-Cyclopropyl-2-((1-(3-(difluoromethyl)-4-fluorophenyl)-1H-1,2,3-triazol-4-yl)methoxy)pyrimidin-4-amine; | 0.008 |
| 691 | N-Ethyl-2-((1-(3-(difluoromethyl)-4-fluorophenyl)-1H-1,2,3-triazol-4-yl)methoxy)pyrimidin-4-amine; | 0.006 |
| 692 | 2-((1-(3-(Difluoromethyl)-4-fluorophenyl)-1H-1,2,3-triazol-4-yl)methoxy)-4-(2-methyl-1H-imidazol-1-yl)pyrimidine; | 1.580 |

TABLE 5-continued

| Ex #. | Compound Name | NR2B IC$_{50}$ (µM) standard assay |
|---|---|---|
| 693 | 2-((1-(3-(Difluoromethyl)-4-fluorophenyl)-1H-1,2,3-triazol-4-yl)methoxy)-5-(2-methyl-1H-imidazol-1-yl)pyrimidine; | NT |
| 694 | 2-((1-(3-(Difluoromethyl)-4-fluorophenyl)-1H-1,2,3-triazol-4-yl)methoxy)-5(1H-pyrazol-5-yl)pyrimidine; | NT |
| 695 | 2-((1-(3-(Difluoromethyl)-4-fluorophenyl)-1H-1,2,3-triazol-4-yl)methoxy)-4-(1H-pyrazol-5-yl)pyrimidine; | NT |
| 696 | 4-(1,1-Difluoroethyl)-2-((1-(3-(difluoromethyl)-4-fluorophenyl)-1H-1,2,3-triazol-4-yl)methoxy)pyrimidine; | 0.958 |
| 697 | 4-((Difluoromethoxy)methyl)-2-((1-(3-(difluoromethyl)-4-fluorophenyl)-1H-1,2,3-triazol-4-yl)methoxy)pyrimidine; | NT |
| 698 | 2-((1-(3-(Difluoromethyl)-4-fluorophenyl)-1H-1,2,3-triazol-4-yl)methoxy)-5-(1H-pyrazol-1-yl)pyrimidine; | NT |
| 699 | 2-((1-(3-(Difluoromethyl)-4-fluorophenyl)-1H-1,2,3-triazol-4-yl)methoxy)-4-(1H-pyrazol-1-yl)pyrimidine; | 0.389 |
| 700 | (E)-1-(2-((1-(3-(Difluoromethyl)-4-fluorophenyl)-1H-1,2,3-triazol-4-yl)methoxy)pyrimidin-5-yl)ethan-1-one oxime; | NT |
| 701 | 5-(1,1-Difluoroethyl)-2-((1-(3-(difluoromethyl)-4-fluorophenyl)-1H-1,2,3-triazol-4-yl)methoxy)pyrimidine; | 0.958 |
| 702 | (Z)-1-(2-((1-(3-(Difluoromethyl)-4-fluorophenyl)-1H-1,2,3-triazol-4-yl)methoxy)pyrimidin-4-yl)ethan-1-one oxime; | NT |
| 703 | (2-((1-(3-(Difluoromethoxy)-4-fluorophenyl)-1H-1,2,3-triazol-4-yl)methoxy)-5-fluoropyrimidin-4-yl)methanol; | NT |
| 704 | 2-((1-(3-(Difluoromethoxy)-4-fluorophenyl)-1H-1,2,3-triazol-4-yl)methoxy)-4-((difluoromethoxy)methyl)-5-fluoropyrimidine; | NT |
| 705 | 2-((1-(3-(Difluoromethoxy)-4-fluorophenyl)-1H-1,2,3-triazol-4-yl)methoxy)-4-((difluoromethoxy)methyl)pyrimidine; | NT |
| 706 | 2-((1-(3-(Difluoromethoxy)-4-fluoropheny)-1H-1,2,3-triazol-4-yl)methoxy)-5-fluoro-4-((trifluoromethoxy)methyl)pyrimidine; | NT |
| 707 | 2-((1-(3-(Difluoromethoxy)-4-fluorophenyl)-1H-1,2,3-triazol-4-yl)methoxy)-4-((trifluoromethoxy)methyl)pyrimidine; | NT |
| 708 | 2-((1-(3-(Difluoromethoxy)-4-fluorophenyl)-1H-1,2,3-triazol-4-y)methoxy)-4-(methoxymethyl-d2)pyrimidine; | NT |
| 709 | 2-((1-(3-(Difluoromethoxy)-4-fluoropheny)-1H-1,2,3-triazol-4-yl)methoxy)-4-((methoxy-d3)methyl-d2)pyrimidine; | NT |
| 710 | 2-((1-(3-(Difluoromethoxy)-4-fluorophenyl)-1H-1,2,3-triazol-4-yl)methoxy)-4-((methoxy-d3)methyl)pyrimidine; | NT |
| 711 | 2-((1-(3-(Difluoromethoxy)-4-fluorophenyl)-1H-1,2,3-triazol-4-yl)methoxy)-4-(ethoxymethyl)pyrimidine; | 0.043 |
| 712 | 2-((1-(3-(Difluoromethoxy)-4-fluorophenyl)-1H-1,2,3-triazol-4-yl)methoxy)-4-(1-methoxyethyl)pyrimidine; | NT |
| 713 | 1-(2-((1-(3-(Difluoromethoxy)-4-fluorophenyl)-1H-1,2,3-triazol-4-yl)methoxy)pyrimidin-4-yl)ethan-1-ol; | NT |
| 714 | 2-((1-(3-(Difluoromethoxy)-4-fluorophenyl)-1H-1,2,3-triazol-4-yl)methoxy)-4-(2-methoxypropan-2-yl)pyrimidine; | NT |
| 715 | 2-(2-((1-(3-(Difluoromethoxy)-4-fluorophenyl)-1H-1,2,3-triazol-4-yl)methoxy)pyrimidin-4-yl)propan-2-ol; and | NT |
| 716 | 4-((2,2-Difluoroethoxy)methyl)-2-((1-(3-(difluoromethoxy)-4-fluorophenyl)-1H-1,2,3-triazol-4-yl)methoxy)pyrimidine. | 0.049 |

NT means not tested.

What is claimed:

1. A method of treating a subject suffering from or diagnosed with a disease, disorder, or medical condition mediated by NR2B receptor activity, comprising administering to a subject in need of such treatment an effective amount of at least one compound selected from compounds of Formula (I):

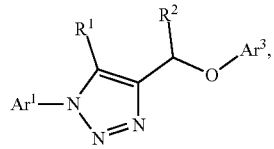

(I)

wherein:
Ar$^1$ is selected from the group consisting of:
  (a) phenyl substituted with one substituent selected from the group consisting of: halo, C$_{1-6}$alkyl, C$_{1-6}$perhaloalkyl, and OC$_{1-6}$perhaloalkyl; phenyl substituted with two or three substituents each independently selected from the group consisting of: halo, C$_{1-6}$alkyl, C$_{1-6}$perhaloalkyl, OC$_{1-6}$alkyl, OC$_{1-6}$perhaloalkyl, C$_{3-6}$-cycloalkyl, and azetidinyl;
  (b) pyridinyl; pyridinyl substituted with one or two members each independently selected from the group consisting of: halo, CH$_3$, CF$_3$, and CF$_2$H; and
  (c) thienyl substituted with CF$_3$; 1-(2,2-difluorobenzo[d][1,3]dioxol-5-yl; or 2,3-dihydro-1H-inden-5-yl;
R$^1$ is H, halo, or CH$_3$;
R$^2$ is H or CH$_3$; and
Ar$^3$ is selected from the group consisting of:
  (a) pyridinyl; pyridinyl substituted with one or two substituents each independently selected from the group consisting of: Cl, F, CH$_3$, OCH$_3$, CF$_3$, C(CH$_3$)$_2$ OH; azetidin-1-yl; 3-fluoroazetidin-1-yl; and 3,3-difluoroazetidin-1-yl;
  (b) pyridazinyl; pyridazinyl substituted with one or two substituents each independently selected from the group consisting of: CH$_3$, OCH$_3$, and CF$_3$;
  (c) pyrimidin-4-yl; pyrimidin-4-yl substituted with one or two substituents each independently selected from the group consisting of: Cl, CH$_3$, CF$_3$, and OCH$_3$; pyrimidin-2-yl; pyrimidin-2-yl substituted one or two members each independently selected from the group consisting of: halo, C$_{1-6}$alkyl, C$_{1-6}$alkyl substituted with OH or OCH$_3$, C(OH)(CH$_3$)(CF$_3$), CH$_2$OCHF$_2$, CH$_2$OCF$_3$, CH$_2$OCH$_2$CH$_3$, CH(NH$_2$)CH$_3$, CH$_2$NH(CH$_3$), C$_{1-6}$perhaloalkyl, OC$_{1-6}$alkyl, OC$_{1-6}$perhaloalkyl, C(=N—OH)(CH$_3$), NH$_2$, NH(CH$_3$), N(CH$_3$)$_2$; NH(CH$_2$CH$_3$), NH(CH$_2$CHF$_2$), NH(cyclopropyl), NH(difluorocyclobutyl), NH-oxetanyl, CN, C(=O)CH$_3$, C(=O)NH(CH$_3$), C(=O)N(CH$_3$)$_2$, SO$_2$CH$_3$, CO$_2$CH$_3$, C(CH$_3$)(=N—OH), cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholinyl, 1H-pyrrol-2-yl, 2-furyl, 1H-pyrazol-4-yl, 1H-pyrazol-5-yl, 1H-pyrazol-1-yl, 2-methyl-1H-imidazol-1-yl, 1-methylpyrazol-3-yl, and phenyl;
  (d) 5-fluoro-pyrazin-2-yl; 5-methylpyrazin-2-yl; 6-methylpyrazin-2-yl; pyrazin-4-yl; (2-thienyl)pyrazin-2-yl, and 2,3-dimethylpyrazin-5-yl; and
  (e) 5-methyl-1H-imidazol-2-yl; 5-methylthiazol-2-yl; and pharmaceutically acceptable salts of compounds of Formula (I).

2. A method of treating a subject suffering from or diagnosed with a disease, disorder, or medical condition mediated by NR2B receptor activity, comprising administering to a subject in need of such treatment an effective amount of at least one compound selected from compounds of Formula (II):

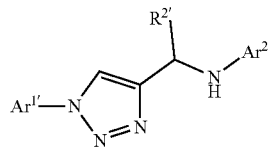

wherein:
$Ar^{1'}$ is phenyl substituted with $C_{1-6}$perhaloalkyl; or phenyl substituted with two substituents each independently selected from the group consisting of: halo, $C_{1-3}$alkyl, $C_{1-6}$perhaloalkyl, and $OC_{1-6}$perhaloalkyl;
$R^{2'}$ is H or $CH_3$; and
$Ar^2$ is selected from the group consisting of:
(a) pyridin-2-yl; pyridazin-3-yl; pyrimidin-4-yl; pyrimidin-2-yl; or pyrimidin-2-yl substituted with one or two substituents each independently selected from the group consisting of halo, $C_{1-3}$alkyl, $C(CH_3)_2$ OH, $C_{1-6}$perhaloalkyl, $OCH_3$, and cyclopropyl; and
(b) 1-methyl-imidazol-2-yl; oxazol-2-yl; 1-methyl-pyrazol-4-yl; 1-methyl-pyrazol-3-yl; or 1-methyl-1H-pyrazol-5-yl;
and pharmaceutically acceptable salts of compounds of Formula (II).

3. The method of claim 1, wherein the disorder, disease or medical condition mediated by NR2B receptor activity is selected from the group consisting of: bipolar disorder, major depressive disorder, treatment-resistant depression, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with bacterial or chronic infections, pain, diabetic neuropathy, migraine, cerebral ischemia, schizophrenia, encephalitis, autism and autism spectrum disorders, memory and learning disorders, obsessive compulsive disorder, attention deficit hyperactivity disorder (ADHD) and addictive illnesses.

4. The method of claim 1, wherein the disorder, disease or medical condition mediated by NR2B receptor activity is selected from the group consisting of treatment resistant depression and major depressive disorder.

5. The method of claim 1, wherein the disorder, disease or medical condition mediated by NR2B receptor activity is a neurologic or psychiatric disorder.

6. The method of claim 5, wherein the neurologic disorder is epilepsy.

7. The method of claim 5, wherein the psychiatric disorder is a mood disorder, treatment-resistant depression or major depressive disorder.

8. The method of claim 1, wherein:
$Ar^1$ is phenyl substituted with two substituents each independently selected from the group consisting of: halo, $C_{1-6}$alkyl, $C_{1-6}$perhaloalkyl, $OC_{1-6}$alkyl, $OC_{1-6}$perhaloalkyl, $C_{3-6}$cycloalkyl, and azetidinyl;
$R^1$ is H, halo, or $CH_3$;
$R^2$ is H or $CH_3$; and
and
$Ar^3$ is pyrimidin-4-yl; pyrimidin-4-yl substituted with one or two substituents each independently selected from the group consisting of: Cl, $CH_3$, $CF_3$, and $OCH_3$; pyrimidin-2-yl; pyrimidin-2-yl substituted one of two members each independently selected from the group consisting of: halo, $C_{1-6}$alkyl, $C_{1-6}$alkyl substituted with OH or $OCH_3$, $C(OH)(CH_3)(CF_3)$, $CH_2OCHF_2$, $CH_2OCF_3$, $CH_2OCH_2CH_3$, $CH(NH_2)CH_3$, $CH_2NH(CH_3)$, $C_{1-6}$perhaloalkyl, $OC_{1-6}$alkyl, $OC_{1-6}$perhaloalkyl, $C(=N-OH)(CH_3)$, $NH_2$, $NH(CH_3)$, $N(CH_3)_2$; $NH(CH_2CH_3)$, $NH(CH_2CHF_2)$, NH(cyclopropyl), NH(difluorocyclobutyl), NH-oxetanyl, CN, $C(=O)CH_3$, $C(=O)NH(CH_3)$, $C(=O)N(CH_3)_2$, $C(CH_3)(=N-OH)$, cyclopropyl, azetidin-1-yl, 3-fluoroazetidin-1-yl, 3,3-difluoroazetidin-1-yl, b 3-(difluoromethyl)azetidin-1-yl, 3-methoxyazetidin-1-yl, 3-fluoro-30methyl-azetidin-yl, pyrrolidin-1-yl, 3-fluoropyrrolidin-1-yl, 3,3-difluoropyrrolidin-1-yl, piperidin-1-yl, morpholinyl, 1H-pyrrol-2-yl, 2-furyl, 1H-pyrazol-4-yl, 1H-pyrazol-5-yl, 1H-pyrazol-1-yl, 2-methyl-1H-imidazol-1-yl, 1-methylpyrazol-3-yl, and phenyl.

9. The method of claim 8, wherein $R^1$ is H, F, I or $CH_3$.
10. The method of claim 8, wherein $R^1$ is H.
11. The method of claim 8, wherein $R^2$ is H.
12. The method of claim 8, wherein $Ar^1$ is phenyl substituted with two substituents each independently selected from the group consisting of: Br, Cl, F, $CH_3$, $CH_2CH_3$, $CH(CH_3)_2$, $CF_3$, $CF_2H$, $CF_2CH_3$, $CH_2CH_2CH_2Cl$, $CH_2CH_2CH_2F$, $OCH_3,OCF_2H$, $OCH_2CH_2F$, cyclopropyl, and azetidin-1-yl.
13. The method of claim 8, wherein $Ar^1$ is 4-chloro-3-(difluoromethoxy)phenyl, 3-(difluoromethyl)-4-fluoro-phenyl, 4-chloro-3-(1,1-difluoroethyl)phenyl, 3-(1,1-difluoroethyl)-4-fluoro-phenyl, 3-(difluoromethoxy)-4-fluoro-phenyl, 4-chloro-3-(difluoromethyl)phenyl, 4-chloro-3-(2-fluoroethoxy)phenyl, 3-(3-chloropropyl)-4-fluoro-phenyl, or 5-(trifluoromethyl)thiophen-2-yl.
14. The method of claim 8, wherein $Ar^3$ is pyrimidin-2-yl; pyrimidin-2-yl substituted one or two member each independently selected from the group consisting of: halo, $C_{1-3}$alkyl, $C_{1-3}$alkyl substituted with OH or $OCH_3$, $C(OH)(CH_3)(CF_3)$, $CH(NH_2)CH_3$, $CH_2NH(CH_3)$, $C_{1-3}$perhaloalkyl, $OC_{1-3}$alkyl, $OC_{1-3}$perhaloalkyl, $NH_2$; $NH(CH_3)$, $N(CH_3)_2$, $NH(CH_2CH_3)$, $NH(CH_2CHF_2)$, CN, $C(=O)CH_3$, $C(=O)NH(CH_3)$, $C(=O)N(CH_3)_2$, $SO_2CH_3,CO_2CH_3$, cyclopropyl, azetidin-1-yl, 3-fluoroazetidin-1-yl, 3,3-difluoroazetidin-1-yl, 3-(difluoromethyl)azetidin-1-yl, 3-methoxyazetidin-1-yl, 3-fluoro-3-methyl-azetidin-1-yl, pyrrolidin-1-yl, 3-fluoropyrrolidin-1-yl, 3,3-difluoropyrrolidin-1-yl, piperidin-1-yl, morpholinyl, 2-furyl, 1H-pyrazol-4-yl, and 1-methylpyrazol-3-yl.
15. The method of claim 8, wherin $Ar^3$ is pyrimidin-2-yl substituted one or two members each independently selected from the group consisting of: halo, $C_{1-6}$-alkyl, $C_{1-6}$alkyl substituted with OH or $CH_3$, $C_{1-6}$perhaloalkyl, $OC_{1-6}$alkyl, $OC_{1-6}$perhaloalkyl, and azetidine-1-yl.
16. The method of claim 8, wherin the compound has or pharmaceutically acceptable salt thereof has the structure of Formula (IB):

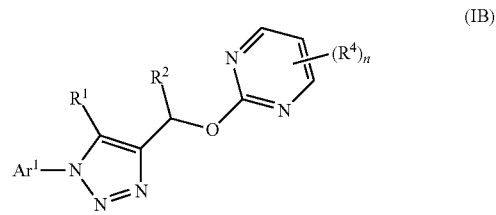

wherein

Ar¹ is phenyl substituted with two substituents each independently selected from the group consisting of: halo, $C_{1-3}$alkyl, $C_{1-3}$perhaloalkyl, $OCH_3$, and $OC_{1-3perhaloalkyl}$;

R¹ is selected from the group consisting of: H, F, I, and $CH_3$;

R² is H or $CH_3$;

n is 0, 1, or 2; and each R⁴ is independently selected from the group consisting of: halo, $C_{1-6}$alkyl, $C_{1-6}$alkyl substituted with OH or $OCH_3$, $C(OH)(CH_3)(CF_3)$, $CH(NH_2)CH_3$, $CH_2NH(CH_3)$, $C_{1-6}$perhaloalkyl, $OC_{1-6}$alkyl, $OC_{1-6}$perhaloalkyl, $NH_2$, $NH(CH_3)$, $N(CH_3)_2$, $NH(CH_2CH_3)$, $NH(CH_2CHF_2)$, CN, $C(=O)CH_3$, $C(=O)NH(CH_3)$, $C(=O)N(CH_3)_2$, $SO_2CH_3$, $CO_2CH_3$, cyclopropyl, azetidin-1-yl, 3-fluoroazetidin-1-yl, 3-fluoro-3methyl-azetidin-1-yl, pyrrolidin-1-yl, 3-fluoropyrrolidin-1-yl, 3,3-difluoropyrrolidin-1-yl, piperidin-1-yl, morpholine, 2-furyl, 1H-pyrazol-4-yl, and 1-methylpyrazol-3-yl.

17. The method of claim 16, wherein

Ar¹ is selected from the group consisting of: 4-chloro-3-(difluoromethoxy)phenyl, 3-(difluoromethoxy)-4-fluoro-phenyl, 3-(difluoromethoxy)-4-methyl-phenyl, 4-chloro-3-(1,1-difluoroethyl)phenyl, 3-(1,1-difluoroethyl-4-fluoro-phenyl, 4-chloro-3-(2-fluoroethoxy) phenyl, 3-(6-chloropropyl)-4-fluoro-phenyl, 4-fluoro-3-(3-floropropyl)phenyl, 3-bromo-4-fluoro-phenyl, 2-fluoro-3-(trifluoromethyl)phenyl, 3-(difluoromethyl)-4-fluoro-phenyl, 4-chloro-3-(difluoromethyl) phenyl, 4-chloro-3-methoxy-phenyl), 4-fluoro-3-isopropyl-phenyl, 3-chloro-4-fluoro-phenyl, 3-ehtyl-4-fluoro-phenyl, 3,4-difluorophenyl, 4-difluorophenyl, 4-fluoro-3-methyl-phenyl, and 3,5-dimethylphenyl;

R¹ is H;

R² is H;

n is 1 or 2; and each R⁴ is independently selected from the group consistion of: CI, F, $C_{1-3}$alkyl, $C_{1-3}$perhaloalkyl, $CH_2OH$, $CH_2OCH_3$, $C(CH_3)_2(OH)$, $OCH_3$, $OC_{1-3}$perhaloalkyl, $C(=O)CH_3$, and azetidine-1-yl.

18. The method of claim 2, wherein the compound of pharmaceutically acceptable salt thereof has the structure of Formula (IIA):

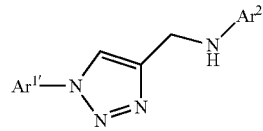

(IIA)

wherein:

Ar¹ is selected from the group consisting of: 4-chloro-3-(difluoromethoxy)phenyl, 3-(difluoromethoxy)-4-fluoro-phenyl, 4-fluoro-3-(trifluoromethyl)phenyl, 3-(difluoromethyl)-4-fluoro-phenyl, and 4-chloro-3-(difluoromethyl)phenyl; and Ar² is selected from the group consisting of: oxazol-2-yl, pyrimidin-4-yl, 1-methyl-pyrazol-3-yl, 1-methyl-imidazol-2-yl, and 1-methyl-pyrazol-4-yl.

19. The method of claim 2, wherein the compound or pharmaceutically acceptable salt thereof has the structure of Formula (IIB):

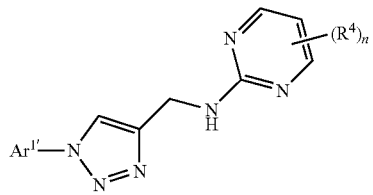

(IIB)

wherein:

Ar¹ is selected from the group consisting of: 3-(difluoromethyl)phenyl, 4-fluoro-3-methyl-phenyl, 4-chloro-3-(difluoromethoxy)phenyl, 3-(difluoromethoxy)-4-fluoro-phenyl, 4-fluoro-3-(trifluoromethyl)phenyl, 3-(difluoromethyl)-4-fluoro-phenyl, 4-chloro-3-(difluoromethyl)phenyl, and 3-(1,1-difluoroethyl)-4-fluoro-phenyl;

n is 1 or 2; and each R⁴ is independently selected from the group consisting of halo, $C_{1-3}$alkyl, $C(CH_3)_2OH$, $C_{1-3}$perhaloalkyl, $OCH_3$, and cyclopropyl.

20. The method of claim 8, wherein the compound is 2-[[1-[1-(difluoromethoxy)-4-fluoro-phenyl]triazol-4-yl] methoxy]-4-(methoxymethyl)pyrimidine or a pharmaceutically acceptable salt thereof.

* * * * *